United States Patent
Astsaturov et al.

(10) Patent No.: US 10,450,613 B2
(45) Date of Patent: Oct. 22, 2019

(54) EGFR/NEDD9/TGF-β INTERACTOME AND METHODS OF USE THEREOF FOR THE IDENTIFICATION OF AGENTS HAVING EFFICACY IN THE TREATMENT OF HYPERPROLIFERATIVE DISORDERS

(71) Applicant: Fox Chase Cancer Center, Philadelphia, PA (US)

(72) Inventors: Igor Astsaturov, Philadelphia, PA (US); Erica A. Golemis, Oreland, PA (US); Ilya G. Serebriiskii, Rockledge, PA (US); Louis M. Weiner, Washington, DC (US)

(73) Assignee: Fox Chase Cancer Center, Philadelphia, PA (US)

( * ) Notice: Subject to any disclaimer, the term of this patent is extended or adjusted under 35 U.S.C. 154(b) by 0 days.

(21) Appl. No.: 15/171,663

(22) Filed: Jun. 2, 2016

(65) Prior Publication Data
US 2017/0002426 A1    Jan. 5, 2017

Related U.S. Application Data

(63) Continuation of application No. 13/942,032, filed on Jul. 15, 2013, now abandoned, which is a continuation of application No. 12/777,112, filed on May 10, 2010, now abandoned, which is a continuation-in-part of application No. PCT/US2008/083067, filed on Nov. 10, 2008.

(60) Provisional application No. 60/986,964, filed on Nov. 9, 2007.

(51) Int. Cl.
| | |
|---|---|
| C12N 15/11 | (2006.01) |
| C12Q 1/6886 | (2018.01) |
| G01N 33/50 | (2006.01) |
| G01N 33/574 | (2006.01) |

(52) U.S. Cl.
CPC ......... *C12Q 1/6886* (2013.01); *G01N 33/502* (2013.01); *G01N 33/5044* (2013.01); *G01N 33/574* (2013.01); *G01N 33/57415* (2013.01); *G01N 33/57423* (2013.01); *G01N 33/57438* (2013.01); *G01N 33/57449* (2013.01); *C12Q 2600/136* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 7,491,720 B2 | 2/2009 | Ohkubo et al. |
| 7,947,653 B1 | 5/2011 | Sordella et al. |
| 8,110,572 B2 | 2/2012 | Dai et al. |
| 2005/0266409 A1 | 12/2005 | Brown et al. |
| 2006/0019256 A1 | 1/2006 | Clarke et al. |
| 2006/0030536 A1 | 2/2006 | Yu et al. |
| 2006/0099645 A1 | 5/2006 | Wrana et al. |
| 2006/0216288 A1 | 9/2006 | Chang |
| 2007/0009530 A1 | 1/2007 | Altaba et al. |
| 2007/0038385 A1 | 2/2007 | Nikolskaya et al. |
| 2007/0077553 A1 | 4/2007 | Bentwich |
| 2007/0172847 A1 | 7/2007 | Bonavida et al. |
| 2007/0212738 A1 | 9/2007 | Haley et al. |
| 2007/0259375 A1 | 11/2007 | Ford et al. |
| 2007/0270505 A1 | 11/2007 | Bunn, Jr. et al. |
| 2008/0102068 A1 | 5/2008 | Coleman et al. |
| 2008/0255065 A1 | 10/2008 | Young et al. |
| 2008/0286771 A1 | 11/2008 | Hudson et al. |
| 2009/0274626 A1* | 11/2009 | Kenny ............... C07K 14/485 514/1.1 |
| 2010/0310503 A1 | 12/2010 | Li et al. |
| 2011/0081356 A1 | 4/2011 | Tahara et al. |

FOREIGN PATENT DOCUMENTS

| | | |
|---|---|---|
| EP | 2226638 A2 | 9/2010 |
| WO | 2012/166579 A1 | 12/2012 |

OTHER PUBLICATIONS

Kraemer et al., Microarray analysis in bladder cancer cells: Inhibition of hTERT expression down-regulates EGFR, 2006, International Journal of Cancer, vol. 119, pp. 1276-1284.*
Sukhanova et al., Targeting the cholesterol pathway gene SC4MOL sensitizes cancer to EGFR inhibitors, Abstract 5098, Cancer Research, vol. 70, issue 8 supplement. (Year: 2010).*
Wiedmann, M.W., et al. "Molecularly targeted therapy for gastrointestinal cancer." Curr Cancer Drug Targets. May 2005;5(3):171-93.
Baselga, J., "The EGFR as a target for anticancer therapy—focus on cetuxamib", European Journal of Cancer, 37: S16-S22 (2001).
Saydam et al., Herpes simplx virus 1 amplicon vector-mediated siRNA targeting epidermal growth factor receptor inhibits growth of human glioma cells in vivo, Molecular Therapy, 12: 803-812 (2005).

\* cited by examiner

*Primary Examiner* — Dana H Shin
(74) *Attorney, Agent, or Firm* — Kathleen K. Rigaut; Howson & Howson LLP

(57) ABSTRACT

Compositions and methods for the treatment and diagnosis of cancer are disclosed.

2 Claims, 33 Drawing Sheets
(18 of 33 Drawing Sheet(s) Filed in Color)
Specification includes a Sequence Listing.

| Source | Total | High Confidence or Overlap |
|---|---|---|
| Experts: STKE, Biocarta, Systems-biology.org, NetPath, Protein Lounge | 277 | 76 |
| PPIs: BOND, Biogrid, EMBL IntAct, HPRD, KEGG, Prolinks | 1439 ($1^{st}$ and $2^{nd}$ rank) | 215 |
| Microarray: GEO (NIH) | 348 | 93 |
| Model Organisms: Michigan Proteome Consortium, fly -> human orthologs | 105; 65 have 1 or more orthologs | 119 |
| Paralogous clusters for key genes | | 125 |
| Selected based on literature | | ~10 |

Figure 9B

Visual Legend for hits by letters

| Node Color | hit set |
|---|---|
| ● | CPT11 only |
| ● | Erlotinib only |
| ● | CPT11 and Erlotinib |
| ● | Panitumumab only |
| ○ | Panitumumab |

| Edge Color | interaction |
|---|---|
| ........... | pathway maps and text mining |
| ———— | protein-protein | cellular localizations are according to GO

| Cell line | Inhibitors | | Molar Ratio | Coefficient of Interaction (average ± std. dev.) | | |
|---|---|---|---|---|---|---|
| | | | | ED50 | ED75 | ED90 |
| HCT116 | erlotinib | PHA-680632 | 50:1 | 0.80 ± 0.04 | 0.28 ± 0.18 | 0.14 ± 0.13 |
| | | | 100:1 | 0.58 ± 0.16 | 0.31 ± 0.12 | 0.21 ± 0.06 |
| | cetuximab | PHA-680632 | 16:1 | 0.46 ± 0.27 | 0.62 ± 0.05 | 1.07 ± 0.78 |
| | | | 33:1 | 0.31 ± 0.10 | 0.45 ± 0.06 | 0.73 ± 0.39 |
| | erlotinib | C1368 | 25:1 | 0.64 ± 0.12 | 0.71 ± 0.17 | 0.89 ± 0.56 |
| | cetuximab | C1368 | 8:1 | 0.42 ± 0.18 | 0.31 ± 0.10 | 0.24 ± 0.06 |
| A431 | erlotinib | PHA-680632 | 5:1 | 0.46 ± 0.11 | 0.37 ± 0.17 | 0.34 ± 0.23 |

```
                           SEQUENCE LISTING

<160> NUMBER OF SEQ ID NOS: 1276

<210> SEQ ID NO 1
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1
aaggttctac ttgagcaaga a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic sequence

<400> SEQUENCE: 2
caccatgagc gacgtggcta t                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic sequence

<400> SEQUENCE: 3
aagtgctttc actgtggagg a                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic sequence

<400> SEQUENCE: 4
accaaggaca tgtttgataa a                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic sequence

<400> SEQUENCE: 5
ccctactgtc tttgagaact a                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic sequence

<400> SEQUENCE: 6
gccctcggtg tcctacttca a                                              21
```

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7
gcgagccatg ctagtttgat a                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8
cgccaagaaa gatacgagat a                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence

<400> SEQUENCE: 9
tacctcttcc caggacatta a                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic sequence

<400> SEQUENCE: 10
caggtgttgc agcatcattg a                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic sequence

<400> SEQUENCE: 11
aacggctgat gtggactgtc t                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic sequence

<400> SEQUENCE: 12
aaggtacttc gatgatgaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic sequence

<400> SEQUENCE: 13
ctggtcttca attaccaaga a                                                 21

<210> SEQ ID NO 14
<211> LENGTH: 21
<212> TYPE: DNA
<213> ORGANISM: Artificial Sequence
<220> FEATURE:
<223> OTHER INFORMATION: Synthetic sequence

<400> SEQUENCE: 14
ttcgcggatc ttcgggaaga a                                                 21

<210> SEQ ID NO 15
<211> LENGTH: 21
<212> TYPE: DNA
<213> ORGANISM: Artificial Sequence
<220> FEATURE:
<223> OTHER INFORMATION: Synthetic sequence

<400> SEQUENCE: 15
cacgctgtgc gctacctcga a                                                 21

<210> SEQ ID NO 16
<211> LENGTH: 21
<212> TYPE: DNA
<213> ORGANISM: Artificial Sequence
<220> FEATURE:
<223> OTHER INFORMATION: Synthetic sequence

<400> SEQUENCE: 16
caacgtgaac gcgcaaatgt a                                                 21

<210> SEQ ID NO 17
<211> LENGTH: 21
<212> TYPE: DNA
<213> ORGANISM: Artificial Sequence
<220> FEATURE:
<223> OTHER INFORMATION: Synthetic sequence

<400> SEQUENCE: 17
gcggcagaca ttaaaggtac a                                                 21

<210> SEQ ID NO 18
<211> LENGTH: 21
<212> TYPE: DNA
<213> ORGANISM: Artificial Sequence
<220> FEATURE:
<223> OTHER INFORMATION: Synthetic sequence

<400> SEQUENCE: 18
ctggttgtat cttattagca a                                                 21

<210> SEQ ID NO 19
<211> LENGTH: 21
<212> TYPE: DNA
<213> ORGANISM: Artificial Sequence
<220> FEATURE:
<223> OTHER INFORMATION: Synthetic sequence

<400> SEQUENCE: 19
aagcaagtgt acgacgcgca c                                                 21

<210> SEQ ID NO 20

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 20
cagggccgtg cgggaccgca a                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic sequence

<400> SEQUENCE: 21
ctgatcgtat gcagaaggaa a                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic sequence

<400> SEQUENCE: 22
ctgggcctgt ataccggata a                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic sequence

<400> SEQUENCE: 23
ccgggatggc atgagtgtct a                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic sequence

<400> SEQUENCE: 24
agcgccaagt ccagaaccat a                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic sequence

<400> SEQUENCE: 25
ccagttgtac ttcagcacca a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic sequence

<400> SEQUENCE: 26
```

-continued aaggtcaacg acaaagaggt g                                            21

<210> SEQ ID NO 27
<211> LENGTH: 21
<212> TYPE: DNA
<213> ORGANISM: Artificial Sequence
<220> FEATURE:
<223> OTHER INFORMATION: Synthetic sequence

<400> SEQUENCE: 27
acggatattg tttcacgatg a                                            21

<210> SEQ ID NO 28
<211> LENGTH: 21
<212> TYPE: DNA
<213> ORGANISM: Artificial Sequence
<220> FEATURE:
<223> OTHER INFORMATION: Synthetic sequence

<400> SEQUENCE: 28
aagcccttct gcacatctaa a                                            21

<210> SEQ ID NO 29
<211> LENGTH: 21
<212> TYPE: DNA
<213> ORGANISM: Artificial Sequence
<220> FEATURE:
<223> OTHER INFORMATION: Synthetic sequence

<400> SEQUENCE: 29
acgctaataa gtgacaaata a                                            21

<210> SEQ ID NO 30
<211> LENGTH: 21
<212> TYPE: DNA
<213> ORGANISM: Artificial Sequence
<220> FEATURE:
<223> OTHER INFORMATION: Synthetic sequence

<400> SEQUENCE: 30
catgcggaag atgctggctt a                                            21

<210> SEQ ID NO 31
<211> LENGTH: 21
<212> TYPE: DNA
<213> ORGANISM: Artificial Sequence
<220> FEATURE:
<223> OTHER INFORMATION: Synthetic sequence

<400> SEQUENCE: 31
cccgcaaatc atcaactcca a                                            21

<210> SEQ ID NO 32
<211> LENGTH: 21
<212> TYPE: DNA
<213> ORGANISM: Artificial Sequence
<220> FEATURE:
<223> OTHER INFORMATION: Synthetic sequence

<400> SEQUENCE: 32
ccaataaaga ccagcaagca a                                            21

<210> SEQ ID NO 33
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 33
atgattgaca gtagtttatc a                                              21

<210> SEQ ID NO 34
<211> LENGTH: 21
<212> TYPE: DNA
<213> ORGANISM: Artificial Sequence
<220> FEATURE:
<223> OTHER INFORMATION: Synthetic sequence

<400> SEQUENCE: 34
aaccttgtat ctcttctgca a                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic sequence

<400> SEQUENCE: 35
ctcgacttct ccagctggtt a                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic sequence

<400> SEQUENCE: 36
ctccatccgt tggttcttca a                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic sequence

<400> SEQUENCE: 37
aacatataga ggccctattg g                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic sequence

<400> SEQUENCE: 38
ccgcagagct gcgtcacgta a                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic sequence

<400> SEQUENCE: 39
cagctttgac ggcgtgtgga a                                              21
```

```
<210> SEQ ID NO 40
<211> LENGTH: 21
<212> TYPE: DNA
<213> ORGANISM: Artificial Sequence
<220> FEATURE:
<223> OTHER INFORMATION: Synthetic sequence

<400> SEQUENCE: 40
aaggcaaacg tgaccgtttt t                                              21

<210> SEQ ID NO 41
<211> LENGTH: 21
<212> TYPE: DNA
<213> ORGANISM: Artificial Sequence
<220> FEATURE:
<223> OTHER INFORMATION: Synthetic sequence

<400> SEQUENCE: 41
caccgtcatc aatgccctca a                                              21

<210> SEQ ID NO 42
<211> LENGTH: 21
<212> TYPE: DNA
<213> ORGANISM: Artificial Sequence
<220> FEATURE:
<223> OTHER INFORMATION: Synthetic sequence

<400> SEQUENCE: 42
cacggcctga gcgtccagaa a                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic sequence

<400> SEQUENCE: 43
agggaagacc acgatcctct a                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic sequence

<400> SEQUENCE: 44
taccttatag ttactgtgta a                                              21

<210> SEQ ID NO 45
<211> LENGTH: 21
<212> TYPE: DNA
<213> ORGANISM: Artificial Sequence
<220> FEATURE:
<223> OTHER INFORMATION: Synthetic sequence

<400> SEQUENCE: 45
aaggatagat tgtgtttcaa a                                              21

<210> SEQ ID NO 46
<211> LENGTH: 21
<212> TYPE: DNA
<213> ORGANISM: Artificial Sequence
<220> FEATURE:
```

<223> OTHER INFORMATION: Synthetic sequence

<400> SEQUENCE: 46
ctggtaagcg actgtcatca a                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic sequence

<400> SEQUENCE: 47
atccatgaga tagctattat a                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic sequence

<400> SEQUENCE: 48
ctcggatatg tcgacttctg a                                              21

<210> SEQ ID NO 49
<211> LENGTH: 21
<212> TYPE: DNA
<213> ORGANISM: Artificial Sequence
<220> FEATURE:
<223> OTHER INFORMATION: Synthetic sequence

<400> SEQUENCE: 49
caggatacaa ggcagatcca a                                              21

<210> SEQ ID NO 50
<211> LENGTH: 21
<212> TYPE: DNA
<213> ORGANISM: Artificial Sequence
<220> FEATURE:
<223> OTHER INFORMATION: Synthetic sequence

<400> SEQUENCE: 50
ctcagtatcc tggatctgaa a                                              21

<210> SEQ ID NO 51
<211> LENGTH: 21
<212> TYPE: DNA
<213> ORGANISM: Artificial Sequence
<220> FEATURE:
<223> OTHER INFORMATION: Synthetic sequence

<400> SEQUENCE: 51
aggctcttga tggctatagt a                                              21

<210> SEQ ID NO 52
<211> LENGTH: 21
<212> TYPE: DNA
<213> ORGANISM: Artificial Sequence
<220> FEATURE:
<223> OTHER INFORMATION: Synthetic sequence

<400> SEQUENCE: 52
ccgacaaact ttacaaatcc a                                              21

```
<210> SEQ ID NO 53
<211> LENGTH: 21
<212> TYPE: DNA
<213> ORGANISM: Artificial Sequence
<220> FEATURE:
<223> OTHER INFORMATION: Synthetic sequence

<400> SEQUENCE: 53
cacctatatg accaatccct a                                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic sequence

<400> SEQUENCE: 54
cccggactcg ctggagaaca t                                              21

<210> SEQ ID NO 55
<211> LENGTH: 21
<212> TYPE: DNA
<213> ORGANISM: Artificial Sequence
<220> FEATURE:
<223> OTHER INFORMATION: Synthetic sequence

<400> SEQUENCE: 55
tccaagattc tagatgatta a                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic sequence

<400> SEQUENCE: 56
caccgaatta atatttatga a                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic sequence

<400> SEQUENCE: 57
caggaatgat ttcctgaaag a                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic sequence

<400> SEQUENCE: 58
agggctgagt ttgtattatt a                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 59
ccgtactatc ttgtcaagat a                                              21

<210> SEQ ID NO 60
<211> LENGTH: 21
<212> TYPE: DNA
<213> ORGANISM: Artificial Sequence
<220> FEATURE:
<223> OTHER INFORMATION: Synthetic sequence

<400> SEQUENCE: 60
aacgagctca atctaggacg a                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic sequence

<400> SEQUENCE: 61
cccaagatac tcatcagtca a                                              21

<210> SEQ ID NO 62
<211> LENGTH: 21
<212> TYPE: DNA
<213> ORGANISM: Artificial Sequence
<220> FEATURE:
<223> OTHER INFORMATION: Synthetic sequence

<400> SEQUENCE: 62
cacgcttggt cccgaggcca a                                              21

<210> SEQ ID NO 63
<211> LENGTH: 21
<212> TYPE: DNA
<213> ORGANISM: Artificial Sequence
<220> FEATURE:
<223> OTHER INFORMATION: Synthetic sequence

<400> SEQUENCE: 63
ggccggaatc ttaatattcg a                                              21

<210> SEQ ID NO 64
<211> LENGTH: 21
<212> TYPE: DNA
<213> ORGANISM: Artificial Sequence
<220> FEATURE:
<223> OTHER INFORMATION: Synthetic sequence

<400> SEQUENCE: 64
cccatttgga attattccta a                                              21

<210> SEQ ID NO 65
<211> LENGTH: 21
<212> TYPE: DNA
<213> ORGANISM: Artificial Sequence
<220> FEATURE:
<223> OTHER INFORMATION: Synthetic sequence

<400> SEQUENCE: 65
caccatggct gcaatccgaa a                                              21

<210> SEQ ID NO 66
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 66
aacaccagct cctgtgctgc g                                        21

<210> SEQ ID NO 67
<211> LENGTH: 21
<212> TYPE: DNA
<213> ORGANISM: Artificial Sequence
<220> FEATURE:
<223> OTHER INFORMATION: Synthetic sequence

<400> SEQUENCE: 67
cagcagcatc cctgagaacg a                                        21

<210> SEQ ID NO 68
<211> LENGTH: 21
<212> TYPE: DNA
<213> ORGANISM: Artificial Sequence
<220> FEATURE:
<223> OTHER INFORMATION: Synthetic sequence

<400> SEQUENCE: 68
atggatcaaa gtttgaatta a                                        21

<210> SEQ ID NO 69
<211> LENGTH: 21
<212> TYPE: DNA
<213> ORGANISM: Artificial Sequence
<220> FEATURE:
<223> OTHER INFORMATION: Synthetic sequence

<400> SEQUENCE: 69
ctcattgaac atatgcaaga a                                        21

<210> SEQ ID NO 70
<211> LENGTH: 21
<212> TYPE: DNA
<213> ORGANISM: Artificial Sequence
<220> FEATURE:
<223> OTHER INFORMATION: Synthetic sequence

<400> SEQUENCE: 70
acgggcaata agactcttta a                                        21

<210> SEQ ID NO 71
<211> LENGTH: 21
<212> TYPE: DNA
<213> ORGANISM: Artificial Sequence
<220> FEATURE:
<223> OTHER INFORMATION: Synthetic sequence

<400> SEQUENCE: 71
aaccaagcct ttgaaacaat g                                        21

<210> SEQ ID NO 72
<211> LENGTH: 21
<212> TYPE: DNA
<213> ORGANISM: Artificial Sequence
<220> FEATURE:
<223> OTHER INFORMATION: Synthetic sequence

<400> SEQUENCE: 72
```

```
aacaacttct ccgtagcaga a                                              21

<210> SEQ ID NO 73
<211> LENGTH: 21
<212> TYPE: DNA
<213> ORGANISM: Artificial Sequence
<220> FEATURE:
<223> OTHER INFORMATION: Synthetic sequence

<400> SEQUENCE: 73
acccaattaa gtcctacttt a                                              21

<210> SEQ ID NO 74
<211> LENGTH: 21
<212> TYPE: DNA
<213> ORGANISM: Artificial Sequence
<220> FEATURE:
<223> OTHER INFORMATION: Synthetic sequence

<400> SEQUENCE: 74
catctttgtg gtggacagta a                                              21

<210> SEQ ID NO 75
<211> LENGTH: 21
<212> TYPE: DNA
<213> ORGANISM: Artificial Sequence
<220> FEATURE:
<223> OTHER INFORMATION: Synthetic sequence

<400> SEQUENCE: 75
gagaaggtga atgtaccta a                                               21

<210> SEQ ID NO 76
<211> LENGTH: 21
<212> TYPE: DNA
<213> ORGANISM: Artificial Sequence
<220> FEATURE:
<223> OTHER INFORMATION: Synthetic sequence

<400> SEQUENCE: 76
ccggccggag gcgctttact a                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic sequence

<400> SEQUENCE: 77
cagctacgcc ggacaataga a                                              21

<210> SEQ ID NO 78
<211> LENGTH: 21
<212> TYPE: DNA
<213> ORGANISM: Artificial Sequence
<220> FEATURE:
<223> OTHER INFORMATION: Synthetic sequence

<400> SEQUENCE: 78
cggcaactta cacacattga a                                              21

<210> SEQ ID NO 79
<211> LENGTH: 21
<212> TYPE: DNA
<213> ORGANISM: Artificial Sequence
```

```
<220> FEATURE:
<223> OTHER INFORMATION: Synthetic sequence

<400> SEQUENCE: 79
caccttcact gtgacgaaat a                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetic sequence

<400> SEQUENCE: 80
aagaaataga cttgcacctt a                                              21

<210> SEQ ID NO 81
<211> LENGTH: 21
<212> TYPE: DNA
<213> ORGANISM: Artificial Sequence
<220> FEATURE:
<223> OTHER INFORMATION: Synthetic sequence

<400> SEQUENCE: 81
tcctagcacc atgaagatta a                                              21

<210> SEQ ID NO 82
<211> LENGTH: 21
<212> TYPE: DNA
<213> ORGANISM: Artificial Sequence
<220> FEATURE:
<223> OTHER INFORMATION: Synthetic sequence

<400> SEQUENCE: 82
cacctacgta tttaagatga a                                              21

<210> SEQ ID NO 83
<211> LENGTH: 21
<212> TYPE: DNA
<213> ORGANISM: Artificial Sequence
<220> FEATURE:
<223> OTHER INFORMATION: Synthetic sequence

<400> SEQUENCE: 83
ccgactcatc aagggacgaa a                                              21

<210> SEQ ID NO 84
<211> LENGTH: 21
<212> TYPE: DNA
<213> ORGANISM: Artificial Sequence
<220> FEATURE:
<223> OTHER INFORMATION: Synthetic sequence

<400> SEQUENCE: 84
aagcatagag ttatccttct a                                              21

<210> SEQ ID NO 85
<211> LENGTH: 21
<212> TYPE: DNA
<213> ORGANISM: Artificial Sequence
<220> FEATURE:
<223> OTHER INFORMATION: Synthetic sequence

<400> SEQUENCE: 85
acgcgttata gtaactccca t                                              21
```

```
<210> SEQ ID NO 86
<211> LENGTH: 21
<212> TYPE: DNA
<213> ORGANISM: Artificial Sequence
<220> FEATURE:
<223> OTHER INFORMATION: Synthetic sequence

<400> SEQUENCE: 86
cagcattccg ctgaccatca a                                        21

<210> SEQ ID NO 87
<211> LENGTH: 21
<212> TYPE: DNA
<213> ORGANISM: Artificial Sequence
<220> FEATURE:
<223> OTHER INFORMATION: Synthetic sequence

<400> SEQUENCE: 87
aacgaatgta ataaagacct a                                        21

<210> SEQ ID NO 88
<211> LENGTH: 21
<212> TYPE: DNA
<213> ORGANISM: Artificial Sequence
<220> FEATURE:
<223> OTHER INFORMATION: Synthetic sequence

<400> SEQUENCE: 88
gaccttgtac agaatgtgtt a                                        21

<210> SEQ ID NO 89
<211> LENGTH: 21
<212> TYPE: DNA
<213> ORGANISM: Artificial Sequence
<220> FEATURE:
<223> OTHER INFORMATION: Synthetic sequence

<400> SEQUENCE: 89
ccggctcaac tcgcatctca a                                        21

<210> SEQ ID NO 90
<211> LENGTH: 21
<212> TYPE: DNA
<213> ORGANISM: Artificial Sequence
<220> FEATURE:
<223> OTHER INFORMATION: Synthetic sequence

<400> SEQUENCE: 90
tgggacagaa ttggatacat a                                        21

<210> SEQ ID NO 91
<211> LENGTH: 21
<212> TYPE: DNA
<213> ORGANISM: Artificial Sequence
<220> FEATURE:
<223> OTHER INFORMATION: Synthetic sequence

<400> SEQUENCE: 91
acgcagcatc gtggactaca a                                        21

<210> SEQ ID NO 92
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 92
caggccatcc gcggaactcg a                                              21

<210> SEQ ID NO 93
<211> LENGTH: 21
<212> TYPE: DNA
<213> ORGANISM: Artificial Sequence
<220> FEATURE:
<223> OTHER INFORMATION: Synthetic sequence

<400> SEQUENCE: 93
atggatttga ggttacctca a                                              21

<210> SEQ ID NO 94
<211> LENGTH: 21
<212> TYPE: DNA
<213> ORGANISM: Artificial Sequence
<220> FEATURE:
<223> OTHER INFORMATION: Synthetic sequence

<400> SEQUENCE: 94
ttggataacc ttccttctaa a                                              21

<210> SEQ ID NO 95
<211> LENGTH: 21
<212> TYPE: DNA
<213> ORGANISM: Artificial Sequence
<220> FEATURE:
<223> OTHER INFORMATION: Synthetic sequence

<400> SEQUENCE: 95
ccgcgtgaag ctggtgaact t                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetic sequence

<400> SEQUENCE: 96
caagacgatc atagtcactg a                                              21

<210> SEQ ID NO 97
<211> LENGTH: 21
<212> TYPE: DNA
<213> ORGANISM: Artificial Sequence
<220> FEATURE:
<223> OTHER INFORMATION: Synthetic sequence

<400> SEQUENCE: 97
ttgcttatat gttaaattga a                                              21

<210> SEQ ID NO 98
<211> LENGTH: 21
<212> TYPE: DNA
<213> ORGANISM: Artificial Sequence
<220> FEATURE:
<223> OTHER INFORMATION: Synthetic sequence

<400> SEQUENCE: 98
caccaattga ttgactgaga a                                              21

<210> SEQ ID NO 99

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 99
ttgcgttcac ttgtactgta a                                              21

<210> SEQ ID NO 100
<211> LENGTH: 21
<212> TYPE: DNA
<213> ORGANISM: Artificial Sequence
<220> FEATURE:
<223> OTHER INFORMATION: Synthetic sequence

<400> SEQUENCE: 100
caagatttct ttgaccggta t                                              21

<210> SEQ ID NO 101
<211> LENGTH: 21
<212> TYPE: DNA
<213> ORGANISM: Artificial Sequence
<220> FEATURE:
<223> OTHER INFORMATION: Synthetic sequence

<400> SEQUENCE: 101
ttggatggct acagtaagaa a                                              21

<210> SEQ ID NO 102
<211> LENGTH: 21
<212> TYPE: DNA
<213> ORGANISM: Artificial Sequence
<220> FEATURE:
<223> OTHER INFORMATION: Synthetic sequence

<400> SEQUENCE: 102
cggcaagtcc ctgtactatt a                                              21

<210> SEQ ID NO 103
<211> LENGTH: 21
<212> TYPE: DNA
<213> ORGANISM: Artificial Sequence
<220> FEATURE:
<223> OTHER INFORMATION: Synthetic sequence

<400> SEQUENCE: 103
cacgatcctc tacaagctta a                                              21

<210> SEQ ID NO 104
<211> LENGTH: 21
<212> TYPE: DNA
<213> ORGANISM: Artificial Sequence
<220> FEATURE:
<223> OTHER INFORMATION: Synthetic sequence

<400> SEQUENCE: 104
caagctagac gtgggaagaa a                                              21

<210> SEQ ID NO 105
<211> LENGTH: 21
<212> TYPE: DNA
<213> ORGANISM: Artificial Sequence
<220> FEATURE:
<223> OTHER INFORMATION: Synthetic sequence

<400> SEQUENCE: 105
```
caggatgatc gtgacaagtt t                                              21

<210> SEQ ID NO 106
<211> LENGTH: 21
<212> TYPE: DNA
<213> ORGANISM: Artificial Sequence
<220> FEATURE:
<223> OTHER INFORMATION: Synthetic sequence

<400> SEQUENCE: 106
caacatgaag gtggccatta a                                              21

<210> SEQ ID NO 107
<211> LENGTH: 21
<212> TYPE: DNA
<213> ORGANISM: Artificial Sequence
<220> FEATURE:
<223> OTHER INFORMATION: Synthetic sequence

<400> SEQUENCE: 107
caccagaagt cctgaaacta a                                              21

<210> SEQ ID NO 108
<211> LENGTH: 21
<212> TYPE: DNA
<213> ORGANISM: Artificial Sequence
<220> FEATURE:
<223> OTHER INFORMATION: Synthetic sequence

<400> SEQUENCE: 108
ccgatgagaa acctcgtgtt a                                              21

<210> SEQ ID NO 109
<211> LENGTH: 21
<212> TYPE: DNA
<213> ORGANISM: Artificial Sequence
<220> FEATURE:
<223> OTHER INFORMATION: Synthetic sequence

<400> SEQUENCE: 109
caggtcgttc ttatctagag a                                              21

<210> SEQ ID NO 110
<211> LENGTH: 21
<212> TYPE: DNA
<213> ORGANISM: Artificial Sequence
<220> FEATURE:
<223> OTHER INFORMATION: Synthetic sequence

<400> SEQUENCE: 110
cacaattgtc atagtggaca t                                              21

<210> SEQ ID NO 111
<211> LENGTH: 21
<212> TYPE: DNA
<213> ORGANISM: Artificial Sequence
<220> FEATURE:
<223> OTHER INFORMATION: Synthetic sequence

<400> SEQUENCE: 111
tcggatatcc gcaactgtaa a                                              21

<210> SEQ ID NO 112
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 112
aaggctcttc aaggctatga a                                              21

<210> SEQ ID NO 113
<211> LENGTH: 21
<212> TYPE: DNA
<213> ORGANISM: Artificial Sequence
<220> FEATURE:
<223> OTHER INFORMATION: Synthetic sequence

<400> SEQUENCE: 113
ttccaattta ctggatttaa a                                              21

<210> SEQ ID NO 114
<211> LENGTH: 21
<212> TYPE: DNA
<213> ORGANISM: Artificial Sequence
<220> FEATURE:
<223> OTHER INFORMATION: Synthetic sequence

<400> SEQUENCE: 114
acaaggcatt ctctaaagct a                                              21

<210> SEQ ID NO 115
<211> LENGTH: 21
<212> TYPE: DNA
<213> ORGANISM: Artificial Sequence
<220> FEATURE:
<223> OTHER INFORMATION: Synthetic sequence

<400> SEQUENCE: 115
ccggtgttct aagatgtgat a                                              21

<210> SEQ ID NO 116
<211> LENGTH: 21
<212> TYPE: DNA
<213> ORGANISM: Artificial Sequence
<220> FEATURE:
<223> OTHER INFORMATION: Synthetic sequence

<400> SEQUENCE: 116
ctcagcatgt tcggcctgaa a                                              21

<210> SEQ ID NO 117
<211> LENGTH: 21
<212> TYPE: DNA
<213> ORGANISM: Artificial Sequence
<220> FEATURE:
<223> OTHER INFORMATION: Synthetic sequence

<400> SEQUENCE: 117
acggtgtgaa tcacacatcc a                                              21

<210> SEQ ID NO 118
<211> LENGTH: 21
<212> TYPE: DNA
<213> ORGANISM: Artificial Sequence
<220> FEATURE:
<223> OTHER INFORMATION: Synthetic sequence

<400> SEQUENCE: 118
atcgatcaat ggatacctat a                                              21
```

```
<210> SEQ ID NO 119
<211> LENGTH: 21
<212> TYPE: DNA
<213> ORGANISM: Artificial Sequence
<220> FEATURE:
<223> OTHER INFORMATION: Synthetic sequence

<400> SEQUENCE: 119
cccgccgaac tctctcagat a                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic sequence

<400> SEQUENCE: 120
caggaaggcc tgtacaatga a                                              21

<210> SEQ ID NO 121
<211> LENGTH: 21
<212> TYPE: DNA
<213> ORGANISM: Artificial Sequence
<220> FEATURE:
<223> OTHER INFORMATION: Synthetic sequence

<400> SEQUENCE: 121
aagcagaata cattcacgct a                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic sequence

<400> SEQUENCE: 122
tcggcctgaa gtgactcgta a                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic sequence

<400> SEQUENCE: 123
cacggagatg ttctgctgct a                                              21

<210> SEQ ID NO 124
<211> LENGTH: 21
<212> TYPE: DNA
<213> ORGANISM: Artificial Sequence
<220> FEATURE:
<223> OTHER INFORMATION: Synthetic sequence

<400> SEQUENCE: 124
caggaagatc tgtggaccaa a                                              21

<210> SEQ ID NO 125
<211> LENGTH: 21
<212> TYPE: DNA
<213> ORGANISM: Artificial Sequence
<220> FEATURE:
```

<223> OTHER INFORMATION: Synthetic sequence

<400> SEQUENCE: 125
ccaggcgatc tgcatacttt a                                              21

<210> SEQ ID NO 126
<211> LENGTH: 21
<212> TYPE: DNA
<213> ORGANISM: Artificial Sequence
<220> FEATURE:
<223> OTHER INFORMATION: Synthetic sequence

<400> SEQUENCE: 126
ctcgggatgt tcacaaccga a                                              21

<210> SEQ ID NO 127
<211> LENGTH: 21
<212> TYPE: DNA
<213> ORGANISM: Artificial Sequence
<220> FEATURE:
<223> OTHER INFORMATION: Synthetic sequence

<400> SEQUENCE: 127
caggatatga gttgcaggtg a                                              21

<210> SEQ ID NO 128
<211> LENGTH: 21
<212> TYPE: DNA
<213> ORGANISM: Artificial Sequence
<220> FEATURE:
<223> OTHER INFORMATION: Synthetic sequence

<400> SEQUENCE: 128
aaggactccg aatacataat a                                              21

<210> SEQ ID NO 129
<211> LENGTH: 21
<212> TYPE: DNA
<213> ORGANISM: Artificial Sequence
<220> FEATURE:
<223> OTHER INFORMATION: Synthetic sequence

<400> SEQUENCE: 129
caggtcggag accatgagaa a                                              21

<210> SEQ ID NO 130
<211> LENGTH: 21
<212> TYPE: DNA
<213> ORGANISM: Artificial Sequence
<220> FEATURE:
<223> OTHER INFORMATION: Synthetic sequence

<400> SEQUENCE: 130
gagcgaggag caattgatta a                                              21

<210> SEQ ID NO 131
<211> LENGTH: 21
<212> TYPE: DNA
<213> ORGANISM: Artificial Sequence
<220> FEATURE:
<223> OTHER INFORMATION: Synthetic sequence

<400> SEQUENCE: 131
aactccatct gtgcagcaaa c                                              21

```
<210> SEQ ID NO 132
<211> LENGTH: 21
<212> TYPE: DNA
<213> ORGANISM: Artificial Sequence
<220> FEATURE:
<223> OTHER INFORMATION: Synthetic sequence

<400> SEQUENCE: 132
aagcctctta cctgccgtaa a                                              21

<210> SEQ ID NO 133
<211> LENGTH: 21
<212> TYPE: DNA
<213> ORGANISM: Artificial Sequence
<220> FEATURE:
<223> OTHER INFORMATION: Synthetic sequence

<400> SEQUENCE: 133
gaccatggag cggtacctaa a                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetic sequence

<400> SEQUENCE: 134
aagcccagcc acagattgcc a                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetic sequence

<400> SEQUENCE: 135
aagtacaact tccacggcac t                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic sequence

<400> SEQUENCE: 136
ctggtgttga tcaacaaatc a                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetic sequence

<400> SEQUENCE: 137
caggtcatgc ttctcatcga t                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 138
gtcggaaatg gcgatcagca a    21

<210> SEQ ID NO 139
<211> LENGTH: 21
<212> TYPE: DNA
<213> ORGANISM: Artificial Sequence
<220> FEATURE:
<223> OTHER INFORMATION: Synthetic sequence

<400> SEQUENCE: 139
cagaatagga acaaggttct a    21

<210> SEQ ID NO 140
<211> LENGTH: 21
<212> TYPE: DNA
<213> ORGANISM: Artificial Sequence
<220> FEATURE:
<223> OTHER INFORMATION: Synthetic sequence

<400> SEQUENCE: 140
cggcaacaag accgtgacct a    21

<210> SEQ ID NO 141
<211> LENGTH: 21
<212> TYPE: DNA
<213> ORGANISM: Artificial Sequence
<220> FEATURE:
<223> OTHER INFORMATION: Synthetic sequence

<400> SEQUENCE: 141
taggtgtgac ttgaactaga t    21

<210> SEQ ID NO 142
<211> LENGTH: 21
<212> TYPE: DNA
<213> ORGANISM: Artificial Sequence
<220> FEATURE:
<223> OTHER INFORMATION: Synthetic sequence

<400> SEQUENCE: 142
caaggacata acaccacgaa a    21

<210> SEQ ID NO 143
<211> LENGTH: 21
<212> TYPE: DNA
<213> ORGANISM: Artificial Sequence
<220> FEATURE:
<223> OTHER INFORMATION: Synthetic sequence

<400> SEQUENCE: 143
aagcagaaga ttattgatct a    21

<210> SEQ ID NO 144
<211> LENGTH: 21
<212> TYPE: DNA
<213> ORGANISM: Artificial Sequence
<220> FEATURE:
<223> OTHER INFORMATION: Synthetic sequence

<400> SEQUENCE: 144
aatccgggac aagcctgaag a    21

<210> SEQ ID NO 145
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 145
ctggtcgctt acatcacttt a                                              21

<210> SEQ ID NO 146
<211> LENGTH: 21
<212> TYPE: DNA
<213> ORGANISM: Artificial Sequence
<220> FEATURE:
<223> OTHER INFORMATION: Synthetic sequence

<400> SEQUENCE: 146
aacagaatta tttgacctga a                                              21

<210> SEQ ID NO 147
<211> LENGTH: 21
<212> TYPE: DNA
<213> ORGANISM: Artificial Sequence
<220> FEATURE:
<223> OTHER INFORMATION: Synthetic sequence

<400> SEQUENCE: 147
aacgaggtcc agcgatttga a                                              21

<210> SEQ ID NO 148
<211> LENGTH: 21
<212> TYPE: DNA
<213> ORGANISM: Artificial Sequence
<220> FEATURE:
<223> OTHER INFORMATION: Synthetic sequence

<400> SEQUENCE: 148
caaggtggtt tcaacaagtt t                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic sequence

<400> SEQUENCE: 149
ctggaagttc gagaccacca a                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetic sequence

<400> SEQUENCE: 150
tcggacagac atataggata t                                              21

<210> SEQ ID NO 151
<211> LENGTH: 21
<212> TYPE: DNA
<213> ORGANISM: Artificial Sequence
<220> FEATURE:
<223> OTHER INFORMATION: Synthetic sequence

<400> SEQUENCE: 151
```
ccggcgacga tttgtgcgta a                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetic sequence

<400> SEQUENCE: 152
aagatggacg gagcttgtta t                                              21

<210> SEQ ID NO 153
<211> LENGTH: 21
<212> TYPE: DNA
<213> ORGANISM: Artificial Sequence
<220> FEATURE:
<223> OTHER INFORMATION: Synthetic sequence

<400> SEQUENCE: 153
gacggaagag ttgagaccta a                                              21

<210> SEQ ID NO 154
<211> LENGTH: 21
<212> TYPE: DNA
<213> ORGANISM: Artificial Sequence
<220> FEATURE:
<223> OTHER INFORMATION: Synthetic sequence

<400> SEQUENCE: 154
tagtttatca ttaaccactt a                                              21

<210> SEQ ID NO 155
<211> LENGTH: 21
<212> TYPE: DNA
<213> ORGANISM: Artificial Sequence
<220> FEATURE:
<223> OTHER INFORMATION: Synthetic sequence

<400> SEQUENCE: 155
tacgctggga atattctgta t                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetic sequence

<400> SEQUENCE: 156
tagagcatga acatccagta a                                              21

<210> SEQ ID NO 157
<211> LENGTH: 21
<212> TYPE: DNA
<213> ORGANISM: Artificial Sequence
<220> FEATURE:
<223> OTHER INFORMATION: Synthetic sequence

<400> SEQUENCE: 157
cccggttaca gctgagaatg a                                              21

<210> SEQ ID NO 158
<211> LENGTH: 21
<212> TYPE: DNA
<213> ORGANISM: Artificial Sequence
<220> FEATURE:
<223> OTHER INFORMATION: Synthetic sequence

<400> SEQUENCE: 158
ctgaataaac agtttattta a                                              21

<210> SEQ ID NO 159
<211> LENGTH: 21
<212> TYPE: DNA
<213> ORGANISM: Artificial Sequence
<220> FEATURE:
<223> OTHER INFORMATION: Synthetic sequence

<400> SEQUENCE: 159
gcggttgttc ctcacccgat a                                              21

<210> SEQ ID NO 160
<211> LENGTH: 21
<212> TYPE: DNA
<213> ORGANISM: Artificial Sequence
<220> FEATURE:
<223> OTHER INFORMATION: Synthetic sequence

<400> SEQUENCE: 160
acgagacgtg attatgaggg a                                              21

<210> SEQ ID NO 161
<211> LENGTH: 21
<212> TYPE: DNA
<213> ORGANISM: Artificial Sequence
<220> FEATURE:
<223> OTHER INFORMATION: Synthetic sequence

<400> SEQUENCE: 161
aagggttatc tctttcatac a                                              21

<210> SEQ ID NO 162
<211> LENGTH: 21
<212> TYPE: DNA
<213> ORGANISM: Artificial Sequence
<220> FEATURE:
<223> OTHER INFORMATION: Synthetic sequence

<400> SEQUENCE: 162
ccggacttgg tgcgtctaag a                                              21

<210> SEQ ID NO 163
<211> LENGTH: 21
<212> TYPE: DNA
<213> ORGANISM: Artificial Sequence
<220> FEATURE:
<223> OTHER INFORMATION: Synthetic sequence

<400> SEQUENCE: 163
ctggtcgtcc tcatcttaat a                                              21

<210> SEQ ID NO 164
<211> LENGTH: 21
<212> TYPE: DNA
<213> ORGANISM: Artificial Sequence
<220> FEATURE:
<223> OTHER INFORMATION: Synthetic sequence

<400> SEQUENCE: 164
ctcagtgata cgtacagcca a                                              21

<210> SEQ ID NO 165
<211> LENGTH: 21
<212> TYPE: DNA
<213> ORGANISM: Artificial Sequence
<220> FEATURE:
<223> OTHER INFORMATION: Synthetic sequence

<400> SEQUENCE: 165
aaagattccc acccaattca a                                              21

<210> SEQ ID NO 166
<211> LENGTH: 21
<212> TYPE: DNA
<213> ORGANISM: Artificial Sequence
<220> FEATURE:
<223> OTHER INFORMATION: Synthetic sequence

<400> SEQUENCE: 166
caagaagatt gccttggtaa a                                              21

<210> SEQ ID NO 167
<211> LENGTH: 21
<212> TYPE: DNA
<213> ORGANISM: Artificial Sequence
<220> FEATURE:
<223> OTHER INFORMATION: Synthetic sequence

<400> SEQUENCE: 167
tcccataatt gctttgccaa a                                              21

<210> SEQ ID NO 168
<211> LENGTH: 21
<212> TYPE: DNA
<213> ORGANISM: Artificial Sequence
<220> FEATURE:
<223> OTHER INFORMATION: Synthetic sequence

<400> SEQUENCE: 168
gacggcgttc tggatctcaa a                                              21

<210> SEQ ID NO 169
<211> LENGTH: 21
<212> TYPE: DNA
<213> ORGANISM: Artificial Sequence
<220> FEATURE:
<223> OTHER INFORMATION: Synthetic sequence

<400> SEQUENCE: 169
caggaactgg atattctgaa a                                              21

<210> SEQ ID NO 170
<211> LENGTH: 21
<212> TYPE: DNA
<213> ORGANISM: Artificial Sequence
<220> FEATURE:
<223> OTHER INFORMATION: Synthetic sequence

<400> SEQUENCE: 170
tgccatattg cacatgtctt a                                              21

<210> SEQ ID NO 171
<211> LENGTH: 21
<212> TYPE: DNA
<213> ORGANISM: Artificial Sequence
<220> FEATURE:
<223> OTHER INFORMATION: Synthetic sequence

<400> SEQUENCE: 171
catcagattt gaaatattta a                                               21

<210> SEQ ID NO 172
<211> LENGTH: 21
<212> TYPE: DNA
<213> ORGANISM: Artificial Sequence
<220> FEATURE:
<223> OTHER INFORMATION: Synthetic sequence

<400> SEQUENCE: 172
cgggccctga gtaatcgctt a                                               21

<210> SEQ ID NO 173
<211> LENGTH: 21
<212> TYPE: DNA
<213> ORGANISM: Artificial Sequence
<220> FEATURE:
<223> OTHER INFORMATION: Synthetic sequence

<400> SEQUENCE: 173
aagatggatt atcaagtgtc a                                               21

<210> SEQ ID NO 174
<211> LENGTH: 21
<212> TYPE: DNA
<213> ORGANISM: Artificial Sequence
<220> FEATURE:
<223> OTHER INFORMATION: Synthetic sequence

<400> SEQUENCE: 174
aaggacagcc ctgtggctat a                                               21

<210> SEQ ID NO 175
<211> LENGTH: 21
<212> TYPE: DNA
<213> ORGANISM: Artificial Sequence
<220> FEATURE:
<223> OTHER INFORMATION: Synthetic sequence

<400> SEQUENCE: 175
caccctgatg tcgcagccta t                                               21

<210> SEQ ID NO 176
<211> LENGTH: 21
<212> TYPE: DNA
<213> ORGANISM: Artificial Sequence
<220> FEATURE:
<223> OTHER INFORMATION: Synthetic sequence

<400> SEQUENCE: 176
aagctagata ctggaaacct a                                               21

<210> SEQ ID NO 177
<211> LENGTH: 21
<212> TYPE: DNA
<213> ORGANISM: Artificial Sequence
<220> FEATURE:
<223> OTHER INFORMATION: Synthetic sequence

<400> SEQUENCE: 177
ctggttcaac gaggccattg a                                               21

<210> SEQ ID NO 178

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 178
tacaagggac actataaata a                                              21

<210> SEQ ID NO 179
<211> LENGTH: 21
<212> TYPE: DNA
<213> ORGANISM: Artificial Sequence
<220> FEATURE:
<223> OTHER INFORMATION: Synthetic sequence

<400> SEQUENCE: 179
cccgtcggtg gccaccacgt a                                              21

<210> SEQ ID NO 180
<211> LENGTH: 21
<212> TYPE: DNA
<213> ORGANISM: Artificial Sequence
<220> FEATURE:
<223> OTHER INFORMATION: Synthetic sequence

<400> SEQUENCE: 180
tcagatgtac atagagatct a                                              21

<210> SEQ ID NO 181
<211> LENGTH: 21
<212> TYPE: DNA
<213> ORGANISM: Artificial Sequence
<220> FEATURE:
<223> OTHER INFORMATION: Synthetic sequence

<400> SEQUENCE: 181
cacgaatatt atgcccagtt t                                              21

<210> SEQ ID NO 182
<211> LENGTH: 21
<212> TYPE: DNA
<213> ORGANISM: Artificial Sequence
<220> FEATURE:
<223> OTHER INFORMATION: Synthetic sequence

<400> SEQUENCE: 182
ctaggtattg tctactctga a                                              21

<210> SEQ ID NO 183
<211> LENGTH: 21
<212> TYPE: DNA
<213> ORGANISM: Artificial Sequence
<220> FEATURE:
<223> OTHER INFORMATION: Synthetic sequence

<400> SEQUENCE: 183
cccgagatgt tcatggatga a                                              21

<210> SEQ ID NO 184
<211> LENGTH: 21
<212> TYPE: DNA
<213> ORGANISM: Artificial Sequence
<220> FEATURE:
<223> OTHER INFORMATION: Synthetic sequence

<400> SEQUENCE: 184
```

```
cacggccaag tttacctccg a                                              21

<210> SEQ ID NO 185
<211> LENGTH: 21
<212> TYPE: DNA
<213> ORGANISM: Artificial Sequence
<220> FEATURE:
<223> OTHER INFORMATION: Synthetic sequence

<400> SEQUENCE: 185
tcctataact tcagtattgt a                                              21

<210> SEQ ID NO 186
<211> LENGTH: 21
<212> TYPE: DNA
<213> ORGANISM: Artificial Sequence
<220> FEATURE:
<223> OTHER INFORMATION: Synthetic sequence

<400> SEQUENCE: 186
taagaattga gtaatggtgt a                                              21

<210> SEQ ID NO 187
<211> LENGTH: 21
<212> TYPE: DNA
<213> ORGANISM: Artificial Sequence
<220> FEATURE:
<223> OTHER INFORMATION: Synthetic sequence

<400> SEQUENCE: 187
gacgagagtg gtcaaggtta a                                              21

<210> SEQ ID NO 188
<211> LENGTH: 21
<212> TYPE: DNA
<213> ORGANISM: Artificial Sequence
<220> FEATURE:
<223> OTHER INFORMATION: Synthetic sequence

<400> SEQUENCE: 188
tacccagaat tctgttctaa a                                              21

<210> SEQ ID NO 189
<211> LENGTH: 21
<212> TYPE: DNA
<213> ORGANISM: Artificial Sequence
<220> FEATURE:
<223> OTHER INFORMATION: Synthetic sequence

<400> SEQUENCE: 189
accgagcaca ttggtgacag a                                              21

<210> SEQ ID NO 190
<211> LENGTH: 21
<212> TYPE: DNA
<213> ORGANISM: Artificial Sequence
<220> FEATURE:
<223> OTHER INFORMATION: Synthetic sequence

<400> SEQUENCE: 190
tccactctct acaatccgta a                                              21

<210> SEQ ID NO 191
<211> LENGTH: 21
<212> TYPE: DNA
```

```
<213> ORGANISM: Artificial Sequence
<220> FEATURE:
<223> OTHER INFORMATION: Synthetic sequence

<400> SEQUENCE: 191
ctggcgcaga tcgatttgaa t                                             21

<210> SEQ ID NO 192
<211> LENGTH: 21
<212> TYPE: DNA
<213> ORGANISM: Artificial Sequence
<220> FEATURE:
<223> OTHER INFORMATION: Synthetic sequence

<400> SEQUENCE: 192
cagatgaaat cggcaacttt a                                             21

<210> SEQ ID NO 193
<211> LENGTH: 21
<212> TYPE: DNA
<213> ORGANISM: Artificial Sequence
<220> FEATURE:
<223> OTHER INFORMATION: Synthetic sequence

<400> SEQUENCE: 193
ctggtagaag tcagtcggta t                                             21

<210> SEQ ID NO 194
<211> LENGTH: 21
<212> TYPE: DNA
<213> ORGANISM: Artificial Sequence
<220> FEATURE:
<223> OTHER INFORMATION: Synthetic sequence

<400> SEQUENCE: 194
aactgattcc caaaagcgaa g                                             21

<210> SEQ ID NO 195
<211> LENGTH: 21
<212> TYPE: DNA
<213> ORGANISM: Artificial Sequence
<220> FEATURE:
<223> OTHER INFORMATION: Synthetic sequence

<400> SEQUENCE: 195
tacgcgcctc attaaaccaa a                                             21

<210> SEQ ID NO 196
<211> LENGTH: 21
<212> TYPE: DNA
<213> ORGANISM: Artificial Sequence
<220> FEATURE:
<223> OTHER INFORMATION: Synthetic sequence

<400> SEQUENCE: 196
aagggttaag atctatggga a                                             21

<210> SEQ ID NO 197
<211> LENGTH: 21
<212> TYPE: DNA
<213> ORGANISM: Artificial Sequence
<220> FEATURE:
<223> OTHER INFORMATION: Synthetic sequence

<400> SEQUENCE: 197
gaggaatgtc tacaaggatt a                                             21
```

<210> SEQ ID NO 198
<211> LENGTH: 21
<212> TYPE: DNA
<213> ORGANISM: Artificial Sequence
<220> FEATURE:
<223> OTHER INFORMATION: Synthetic sequence

<400> SEQUENCE: 198
tacggacact attatcacta a                                              21

<210> SEQ ID NO 199
<211> LENGTH: 21
<212> TYPE: DNA
<213> ORGANISM: Artificial Sequence
<220> FEATURE:
<223> OTHER INFORMATION: Synthetic sequence

<400> SEQUENCE: 199
caccgagaca tttaggtgaa a                                              21

<210> SEQ ID NO 200
<211> LENGTH: 21
<212> TYPE: DNA
<213> ORGANISM: Artificial Sequence
<220> FEATURE:
<223> OTHER INFORMATION: Synthetic sequence

<400> SEQUENCE: 200
cagcgactcg gtagtccatt a                                              21

<210> SEQ ID NO 201
<211> LENGTH: 21
<212> TYPE: DNA
<213> ORGANISM: Artificial Sequence
<220> FEATURE:
<223> OTHER INFORMATION: Synthetic sequence

<400> SEQUENCE: 201
caaagctggg ttacaagtgt a                                              21

<210> SEQ ID NO 202
<211> LENGTH: 21
<212> TYPE: DNA
<213> ORGANISM: Artificial Sequence
<220> FEATURE:
<223> OTHER INFORMATION: Synthetic sequence

<400> SEQUENCE: 202
accacgaaac gtgaagttca a                                              21

<210> SEQ ID NO 203
<211> LENGTH: 21
<212> TYPE: DNA
<213> ORGANISM: Artificial Sequence
<220> FEATURE:
<223> OTHER INFORMATION: Synthetic sequence

<400> SEQUENCE: 203
ttccataagc ttggtgacaa a                                              21

<210> SEQ ID NO 204
<211> LENGTH: 21
<212> TYPE: DNA
<213> ORGANISM: Artificial Sequence
<220> FEATURE:

<223> OTHER INFORMATION: Synthetic sequence

<400> SEQUENCE: 204
caggatgtac cgagcacttt a                                           21

<210> SEQ ID NO 205
<211> LENGTH: 21
<212> TYPE: DNA
<213> ORGANISM: Artificial Sequence
<220> FEATURE:
<223> OTHER INFORMATION: Synthetic sequence

<400> SEQUENCE: 205
tccattgaag ctgaaatggt a                                           21

<210> SEQ ID NO 206
<211> LENGTH: 21
<212> TYPE: DNA
<213> ORGANISM: Artificial Sequence
<220> FEATURE:
<223> OTHER INFORMATION: Synthetic sequence

<400> SEQUENCE: 206
cagcgcctgc acgatattga a                                           21

<210> SEQ ID NO 207
<211> LENGTH: 21
<212> TYPE: DNA
<213> ORGANISM: Artificial Sequence
<220> FEATURE:
<223> OTHER INFORMATION: Synthetic sequence

<400> SEQUENCE: 207
ccgaggttac acgttacgaa a                                           21

<210> SEQ ID NO 208
<211> LENGTH: 21
<212> TYPE: DNA
<213> ORGANISM: Artificial Sequence
<220> FEATURE:
<223> OTHER INFORMATION: Synthetic sequence

<400> SEQUENCE: 208
tacgactttg tcaagaggaa a                                           21

<210> SEQ ID NO 209
<211> LENGTH: 21
<212> TYPE: DNA
<213> ORGANISM: Artificial Sequence
<220> FEATURE:
<223> OTHER INFORMATION: Synthetic sequence

<400> SEQUENCE: 209
caaggagaag acccacatca a                                           21

<210> SEQ ID NO 210
<211> LENGTH: 21
<212> TYPE: DNA
<213> ORGANISM: Artificial Sequence
<220> FEATURE:
<223> OTHER INFORMATION: Synthetic sequence

<400> SEQUENCE: 210
cagcgccaag taaacagggt a                                           21

```
<210> SEQ ID NO 211
<211> LENGTH: 21
<212> TYPE: DNA
<213> ORGANISM: Artificial Sequence
<220> FEATURE:
<223> OTHER INFORMATION: Synthetic sequence

<400> SEQUENCE: 211
caggccattc ttaattacct a                                              21

<210> SEQ ID NO 212
<211> LENGTH: 21
<212> TYPE: DNA
<213> ORGANISM: Artificial Sequence
<220> FEATURE:
<223> OTHER INFORMATION: Synthetic sequence

<400> SEQUENCE: 212
aacttgcctt aaacactcac c                                              21

<210> SEQ ID NO 213
<211> LENGTH: 21
<212> TYPE: DNA
<213> ORGANISM: Artificial Sequence
<220> FEATURE:
<223> OTHER INFORMATION: Synthetic sequence

<400> SEQUENCE: 213
ctggatcgac tacaagttga a                                              21

<210> SEQ ID NO 214
<211> LENGTH: 21
<212> TYPE: DNA
<213> ORGANISM: Artificial Sequence
<220> FEATURE:
<223> OTHER INFORMATION: Synthetic sequence

<400> SEQUENCE: 214
caggtgttta taattaatcc t                                              21

<210> SEQ ID NO 215
<211> LENGTH: 21
<212> TYPE: DNA
<213> ORGANISM: Artificial Sequence
<220> FEATURE:
<223> OTHER INFORMATION: Synthetic sequence

<400> SEQUENCE: 215
cacggtgagg gatgtaaatg a                                              21

<210> SEQ ID NO 216
<211> LENGTH: 21
<212> TYPE: DNA
<213> ORGANISM: Artificial Sequence
<220> FEATURE:
<223> OTHER INFORMATION: Synthetic sequence

<400> SEQUENCE: 216
aaggttggcc ttagtagtca a                                              21

<210> SEQ ID NO 217
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 217
caggtctatg ctgcgctcat a                                              21

<210> SEQ ID NO 218
<211> LENGTH: 21
<212> TYPE: DNA
<213> ORGANISM: Artificial Sequence
<220> FEATURE:
<223> OTHER INFORMATION: Synthetic sequence

<400> SEQUENCE: 218
ccgggattcc gccaatttgg a                                              21

<210> SEQ ID NO 219
<211> LENGTH: 21
<212> TYPE: DNA
<213> ORGANISM: Artificial Sequence
<220> FEATURE:
<223> OTHER INFORMATION: Synthetic sequence

<400> SEQUENCE: 219
tacgactaat cacctactca a                                              21

<210> SEQ ID NO 220
<211> LENGTH: 21
<212> TYPE: DNA
<213> ORGANISM: Artificial Sequence
<220> FEATURE:
<223> OTHER INFORMATION: Synthetic sequence

<400> SEQUENCE: 220
agggatggac atcttgtcat t                                              21

<210> SEQ ID NO 221
<211> LENGTH: 21
<212> TYPE: DNA
<213> ORGANISM: Artificial Sequence
<220> FEATURE:
<223> OTHER INFORMATION: Synthetic sequence

<400> SEQUENCE: 221
ctggccaaat agcaaagaca a                                              21

<210> SEQ ID NO 222
<211> LENGTH: 21
<212> TYPE: DNA
<213> ORGANISM: Artificial Sequence
<220> FEATURE:
<223> OTHER INFORMATION: Synthetic sequence

<400> SEQUENCE: 222
cccggcaact ctagtattta g                                              21

<210> SEQ ID NO 223
<211> LENGTH: 21
<212> TYPE: DNA
<213> ORGANISM: Artificial Sequence
<220> FEATURE:
<223> OTHER INFORMATION: Synthetic sequence

<400> SEQUENCE: 223
agggctgtat cacatcggtt a                                              21

<210> SEQ ID NO 224
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 224
cagagaactg cggttactta a                                               21

<210> SEQ ID NO 225
<211> LENGTH: 21
<212> TYPE: DNA
<213> ORGANISM: Artificial Sequence
<220> FEATURE:
<223> OTHER INFORMATION: Synthetic sequence

<400> SEQUENCE: 225
ctgatcgttc aaagcatgaa a                                               21

<210> SEQ ID NO 226
<211> LENGTH: 21
<212> TYPE: DNA
<213> ORGANISM: Artificial Sequence
<220> FEATURE:
<223> OTHER INFORMATION: Synthetic sequence

<400> SEQUENCE: 226
aagggtgtgc attacatttc a                                               21

<210> SEQ ID NO 227
<211> LENGTH: 21
<212> TYPE: DNA
<213> ORGANISM: Artificial Sequence
<220> FEATURE:
<223> OTHER INFORMATION: Synthetic sequence

<400> SEQUENCE: 227
gtgctggatt tgatgagtta a                                               21

<210> SEQ ID NO 228
<211> LENGTH: 21
<212> TYPE: DNA
<213> ORGANISM: Artificial Sequence
<220> FEATURE:
<223> OTHER INFORMATION: Synthetic sequence

<400> SEQUENCE: 228
ctggaggtac ccattccaga a                                               21

<210> SEQ ID NO 229
<211> LENGTH: 21
<212> TYPE: DNA
<213> ORGANISM: Artificial Sequence
<220> FEATURE:
<223> OTHER INFORMATION: Synthetic sequence

<400> SEQUENCE: 229
ataggtattg gtgaatttaa a                                               21

<210> SEQ ID NO 230
<211> LENGTH: 21
<212> TYPE: DNA
<213> ORGANISM: Artificial Sequence
<220> FEATURE:
<223> OTHER INFORMATION: Synthetic sequence

<400> SEQUENCE: 230
```
aaagatataa gtgctgtata a                                              21

<210> SEQ ID NO 231
<211> LENGTH: 21
<212> TYPE: DNA
<213> ORGANISM: Artificial Sequence
<220> FEATURE:
<223> OTHER INFORMATION: Synthetic sequence

<400> SEQUENCE: 231
tacaattgtg gttaccttca a                                              21

<210> SEQ ID NO 232
<211> LENGTH: 21
<212> TYPE: DNA
<213> ORGANISM: Artificial Sequence
<220> FEATURE:
<223> OTHER INFORMATION: Synthetic sequence

<400> SEQUENCE: 232
caccctgcgg aacttgttca a                                              21

<210> SEQ ID NO 233
<211> LENGTH: 21
<212> TYPE: DNA
<213> ORGANISM: Artificial Sequence
<220> FEATURE:
<223> OTHER INFORMATION: Synthetic sequence

<400> SEQUENCE: 233
aagggacata ttcatttgga a                                              21

<210> SEQ ID NO 234
<211> LENGTH: 21
<212> TYPE: DNA
<213> ORGANISM: Artificial Sequence
<220> FEATURE:
<223> OTHER INFORMATION: Synthetic sequence

<400> SEQUENCE: 234
aagcatgtct gtgatccacc a                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic sequence

<400> SEQUENCE: 235
gcgaattgtg gcagagtgta a                                              21

<210> SEQ ID NO 236
<211> LENGTH: 21
<212> TYPE: DNA
<213> ORGANISM: Artificial Sequence
<220> FEATURE:
<223> OTHER INFORMATION: Synthetic sequence

<400> SEQUENCE: 236
tacgtgcgct ctgccattca a                                              21

<210> SEQ ID NO 237
<211> LENGTH: 21
<212> TYPE: DNA
<213> ORGANISM: Artificial Sequence -continued

```
<220> FEATURE:
<223> OTHER INFORMATION: Synthetic sequence

<400> SEQUENCE: 237
cagttgtatg tttgctgatt a                                    21

<210> SEQ ID NO 238
<211> LENGTH: 21
<212> TYPE: DNA
<213> ORGANISM: Artificial Sequence
<220> FEATURE:
<223> OTHER INFORMATION: Synthetic sequence

<400> SEQUENCE: 238
agggtgttgg ttaaagttgt a                                    21

<210> SEQ ID NO 239
<211> LENGTH: 21
<212> TYPE: DNA
<213> ORGANISM: Artificial Sequence
<220> FEATURE:
<223> OTHER INFORMATION: Synthetic sequence

<400> SEQUENCE: 239
caggacaatt gaaatttgct a                                    21

<210> SEQ ID NO 240
<211> LENGTH: 21
<212> TYPE: DNA
<213> ORGANISM: Artificial Sequence
<220> FEATURE:
<223> OTHER INFORMATION: Synthetic sequence

<400> SEQUENCE: 240
cagactctga caatcattaa a                                    21

<210> SEQ ID NO 241
<211> LENGTH: 21
<212> TYPE: DNA
<213> ORGANISM: Artificial Sequence
<220> FEATURE:
<223> OTHER INFORMATION: Synthetic sequence

<400> SEQUENCE: 241
agggagtcat ctcttcctat a                                    21

<210> SEQ ID NO 242
<211> LENGTH: 21
<212> TYPE: DNA
<213> ORGANISM: Artificial Sequence
<220> FEATURE:
<223> OTHER INFORMATION: Synthetic sequence

<400> SEQUENCE: 242
accagttgga tctccaatga a                                    21

<210> SEQ ID NO 243
<211> LENGTH: 21
<212> TYPE: DNA
<213> ORGANISM: Artificial Sequence
<220> FEATURE:
<223> OTHER INFORMATION: Synthetic sequence

<400> SEQUENCE: 243
cccagtgaga aggctaacaa a                                    21
```

```
<210> SEQ ID NO 244
<211> LENGTH: 21
<212> TYPE: DNA
<213> ORGANISM: Artificial Sequence
<220> FEATURE:
<223> OTHER INFORMATION: Synthetic sequence

<400> SEQUENCE: 244
tagcattaag caggaacgaa t                                              21

<210> SEQ ID NO 245
<211> LENGTH: 21
<212> TYPE: DNA
<213> ORGANISM: Artificial Sequence
<220> FEATURE:
<223> OTHER INFORMATION: Synthetic sequence

<400> SEQUENCE: 245
ctggcggttc atggagagca a                                              21

<210> SEQ ID NO 246
<211> LENGTH: 21
<212> TYPE: DNA
<213> ORGANISM: Artificial Sequence
<220> FEATURE:
<223> OTHER INFORMATION: Synthetic sequence

<400> SEQUENCE: 246
caggctcttc cggcaagtca a                                              21

<210> SEQ ID NO 247
<211> LENGTH: 21
<212> TYPE: DNA
<213> ORGANISM: Artificial Sequence
<220> FEATURE:
<223> OTHER INFORMATION: Synthetic sequence

<400> SEQUENCE: 247
tacgttgatt tcagagaata t                                              21

<210> SEQ ID NO 248
<211> LENGTH: 21
<212> TYPE: DNA
<213> ORGANISM: Artificial Sequence
<220> FEATURE:
<223> OTHER INFORMATION: Synthetic sequence

<400> SEQUENCE: 248
aagaagcagg atgctgatct a                                              21

<210> SEQ ID NO 249
<211> LENGTH: 21
<212> TYPE: DNA
<213> ORGANISM: Artificial Sequence
<220> FEATURE:
<223> OTHER INFORMATION: Synthetic sequence

<400> SEQUENCE: 249
caggtgagcg acattacacc a                                              21

<210> SEQ ID NO 250
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 250
ccgggcggtt gtctacagca a                                              21

<210> SEQ ID NO 251
<211> LENGTH: 21
<212> TYPE: DNA
<213> ORGANISM: Artificial Sequence
<220> FEATURE:
<223> OTHER INFORMATION: Synthetic sequence

<400> SEQUENCE: 251
atgcaactta ttgtatctga a                                              21

<210> SEQ ID NO 252
<211> LENGTH: 21
<212> TYPE: DNA
<213> ORGANISM: Artificial Sequence
<220> FEATURE:
<223> OTHER INFORMATION: Synthetic sequence

<400> SEQUENCE: 252
caggctgcga aggaagtact a                                              21

<210> SEQ ID NO 253
<211> LENGTH: 21
<212> TYPE: DNA
<213> ORGANISM: Artificial Sequence
<220> FEATURE:
<223> OTHER INFORMATION: Synthetic sequence

<400> SEQUENCE: 253
tcgggatttg gcagcccgta a                                              21

<210> SEQ ID NO 254
<211> LENGTH: 21
<212> TYPE: DNA
<213> ORGANISM: Artificial Sequence
<220> FEATURE:
<223> OTHER INFORMATION: Synthetic sequence

<400> SEQUENCE: 254
ctcaccgtat ccagcacatt a                                              21

<210> SEQ ID NO 255
<211> LENGTH: 21
<212> TYPE: DNA
<213> ORGANISM: Artificial Sequence
<220> FEATURE:
<223> OTHER INFORMATION: Synthetic sequence

<400> SEQUENCE: 255
cagaacaact tagtaggata a                                              21

<210> SEQ ID NO 256
<211> LENGTH: 21
<212> TYPE: DNA
<213> ORGANISM: Artificial Sequence
<220> FEATURE:
<223> OTHER INFORMATION: Synthetic sequence

<400> SEQUENCE: 256
caccacacgg gttcagttca a                                              21

<210> SEQ ID NO 257
```

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 257
cacgctcttg gtcaacagga a                                              21

<210> SEQ ID NO 258
<211> LENGTH: 21
<212> TYPE: DNA
<213> ORGANISM: Artificial Sequence
<220> FEATURE:
<223> OTHER INFORMATION: Synthetic sequence

<400> SEQUENCE: 258
accgagggcg atgaagaagc a                                              21

<210> SEQ ID NO 259
<211> LENGTH: 21
<212> TYPE: DNA
<213> ORGANISM: Artificial Sequence
<220> FEATURE:
<223> OTHER INFORMATION: Synthetic sequence

<400> SEQUENCE: 259
atgcttagag tggactatta a                                              21

<210> SEQ ID NO 260
<211> LENGTH: 21
<212> TYPE: DNA
<213> ORGANISM: Artificial Sequence
<220> FEATURE:
<223> OTHER INFORMATION: Synthetic sequence

<400> SEQUENCE: 260
cagatgatgc ccggcaatta t                                              21

<210> SEQ ID NO 261
<211> LENGTH: 21
<212> TYPE: DNA
<213> ORGANISM: Artificial Sequence
<220> FEATURE:
<223> OTHER INFORMATION: Synthetic sequence

<400> SEQUENCE: 261
gaaggagtag atatcatcct a                                              21

<210> SEQ ID NO 262
<211> LENGTH: 21
<212> TYPE: DNA
<213> ORGANISM: Artificial Sequence
<220> FEATURE:
<223> OTHER INFORMATION: Synthetic sequence

<400> SEQUENCE: 262
cagatgatca gggatccaat a                                              21

<210> SEQ ID NO 263
<211> LENGTH: 21
<212> TYPE: DNA
<213> ORGANISM: Artificial Sequence
<220> FEATURE:
<223> OTHER INFORMATION: Synthetic sequence

<400> SEQUENCE: 263
```

```
caggaatatt aagttctata a                                              21

<210> SEQ ID NO 264
<211> LENGTH: 21
<212> TYPE: DNA
<213> ORGANISM: Artificial Sequence
<220> FEATURE:
<223> OTHER INFORMATION: Synthetic sequence

<400> SEQUENCE: 264
tgggtgcttt gtgatggata a                                              21

<210> SEQ ID NO 265
<211> LENGTH: 21
<212> TYPE: DNA
<213> ORGANISM: Artificial Sequence
<220> FEATURE:
<223> OTHER INFORMATION: Synthetic sequence

<400> SEQUENCE: 265
cagcctgagg ctgagtacca a                                              21

<210> SEQ ID NO 266
<211> LENGTH: 21
<212> TYPE: DNA
<213> ORGANISM: Artificial Sequence
<220> FEATURE:
<223> OTHER INFORMATION: Synthetic sequence

<400> SEQUENCE: 266
ttctatgaca ttgaaacact a                                              21

<210> SEQ ID NO 267
<211> LENGTH: 21
<212> TYPE: DNA
<213> ORGANISM: Artificial Sequence
<220> FEATURE:
<223> OTHER INFORMATION: Synthetic sequence

<400> SEQUENCE: 267
tgggttcatt attggaatta a                                              21

<210> SEQ ID NO 268
<211> LENGTH: 21
<212> TYPE: DNA
<213> ORGANISM: Artificial Sequence
<220> FEATURE:
<223> OTHER INFORMATION: Synthetic sequence

<400> SEQUENCE: 268
tagatgctgg attgacattt a                                              21

<210> SEQ ID NO 269
<211> LENGTH: 21
<212> TYPE: DNA
<213> ORGANISM: Artificial Sequence
<220> FEATURE:
<223> OTHER INFORMATION: Synthetic sequence

<400> SEQUENCE: 269
tacccgggct acagtccgca a                                              21

<210> SEQ ID NO 270
<211> LENGTH: 21
<212> TYPE: DNA
```

```
<213> ORGANISM: Artificial Sequence
<220> FEATURE:
<223> OTHER INFORMATION: Synthetic sequence

<400> SEQUENCE: 270
ccgggagtat caactcaacg a                                              21

<210> SEQ ID NO 271
<211> LENGTH: 21
<212> TYPE: DNA
<213> ORGANISM: Artificial Sequence
<220> FEATURE:
<223> OTHER INFORMATION: Synthetic sequence

<400> SEQUENCE: 271
cacgttacag ttagcagacg a                                              21

<210> SEQ ID NO 272
<211> LENGTH: 21
<212> TYPE: DNA
<213> ORGANISM: Artificial Sequence
<220> FEATURE:
<223> OTHER INFORMATION: Synthetic sequence

<400> SEQUENCE: 272
tacctttgtc ctggatcgga a                                              21

<210> SEQ ID NO 273
<211> LENGTH: 21
<212> TYPE: DNA
<213> ORGANISM: Artificial Sequence
<220> FEATURE:
<223> OTHER INFORMATION: Synthetic sequence

<400> SEQUENCE: 273
cagctttagc aaagaactct t                                              21

<210> SEQ ID NO 274
<211> LENGTH: 21
<212> TYPE: DNA
<213> ORGANISM: Artificial Sequence
<220> FEATURE:
<223> OTHER INFORMATION: Synthetic sequence

<400> SEQUENCE: 274
cagactcaat accagacact a                                              21

<210> SEQ ID NO 275
<211> LENGTH: 21
<212> TYPE: DNA
<213> ORGANISM: Artificial Sequence
<220> FEATURE:
<223> OTHER INFORMATION: Synthetic sequence

<400> SEQUENCE: 275
ccggcctcta tgcttgcgta a                                              21

<210> SEQ ID NO 276
<211> LENGTH: 21
<212> TYPE: DNA
<213> ORGANISM: Artificial Sequence
<220> FEATURE:
<223> OTHER INFORMATION: Synthetic sequence

<400> SEQUENCE: 276
cccgagttta gtaacagtgc a                                              21
```

```
<210> SEQ ID NO 277
<211> LENGTH: 21
<212> TYPE: DNA
<213> ORGANISM: Artificial Sequence
<220> FEATURE:
<223> OTHER INFORMATION: Synthetic sequence

<400> SEQUENCE: 277
ttcctggttt ccgaaaggca a                                              21

<210> SEQ ID NO 278
<211> LENGTH: 21
<212> TYPE: DNA
<213> ORGANISM: Artificial Sequence
<220> FEATURE:
<223> OTHER INFORMATION: Synthetic sequence

<400> SEQUENCE: 278
aaggtcggag tcaacggatt t                                              21

<210> SEQ ID NO 279
<211> LENGTH: 21
<212> TYPE: DNA
<213> ORGANISM: Artificial Sequence
<220> FEATURE:
<223> OTHER INFORMATION: Synthetic sequence

<400> SEQUENCE: 279
ctgaccgatg gaggtagtat a                                              21

<210> SEQ ID NO 280
<211> LENGTH: 21
<212> TYPE: DNA
<213> ORGANISM: Artificial Sequence
<220> FEATURE:
<223> OTHER INFORMATION: Synthetic sequence

<400> SEQUENCE: 280
ccgggagaag gtggagactg a                                              21

<210> SEQ ID NO 281
<211> LENGTH: 21
<212> TYPE: DNA
<213> ORGANISM: Artificial Sequence
<220> FEATURE:
<223> OTHER INFORMATION: Synthetic sequence

<400> SEQUENCE: 281
tcccatgcat ttaatatatt a                                              21

<210> SEQ ID NO 282
<211> LENGTH: 21
<212> TYPE: DNA
<213> ORGANISM: Artificial Sequence
<220> FEATURE:
<223> OTHER INFORMATION: Synthetic sequence

<400> SEQUENCE: 282
tacatcggta gaaacgttga a                                              21

<210> SEQ ID NO 283
<211> LENGTH: 21
<212> TYPE: DNA
<213> ORGANISM: Artificial Sequence
<220> FEATURE:
```

```
<223> OTHER INFORMATION: Synthetic sequence

<400> SEQUENCE: 283
gagacttgaa ttaataagtg a                                              21

<210> SEQ ID NO 284
<211> LENGTH: 21
<212> TYPE: DNA
<213> ORGANISM: Artificial Sequence
<220> FEATURE:
<223> OTHER INFORMATION: Synthetic sequence

<400> SEQUENCE: 284
caggagaact taaagcccaa a                                              21

<210> SEQ ID NO 285
<211> LENGTH: 21
<212> TYPE: DNA
<213> ORGANISM: Artificial Sequence
<220> FEATURE:
<223> OTHER INFORMATION: Synthetic sequence

<400> SEQUENCE: 285
ccgatgttat tagatgttac a                                              21

<210> SEQ ID NO 286
<211> LENGTH: 21
<212> TYPE: DNA
<213> ORGANISM: Artificial Sequence
<220> FEATURE:
<223> OTHER INFORMATION: Synthetic sequence

<400> SEQUENCE: 286
gtggaagaag atccagcaga a                                              21

<210> SEQ ID NO 287
<211> LENGTH: 21
<212> TYPE: DNA
<213> ORGANISM: Artificial Sequence
<220> FEATURE:
<223> OTHER INFORMATION: Synthetic sequence

<400> SEQUENCE: 287
ctgggagtac ctagaaccct a                                              21

<210> SEQ ID NO 288
<211> LENGTH: 21
<212> TYPE: DNA
<213> ORGANISM: Artificial Sequence
<220> FEATURE:
<223> OTHER INFORMATION: Synthetic sequence

<400> SEQUENCE: 288
tcggtgcttc cagccacata a                                              21

<210> SEQ ID NO 289
<211> LENGTH: 21
<212> TYPE: DNA
<213> ORGANISM: Artificial Sequence
<220> FEATURE:
<223> OTHER INFORMATION: Synthetic sequence

<400> SEQUENCE: 289
cggccgcgag ttcgaccaga a                                              21
```

-continued

```
<210> SEQ ID NO 290
<211> LENGTH: 21
<212> TYPE: DNA
<213> ORGANISM: Artificial Sequence
<220> FEATURE:
<223> OTHER INFORMATION: Synthetic sequence

<400> SEQUENCE: 290
caagaactac atagaaatga a                                                  21

<210> SEQ ID NO 291
<211> LENGTH: 21
<212> TYPE: DNA
<213> ORGANISM: Artificial Sequence
<220> FEATURE:
<223> OTHER INFORMATION: Synthetic sequence

<400> SEQUENCE: 291
ttggatagtt tcctacgtaa a                                                  21

<210> SEQ ID NO 292
<211> LENGTH: 21
<212> TYPE: DNA
<213> ORGANISM: Artificial Sequence
<220> FEATURE:
<223> OTHER INFORMATION: Synthetic sequence

<400> SEQUENCE: 292
cacgtttgag tccatgccca a                                                  21

<210> SEQ ID NO 293
<211> LENGTH: 21
<212> TYPE: DNA
<213> ORGANISM: Artificial Sequence
<220> FEATURE:
<223> OTHER INFORMATION: Synthetic sequence

<400> SEQUENCE: 293
ttggaactgc atctaacatt a                                                  21

<210> SEQ ID NO 294
<211> LENGTH: 21
<212> TYPE: DNA
<213> ORGANISM: Artificial Sequence
<220> FEATURE:
<223> OTHER INFORMATION: Synthetic sequence

<400> SEQUENCE: 294
ctggaaggac cataaattta a                                                  21

<210> SEQ ID NO 295
<211> LENGTH: 21
<212> TYPE: DNA
<213> ORGANISM: Artificial Sequence
<220> FEATURE:
<223> OTHER INFORMATION: Synthetic sequence

<400> SEQUENCE: 295
cagcatatgt gtaaagattt a                                                  21

<210> SEQ ID NO 296
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 296
cactacagta ttagcaagca a                                              21

<210> SEQ ID NO 297
<211> LENGTH: 21
<212> TYPE: DNA
<213> ORGANISM: Artificial Sequence
<220> FEATURE:
<223> OTHER INFORMATION: Synthetic sequence

<400> SEQUENCE: 297
aagatcaatc ctccatgagt a                                              21

<210> SEQ ID NO 298
<211> LENGTH: 21
<212> TYPE: DNA
<213> ORGANISM: Artificial Sequence
<220> FEATURE:
<223> OTHER INFORMATION: Synthetic sequence

<400> SEQUENCE: 298
ggcgggagac actatattca a                                              21

<210> SEQ ID NO 299
<211> LENGTH: 21
<212> TYPE: DNA
<213> ORGANISM: Artificial Sequence
<220> FEATURE:
<223> OTHER INFORMATION: Synthetic sequence

<400> SEQUENCE: 299
tacgacctgg ttctagctga a                                              21

<210> SEQ ID NO 300
<211> LENGTH: 21
<212> TYPE: DNA
<213> ORGANISM: Artificial Sequence
<220> FEATURE:
<223> OTHER INFORMATION: Synthetic sequence

<400> SEQUENCE: 300
ctggatctgt ctccacctca t                                              21

<210> SEQ ID NO 301
<211> LENGTH: 21
<212> TYPE: DNA
<213> ORGANISM: Artificial Sequence
<220> FEATURE:
<223> OTHER INFORMATION: Synthetic sequence

<400> SEQUENCE: 301
ctgctgagag agcaaggcaa t                                              21

<210> SEQ ID NO 302
<211> LENGTH: 21
<212> TYPE: DNA
<213> ORGANISM: Artificial Sequence
<220> FEATURE:
<223> OTHER INFORMATION: Synthetic sequence

<400> SEQUENCE: 302
cccggcagta tgtgtctgta a                                              21

<210> SEQ ID NO 303
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 303
cttcgtcatg ttgaactata a                                              21

<210> SEQ ID NO 304
<211> LENGTH: 21
<212> TYPE: DNA
<213> ORGANISM: Artificial Sequence
<220> FEATURE:
<223> OTHER INFORMATION: Synthetic sequence

<400> SEQUENCE: 304
gcgccactac tacaaactaa a                                              21

<210> SEQ ID NO 305
<211> LENGTH: 21
<212> TYPE: DNA
<213> ORGANISM: Artificial Sequence
<220> FEATURE:
<223> OTHER INFORMATION: Synthetic sequence

<400> SEQUENCE: 305
ttgaatgttc gtaatagtag a                                              21

<210> SEQ ID NO 306
<211> LENGTH: 21
<212> TYPE: DNA
<213> ORGANISM: Artificial Sequence
<220> FEATURE:
<223> OTHER INFORMATION: Synthetic sequence

<400> SEQUENCE: 306
ccgcctgacc ttcggaccct a                                              21

<210> SEQ ID NO 307
<211> LENGTH: 21
<212> TYPE: DNA
<213> ORGANISM: Artificial Sequence
<220> FEATURE:
<223> OTHER INFORMATION: Synthetic sequence

<400> SEQUENCE: 307
accaattcaa gtgaagatta t                                              21

<210> SEQ ID NO 308
<211> LENGTH: 21
<212> TYPE: DNA
<213> ORGANISM: Artificial Sequence
<220> FEATURE:
<223> OTHER INFORMATION: Synthetic sequence

<400> SEQUENCE: 308
gtggcccttt atgactatga a                                              21

<210> SEQ ID NO 309
<211> LENGTH: 21
<212> TYPE: DNA
<213> ORGANISM: Artificial Sequence
<220> FEATURE:
<223> OTHER INFORMATION: Synthetic sequence

<400> SEQUENCE: 309
```
aagtgttaat ccaggcctaa a					21

<210> SEQ ID NO 310
<211> LENGTH: 21
<212> TYPE: DNA
<213> ORGANISM: Artificial Sequence
<220> FEATURE:
<223> OTHER INFORMATION: Synthetic sequence

<400> SEQUENCE: 310
cagcccaagt ccaaatgttt a					21

<210> SEQ ID NO 311
<211> LENGTH: 21
<212> TYPE: DNA
<213> ORGANISM: Artificial Sequence
<220> FEATURE:
<223> OTHER INFORMATION: Synthetic sequence

<400> SEQUENCE: 311
caccaggagc atatcaacat a					21

<210> SEQ ID NO 312
<211> LENGTH: 21
<212> TYPE: DNA
<213> ORGANISM: Artificial Sequence
<220> FEATURE:
<223> OTHER INFORMATION: Synthetic sequence

<400> SEQUENCE: 312
accagtcatg atagtaatag a					21

<210> SEQ ID NO 313
<211> LENGTH: 21
<212> TYPE: DNA
<213> ORGANISM: Artificial Sequence
<220> FEATURE:
<223> OTHER INFORMATION: Synthetic sequence

<400> SEQUENCE: 313
ctacgtgtta gtggctctta a					21

<210> SEQ ID NO 314
<211> LENGTH: 21
<212> TYPE: DNA
<213> ORGANISM: Artificial Sequence
<220> FEATURE:
<223> OTHER INFORMATION: Synthetic sequence

<400> SEQUENCE: 314
agccgacggg tctttaaaca a					21

<210> SEQ ID NO 315
<211> LENGTH: 21
<212> TYPE: DNA
<213> ORGANISM: Artificial Sequence
<220> FEATURE:
<223> OTHER INFORMATION: Synthetic sequence

<400> SEQUENCE: 315
cagatagatc ctagtacaga a					21

<210> SEQ ID NO 316
<211> LENGTH: 21
<212> TYPE: DNA
<213> ORGANISM: Artificial Sequence
<220> FEATURE:
<223> OTHER INFORMATION: Synthetic sequence

<400> SEQUENCE: 316
cacgtggaac ggcagcacta a                                              21

<210> SEQ ID NO 317
<211> LENGTH: 21
<212> TYPE: DNA
<213> ORGANISM: Artificial Sequence
<220> FEATURE:
<223> OTHER INFORMATION: Synthetic sequence

<400> SEQUENCE: 317
caccgtgtgg gctgagttta a                                              21

<210> SEQ ID NO 318
<211> LENGTH: 21
<212> TYPE: DNA
<213> ORGANISM: Artificial Sequence
<220> FEATURE:
<223> OTHER INFORMATION: Synthetic sequence

<400> SEQUENCE: 318
aagctctatc gggaaacaaa t                                              21

<210> SEQ ID NO 319
<211> LENGTH: 21
<212> TYPE: DNA
<213> ORGANISM: Artificial Sequence
<220> FEATURE:
<223> OTHER INFORMATION: Synthetic sequence

<400> SEQUENCE: 319
cagggaatca agccatgctt a                                              21

<210> SEQ ID NO 320
<211> LENGTH: 21
<212> TYPE: DNA
<213> ORGANISM: Artificial Sequence
<220> FEATURE:
<223> OTHER INFORMATION: Synthetic sequence

<400> SEQUENCE: 320
aaagtgtgat tcgatcgtca a                                              21

<210> SEQ ID NO 321
<211> LENGTH: 21
<212> TYPE: DNA
<213> ORGANISM: Artificial Sequence
<220> FEATURE:
<223> OTHER INFORMATION: Synthetic sequence

<400> SEQUENCE: 321
ttcgagcgta cagcaagtaa a                                              21

<210> SEQ ID NO 322
<211> LENGTH: 21
<212> TYPE: DNA
<213> ORGANISM: Artificial Sequence
<220> FEATURE:
<223> OTHER INFORMATION: Synthetic sequence

<400> SEQUENCE: 322
ccagtgcaga ctcaagactt a                                              21

<210> SEQ ID NO 323
<211> LENGTH: 21
<212> TYPE: DNA
<213> ORGANISM: Artificial Sequence
<220> FEATURE:
<223> OTHER INFORMATION: Synthetic sequence

<400> SEQUENCE: 323
caccatggta tcatatatta a                                              21

<210> SEQ ID NO 324
<211> LENGTH: 21
<212> TYPE: DNA
<213> ORGANISM: Artificial Sequence
<220> FEATURE:
<223> OTHER INFORMATION: Synthetic sequence

<400> SEQUENCE: 324
aaggcagttc aagctgttga a                                              21

<210> SEQ ID NO 325
<211> LENGTH: 21
<212> TYPE: DNA
<213> ORGANISM: Artificial Sequence
<220> FEATURE:
<223> OTHER INFORMATION: Synthetic sequence

<400> SEQUENCE: 325
aaggccaagt ttctacagga a                                              21

<210> SEQ ID NO 326
<211> LENGTH: 21
<212> TYPE: DNA
<213> ORGANISM: Artificial Sequence
<220> FEATURE:
<223> OTHER INFORMATION: Synthetic sequence

<400> SEQUENCE: 326
caggttgtaa gtgcttgcca a                                              21

<210> SEQ ID NO 327
<211> LENGTH: 21
<212> TYPE: DNA
<213> ORGANISM: Artificial Sequence
<220> FEATURE:
<223> OTHER INFORMATION: Synthetic sequence

<400> SEQUENCE: 327
gaccaatatt atactaagaa a                                              21

<210> SEQ ID NO 328
<211> LENGTH: 21
<212> TYPE: DNA
<213> ORGANISM: Artificial Sequence
<220> FEATURE:
<223> OTHER INFORMATION: Synthetic sequence

<400> SEQUENCE: 328
cccgaccaga ttcagtgcat a                                              21

<210> SEQ ID NO 329
<211> LENGTH: 21
<212> TYPE: DNA
<213> ORGANISM: Artificial Sequence
<220> FEATURE:
<223> OTHER INFORMATION: Synthetic sequence

<400> SEQUENCE: 329
ctcgctagtg gcctacatca a                                              21

<210> SEQ ID NO 330
<211> LENGTH: 21
<212> TYPE: DNA
<213> ORGANISM: Artificial Sequence
<220> FEATURE:
<223> OTHER INFORMATION: Synthetic sequence

<400> SEQUENCE: 330
atggacactt tgggcatcga a                                              21

<210> SEQ ID NO 331
<211> LENGTH: 21
<212> TYPE: DNA
<213> ORGANISM: Artificial Sequence
<220> FEATURE:
<223> OTHER INFORMATION: Synthetic sequence

<400> SEQUENCE: 331
cagagtctcc gctatggata a                                              21

<210> SEQ ID NO 332
<211> LENGTH: 21
<212> TYPE: DNA
<213> ORGANISM: Artificial Sequence
<220> FEATURE:
<223> OTHER INFORMATION: Synthetic sequence

<400> SEQUENCE: 332
caggtggatg ttagaagtcg a                                              21

<210> SEQ ID NO 333
<211> LENGTH: 21
<212> TYPE: DNA
<213> ORGANISM: Artificial Sequence
<220> FEATURE:
<223> OTHER INFORMATION: Synthetic sequence

<400> SEQUENCE: 333
ctgggtcagt aattacaagt a                                              21

<210> SEQ ID NO 334
<211> LENGTH: 21
<212> TYPE: DNA
<213> ORGANISM: Artificial Sequence
<220> FEATURE:
<223> OTHER INFORMATION: Synthetic sequence

<400> SEQUENCE: 334
cagtcacata agtataataa a                                              21

<210> SEQ ID NO 335
<211> LENGTH: 21
<212> TYPE: DNA
<213> ORGANISM: Artificial Sequence
<220> FEATURE:
<223> OTHER INFORMATION: Synthetic sequence

<400> SEQUENCE: 335
cagagattta cccatcgggt a                                              21

<210> SEQ ID NO 336

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 336
aaccaagtag cctgttatca a                                              21

<210> SEQ ID NO 337
<211> LENGTH: 21
<212> TYPE: DNA
<213> ORGANISM: Artificial Sequence
<220> FEATURE:
<223> OTHER INFORMATION: Synthetic sequence

<400> SEQUENCE: 337
aagggtgcgc cgggaacgaa a                                              21

<210> SEQ ID NO 338
<211> LENGTH: 21
<212> TYPE: DNA
<213> ORGANISM: Artificial Sequence
<220> FEATURE:
<223> OTHER INFORMATION: Synthetic sequence

<400> SEQUENCE: 338
ccgagccaca tcgctcagac a                                              21

<210> SEQ ID NO 339
<211> LENGTH: 21
<212> TYPE: DNA
<213> ORGANISM: Artificial Sequence
<220> FEATURE:
<223> OTHER INFORMATION: Synthetic sequence

<400> SEQUENCE: 339
ccgccttatc tagtagccct a                                              21

<210> SEQ ID NO 340
<211> LENGTH: 21
<212> TYPE: DNA
<213> ORGANISM: Artificial Sequence
<220> FEATURE:
<223> OTHER INFORMATION: Synthetic sequence

<400> SEQUENCE: 340
accatgtttc ctctcaataa a                                              21

<210> SEQ ID NO 341
<211> LENGTH: 21
<212> TYPE: DNA
<213> ORGANISM: Artificial Sequence
<220> FEATURE:
<223> OTHER INFORMATION: Synthetic sequence

<400> SEQUENCE: 341
caggctaagg gtgatgctga a                                              21

<210> SEQ ID NO 342
<211> LENGTH: 21
<212> TYPE: DNA
<213> ORGANISM: Artificial Sequence
<220> FEATURE:
<223> OTHER INFORMATION: Synthetic sequence

<400> SEQUENCE: 342
```
tagcctataa ataaattcca a       21

<210> SEQ ID NO 343
<211> LENGTH: 21
<212> TYPE: DNA
<213> ORGANISM: Artificial Sequence
<220> FEATURE:
<223> OTHER INFORMATION: Synthetic sequence

<400> SEQUENCE: 343
tccgagtatg atcctaccag a       21

<210> SEQ ID NO 344
<211> LENGTH: 21
<212> TYPE: DNA
<213> ORGANISM: Artificial Sequence
<220> FEATURE:
<223> OTHER INFORMATION: Synthetic sequence

<400> SEQUENCE: 344
aagctgatcg gcatcattga a       21

<210> SEQ ID NO 345
<211> LENGTH: 21
<212> TYPE: DNA
<213> ORGANISM: Artificial Sequence
<220> FEATURE:
<223> OTHER INFORMATION: Synthetic sequence

<400> SEQUENCE: 345
accctacgtt accgtgctca a       21

<210> SEQ ID NO 346
<211> LENGTH: 21
<212> TYPE: DNA
<213> ORGANISM: Artificial Sequence
<220> FEATURE:
<223> OTHER INFORMATION: Synthetic sequence

<400> SEQUENCE: 346
cacccatgga gtagtgaaca a       21

<210> SEQ ID NO 347
<211> LENGTH: 21
<212> TYPE: DNA
<213> ORGANISM: Artificial Sequence
<220> FEATURE:
<223> OTHER INFORMATION: Synthetic sequence

<400> SEQUENCE: 347
caggacagtc aaggtgatat a       21

<210> SEQ ID NO 348
<211> LENGTH: 21
<212> TYPE: DNA
<213> ORGANISM: Artificial Sequence
<220> FEATURE:
<223> OTHER INFORMATION: Synthetic sequence

<400> SEQUENCE: 348
aaggcagtgc gtggcgggca a       21

<210> SEQ ID NO 349
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 349
gtccgtttaa ctcgatagaa a                                             21

<210> SEQ ID NO 350
<211> LENGTH: 21
<212> TYPE: DNA
<213> ORGANISM: Artificial Sequence
<220> FEATURE:
<223> OTHER INFORMATION: Synthetic sequence

<400> SEQUENCE: 350
aagtttggaa acgatgtgca g                                             21

<210> SEQ ID NO 351
<211> LENGTH: 21
<212> TYPE: DNA
<213> ORGANISM: Artificial Sequence
<220> FEATURE:
<223> OTHER INFORMATION: Synthetic sequence

<400> SEQUENCE: 351
tcggatatga ttgtttctca a                                             21

<210> SEQ ID NO 352
<211> LENGTH: 21
<212> TYPE: DNA
<213> ORGANISM: Artificial Sequence
<220> FEATURE:
<223> OTHER INFORMATION: Synthetic sequence

<400> SEQUENCE: 352
aacaaagaaa tcttagacga a                                             21

<210> SEQ ID NO 353
<211> LENGTH: 21
<212> TYPE: DNA
<213> ORGANISM: Artificial Sequence
<220> FEATURE:
<223> OTHER INFORMATION: Synthetic sequence

<400> SEQUENCE: 353
agggagtatg tcttaaatgt a                                             21

<210> SEQ ID NO 354
<211> LENGTH: 21
<212> TYPE: DNA
<213> ORGANISM: Artificial Sequence
<220> FEATURE:
<223> OTHER INFORMATION: Synthetic sequence

<400> SEQUENCE: 354
caagttgcta agtgaacaga a                                             21

<210> SEQ ID NO 355
<211> LENGTH: 21
<212> TYPE: DNA
<213> ORGANISM: Artificial Sequence
<220> FEATURE:
<223> OTHER INFORMATION: Synthetic sequence

<400> SEQUENCE: 355
ttagttgagg ataccacatt a                                             21
```

<210> SEQ ID NO 356
<211> LENGTH: 21
<212> TYPE: DNA
<213> ORGANISM: Artificial Sequence
<220> FEATURE:
<223> OTHER INFORMATION: Synthetic sequence

<400> SEQUENCE: 356
accgcatatg gtatccctca a                                              21

<210> SEQ ID NO 357
<211> LENGTH: 21
<212> TYPE: DNA
<213> ORGANISM: Artificial Sequence
<220> FEATURE:
<223> OTHER INFORMATION: Synthetic sequence

<400> SEQUENCE: 357
acaggataat tcagacaaca a                                              21

<210> SEQ ID NO 358
<211> LENGTH: 21
<212> TYPE: DNA
<213> ORGANISM: Artificial Sequence
<220> FEATURE:
<223> OTHER INFORMATION: Synthetic sequence

<400> SEQUENCE: 358
cagaggtttg accgaattgc a                                              21

<210> SEQ ID NO 359
<211> LENGTH: 21
<212> TYPE: DNA
<213> ORGANISM: Artificial Sequence
<220> FEATURE:
<223> OTHER INFORMATION: Synthetic sequence

<400> SEQUENCE: 359
cgggcggatg atgcacgcca a                                              21

<210> SEQ ID NO 360
<211> LENGTH: 21
<212> TYPE: DNA
<213> ORGANISM: Artificial Sequence
<220> FEATURE:
<223> OTHER INFORMATION: Synthetic sequence

<400> SEQUENCE: 360
cctgcagaaa gtgaagcatt a                                              21

<210> SEQ ID NO 361
<211> LENGTH: 21
<212> TYPE: DNA
<213> ORGANISM: Artificial Sequence
<220> FEATURE:
<223> OTHER INFORMATION: Synthetic sequence

<400> SEQUENCE: 361
ctagatgacg ggaacaccaa a                                              21

<210> SEQ ID NO 362
<211> LENGTH: 21
<212> TYPE: DNA
<213> ORGANISM: Artificial Sequence
<220> FEATURE:

<223> OTHER INFORMATION: Synthetic sequence

<400> SEQUENCE: 362
cccgctgaca tttccgttgt a                                    21

<210> SEQ ID NO 363
<211> LENGTH: 21
<212> TYPE: DNA
<213> ORGANISM: Artificial Sequence
<220> FEATURE:
<223> OTHER INFORMATION: Synthetic sequence

<400> SEQUENCE: 363
ctccagtggc tctgactact a                                    21

<210> SEQ ID NO 364
<211> LENGTH: 21
<212> TYPE: DNA
<213> ORGANISM: Artificial Sequence
<220> FEATURE:
<223> OTHER INFORMATION: Synthetic sequence

<400> SEQUENCE: 364
aggaaataac attgcacttt a                                    21

<210> SEQ ID NO 365
<211> LENGTH: 21
<212> TYPE: DNA
<213> ORGANISM: Artificial Sequence
<220> FEATURE:
<223> OTHER INFORMATION: Synthetic sequence

<400> SEQUENCE: 365
ttggactgtg atattcgtta t                                    21

<210> SEQ ID NO 366
<211> LENGTH: 21
<212> TYPE: DNA
<213> ORGANISM: Artificial Sequence
<220> FEATURE:
<223> OTHER INFORMATION: Synthetic sequence

<400> SEQUENCE: 366
aagaactcgg ataatgataa a                                    21

<210> SEQ ID NO 367
<211> LENGTH: 21
<212> TYPE: DNA
<213> ORGANISM: Artificial Sequence
<220> FEATURE:
<223> OTHER INFORMATION: Synthetic sequence

<400> SEQUENCE: 367
tccgggtacc gcgaagggca a                                    21

<210> SEQ ID NO 368
<211> LENGTH: 21
<212> TYPE: DNA
<213> ORGANISM: Artificial Sequence
<220> FEATURE:
<223> OTHER INFORMATION: Synthetic sequence

<400> SEQUENCE: 368
cacggataac atcagcttca t                                    21

```
<210> SEQ ID NO 369
<211> LENGTH: 21
<212> TYPE: DNA
<213> ORGANISM: Artificial Sequence
<220> FEATURE:
<223> OTHER INFORMATION: Synthetic sequence

<400> SEQUENCE: 369
cggctgggtc agcttctaca a                                              21

<210> SEQ ID NO 370
<211> LENGTH: 21
<212> TYPE: DNA
<213> ORGANISM: Artificial Sequence
<220> FEATURE:
<223> OTHER INFORMATION: Synthetic sequence

<400> SEQUENCE: 370
ccgcgaggtc accattaacc a                                              21

<210> SEQ ID NO 371
<211> LENGTH: 21
<212> TYPE: DNA
<213> ORGANISM: Artificial Sequence
<220> FEATURE:
<223> OTHER INFORMATION: Synthetic sequence

<400> SEQUENCE: 371
cagacctatt tcccaaagca a                                              21

<210> SEQ ID NO 372
<211> LENGTH: 21
<212> TYPE: DNA
<213> ORGANISM: Artificial Sequence
<220> FEATURE:
<223> OTHER INFORMATION: Synthetic sequence

<400> SEQUENCE: 372
cacccggagg aaagtctgtt a                                              21

<210> SEQ ID NO 373
<211> LENGTH: 21
<212> TYPE: DNA
<213> ORGANISM: Artificial Sequence
<220> FEATURE:
<223> OTHER INFORMATION: Synthetic sequence

<400> SEQUENCE: 373
aatcatgact gaccgaggca g                                              21

<210> SEQ ID NO 374
<211> LENGTH: 21
<212> TYPE: DNA
<213> ORGANISM: Artificial Sequence
<220> FEATURE:
<223> OTHER INFORMATION: Synthetic sequence

<400> SEQUENCE: 374
aattgtattc tccgagtcag a                                              21

<210> SEQ ID NO 375
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 375
ctggactcag tacgccgttt a                                                    21

<210> SEQ ID NO 376
<211> LENGTH: 21
<212> TYPE: DNA
<213> ORGANISM: Artificial Sequence
<220> FEATURE:
<223> OTHER INFORMATION: Synthetic sequence

<400> SEQUENCE: 376
cacgtgtatc cctgagaaca a                                                    21

<210> SEQ ID NO 377
<211> LENGTH: 21
<212> TYPE: DNA
<213> ORGANISM: Artificial Sequence
<220> FEATURE:
<223> OTHER INFORMATION: Synthetic sequence

<400> SEQUENCE: 377
caagatctac ttcgccttca a                                                    21

<210> SEQ ID NO 378
<211> LENGTH: 21
<212> TYPE: DNA
<213> ORGANISM: Artificial Sequence
<220> FEATURE:
<223> OTHER INFORMATION: Synthetic sequence

<400> SEQUENCE: 378
ctgccttacg atgacagaaa t                                                    21

<210> SEQ ID NO 379
<211> LENGTH: 21
<212> TYPE: DNA
<213> ORGANISM: Artificial Sequence
<220> FEATURE:
<223> OTHER INFORMATION: Synthetic sequence

<400> SEQUENCE: 379
aaggctaata caactcttca a                                                    21

<210> SEQ ID NO 380
<211> LENGTH: 21
<212> TYPE: DNA
<213> ORGANISM: Artificial Sequence
<220> FEATURE:
<223> OTHER INFORMATION: Synthetic sequence

<400> SEQUENCE: 380
cctgagagct ctcctcacca a                                                    21

<210> SEQ ID NO 381
<211> LENGTH: 21
<212> TYPE: DNA
<213> ORGANISM: Artificial Sequence
<220> FEATURE:
<223> OTHER INFORMATION: Synthetic sequence

<400> SEQUENCE: 381
ctgggtccgg tccataatca t                                                    21

<210> SEQ ID NO 382
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 382
tagcatgtca agtggagtga a                                              21

<210> SEQ ID NO 383
<211> LENGTH: 21
<212> TYPE: DNA
<213> ORGANISM: Artificial Sequence
<220> FEATURE:
<223> OTHER INFORMATION: Synthetic sequence

<400> SEQUENCE: 383
aatctgatgc tgtggaatgc t                                              21

<210> SEQ ID NO 384
<211> LENGTH: 21
<212> TYPE: DNA
<213> ORGANISM: Artificial Sequence
<220> FEATURE:
<223> OTHER INFORMATION: Synthetic sequence

<400> SEQUENCE: 384
tgcactgtaa gacgtatgta a                                              21

<210> SEQ ID NO 385
<211> LENGTH: 21
<212> TYPE: DNA
<213> ORGANISM: Artificial Sequence
<220> FEATURE:
<223> OTHER INFORMATION: Synthetic sequence

<400> SEQUENCE: 385
caagaacgtc atgatgatcc a                                              21

<210> SEQ ID NO 386
<211> LENGTH: 21
<212> TYPE: DNA
<213> ORGANISM: Artificial Sequence
<220> FEATURE:
<223> OTHER INFORMATION: Synthetic sequence

<400> SEQUENCE: 386
atggaccaac ccaagtatta a                                              21

<210> SEQ ID NO 387
<211> LENGTH: 21
<212> TYPE: DNA
<213> ORGANISM: Artificial Sequence
<220> FEATURE:
<223> OTHER INFORMATION: Synthetic sequence

<400> SEQUENCE: 387
acaataggcc atgttaatta a                                              21

<210> SEQ ID NO 388
<211> LENGTH: 21
<212> TYPE: DNA
<213> ORGANISM: Artificial Sequence
<220> FEATURE:
<223> OTHER INFORMATION: Synthetic sequence

<400> SEQUENCE: 388
```
aagaacgtga cagatgagca g          21

<210> SEQ ID NO 389
<211> LENGTH: 21
<212> TYPE: DNA
<213> ORGANISM: Artificial Sequence
<220> FEATURE:
<223> OTHER INFORMATION: Synthetic sequence

<400> SEQUENCE: 389
aaggagaatt taataaagat a          21

<210> SEQ ID NO 390
<211> LENGTH: 21
<212> TYPE: DNA
<213> ORGANISM: Artificial Sequence
<220> FEATURE:
<223> OTHER INFORMATION: Synthetic sequence

<400> SEQUENCE: 390
tccttgcctg atgacaataa a          21

<210> SEQ ID NO 391
<211> LENGTH: 21
<212> TYPE: DNA
<213> ORGANISM: Artificial Sequence
<220> FEATURE:
<223> OTHER INFORMATION: Synthetic sequence

<400> SEQUENCE: 391
ctgcatttat cgttaaccta a          21

<210> SEQ ID NO 392
<211> LENGTH: 21
<212> TYPE: DNA
<213> ORGANISM: Artificial Sequence
<220> FEATURE:
<223> OTHER INFORMATION: Synthetic sequence

<400> SEQUENCE: 392
tggctgattc tggagagtat a          21

<210> SEQ ID NO 393
<211> LENGTH: 21
<212> TYPE: DNA
<213> ORGANISM: Artificial Sequence
<220> FEATURE:
<223> OTHER INFORMATION: Synthetic sequence

<400> SEQUENCE: 393
aggagcgatg acggaatata a          21

<210> SEQ ID NO 394
<211> LENGTH: 21
<212> TYPE: DNA
<213> ORGANISM: Artificial Sequence
<220> FEATURE:
<223> OTHER INFORMATION: Synthetic sequence

<400> SEQUENCE: 394
cagggtttgg tgacaataga a          21

<210> SEQ ID NO 395
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 395
ctggagaagt acagcgagca a                                              21

<210> SEQ ID NO 396
<211> LENGTH: 21
<212> TYPE: DNA
<213> ORGANISM: Artificial Sequence
<220> FEATURE:
<223> OTHER INFORMATION: Synthetic sequence

<400> SEQUENCE: 396
ctcgcccttg atgccaacaa a                                              21

<210> SEQ ID NO 397
<211> LENGTH: 21
<212> TYPE: DNA
<213> ORGANISM: Artificial Sequence
<220> FEATURE:
<223> OTHER INFORMATION: Synthetic sequence

<400> SEQUENCE: 397
aatccttaat ggctcagaca t                                              21

<210> SEQ ID NO 398
<211> LENGTH: 21
<212> TYPE: DNA
<213> ORGANISM: Artificial Sequence
<220> FEATURE:
<223> OTHER INFORMATION: Synthetic sequence

<400> SEQUENCE: 398
cccgacgacc accatcagct a                                              21

<210> SEQ ID NO 399
<211> LENGTH: 21
<212> TYPE: DNA
<213> ORGANISM: Artificial Sequence
<220> FEATURE:
<223> OTHER INFORMATION: Synthetic sequence

<400> SEQUENCE: 399
acgcatgtct ctgacacctc a                                              21

<210> SEQ ID NO 400
<211> LENGTH: 21
<212> TYPE: DNA
<213> ORGANISM: Artificial Sequence
<220> FEATURE:
<223> OTHER INFORMATION: Synthetic sequence

<400> SEQUENCE: 400
ccgccggata gtggatggca a                                              21

<210> SEQ ID NO 401
<211> LENGTH: 21
<212> TYPE: DNA
<213> ORGANISM: Artificial Sequence
<220> FEATURE:
<223> OTHER INFORMATION: Synthetic sequence

<400> SEQUENCE: 401
cagctacatc attctgtaca a                                              21
```

```
<210> SEQ ID NO 402
<211> LENGTH: 21
<212> TYPE: DNA
<213> ORGANISM: Artificial Sequence
<220> FEATURE:
<223> OTHER INFORMATION: Synthetic sequence

<400> SEQUENCE: 402
caggttaggg tgctagagct a                                              21

<210> SEQ ID NO 403
<211> LENGTH: 21
<212> TYPE: DNA
<213> ORGANISM: Artificial Sequence
<220> FEATURE:
<223> OTHER INFORMATION: Synthetic sequence

<400> SEQUENCE: 403
ccagatcaat gccatgacct a                                              21

<210> SEQ ID NO 404
<211> LENGTH: 21
<212> TYPE: DNA
<213> ORGANISM: Artificial Sequence
<220> FEATURE:
<223> OTHER INFORMATION: Synthetic sequence

<400> SEQUENCE: 404
cacgccttat agagtctcca t                                              21

<210> SEQ ID NO 405
<211> LENGTH: 21
<212> TYPE: DNA
<213> ORGANISM: Artificial Sequence
<220> FEATURE:
<223> OTHER INFORMATION: Synthetic sequence

<400> SEQUENCE: 405
gtgcacctac ttcaagttct a                                              21

<210> SEQ ID NO 406
<211> LENGTH: 21
<212> TYPE: DNA
<213> ORGANISM: Artificial Sequence
<220> FEATURE:
<223> OTHER INFORMATION: Synthetic sequence

<400> SEQUENCE: 406
aacctcctta gggttcgtca a                                              21

<210> SEQ ID NO 407
<211> LENGTH: 21
<212> TYPE: DNA
<213> ORGANISM: Artificial Sequence
<220> FEATURE:
<223> OTHER INFORMATION: Synthetic sequence

<400> SEQUENCE: 407
cacgtgtggc ctgttcttct a                                              21

<210> SEQ ID NO 408
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 408
cgcggccggc agcatgatga a                          21

<210> SEQ ID NO 409
<211> LENGTH: 21
<212> TYPE: DNA
<213> ORGANISM: Artificial Sequence
<220> FEATURE:
<223> OTHER INFORMATION: Synthetic sequence

<400> SEQUENCE: 409
ttcactcttt gcaattgcta a                          21

<210> SEQ ID NO 410
<211> LENGTH: 21
<212> TYPE: DNA
<213> ORGANISM: Artificial Sequence
<220> FEATURE:
<223> OTHER INFORMATION: Synthetic sequence

<400> SEQUENCE: 410
caccctcaag ctgtcgccct a                          21

<210> SEQ ID NO 411
<211> LENGTH: 21
<212> TYPE: DNA
<213> ORGANISM: Artificial Sequence
<220> FEATURE:
<223> OTHER INFORMATION: Synthetic sequence

<400> SEQUENCE: 411
ccgggatagc gagaccacta a                          21

<210> SEQ ID NO 412
<211> LENGTH: 21
<212> TYPE: DNA
<213> ORGANISM: Artificial Sequence
<220> FEATURE:
<223> OTHER INFORMATION: Synthetic sequence

<400> SEQUENCE: 412
tgccgtgatg tggaggagga a                          21

<210> SEQ ID NO 413
<211> LENGTH: 21
<212> TYPE: DNA
<213> ORGANISM: Artificial Sequence
<220> FEATURE:
<223> OTHER INFORMATION: Synthetic sequence

<400> SEQUENCE: 413
tgggataagg aaacacttct a                          21

<210> SEQ ID NO 414
<211> LENGTH: 21
<212> TYPE: DNA
<213> ORGANISM: Artificial Sequence
<220> FEATURE:
<223> OTHER INFORMATION: Synthetic sequence

<400> SEQUENCE: 414
ccagtcgcca agaatcatga a                          21

<210> SEQ ID NO 415

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 415
ctgccaggtg tactttactt a                                              21

<210> SEQ ID NO 416
<211> LENGTH: 21
<212> TYPE: DNA
<213> ORGANISM: Artificial Sequence
<220> FEATURE:
<223> OTHER INFORMATION: Synthetic sequence

<400> SEQUENCE: 416
acccaagaac agcttcaata a                                              21

<210> SEQ ID NO 417
<211> LENGTH: 21
<212> TYPE: DNA
<213> ORGANISM: Artificial Sequence
<220> FEATURE:
<223> OTHER INFORMATION: Synthetic sequence

<400> SEQUENCE: 417
aacgatgaca accgacctat t                                              21

<210> SEQ ID NO 418
<211> LENGTH: 21
<212> TYPE: DNA
<213> ORGANISM: Artificial Sequence
<220> FEATURE:
<223> OTHER INFORMATION: Synthetic sequence

<400> SEQUENCE: 418
ccgcatctcc gaggacaaga a                                              21

<210> SEQ ID NO 419
<211> LENGTH: 21
<212> TYPE: DNA
<213> ORGANISM: Artificial Sequence
<220> FEATURE:
<223> OTHER INFORMATION: Synthetic sequence

<400> SEQUENCE: 419
ctctctttaa ttgctaacca t                                              21

<210> SEQ ID NO 420
<211> LENGTH: 21
<212> TYPE: DNA
<213> ORGANISM: Artificial Sequence
<220> FEATURE:
<223> OTHER INFORMATION: Synthetic sequence

<400> SEQUENCE: 420
aggcatcaag ttgaccatca a                                              21

<210> SEQ ID NO 421
<211> LENGTH: 21
<212> TYPE: DNA
<213> ORGANISM: Artificial Sequence
<220> FEATURE:
<223> OTHER INFORMATION: Synthetic sequence

<400> SEQUENCE: 421
```
ccgccgcaaa gcaggatgtt a                                              21

<210> SEQ ID NO 422
<211> LENGTH: 21
<212> TYPE: DNA
<213> ORGANISM: Artificial Sequence
<220> FEATURE:
<223> OTHER INFORMATION: Synthetic sequence

<400> SEQUENCE: 422
cacacgctaa ctacaaggtc a                                              21

<210> SEQ ID NO 423
<211> LENGTH: 21
<212> TYPE: DNA
<213> ORGANISM: Artificial Sequence
<220> FEATURE:
<223> OTHER INFORMATION: Synthetic sequence

<400> SEQUENCE: 423
cacaggagag tttgacacct t                                              21

<210> SEQ ID NO 424
<211> LENGTH: 21
<212> TYPE: DNA
<213> ORGANISM: Artificial Sequence
<220> FEATURE:
<223> OTHER INFORMATION: Synthetic sequence

<400> SEQUENCE: 424
aacactgtat tgtaagtgga a                                              21

<210> SEQ ID NO 425
<211> LENGTH: 21
<212> TYPE: DNA
<213> ORGANISM: Artificial Sequence
<220> FEATURE:
<223> OTHER INFORMATION: Synthetic sequence

<400> SEQUENCE: 425
aaagtttagt tgtaaactta a                                              21

<210> SEQ ID NO 426
<211> LENGTH: 21
<212> TYPE: DNA
<213> ORGANISM: Artificial Sequence
<220> FEATURE:
<223> OTHER INFORMATION: Synthetic sequence

<400> SEQUENCE: 426
cacgacaatt ctgacgccca a                                              21

<210> SEQ ID NO 427
<211> LENGTH: 21
<212> TYPE: DNA
<213> ORGANISM: Artificial Sequence
<220> FEATURE:
<223> OTHER INFORMATION: Synthetic sequence

<400> SEQUENCE: 427
ttggacggtg gtagacattg a                                              21

<210> SEQ ID NO 428
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 428
accggatgag gttctatttc a                                              21

<210> SEQ ID NO 429
<211> LENGTH: 21
<212> TYPE: DNA
<213> ORGANISM: Artificial Sequence
<220> FEATURE:
<223> OTHER INFORMATION: Synthetic sequence

<400> SEQUENCE: 429
cgcaggtggg ctggacttct a                                              21

<210> SEQ ID NO 430
<211> LENGTH: 21
<212> TYPE: DNA
<213> ORGANISM: Artificial Sequence
<220> FEATURE:
<223> OTHER INFORMATION: Synthetic sequence

<400> SEQUENCE: 430
tgccctgaat gatgagatca a                                              21

<210> SEQ ID NO 431
<211> LENGTH: 21
<212> TYPE: DNA
<213> ORGANISM: Artificial Sequence
<220> FEATURE:
<223> OTHER INFORMATION: Synthetic sequence

<400> SEQUENCE: 431
aagaatgtat ttcacctgca a                                              21

<210> SEQ ID NO 432
<211> LENGTH: 21
<212> TYPE: DNA
<213> ORGANISM: Artificial Sequence
<220> FEATURE:
<223> OTHER INFORMATION: Synthetic sequence

<400> SEQUENCE: 432
cccgttctta actttgaacc a                                              21

<210> SEQ ID NO 433
<211> LENGTH: 21
<212> TYPE: DNA
<213> ORGANISM: Artificial Sequence
<220> FEATURE:
<223> OTHER INFORMATION: Synthetic sequence

<400> SEQUENCE: 433
ctcttaagcc atcttggtaa a                                              21

<210> SEQ ID NO 434
<211> LENGTH: 21
<212> TYPE: DNA
<213> ORGANISM: Artificial Sequence
<220> FEATURE:
<223> OTHER INFORMATION: Synthetic sequence

<400> SEQUENCE: 434
aagagacttc ctgagcagaa a                                              21
```

<210> SEQ ID NO 435
<211> LENGTH: 21
<212> TYPE: DNA
<213> ORGANISM: Artificial Sequence
<220> FEATURE:
<223> OTHER INFORMATION: Synthetic sequence

<400> SEQUENCE: 435
tcgaagaatc gcatcatcat a                                              21

<210> SEQ ID NO 436
<211> LENGTH: 21
<212> TYPE: DNA
<213> ORGANISM: Artificial Sequence
<220> FEATURE:
<223> OTHER INFORMATION: Synthetic sequence

<400> SEQUENCE: 436
aagcccagcg agcatgtgaa a                                              21

<210> SEQ ID NO 437
<211> LENGTH: 21
<212> TYPE: DNA
<213> ORGANISM: Artificial Sequence
<220> FEATURE:
<223> OTHER INFORMATION: Synthetic sequence

<400> SEQUENCE: 437
cagctcggat ttcgagatcc a                                              21

<210> SEQ ID NO 438
<211> LENGTH: 21
<212> TYPE: DNA
<213> ORGANISM: Artificial Sequence
<220> FEATURE:
<223> OTHER INFORMATION: Synthetic sequence

<400> SEQUENCE: 438
agccatcata cgagatctta a                                              21

<210> SEQ ID NO 439
<211> LENGTH: 21
<212> TYPE: DNA
<213> ORGANISM: Artificial Sequence
<220> FEATURE:
<223> OTHER INFORMATION: Synthetic sequence

<400> SEQUENCE: 439
aacgctgaca tgtacggtct a                                              21

<210> SEQ ID NO 440
<211> LENGTH: 21
<212> TYPE: DNA
<213> ORGANISM: Artificial Sequence
<220> FEATURE:
<223> OTHER INFORMATION: Synthetic sequence

<400> SEQUENCE: 440
caccgcagtt acggtcaacc a                                              21

<210> SEQ ID NO 441
<211> LENGTH: 21
<212> TYPE: DNA
<213> ORGANISM: Artificial Sequence
<220> FEATURE:

<223> OTHER INFORMATION: Synthetic sequence

<400> SEQUENCE: 441
caggaaagat tggtgttgt a                                        21

<210> SEQ ID NO 442
<211> LENGTH: 21
<212> TYPE: DNA
<213> ORGANISM: Artificial Sequence
<220> FEATURE:
<223> OTHER INFORMATION: Synthetic sequence

<400> SEQUENCE: 442
ctggagttcc atgataccac a                                       21

<210> SEQ ID NO 443
<211> LENGTH: 21
<212> TYPE: DNA
<213> ORGANISM: Artificial Sequence
<220> FEATURE:
<223> OTHER INFORMATION: Synthetic sequence

<400> SEQUENCE: 443
ttccattgta tgcaaattga a                                       21

<210> SEQ ID NO 444
<211> LENGTH: 21
<212> TYPE: DNA
<213> ORGANISM: Artificial Sequence
<220> FEATURE:
<223> OTHER INFORMATION: Synthetic sequence

<400> SEQUENCE: 444
aaccctgacc attccattat t                                       21

<210> SEQ ID NO 445
<211> LENGTH: 21
<212> TYPE: DNA
<213> ORGANISM: Artificial Sequence
<220> FEATURE:
<223> OTHER INFORMATION: Synthetic sequence

<400> SEQUENCE: 445 aacccttta c aaggccagaa a                                      21

<210> SEQ ID NO 446
<211> LENGTH: 21
<212> TYPE: DNA
<213> ORGANISM: Artificial Sequence
<220> FEATURE:
<223> OTHER INFORMATION: Synthetic sequence

<400> SEQUENCE: 446
cacattgtac atggtacgaa t                                       21

<210> SEQ ID NO 447
<211> LENGTH: 21
<212> TYPE: DNA
<213> ORGANISM: Artificial Sequence
<220> FEATURE:
<223> OTHER INFORMATION: Synthetic sequence

<400> SEQUENCE: 447
ccggtatcgt ttcgcatgga a                                       21

<210> SEQ ID NO 448
<211> LENGTH: 21
<212> TYPE: DNA
<213> ORGANISM: Artificial Sequence
<220> FEATURE:
<223> OTHER INFORMATION: Synthetic sequence

<400> SEQUENCE: 448
cccgagctgg agcgcctgat a         21

<210> SEQ ID NO 449
<211> LENGTH: 21
<212> TYPE: DNA
<213> ORGANISM: Artificial Sequence
<220> FEATURE:
<223> OTHER INFORMATION: Synthetic sequence

<400> SEQUENCE: 449
gtggacgaat atgatccaac a         21

<210> SEQ ID NO 450
<211> LENGTH: 21
<212> TYPE: DNA
<213> ORGANISM: Artificial Sequence
<220> FEATURE:
<223> OTHER INFORMATION: Synthetic sequence

<400> SEQUENCE: 450
caccgtggac aatgccaaca t         21

<210> SEQ ID NO 451
<211> LENGTH: 21
<212> TYPE: DNA
<213> ORGANISM: Artificial Sequence
<220> FEATURE:
<223> OTHER INFORMATION: Synthetic sequence

<400> SEQUENCE: 451
aacactggtc acgtttggaa a         21

<210> SEQ ID NO 452
<211> LENGTH: 21
<212> TYPE: DNA
<213> ORGANISM: Artificial Sequence
<220> FEATURE:
<223> OTHER INFORMATION: Synthetic sequence

<400> SEQUENCE: 452
tcggctgcag gttccaaact a         21

<210> SEQ ID NO 453
<211> LENGTH: 21
<212> TYPE: DNA
<213> ORGANISM: Artificial Sequence
<220> FEATURE:
<223> OTHER INFORMATION: Synthetic sequence

<400> SEQUENCE: 453
cacagatggg atcacagtaa a         21

<210> SEQ ID NO 454
<211> LENGTH: 21
<212> TYPE: DNA
<213> ORGANISM: Artificial Sequence
<220> FEATURE:
<223> OTHER INFORMATION: Synthetic sequence

<400> SEQUENCE: 454
caccaccaga tgagaagtta a                                          21

<210> SEQ ID NO 455
<211> LENGTH: 21
<212> TYPE: DNA
<213> ORGANISM: Artificial Sequence
<220> FEATURE:
<223> OTHER INFORMATION: Synthetic sequence

<400> SEQUENCE: 455
aaaccgagtt tgggatcaca t                                          21

<210> SEQ ID NO 456
<211> LENGTH: 21
<212> TYPE: DNA
<213> ORGANISM: Artificial Sequence
<220> FEATURE:
<223> OTHER INFORMATION: Synthetic sequence

<400> SEQUENCE: 456
cacaaccgcc ctcctggaca a                                          21

<210> SEQ ID NO 457
<211> LENGTH: 21
<212> TYPE: DNA
<213> ORGANISM: Artificial Sequence
<220> FEATURE:
<223> OTHER INFORMATION: Synthetic sequence

<400> SEQUENCE: 457
cagggtctac gtctacctgc a                                          21

<210> SEQ ID NO 458
<211> LENGTH: 21
<212> TYPE: DNA
<213> ORGANISM: Artificial Sequence
<220> FEATURE:
<223> OTHER INFORMATION: Synthetic sequence

<400> SEQUENCE: 458
aaacacgcac ttagtctcta a                                          21

<210> SEQ ID NO 459
<211> LENGTH: 21
<212> TYPE: DNA
<213> ORGANISM: Artificial Sequence
<220> FEATURE:
<223> OTHER INFORMATION: Synthetic sequence

<400> SEQUENCE: 459
aagccgagtc ctggtatcag a                                          21

<210> SEQ ID NO 460
<211> LENGTH: 21
<212> TYPE: DNA
<213> ORGANISM: Artificial Sequence
<220> FEATURE:
<223> OTHER INFORMATION: Synthetic sequence

<400> SEQUENCE: 460
tcgctccacc ttctccacca a                                          21

<210> SEQ ID NO 461
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 461
aacgatgcct tgttctgaa a                                              21

<210> SEQ ID NO 462
<211> LENGTH: 21
<212> TYPE: DNA
<213> ORGANISM: Artificial Sequence
<220> FEATURE:
<223> OTHER INFORMATION: Synthetic sequence

<400> SEQUENCE: 462
cacaacaatg ggtatcctta a                                             21

<210> SEQ ID NO 463
<211> LENGTH: 21
<212> TYPE: DNA
<213> ORGANISM: Artificial Sequence
<220> FEATURE:
<223> OTHER INFORMATION: Synthetic sequence

<400> SEQUENCE: 463
aaagacgaag agcaagaata a                                             21

<210> SEQ ID NO 464
<211> LENGTH: 21
<212> TYPE: DNA
<213> ORGANISM: Artificial Sequence
<220> FEATURE:
<223> OTHER INFORMATION: Synthetic sequence

<400> SEQUENCE: 464
cacgatggct ttgcaggcga t                                             21

<210> SEQ ID NO 465
<211> LENGTH: 21
<212> TYPE: DNA
<213> ORGANISM: Artificial Sequence
<220> FEATURE:
<223> OTHER INFORMATION: Synthetic sequence

<400> SEQUENCE: 465
ctggaggaag tgctaaattt a                                             21

<210> SEQ ID NO 466
<211> LENGTH: 21
<212> TYPE: DNA
<213> ORGANISM: Artificial Sequence
<220> FEATURE:
<223> OTHER INFORMATION: Synthetic sequence

<400> SEQUENCE: 466
cccgggactg ttgacagcca a                                             21

<210> SEQ ID NO 467
<211> LENGTH: 21
<212> TYPE: DNA
<213> ORGANISM: Artificial Sequence
<220> FEATURE:
<223> OTHER INFORMATION: Synthetic sequence

<400> SEQUENCE: 467
```
caagctgaac ctaatagcca t                                               21

<210> SEQ ID NO 468
<211> LENGTH: 21
<212> TYPE: DNA
<213> ORGANISM: Artificial Sequence
<220> FEATURE:
<223> OTHER INFORMATION: Synthetic sequence

<400> SEQUENCE: 468
cccgccgttg tcgcccatcg a                                               21

<210> SEQ ID NO 469
<211> LENGTH: 21
<212> TYPE: DNA
<213> ORGANISM: Artificial Sequence
<220> FEATURE:
<223> OTHER INFORMATION: Synthetic sequence

<400> SEQUENCE: 469
ctggagcttc actgttacta a                                               21

<210> SEQ ID NO 470
<211> LENGTH: 21
<212> TYPE: DNA
<213> ORGANISM: Artificial Sequence
<220> FEATURE:
<223> OTHER INFORMATION: Synthetic sequence

<400> SEQUENCE: 470
ccgcggatac aatgtgacgt a                                               21

<210> SEQ ID NO 471
<211> LENGTH: 21
<212> TYPE: DNA
<213> ORGANISM: Artificial Sequence
<220> FEATURE:
<223> OTHER INFORMATION: Synthetic sequence

<400> SEQUENCE: 471
cggcagggag ataccgtgaa a                                               21

<210> SEQ ID NO 472
<211> LENGTH: 21
<212> TYPE: DNA
<213> ORGANISM: Artificial Sequence
<220> FEATURE:
<223> OTHER INFORMATION: Synthetic sequence

<400> SEQUENCE: 472
tagaacctta gtataaattt a                                               21

<210> SEQ ID NO 473
<211> LENGTH: 21
<212> TYPE: DNA
<213> ORGANISM: Artificial Sequence
<220> FEATURE:
<223> OTHER INFORMATION: Synthetic sequence

<400> SEQUENCE: 473
tagggtgtgt gttcaccttc a                                               21

<210> SEQ ID NO 474
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 474
cagttggagc tgaactcgga a                                              21

<210> SEQ ID NO 475
<211> LENGTH: 21
<212> TYPE: DNA
<213> ORGANISM: Artificial Sequence
<220> FEATURE:
<223> OTHER INFORMATION: Synthetic sequence

<400> SEQUENCE: 475
acagacggcg gtggaaccaa a                                              21

<210> SEQ ID NO 476
<211> LENGTH: 21
<212> TYPE: DNA
<213> ORGANISM: Artificial Sequence
<220> FEATURE:
<223> OTHER INFORMATION: Synthetic sequence

<400> SEQUENCE: 476
caagttcttc atcgagttct a                                              21

<210> SEQ ID NO 477
<211> LENGTH: 21
<212> TYPE: DNA
<213> ORGANISM: Artificial Sequence
<220> FEATURE:
<223> OTHER INFORMATION: Synthetic sequence

<400> SEQUENCE: 477
gtggatgagt tccggaataa a                                              21

<210> SEQ ID NO 478
<211> LENGTH: 21
<212> TYPE: DNA
<213> ORGANISM: Artificial Sequence
<220> FEATURE:
<223> OTHER INFORMATION: Synthetic sequence

<400> SEQUENCE: 478
aaccatcggc ttgatcagga a                                              21

<210> SEQ ID NO 479
<211> LENGTH: 21
<212> TYPE: DNA
<213> ORGANISM: Artificial Sequence
<220> FEATURE:
<223> OTHER INFORMATION: Synthetic sequence

<400> SEQUENCE: 479
tcaggagttc tcatctgaca a                                              21

<210> SEQ ID NO 480
<211> LENGTH: 21
<212> TYPE: DNA
<213> ORGANISM: Artificial Sequence
<220> FEATURE:
<223> OTHER INFORMATION: Synthetic sequence

<400> SEQUENCE: 480
ctacgggaca ttcaccatca a                                              21
```

<210> SEQ ID NO 481
<211> LENGTH: 21
<212> TYPE: DNA
<213> ORGANISM: Artificial Sequence
<220> FEATURE:
<223> OTHER INFORMATION: Synthetic sequence

<400> SEQUENCE: 481
ccgggtgccg attctcagta a                                             21

<210> SEQ ID NO 482
<211> LENGTH: 21
<212> TYPE: DNA
<213> ORGANISM: Artificial Sequence
<220> FEATURE:
<223> OTHER INFORMATION: Synthetic sequence

<400> SEQUENCE: 482
ctggtgctct attgtctact a                                             21

<210> SEQ ID NO 483
<211> LENGTH: 21
<212> TYPE: DNA
<213> ORGANISM: Artificial Sequence
<220> FEATURE:
<223> OTHER INFORMATION: Synthetic sequence

<400> SEQUENCE: 483
gaccacgaga cgggaacatt a                                             21

<210> SEQ ID NO 484
<211> LENGTH: 21
<212> TYPE: DNA
<213> ORGANISM: Artificial Sequence
<220> FEATURE:
<223> OTHER INFORMATION: Synthetic sequence

<400> SEQUENCE: 484
cccgacgtct ggaggactca a                                             21

<210> SEQ ID NO 485
<211> LENGTH: 21
<212> TYPE: DNA
<213> ORGANISM: Artificial Sequence
<220> FEATURE:
<223> OTHER INFORMATION: Synthetic sequence

<400> SEQUENCE: 485
accgttatgc agaataatcc a                                             21

<210> SEQ ID NO 486
<211> LENGTH: 21
<212> TYPE: DNA
<213> ORGANISM: Artificial Sequence
<220> FEATURE:
<223> OTHER INFORMATION: Synthetic sequence

<400> SEQUENCE: 486
ctgagatacg tctgtgactt a                                             21

<210> SEQ ID NO 487
<211> LENGTH: 21
<212> TYPE: DNA
<213> ORGANISM: Artificial Sequence
<220> FEATURE:
<223> OTHER INFORMATION: Synthetic sequence

<400> SEQUENCE: 487
caaggctgcc ttcaattaga a                                              21

<210> SEQ ID NO 488
<211> LENGTH: 21
<212> TYPE: DNA
<213> ORGANISM: Artificial Sequence
<220> FEATURE:
<223> OTHER INFORMATION: Synthetic sequence

<400> SEQUENCE: 488
ttccagtact ttgtacagga a                                              21

<210> SEQ ID NO 489
<211> LENGTH: 21
<212> TYPE: DNA
<213> ORGANISM: Artificial Sequence
<220> FEATURE:
<223> OTHER INFORMATION: Synthetic sequence

<400> SEQUENCE: 489
ctccgtgagg ctacattaat a                                              21

<210> SEQ ID NO 490
<211> LENGTH: 21
<212> TYPE: DNA
<213> ORGANISM: Artificial Sequence
<220> FEATURE:
<223> OTHER INFORMATION: Synthetic sequence

<400> SEQUENCE: 490
cagtatttat tgttcccaca a                                              21

<210> SEQ ID NO 491
<211> LENGTH: 21
<212> TYPE: DNA
<213> ORGANISM: Artificial Sequence
<220> FEATURE:
<223> OTHER INFORMATION: Synthetic sequence

<400> SEQUENCE: 491
caatacaaag ctggataata a                                              21

<210> SEQ ID NO 492
<211> LENGTH: 21
<212> TYPE: DNA
<213> ORGANISM: Artificial Sequence
<220> FEATURE:
<223> OTHER INFORMATION: Synthetic sequence

<400> SEQUENCE: 492
caggtaatgt atcatgatcc a                                              21

<210> SEQ ID NO 493
<211> LENGTH: 21
<212> TYPE: DNA
<213> ORGANISM: Artificial Sequence
<220> FEATURE:
<223> OTHER INFORMATION: Synthetic sequence

<400> SEQUENCE: 493
ctccgggtgt ttcaactaga a                                              21

<210> SEQ ID NO 494

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 494
aggtgtggtg tggaacctat a                                              21

<210> SEQ ID NO 495
<211> LENGTH: 21
<212> TYPE: DNA
<213> ORGANISM: Artificial Sequence
<220> FEATURE:
<223> OTHER INFORMATION: Synthetic sequence

<400> SEQUENCE: 495
cctgaccgtc atagagcaga a                                              21

<210> SEQ ID NO 496
<211> LENGTH: 21
<212> TYPE: DNA
<213> ORGANISM: Artificial Sequence
<220> FEATURE:
<223> OTHER INFORMATION: Synthetic sequence

<400> SEQUENCE: 496
ctgggagtgg ttagccggaa t                                              21

<210> SEQ ID NO 497
<211> LENGTH: 21
<212> TYPE: DNA
<213> ORGANISM: Artificial Sequence
<220> FEATURE:
<223> OTHER INFORMATION: Synthetic sequence

<400> SEQUENCE: 497
caggtctaca gtgatagagc a                                              21

<210> SEQ ID NO 498
<211> LENGTH: 21
<212> TYPE: DNA
<213> ORGANISM: Artificial Sequence
<220> FEATURE:
<223> OTHER INFORMATION: Synthetic sequence

<400> SEQUENCE: 498
aagcgccacc tcagaagata a                                              21

<210> SEQ ID NO 499
<211> LENGTH: 21
<212> TYPE: DNA
<213> ORGANISM: Artificial Sequence
<220> FEATURE:
<223> OTHER INFORMATION: Synthetic sequence

<400> SEQUENCE: 499
tcgggaagct accatttctt a                                              21

<210> SEQ ID NO 500
<211> LENGTH: 21
<212> TYPE: DNA
<213> ORGANISM: Artificial Sequence
<220> FEATURE:
<223> OTHER INFORMATION: Synthetic sequence

<400> SEQUENCE: 500
```
ctgcccgatg gtcttccgta a                                              21

<210> SEQ ID NO 501
<211> LENGTH: 21
<212> TYPE: DNA
<213> ORGANISM: Artificial Sequence
<220> FEATURE:
<223> OTHER INFORMATION: Synthetic sequence

<400> SEQUENCE: 501
ccaggagctt ctggacatca a                                              21

<210> SEQ ID NO 502
<211> LENGTH: 21
<212> TYPE: DNA
<213> ORGANISM: Artificial Sequence
<220> FEATURE:
<223> OTHER INFORMATION: Synthetic sequence

<400> SEQUENCE: 502
atggtgcgag aaggcggtca a                                              21

<210> SEQ ID NO 503
<211> LENGTH: 21
<212> TYPE: DNA
<213> ORGANISM: Artificial Sequence
<220> FEATURE:
<223> OTHER INFORMATION: Synthetic sequence

<400> SEQUENCE: 503
ccacgtgtct gtgcaccaca a                                              21

<210> SEQ ID NO 504
<211> LENGTH: 21
<212> TYPE: DNA
<213> ORGANISM: Artificial Sequence
<220> FEATURE:
<223> OTHER INFORMATION: Synthetic sequence

<400> SEQUENCE: 504
caggtctgcg tagatggtga a                                              21

<210> SEQ ID NO 505
<211> LENGTH: 21
<212> TYPE: DNA
<213> ORGANISM: Artificial Sequence
<220> FEATURE:
<223> OTHER INFORMATION: Synthetic sequence

<400> SEQUENCE: 505
gacgccatct atgacagtaa a                                              21

<210> SEQ ID NO 506
<211> LENGTH: 21
<212> TYPE: DNA
<213> ORGANISM: Artificial Sequence
<220> FEATURE:
<223> OTHER INFORMATION: Synthetic sequence

<400> SEQUENCE: 506
gggctcctta aggataacta a                                              21

<210> SEQ ID NO 507
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 507
cacggttcca cggtataaat a                                              21

<210> SEQ ID NO 508
<211> LENGTH: 21
<212> TYPE: DNA
<213> ORGANISM: Artificial Sequence
<220> FEATURE:
<223> OTHER INFORMATION: Synthetic sequence

<400> SEQUENCE: 508
ctgccgagca actttgatca a                                              21

<210> SEQ ID NO 509
<211> LENGTH: 21
<212> TYPE: DNA
<213> ORGANISM: Artificial Sequence
<220> FEATURE:
<223> OTHER INFORMATION: Synthetic sequence

<400> SEQUENCE: 509
cgccgtgatc gagaaagcca a                                              21

<210> SEQ ID NO 510
<211> LENGTH: 21
<212> TYPE: DNA
<213> ORGANISM: Artificial Sequence
<220> FEATURE:
<223> OTHER INFORMATION: Synthetic sequence

<400> SEQUENCE: 510
ctgcacaata tgagcatgca a                                              21

<210> SEQ ID NO 511
<211> LENGTH: 21
<212> TYPE: DNA
<213> ORGANISM: Artificial Sequence
<220> FEATURE:
<223> OTHER INFORMATION: Synthetic sequence

<400> SEQUENCE: 511
tacgaccgca tcgagacgat a                                              21

<210> SEQ ID NO 512
<211> LENGTH: 21
<212> TYPE: DNA
<213> ORGANISM: Artificial Sequence
<220> FEATURE:
<223> OTHER INFORMATION: Synthetic sequence

<400> SEQUENCE: 512
ctggtgctcg gtcgcctact a                                              21

<210> SEQ ID NO 513
<211> LENGTH: 21
<212> TYPE: DNA
<213> ORGANISM: Artificial Sequence
<220> FEATURE:
<223> OTHER INFORMATION: Synthetic sequence

<400> SEQUENCE: 513
ctcaagcatc gcatagttta a                                              21
```

<210> SEQ ID NO 514
<211> LENGTH: 21
<212> TYPE: DNA
<213> ORGANISM: Artificial Sequence
<220> FEATURE:
<223> OTHER INFORMATION: Synthetic sequence

<400> SEQUENCE: 514
cagcagcctc tcttacacaa a                                              21

<210> SEQ ID NO 515
<211> LENGTH: 21
<212> TYPE: DNA
<213> ORGANISM: Artificial Sequence
<220> FEATURE:
<223> OTHER INFORMATION: Synthetic sequence

<400> SEQUENCE: 515
ccgagcacat agactccttt a                                              21

<210> SEQ ID NO 516
<211> LENGTH: 21
<212> TYPE: DNA
<213> ORGANISM: Artificial Sequence
<220> FEATURE:
<223> OTHER INFORMATION: Synthetic sequence

<400> SEQUENCE: 516
ctggttggag cgaatctgct a                                              21

<210> SEQ ID NO 517
<211> LENGTH: 21
<212> TYPE: DNA
<213> ORGANISM: Artificial Sequence
<220> FEATURE:
<223> OTHER INFORMATION: Synthetic sequence

<400> SEQUENCE: 517
atgcgcatga acactttgtt a                                              21

<210> SEQ ID NO 518
<211> LENGTH: 21
<212> TYPE: DNA
<213> ORGANISM: Artificial Sequence
<220> FEATURE:
<223> OTHER INFORMATION: Synthetic sequence

<400> SEQUENCE: 518
cacgcctaac aggacgtatt a                                              21

<210> SEQ ID NO 519
<211> LENGTH: 21
<212> TYPE: DNA
<213> ORGANISM: Artificial Sequence
<220> FEATURE:
<223> OTHER INFORMATION: Synthetic sequence

<400> SEQUENCE: 519
cacctttact ctataactca a                                              21

<210> SEQ ID NO 520
<211> LENGTH: 21
<212> TYPE: DNA
<213> ORGANISM: Artificial Sequence
<220> FEATURE:

<223> OTHER INFORMATION: Synthetic sequence

<400> SEQUENCE: 520
tccgtctttg gcaagacatt a 21

<210> SEQ ID NO 521
<211> LENGTH: 21
<212> TYPE: DNA
<213> ORGANISM: Artificial Sequence
<220> FEATURE:
<223> OTHER INFORMATION: Synthetic sequence

<400> SEQUENCE: 521
cctgcagatg cttctaataa a 21

<210> SEQ ID NO 522
<211> LENGTH: 21
<212> TYPE: DNA
<213> ORGANISM: Artificial Sequence
<220> FEATURE:
<223> OTHER INFORMATION: Synthetic sequence

<400> SEQUENCE: 522
gacggattct aaggactcta a 21

<210> SEQ ID NO 523
<211> LENGTH: 21
<212> TYPE: DNA
<213> ORGANISM: Artificial Sequence
<220> FEATURE:
<223> OTHER INFORMATION: Synthetic sequence

<400> SEQUENCE: 523
aacgaagcga gccaagggca a 21

<210> SEQ ID NO 524
<211> LENGTH: 21
<212> TYPE: DNA
<213> ORGANISM: Artificial Sequence
<220> FEATURE:
<223> OTHER INFORMATION: Synthetic sequence

<400> SEQUENCE: 524
ctcggtgcag ccgtatttct a 21

<210> SEQ ID NO 525
<211> LENGTH: 21
<212> TYPE: DNA
<213> ORGANISM: Artificial Sequence
<220> FEATURE:
<223> OTHER INFORMATION: Synthetic sequence

<400> SEQUENCE: 525
cagcggtgta ccattgacat t 21

<210> SEQ ID NO 526
<211> LENGTH: 21
<212> TYPE: DNA
<213> ORGANISM: Artificial Sequence
<220> FEATURE:
<223> OTHER INFORMATION: Synthetic sequence

<400> SEQUENCE: 526
cacccacaac ctatgatcca a 21

```
<210> SEQ ID NO 527
<211> LENGTH: 21
<212> TYPE: DNA
<213> ORGANISM: Artificial Sequence
<220> FEATURE:
<223> OTHER INFORMATION: Synthetic sequence

<400> SEQUENCE: 527
ttgaagagaa ctgcaactga a                                              21

<210> SEQ ID NO 528
<211> LENGTH: 21
<212> TYPE: DNA
<213> ORGANISM: Artificial Sequence
<220> FEATURE:
<223> OTHER INFORMATION: Synthetic sequence

<400> SEQUENCE: 528
aaggcctatg attatttcca a                                              21

<210> SEQ ID NO 529
<211> LENGTH: 21
<212> TYPE: DNA
<213> ORGANISM: Artificial Sequence
<220> FEATURE:
<223> OTHER INFORMATION: Synthetic sequence

<400> SEQUENCE: 529
tagctggtta tgaactagta a                                              21

<210> SEQ ID NO 530
<211> LENGTH: 21
<212> TYPE: DNA
<213> ORGANISM: Artificial Sequence
<220> FEATURE:
<223> OTHER INFORMATION: Synthetic sequence

<400> SEQUENCE: 530
caagttcttc ttgacagaca a                                              21

<210> SEQ ID NO 531
<211> LENGTH: 21
<212> TYPE: DNA
<213> ORGANISM: Artificial Sequence
<220> FEATURE:
<223> OTHER INFORMATION: Synthetic sequence

<400> SEQUENCE: 531
cgggaaatat gggatgtata a                                              21

<210> SEQ ID NO 532
<211> LENGTH: 21
<212> TYPE: DNA
<213> ORGANISM: Artificial Sequence
<220> FEATURE:
<223> OTHER INFORMATION: Synthetic sequence

<400> SEQUENCE: 532
gaggtgcaat gagctacgtt a                                              21

<210> SEQ ID NO 533
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 533
caacacccat ccagaatgtc a                                              21

<210> SEQ ID NO 534
<211> LENGTH: 21
<212> TYPE: DNA
<213> ORGANISM: Artificial Sequence
<220> FEATURE:
<223> OTHER INFORMATION: Synthetic sequence

<400> SEQUENCE: 534
caggagcagc tccaggcaga a                                              21

<210> SEQ ID NO 535
<211> LENGTH: 21
<212> TYPE: DNA
<213> ORGANISM: Artificial Sequence
<220> FEATURE:
<223> OTHER INFORMATION: Synthetic sequence

<400> SEQUENCE: 535
ccagttaaag caggcaatag a                                              21

<210> SEQ ID NO 536
<211> LENGTH: 21
<212> TYPE: DNA
<213> ORGANISM: Artificial Sequence
<220> FEATURE:
<223> OTHER INFORMATION: Synthetic sequence

<400> SEQUENCE: 536
tacgacactg tccacctta a                                               21

<210> SEQ ID NO 537
<211> LENGTH: 21
<212> TYPE: DNA
<213> ORGANISM: Artificial Sequence
<220> FEATURE:
<223> OTHER INFORMATION: Synthetic sequence

<400> SEQUENCE: 537
ccggatcata cgaaatcaat t                                              21

<210> SEQ ID NO 538
<211> LENGTH: 21
<212> TYPE: DNA
<213> ORGANISM: Artificial Sequence
<220> FEATURE:
<223> OTHER INFORMATION: Synthetic sequence

<400> SEQUENCE: 538
cactgtagac ttgcttatct a                                              21

<210> SEQ ID NO 539
<211> LENGTH: 21
<212> TYPE: DNA
<213> ORGANISM: Artificial Sequence
<220> FEATURE:
<223> OTHER INFORMATION: Synthetic sequence

<400> SEQUENCE: 539
ttggtacgtg ggcaagatca a                                              21

<210> SEQ ID NO 540
<211> LENGTH: 21
```

-continued

<212> TYPE: DNA
<213> ORGANISM: Artificial Sequence
<220> FEATURE:
<223> OTHER INFORMATION: Synthetic sequence

<400> SEQUENCE: 540
gacgacggtt gtgaatgata a                                      21

<210> SEQ ID NO 541
<211> LENGTH: 21
<212> TYPE: DNA
<213> ORGANISM: Artificial Sequence
<220> FEATURE:
<223> OTHER INFORMATION: Synthetic sequence

<400> SEQUENCE: 541
aagctgctct tagaaagata a                                      21

<210> SEQ ID NO 542
<211> LENGTH: 21
<212> TYPE: DNA
<213> ORGANISM: Artificial Sequence
<220> FEATURE:
<223> OTHER INFORMATION: Synthetic sequence

<400> SEQUENCE: 542
ctcccaatag cagttaccca a                                      21

<210> SEQ ID NO 543
<211> LENGTH: 21
<212> TYPE: DNA
<213> ORGANISM: Artificial Sequence
<220> FEATURE:
<223> OTHER INFORMATION: Synthetic sequence

<400> SEQUENCE: 543
gacctaaaga tgcgtatata a                                      21

<210> SEQ ID NO 544
<211> LENGTH: 21
<212> TYPE: DNA
<213> ORGANISM: Artificial Sequence
<220> FEATURE:
<223> OTHER INFORMATION: Synthetic sequence

<400> SEQUENCE: 544
ccggaggaga aacgtcttcg a                                      21

<210> SEQ ID NO 545
<211> LENGTH: 21
<212> TYPE: DNA
<213> ORGANISM: Artificial Sequence
<220> FEATURE:
<223> OTHER INFORMATION: Synthetic sequence

<400> SEQUENCE: 545
agcagtcgtc aataacctaa a                                      21

<210> SEQ ID NO 546
<211> LENGTH: 21
<212> TYPE: DNA
<213> ORGANISM: Artificial Sequence
<220> FEATURE:
<223> OTHER INFORMATION: Synthetic sequence

<400> SEQUENCE: 546
aacctgtttg ttggacatac t         21

<210> SEQ ID NO 547
<211> LENGTH: 21
<212> TYPE: DNA
<213> ORGANISM: Artificial Sequence
<220> FEATURE:
<223> OTHER INFORMATION: Synthetic sequence

<400> SEQUENCE: 547
ccgcgcgttc ctggtgaaga a         21

<210> SEQ ID NO 548
<211> LENGTH: 21
<212> TYPE: DNA
<213> ORGANISM: Artificial Sequence
<220> FEATURE:
<223> OTHER INFORMATION: Synthetic sequence

<400> SEQUENCE: 548
caagaaggaa ttaattatta a         21

<210> SEQ ID NO 549
<211> LENGTH: 21
<212> TYPE: DNA
<213> ORGANISM: Artificial Sequence
<220> FEATURE:
<223> OTHER INFORMATION: Synthetic sequence

<400> SEQUENCE: 549
ctgagtcagt ataagtatat a         21

<210> SEQ ID NO 550
<211> LENGTH: 21
<212> TYPE: DNA
<213> ORGANISM: Artificial Sequence
<220> FEATURE:
<223> OTHER INFORMATION: Synthetic sequence

<400> SEQUENCE: 550
gaccgccaga ttctcccttataa         21

<210> SEQ ID NO 551
<211> LENGTH: 21
<212> TYPE: DNA
<213> ORGANISM: Artificial Sequence
<220> FEATURE:
<223> OTHER INFORMATION: Synthetic sequence

<400> SEQUENCE: 551
atgcgttatc tgggtctgga a         21

<210> SEQ ID NO 552
<211> LENGTH: 21
<212> TYPE: DNA
<213> ORGANISM: Artificial Sequence
<220> FEATURE:
<223> OTHER INFORMATION: Synthetic sequence

<400> SEQUENCE: 552
aagccgtcta tcagctaact a         21

<210> SEQ ID NO 553
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 553
cacgcatgtc aaattctcat a                                              21

<210> SEQ ID NO 554
<211> LENGTH: 21
<212> TYPE: DNA
<213> ORGANISM: Artificial Sequence
<220> FEATURE:
<223> OTHER INFORMATION: Synthetic sequence

<400> SEQUENCE: 554
caccgttaca agtatactta t                                              21

<210> SEQ ID NO 555
<211> LENGTH: 21
<212> TYPE: DNA
<213> ORGANISM: Artificial Sequence
<220> FEATURE:
<223> OTHER INFORMATION: Synthetic sequence

<400> SEQUENCE: 555
cagaagctct atcaagtgcc a                                              21

<210> SEQ ID NO 556
<211> LENGTH: 21
<212> TYPE: DNA
<213> ORGANISM: Artificial Sequence
<220> FEATURE:
<223> OTHER INFORMATION: Synthetic sequence

<400> SEQUENCE: 556
cacatcatcg agaacccaca a                                              21

<210> SEQ ID NO 557
<211> LENGTH: 21
<212> TYPE: DNA
<213> ORGANISM: Artificial Sequence
<220> FEATURE:
<223> OTHER INFORMATION: Synthetic sequence

<400> SEQUENCE: 557
ccgctatgtc tggctggttt a                                              21

<210> SEQ ID NO 558
<211> LENGTH: 21
<212> TYPE: DNA
<213> ORGANISM: Artificial Sequence
<220> FEATURE:
<223> OTHER INFORMATION: Synthetic sequence

<400> SEQUENCE: 558
cagctttatc aacgagaaga a                                              21

<210> SEQ ID NO 559
<211> LENGTH: 21
<212> TYPE: DNA
<213> ORGANISM: Artificial Sequence
<220> FEATURE:
<223> OTHER INFORMATION: Synthetic sequence

<400> SEQUENCE: 559
cccttcgata agattattga a                                              21
```

```
<210> SEQ ID NO 560
<211> LENGTH: 21
<212> TYPE: DNA
<213> ORGANISM: Artificial Sequence
<220> FEATURE:
<223> OTHER INFORMATION: Synthetic sequence

<400> SEQUENCE: 560
atggaattaa gtgccatgaa a                                              21

<210> SEQ ID NO 561
<211> LENGTH: 21
<212> TYPE: DNA
<213> ORGANISM: Artificial Sequence
<220> FEATURE:
<223> OTHER INFORMATION: Synthetic sequence

<400> SEQUENCE: 561
aactggactt ccagaagaac a                                              21

<210> SEQ ID NO 562
<211> LENGTH: 21
<212> TYPE: DNA
<213> ORGANISM: Artificial Sequence
<220> FEATURE:
<223> OTHER INFORMATION: Synthetic sequence

<400> SEQUENCE: 562
aaggagcacc ttgacagact t                                              21

<210> SEQ ID NO 563
<211> LENGTH: 21
<212> TYPE: DNA
<213> ORGANISM: Artificial Sequence
<220> FEATURE:
<223> OTHER INFORMATION: Synthetic sequence

<400> SEQUENCE: 563
caggaatact cagatcggga a                                              21

<210> SEQ ID NO 564
<211> LENGTH: 21
<212> TYPE: DNA
<213> ORGANISM: Artificial Sequence
<220> FEATURE:
<223> OTHER INFORMATION: Synthetic sequence

<400> SEQUENCE: 564
tcccggtgac acagacacaa a                                              21

<210> SEQ ID NO 565
<211> LENGTH: 21
<212> TYPE: DNA
<213> ORGANISM: Artificial Sequence
<220> FEATURE:
<223> OTHER INFORMATION: Synthetic sequence

<400> SEQUENCE: 565
ctgggtatac ttcatgtgac a                                              21

<210> SEQ ID NO 566
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 566
cagcgcttca gtggttctat a                                              21

<210> SEQ ID NO 567
<211> LENGTH: 21
<212> TYPE: DNA
<213> ORGANISM: Artificial Sequence
<220> FEATURE:
<223> OTHER INFORMATION: Synthetic sequence

<400> SEQUENCE: 567
ctccaactac gcgtatgtga a                                              21

<210> SEQ ID NO 568
<211> LENGTH: 21
<212> TYPE: DNA
<213> ORGANISM: Artificial Sequence
<220> FEATURE:
<223> OTHER INFORMATION: Synthetic sequence

<400> SEQUENCE: 568
ccgagcaact ttgatcaacg a                                              21

<210> SEQ ID NO 569
<211> LENGTH: 21
<212> TYPE: DNA
<213> ORGANISM: Artificial Sequence
<220> FEATURE:
<223> OTHER INFORMATION: Synthetic sequence

<400> SEQUENCE: 569
ccggtcacgc atgaaggcaa a                                              21

<210> SEQ ID NO 570
<211> LENGTH: 21
<212> TYPE: DNA
<213> ORGANISM: Artificial Sequence
<220> FEATURE:
<223> OTHER INFORMATION: Synthetic sequence

<400> SEQUENCE: 570
aaggatggaa gaagagacga a                                              21

<210> SEQ ID NO 571
<211> LENGTH: 21
<212> TYPE: DNA
<213> ORGANISM: Artificial Sequence
<220> FEATURE:
<223> OTHER INFORMATION: Synthetic sequence

<400> SEQUENCE: 571
ctggctattg acttccctga a                                              21

<210> SEQ ID NO 572
<211> LENGTH: 21
<212> TYPE: DNA
<213> ORGANISM: Artificial Sequence
<220> FEATURE:
<223> OTHER INFORMATION: Synthetic sequence

<400> SEQUENCE: 572
cagatgaaac aaagcagtga a                                              21

<210> SEQ ID NO 573
```

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 573
caccaatccc tgaaagatta a                                              21

<210> SEQ ID NO 574
<211> LENGTH: 21
<212> TYPE: DNA
<213> ORGANISM: Artificial Sequence
<220> FEATURE:
<223> OTHER INFORMATION: Synthetic sequence

<400> SEQUENCE: 574
ctggccattg tctatctcat t                                              21

<210> SEQ ID NO 575
<211> LENGTH: 21
<212> TYPE: DNA
<213> ORGANISM: Artificial Sequence
<220> FEATURE:
<223> OTHER INFORMATION: Synthetic sequence

<400> SEQUENCE: 575
cacagcggtg agtgctgcaa a                                              21

<210> SEQ ID NO 576
<211> LENGTH: 21
<212> TYPE: DNA
<213> ORGANISM: Artificial Sequence
<220> FEATURE:
<223> OTHER INFORMATION: Synthetic sequence

<400> SEQUENCE: 576
cacggataac tttatcttgt t                                              21

<210> SEQ ID NO 577
<211> LENGTH: 21
<212> TYPE: DNA
<213> ORGANISM: Artificial Sequence
<220> FEATURE:
<223> OTHER INFORMATION: Synthetic sequence

<400> SEQUENCE: 577
cagaatcttc tgaaccatct a                                              21

<210> SEQ ID NO 578
<211> LENGTH: 21
<212> TYPE: DNA
<213> ORGANISM: Artificial Sequence
<220> FEATURE:
<223> OTHER INFORMATION: Synthetic sequence

<400> SEQUENCE: 578
aagcggttag gctgtgagga a                                              21

<210> SEQ ID NO 579
<211> LENGTH: 21
<212> TYPE: DNA
<213> ORGANISM: Artificial Sequence
<220> FEATURE:
<223> OTHER INFORMATION: Synthetic sequence

<400> SEQUENCE: 579
```

```
atcgaagttt gcagagacaa a                                              21

<210> SEQ ID NO 580
<211> LENGTH: 21
<212> TYPE: DNA
<213> ORGANISM: Artificial Sequence
<220> FEATURE:
<223> OTHER INFORMATION: Synthetic sequence

<400> SEQUENCE: 580
tccggaggtc acccacgctt a                                              21

<210> SEQ ID NO 581
<211> LENGTH: 21
<212> TYPE: DNA
<213> ORGANISM: Artificial Sequence
<220> FEATURE:
<223> OTHER INFORMATION: Synthetic sequence

<400> SEQUENCE: 581
acagatcttt ggagtgccta a                                              21

<210> SEQ ID NO 582
<211> LENGTH: 21
<212> TYPE: DNA
<213> ORGANISM: Artificial Sequence
<220> FEATURE:
<223> OTHER INFORMATION: Synthetic sequence

<400> SEQUENCE: 582
acggattcta aggactctaa a                                              21

<210> SEQ ID NO 583
<211> LENGTH: 21
<212> TYPE: DNA
<213> ORGANISM: Artificial Sequence
<220> FEATURE:
<223> OTHER INFORMATION: Synthetic sequence

<400> SEQUENCE: 583
ccgggaatct atactcaatg a                                              21

<210> SEQ ID NO 584
<211> LENGTH: 21
<212> TYPE: DNA
<213> ORGANISM: Artificial Sequence
<220> FEATURE:
<223> OTHER INFORMATION: Synthetic sequence

<400> SEQUENCE: 584
gatcccggag ttggaaaaca a                                              21

<210> SEQ ID NO 585
<211> LENGTH: 21
<212> TYPE: DNA
<213> ORGANISM: Artificial Sequence
<220> FEATURE:
<223> OTHER INFORMATION: Synthetic sequence

<400> SEQUENCE: 585
ttagatgata atggacaact a                                              21

<210> SEQ ID NO 586
<211> LENGTH: 21
<212> TYPE: DNA
```

```
<213> ORGANISM: Artificial Sequence
<220> FEATURE:
<223> OTHER INFORMATION: Synthetic sequence

<400> SEQUENCE: 586
aaagaagcgt tcacaacaa a                                              21

<210> SEQ ID NO 587
<211> LENGTH: 21
<212> TYPE: DNA
<213> ORGANISM: Artificial Sequence
<220> FEATURE:
<223> OTHER INFORMATION: Synthetic sequence

<400> SEQUENCE: 587
tccactgatt gctgcagcta a                                             21

<210> SEQ ID NO 588
<211> LENGTH: 21
<212> TYPE: DNA
<213> ORGANISM: Artificial Sequence
<220> FEATURE:
<223> OTHER INFORMATION: Synthetic sequence

<400> SEQUENCE: 588
atgactgata ttcacctca a                                              21

<210> SEQ ID NO 589
<211> LENGTH: 21
<212> TYPE: DNA
<213> ORGANISM: Artificial Sequence
<220> FEATURE:
<223> OTHER INFORMATION: Synthetic sequence

<400> SEQUENCE: 589
cagcattaaa ccagacctta t                                             21

<210> SEQ ID NO 590
<211> LENGTH: 21
<212> TYPE: DNA
<213> ORGANISM: Artificial Sequence
<220> FEATURE:
<223> OTHER INFORMATION: Synthetic sequence

<400> SEQUENCE: 590
cacgctctct ttctggcgga a                                             21

<210> SEQ ID NO 591
<211> LENGTH: 21
<212> TYPE: DNA
<213> ORGANISM: Artificial Sequence
<220> FEATURE:
<223> OTHER INFORMATION: Synthetic sequence

<400> SEQUENCE: 591
cccggacgac ttgtctttca a                                             21

<210> SEQ ID NO 592
<211> LENGTH: 21
<212> TYPE: DNA
<213> ORGANISM: Artificial Sequence
<220> FEATURE:
<223> OTHER INFORMATION: Synthetic sequence

<400> SEQUENCE: 592
cagcgtttgg atagggcaca a                                             21
```

<210> SEQ ID NO 593
<211> LENGTH: 21
<212> TYPE: DNA
<213> ORGANISM: Artificial Sequence
<220> FEATURE:
<223> OTHER INFORMATION: Synthetic sequence

<400> SEQUENCE: 593
cgcgccgtga tgaatatcga a                                              21

<210> SEQ ID NO 594
<211> LENGTH: 21
<212> TYPE: DNA
<213> ORGANISM: Artificial Sequence
<220> FEATURE:
<223> OTHER INFORMATION: Synthetic sequence

<400> SEQUENCE: 594
aaccgggacg aagccatcaa a                                              21

<210> SEQ ID NO 595
<211> LENGTH: 21
<212> TYPE: DNA
<213> ORGANISM: Artificial Sequence
<220> FEATURE:
<223> OTHER INFORMATION: Synthetic sequence

<400> SEQUENCE: 595
cagggccttg ctgtgacaat a                                              21

<210> SEQ ID NO 596
<211> LENGTH: 21
<212> TYPE: DNA
<213> ORGANISM: Artificial Sequence
<220> FEATURE:
<223> OTHER INFORMATION: Synthetic sequence

<400> SEQUENCE: 596
ctggatttag aacatggact a                                              21

<210> SEQ ID NO 597
<211> LENGTH: 21
<212> TYPE: DNA
<213> ORGANISM: Artificial Sequence
<220> FEATURE:
<223> OTHER INFORMATION: Synthetic sequence

<400> SEQUENCE: 597
ccgcgaccgg atcatacgaa a                                              21

<210> SEQ ID NO 598
<211> LENGTH: 21
<212> TYPE: DNA
<213> ORGANISM: Artificial Sequence
<220> FEATURE:
<223> OTHER INFORMATION: Synthetic sequence

<400> SEQUENCE: 598
gagggaggag ctaaacggtt a                                              21

<210> SEQ ID NO 599
<211> LENGTH: 21
<212> TYPE: DNA
<213> ORGANISM: Artificial Sequence
<220> FEATURE:

<223> OTHER INFORMATION: Synthetic sequence

<400> SEQUENCE: 599
ccgcgagtat gaccagcttt a              21

<210> SEQ ID NO 600
<211> LENGTH: 21
<212> TYPE: DNA
<213> ORGANISM: Artificial Sequence
<220> FEATURE:
<223> OTHER INFORMATION: Synthetic sequence

<400> SEQUENCE: 600
gggcgggacc ctgaaatact a              21

<210> SEQ ID NO 601
<211> LENGTH: 21
<212> TYPE: DNA
<213> ORGANISM: Artificial Sequence
<220> FEATURE:
<223> OTHER INFORMATION: Synthetic sequence

<400> SEQUENCE: 601
tccgaattga taatctttca a              21

<210> SEQ ID NO 602
<211> LENGTH: 21
<212> TYPE: DNA
<213> ORGANISM: Artificial Sequence
<220> FEATURE:
<223> OTHER INFORMATION: Synthetic sequence

<400> SEQUENCE: 602
cacgccagag ctggccgagc a              21

<210> SEQ ID NO 603
<211> LENGTH: 21
<212> TYPE: DNA
<213> ORGANISM: Artificial Sequence
<220> FEATURE:
<223> OTHER INFORMATION: Synthetic sequence

<400> SEQUENCE: 603
cagaaggtgg tgaaactgaa a              21

<210> SEQ ID NO 604
<211> LENGTH: 21
<212> TYPE: DNA
<213> ORGANISM: Artificial Sequence
<220> FEATURE:
<223> OTHER INFORMATION: Synthetic sequence

<400> SEQUENCE: 604
cagcagcaag tgcaacatca a              21

<210> SEQ ID NO 605
<211> LENGTH: 21
<212> TYPE: DNA
<213> ORGANISM: Artificial Sequence
<220> FEATURE:
<223> OTHER INFORMATION: Synthetic sequence

<400> SEQUENCE: 605
cacaagaagt gtattgataa a              21

```
<210> SEQ ID NO 606
<211> LENGTH: 21
<212> TYPE: DNA
<213> ORGANISM: Artificial Sequence
<220> FEATURE:
<223> OTHER INFORMATION: Synthetic sequence

<400> SEQUENCE: 606
atcgtgaact tgtcctctta a                                              21

<210> SEQ ID NO 607
<211> LENGTH: 21
<212> TYPE: DNA
<213> ORGANISM: Artificial Sequence
<220> FEATURE:
<223> OTHER INFORMATION: Synthetic sequence

<400> SEQUENCE: 607
ttggaatact ctaagagaat a                                              21

<210> SEQ ID NO 608
<211> LENGTH: 21
<212> TYPE: DNA
<213> ORGANISM: Artificial Sequence
<220> FEATURE:
<223> OTHER INFORMATION: Synthetic sequence

<400> SEQUENCE: 608
acggacgttg gttctgcact a                                              21

<210> SEQ ID NO 609
<211> LENGTH: 21
<212> TYPE: DNA
<213> ORGANISM: Artificial Sequence
<220> FEATURE:
<223> OTHER INFORMATION: Synthetic sequence

<400> SEQUENCE: 609
cacgaccatc tgggacggaa t                                              21

<210> SEQ ID NO 610
<211> LENGTH: 21
<212> TYPE: DNA
<213> ORGANISM: Artificial Sequence
<220> FEATURE:
<223> OTHER INFORMATION: Synthetic sequence

<400> SEQUENCE: 610
gacatgcttg ctgatcagct a                                              21

<210> SEQ ID NO 611
<211> LENGTH: 21
<212> TYPE: DNA
<213> ORGANISM: Artificial Sequence
<220> FEATURE:
<223> OTHER INFORMATION: Synthetic sequence

<400> SEQUENCE: 611
cagcaaggtg ctcatcgcag a                                              21

<210> SEQ ID NO 612
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 612
cccgaccagc attgacaaga t                                              21

<210> SEQ ID NO 613
<211> LENGTH: 21
<212> TYPE: DNA
<213> ORGANISM: Artificial Sequence
<220> FEATURE:
<223> OTHER INFORMATION: Synthetic sequence

<400> SEQUENCE: 613
ctgaccaatc aagtacacta a                                              21

<210> SEQ ID NO 614
<211> LENGTH: 21
<212> TYPE: DNA
<213> ORGANISM: Artificial Sequence
<220> FEATURE:
<223> OTHER INFORMATION: Synthetic sequence

<400> SEQUENCE: 614
cacggaaaca cccgtacctt a                                              21

<210> SEQ ID NO 615
<211> LENGTH: 21
<212> TYPE: DNA
<213> ORGANISM: Artificial Sequence
<220> FEATURE:
<223> OTHER INFORMATION: Synthetic sequence

<400> SEQUENCE: 615
gaccaaattt acgccatgaa a                                              21

<210> SEQ ID NO 616
<211> LENGTH: 21
<212> TYPE: DNA
<213> ORGANISM: Artificial Sequence
<220> FEATURE:
<223> OTHER INFORMATION: Synthetic sequence

<400> SEQUENCE: 616
tccgagcaca ataaactcaa a                                              21

<210> SEQ ID NO 617
<211> LENGTH: 21
<212> TYPE: DNA
<213> ORGANISM: Artificial Sequence
<220> FEATURE:
<223> OTHER INFORMATION: Synthetic sequence

<400> SEQUENCE: 617
ccgcacctac ttctacgcca a                                              21

<210> SEQ ID NO 618
<211> LENGTH: 21
<212> TYPE: DNA
<213> ORGANISM: Artificial Sequence
<220> FEATURE:
<223> OTHER INFORMATION: Synthetic sequence

<400> SEQUENCE: 618
cacaaaggag ttacatctta a                                              21

<210> SEQ ID NO 619
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 619
tccgagtatg tctaccattt a                                              21

<210> SEQ ID NO 620
<211> LENGTH: 21
<212> TYPE: DNA
<213> ORGANISM: Artificial Sequence
<220> FEATURE:
<223> OTHER INFORMATION: Synthetic sequence

<400> SEQUENCE: 620
tgggaaatag aagccagtga a                                              21

<210> SEQ ID NO 621
<211> LENGTH: 21
<212> TYPE: DNA
<213> ORGANISM: Artificial Sequence
<220> FEATURE:
<223> OTHER INFORMATION: Synthetic sequence

<400> SEQUENCE: 621
ccagactaat atattaatat a                                              21

<210> SEQ ID NO 622
<211> LENGTH: 21
<212> TYPE: DNA
<213> ORGANISM: Artificial Sequence
<220> FEATURE:
<223> OTHER INFORMATION: Synthetic sequence

<400> SEQUENCE: 622
ttcaagatga ctaatgtcaa a                                              21

<210> SEQ ID NO 623
<211> LENGTH: 21
<212> TYPE: DNA
<213> ORGANISM: Artificial Sequence
<220> FEATURE:
<223> OTHER INFORMATION: Synthetic sequence

<400> SEQUENCE: 623
ctggatcgcc atctatgaga a                                              21

<210> SEQ ID NO 624
<211> LENGTH: 21
<212> TYPE: DNA
<213> ORGANISM: Artificial Sequence
<220> FEATURE:
<223> OTHER INFORMATION: Synthetic sequence

<400> SEQUENCE: 624
ctacgccatc aagatcttga a                                              21

<210> SEQ ID NO 625
<211> LENGTH: 21
<212> TYPE: DNA
<213> ORGANISM: Artificial Sequence
<220> FEATURE:
<223> OTHER INFORMATION: Synthetic sequence

<400> SEQUENCE: 625
```
gaccctgttg acagtacttt a                                              21

<210> SEQ ID NO 626
<211> LENGTH: 21
<212> TYPE: DNA
<213> ORGANISM: Artificial Sequence
<220> FEATURE:
<223> OTHER INFORMATION: Synthetic sequence

<400> SEQUENCE: 626
ctggatcaag tcctgaagaa a                                              21

<210> SEQ ID NO 627
<211> LENGTH: 21
<212> TYPE: DNA
<213> ORGANISM: Artificial Sequence
<220> FEATURE:
<223> OTHER INFORMATION: Synthetic sequence

<400> SEQUENCE: 627
aaggcgtata caggaacaat a                                              21

<210> SEQ ID NO 628
<211> LENGTH: 21
<212> TYPE: DNA
<213> ORGANISM: Artificial Sequence
<220> FEATURE:
<223> OTHER INFORMATION: Synthetic sequence

<400> SEQUENCE: 628
taggccctga tgagaacgct a                                              21

<210> SEQ ID NO 629
<211> LENGTH: 21
<212> TYPE: DNA
<213> ORGANISM: Artificial Sequence
<220> FEATURE:
<223> OTHER INFORMATION: Synthetic sequence

<400> SEQUENCE: 629
tccgactttg atagatttct a                                              21

<210> SEQ ID NO 630
<211> LENGTH: 21
<212> TYPE: DNA
<213> ORGANISM: Artificial Sequence
<220> FEATURE:
<223> OTHER INFORMATION: Synthetic sequence

<400> SEQUENCE: 630
cgcggtgcag attcttctta a                                              21

<210> SEQ ID NO 631
<211> LENGTH: 21
<212> TYPE: DNA
<213> ORGANISM: Artificial Sequence
<220> FEATURE:
<223> OTHER INFORMATION: Synthetic sequence

<400> SEQUENCE: 631
ccagtgtata atcagccagt a                                              21

<210> SEQ ID NO 632
<211> LENGTH: 21
<212> TYPE: DNA
<213> ORGANISM: Artificial Sequence
<220> FEATURE:
<223> OTHER INFORMATION: Synthetic sequence

<400> SEQUENCE: 632
cactattgga tgtgattcta a                                              21

<210> SEQ ID NO 633
<211> LENGTH: 21
<212> TYPE: DNA
<213> ORGANISM: Artificial Sequence
<220> FEATURE:
<223> OTHER INFORMATION: Synthetic sequence

<400> SEQUENCE: 633
ctggaccgac ctagatttga a                                              21

<210> SEQ ID NO 634
<211> LENGTH: 21
<212> TYPE: DNA
<213> ORGANISM: Artificial Sequence
<220> FEATURE:
<223> OTHER INFORMATION: Synthetic sequence

<400> SEQUENCE: 634
gtgccggtac atttacttaa a                                              21

<210> SEQ ID NO 635
<211> LENGTH: 21
<212> TYPE: DNA
<213> ORGANISM: Artificial Sequence
<220> FEATURE:
<223> OTHER INFORMATION: Synthetic sequence

<400> SEQUENCE: 635
atcatggtag tcactaacat a                                              21

<210> SEQ ID NO 636
<211> LENGTH: 21
<212> TYPE: DNA
<213> ORGANISM: Artificial Sequence
<220> FEATURE:
<223> OTHER INFORMATION: Synthetic sequence

<400> SEQUENCE: 636
ccggcctgcc atggccatct t                                              21

<210> SEQ ID NO 637
<211> LENGTH: 21
<212> TYPE: DNA
<213> ORGANISM: Artificial Sequence
<220> FEATURE:
<223> OTHER INFORMATION: Synthetic sequence

<400> SEQUENCE: 637
aggctctatt ccaataaact a                                              21

<210> SEQ ID NO 638
<211> LENGTH: 21
<212> TYPE: DNA
<213> ORGANISM: Artificial Sequence
<220> FEATURE:
<223> OTHER INFORMATION: Synthetic sequence

<400> SEQUENCE: 638
ccgctcatga ctatacgcta a                                              21

```
<210> SEQ ID NO 639
<211> LENGTH: 21
<212> TYPE: DNA
<213> ORGANISM: Artificial Sequence
<220> FEATURE:
<223> OTHER INFORMATION: Synthetic sequence

<400> SEQUENCE: 639
aacccaaact gtatgtcttg a                                              21

<210> SEQ ID NO 640
<211> LENGTH: 21
<212> TYPE: DNA
<213> ORGANISM: Artificial Sequence
<220> FEATURE:
<223> OTHER INFORMATION: Synthetic sequence

<400> SEQUENCE: 640
tgacgagttt gtagaagact a                                              21

<210> SEQ ID NO 641
<211> LENGTH: 21
<212> TYPE: DNA
<213> ORGANISM: Artificial Sequence
<220> FEATURE:
<223> OTHER INFORMATION: Synthetic sequence

<400> SEQUENCE: 641
ccgcccgcgc ccttaattta a                                              21

<210> SEQ ID NO 642
<211> LENGTH: 21
<212> TYPE: DNA
<213> ORGANISM: Artificial Sequence
<220> FEATURE:
<223> OTHER INFORMATION: Synthetic sequence

<400> SEQUENCE: 642
ctcaaacgtc agagcaacgt a                                              21

<210> SEQ ID NO 643
<211> LENGTH: 21
<212> TYPE: DNA
<213> ORGANISM: Artificial Sequence
<220> FEATURE:
<223> OTHER INFORMATION: Synthetic sequence

<400> SEQUENCE: 643
tacaagttgc ttaaccaaga a                                              21

<210> SEQ ID NO 644
<211> LENGTH: 21
<212> TYPE: DNA
<213> ORGANISM: Artificial Sequence
<220> FEATURE:
<223> OTHER INFORMATION: Synthetic sequence

<400> SEQUENCE: 644
cacgtcaaag tatgatatct a                                              21

<210> SEQ ID NO 645
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 645
ctccctgacc cgtctaatat a                                              21

<210> SEQ ID NO 646
<211> LENGTH: 21
<212> TYPE: DNA
<213> ORGANISM: Artificial Sequence
<220> FEATURE:
<223> OTHER INFORMATION: Synthetic sequence

<400> SEQUENCE: 646
ccgggccacc gtgaactcac a                                              21

<210> SEQ ID NO 647
<211> LENGTH: 21
<212> TYPE: DNA
<213> ORGANISM: Artificial Sequence
<220> FEATURE:
<223> OTHER INFORMATION: Synthetic sequence

<400> SEQUENCE: 647
ccggtcgaat gataaggtgt a                                              21

<210> SEQ ID NO 648
<211> LENGTH: 21
<212> TYPE: DNA
<213> ORGANISM: Artificial Sequence
<220> FEATURE:
<223> OTHER INFORMATION: Synthetic sequence

<400> SEQUENCE: 648
aagcttaatg aggaaatatc a                                              21

<210> SEQ ID NO 649
<211> LENGTH: 21
<212> TYPE: DNA
<213> ORGANISM: Artificial Sequence
<220> FEATURE:
<223> OTHER INFORMATION: Synthetic sequence

<400> SEQUENCE: 649
atgcatttcc tggagaatat a                                              21

<210> SEQ ID NO 650
<211> LENGTH: 21
<212> TYPE: DNA
<213> ORGANISM: Artificial Sequence
<220> FEATURE:
<223> OTHER INFORMATION: Synthetic sequence

<400> SEQUENCE: 650
cagggccaga atttagcaag a                                              21

<210> SEQ ID NO 651
<211> LENGTH: 21
<212> TYPE: DNA
<213> ORGANISM: Artificial Sequence
<220> FEATURE:
<223> OTHER INFORMATION: Synthetic sequence

<400> SEQUENCE: 651
tacccgcttt atcgaaggca a                                              21

<210> SEQ ID NO 652

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 652
cagcgtattc tgatatagta a                                            21

<210> SEQ ID NO 653
<211> LENGTH: 21
<212> TYPE: DNA
<213> ORGANISM: Artificial Sequence
<220> FEATURE:
<223> OTHER INFORMATION: Synthetic sequence

<400> SEQUENCE: 653
ccggatgaaa ctgaccgatt t                                            21

<210> SEQ ID NO 654
<211> LENGTH: 21
<212> TYPE: DNA
<213> ORGANISM: Artificial Sequence
<220> FEATURE:
<223> OTHER INFORMATION: Synthetic sequence

<400> SEQUENCE: 654
aagcggcaca ttcccattta a                                            21

<210> SEQ ID NO 655
<211> LENGTH: 21
<212> TYPE: DNA
<213> ORGANISM: Artificial Sequence
<220> FEATURE:
<223> OTHER INFORMATION: Synthetic sequence

<400> SEQUENCE: 655
atgatgtgtc ttcaatgtca a                                            21

<210> SEQ ID NO 656
<211> LENGTH: 21
<212> TYPE: DNA
<213> ORGANISM: Artificial Sequence
<220> FEATURE:
<223> OTHER INFORMATION: Synthetic sequence

<400> SEQUENCE: 656
caggaagaga ccaaagtata a                                            21

<210> SEQ ID NO 657
<211> LENGTH: 21
<212> TYPE: DNA
<213> ORGANISM: Artificial Sequence
<220> FEATURE:
<223> OTHER INFORMATION: Synthetic sequence

<400> SEQUENCE: 657
ctccgcgact ctgatgagaa a                                            21

<210> SEQ ID NO 658
<211> LENGTH: 21
<212> TYPE: DNA
<213> ORGANISM: Artificial Sequence
<220> FEATURE:
<223> OTHER INFORMATION: Synthetic sequence

<400> SEQUENCE: 658
```
catcgtgttt gcaaaggtta a                                               21

<210> SEQ ID NO 659
<211> LENGTH: 21
<212> TYPE: DNA
<213> ORGANISM: Artificial Sequence
<220> FEATURE:
<223> OTHER INFORMATION: Synthetic sequence

<400> SEQUENCE: 659
aactattcag ccaatgtgat g                                               21

<210> SEQ ID NO 660
<211> LENGTH: 21
<212> TYPE: DNA
<213> ORGANISM: Artificial Sequence
<220> FEATURE:
<223> OTHER INFORMATION: Synthetic sequence

<400> SEQUENCE: 660
cagtataatg tcttagatta a                                               21

<210> SEQ ID NO 661
<211> LENGTH: 21
<212> TYPE: DNA
<213> ORGANISM: Artificial Sequence
<220> FEATURE:
<223> OTHER INFORMATION: Synthetic sequence

<400> SEQUENCE: 661
atgggatatt tgattacgta a                                               21

<210> SEQ ID NO 662
<211> LENGTH: 21
<212> TYPE: DNA
<213> ORGANISM: Artificial Sequence
<220> FEATURE:
<223> OTHER INFORMATION: Synthetic sequence

<400> SEQUENCE: 662
cggctctatt gtgcactcgg a                                               21

<210> SEQ ID NO 663
<211> LENGTH: 21
<212> TYPE: DNA
<213> ORGANISM: Artificial Sequence
<220> FEATURE:
<223> OTHER INFORMATION: Synthetic sequence

<400> SEQUENCE: 663
caaggacaac tcaaacttat a                                               21

<210> SEQ ID NO 664
<211> LENGTH: 21
<212> TYPE: DNA
<213> ORGANISM: Artificial Sequence
<220> FEATURE:
<223> OTHER INFORMATION: Synthetic sequence

<400> SEQUENCE: 664
aactctaccg tgccacgttt t                                               21

<210> SEQ ID NO 665
<211> LENGTH: 21
<212> TYPE: DNA

<213> ORGANISM: Artificial Sequence
<220> FEATURE:
<223> OTHER INFORMATION: Synthetic sequence

<400> SEQUENCE: 665
aaccatagtt atttacttga a                                              21

<210> SEQ ID NO 666
<211> LENGTH: 21
<212> TYPE: DNA
<213> ORGANISM: Artificial Sequence
<220> FEATURE:
<223> OTHER INFORMATION: Synthetic sequence

<400> SEQUENCE: 666
aaagtcgatt tatgtgtatt a                                              21

<210> SEQ ID NO 667
<211> LENGTH: 21
<212> TYPE: DNA
<213> ORGANISM: Artificial Sequence
<220> FEATURE:
<223> OTHER INFORMATION: Synthetic sequence

<400> SEQUENCE: 667
cggatgggat tcacttaaga a                                              21

<210> SEQ ID NO 668
<211> LENGTH: 21
<212> TYPE: DNA
<213> ORGANISM: Artificial Sequence
<220> FEATURE:
<223> OTHER INFORMATION: Synthetic sequence

<400> SEQUENCE: 668
caggaatagg catttgccta a                                              21

<210> SEQ ID NO 669
<211> LENGTH: 21
<212> TYPE: DNA
<213> ORGANISM: Artificial Sequence
<220> FEATURE:
<223> OTHER INFORMATION: Synthetic sequence

<400> SEQUENCE: 669
atcaccgtgg atagacttga a                                              21

<210> SEQ ID NO 670
<211> LENGTH: 21
<212> TYPE: DNA
<213> ORGANISM: Artificial Sequence
<220> FEATURE:
<223> OTHER INFORMATION: Synthetic sequence

<400> SEQUENCE: 670
ccgggagatt ggctctgtga a                                              21

<210> SEQ ID NO 671
<211> LENGTH: 21
<212> TYPE: DNA
<213> ORGANISM: Artificial Sequence
<220> FEATURE:
<223> OTHER INFORMATION: Synthetic sequence

<400> SEQUENCE: 671
tgggcggacg gttctgaaca a                                              21

```
<210> SEQ ID NO 672
<211> LENGTH: 21
<212> TYPE: DNA
<213> ORGANISM: Artificial Sequence
<220> FEATURE:
<223> OTHER INFORMATION: Synthetic sequence

<400> SEQUENCE: 672
cagaaacttc tccaaagtga t                                         21

<210> SEQ ID NO 673
<211> LENGTH: 21
<212> TYPE: DNA
<213> ORGANISM: Artificial Sequence
<220> FEATURE:
<223> OTHER INFORMATION: Synthetic sequence

<400> SEQUENCE: 673
cagcctgtgt agtgtgacaa a                                         21

<210> SEQ ID NO 674
<211> LENGTH: 21
<212> TYPE: DNA
<213> ORGANISM: Artificial Sequence
<220> FEATURE:
<223> OTHER INFORMATION: Synthetic sequence

<400> SEQUENCE: 674
cccgaccatg gtagtgttca a                                         21

<210> SEQ ID NO 675
<211> LENGTH: 21
<212> TYPE: DNA
<213> ORGANISM: Artificial Sequence
<220> FEATURE:
<223> OTHER INFORMATION: Synthetic sequence

<400> SEQUENCE: 675
cggaagcatg acagcattaa a                                         21

<210> SEQ ID NO 676
<211> LENGTH: 21
<212> TYPE: DNA
<213> ORGANISM: Artificial Sequence
<220> FEATURE:
<223> OTHER INFORMATION: Synthetic sequence

<400> SEQUENCE: 676
ccgcatgtgt ctgtattcat a                                         21

<210> SEQ ID NO 677
<211> LENGTH: 21
<212> TYPE: DNA
<213> ORGANISM: Artificial Sequence
<220> FEATURE:
<223> OTHER INFORMATION: Synthetic sequence

<400> SEQUENCE: 677
ctggcatttg tcaggaatat a                                         21

<210> SEQ ID NO 678
<211> LENGTH: 21
<212> TYPE: DNA
<213> ORGANISM: Artificial Sequence
<220> FEATURE:
```

```
<223> OTHER INFORMATION: Synthetic sequence

<400> SEQUENCE: 678
ccgctgtact tggaaattcg a                                              21

<210> SEQ ID NO 679
<211> LENGTH: 21
<212> TYPE: DNA
<213> ORGANISM: Artificial Sequence
<220> FEATURE:
<223> OTHER INFORMATION: Synthetic sequence

<400> SEQUENCE: 679
tcgggtagaa ataaccacca a                                              21

<210> SEQ ID NO 680
<211> LENGTH: 21
<212> TYPE: DNA
<213> ORGANISM: Artificial Sequence
<220> FEATURE:
<223> OTHER INFORMATION: Synthetic sequence

<400> SEQUENCE: 680
cagatcttag taagctatat a                                              21

<210> SEQ ID NO 681
<211> LENGTH: 21
<212> TYPE: DNA
<213> ORGANISM: Artificial Sequence
<220> FEATURE:
<223> OTHER INFORMATION: Synthetic sequence

<400> SEQUENCE: 681
ccgccaggtg aagctggtga a                                              21

<210> SEQ ID NO 682
<211> LENGTH: 21
<212> TYPE: DNA
<213> ORGANISM: Artificial Sequence
<220> FEATURE:
<223> OTHER INFORMATION: Synthetic sequence

<400> SEQUENCE: 682
cagtaatggg ttacttctga a                                              21

<210> SEQ ID NO 683
<211> LENGTH: 21
<212> TYPE: DNA
<213> ORGANISM: Artificial Sequence
<220> FEATURE:
<223> OTHER INFORMATION: Synthetic sequence

<400> SEQUENCE: 683
aaccagctgg atcgccatct a                                              21

<210> SEQ ID NO 684
<211> LENGTH: 21
<212> TYPE: DNA
<213> ORGANISM: Artificial Sequence
<220> FEATURE:
<223> OTHER INFORMATION: Synthetic sequence

<400> SEQUENCE: 684
cccggagatc attgcctacc a                                              21
```

```
<210> SEQ ID NO 685
<211> LENGTH: 21
<212> TYPE: DNA
<213> ORGANISM: Artificial Sequence
<220> FEATURE:
<223> OTHER INFORMATION: Synthetic sequence

<400> SEQUENCE: 685
ttcggctaac tcgccagttt a                                              21

<210> SEQ ID NO 686
<211> LENGTH: 21
<212> TYPE: DNA
<213> ORGANISM: Artificial Sequence
<220> FEATURE:
<223> OTHER INFORMATION: Synthetic sequence

<400> SEQUENCE: 686
ctggaagaat tcctgaacaa a                                              21

<210> SEQ ID NO 687
<211> LENGTH: 21
<212> TYPE: DNA
<213> ORGANISM: Artificial Sequence
<220> FEATURE:
<223> OTHER INFORMATION: Synthetic sequence

<400> SEQUENCE: 687
tcgacttaga cttgacctat a                                              21

<210> SEQ ID NO 688
<211> LENGTH: 21
<212> TYPE: DNA
<213> ORGANISM: Artificial Sequence
<220> FEATURE:
<223> OTHER INFORMATION: Synthetic sequence

<400> SEQUENCE: 688
ccggaacaaa tgcgtcccat a                                              21

<210> SEQ ID NO 689
<211> LENGTH: 21
<212> TYPE: DNA
<213> ORGANISM: Artificial Sequence
<220> FEATURE:
<223> OTHER INFORMATION: Synthetic sequence

<400> SEQUENCE: 689
ccgactgaaa ctggaaccct t                                              21

<210> SEQ ID NO 690
<211> LENGTH: 21
<212> TYPE: DNA
<213> ORGANISM: Artificial Sequence
<220> FEATURE:
<223> OTHER INFORMATION: Synthetic sequence

<400> SEQUENCE: 690
taggaactca ctctttagat a                                              21

<210> SEQ ID NO 691
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 691
cagcgccaca gcctccatta a                                              21

<210> SEQ ID NO 692
<211> LENGTH: 21
<212> TYPE: DNA
<213> ORGANISM: Artificial Sequence
<220> FEATURE:
<223> OTHER INFORMATION: Synthetic sequence

<400> SEQUENCE: 692
tacgaggatg tcgtccagga a                                              21

<210> SEQ ID NO 693
<211> LENGTH: 21
<212> TYPE: DNA
<213> ORGANISM: Artificial Sequence
<220> FEATURE:
<223> OTHER INFORMATION: Synthetic sequence

<400> SEQUENCE: 693
cagctagtgc caaataattg a                                              21

<210> SEQ ID NO 694
<211> LENGTH: 21
<212> TYPE: DNA
<213> ORGANISM: Artificial Sequence
<220> FEATURE:
<223> OTHER INFORMATION: Synthetic sequence

<400> SEQUENCE: 694
cagattgttc tttgttatag a                                              21

<210> SEQ ID NO 695
<211> LENGTH: 21
<212> TYPE: DNA
<213> ORGANISM: Artificial Sequence
<220> FEATURE:
<223> OTHER INFORMATION: Synthetic sequence

<400> SEQUENCE: 695
aacacttgtc aagaagcgtt a                                              21

<210> SEQ ID NO 696
<211> LENGTH: 21
<212> TYPE: DNA
<213> ORGANISM: Artificial Sequence
<220> FEATURE:
<223> OTHER INFORMATION: Synthetic sequence

<400> SEQUENCE: 696
cagcatttgc atggaacaca t                                              21

<210> SEQ ID NO 697
<211> LENGTH: 21
<212> TYPE: DNA
<213> ORGANISM: Artificial Sequence
<220> FEATURE:
<223> OTHER INFORMATION: Synthetic sequence

<400> SEQUENCE: 697
acccataatt gaagtgtata a                                              21

<210> SEQ ID NO 698
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 698
cagaagcaca gtaccgattt a                                             21

<210> SEQ ID NO 699
<211> LENGTH: 21
<212> TYPE: DNA
<213> ORGANISM: Artificial Sequence
<220> FEATURE:
<223> OTHER INFORMATION: Synthetic sequence

<400> SEQUENCE: 699
attcatggag acatccgcta a                                             21

<210> SEQ ID NO 700
<211> LENGTH: 21
<212> TYPE: DNA
<213> ORGANISM: Artificial Sequence
<220> FEATURE:
<223> OTHER INFORMATION: Synthetic sequence

<400> SEQUENCE: 700
caaggtgttc tttgacctaa t                                             21

<210> SEQ ID NO 701
<211> LENGTH: 21
<212> TYPE: DNA
<213> ORGANISM: Artificial Sequence
<220> FEATURE:
<223> OTHER INFORMATION: Synthetic sequence

<400> SEQUENCE: 701
cccgcccatg gacgatgtat a                                             21

<210> SEQ ID NO 702
<211> LENGTH: 21
<212> TYPE: DNA
<213> ORGANISM: Artificial Sequence
<220> FEATURE:
<223> OTHER INFORMATION: Synthetic sequence

<400> SEQUENCE: 702
aagcaatagt caggagcgat a                                             21

<210> SEQ ID NO 703
<211> LENGTH: 21
<212> TYPE: DNA
<213> ORGANISM: Artificial Sequence
<220> FEATURE:
<223> OTHER INFORMATION: Synthetic sequence

<400> SEQUENCE: 703
cgcagtggaa tgagtccttt a                                             21

<210> SEQ ID NO 704
<211> LENGTH: 21
<212> TYPE: DNA
<213> ORGANISM: Artificial Sequence
<220> FEATURE:
<223> OTHER INFORMATION: Synthetic sequence

<400> SEQUENCE: 704
```

```
aaagtatgat atctacgcaa a                                           21

<210> SEQ ID NO 705
<211> LENGTH: 21
<212> TYPE: DNA
<213> ORGANISM: Artificial Sequence
<220> FEATURE:
<223> OTHER INFORMATION: Synthetic sequence

<400> SEQUENCE: 705
cccgtctaat atataaatat a                                           21

<210> SEQ ID NO 706
<211> LENGTH: 21
<212> TYPE: DNA
<213> ORGANISM: Artificial Sequence
<220> FEATURE:
<223> OTHER INFORMATION: Synthetic sequence

<400> SEQUENCE: 706
acggatatcc tgcatgtcca a                                           21

<210> SEQ ID NO 707
<211> LENGTH: 21
<212> TYPE: DNA
<213> ORGANISM: Artificial Sequence
<220> FEATURE:
<223> OTHER INFORMATION: Synthetic sequence

<400> SEQUENCE: 707
aatcacacac caaattcgag t                                           21

<210> SEQ ID NO 708
<211> LENGTH: 21
<212> TYPE: DNA
<213> ORGANISM: Artificial Sequence
<220> FEATURE:
<223> OTHER INFORMATION: Synthetic sequence

<400> SEQUENCE: 708
ttgcaggtta tcagagatca a                                           21

<210> SEQ ID NO 709
<211> LENGTH: 21
<212> TYPE: DNA
<213> ORGANISM: Artificial Sequence
<220> FEATURE:
<223> OTHER INFORMATION: Synthetic sequence

<400> SEQUENCE: 709
cagcacgtgt tcccgacata a                                           21

<210> SEQ ID NO 710
<211> LENGTH: 21
<212> TYPE: DNA
<213> ORGANISM: Artificial Sequence
<220> FEATURE:
<223> OTHER INFORMATION: Synthetic sequence

<400> SEQUENCE: 710
cccaacgata gaagattcct a                                           21

<210> SEQ ID NO 711
<211> LENGTH: 21
<212> TYPE: DNA
<213> ORGANISM: Artificial Sequence
```

<220> FEATURE:
<223> OTHER INFORMATION: Synthetic sequence

<400> SEQUENCE: 711
ccgcagcgtc taaccactac a                                              21

<210> SEQ ID NO 712
<211> LENGTH: 21
<212> TYPE: DNA
<213> ORGANISM: Artificial Sequence
<220> FEATURE:
<223> OTHER INFORMATION: Synthetic sequence

<400> SEQUENCE: 712
ctgtatcatg gccatagtat a                                              21

<210> SEQ ID NO 713
<211> LENGTH: 21
<212> TYPE: DNA
<213> ORGANISM: Artificial Sequence
<220> FEATURE:
<223> OTHER INFORMATION: Synthetic sequence

<400> SEQUENCE: 713
caagagctaa gtagatgtgt a                                              21

<210> SEQ ID NO 714
<211> LENGTH: 21
<212> TYPE: DNA
<213> ORGANISM: Artificial Sequence
<220> FEATURE:
<223> OTHER INFORMATION: Synthetic sequence

<400> SEQUENCE: 714
tcgattattt ccagtgttct a                                              21

<210> SEQ ID NO 715
<211> LENGTH: 21
<212> TYPE: DNA
<213> ORGANISM: Artificial Sequence
<220> FEATURE:
<223> OTHER INFORMATION: Synthetic sequence

<400> SEQUENCE: 715
atgaaatgtg ttaatcacaa a                                              21

<210> SEQ ID NO 716
<211> LENGTH: 21
<212> TYPE: DNA
<213> ORGANISM: Artificial Sequence
<220> FEATURE:
<223> OTHER INFORMATION: Synthetic sequence

<400> SEQUENCE: 716
aaagatgaca gtggcgattg t                                              21

<210> SEQ ID NO 717
<211> LENGTH: 21
<212> TYPE: DNA
<213> ORGANISM: Artificial Sequence
<220> FEATURE:
<223> OTHER INFORMATION: Synthetic sequence

<400> SEQUENCE: 717
acgcgtgtgc tcctctcctt a                                              21

<210> SEQ ID NO 718
<211> LENGTH: 21
<212> TYPE: DNA
<213> ORGANISM: Artificial Sequence
<220> FEATURE:
<223> OTHER INFORMATION: Synthetic sequence

<400> SEQUENCE: 718
cagcgctatc tagataggta a                                         21

<210> SEQ ID NO 719
<211> LENGTH: 21
<212> TYPE: DNA
<213> ORGANISM: Artificial Sequence
<220> FEATURE:
<223> OTHER INFORMATION: Synthetic sequence

<400> SEQUENCE: 719
caatgtgatg gtggacagca a                                         21

<210> SEQ ID NO 720
<211> LENGTH: 21
<212> TYPE: DNA
<213> ORGANISM: Artificial Sequence
<220> FEATURE:
<223> OTHER INFORMATION: Synthetic sequence

<400> SEQUENCE: 720
gacgagtact gtggatgtga a                                         21

<210> SEQ ID NO 721
<211> LENGTH: 21
<212> TYPE: DNA
<213> ORGANISM: Artificial Sequence
<220> FEATURE:
<223> OTHER INFORMATION: Synthetic sequence

<400> SEQUENCE: 721
ccagtgtatt ccgtcaagta a                                         21

<210> SEQ ID NO 722
<211> LENGTH: 21
<212> TYPE: DNA
<213> ORGANISM: Artificial Sequence
<220> FEATURE:
<223> OTHER INFORMATION: Synthetic sequence

<400> SEQUENCE: 722
cagggttgtg tcgaaattgg a                                         21

<210> SEQ ID NO 723
<211> LENGTH: 21
<212> TYPE: DNA
<213> ORGANISM: Artificial Sequence
<220> FEATURE:
<223> OTHER INFORMATION: Synthetic sequence

<400> SEQUENCE: 723
cagcttaggg ataagtgtct a                                         21

<210> SEQ ID NO 724
<211> LENGTH: 21
<212> TYPE: DNA
<213> ORGANISM: Artificial Sequence
<220> FEATURE:
<223> OTHER INFORMATION: Synthetic sequence

<400> SEQUENCE: 724
tccaaacatt atcactctaa a                                              21

<210> SEQ ID NO 725
<211> LENGTH: 21
<212> TYPE: DNA
<213> ORGANISM: Artificial Sequence
<220> FEATURE:
<223> OTHER INFORMATION: Synthetic sequence

<400> SEQUENCE: 725
ttggacgagg agcttatggt t                                              21

<210> SEQ ID NO 726
<211> LENGTH: 21
<212> TYPE: DNA
<213> ORGANISM: Artificial Sequence
<220> FEATURE:
<223> OTHER INFORMATION: Synthetic sequence

<400> SEQUENCE: 726
atggatgtat tcatgaaagg a                                              21

<210> SEQ ID NO 727
<211> LENGTH: 21
<212> TYPE: DNA
<213> ORGANISM: Artificial Sequence
<220> FEATURE:
<223> OTHER INFORMATION: Synthetic sequence

<400> SEQUENCE: 727
aagcatttga tccttatgaa a                                              21

<210> SEQ ID NO 728
<211> LENGTH: 21
<212> TYPE: DNA
<213> ORGANISM: Artificial Sequence
<220> FEATURE:
<223> OTHER INFORMATION: Synthetic sequence

<400> SEQUENCE: 728
caagatggag ttcatcgaca a                                              21

<210> SEQ ID NO 729
<211> LENGTH: 21
<212> TYPE: DNA
<213> ORGANISM: Artificial Sequence
<220> FEATURE:
<223> OTHER INFORMATION: Synthetic sequence

<400> SEQUENCE: 729
aggcacgtgg aggaactctt a                                              21

<210> SEQ ID NO 730
<211> LENGTH: 21
<212> TYPE: DNA
<213> ORGANISM: Artificial Sequence
<220> FEATURE:
<223> OTHER INFORMATION: Synthetic sequence

<400> SEQUENCE: 730
cccgcatgtc acttagtcta a                                              21

<210> SEQ ID NO 731

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 731
caggaaatgt tggagaactc a                                              21

<210> SEQ ID NO 732
<211> LENGTH: 21
<212> TYPE: DNA
<213> ORGANISM: Artificial Sequence
<220> FEATURE:
<223> OTHER INFORMATION: Synthetic sequence

<400> SEQUENCE: 732
cagctatccc tctatataat a                                              21

<210> SEQ ID NO 733
<211> LENGTH: 21
<212> TYPE: DNA
<213> ORGANISM: Artificial Sequence
<220> FEATURE:
<223> OTHER INFORMATION: Synthetic sequence

<400> SEQUENCE: 733
caccttagga ttcattataa a                                              21

<210> SEQ ID NO 734
<211> LENGTH: 21
<212> TYPE: DNA
<213> ORGANISM: Artificial Sequence
<220> FEATURE:
<223> OTHER INFORMATION: Synthetic sequence

<400> SEQUENCE: 734
ctcggccaaa ctgcgtctca a                                              21

<210> SEQ ID NO 735
<211> LENGTH: 21
<212> TYPE: DNA
<213> ORGANISM: Artificial Sequence
<220> FEATURE:
<223> OTHER INFORMATION: Synthetic sequence

<400> SEQUENCE: 735
caaggagaat taggatttaa a                                              21

<210> SEQ ID NO 736
<211> LENGTH: 21
<212> TYPE: DNA
<213> ORGANISM: Artificial Sequence
<220> FEATURE:
<223> OTHER INFORMATION: Synthetic sequence

<400> SEQUENCE: 736
ctgagcctta tttctctgga a                                              21

<210> SEQ ID NO 737
<211> LENGTH: 21
<212> TYPE: DNA
<213> ORGANISM: Artificial Sequence
<220> FEATURE:
<223> OTHER INFORMATION: Synthetic sequence

<400> SEQUENCE: 737
```
caggtcagtt ggcagactct a                    21

<210> SEQ ID NO 738
<211> LENGTH: 21
<212> TYPE: DNA
<213> ORGANISM: Artificial Sequence
<220> FEATURE:
<223> OTHER INFORMATION: Synthetic sequence

<400> SEQUENCE: 738
ctccgcgctc ttcttcggaa a                    21

<210> SEQ ID NO 739
<211> LENGTH: 21
<212> TYPE: DNA
<213> ORGANISM: Artificial Sequence
<220> FEATURE:
<223> OTHER INFORMATION: Synthetic sequence

<400> SEQUENCE: 739
atgggactca gtagatcttg a                    21

<210> SEQ ID NO 740
<211> LENGTH: 21
<212> TYPE: DNA
<213> ORGANISM: Artificial Sequence
<220> FEATURE:
<223> OTHER INFORMATION: Synthetic sequence

<400> SEQUENCE: 740
gacgacaaga aggatatcaa a                    21

<210> SEQ ID NO 741
<211> LENGTH: 21
<212> TYPE: DNA
<213> ORGANISM: Artificial Sequence
<220> FEATURE:
<223> OTHER INFORMATION: Synthetic sequence

<400> SEQUENCE: 741
gagcgtgtaa ttaccttgaa a                    21

<210> SEQ ID NO 742
<211> LENGTH: 21
<212> TYPE: DNA
<213> ORGANISM: Artificial Sequence
<220> FEATURE:
<223> OTHER INFORMATION: Synthetic sequence

<400> SEQUENCE: 742
ccgacgcaag atggcgagta a                    21

<210> SEQ ID NO 743
<211> LENGTH: 21
<212> TYPE: DNA
<213> ORGANISM: Artificial Sequence
<220> FEATURE:
<223> OTHER INFORMATION: Synthetic sequence

<400> SEQUENCE: 743
accgagaagg gttaaactat a                    21

<210> SEQ ID NO 744
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 744
cggaggtgca tcagcgagca a                                              21

<210> SEQ ID NO 745
<211> LENGTH: 21
<212> TYPE: DNA
<213> ORGANISM: Artificial Sequence
<220> FEATURE:
<223> OTHER INFORMATION: Synthetic sequence

<400> SEQUENCE: 745
ctgaaatttg ctggaatgcc a                                              21

<210> SEQ ID NO 746
<211> LENGTH: 21
<212> TYPE: DNA
<213> ORGANISM: Artificial Sequence
<220> FEATURE:
<223> OTHER INFORMATION: Synthetic sequence

<400> SEQUENCE: 746
tgccattggt gttgagaata a                                              21

<210> SEQ ID NO 747
<211> LENGTH: 21
<212> TYPE: DNA
<213> ORGANISM: Artificial Sequence
<220> FEATURE:
<223> OTHER INFORMATION: Synthetic sequence

<400> SEQUENCE: 747
aaggttgaag cagaagaata a                                              21

<210> SEQ ID NO 748
<211> LENGTH: 21
<212> TYPE: DNA
<213> ORGANISM: Artificial Sequence
<220> FEATURE:
<223> OTHER INFORMATION: Synthetic sequence

<400> SEQUENCE: 748
ccagatgtct atgatcattt a                                              21

<210> SEQ ID NO 749
<211> LENGTH: 21
<212> TYPE: DNA
<213> ORGANISM: Artificial Sequence
<220> FEATURE:
<223> OTHER INFORMATION: Synthetic sequence

<400> SEQUENCE: 749
acggataggc aggaacatac a                                              21

<210> SEQ ID NO 750
<211> LENGTH: 21
<212> TYPE: DNA
<213> ORGANISM: Artificial Sequence
<220> FEATURE:
<223> OTHER INFORMATION: Synthetic sequence

<400> SEQUENCE: 750
gagcggaacc tgaatcccaa a                                              21
```

<210> SEQ ID NO 751
<211> LENGTH: 21
<212> TYPE: DNA
<213> ORGANISM: Artificial Sequence
<220> FEATURE:
<223> OTHER INFORMATION: Synthetic sequence

<400> SEQUENCE: 751
tcctgtttcg ccggacttga a                                          21

<210> SEQ ID NO 752
<211> LENGTH: 21
<212> TYPE: DNA
<213> ORGANISM: Artificial Sequence
<220> FEATURE:
<223> OTHER INFORMATION: Synthetic sequence

<400> SEQUENCE: 752
taggctggtt ctcaaccgga a                                          21

<210> SEQ ID NO 753
<211> LENGTH: 21
<212> TYPE: DNA
<213> ORGANISM: Artificial Sequence
<220> FEATURE:
<223> OTHER INFORMATION: Synthetic sequence

<400> SEQUENCE: 753
cagcaaagcc ttgcaatccc a                                          21

<210> SEQ ID NO 754
<211> LENGTH: 21
<212> TYPE: DNA
<213> ORGANISM: Artificial Sequence
<220> FEATURE:
<223> OTHER INFORMATION: Synthetic sequence

<400> SEQUENCE: 754
ccgctatggc ctcctcataa a                                          21

<210> SEQ ID NO 755
<211> LENGTH: 21
<212> TYPE: DNA
<213> ORGANISM: Artificial Sequence
<220> FEATURE:
<223> OTHER INFORMATION: Synthetic sequence

<400> SEQUENCE: 755
ttggttcagg gctcaactaa a                                          21

<210> SEQ ID NO 756
<211> LENGTH: 21
<212> TYPE: DNA
<213> ORGANISM: Artificial Sequence
<220> FEATURE:
<223> OTHER INFORMATION: Synthetic sequence

<400> SEQUENCE: 756
gagggccgct ttagaaaggt a                                          21

<210> SEQ ID NO 757
<211> LENGTH: 21
<212> TYPE: DNA
<213> ORGANISM: Artificial Sequence
<220> FEATURE:

<223> OTHER INFORMATION: Synthetic sequence

<400> SEQUENCE: 757
aacgcttcct tgctgacttc c                                              21

<210> SEQ ID NO 758
<211> LENGTH: 21
<212> TYPE: DNA
<213> ORGANISM: Artificial Sequence
<220> FEATURE:
<223> OTHER INFORMATION: Synthetic sequence

<400> SEQUENCE: 758
aacgttcagg tggttcagga a                                              21

<210> SEQ ID NO 759
<211> LENGTH: 21
<212> TYPE: DNA
<213> ORGANISM: Artificial Sequence
<220> FEATURE:
<223> OTHER INFORMATION: Synthetic sequence

<400> SEQUENCE: 759
cggcgcctaa gagtaaacta a                                              21

<210> SEQ ID NO 760
<211> LENGTH: 21
<212> TYPE: DNA
<213> ORGANISM: Artificial Sequence
<220> FEATURE:
<223> OTHER INFORMATION: Synthetic sequence

<400> SEQUENCE: 760
atggttggaa ctcatcggga a                                              21

<210> SEQ ID NO 761
<211> LENGTH: 21
<212> TYPE: DNA
<213> ORGANISM: Artificial Sequence
<220> FEATURE:
<223> OTHER INFORMATION: Synthetic sequence

<400> SEQUENCE: 761
cagacctaat aggttattac a                                              21

<210> SEQ ID NO 762
<211> LENGTH: 21
<212> TYPE: DNA
<213> ORGANISM: Artificial Sequence
<220> FEATURE:
<223> OTHER INFORMATION: Synthetic sequence

<400> SEQUENCE: 762
ctggtccctc agtgtgccta a                                              21

<210> SEQ ID NO 763
<211> LENGTH: 21
<212> TYPE: DNA
<213> ORGANISM: Artificial Sequence
<220> FEATURE:
<223> OTHER INFORMATION: Synthetic sequence

<400> SEQUENCE: 763
tgccacgtac tccgcactca a                                              21

```
<210> SEQ ID NO 764
<211> LENGTH: 21
<212> TYPE: DNA
<213> ORGANISM: Artificial Sequence
<220> FEATURE:
<223> OTHER INFORMATION: Synthetic sequence

<400> SEQUENCE: 764
ttgaagatac ttggcactat t                                       21

<210> SEQ ID NO 765
<211> LENGTH: 21
<212> TYPE: DNA
<213> ORGANISM: Artificial Sequence
<220> FEATURE:
<223> OTHER INFORMATION: Synthetic sequence

<400> SEQUENCE: 765
aaggctctgg aaagtccttc a                                       21

<210> SEQ ID NO 766
<211> LENGTH: 21
<212> TYPE: DNA
<213> ORGANISM: Artificial Sequence
<220> FEATURE:
<223> OTHER INFORMATION: Synthetic sequence

<400> SEQUENCE: 766
aagtgctgcc atgttaggta a                                       21

<210> SEQ ID NO 767
<211> LENGTH: 21
<212> TYPE: DNA
<213> ORGANISM: Artificial Sequence
<220> FEATURE:
<223> OTHER INFORMATION: Synthetic sequence

<400> SEQUENCE: 767
tgggagacgc atataatatg a                                       21

<210> SEQ ID NO 768
<211> LENGTH: 21
<212> TYPE: DNA
<213> ORGANISM: Artificial Sequence
<220> FEATURE:
<223> OTHER INFORMATION: Synthetic sequence

<400> SEQUENCE: 768
caggctggta atttatataa t                                       21

<210> SEQ ID NO 769
<211> LENGTH: 21
<212> TYPE: DNA
<213> ORGANISM: Artificial Sequence
<220> FEATURE:
<223> OTHER INFORMATION: Synthetic sequence

<400> SEQUENCE: 769
caccatttgc tgtgcgaatt a                                       21

<210> SEQ ID NO 770
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 770
catgatgaca tagaagtact a    21

<210> SEQ ID NO 771
<211> LENGTH: 21
<212> TYPE: DNA
<213> ORGANISM: Artificial Sequence
<220> FEATURE:
<223> OTHER INFORMATION: Synthetic sequence

<400> SEQUENCE: 771
ccgcagttta atgaaatctt t    21

<210> SEQ ID NO 772
<211> LENGTH: 21
<212> TYPE: DNA
<213> ORGANISM: Artificial Sequence
<220> FEATURE:
<223> OTHER INFORMATION: Synthetic sequence

<400> SEQUENCE: 772
caggaccatg gcacccttag a    21

<210> SEQ ID NO 773
<211> LENGTH: 21
<212> TYPE: DNA
<213> ORGANISM: Artificial Sequence
<220> FEATURE:
<223> OTHER INFORMATION: Synthetic sequence

<400> SEQUENCE: 773
ccggaggtcc tgaagcgtca a    21

<210> SEQ ID NO 774
<211> LENGTH: 21
<212> TYPE: DNA
<213> ORGANISM: Artificial Sequence
<220> FEATURE:
<223> OTHER INFORMATION: Synthetic sequence

<400> SEQUENCE: 774
gtgcattgac ccgaagctaa a    21

<210> SEQ ID NO 775
<211> LENGTH: 21
<212> TYPE: DNA
<213> ORGANISM: Artificial Sequence
<220> FEATURE:
<223> OTHER INFORMATION: Synthetic sequence

<400> SEQUENCE: 775
ctccacaacc atcaacagga a    21

<210> SEQ ID NO 776
<211> LENGTH: 21
<212> TYPE: DNA
<213> ORGANISM: Artificial Sequence
<220> FEATURE:
<223> OTHER INFORMATION: Synthetic sequence

<400> SEQUENCE: 776
aaggaggtcc taggttataa a    21

<210> SEQ ID NO 777
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 777
ctccatgtgc gtccatattt a                                              21

<210> SEQ ID NO 778
<211> LENGTH: 21
<212> TYPE: DNA
<213> ORGANISM: Artificial Sequence
<220> FEATURE:
<223> OTHER INFORMATION: Synthetic sequence

<400> SEQUENCE: 778
tcagaggccg ttggtactta a                                              21

<210> SEQ ID NO 779
<211> LENGTH: 21
<212> TYPE: DNA
<213> ORGANISM: Artificial Sequence
<220> FEATURE:
<223> OTHER INFORMATION: Synthetic sequence

<400> SEQUENCE: 779
caccttcggc atcctaatat t                                              21

<210> SEQ ID NO 780
<211> LENGTH: 21
<212> TYPE: DNA
<213> ORGANISM: Artificial Sequence
<220> FEATURE:
<223> OTHER INFORMATION: Synthetic sequence

<400> SEQUENCE: 780
ctggctgtcc ttatcatcac a                                              21

<210> SEQ ID NO 781
<211> LENGTH: 21
<212> TYPE: DNA
<213> ORGANISM: Artificial Sequence
<220> FEATURE:
<223> OTHER INFORMATION: Synthetic sequence

<400> SEQUENCE: 781
accggcacct tcatcgagaa a                                              21

<210> SEQ ID NO 782
<211> LENGTH: 21
<212> TYPE: DNA
<213> ORGANISM: Artificial Sequence
<220> FEATURE:
<223> OTHER INFORMATION: Synthetic sequence

<400> SEQUENCE: 782
cgcgtgtaaa ttctactgca a                                              21

<210> SEQ ID NO 783
<211> LENGTH: 21
<212> TYPE: DNA
<213> ORGANISM: Artificial Sequence
<220> FEATURE:
<223> OTHER INFORMATION: Synthetic sequence

<400> SEQUENCE: 783
```
ccacatttaa ttaacagctg a                         21

<210> SEQ ID NO 784
<211> LENGTH: 21
<212> TYPE: DNA
<213> ORGANISM: Artificial Sequence
<220> FEATURE:
<223> OTHER INFORMATION: Synthetic sequence

<400> SEQUENCE: 784
agcgctgaga atggacagca a                         21

<210> SEQ ID NO 785
<211> LENGTH: 21
<212> TYPE: DNA
<213> ORGANISM: Artificial Sequence
<220> FEATURE:
<223> OTHER INFORMATION: Synthetic sequence

<400> SEQUENCE: 785
agggtgtata gtgttcacaa a                         21

<210> SEQ ID NO 786
<211> LENGTH: 21
<212> TYPE: DNA
<213> ORGANISM: Artificial Sequence
<220> FEATURE:
<223> OTHER INFORMATION: Synthetic sequence

<400> SEQUENCE: 786
aaagagggtg ttctctatgt a                         21

<210> SEQ ID NO 787
<211> LENGTH: 21
<212> TYPE: DNA
<213> ORGANISM: Artificial Sequence
<220> FEATURE:
<223> OTHER INFORMATION: Synthetic sequence

<400> SEQUENCE: 787
cagcataata tttgctgcta a                         21

<210> SEQ ID NO 788
<211> LENGTH: 21
<212> TYPE: DNA
<213> ORGANISM: Artificial Sequence
<220> FEATURE:
<223> OTHER INFORMATION: Synthetic sequence

<400> SEQUENCE: 788
aaggagcggc ctcgccataa a                         21

<210> SEQ ID NO 789
<211> LENGTH: 21
<212> TYPE: DNA
<213> ORGANISM: Artificial Sequence
<220> FEATURE:
<223> OTHER INFORMATION: Synthetic sequence

<400> SEQUENCE: 789
ttcgaagtta ggaggactca a                         21

<210> SEQ ID NO 790
<211> LENGTH: 21
<212> TYPE: DNA
<213> ORGANISM: Artificial Sequence
<220> FEATURE:
<223> OTHER INFORMATION: Synthetic sequence

<400> SEQUENCE: 790
tagagtcatc cctgtaatca a         21

<210> SEQ ID NO 791
<211> LENGTH: 21
<212> TYPE: DNA
<213> ORGANISM: Artificial Sequence
<220> FEATURE:
<223> OTHER INFORMATION: Synthetic sequence

<400> SEQUENCE: 791
cactgagatc tactggataa a         21

<210> SEQ ID NO 792
<211> LENGTH: 21
<212> TYPE: DNA
<213> ORGANISM: Artificial Sequence
<220> FEATURE:
<223> OTHER INFORMATION: Synthetic sequence

<400> SEQUENCE: 792
aagactcctt ccagtgatgt t         21

<210> SEQ ID NO 793
<211> LENGTH: 21
<212> TYPE: DNA
<213> ORGANISM: Artificial Sequence
<220> FEATURE:
<223> OTHER INFORMATION: Synthetic sequence

<400> SEQUENCE: 793
aaggatgaat gtagttctga a         21

<210> SEQ ID NO 794
<211> LENGTH: 21
<212> TYPE: DNA
<213> ORGANISM: Artificial Sequence
<220> FEATURE:
<223> OTHER INFORMATION: Synthetic sequence

<400> SEQUENCE: 794
ccgggtcact gctgtatata a         21

<210> SEQ ID NO 795
<211> LENGTH: 21
<212> TYPE: DNA
<213> ORGANISM: Artificial Sequence
<220> FEATURE:
<223> OTHER INFORMATION: Synthetic sequence

<400> SEQUENCE: 795
cgcctggatt acgattataa a         21

<210> SEQ ID NO 796
<211> LENGTH: 21
<212> TYPE: DNA
<213> ORGANISM: Artificial Sequence
<220> FEATURE:
<223> OTHER INFORMATION: Synthetic sequence

<400> SEQUENCE: 796
cagctgctac tttgacatcg a         21

```
<210> SEQ ID NO 797
<211> LENGTH: 21
<212> TYPE: DNA
<213> ORGANISM: Artificial Sequence
<220> FEATURE:
<223> OTHER INFORMATION: Synthetic sequence

<400> SEQUENCE: 797
atgcctaata ttcagtatca a                                      21

<210> SEQ ID NO 798
<211> LENGTH: 21
<212> TYPE: DNA
<213> ORGANISM: Artificial Sequence
<220> FEATURE:
<223> OTHER INFORMATION: Synthetic sequence

<400> SEQUENCE: 798
cagccgcaat ctctcggcca a                                      21

<210> SEQ ID NO 799
<211> LENGTH: 21
<212> TYPE: DNA
<213> ORGANISM: Artificial Sequence
<220> FEATURE:
<223> OTHER INFORMATION: Synthetic sequence

<400> SEQUENCE: 799
gccaccctaa tttgacatca a                                      21

<210> SEQ ID NO 800
<211> LENGTH: 21
<212> TYPE: DNA
<213> ORGANISM: Artificial Sequence
<220> FEATURE:
<223> OTHER INFORMATION: Synthetic sequence

<400> SEQUENCE: 800
agccgaattg aagatcgttt a                                      21

<210> SEQ ID NO 801
<211> LENGTH: 21
<212> TYPE: DNA
<213> ORGANISM: Artificial Sequence
<220> FEATURE:
<223> OTHER INFORMATION: Synthetic sequence

<400> SEQUENCE: 801
ctgccagttc agttaatcaa a                                      21

<210> SEQ ID NO 802
<211> LENGTH: 21
<212> TYPE: DNA
<213> ORGANISM: Artificial Sequence
<220> FEATURE:
<223> OTHER INFORMATION: Synthetic sequence

<400> SEQUENCE: 802
gcggataaga ccgtagcttt a                                      21

<210> SEQ ID NO 803
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 803
aaggtaattg ctctaacttt a                                              21

<210> SEQ ID NO 804
<211> LENGTH: 21
<212> TYPE: DNA
<213> ORGANISM: Artificial Sequence
<220> FEATURE:
<223> OTHER INFORMATION: Synthetic sequence

<400> SEQUENCE: 804
aacgcgcttg tccacaaaca a                                              21

<210> SEQ ID NO 805
<211> LENGTH: 21
<212> TYPE: DNA
<213> ORGANISM: Artificial Sequence
<220> FEATURE:
<223> OTHER INFORMATION: Synthetic sequence

<400> SEQUENCE: 805
aagagccacc tgaccatcag t                                              21

<210> SEQ ID NO 806
<211> LENGTH: 21
<212> TYPE: DNA
<213> ORGANISM: Artificial Sequence
<220> FEATURE:
<223> OTHER INFORMATION: Synthetic sequence

<400> SEQUENCE: 806
ccgcaacaat aagaaactcc t                                              21

<210> SEQ ID NO 807
<211> LENGTH: 21
<212> TYPE: DNA
<213> ORGANISM: Artificial Sequence
<220> FEATURE:
<223> OTHER INFORMATION: Synthetic sequence

<400> SEQUENCE: 807
gagcgacgtg gtggaagtct a                                              21

<210> SEQ ID NO 808
<211> LENGTH: 21
<212> TYPE: DNA
<213> ORGANISM: Artificial Sequence
<220> FEATURE:
<223> OTHER INFORMATION: Synthetic sequence

<400> SEQUENCE: 808
cagaaagagc ttgacagtaa a                                              21

<210> SEQ ID NO 809
<211> LENGTH: 21
<212> TYPE: DNA
<213> ORGANISM: Artificial Sequence
<220> FEATURE:
<223> OTHER INFORMATION: Synthetic sequence

<400> SEQUENCE: 809
cagcggctct atgtcgactt t                                              21

<210> SEQ ID NO 810

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 810
ctggatgatt gggactttaa a                                              21

<210> SEQ ID NO 811
<211> LENGTH: 21
<212> TYPE: DNA
<213> ORGANISM: Artificial Sequence
<220> FEATURE:
<223> OTHER INFORMATION: Synthetic sequence

<400> SEQUENCE: 811
tacgactgta tggaaacgtt t                                              21

<210> SEQ ID NO 812
<211> LENGTH: 21
<212> TYPE: DNA
<213> ORGANISM: Artificial Sequence
<220> FEATURE:
<223> OTHER INFORMATION: Synthetic sequence

<400> SEQUENCE: 812
ccgctggtgg actgtaataa t                                              21

<210> SEQ ID NO 813
<211> LENGTH: 21
<212> TYPE: DNA
<213> ORGANISM: Artificial Sequence
<220> FEATURE:
<223> OTHER INFORMATION: Synthetic sequence

<400> SEQUENCE: 813
cagaaacagg ttgacaactc a                                              21

<210> SEQ ID NO 814
<211> LENGTH: 21
<212> TYPE: DNA
<213> ORGANISM: Artificial Sequence
<220> FEATURE:
<223> OTHER INFORMATION: Synthetic sequence

<400> SEQUENCE: 814
ctgggaatgg acgatagaga a                                              21

<210> SEQ ID NO 815
<211> LENGTH: 21
<212> TYPE: DNA
<213> ORGANISM: Artificial Sequence
<220> FEATURE:
<223> OTHER INFORMATION: Synthetic sequence

<400> SEQUENCE: 815
aggcaagtaa gtccatatca a                                              21

<210> SEQ ID NO 816
<211> LENGTH: 21
<212> TYPE: DNA
<213> ORGANISM: Artificial Sequence
<220> FEATURE:
<223> OTHER INFORMATION: Synthetic sequence

<400> SEQUENCE: 816
```
ctgggtcttt atgagaagct t    21

<210> SEQ ID NO 817
<211> LENGTH: 21
<212> TYPE: DNA
<213> ORGANISM: Artificial Sequence
<220> FEATURE:
<223> OTHER INFORMATION: Synthetic sequence

<400> SEQUENCE: 817
ccggctgcgt acgtgaagaa a    21

<210> SEQ ID NO 818
<211> LENGTH: 21
<212> TYPE: DNA
<213> ORGANISM: Artificial Sequence
<220> FEATURE:
<223> OTHER INFORMATION: Synthetic sequence

<400> SEQUENCE: 818
taggccgatt aactaccta a    21

<210> SEQ ID NO 819
<211> LENGTH: 21
<212> TYPE: DNA
<213> ORGANISM: Artificial Sequence
<220> FEATURE:
<223> OTHER INFORMATION: Synthetic sequence

<400> SEQUENCE: 819
ccggcgccta agagtaaact a    21

<210> SEQ ID NO 820
<211> LENGTH: 21
<212> TYPE: DNA
<213> ORGANISM: Artificial Sequence
<220> FEATURE:
<223> OTHER INFORMATION: Synthetic sequence

<400> SEQUENCE: 820
aaccgtgaat ctcctagtta t    21

<210> SEQ ID NO 821
<211> LENGTH: 21
<212> TYPE: DNA
<213> ORGANISM: Artificial Sequence
<220> FEATURE:
<223> OTHER INFORMATION: Synthetic sequence

<400> SEQUENCE: 821
acggacctgt cccgtgattt a    21

<210> SEQ ID NO 822
<211> LENGTH: 21
<212> TYPE: DNA
<213> ORGANISM: Artificial Sequence
<220> FEATURE:
<223> OTHER INFORMATION: Synthetic sequence

<400> SEQUENCE: 822
ctggattctt gcaccaggga a    21

<210> SEQ ID NO 823
<211> LENGTH: 21
<212> TYPE: DNA

<213> ORGANISM: Artificial Sequence
<220> FEATURE:
<223> OTHER INFORMATION: Synthetic sequence

<400> SEQUENCE: 823
cccaacatca tcactctgaa a                                            21

<210> SEQ ID NO 824
<211> LENGTH: 21
<212> TYPE: DNA
<213> ORGANISM: Artificial Sequence
<220> FEATURE:
<223> OTHER INFORMATION: Synthetic sequence

<400> SEQUENCE: 824
ctctcagtat aatgcctata a                                            21

<210> SEQ ID NO 825
<211> LENGTH: 21
<212> TYPE: DNA
<213> ORGANISM: Artificial Sequence
<220> FEATURE:
<223> OTHER INFORMATION: Synthetic sequence

<400> SEQUENCE: 825
cagtgcctta gatacaagaa a                                            21

<210> SEQ ID NO 826
<211> LENGTH: 21
<212> TYPE: DNA
<213> ORGANISM: Artificial Sequence
<220> FEATURE:
<223> OTHER INFORMATION: Synthetic sequence

<400> SEQUENCE: 826
ctggatcagc aacttaggaa a                                            21

<210> SEQ ID NO 827
<211> LENGTH: 21
<212> TYPE: DNA
<213> ORGANISM: Artificial Sequence
<220> FEATURE:
<223> OTHER INFORMATION: Synthetic sequence

<400> SEQUENCE: 827
ctcgagtact tgttgacatt a                                            21

<210> SEQ ID NO 828
<211> LENGTH: 21
<212> TYPE: DNA
<213> ORGANISM: Artificial Sequence
<220> FEATURE:
<223> OTHER INFORMATION: Synthetic sequence

<400> SEQUENCE: 828
cagcctctct gcagaattca a                                            21

<210> SEQ ID NO 829
<211> LENGTH: 21
<212> TYPE: DNA
<213> ORGANISM: Artificial Sequence
<220> FEATURE:
<223> OTHER INFORMATION: Synthetic sequence

<400> SEQUENCE: 829
aggattcata gcatcactat a                                            21

```
<210> SEQ ID NO 830
<211> LENGTH: 21
<212> TYPE: DNA
<213> ORGANISM: Artificial Sequence
<220> FEATURE:
<223> OTHER INFORMATION: Synthetic sequence

<400> SEQUENCE: 830
cagaggcgga tagaacggat a                                              21

<210> SEQ ID NO 831
<211> LENGTH: 21
<212> TYPE: DNA
<213> ORGANISM: Artificial Sequence
<220> FEATURE:
<223> OTHER INFORMATION: Synthetic sequence

<400> SEQUENCE: 831
ctacctgaaa gtaacattaa a                                              21

<210> SEQ ID NO 832
<211> LENGTH: 21
<212> TYPE: DNA
<213> ORGANISM: Artificial Sequence
<220> FEATURE:
<223> OTHER INFORMATION: Synthetic sequence

<400> SEQUENCE: 832
cagactgttc tgggcacgga a                                              21

<210> SEQ ID NO 833
<211> LENGTH: 21
<212> TYPE: DNA
<213> ORGANISM: Artificial Sequence
<220> FEATURE:
<223> OTHER INFORMATION: Synthetic sequence

<400> SEQUENCE: 833
ccgagtgaga tcgaagatgg a                                              21

<210> SEQ ID NO 834
<211> LENGTH: 21
<212> TYPE: DNA
<213> ORGANISM: Artificial Sequence
<220> FEATURE:
<223> OTHER INFORMATION: Synthetic sequence

<400> SEQUENCE: 834
ctgaagaaca acaacagaca a                                              21

<210> SEQ ID NO 835
<211> LENGTH: 21
<212> TYPE: DNA
<213> ORGANISM: Artificial Sequence
<220> FEATURE:
<223> OTHER INFORMATION: Synthetic sequence

<400> SEQUENCE: 835
accagagaag tttgccctga a                                              21

<210> SEQ ID NO 836
<211> LENGTH: 21
<212> TYPE: DNA
<213> ORGANISM: Artificial Sequence
<220> FEATURE:
```

<223> OTHER INFORMATION: Synthetic sequence

<400> SEQUENCE: 836
tgggttgaat ccatcactaa a                                              21

<210> SEQ ID NO 837
<211> LENGTH: 21
<212> TYPE: DNA
<213> ORGANISM: Artificial Sequence
<220> FEATURE:
<223> OTHER INFORMATION: Synthetic sequence

<400> SEQUENCE: 837
cggcttgtgg gtgatgtttg a                                              21

<210> SEQ ID NO 838
<211> LENGTH: 21
<212> TYPE: DNA
<213> ORGANISM: Artificial Sequence
<220> FEATURE:
<223> OTHER INFORMATION: Synthetic sequence

<400> SEQUENCE: 838
tggaatcaag tccaacagtt a                                              21

<210> SEQ ID NO 839
<211> LENGTH: 21
<212> TYPE: DNA
<213> ORGANISM: Artificial Sequence
<220> FEATURE:
<223> OTHER INFORMATION: Synthetic sequence

<400> SEQUENCE: 839
tcccagcgca ttcctttgca a                                              21

<210> SEQ ID NO 840
<211> LENGTH: 21
<212> TYPE: DNA
<213> ORGANISM: Artificial Sequence
<220> FEATURE:
<223> OTHER INFORMATION: Synthetic sequence

<400> SEQUENCE: 840
aagccggtaa atgcctcaat a                                              21

<210> SEQ ID NO 841
<211> LENGTH: 21
<212> TYPE: DNA
<213> ORGANISM: Artificial Sequence
<220> FEATURE:
<223> OTHER INFORMATION: Synthetic sequence

<400> SEQUENCE: 841
ctgccttatt atgatcttgt a                                              21

<210> SEQ ID NO 842
<211> LENGTH: 21
<212> TYPE: DNA
<213> ORGANISM: Artificial Sequence
<220> FEATURE:
<223> OTHER INFORMATION: Synthetic sequence

<400> SEQUENCE: 842
cccagacaag aagataaaga t                                              21

```
<210> SEQ ID NO 843
<211> LENGTH: 21
<212> TYPE: DNA
<213> ORGANISM: Artificial Sequence
<220> FEATURE:
<223> OTHER INFORMATION: Synthetic sequence

<400> SEQUENCE: 843
tggatttaag gtgggcatta a                                              21

<210> SEQ ID NO 844
<211> LENGTH: 21
<212> TYPE: DNA
<213> ORGANISM: Artificial Sequence
<220> FEATURE:
<223> OTHER INFORMATION: Synthetic sequence

<400> SEQUENCE: 844
aagcgagtaa ccagctcata a                                              21

<210> SEQ ID NO 845
<211> LENGTH: 21
<212> TYPE: DNA
<213> ORGANISM: Artificial Sequence
<220> FEATURE:
<223> OTHER INFORMATION: Synthetic sequence

<400> SEQUENCE: 845
ttggccatgt ttatgatttg a                                              21

<210> SEQ ID NO 846
<211> LENGTH: 21
<212> TYPE: DNA
<213> ORGANISM: Artificial Sequence
<220> FEATURE:
<223> OTHER INFORMATION: Synthetic sequence

<400> SEQUENCE: 846
cacgatcaat gagctgagca a                                              21

<210> SEQ ID NO 847
<211> LENGTH: 21
<212> TYPE: DNA
<213> ORGANISM: Artificial Sequence
<220> FEATURE:
<223> OTHER INFORMATION: Synthetic sequence

<400> SEQUENCE: 847
tacgtatctg gaagttatca a                                              21

<210> SEQ ID NO 848
<211> LENGTH: 21
<212> TYPE: DNA
<213> ORGANISM: Artificial Sequence
<220> FEATURE:
<223> OTHER INFORMATION: Synthetic sequence

<400> SEQUENCE: 848
ccgacatttc ctggcattga a                                              21

<210> SEQ ID NO 849
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 849
cttgtcgaac atcaagtaga a                                              21

<210> SEQ ID NO 850
<211> LENGTH: 21
<212> TYPE: DNA
<213> ORGANISM: Artificial Sequence
<220> FEATURE:
<223> OTHER INFORMATION: Synthetic sequence

<400> SEQUENCE: 850
atgattctgt attaatgtaa a                                              21

<210> SEQ ID NO 851
<211> LENGTH: 21
<212> TYPE: DNA
<213> ORGANISM: Artificial Sequence
<220> FEATURE:
<223> OTHER INFORMATION: Synthetic sequence

<400> SEQUENCE: 851
ccggcggttc atgaggagtg a                                              21

<210> SEQ ID NO 852
<211> LENGTH: 21
<212> TYPE: DNA
<213> ORGANISM: Artificial Sequence
<220> FEATURE:
<223> OTHER INFORMATION: Synthetic sequence

<400> SEQUENCE: 852
aaggaaattt gcgtgtggag t                                              21

<210> SEQ ID NO 853
<211> LENGTH: 21
<212> TYPE: DNA
<213> ORGANISM: Artificial Sequence
<220> FEATURE:
<223> OTHER INFORMATION: Synthetic sequence

<400> SEQUENCE: 853
ccgcactagt agagaatcca t                                              21

<210> SEQ ID NO 854
<211> LENGTH: 21
<212> TYPE: DNA
<213> ORGANISM: Artificial Sequence
<220> FEATURE:
<223> OTHER INFORMATION: Synthetic sequence

<400> SEQUENCE: 854
gaggctcctg cttatttata a                                              21

<210> SEQ ID NO 855
<211> LENGTH: 21
<212> TYPE: DNA
<213> ORGANISM: Artificial Sequence
<220> FEATURE:
<223> OTHER INFORMATION: Synthetic sequence

<400> SEQUENCE: 855
aaggtgagca gtattgattt g                                              21

<210> SEQ ID NO 856
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 856
ccggaactct ggcgtcaact a                                              21

<210> SEQ ID NO 857
<211> LENGTH: 21
<212> TYPE: DNA
<213> ORGANISM: Artificial Sequence
<220> FEATURE:
<223> OTHER INFORMATION: Synthetic sequence

<400> SEQUENCE: 857
tacccagtat ctttgcacaa a                                              21

<210> SEQ ID NO 858
<211> LENGTH: 21
<212> TYPE: DNA
<213> ORGANISM: Artificial Sequence
<220> FEATURE:
<223> OTHER INFORMATION: Synthetic sequence

<400> SEQUENCE: 858
aactttgatg tgattaaggg a                                              21

<210> SEQ ID NO 859
<211> LENGTH: 21
<212> TYPE: DNA
<213> ORGANISM: Artificial Sequence
<220> FEATURE:
<223> OTHER INFORMATION: Synthetic sequence

<400> SEQUENCE: 859
caggatgagc aacaacagta a                                              21

<210> SEQ ID NO 860
<211> LENGTH: 21
<212> TYPE: DNA
<213> ORGANISM: Artificial Sequence
<220> FEATURE:
<223> OTHER INFORMATION: Synthetic sequence

<400> SEQUENCE: 860
ctccaagttg atgctcttaa a                                              21

<210> SEQ ID NO 861
<211> LENGTH: 21
<212> TYPE: DNA
<213> ORGANISM: Artificial Sequence
<220> FEATURE:
<223> OTHER INFORMATION: Synthetic sequence

<400> SEQUENCE: 861
ccagtatctg ataatgaaga a                                              21

<210> SEQ ID NO 862
<211> LENGTH: 21
<212> TYPE: DNA
<213> ORGANISM: Artificial Sequence
<220> FEATURE:
<223> OTHER INFORMATION: Synthetic sequence

<400> SEQUENCE: 862
```
ctggcccaac ttcatttcca t					21

<210> SEQ ID NO 863
<211> LENGTH: 21
<212> TYPE: DNA
<213> ORGANISM: Artificial Sequence
<220> FEATURE:
<223> OTHER INFORMATION: Synthetic sequence

<400> SEQUENCE: 863
tagatagtac gaagtcttca a					21

<210> SEQ ID NO 864
<211> LENGTH: 21
<212> TYPE: DNA
<213> ORGANISM: Artificial Sequence
<220> FEATURE:
<223> OTHER INFORMATION: Synthetic sequence

<400> SEQUENCE: 864
aaagagtacc gtgagaagat a					21

<210> SEQ ID NO 865
<211> LENGTH: 21
<212> TYPE: DNA
<213> ORGANISM: Artificial Sequence
<220> FEATURE:
<223> OTHER INFORMATION: Synthetic sequence

<400> SEQUENCE: 865
aagttgtggt ctgatcagtt a					21

<210> SEQ ID NO 866
<211> LENGTH: 21
<212> TYPE: DNA
<213> ORGANISM: Artificial Sequence
<220> FEATURE:
<223> OTHER INFORMATION: Synthetic sequence

<400> SEQUENCE: 866
gacgggctat gtaccgtcca a					21

<210> SEQ ID NO 867
<211> LENGTH: 21
<212> TYPE: DNA
<213> ORGANISM: Artificial Sequence
<220> FEATURE:
<223> OTHER INFORMATION: Synthetic sequence

<400> SEQUENCE: 867
cagaatagcc tacatttgta t					21

<210> SEQ ID NO 868
<211> LENGTH: 21
<212> TYPE: DNA
<213> ORGANISM: Artificial Sequence
<220> FEATURE:
<223> OTHER INFORMATION: Synthetic sequence

<400> SEQUENCE: 868
cagaacggtc cagtcaccaa a					21

<210> SEQ ID NO 869
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 869
aaccttaatg taatttactt a                                              21

<210> SEQ ID NO 870
<211> LENGTH: 21
<212> TYPE: DNA
<213> ORGANISM: Artificial Sequence
<220> FEATURE:
<223> OTHER INFORMATION: Synthetic sequence

<400> SEQUENCE: 870
ctgtggcata tttgtcacta a                                              21

<210> SEQ ID NO 871
<211> LENGTH: 21
<212> TYPE: DNA
<213> ORGANISM: Artificial Sequence
<220> FEATURE:
<223> OTHER INFORMATION: Synthetic sequence

<400> SEQUENCE: 871
caccatgaac tcgatcacag a                                              21

<210> SEQ ID NO 872
<211> LENGTH: 21
<212> TYPE: DNA
<213> ORGANISM: Artificial Sequence
<220> FEATURE:
<223> OTHER INFORMATION: Synthetic sequence

<400> SEQUENCE: 872
cagcgtgata tgtaccgtat t                                              21

<210> SEQ ID NO 873
<211> LENGTH: 21
<212> TYPE: DNA
<213> ORGANISM: Artificial Sequence
<220> FEATURE:
<223> OTHER INFORMATION: Synthetic sequence

<400> SEQUENCE: 873
caaggagagg ttcctcgtct a                                              21

<210> SEQ ID NO 874
<211> LENGTH: 21
<212> TYPE: DNA
<213> ORGANISM: Artificial Sequence
<220> FEATURE:
<223> OTHER INFORMATION: Synthetic sequence

<400> SEQUENCE: 874
accattagca aatggaaatt a                                              21

<210> SEQ ID NO 875
<211> LENGTH: 21
<212> TYPE: DNA
<213> ORGANISM: Artificial Sequence
<220> FEATURE:
<223> OTHER INFORMATION: Synthetic sequence

<400> SEQUENCE: 875
cacgctcagg ttgaaggtcg a                                              21
```

```
<210> SEQ ID NO 876
<211> LENGTH: 21
<212> TYPE: DNA
<213> ORGANISM: Artificial Sequence
<220> FEATURE:
<223> OTHER INFORMATION: Synthetic sequence

<400> SEQUENCE: 876
ctcagtgtag tggaagtgat a                                        21

<210> SEQ ID NO 877
<211> LENGTH: 21
<212> TYPE: DNA
<213> ORGANISM: Artificial Sequence
<220> FEATURE:
<223> OTHER INFORMATION: Synthetic sequence

<400> SEQUENCE: 877
cagtgtattg acgcatattt a                                        21

<210> SEQ ID NO 878
<211> LENGTH: 21
<212> TYPE: DNA
<213> ORGANISM: Artificial Sequence
<220> FEATURE:
<223> OTHER INFORMATION: Synthetic sequence

<400> SEQUENCE: 878
cccatttata tctctcgcat a                                        21

<210> SEQ ID NO 879
<211> LENGTH: 21
<212> TYPE: DNA
<213> ORGANISM: Artificial Sequence
<220> FEATURE:
<223> OTHER INFORMATION: Synthetic sequence

<400> SEQUENCE: 879
tacctagtgc atgctctgca a                                        21

<210> SEQ ID NO 880
<211> LENGTH: 21
<212> TYPE: DNA
<213> ORGANISM: Artificial Sequence
<220> FEATURE:
<223> OTHER INFORMATION: Synthetic sequence

<400> SEQUENCE: 880
ctggatctct tacgtaattc a                                        21

<210> SEQ ID NO 881
<211> LENGTH: 21
<212> TYPE: DNA
<213> ORGANISM: Artificial Sequence
<220> FEATURE:
<223> OTHER INFORMATION: Synthetic sequence

<400> SEQUENCE: 881
aacagagacc cctgaagatc c                                        21

<210> SEQ ID NO 882
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 882
tcgcctcagt ttgaacattg a                                              21

<210> SEQ ID NO 883
<211> LENGTH: 21
<212> TYPE: DNA
<213> ORGANISM: Artificial Sequence
<220> FEATURE:
<223> OTHER INFORMATION: Synthetic sequence

<400> SEQUENCE: 883
ctgaaagtct gccacgataa a                                              21

<210> SEQ ID NO 884
<211> LENGTH: 21
<212> TYPE: DNA
<213> ORGANISM: Artificial Sequence
<220> FEATURE:
<223> OTHER INFORMATION: Synthetic sequence

<400> SEQUENCE: 884
caatccaagc ataattgtta a                                              21

<210> SEQ ID NO 885
<211> LENGTH: 21
<212> TYPE: DNA
<213> ORGANISM: Artificial Sequence
<220> FEATURE:
<223> OTHER INFORMATION: Synthetic sequence

<400> SEQUENCE: 885
ccctgccttg ataatatgtt a                                              21

<210> SEQ ID NO 886
<211> LENGTH: 21
<212> TYPE: DNA
<213> ORGANISM: Artificial Sequence
<220> FEATURE:
<223> OTHER INFORMATION: Synthetic sequence

<400> SEQUENCE: 886
atgaattatg ataaattgaa a                                              21

<210> SEQ ID NO 887
<211> LENGTH: 21
<212> TYPE: DNA
<213> ORGANISM: Artificial Sequence
<220> FEATURE:
<223> OTHER INFORMATION: Synthetic sequence

<400> SEQUENCE: 887
ccgcacttcc atattctgga a                                              21

<210> SEQ ID NO 888
<211> LENGTH: 21
<212> TYPE: DNA
<213> ORGANISM: Artificial Sequence
<220> FEATURE:
<223> OTHER INFORMATION: Synthetic sequence

<400> SEQUENCE: 888
aaggagacgt cagaacgtgg c                                              21

<210> SEQ ID NO 889

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 889
tcgggagttc ctggaccagt a                                              21

<210> SEQ ID NO 890
<211> LENGTH: 21
<212> TYPE: DNA
<213> ORGANISM: Artificial Sequence
<220> FEATURE:
<223> OTHER INFORMATION: Synthetic sequence

<400> SEQUENCE: 890
ctgagcatcg atggcgagaa t                                              21

<210> SEQ ID NO 891
<211> LENGTH: 21
<212> TYPE: DNA
<213> ORGANISM: Artificial Sequence
<220> FEATURE:
<223> OTHER INFORMATION: Synthetic sequence

<400> SEQUENCE: 891
tccgaagatg attcacctag a                                              21

<210> SEQ ID NO 892
<211> LENGTH: 21
<212> TYPE: DNA
<213> ORGANISM: Artificial Sequence
<220> FEATURE:
<223> OTHER INFORMATION: Synthetic sequence

<400> SEQUENCE: 892
caggaggaga ctgtgagaat t                                              21

<210> SEQ ID NO 893
<211> LENGTH: 21
<212> TYPE: DNA
<213> ORGANISM: Artificial Sequence
<220> FEATURE:
<223> OTHER INFORMATION: Synthetic sequence

<400> SEQUENCE: 893
ttgctgcagc acattataat a                                              21

<210> SEQ ID NO 894
<211> LENGTH: 21
<212> TYPE: DNA
<213> ORGANISM: Artificial Sequence
<220> FEATURE:
<223> OTHER INFORMATION: Synthetic sequence

<400> SEQUENCE: 894
cacggaagag atgatgcgcg a                                              21

<210> SEQ ID NO 895
<211> LENGTH: 21
<212> TYPE: DNA
<213> ORGANISM: Artificial Sequence
<220> FEATURE:
<223> OTHER INFORMATION: Synthetic sequence

<400> SEQUENCE: 895
```
aagggttacc ttccagttca a                                        21

<210> SEQ ID NO 896
<211> LENGTH: 21
<212> TYPE: DNA
<213> ORGANISM: Artificial Sequence
<220> FEATURE:
<223> OTHER INFORMATION: Synthetic sequence

<400> SEQUENCE: 896
ttcggaaatg cctcacatat a                                        21

<210> SEQ ID NO 897
<211> LENGTH: 21
<212> TYPE: DNA
<213> ORGANISM: Artificial Sequence
<220> FEATURE:
<223> OTHER INFORMATION: Synthetic sequence

<400> SEQUENCE: 897
tggcggcgat atagtgaatt t                                        21

<210> SEQ ID NO 898
<211> LENGTH: 21
<212> TYPE: DNA
<213> ORGANISM: Artificial Sequence
<220> FEATURE:
<223> OTHER INFORMATION: Synthetic sequence

<400> SEQUENCE: 898
taggaggaaa cccagaaatg a                                        21

<210> SEQ ID NO 899
<211> LENGTH: 21
<212> TYPE: DNA
<213> ORGANISM: Artificial Sequence
<220> FEATURE:
<223> OTHER INFORMATION: Synthetic sequence

<400> SEQUENCE: 899
gagtatgaca atgttgtact a                                        21

<210> SEQ ID NO 900
<211> LENGTH: 21
<212> TYPE: DNA
<213> ORGANISM: Artificial Sequence
<220> FEATURE:
<223> OTHER INFORMATION: Synthetic sequence

<400> SEQUENCE: 900
ctacgagcag atcaagataa a                                        21

<210> SEQ ID NO 901
<211> LENGTH: 21
<212> TYPE: DNA
<213> ORGANISM: Artificial Sequence
<220> FEATURE:
<223> OTHER INFORMATION: Synthetic sequence

<400> SEQUENCE: 901
tgggattgta ctataccagt a                                        21

<210> SEQ ID NO 902
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 902
tagatgtaac agagctcact a                                              21

<210> SEQ ID NO 903
<211> LENGTH: 21
<212> TYPE: DNA
<213> ORGANISM: Artificial Sequence
<220> FEATURE:
<223> OTHER INFORMATION: Synthetic sequence

<400> SEQUENCE: 903
cagctgatca ccgggaagga a                                              21

<210> SEQ ID NO 904
<211> LENGTH: 21
<212> TYPE: DNA
<213> ORGANISM: Artificial Sequence
<220> FEATURE:
<223> OTHER INFORMATION: Synthetic sequence

<400> SEQUENCE: 904
aagcataact atgagtgttt a                                              21

<210> SEQ ID NO 905
<211> LENGTH: 21
<212> TYPE: DNA
<213> ORGANISM: Artificial Sequence
<220> FEATURE:
<223> OTHER INFORMATION: Synthetic sequence

<400> SEQUENCE: 905
taccaacagt tatctcatgt a                                              21

<210> SEQ ID NO 906
<211> LENGTH: 21
<212> TYPE: DNA
<213> ORGANISM: Artificial Sequence
<220> FEATURE:
<223> OTHER INFORMATION: Synthetic sequence

<400> SEQUENCE: 906
gcggagatgc acaacatctt a                                              21

<210> SEQ ID NO 907
<211> LENGTH: 21
<212> TYPE: DNA
<213> ORGANISM: Artificial Sequence
<220> FEATURE:
<223> OTHER INFORMATION: Synthetic sequence

<400> SEQUENCE: 907
atgcgtttgg cagttgcatt a                                              21

<210> SEQ ID NO 908
<211> LENGTH: 21
<212> TYPE: DNA
<213> ORGANISM: Artificial Sequence
<220> FEATURE:
<223> OTHER INFORMATION: Synthetic sequence

<400> SEQUENCE: 908
taccactagt ctgacggata a                                              21
```

<210> SEQ ID NO 909
<211> LENGTH: 21
<212> TYPE: DNA
<213> ORGANISM: Artificial Sequence
<220> FEATURE:
<223> OTHER INFORMATION: Synthetic sequence

<400> SEQUENCE: 909
cagaaggaga atccagcacg a                                           21

<210> SEQ ID NO 910
<211> LENGTH: 21
<212> TYPE: DNA
<213> ORGANISM: Artificial Sequence
<220> FEATURE:
<223> OTHER INFORMATION: Synthetic sequence

<400> SEQUENCE: 910
tccgacctct ttatttctat a                                           21

<210> SEQ ID NO 911
<211> LENGTH: 21
<212> TYPE: DNA
<213> ORGANISM: Artificial Sequence
<220> FEATURE:
<223> OTHER INFORMATION: Synthetic sequence

<400> SEQUENCE: 911
agcccgttgt gcagagttca a                                           21

<210> SEQ ID NO 912
<211> LENGTH: 21
<212> TYPE: DNA
<213> ORGANISM: Artificial Sequence
<220> FEATURE:
<223> OTHER INFORMATION: Synthetic sequence

<400> SEQUENCE: 912
cagagtgcat tgtgagggtt a                                           21

<210> SEQ ID NO 913
<211> LENGTH: 21
<212> TYPE: DNA
<213> ORGANISM: Artificial Sequence
<220> FEATURE:
<223> OTHER INFORMATION: Synthetic sequence

<400> SEQUENCE: 913
cacactccag tttgtaataa a                                           21

<210> SEQ ID NO 914
<211> LENGTH: 21
<212> TYPE: DNA
<213> ORGANISM: Artificial Sequence
<220> FEATURE:
<223> OTHER INFORMATION: Synthetic sequence

<400> SEQUENCE: 914
ccagcctaca ttcacttcta a                                           21

<210> SEQ ID NO 915
<211> LENGTH: 21
<212> TYPE: DNA
<213> ORGANISM: Artificial Sequence
<220> FEATURE:

<223> OTHER INFORMATION: Synthetic sequence

<400> SEQUENCE: 915
accaagaatg atcctttcaa a                                              21

<210> SEQ ID NO 916
<211> LENGTH: 21
<212> TYPE: DNA
<213> ORGANISM: Artificial Sequence
<220> FEATURE:
<223> OTHER INFORMATION: Synthetic sequence

<400> SEQUENCE: 916
ccgagcggcc actctgagta a                                              21

<210> SEQ ID NO 917
<211> LENGTH: 21
<212> TYPE: DNA
<213> ORGANISM: Artificial Sequence
<220> FEATURE:
<223> OTHER INFORMATION: Synthetic sequence

<400> SEQUENCE: 917
taaagtcagt ttaggtaata a                                              21

<210> SEQ ID NO 918
<211> LENGTH: 21
<212> TYPE: DNA
<213> ORGANISM: Artificial Sequence
<220> FEATURE:
<223> OTHER INFORMATION: Synthetic sequence

<400> SEQUENCE: 918
acggaaattt gaacagttga a                                              21

<210> SEQ ID NO 919
<211> LENGTH: 21
<212> TYPE: DNA
<213> ORGANISM: Artificial Sequence
<220> FEATURE:
<223> OTHER INFORMATION: Synthetic sequence

<400> SEQUENCE: 919
cacgttgatt caccattgtg a                                              21

<210> SEQ ID NO 920
<211> LENGTH: 21
<212> TYPE: DNA
<213> ORGANISM: Artificial Sequence
<220> FEATURE:
<223> OTHER INFORMATION: Synthetic sequence

<400> SEQUENCE: 920
aagaagagta ttaaatatat a                                              21

<210> SEQ ID NO 921
<211> LENGTH: 21
<212> TYPE: DNA
<213> ORGANISM: Artificial Sequence
<220> FEATURE:
<223> OTHER INFORMATION: Synthetic sequence

<400> SEQUENCE: 921
aaggatccat atcccgagga a                                              21

<210> SEQ ID NO 922
<211> LENGTH: 21
<212> TYPE: DNA
<213> ORGANISM: Artificial Sequence
<220> FEATURE:
<223> OTHER INFORMATION: Synthetic sequence

<400> SEQUENCE: 922
ttgcatattt ccttcattct a                                              21

<210> SEQ ID NO 923
<211> LENGTH: 21
<212> TYPE: DNA
<213> ORGANISM: Artificial Sequence
<220> FEATURE:
<223> OTHER INFORMATION: Synthetic sequence

<400> SEQUENCE: 923
atgctcagtc atacacgcga a                                              21

<210> SEQ ID NO 924
<211> LENGTH: 21
<212> TYPE: DNA
<213> ORGANISM: Artificial Sequence
<220> FEATURE:
<223> OTHER INFORMATION: Synthetic sequence

<400> SEQUENCE: 924
cagcaatatg ttcactatgt t                                              21

<210> SEQ ID NO 925
<211> LENGTH: 21
<212> TYPE: DNA
<213> ORGANISM: Artificial Sequence
<220> FEATURE:
<223> OTHER INFORMATION: Synthetic sequence

<400> SEQUENCE: 925
tccaacctat actaacctga a                                              21

<210> SEQ ID NO 926
<211> LENGTH: 21
<212> TYPE: DNA
<213> ORGANISM: Artificial Sequence
<220> FEATURE:
<223> OTHER INFORMATION: Synthetic sequence

<400> SEQUENCE: 926
gacactaata cagatgatta a                                              21

<210> SEQ ID NO 927
<211> LENGTH: 21
<212> TYPE: DNA
<213> ORGANISM: Artificial Sequence
<220> FEATURE:
<223> OTHER INFORMATION: Synthetic sequence

<400> SEQUENCE: 927
cacacccagt gatccatcca a                                              21

<210> SEQ ID NO 928
<211> LENGTH: 21
<212> TYPE: DNA
<213> ORGANISM: Artificial Sequence
<220> FEATURE:
<223> OTHER INFORMATION: Synthetic sequence

<400> SEQUENCE: 928
ccgagactta tctaaaccag a                                      21

<210> SEQ ID NO 929
<211> LENGTH: 21
<212> TYPE: DNA
<213> ORGANISM: Artificial Sequence
<220> FEATURE:
<223> OTHER INFORMATION: Synthetic sequence

<400> SEQUENCE: 929
cagatacgac agggtatcca a                                      21

<210> SEQ ID NO 930
<211> LENGTH: 21
<212> TYPE: DNA
<213> ORGANISM: Artificial Sequence
<220> FEATURE:
<223> OTHER INFORMATION: Synthetic sequence

<400> SEQUENCE: 930
ttgcctgttt gtcgactata a                                      21

<210> SEQ ID NO 931
<211> LENGTH: 21
<212> TYPE: DNA
<213> ORGANISM: Artificial Sequence
<220> FEATURE:
<223> OTHER INFORMATION: Synthetic sequence

<400> SEQUENCE: 931
cccgggcagc cgggatttaa a                                      21

<210> SEQ ID NO 932
<211> LENGTH: 21
<212> TYPE: DNA
<213> ORGANISM: Artificial Sequence
<220> FEATURE:
<223> OTHER INFORMATION: Synthetic sequence

<400> SEQUENCE: 932
gagggtgaag atagtaatga a                                      21

<210> SEQ ID NO 933
<211> LENGTH: 21
<212> TYPE: DNA
<213> ORGANISM: Artificial Sequence
<220> FEATURE:
<223> OTHER INFORMATION: Synthetic sequence

<400> SEQUENCE: 933
gtcgaggtca agcacattaa a                                      21

<210> SEQ ID NO 934
<211> LENGTH: 21
<212> TYPE: DNA
<213> ORGANISM: Artificial Sequence
<220> FEATURE:
<223> OTHER INFORMATION: Synthetic sequence

<400> SEQUENCE: 934
aagcatctaa gagagaggtt a                                      21

<210> SEQ ID NO 935
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 935
cacgagcagc agattaagga t                                              21

<210> SEQ ID NO 936
<211> LENGTH: 21
<212> TYPE: DNA
<213> ORGANISM: Artificial Sequence
<220> FEATURE:
<223> OTHER INFORMATION: Synthetic sequence

<400> SEQUENCE: 936
aagcggatca ttggtgggaa a                                              21

<210> SEQ ID NO 937
<211> LENGTH: 21
<212> TYPE: DNA
<213> ORGANISM: Artificial Sequence
<220> FEATURE:
<223> OTHER INFORMATION: Synthetic sequence

<400> SEQUENCE: 937
tcgctataga ataatgcatt a                                              21

<210> SEQ ID NO 938
<211> LENGTH: 21
<212> TYPE: DNA
<213> ORGANISM: Artificial Sequence
<220> FEATURE:
<223> OTHER INFORMATION: Synthetic sequence

<400> SEQUENCE: 938
ttcgagaggt gtatcaatat a                                              21

<210> SEQ ID NO 939
<211> LENGTH: 21
<212> TYPE: DNA
<213> ORGANISM: Artificial Sequence
<220> FEATURE:
<223> OTHER INFORMATION: Synthetic sequence

<400> SEQUENCE: 939
cacatgcatg tgactcctca a                                              21

<210> SEQ ID NO 940
<211> LENGTH: 21
<212> TYPE: DNA
<213> ORGANISM: Artificial Sequence
<220> FEATURE:
<223> OTHER INFORMATION: Synthetic sequence

<400> SEQUENCE: 940
aagccagtca ttcgagatga a                                              21

<210> SEQ ID NO 941
<211> LENGTH: 21
<212> TYPE: DNA
<213> ORGANISM: Artificial Sequence
<220> FEATURE:
<223> OTHER INFORMATION: Synthetic sequence

<400> SEQUENCE: 941
```
tgggaaagct ttggactact a                                              21

<210> SEQ ID NO 942
<211> LENGTH: 21
<212> TYPE: DNA
<213> ORGANISM: Artificial Sequence
<220> FEATURE:
<223> OTHER INFORMATION: Synthetic sequence

<400> SEQUENCE: 942
aagttgatgt ggatggtaca t                                              21

<210> SEQ ID NO 943
<211> LENGTH: 21
<212> TYPE: DNA
<213> ORGANISM: Artificial Sequence
<220> FEATURE:
<223> OTHER INFORMATION: Synthetic sequence

<400> SEQUENCE: 943
ttggcgatgt acatcaatga a                                              21

<210> SEQ ID NO 944
<211> LENGTH: 21
<212> TYPE: DNA
<213> ORGANISM: Artificial Sequence
<220> FEATURE:
<223> OTHER INFORMATION: Synthetic sequence

<400> SEQUENCE: 944
caggtttatg ttacttctat t                                              21

<210> SEQ ID NO 945
<211> LENGTH: 21
<212> TYPE: DNA
<213> ORGANISM: Artificial Sequence
<220> FEATURE:
<223> OTHER INFORMATION: Synthetic sequence

<400> SEQUENCE: 945
cagcctcttg atgtcaatcc a                                              21

<210> SEQ ID NO 946
<211> LENGTH: 21
<212> TYPE: DNA
<213> ORGANISM: Artificial Sequence
<220> FEATURE:
<223> OTHER INFORMATION: Synthetic sequence

<400> SEQUENCE: 946
cagggctgta gtattcagta a                                              21

<210> SEQ ID NO 947
<211> LENGTH: 21
<212> TYPE: DNA
<213> ORGANISM: Artificial Sequence
<220> FEATURE:
<223> OTHER INFORMATION: Synthetic sequence

<400> SEQUENCE: 947
caggttgaac atggaaataa a                                              21

<210> SEQ ID NO 948
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 948
tcctatggtt gtggtccgaa a                                              21

<210> SEQ ID NO 949
<211> LENGTH: 21
<212> TYPE: DNA
<213> ORGANISM: Artificial Sequence
<220> FEATURE:
<223> OTHER INFORMATION: Synthetic sequence

<400> SEQUENCE: 949
cagaagagcc tattacatct a                                              21

<210> SEQ ID NO 950
<211> LENGTH: 21
<212> TYPE: DNA
<213> ORGANISM: Artificial Sequence
<220> FEATURE:
<223> OTHER INFORMATION: Synthetic sequence

<400> SEQUENCE: 950
aggcaccgag ttcatgcaag a                                              21

<210> SEQ ID NO 951
<211> LENGTH: 21
<212> TYPE: DNA
<213> ORGANISM: Artificial Sequence
<220> FEATURE:
<223> OTHER INFORMATION: Synthetic sequence

<400> SEQUENCE: 951
ctggttaata gtgatagttg a                                              21

<210> SEQ ID NO 952
<211> LENGTH: 21
<212> TYPE: DNA
<213> ORGANISM: Artificial Sequence
<220> FEATURE:
<223> OTHER INFORMATION: Synthetic sequence

<400> SEQUENCE: 952
tgggctgctt tgtatgttct a                                              21

<210> SEQ ID NO 953
<211> LENGTH: 21
<212> TYPE: DNA
<213> ORGANISM: Artificial Sequence
<220> FEATURE:
<223> OTHER INFORMATION: Synthetic sequence

<400> SEQUENCE: 953
cacggcttat gcaagcaaag a                                              21

<210> SEQ ID NO 954
<211> LENGTH: 21
<212> TYPE: DNA
<213> ORGANISM: Artificial Sequence
<220> FEATURE:
<223> OTHER INFORMATION: Synthetic sequence

<400> SEQUENCE: 954
ccgcaacgtc ctgctggtta a                                              21
```

```
<210> SEQ ID NO 955
<211> LENGTH: 21
<212> TYPE: DNA
<213> ORGANISM: Artificial Sequence
<220> FEATURE:
<223> OTHER INFORMATION: Synthetic sequence

<400> SEQUENCE: 955
tacactctat tcaaacagca a                                              21

<210> SEQ ID NO 956
<211> LENGTH: 21
<212> TYPE: DNA
<213> ORGANISM: Artificial Sequence
<220> FEATURE:
<223> OTHER INFORMATION: Synthetic sequence

<400> SEQUENCE: 956
ctcctctagt tcagagacat a                                              21

<210> SEQ ID NO 957
<211> LENGTH: 21
<212> TYPE: DNA
<213> ORGANISM: Artificial Sequence
<220> FEATURE:
<223> OTHER INFORMATION: Synthetic sequence

<400> SEQUENCE: 957
aggcgacgga ttggtttaga a                                              21

<210> SEQ ID NO 958
<211> LENGTH: 21
<212> TYPE: DNA
<213> ORGANISM: Artificial Sequence
<220> FEATURE:
<223> OTHER INFORMATION: Synthetic sequence

<400> SEQUENCE: 958
cagcttgtga tgcaagtgtg a                                              21

<210> SEQ ID NO 959
<211> LENGTH: 21
<212> TYPE: DNA
<213> ORGANISM: Artificial Sequence
<220> FEATURE:
<223> OTHER INFORMATION: Synthetic sequence

<400> SEQUENCE: 959
ttgggctgct tggctatgca a                                              21

<210> SEQ ID NO 960
<211> LENGTH: 21
<212> TYPE: DNA
<213> ORGANISM: Artificial Sequence
<220> FEATURE:
<223> OTHER INFORMATION: Synthetic sequence

<400> SEQUENCE: 960
cgccatcatc gatgactaca a                                              21

<210> SEQ ID NO 961
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 961
cagatgtttc atcatttgaa a                                              21

<210> SEQ ID NO 962
<211> LENGTH: 21
<212> TYPE: DNA
<213> ORGANISM: Artificial Sequence
<220> FEATURE:
<223> OTHER INFORMATION: Synthetic sequence

<400> SEQUENCE: 962
aagcagtttg aacgactgga a                                              21

<210> SEQ ID NO 963
<211> LENGTH: 21
<212> TYPE: DNA
<213> ORGANISM: Artificial Sequence
<220> FEATURE:
<223> OTHER INFORMATION: Synthetic sequence

<400> SEQUENCE: 963
cccgttgatt atgcaaggca a                                              21

<210> SEQ ID NO 964
<211> LENGTH: 21
<212> TYPE: DNA
<213> ORGANISM: Artificial Sequence
<220> FEATURE:
<223> OTHER INFORMATION: Synthetic sequence

<400> SEQUENCE: 964
taggatactg ggcgttacca a                                              21

<210> SEQ ID NO 965
<211> LENGTH: 21
<212> TYPE: DNA
<213> ORGANISM: Artificial Sequence
<220> FEATURE:
<223> OTHER INFORMATION: Synthetic sequence

<400> SEQUENCE: 965
cggcagtcag atcctgcata a                                              21

<210> SEQ ID NO 966
<211> LENGTH: 21
<212> TYPE: DNA
<213> ORGANISM: Artificial Sequence
<220> FEATURE:
<223> OTHER INFORMATION: Synthetic sequence

<400> SEQUENCE: 966
cagcactgca ctgttagctg a                                              21

<210> SEQ ID NO 967
<211> LENGTH: 21
<212> TYPE: DNA
<213> ORGANISM: Artificial Sequence
<220> FEATURE:
<223> OTHER INFORMATION: Synthetic sequence

<400> SEQUENCE: 967
cgggactttc tattaatatc a                                              21

<210> SEQ ID NO 968
```

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 968
tcgggagaaa gtggagtccg a                                              21

<210> SEQ ID NO 969
<211> LENGTH: 21
<212> TYPE: DNA
<213> ORGANISM: Artificial Sequence
<220> FEATURE:
<223> OTHER INFORMATION: Synthetic sequence

<400> SEQUENCE: 969
tagcgaagac caagggataa a                                              21

<210> SEQ ID NO 970
<211> LENGTH: 21
<212> TYPE: DNA
<213> ORGANISM: Artificial Sequence
<220> FEATURE:
<223> OTHER INFORMATION: Synthetic sequence

<400> SEQUENCE: 970
taggattaaa ttggtttcct a                                              21

<210> SEQ ID NO 971
<211> LENGTH: 21
<212> TYPE: DNA
<213> ORGANISM: Artificial Sequence
<220> FEATURE:
<223> OTHER INFORMATION: Synthetic sequence

<400> SEQUENCE: 971
tcccagtgtc ctttgaatcg a                                              21

<210> SEQ ID NO 972
<211> LENGTH: 21
<212> TYPE: DNA
<213> ORGANISM: Artificial Sequence
<220> FEATURE:
<223> OTHER INFORMATION: Synthetic sequence

<400> SEQUENCE: 972
cgccgtcgag tcgccatgga a                                              21

<210> SEQ ID NO 973
<211> LENGTH: 21
<212> TYPE: DNA
<213> ORGANISM: Artificial Sequence
<220> FEATURE:
<223> OTHER INFORMATION: Synthetic sequence

<400> SEQUENCE: 973
cacttggcta cccatcaaca a                                              21

<210> SEQ ID NO 974
<211> LENGTH: 21
<212> TYPE: DNA
<213> ORGANISM: Artificial Sequence
<220> FEATURE:
<223> OTHER INFORMATION: Synthetic sequence

<400> SEQUENCE: 974
```
gccgtgattt ctagcagttg a    21

<210> SEQ ID NO 975
<211> LENGTH: 21
<212> TYPE: DNA
<213> ORGANISM: Artificial Sequence
<220> FEATURE:
<223> OTHER INFORMATION: Synthetic sequence

<400> SEQUENCE: 975
cagggactga acaaatggaa a    21

<210> SEQ ID NO 976
<211> LENGTH: 21
<212> TYPE: DNA
<213> ORGANISM: Artificial Sequence
<220> FEATURE:
<223> OTHER INFORMATION: Synthetic sequence

<400> SEQUENCE: 976
cagcttaact gacagacgtt a    21

<210> SEQ ID NO 977
<211> LENGTH: 21
<212> TYPE: DNA
<213> ORGANISM: Artificial Sequence
<220> FEATURE:
<223> OTHER INFORMATION: Synthetic sequence

<400> SEQUENCE: 977
aagagccaat ttaacaaact a    21

<210> SEQ ID NO 978
<211> LENGTH: 21
<212> TYPE: DNA
<213> ORGANISM: Artificial Sequence
<220> FEATURE:
<223> OTHER INFORMATION: Synthetic sequence

<400> SEQUENCE: 978
ctggactaag gatcaccatt a    21

<210> SEQ ID NO 979
<211> LENGTH: 21
<212> TYPE: DNA
<213> ORGANISM: Artificial Sequence
<220> FEATURE:
<223> OTHER INFORMATION: Synthetic sequence

<400> SEQUENCE: 979
tacgtgggtg tactccatca a    21

<210> SEQ ID NO 980
<211> LENGTH: 21
<212> TYPE: DNA
<213> ORGANISM: Artificial Sequence
<220> FEATURE:
<223> OTHER INFORMATION: Synthetic sequence

<400> SEQUENCE: 980
cagagatgat ccggtcatat a    21

<210> SEQ ID NO 981
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 981
cacagttaat ggatctgtaa a                                              21

<210> SEQ ID NO 982
<211> LENGTH: 21
<212> TYPE: DNA
<213> ORGANISM: Artificial Sequence
<220> FEATURE:
<223> OTHER INFORMATION: Synthetic sequence

<400> SEQUENCE: 982
ccggagctgg aagtacaagt a                                              21

<210> SEQ ID NO 983
<211> LENGTH: 21
<212> TYPE: DNA
<213> ORGANISM: Artificial Sequence
<220> FEATURE:
<223> OTHER INFORMATION: Synthetic sequence

<400> SEQUENCE: 983
aaagtgcgtc atcctaagga a                                              21

<210> SEQ ID NO 984
<211> LENGTH: 21
<212> TYPE: DNA
<213> ORGANISM: Artificial Sequence
<220> FEATURE:
<223> OTHER INFORMATION: Synthetic sequence

<400> SEQUENCE: 984
atcgatgttg gttatgagag a                                              21

<210> SEQ ID NO 985
<211> LENGTH: 21
<212> TYPE: DNA
<213> ORGANISM: Artificial Sequence
<220> FEATURE:
<223> OTHER INFORMATION: Synthetic sequence

<400> SEQUENCE: 985
ctgaagggag aagctgagca a                                              21

<210> SEQ ID NO 986
<211> LENGTH: 21
<212> TYPE: DNA
<213> ORGANISM: Artificial Sequence
<220> FEATURE:
<223> OTHER INFORMATION: Synthetic sequence

<400> SEQUENCE: 986
cacatccaat gtcttcgcaa t                                              21

<210> SEQ ID NO 987
<211> LENGTH: 21
<212> TYPE: DNA
<213> ORGANISM: Artificial Sequence
<220> FEATURE:
<223> OTHER INFORMATION: Synthetic sequence

<400> SEQUENCE: 987
caggaaataa tttatccacc a                                              21
```

<210> SEQ ID NO 988
<211> LENGTH: 21
<212> TYPE: DNA
<213> ORGANISM: Artificial Sequence
<220> FEATURE:
<223> OTHER INFORMATION: Synthetic sequence

<400> SEQUENCE: 988
accgtcatga cgattattac a                                              21

<210> SEQ ID NO 989
<211> LENGTH: 21
<212> TYPE: DNA
<213> ORGANISM: Artificial Sequence
<220> FEATURE:
<223> OTHER INFORMATION: Synthetic sequence

<400> SEQUENCE: 989
aacagttagc acggcagctt a                                              21

<210> SEQ ID NO 990
<211> LENGTH: 21
<212> TYPE: DNA
<213> ORGANISM: Artificial Sequence
<220> FEATURE:
<223> OTHER INFORMATION: Synthetic sequence

<400> SEQUENCE: 990
tcccactaaa gcatagttgt a                                              21

<210> SEQ ID NO 991
<211> LENGTH: 21
<212> TYPE: DNA
<213> ORGANISM: Artificial Sequence
<220> FEATURE:
<223> OTHER INFORMATION: Synthetic sequence

<400> SEQUENCE: 991
cacctcggcg gcctttattt a                                              21

<210> SEQ ID NO 992
<211> LENGTH: 21
<212> TYPE: DNA
<213> ORGANISM: Artificial Sequence
<220> FEATURE:
<223> OTHER INFORMATION: Synthetic sequence

<400> SEQUENCE: 992
gcggacggtc gtgatggata a                                              21

<210> SEQ ID NO 993
<211> LENGTH: 21
<212> TYPE: DNA
<213> ORGANISM: Artificial Sequence
<220> FEATURE:
<223> OTHER INFORMATION: Synthetic sequence

<400> SEQUENCE: 993
accagaggtg ttagaagata a                                              21

<210> SEQ ID NO 994
<211> LENGTH: 21
<212> TYPE: DNA
<213> ORGANISM: Artificial Sequence
<220> FEATURE:

<223> OTHER INFORMATION: Synthetic sequence

<400> SEQUENCE: 994
ccagcctgtt atggctaact a                                    21

<210> SEQ ID NO 995
<211> LENGTH: 21
<212> TYPE: DNA
<213> ORGANISM: Artificial Sequence
<220> FEATURE:
<223> OTHER INFORMATION: Synthetic sequence

<400> SEQUENCE: 995
aagcatgaaa ggactcatga a                                    21

<210> SEQ ID NO 996
<211> LENGTH: 21
<212> TYPE: DNA
<213> ORGANISM: Artificial Sequence
<220> FEATURE:
<223> OTHER INFORMATION: Synthetic sequence

<400> SEQUENCE: 996
accagggatg agaccaacta t                                    21

<210> SEQ ID NO 997
<211> LENGTH: 21
<212> TYPE: DNA
<213> ORGANISM: Artificial Sequence
<220> FEATURE:
<223> OTHER INFORMATION: Synthetic sequence

<400> SEQUENCE: 997
tggcttcttc ccacggagtt a                                    21

<210> SEQ ID NO 998
<211> LENGTH: 21
<212> TYPE: DNA
<213> ORGANISM: Artificial Sequence
<220> FEATURE:
<223> OTHER INFORMATION: Synthetic sequence

<400> SEQUENCE: 998
ttcgttgact acgcccagaa a                                    21

<210> SEQ ID NO 999
<211> LENGTH: 21
<212> TYPE: DNA
<213> ORGANISM: Artificial Sequence
<220> FEATURE:
<223> OTHER INFORMATION: Synthetic sequence

<400> SEQUENCE: 999
aacctgaagt ttggagatga a                                    21

<210> SEQ ID NO 1000
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1000
tggcgtttcc acggtaccaa a                                    21

```
<210> SEQ ID NO 1001
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1001
ctcaactcgt ttataaataa a                                              21

<210> SEQ ID NO 1002
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1002
cctgatgaat ctactgctaa a                                              21

<210> SEQ ID NO 1003
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1003
ctagtgttgc ttatcaaata a                                              21

<210> SEQ ID NO 1004
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1004
tggatcgatt tgtataccga a                                              21

<210> SEQ ID NO 1005
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1005
caggtccatt cttctgcacg a                                              21

<210> SEQ ID NO 1006
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1006
aagagggagt tcattcagga a                                              21

<210> SEQ ID NO 1007
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 1007
acccaaggaa atgattataa a                                              21

<210> SEQ ID NO 1008
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1008
cagttctatt taactgaatt a                                              21

<210> SEQ ID NO 1009
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1009
cccgatcacg ccgcaagcga a                                              21

<210> SEQ ID NO 1010
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1010
tagcaagtct tgtacaacga a                                              21

<210> SEQ ID NO 1011
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1011
cagcctcaag tcagtgcagg a                                              21

<210> SEQ ID NO 1012
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1012
ccgcatcttg gtgaaacgtg a                                              21

<210> SEQ ID NO 1013
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1013
cacttcgaag cgaaatatta a                                              21

<210> SEQ ID NO 1014
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 1014
tacgtgcagg tgtctcgtga a                                             21

<210> SEQ ID NO 1015
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1015
tacgcgaacg cccacccatta a                                            21

<210> SEQ ID NO 1016
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1016
cacgactttc tcgaacacct a                                             21

<210> SEQ ID NO 1017
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1017
ccaggacgcc ttcctcttca a                                             21

<210> SEQ ID NO 1018
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1018
tacccgcacc accaccttta a                                             21

<210> SEQ ID NO 1019
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1019
ctgcacgttc ataaccaaca a                                             21

<210> SEQ ID NO 1020
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1020
```
ctcacctatg atgaggtcca a                                              21

<210> SEQ ID NO 1021
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1021
cagtgctagt ccagactaca a                                              21

<210> SEQ ID NO 1022
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1022
ctggatggag gactatgact a                                              21

<210> SEQ ID NO 1023
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1023
cagcgttgag agtcaagaca a                                              21

<210> SEQ ID NO 1024
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1024
ccggcgctat gagaagttcg a                                              21

<210> SEQ ID NO 1025
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1025
acgcaagtcg tggatgagta a                                              21

<210> SEQ ID NO 1026
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1026
acgagcgtca gccttactca a                                              21

<210> SEQ ID NO 1027
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 1027
ttgggcatat gtatctttat a                                      21

<210> SEQ ID NO 1028
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1028
ctgcatgaag gcagtgaccg a                                      21

<210> SEQ ID NO 1029
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1029
ccgactcggt gtactgcagt a                                      21

<210> SEQ ID NO 1030
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1030
cacgtgtagt tctttattat a                                      21

<210> SEQ ID NO 1031
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1031
ggcgttaaag ttcatatccc a                                      21

<210> SEQ ID NO 1032
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1032
agcaagaaag cccgtctgga a                                      21

<210> SEQ ID NO 1033
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1033
caccaattct gaagacaact a                                      21
```

<210> SEQ ID NO 1034
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1034
caggtgccac aggatggaga a    21

<210> SEQ ID NO 1035
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1035
cagcaggaag tccaattcaa a    21

<210> SEQ ID NO 1036
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1036
cccgccctag tgcgttactt a    21

<210> SEQ ID NO 1037
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1037
tgcaacatcc ttcgagttga a    21

<210> SEQ ID NO 1038
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1038
atgcaatcgg gtggtatcat a    21

<210> SEQ ID NO 1039
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1039
ctgactaaga gtcccaagaa a    21

<210> SEQ ID NO 1040
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1040
tcgagattac atggatgtta a                                              21

<210> SEQ ID NO 1041
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1041
ctggtaatta gttgatgcaa a                                              21

<210> SEQ ID NO 1042
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1042
ctgcaggagt tcctcagtga a                                              21

<210> SEQ ID NO 1043
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1043
cagtaacagt ttgcacatga a                                              21

<210> SEQ ID NO 1044
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1044
ccggctgaaa ttaagtgagg a                                              21

<210> SEQ ID NO 1045
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1045
cagggtagta tgagtaagga a                                              21

<210> SEQ ID NO 1046
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1046
cgccaaggat aaagacgact a                                              21

<210> SEQ ID NO 1047

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1047
ctggaccaaa gtggaaccaa a                                              21

<210> SEQ ID NO 1048
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1048
tagatgtagt gttgtaataa a                                              21

<210> SEQ ID NO 1049
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1049
tagtcctttc tgtgaagcta a                                              21

<210> SEQ ID NO 1050
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1050
gagaataaat atcaaatcta a                                              21

<210> SEQ ID NO 1051
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1051
tcgcctcacc atcaagaagt a                                              21

<210> SEQ ID NO 1052
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1052
ccggacctac aaatcggtct a                                              21

<210> SEQ ID NO 1053
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1053
```
cagcaggcac gttaactcga a                                              21

<210> SEQ ID NO 1054
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1054
accaagttcg gctctaccaa a                                              21

<210> SEQ ID NO 1055
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1055
ttggatagcc gtcagagatt a                                              21

<210> SEQ ID NO 1056
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1056
ttggcacacg ctagaagttt a                                              21

<210> SEQ ID NO 1057
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1057
ccgccgtggc gacatcattg a                                              21

<210> SEQ ID NO 1058
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1058
acgatccgtt ggtgcatgaa a                                              21

<210> SEQ ID NO 1059
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1059
taggaacttt cttgtcacaa a                                              21

<210> SEQ ID NO 1060
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 1060
ccggcctgtg aaacctccaa a                                      21

<210> SEQ ID NO 1061
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1061
ccgggtgtat cccatgtgca a                                      21

<210> SEQ ID NO 1062
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1062
taggcagttc tgtgagtcaa a                                      21

<210> SEQ ID NO 1063
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1063
gagggcgctg atcgagagtt a                                      21

<210> SEQ ID NO 1064
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1064
cagtaccaca ccgaaagtaa a                                      21

<210> SEQ ID NO 1065
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1065
aaccaacata gcatcattaa t                                      21

<210> SEQ ID NO 1066
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1066
tgggcaaggg attataatta a                                      21
```

<210> SEQ ID NO 1067
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1067
cccagagatg gtcatattta a                                    21

<210> SEQ ID NO 1068
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1068
aaggattcat tgagcagcat a                                    21

<210> SEQ ID NO 1069
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1069
cagaactgcc tttgcactaa a                                    21

<210> SEQ ID NO 1070
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1070
aagcgtcagt gtaaagttct t                                    21

<210> SEQ ID NO 1071
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1071
cagaaagaac tcacgactac a                                    21

<210> SEQ ID NO 1072
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1072
atgattcgtc gcagaagcct a                                    21

<210> SEQ ID NO 1073
<211> LENGTH: 21
<212> TYPE: DNA
<213> ORGANISM: Artificial Sequence
<220> FEATURE:

```
<223> OTHER INFORMATION: Synthetic sequence

<400> SEQUENCE: 1073
caccgtcaac gtggcatgga a                                              21

<210> SEQ ID NO 1074
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1074
cggaacgttc cctggaaatt a                                              21

<210> SEQ ID NO 1075
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1075
cccgagcgcg caggagctca a                                              21

<210> SEQ ID NO 1076
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1076
atggactgcg aagaactcct a                                              21

<210> SEQ ID NO 1077
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1077
aaccgttaca gccacaacca a                                              21

<210> SEQ ID NO 1078
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1078
ctgcgctact ttgacgagaa a                                              21

<210> SEQ ID NO 1079
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1079
taaccttata tttacaataa a                                              21
```

```
<210> SEQ ID NO 1080
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1080
atggccaaca ctcctcaaga a                                    21

<210> SEQ ID NO 1081
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1081
cacgtcggct gctgatgtct a                                    21

<210> SEQ ID NO 1082
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1082
cagactggat atggcgcaag a                                    21

<210> SEQ ID NO 1083
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1083
tagcttatat atgacggtat a                                    21

<210> SEQ ID NO 1084
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1084
cagctgctcc ttgatacccg a                                    21

<210> SEQ ID NO 1085
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1085
ccgggtcatc tgcagtgaca a                                    21

<210> SEQ ID NO 1086
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 1086
caagatgtta tcaattggtt a                                              21

<210> SEQ ID NO 1087
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1087
cagaattaca ctgaagaagt a                                              21

<210> SEQ ID NO 1088
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1088
ctcgaggttg aaaccacaga t                                              21

<210> SEQ ID NO 1089
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1089
aaggagctat ctgtttatgt a                                              21

<210> SEQ ID NO 1090
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1090
ctgacaaagt acgaggttta a                                              21

<210> SEQ ID NO 1091
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1091
ttcggatcgg tttgtaatta a                                              21

<210> SEQ ID NO 1092
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1092
aaggatgagt gcgtcatagc a                                              21

<210> SEQ ID NO 1093
<211> LENGTH: 21

```
<212> TYPE: DNA
<213> ORGANISM: Artificial Sequence
<220> FEATURE:
<223> OTHER INFORMATION: Synthetic sequence

<400> SEQUENCE: 1093
caccttggat tctttgttaa a                                              21

<210> SEQ ID NO 1094
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1094
acactcgcag ttaatatcat a                                              21

<210> SEQ ID NO 1095
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1095
ctgctagcgt atattcataa a                                              21

<210> SEQ ID NO 1096
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1096
taggtatagc tgacgagact a                                              21

<210> SEQ ID NO 1097
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1097
tacctcggat ccattcacga a                                              21

<210> SEQ ID NO 1098
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1098
ccaaggaatc tgtgcgggta a                                              21

<210> SEQ ID NO 1099
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1099
```
caagatatcc atggtgaata a                                              21

<210> SEQ ID NO 1100
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1100
cacgaacagc gtcatctgca a                                              21

<210> SEQ ID NO 1101
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1101
cacgagcatc actctgacca t                                              21

<210> SEQ ID NO 1102
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1102
gccgctgagg atgtcccgaa a                                              21

<210> SEQ ID NO 1103
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1103
ccaggtttcc tcagtcatag a                                              21

<210> SEQ ID NO 1104
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1104
cagagtatga accaagggtt a                                              21

<210> SEQ ID NO 1105
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1105
aaggaaacaa ctcgtactga a                                              21

<210> SEQ ID NO 1106
<211> LENGTH: 21
<212> TYPE: DNA
<213> ORGANISM: Artificial Sequence

```
<220> FEATURE:
<223> OTHER INFORMATION: Synthetic sequence

<400> SEQUENCE: 1106
aagtgtatat gaagttattt a                                              21

<210> SEQ ID NO 1107
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1107
ccgcggactt aaagcaataa a                                              21

<210> SEQ ID NO 1108
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1108
ctacagctcg ttgacaagaa a                                              21

<210> SEQ ID NO 1109
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1109
aacatcctag accctgacga a                                              21

<210> SEQ ID NO 1110
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1110
aggcttcatc atcgacccaa a                                              21

<210> SEQ ID NO 1111
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1111
cgggagaaga agcgtctaga a                                              21

<210> SEQ ID NO 1112
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1112
ccctcggagc acgaatatat a                                              21
```

<210> SEQ ID NO 1113
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1113
cgcggtcgga tagttacact a                                              21

<210> SEQ ID NO 1114
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1114
gagggtggat ttatcttctc a                                              21

<210> SEQ ID NO 1115
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1115
aagggaaaca tcagtaagaa a                                              21

<210> SEQ ID NO 1116
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1116
ctggaccagg attcaactac a                                              21

<210> SEQ ID NO 1117
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1117
tagccgagtt gtgcagcgta a                                              21

<210> SEQ ID NO 1118
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1118
aaccctgatg tctgccaact a                                              21

<210> SEQ ID NO 1119
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1119
cggcgttgat atcggtggta a                                             21

<210> SEQ ID NO 1120
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1120
tgccgccgac aaatacaaat a                                             21

<210> SEQ ID NO 1121
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1121
aagaaataaa ttcaccaaca a                                             21

<210> SEQ ID NO 1122
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1122
ctggtagata gaagagctaa a                                             21

<210> SEQ ID NO 1123
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1123
cgggtcgatc ttccacattc a                                             21

<210> SEQ ID NO 1124
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1124
ctccaaacag atcatagcga a                                             21

<210> SEQ ID NO 1125
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1125
tcaaccgtac atcaaattat a                                             21

<210> SEQ ID NO 1126

-continued

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1126
tacgtgggct atactgtatt a                                              21

<210> SEQ ID NO 1127
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1127
aaagagatac ctcatatcgt a                                              21

<210> SEQ ID NO 1128
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1128
aagaaatcaa gaaacaatta a                                              21

<210> SEQ ID NO 1129
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1129
tcccaattag tctgtatcta t                                              21

<210> SEQ ID NO 1130
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1130
ctgtaaatgt ctattgccgt a                                              21

<210> SEQ ID NO 1131
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1131
ttaaagcatt cctttcttta a                                              21

<210> SEQ ID NO 1132
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1132
```
ccggaagacg ccggagtcat t                                              21

<210> SEQ ID NO 1133
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1133
aaagtcatat agaaatatta a                                              21

<210> SEQ ID NO 1134
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1134
aaccaattag ttactatcgt a                                              21

<210> SEQ ID NO 1135
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1135
ctgcttgtat gaaactgtga a                                              21

<210> SEQ ID NO 1136
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1136
aaggcctatc agccaattaa a                                              21

<210> SEQ ID NO 1137
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1137
tagactagag gcaagcattt a                                              21

<210> SEQ ID NO 1138
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1138
tggcggtgtt ccagaagcag a                                              21

<210> SEQ ID NO 1139
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 1139
tcgcatcatc gcagagctag a                                              21

<210> SEQ ID NO 1140
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1140
aaacatgatt cctttaataa a                                              21

<210> SEQ ID NO 1141
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1141
aagggacagt atacgcacaa a                                              21

<210> SEQ ID NO 1142
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1142
ctggtacata aagatgagta a                                              21

<210> SEQ ID NO 1143
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1143
ctctgagatc tcaatgcgaa a                                              21

<210> SEQ ID NO 1144
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1144
cacgtgcaag ccagatgtga a                                              21

<210> SEQ ID NO 1145
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1145
ttcgggctgt catgaacaga a                                              21
```

<210> SEQ ID NO 1146
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1146
cccgaagagc caaatataat a                                            21

<210> SEQ ID NO 1147
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1147
cacgaaagag atgatgataa t                                            21

<210> SEQ ID NO 1148
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1148
ctccgctatc cgagaggtgt a                                            21

<210> SEQ ID NO 1149
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1149
tagcacctta gggcagcata a                                            21

<210> SEQ ID NO 1150
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1150
ccaggaaata ctggaagtca a                                            21

<210> SEQ ID NO 1151
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1151
acggaaccat ttcgccttta a                                            21

<210> SEQ ID NO 1152
<211> LENGTH: 21
<212> TYPE: DNA
<213> ORGANISM: Artificial Sequence
<220> FEATURE:

<223> OTHER INFORMATION: Synthetic sequence

<400> SEQUENCE: 1152
ccgcgtgtgc ctcaagcact a                                              21

<210> SEQ ID NO 1153
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1153
caccttcaag tcaattcata a                                              21

<210> SEQ ID NO 1154
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1154
cggatttgct tgttccagta a                                              21

<210> SEQ ID NO 1155
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1155
cctgtaagat ctatcgttca a                                              21

<210> SEQ ID NO 1156
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1156
cagcttaaga aaggtacaga a                                              21

<210> SEQ ID NO 1157
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1157
caccgcctaa atttcacgac a                                              21

<210> SEQ ID NO 1158
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1158
caggctaagg gtggccagag a                                              21

```
<210> SEQ ID NO 1159
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1159
ttgcataata cttgtcttaa a                                              21

<210> SEQ ID NO 1160
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1160
ctgaatgtac tgatttagaa a                                              21

<210> SEQ ID NO 1161
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1161
ctagttaagg tttaaatgct a                                              21

<210> SEQ ID NO 1162
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1162
cagccttgac ttatccgaat t                                              21

<210> SEQ ID NO 1163
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1163
atcgtcgagg tgaagagcaa a                                              21

<210> SEQ ID NO 1164
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1164
cagaagtttc atcttaggat a                                              21

<210> SEQ ID NO 1165
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 1165
cagcaagagt cctaacatct a                                              21

<210> SEQ ID NO 1166
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1166
caggactaaa tggaagcgac a                                              21

<210> SEQ ID NO 1167
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1167
caggccgaaa cttcccaaca a                                              21

<210> SEQ ID NO 1168
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1168
ccagcggttg tcctccctta a                                              21

<210> SEQ ID NO 1169
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1169
cacattcagc ttataatgga a                                              21

<210> SEQ ID NO 1170
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1170
aagcaggaaa ccagcaacaa a                                              21

<210> SEQ ID NO 1171
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1171
ctctgtcatt cgtgaactta a                                              21

<210> SEQ ID NO 1172
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 1172
cacgagagcc ttctaatgcc a                                              21

<210> SEQ ID NO 1173
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1173
agggattgga accctgatct a                                              21

<210> SEQ ID NO 1174
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1174
ccgcaaggtc tcggtgcagt a                                              21

<210> SEQ ID NO 1175
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1175
atggatctat acaacaaata a                                              21

<210> SEQ ID NO 1176
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1176
ctgatactat ctcaaagacg a                                              21

<210> SEQ ID NO 1177
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1177
cagcaagaag atgaaccttc a                                              21

<210> SEQ ID NO 1178
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1178
```
aagatgcaag aaggagtgaa a                                        21

<210> SEQ ID NO 1179
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1179
ttggtgcagt taagaattaa a                                        21

<210> SEQ ID NO 1180
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1180
atgggtagcc tcaccatgaa a                                        21

<210> SEQ ID NO 1181
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1181
cgggatgtgg atgatagcaa a                                        21

<210> SEQ ID NO 1182
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1182
caggtggatg tagagatcaa a                                        21

<210> SEQ ID NO 1183
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1183
tgcagtgacg ctgtcattaa a                                        21

<210> SEQ ID NO 1184
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1184
cagcaaacac ctttaaggca a                                        21

<210> SEQ ID NO 1185
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1185
tggcatattg accctatata a                                              21

<210> SEQ ID NO 1186
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1186
tacgagaatc agtctaacag a                                              21

<210> SEQ ID NO 1187
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1187
aagcactaga atatccagct a                                              21

<210> SEQ ID NO 1188
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1188
cacaagaatg gaacaaatct a                                              21

<210> SEQ ID NO 1189
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1189
tccattgaca acaaggcttt a                                              21

<210> SEQ ID NO 1190
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1190
attgccgtaa attgttaata a                                              21

<210> SEQ ID NO 1191
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1191
atgccaggtc tagcaaacat a                                              21

```
<210> SEQ ID NO 1192
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1192
cccgacgagt tctctgactt t                                              21

<210> SEQ ID NO 1193
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1193
aagcacatag ttattgctga a                                              21

<210> SEQ ID NO 1194
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1194
tagactgtat taataaacat a                                              21

<210> SEQ ID NO 1195
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1195
aacagagagc cttaatcttt a                                              21

<210> SEQ ID NO 1196
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1196
caggtttaat ttgatggtct a                                              21

<210> SEQ ID NO 1197
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1197
cggattccta tttatgccct a                                              21

<210> SEQ ID NO 1198
<211> LENGTH: 21
<212> TYPE: DNA
<213> ORGANISM: Artificial Sequence
<220> FEATURE:
<223> OTHER INFORMATION: Synthetic sequence
```

<400> SEQUENCE: 1198
caggaagtgg gtatcaaatt g                                              21

<210> SEQ ID NO 1199
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1199
caggccacta aaccatctaa a                                              21

<210> SEQ ID NO 1200
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1200
cagcaactca tttatatata t                                              21

<210> SEQ ID NO 1201
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1201
cccaaagatc atgatattcc a                                              21

<210> SEQ ID NO 1202
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1202
gagcaagaac ctggtgcgca a                                              21

<210> SEQ ID NO 1203
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1203
taggacatgc tccaaagaag a                                              21

<210> SEQ ID NO 1204
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1204
ccgcaccaag ctgcagaaca a                                              21

<210> SEQ ID NO 1205

```
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1205
gagatggtct atcctaacca a                                              21

<210> SEQ ID NO 1206
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1206
ttcaacaaag ctacagagtt a                                              21

<210> SEQ ID NO 1207
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1207
cacgatggga ggacaagttc a                                              21

<210> SEQ ID NO 1208
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1208
ctggatgaca gttgggtgat a                                              21

<210> SEQ ID NO 1209
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1209
cagggccaat caatttcacc a                                              21

<210> SEQ ID NO 1210
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1210
tccacacatc ataaagcttt a                                              21

<210> SEQ ID NO 1211
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1211
```
caggctgaat ggcgaaggca t                                              21

<210> SEQ ID NO 1212
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1212
ttcaacaaag ctacagagtt a                                              21

<210> SEQ ID NO 1213
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1213
ccaagtctga gtggttggat a                                              21

<210> SEQ ID NO 1214
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1214
caggatactg tttccttact a                                              21

<210> SEQ ID NO 1215
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1215
aacgctcttc aagctcacaa a                                              21

<210> SEQ ID NO 1216
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1216
ctggatgcga taagacatcg a                                              21

<210> SEQ ID NO 1217
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1217
caaggagaaa ctatacagga a                                              21

<210> SEQ ID NO 1218
<211> LENGTH: 21
<212> TYPE: DNA

```
<213> ORGANISM: Artificial Sequence
<220> FEATURE:
<223> OTHER INFORMATION: Synthetic sequence

<400> SEQUENCE: 1218
ctccctgttc ggagattgat a                                              21

<210> SEQ ID NO 1219
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1219
tggagtgttc tgcacttaca a                                              21

<210> SEQ ID NO 1220
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1220
cccggccttc aacgagttct a                                              21

<210> SEQ ID NO 1221
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1221
aactaccgag attatttgat a                                              21

<210> SEQ ID NO 1222
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1222
tagttaaatt agaatggtgt a                                              21

<210> SEQ ID NO 1223
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1223
aaagttgtag ctaaatattt a                                              21

<210> SEQ ID NO 1224
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1224
atgaagctcc aggaacttta a                                              21
```

-continued

<210> SEQ ID NO 1225
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1225
ctagagtatg cagctggtaa a                                        21

<210> SEQ ID NO 1226
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1226
cccggcaggg ttgtttctta a                                        21

<210> SEQ ID NO 1227
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1227
ttcgctctga aatggaacaa a                                        21

<210> SEQ ID NO 1228
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1228
ctgcatggac tgtatactcg a                                        21

<210> SEQ ID NO 1229
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1229
ttggattact attaagtggt t                                        21

<210> SEQ ID NO 1230
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1230
ccgcctgttg ttaccggtat t                                        21

<210> SEQ ID NO 1231
<211> LENGTH: 21
<212> TYPE: DNA
<213> ORGANISM: Artificial Sequence
<220> FEATURE:

<223> OTHER INFORMATION: Synthetic sequence

<400> SEQUENCE: 1231
ccaagtctga gtggttggat a                                              21

<210> SEQ ID NO 1232
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1232
cagagtatga accaagggtt a                                              21

<210> SEQ ID NO 1233
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1233
ccaaatgtcg atggaacatc a                                              21

<210> SEQ ID NO 1234
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1234
ccagaagatt catatctcca a                                              21

<210> SEQ ID NO 1235
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1235
aaggaaatcc attacttcaa a                                              21

<210> SEQ ID NO 1236
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1236
caagatgaaa gaaggcataa a                                              21

<210> SEQ ID NO 1237
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1237
catggaatta ttggttataa a                                              21

```
<210> SEQ ID NO 1238
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1238
cacagaagac gaagagacta t                                              21

<210> SEQ ID NO 1239
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1239
ctgctaggca accaaattta a                                              21

<210> SEQ ID NO 1240
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1240
cacctccatg acctccgtca a                                              21

<210> SEQ ID NO 1241
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1241
atgaagcagc ttcatatcta a                                              21

<210> SEQ ID NO 1242
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1242
tcccttcagt gtgccactga a                                              21

<210> SEQ ID NO 1243
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1243
cagagaagcg cctattaaca a                                              21

<210> SEQ ID NO 1244
<211> LENGTH: 21
<212> TYPE: DNA
<213> ORGANISM: Artificial Sequence
<220> FEATURE:
<223> OTHER INFORMATION: Synthetic sequence
```

```
<400> SEQUENCE: 1244
gaccgaatgt ctaggattta a                                              21

<210> SEQ ID NO 1245
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1245
acgaactggt ataatgattt a                                              21

<210> SEQ ID NO 1246
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1246
aggagtagaa ggctcaaaca a                                              21

<210> SEQ ID NO 1247
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1247
actgaaagaa ctttagctaa a                                              21

<210> SEQ ID NO 1248
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1248
tacctcggac gtctacggaa a                                              21

<210> SEQ ID NO 1249
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1249
cagccctctc atctcctgga a                                              21

<210> SEQ ID NO 1250
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1250
gaccgaatgt ctaggattta a                                              21

<210> SEQ ID NO 1251
<211> LENGTH: 21
```

```
<212> TYPE: DNA
<213> ORGANISM: Artificial Sequence
<220> FEATURE:
<223> OTHER INFORMATION: Synthetic sequence

<400> SEQUENCE: 1251
caggtcctgg catattgtcc a                                              21

<210> SEQ ID NO 1252
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1252
caacgtgtca agctacttaa a                                              21

<210> SEQ ID NO 1253
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1253
atggctatga tttaccagaa a                                              21

<210> SEQ ID NO 1254
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1254
aagcaccttc tttaacaata a                                              21

<210> SEQ ID NO 1255
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1255
aagaggcaaa tttgcagcaa a                                              21

<210> SEQ ID NO 1256
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1256
tccgaccacc agctcaatca a                                              21

<210> SEQ ID NO 1257
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1257
```
ggcgatggtg ctgttagtaa a                            21

<210> SEQ ID NO 1258
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1258
cccgatgggt ttcctaaatt t                            21

<210> SEQ ID NO 1259
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1259
ctgctgaaat gtaaacaaga a                            21

<210> SEQ ID NO 1260
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1260
aagagtcact ccctaaacct a                            21

<210> SEQ ID NO 1261
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1261
tacactacaa ttgttaataa a                            21

<210> SEQ ID NO 1262
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1262
ttggagaata tttctactac a                            21

<210> SEQ ID NO 1263
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1263
cgcccagatt caggcgtgta a                            21

<210> SEQ ID NO 1264
<211> LENGTH: 21
<212> TYPE: DNA
<213> ORGANISM: Artificial Sequence -continued

```
<220> FEATURE:
<223> OTHER INFORMATION: Synthetic sequence

<400> SEQUENCE: 1264
aaaggtaaat aagctccctaa a                                          21

<210> SEQ ID NO 1265
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1265
caggagtgta tatgtttcat a                                           21

<210> SEQ ID NO 1266
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1266
ttgacaagaa atataaccct a                                           21

<210> SEQ ID NO 1267
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1267
ctgctatata agaaagaggt a                                           21

<210> SEQ ID NO 1268
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1268
caccaataaa ttctactaac t                                           21

<210> SEQ ID NO 1269
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1269
caggtcctgg catattgtcc a                                           21

<210> SEQ ID NO 1270
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1270
cagaagtttc atcttaggat a                                           21
```

<210> SEQ ID NO 1271
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1271
cagcaacaaa tggtacagga a          21

<210> SEQ ID NO 1272
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1272
ccgtatttgt gccaacaaat a          21

<210> SEQ ID NO 1273
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1273
caggcttacc gtggacgcct a          21

<210> SEQ ID NO 1274
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1274
ttcttcaaca ttgccatcaa t          21

<210> SEQ ID NO 1275
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1275
atcctatgca atatatctaa a          21

<210> SEQ ID NO 1276
<211> LENGTH: 21
<212> TYPE: DNA
<213> ORGANISM: Artificial Sequence
<220> FEATURE:
<223> OTHER INFORMATION: Synthetic sequence

<400> SEQUENCE: 1276
ttgaactaca gtacagaaag a          21

EGFR/NEDD9/TGF-β INTERACTOME AND METHODS OF USE THEREOF FOR THE IDENTIFICATION OF AGENTS HAVING EFFICACY IN THE TREATMENT OF HYPERPROLIFERATIVE DISORDERS

This application is a continuation application of U.S. patent application Ser. No. 13/942,032, filed Jul. 15, 2013, now abandoned, which is a continuation application of U.S. patent application Ser. No. 12/777,112, filed May 10, 2010, now abandoned, which is a continuation-in-part of PCT/US08/83067, filed Nov. 10, 2008, which in turn claims priority under 35 U.S.C. § 119(e) to U.S. Provisional Application 60/986,964 filed Nov. 9, 2007, the entire contents of each being incorporated by reference herein as though set forth in full.

Incorporated herein by reference in its entirety is the Sequence Listing being concurrently submitted via EFS-Web as a text file named SeqList.txt, created Jun. 20, 2016, and having a size of 230,641 bytes.

FIELD OF THE INVENTION

This invention relates to the fields of system biology, pharmacology and drug discovery. More specifically, the invention provides an EGFR/NEDD9/TGF-β interactome that facilitates the identification of agents for the treatment of proliferative disorders, particularly metastatic cancer. Anti-cancer agents having efficacy when used alone and in combination identified using the methods described herein are also provided.

BACKGROUND OF THE INVENTION

Several publications and patent documents are cited throughout the specification in order to describe the state of the art to which this invention pertains. Each of these citations is incorporated herein by reference as though set forth in full.

Cancer is a leading cause of death in the United States. Treatments for metastatic cancer are generally limited, and include radiation, chemotherapy with non-specific cytotoxic agents, and therapy with drugs targeted at specific proteins that have been identified as marking cancer cells, and actively contributing to the aggressiveness of cancer growth. Taking metastatic colorectal cancer as an example, among the relatively limited drugs available for treatment of this disease, the DNA damaging agent irenotecan (a pro-drug for camptothecin), and antibodies (cetuximab, panitumumab) and small molecules (erlotinib, gefitinib) targeting the receptor tyrosine kinase (RTK) EGFR, an upstream regulator of the Ras pathway, have shown some efficacy (1-3). It is likely that improvement of therapies directed against EGFR and its family members (e.g., ERBB2/HER2/NEU, ERBB3/HER3) will be beneficial for treatment of numerous metastatic cancers, including those of breast, lung, and pancreas, as these proteins are often abnormally abundant or active in these tumors (e.g. 4,5), and EGFR-family targeting agents such as erlotinib and cetuximab have recently been approved for use in combination therapies in these cancers (1).

While combination of DNA damaging agents such as irenotecan and EGFR-targeting antibodies in the clinic, in some cases, produces substantial therapeutic benefit, in other cases, patients fail to respond. It is extremely likely that the failed response arises from secondary mutations in cancer cells that confer resistance to DNA damage, or relieve dependence of cells on EGFR: for example, mutations in K-Ras are becoming appreciated as a resistance factor for EGFR-directed therapies (6). In other cases, the sources of resistance or sensitivity are obscure (7).

SUMMARY OF THE INVENTION

In accordance with the present invention, a method for identifying compounds, particularly siRNA molecules which modulate sensitivity to EGFR/MEK-1 targeting agents is provided.

An exemplary method entails providing an EGFR/NEDD9/TGF-β interactome, comprising genes which are involved in cellular proliferation and EGFR/MEK-1 signaling; synthesizing at least one compound (e.g., an siRNA molecule) which targets EGFR/NEDD9/TGF-β interactome genes; contacting a cancer cell with at least one EGFR-MEK-1 targeting agent in the presence and absence of at least one compound from above; and determining cell viability in the presence of said agent alone and in the presence and absence of said at least one compound, compounds which increase or decrease sensitivity modulating cell sensitivity to said agent. Compounds for use in the invention include, without limitation, siRNA, phosphatase inhibitors, kinase inhibitors, inhibitory antibodies, and cholesterol synthesis inhibitors. The method may further include examining the cells for the presence of at least one parameter selected from the group consisting of morphological alterations, altered migratory properties, altered levels of apoptosis, altered angiogenic properties, and altered chromosomal or DNA integrity.

In a preferred embodiment, the EGFR-MEK-1 targeting agent is selected from the group consisting of cetuximab, panitumumab, erlotinib, lapatinib, gefitinib, and U0126. Sequences for the siRNA molecules disclosed herein are provided in Table 3. Sensitizing siRNAs are provided in Table 2.

In yet another aspect of the invention, a pharmaceutical composition comprising an effective amount of at least one EGFR-MEK-1 targeting agent listed above and at least one sensitizing siRNA provided in Table 2, in a pharmaceutically acceptable carrier is provided. Methods of administering the same to patients in need thereof for the treatment of malignancy are also disclosed.

In one embodiment, the cancer cell to be screened is obtained from a cancer cell line. In a particularly preferred embodiment, the cancer cell is isolated from a patient.

Also provided herein is a plurality of biomarkers associated with chemoresistance. Exemplary markers are provided in Table 2.

In yet another aspect, a method for determining whether a patient will respond to EGFR/MEK-1 targeting therapy is provided. An exemplary method comprises assessing a cancer cell from said patient for expression levels of at least one of the biomarkers listed in Table 2.

BRIEF DESCRIPTION OF THE DRAWINGS

The file of this application contains at least one drawing executed in color. Copies of this patent with color drawings will be provided by the Patent and Trademark Office upon request and payment of the necessary fee.

FIG. 9B: color code of map.

DETAILED DESCRIPTION OF THE INVENTION

Figure 1:
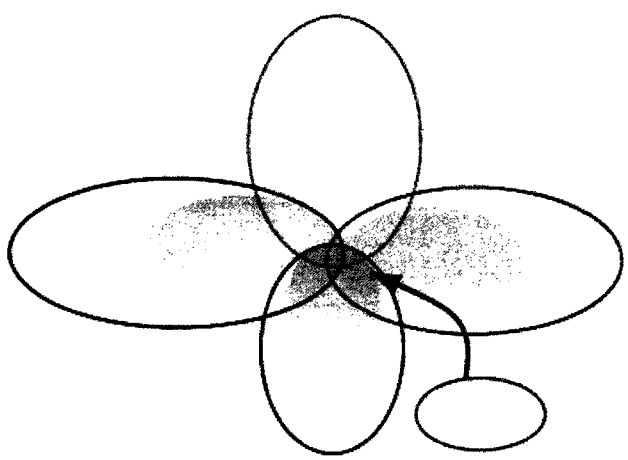
FIG. 1. Selection of siRNAs for targeted library.

In accordance with the present invention, compositions and methods are provided to better improve the treatment of cancer. Using small interfering RNA (siRNA) technology to identify proteins that contribute to resistance to clinically important therapeutic agents, we have identified suitable candidates which inhibit the action of identified resistance proteins thereby enhancing therapy. Such proteins also provide novel biomarkers to better select individual patients for specific treatment regimens.

An effective strategy has been devised to enhance the potency of EGFR-targeting agents. First, systems biology studies in model organisms have begun to establish that synthetic lethal relationships commonly involve genes that are involved in redundant, parallel pathways, or are vertically linked in the same pathway (8). It is instructive that in a seminal genome-wide screen to identify sensitizers to the microtubule-targeting agent paclitaxel, many hits could be clustered into coherent groups of genes associated with the proteasome or mitotic spindle (9), which a priori had been linked to paclitaxel activity based on existing pathway knowledge. Further, in the design of combination therapies in the clinic, the selection strategy for drugs to combine frequently involves common principles: that is, identifying two drugs that 1) inhibit the same target, 2) inhibit functionally linked and/or semi-redundant targets, or 3) inhibit vertically linked targets (10). Together, these observations suggested that generation of a mid-throughput siRNA library (~500-800 genes) that is large enough to fully represent genes functionally linked to the EGFR-Ras-MAPK signaling axis, would greatly increase the useful "hit" rate for genes that chemosensitize EGFR-targeted therapies.

This strategy has produced numerous gains, outlined below in detail: 1) we have been able to conduct reiterative screens to test strategies of hits selection and validation; 2) we have been able to test drive our experimental system to identify systematic errors and biases and apply statistical and bioinformatics tools to compensate for these biases; 3) the EGFR-centered library allowed us to validate the siRNA screening as successful strategy to identify interesting chemosensitizing hits; 4) we have identified siRNA molecules that sensitize chemoresistance cancer cells to EGFR based therapies.

Definitions

As used herein, the phrase "EGFR/MEK1 targeting agent refers to small molecules, antibodies, or RNA agents targeting EGFR, EGFR-related family members, or immediate effectors in the EGFR cascade including but not limited to Ras, Raf, and MEK1.

The phrase "EGFR/NEDD9/TGF-β interactome" refers to proteins linked by close physical or functional association with EGFR, or with the proteins NEDD9, TGF-beta, or their binding partners.

A "small nucleic acid inhibitor" refers to any sequence based nucleic acid molecule which, when introduced into a cell expressing the target nucleic acid, is capable of modulating expression of that target. While siRNA molecules are exemplified herein, antisense, miRNA, shRNA and the like may be utilized in the methods of the invention.

As used herein, the phrase "effective amount" of a compound or pharmaceutical composition refers to an amount sufficient to modulate tumor growth or metastasis in an animal, especially a human, including without limitation decreasing tumor growth or size or preventing formation of tumor growth in an animal lacking any tumor formation prior to administration, i.e., prophylactic administration.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers, for example to a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A pharmaceutical composition of the present invention can be administered by any suitable route, for example, by injection, by oral, pulmonary, nasal or other forms of administration. In general, pharmaceutical compositions contemplated to be within the scope of the invention, comprise, inter alia, pharmaceutically acceptable diluents, preservatives, solubilizers, emulsifiers, adjuvants and/or carriers. Such compositions can include diluents of various buffer content (e.g., Tris HCl, acetate, phosphate), pH and ionic strength; additives such as detergents and solubilizing agents (e.g., Tween 80, Polysorbate 80), anti oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington's Pharmaceutical Sciences, 18th Ed. (1990, Mack Publishing Co., Easton, Pa. 18042) pages 1435 1712 which are herein incorporated by reference. A pharmaceutical composition of the present invention can be prepared, for example, in liquid form, or can be in dried powder, such as lyophilized form. Particular methods of administering such compositions are described infra.

In yet another embodiment, a pharmaceutical composition of the present invention can be delivered in a controlled release system, such as using an intravenous infusion, an implantable osmotic pump, a transdermal patch, liposomes, or other modes of administration. In a particular embodiment, a pump may be used [see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)]. In another embodiment, polymeric materials can be used [see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)]. In yet another embodiment, a controlled release system can be placed in proximity of the target tissues of the animal, thus requiring only a fraction of the systemic dose [see, e.g., Goodson, in Medical Applications of Controlled Release, supra, vol. 2, pp. 115 138 (1984)]. In particular, a controlled release device can be introduced into an animal in proximity of the site of inappropriate immune activation or a tumor. Other controlled release systems are discussed in the review by Langer [Science 249:1527 1533 (1990)].

As used herein the term "biomarker" refers to a characteristic that is objectively measured and evaluated as an indicator of normal biologic processes, pathogenic processes, or pharmacologic responses to a therapeutic intervention.

As used herein, the terms "modulate", "modulating" or "modulation" refer to changing the rate at which a particular process occurs, inhibiting a particular process, reversing a particular process, and/or preventing the initiation of a particular process. Accordingly, if the particular process is tumor growth or metastasis, the term "modulation" includes, without limitation, decreasing the rate at which tumor growth and/or metastasis occurs; inhibiting tumor growth and/or metastasis; reversing tumor growth and/or metastasis (including tumor shrinkage and/or eradication) and/or preventing tumor growth and/or metastasis.

As used herein, the terms "tumor", "tumor growth" or "tumor tissue" can be used interchangeably, and refer to an abnormal growth of tissue resulting from uncontrolled progressive multiplication of cells and serving no physiological function. A solid tumor can be malignant, e.g. tending to metastasize and being life threatening, or benign. Examples of solid tumors that can be treated or prevented according to a method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, gastic cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, liver metastases, bile duct carcinoma, choriocarcinoma, seminoma, embryonal carcinoma, thyroid carcinoma such as anaplastic thyroid cancer, Wilms' tumor, cervical cancer, testicular tumor, lung carcinoma such as small cell lung carcinoma and non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Moreover, tumors comprising dysproliferative changes (such as metaplasias and dysplasias) can be treated or prevented with a pharmaceutical composition or method of the present invention in epithelial tissues such as those in the cervix, esophagus, and lung. Thus, the present invention provides for treatment of conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, 1976, Basic Pathology, 2d Ed., W.B. Saunders Co., Philadelphia, pp. 68 to 79). Hyperplasia is a form of controlled cell proliferation involving an increase in cell number in a tissue or organ, without significant alteration in structure or function. For example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. For a review of such disorders, see Fishman et al., 1985, Medicine, 2d Ed., J. B. Lippincott Co., Philadelphia.

Other examples of tumors that are benign and can be treated or prevented in accordance with a method of the present invention include arteriovenous (AV) malformations, particularly in intracranial sites and myoleomas.

Methods for Modulating Tumor Growth or Metastasis

As explained above, the present invention is directed towards methods for modulating tumor growth and metastasis comprising, inter alia, the administration of a EGFR/Mek-1 targeting agent and at least one sensitizing siRNA molecule. The agents of the invention can be administered separately (e.g, formulated and administered separately), or in combination as a pharmaceutical composition of the present invention.

The present invention provides for both prophylactic and therapeutic methods of treating a subject at risk of (or susceptible to) a disorder or having a disorder associated with aberrant or unwanted target gene expression or activity. In one embodiment, the subject is administered a lipid/therapeutic agent complex, for example, a liposome comprising an siRNA for suppressing the expression of an the undesired gene product. It is understood that "treatment" or "treating" as used herein, is defined as the application or administration of a therapeutic agent (e.g., an RNAi agent or vector or transgene encoding same, a polypeptide, e.g., an antibody or fragment thereof, or small molecule) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In another aspect, the invention provides a method for preventing in a subject, a disease or condition associated with an aberrant or unwanted target gene expression or activity, by administering to the subject a lipid/therapeutic agent complex of the invention (e.g., an siRNA agent or vector or transgene encoding same, a polypeptide, e.g., an antibody or fragment thereof, or small molecule). Subjects at risk for a disease which is caused, or contributed to, by aberrant or unwanted target gene expression or activity can be identified by, for example, any or a combination of diagnostic or prognostic assays as described herein. Administration of a prophylactic agent can occur prior to the manifestation of symptoms characteristic of the target gene aberrancy, such that a disease or disorder is prevented or, alternatively, delayed in its progression. Depending on the type of target gene aberrancy, for example, a target gene, target gene agonist or target gene antagonist agent can be used for treating the subject. The appropriate agent can be determined based on screening assays described herein.

In yet another aspect, the invention pertains to methods of modulating target gene expression, protein expression or activity for therapeutic purposes. Accordingly, in an exemplary embodiment, the modulatory method of the invention involves contacting a cell capable of expressing target gene with a lipid/therapeutic agent complex (e.g., an siRNA agent or vector or transgene encoding same) that is specific for the target gene or protein (e.g., is specific for the mRNA encoded by said gene or specifying the amino acid sequence of said protein) such that expression or one or more of the activities of target protein is modulated. These modulatory methods can be performed in vitro (e.g., by culturing the cell with the agent), in vivo (e.g., by administering the agent to a subject), or ex vivo. As such, the present invention provides methods of treating an individual afflicted with a disease or disorder characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

When employing the methods or compositions of the present invention, other agents used in the modulation of tumor growth or metastasis in a clinical setting, such as antiemetics, can also be administered as desired.

Materials and methods are provided herein to facilitate the practice of the present invention.

Cell Lines, Compounds, Antibodies.

The A431 cervical adenocarcinoma (K-Ras wt, p53 mutant (Kwok et al. (1994) Cancer Res. 54:2834), HCT116 and LoVo (K-Ras mutant, p53 wt) colorectal carcinoma and the PANC-1 (K-Ras mutant, p53 mutant) and MIA PaCa-2 (K-Ras mutant, p53 and p16 mutant) pancreatic adenocarcinoma (Brunner et al., (2005) Cancer Res. 65:8433) cell lines were obtained from the ATCC (USA). The DLD-1 (K-Ras mutant, p53 mutant) and DKS-8 (with the activated K-Ras allele disrupted [derived from DLD-1], p53 mutant; Sarthy et al. (2007) Mol. Cancer Ther. 6:269) were a kind gift of Dr. Robert J. Coffey (Vanderbilt University, TN). SCC61 cells (K-Ras wt, p53 mutant), derived from squamous cell carcinomas of the head and neck, were kindly provided by Dr. Tanguy Y. Seiwert (University of Chicago). All cell lines were maintained in DMEM supplemented with 10% v/v fetal bovine serum (FBS) and L-glutamine without antibiotics. Cetuximab, panitumumab and erlotinib were purchased from the Fox Chase Cancer Center pharmacy; CPT11 and C1368 from Sigma-Aldrich (USA); Stattic and Ro-318220 from EMD Chemicals (Gibbstown, N.J., USA). PHA-680632 was obtained from Nerviano Medical Sciences (Nerviano, Italy), as a kind gift of Dr. Jurgen Moll. Enzastaurin was generously provided by the Elli Lilly Company (Indianapolis, Ind.). All antibodies used in Western blot experiments were purchased from Cell Signaling (Danvers, Mass., USA), except anti-p53 mouse monoclonal antibody was from Calbiochem (EMD Biosciences, USA).

EGFR Network Construction.

Methods for Library Construction.

Four sources of information were used, including 1) published EGFR pathway maps, 2) human protein-protein interaction (PPI) data, gleaned from various databases, 3) human orthologs of PPIs and genetic interactions modeled from *Drosophila*, and 4) microarray data obtained at brief intervals after treatment of cells with stimulators or inhibitors of EGFR/ErbB2. Following initial assembly of a larger gene list, genes were parsed into high confidence ("core", denoted as "1" after the corresponding letter code) versus lower confidence sets (denoted as "2"), based on the confidence criteria outlined for each section below. For each category of information, all "core" components were included in the final library, as were genes noted as lower confidence but included in at least two categories of search criteria (e.g., second order protein-protein interaction and microarray linkage). Finally, for the assembled set of EGFR interactors, multiple paralogous genes were identified in humans using the KEGG Sequence Similarity DataBase (SSDB) resource, see the world wide web at .genome.jp/kegg/ssdb/. 77 paralogs of the best-characterized and biologically significant genes were added to the set. All data storage, handling and analysis were done primarily in Cytoscape (on the world wide web at cytoscape.org).

1) Pathway map sources. Protein names for were extracted from the following pathway maps focused on EGFR: STKE (on the world wide web at stke.sciencemag.org/cgi/cm/stkecm %3BCMP_14987); Biocarta (on the world wide web at biocarta.com/pathfiles/PathwayProteinList.asp?showP-FID=102); the Systems Biology model repository (on the world wide web at systems biology.org/001/005.html); Net-Path (on the world wide web at netpath.org/pathways?path_id=NetPath_4); and from Protein Lounge (on the world wide web at proteinlounge.com/pop_pathwaysl.asp?id=EGF+Pathway). Protein names were individually inspected and, where necessary, converted to the corresponding official (NCBI/EMBL) symbols. Proteins mentioned on at least two EGFR-centered pathways were designated as "pathway core"; we note, significant divergence was seen among different interpretations of the "EGFR pathway" by the 5 sources.

2) PPIs. EGFR/ERBB1 and ErbB2 were used as seeds for PPI searches. Curated information regarding human PPIs of these seeds was collected from the following databases: Biomolecular Object Network Databank (BOND) (on the world wide web at bond.unleashedinformatics.com/); General Repository for Interaction Datasets (on the web at thebiogrid.org/); EMBL_EBI IntAct on the web at ebi.ac.uk/intact/site/index.jsf); The Human Protein Reference Database (on the web at hprd.orgf); Kyoto Encyclopedia of Genes and Genomes (KEGG) (on the web at genome.jp/about_genomenet/service.html); and Prolinks Database 2.0 (on the web at mysql5.mbi.ucla.edu/cgi-bin/functionator/pronav). Data for first rank (direct) interactors were collected both by export from the corresponding database and subsequent import into Cytoscape, and by directly querying those databases using the BioNetBuilder plugin (on the web at err.bio.nyu.edu/cytoscape/bionetbuilder/), and then cross-comparing retrieved results. Data for the second order interactions were obtained by using EGFR and ERBB2 first rank interactors as seeds for an additional round of query, and only through the BioNetBuilder plugin. Finally, an orthogonal set of second rank interactors was obtained by analysis of protein complexes with more than 2 subunits, which included EGFR. Information for complexes was obtained from BOND and IntAct, and manually compared to the lists in the corresponding publications. We also used the SHC1 and SHC3 adaptors, which bridge between EGFR and downstream signaling effectors, and the CAS (EFS, BCAR1, and NEDD9) scaffolding proteins, which connect EGFR to the SRC and TGF-β core signaling cascades (O'Neill et al., (2000) Trends Cell Biol. 10:111; Defilippi et al. (2006) Trends Cell Biol. 16:257), as seeds for first order PPI searches. Second order PPIs EGFR and ErbB2 were ranked higher (i.e., P1) if they were also first order interactors of SHC or CAS proteins.

3) To extract a set of EGFR-centered interactions potentially conserved between humans and *D. melanogaster*, information assembled by the Michigan Proteomics Consortium in the *Drosophila* Interactions Database (DIP) (on the web at proteome.wayne.edu/PIMdb.htm) was used. Briefly, this database integrates genetic and or protein interaction data from a variety of non-mammalian species (yeast, worms, flies). Of 105 EGFR interactors (almost exclusively from *Drosophila* genetic interactions), 65 had 1-2 conserved human orthologs (117 genes).

4) Microarray data were obtained from The Gene Expression Omnibus (GEO, release date Dec. 15, 2006). In the selected dataset (GSE6521; raw data available at on the web at ncbi.nlm.nih.gov/geo/query/acc.cgi?acc=GSE6521), MCF-7 human breast cancer cells were incubated with the growth hormone heregulin (HRG), or AG1478 (an EGFR kinase inhibitor), or both growth hormone and AG1478. Controls were set as growth hormone/inhibitor non-treated cells. A total of 348 genes with a >1.5 fold change (+ or −) upon AG1478 treatment was identified. In this group, the core set includes 89 genes which showed a >2-fold change in expression level upon AG1478 treatment, or which were inducible by HRG (>1.5 fold) and repressible by AG1478 (>1.5 fold).

High Throughput siRNA Screening Methods.

The custom siRNA library targeting 638 human genes was designed and synthesized with two siRNA duplexes for each gene target (Qiagen, Valencia, Calif.). Transfection conditions were established for the A431 cervical adenocarcinoma (K-Ras wt, p53 mutant) cell line (data not shown) using PLK1 & GL2 siRNA controls to achieve Z' values of 0.5 or greater. IC values using erlotinib, panitumumab, and camptothecin (CPT11) were established (data not shown). Details of establishment of Z' factor for transfections, and statistical consideration for selection of preliminary positive candidates graphically outlined in FIG. 4B, and based on standard approaches described in detail in Whitehurst et al., (2007) Nature 446:815). For each gene targeted, two independent siRNA duplexes were combined and arrayed in 96-well plates with a layout intended to seed in regular positive siRNA (targeting PLK1) and negative control siRNA (targeting insect luciferase GL2, Thermo Fisher Scientific, USA) amongst test siRNAs. A reverse transfection protocol was used where siRNA at final concentration of 50 nM was mixed with Dharmafect 1 transfection reagent according to the manufacturer's instructions (Thermo Fisher, USA). Cells (3500 per well, resuspended in 1% FBS/DMEM) were added directly to wells using an automated liquid dispenser. At 24 hr following transfection, two replica plates were treated with drugs at previously established IC30 or 0.02% DMSO diluted in culture media. The viability at 96 hr post-transfection was assessed using Alamar blue (CellTiter Blue Viability Assay, Promega, USA). Dose-responses for each drug and cell line were retested in parallel with each screen.

For screening, A431 cells were transfected with siRNA followed by exposure to vehicle (0.02% DMSO), or drug used at inhibitory concentrations of 30% KA. Viability was determined for each target gene and normalized to the averaged GL2 viability on each plate. Sensitization index (SI) was calculated for each individual well on a 96-well plate as $SI=(V_{drug}/GL2_{drug})/(V_{DMSO}/GL2_{DMSO})$, where V was viability in wells transfected with targeting duplexes and GL2 was the averaged viability of 4 wells with non-targeting negative control siRNA on the same plate. All calculations were automated using cellHTS package within open source Bioconductor Package (on the web at bioconductor.org) (Gentleman et al. (2004) Genome Biol. 5:R80). The effect of drug treatment on viability was measured based on the normalized viabilities in the drug treated and vehicle wells using Limma (Smyth, G. K. (2004) Statistical Applications in genetics and molecular biology 3, Article 3). Limma borrows strength across genes based on an empirical Bayes approach and identifies statistically significant changes in viability by combining information from a set of gene-specific tests. Hits were identified based on statistical significance as well as biological significance. Statistical significance was determined by p-value controlled for the false discovery rate (FDR) using the Benjamini-Hochberg step-up method (Benjamini et al. (1995) J. Royal Stat Soc B 57:289) to account for multiple testing. Hits showing an FDR of less than 20% were considered statistically significant. Biological significance was arbitrarily defined as an increase or decrease in SI greater than 15%. Hits identified as statistically and biologically significant were further validated.

Primary sensitizing hits obtained with erlotinib and/or cetuximab were further tested with erlotinib and DMSO in the A431 cell line by using 4 siRNA duplexes individually (the two originally used in the screen, plus two new non-overlapping RNA oligoribonucleotides), to confirm the sensitization phenotype at 10 nM and 50 nM concentrations. Hits were considered as validated by this method if at least 2 out of 4 siRNA reproduced the sensitization phenotype with SI≤0.85, FDR≤20% for each individual siRNA sequence in at least two independent experiments. For a number of hits, we additionally confirmed sensitizing siRNAs reduced mRNA levels for the targeted genes, using qRT-PCR; and used Western analysis to confirm protein knockdown (data not shown).

Cell line specificity of hit activity. Of the confirmed set of 61 siRNA targets identified for erlotinib in A431 cells, 45 were further tested for sensitization to erlotinib, cetuximab and camptothecin in A431 versus refractory adenocarcinoma cell lines for which optimal transfection conditions and drug sensitivity had been established. In this analysis, for each target, the two most active siRNA duplexes identified during the validation stage were pooled in a 96-well format, cells were reverse-transfected and drug-treated under conditions similar to those described above for the initial A431 screen. SI and statistical significance were calculated as in the validation experiments. All experiments were performed at least three times independently.

In subsequent data analysis, two approaches were used. For the relative ranking approach, for each experiment, SI values for each siRNA pool were ranked from the strongest (assigned a value of 0) to the weakest (assigned as 1). For all experiments performed with a given cell:drug combination (e.g., A431:erlotinib, or HCT116:CPT11) averages were determined based on at least three experimental runs. The averaged data were imported and clustered in MultiExperiment Viewer (MeV_4_3) software (Saeed et al. (2003) Biotechniques 34:374), and dendrograms were created using HCL Support Trees (using Euclidian Distance as a metric, and bootstrapping with 100 iterations). For the absolute threshold approach, specific SI thresholds were applied for each data point, considering only data with an FDR≤20% in each independent experiment. Data were visualized in MultiExperiment Viewer using color assignments to indicate SI cutoffs obtained in at least two independent experiments, as described in figure legends. The resulting output of both analytic strategies was processed in standard graphic software to improve visualization of data.

Quantitative RT-PCR.

For evaluation of expression of validated target genes, each of the cell lines was grown to 70% confluency in full DMEM media, then total RNA was extracted using RNeasy Minikit (Qiagen, Valencia, Calif.). To confirm mRNA depletion by siRNA, 48 hrs after transfection of A431 cells grown in 96-well plates, total RNA was extracted at using a Cell-to-Ct kit (Applied Biosystems, Foster City, Calif.). Subsequent quantitative RT-PCR reactions were performed using TaqMan probes and primers designed by the manufacturer, using an ABI PRISM 7700 detection system (Applied Biosystems, Foster City, Calif.). The results were analyzed using the comparative Ct method to establish relative expression curves.

To assess whether gene expression levels correlated with the ability of gene-targeted siRNAs to inhibit intrinsic cell growth, we used a Pearson correlation of the mean values of gene expression relative to that obtained in A431 cells measured by RT-PCR, against the mean growth observed in DMSO-treated cells in all experiments. To test significance, we performed 100 permutations of the cell line labels in the RT-PCR measurements and generated Pearson correlation values. Significance was defined as a false discovery rate (FDR) of 5%, setting Pearson correlation greater than 0.745 or less than −0.71 for positive correlated or negative-correlated, respectively. Positive correlation indicates that higher expression (lower number of RT-PCR cycles) is correlated with greater growth inhibition, while negative correlation indicates higher expression is correlated with lower inhibition.

Network Analysis with Hits.

For all genes in the library, the String search engine (Jensen et al., (2009) Nucleic Acids Res. 37:D412) was used in subsequent analysis to augment information on PPIs in human cells, PPIs between homologous genes in model organisms, database/pathway links, and textmining (coappearance of gene names in PubMed). Data regarding experimentally proven interactions in human and model organisms were merged. Topological properties of the library network were assessed using NetworkAnalyzer plugin for Cytoscape (Assenov et al., (2008) Bioinformatics 24: 282), based on STRING-expanded defined interactions among genes in the library (based only on experimental data). In this analysis, for each node, degree (reflecting the number of edges linked to it), stress (reflecting how frequently it lies in the shortest paths connecting other nodes), and neighborhood connectivity (the average number of neighbors for each direct interactor of the node) were separately assessed. The topological coefficient was calculated to provide an estimate for the trend of the nodes in the network to have shared neighbors. To provide additional context in some analyses (FIG. 14) STRING-extracted information from pathway databases and textmining data were merged, and displayed using Cytoscape as indicated in figure legends.

Apoptosis Assays.

Apoptosis was measured using the Annexin V assay (Guava Technologies, Hayward, Calif.). Annexin V-positive A431 cells were counted using Guava flow cytometry 72 hours post transfection, 48 hours after treatment. Statistical significance versus control GL2 siRNA was determined by logistic regression models to identify genes increasing apoptosis with erlotinib relative to vehicle.

Pathway Analysis.

To measure the effect of siRNAs on the activity of EGFR effectors, cells were transfected with siRNA, and the culture media replaced with glutamine-supplemented serum-free DMEM at 24 hrs post-transfection. After overnight incubation, cells were treated with DMSO, erlotinib or PHA-680632 for 2 hrs, then either left untreated, or stimulated with EGF at 15 ng/ml for 15 minutes. Cell extracts were prepared using M-PER™ mammalian protein extraction buffer (Thermo Scientific, Rockford, Ill.) supplemented with the Halt™ phosphatase inhibitor cocktail (Thermo Scientific, Rockford, Ill.) and the Complete Mini™ protease inhibitor cocktail (Roche Diagnostics Gmbh, Manheim, Germany). Extracts were centrifuged at 15,000 g for 10 min at 4° C. Western signal detection was performed using antibodies to indicated proteins with LiCor technology (Lincoln, Nebr., USA) or standard X-ray film.

Figure 19A:
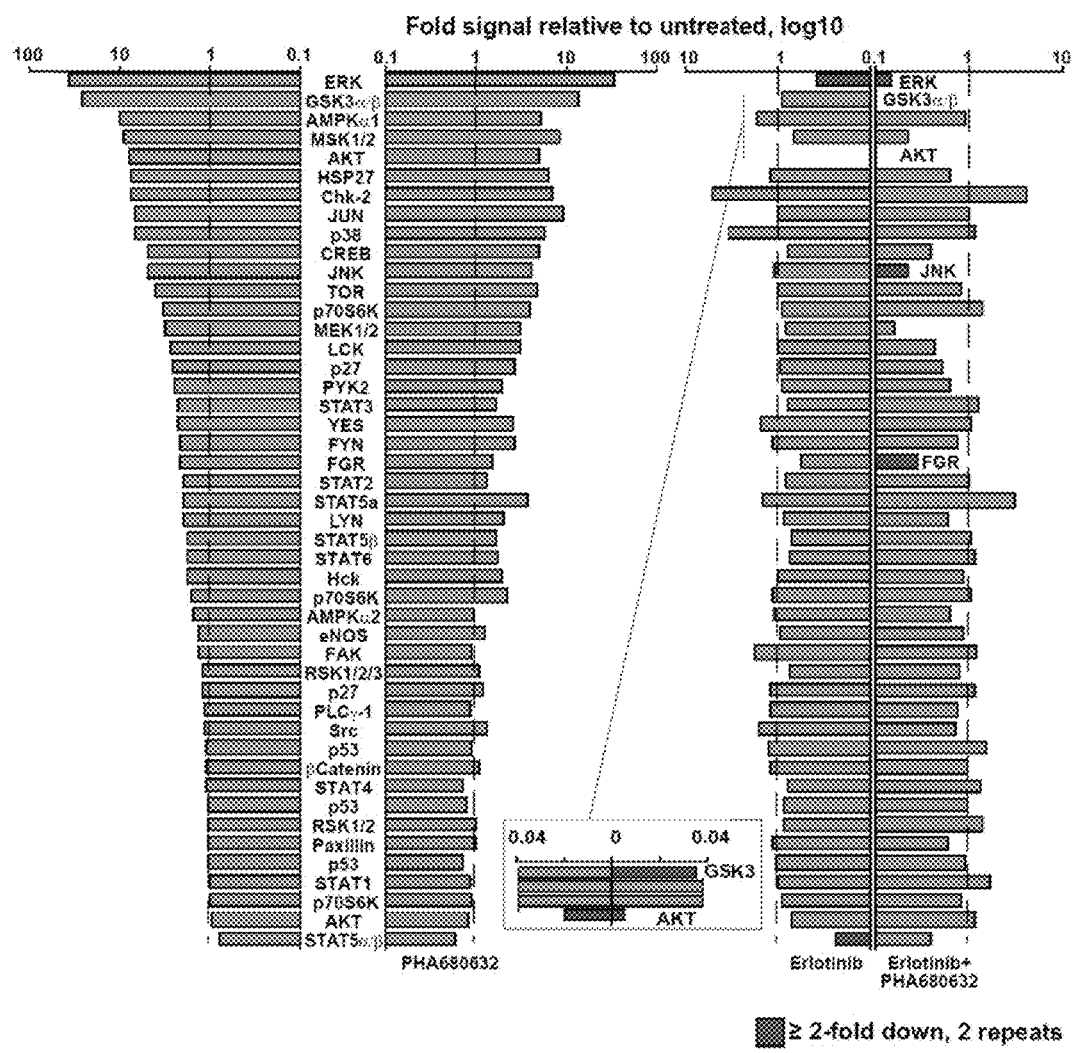
FIGS. 19A-19B: Dual inhibition of Aurora-A and EGFR suppresses activation of multiple signaling nodes. Ranked fold increase in phosphorylation signal of 46 proteins in A431 cells stimulated with EGF (FIG. 19A) or grown in 1% serum media (FIG. 19B) and treated with indicated drugs. Inset, graphs illustrate magnified scale of indicated phosphoproteins. Proteins showed in red have consistent decrease of >2-fold in signal intensity in independent biological replicates, as indicated.

For phosphoproteomic analysis, we used the Proteome Profiler™ array (R&D Systems, Minneapolis, Minn., USA) according to the manufacturer's protocol. In brief, A431 cells were grown for 24 hours in DMEM supplemented with L-glutamine and 1% FBS to 70% confluency. Cells then were either serum starved overnight or remained in the same media. Serum starved and cells incubated in 1% serum were either left untreated or incubated with $IC_{30}$ concentrations of inhibitors for 3 hours. For FIG. 19A, we used erlotinib at 0.5 μM and PHA-680632☐ at μM alone or in combination; for FIG. 19B, erlotinib at 1 μM and PHA680632 at 0.5 μM individually, and erlotinib at 0.5 μM plus PHA at 0.1 μM in combination. Serum-starved cells were subsequently stimulated with recombinant EGF (Sigma-Aldrich, USA) at 15 ng/mL for 15 minutes before lysis. For a subset of phosphoproteins, phosphorylation status was confirmed by Western blot. Quantification was done using ImageJ software.

Drug Synergy Testing.

The coefficient of interaction (CI) between pharmacological inhibitors was established by the Chou-Talalay method (Chou et al., (1984) Adv Enzyme Regul 22:27). The software package CalcuSyn (BioSoft, UK) was used to automate calculations. Briefly, for each drug tested, an $IC_{50}$ curve was established in each cell line, and used to select combination doses of drugs for subsequent synergy tests. 3500 cells were plated per well in 96-well plates. After 24 hours, cells were treated with serial dilutions of individual inhibitors, or combinations of two inhibitors maintained at a constant molar ratio. After 72 hours incubation, cell viability was measured using either CellTiter Blue (Promega, USA) or a WST1 assay (Roche Applied Science, Indianapolis, Ind.). The CI values for each dose and corresponding cytotoxicity were expressed as the fraction affected (Fa) and were calculated using CalcuSyn computer software and presented as Fa-CI plots. CI values <1 indicate synergy, and <0.5 strong synergy, between the two agents in producing cytotoxic effect.

Anchorage-Independent Growth and Cell Motility.

Soft agar assays were done essentially as described (10). Cells were seeded at 2000 cells per well and grown for 2-3 weeks. Colonies were stained with thiazolyl blue tetrazolium bromide, and scored using a Nikon SMZ1500 microscope coupled with Cool Snap charge coupled device camera (Roper Scientific, Inc., Tucson, Ariz.) with Image Pro-Plus software (Media Cybernetics, Silver Spring, Md.). Survival curves were based on at least two concentration points, with values determined in at least two separate experiments, with each assay done in duplicate. Drug interactions were calculated as above using CalcuSyn software (Biosoft, Ferguson, Mo.) to establish the combination index (CI). For motility assays, movement of A431 cells grown in 1% FCS into a scratched area of the monolayer was monitored with a phase contrast 10× objective using an inverted microscope (Nikon TE2000). Images were obtained every 20 min for 18 hours. Areas of migration were estimated using MetaMorph software. For both studies, analysis of variance was used to determine the treatment effect for each comparison. The logarithm of normalized ratios (to vehicle control) was used in the analysis. Multiple hypothesis testing was accounted for by the false discovery rate method of Benjamini & Hochberg (supra).

Tumor Formation In Vivo.

Male CB.17/scid mice aged 6-8 weeks were obtained from the Fox Chase Cancer Center breeding colony. All experiments were carried out according to protocols approved by the institutional animal use committee. Mice were injected with $3 \times 10^6$ A431 cells subcutaneously into the flanks. Palpable tumors appeared in all animals in 10-14 days, and were measured 3 times a week in two dimension and volume calculated by modified ellipsoidal formula as Length×Width$^2$×0.52. Mice were randomized and treatments commenced when tumor volume exceeded 65 mm$^3$. Erlotinib at doses 10-20 mg/kg was given by oral gavage as in 10% DMSO/saline. Enzastaurin was suspended in 5% dextrose in water and dosed at 75 mg/kg by gavage twice daily. PHA-680632 was freshly dissolved in acidified 5% dextrose in water and administered intraperitoneally twice daily at 15 mg/kg dose. The generalized estimating equations approach (with an autoregressive correlation structure) was used to model tumor growth. A linear time-effect was included in the model for the logarithm of tumor volume and interacted with the treatments in each comparison.

The following examples are provided to illustrate certain embodiments of the invention. They are not intended to limit the invention in any way.

Example I

Identification of Sensitizing siRNA Molecules

To generate an EGFR interactome library, we extensively mined public access databases containing information about protein-protein interactions and mRNA expression profiles generated in humans. These databases included among others NetPath, BioGrid, DIP, BIND, KEGG, HPRD, CellCircuits, and NCBI GEO, as well as five different "expert systems" focused on pathway analysis (NetPath, Protein Lounge, Molecular Systems Biology, Biocarta, Science's STKE). This approach identified a set of genes for which the encoded proteins either directly bound EGFR, EGFR-family members such as ERBB2 and ERBB3, and their immediate downstream effectors, or were purified in complexes including these proteins; a set of genes transcriptionally upregulated by EGFR family stimulation and downregulated by EGFR pathway inhibition; and a set of genes otherwise involved in EGFR signaling based on published literature. We also incorporated data generated from genetic interactions reported in Drosophila, C. elegans, and other organisms for strongly conserved evolutionary orthologs of genes in this pathway (11, 12). Using resources in the systems analysis programs Cytoscape and Osprey, we then identified a core high value set of genes that fell into at least two of these linkage categories, and based on other weighting functions. FIG. 1 schematically represents the source for each of the genes in the final custom library.

Figure 2:
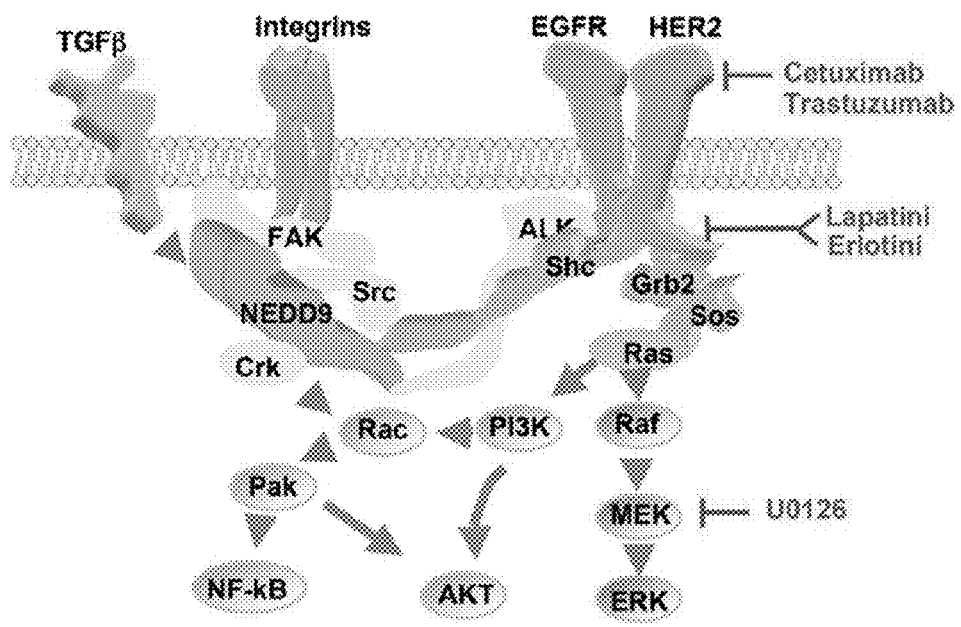
FIG. 2. EGFR/HER2 and connected pro-survival signaling pathways. While EGFR/HER2 directly signal through Ras to ERK and PI3K, cross signaling by the TGFβ/integrin-regulated proteins, Src, FAK, and NEDD9 contribute to activation of pro-survival endpoints, Akt and NF-κB. Drugs inhibiting EGFR/HER2 and Ras/Mek1 cascade are indicated.
Figure 3:
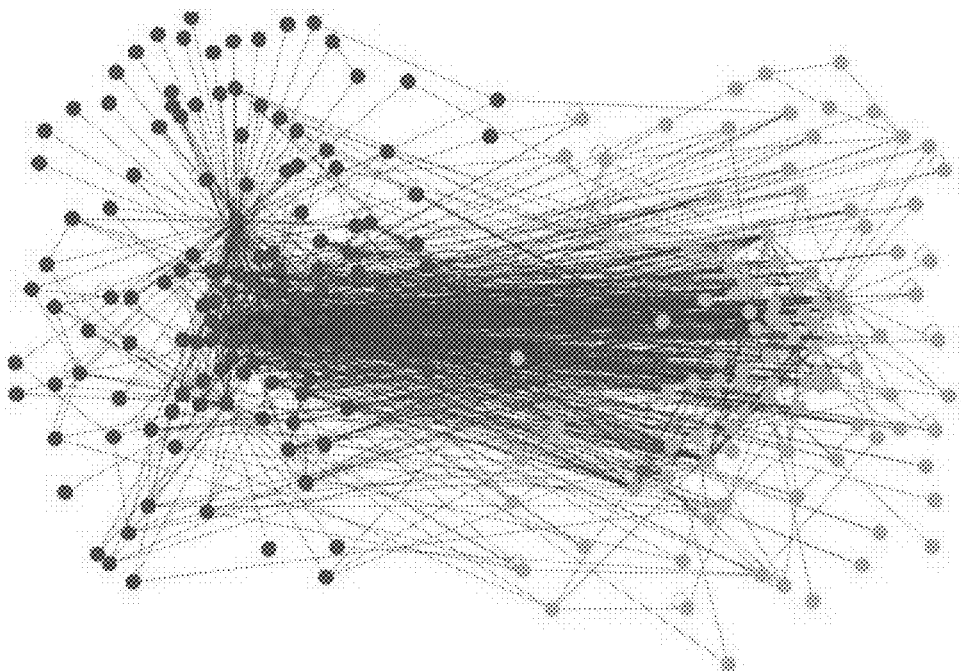
FIG. 3. Representative dataset indicating convergence of EGFR/HER2-centered and NEDD9/SRC/TGFβ-centered protein interaction networks. Filled circles represent proteins, lines direct physical interactions. Proteins directly binding EGFR, HER2, or their proximal effectors are indicated in green to left; those directly binding NEDD9 and proximal partners are indicated in red, to right. This is one component of the meta-analysis employed to select components of the 638 siRNA library (see FIG. 1).

Drug resistance and propensity to metastasis commonly both characterize the most aggressive tumors. A growing number of proteins that function in pro-metastatic signaling pathways related to cellular invasiveness are also known to function in promoting apoptosis resistance (via modulation of integrin- and cadherin-dependent signaling cascades). To enrich our candidate siRNA set, we then performed a similar analysis for genes physically and functionally linked to TGFβ, Src and NEDD9. It is becoming well established that cancer metastasis requires parallel inputs from EGFR superfamily members, and the Src and TGFβ signaling pathways (13, 14). NEDD9 (also known as HEF1) has long been studied in the Golemis laboratory (15, 16), and elevated expression of NEDD9 has recently been shown to be a critical driver of melanoma metastasis, and linked to metastasis in lung cancers (17, 18); moreover, NEDD9 physically interacts with multiple components of the EGFR/Ras, TGFβ, and Src signaling pathways (19, 20). FIGS. 2 and 3 show an example of the degree of functional overlap between EGFR family and TGF-β/NEDD9 signaling networks.

From these combined data mining efforts, we selected a set of 638 target genes (see Table 1). These genes were ordered as a custom library from Qiagen. Two independent siRNAs for each gene were pooled and arrayed in wells. For the screening experiment, aliquots of the library were transferred to the inner 60 wells of 11 assay plates with a layout intended to seed in negative control siRNA (siControl targeting insect luciferase transcript, Dharmacon), positive control cytotoxic siRNA (targeting Polo-like kinase1), and cytotoxic drug (0.7 mM campthotecin). The siRNA was mixed with the transfection reagent (Dharmafect 1, Dharmacon) diluted 1:100 in Hank's balanced saline in a total volume of 22 ml to produce 25 nM final concentration of each siRNA oligo. The mixture was incubated for 45 minutes. A reverse transfection protocol was used (9) where cells resuspended in DMEM/1% FBS/Glutamine were added at 4000 per well to the assay plates using a Thermo Multidrop bulk reagent dispenser. After overnight incubation, 10 ml per well of the drug was added. For each screening experiment, the effective inhibitory concentration (IC) of the screen drug was pre-determined by rigorous IC50 testing, and screens were consistently performed aiming for IC30-40 range. Viability was measured in the Perkin Elmer Envision plate reader using fluorescent metabolite of Alamar blue (CellTiterBlue™, Promega).

Screening Conditions: Initial Selection and Optimization.

Our initial screens were performed in A431 cells, for two compelling reasons. First, we wanted to maximize our chances of obtaining any hits that would sensitize to EGFR-targeting antibodies. A431 cells are well known to overexpress the EGFR receptor, and to be exquisitely sensitive to inhibition of EGFR-dependent signaling. Second, as outlined below, we have had the opportunity to add value to our screening strategy based on addition of a high throughput microscope-based detection system: based on their regular growth properties, A431 cells have proven excellent for this purpose.

As a second conservative approach, initial EGFR-pathway sensitization screens were performed with panitumumab, and also with the small molecule erlotinib. This was done because of literature suggesting that a significant component of the anti-tumor effect of EGFR-targeting antibodies arises from cell-mediated immunity, which would not apply in cultured cell lines. This restriction should not apply with erlotinib. Because of the relatively low cost of screening, this project also serves as an opportunity to probe the overall "resistance structure" of the EGFR signaling pathway, by examining the overlapping pattern of "hits" arising from drugs targeting different points along the pathway. Hence, we have now screened A431 cells for siRNA sensitizers to erlotinib, panitumumab, and U0126 (targets MEK1), in each case normalizing against the base line inhibitory profile of each siRNA in cells treated with a DMSO (vehicle) control. We have also screened the A431 cell line with CPT11 (an active camptothecin analog of irenotecan). We anticipated that comparison of the CPT11 hit pattern with the EGFR-Ras-MEK1 inhibitor pattern would segment siRNAs into 3 classes: those that sensitize to CPT11 and EGFR-Ras-MEK1 inhibitors, targeting general apoptosis-resistance genes; and those specific either to CPT11 or the EGFR-Ras-MEK1 pathway. Knowledge of each these classes has specific value for specific therapeutic/biomarker applications.

Library Screening: Additional Cell Line Models, Strategy.

A growing consensus among clinicians is that a major source of resistance to EGFR-targeted therapies is the presence of an activating K-Ras mutation (present in up to 70% of resistant tumors) or an activating B-Raf mutation (present in up to 10% of resistant tumors). The colon cancer cell lines HCT116 harbors an activating K-Ras mutation, conferring relative resistance to the EGFR antagonists in vitro. The HCT116 colorectal carcinoma cell line offers advantage of comparison between p53null and p53-positive (intact apoptotic checkpoint) isogenic variants (9) which will be important to determine the p53-dependancy of the synthetic lethal phenotype and the mechanism of apoptosis induction. Conditions for these cell lines have been established for siRNA-based screening with high siRNA transfection efficiency (>75% depletion of two housekeeping genes GADPH, PLK1); and consistency in Alamar Blue viability yielding robust Z'-scores with control drugs (see Results below). Additional cell lines with activating mutations in B-Raf will also be worked up for hit validation.

Figure 4A:
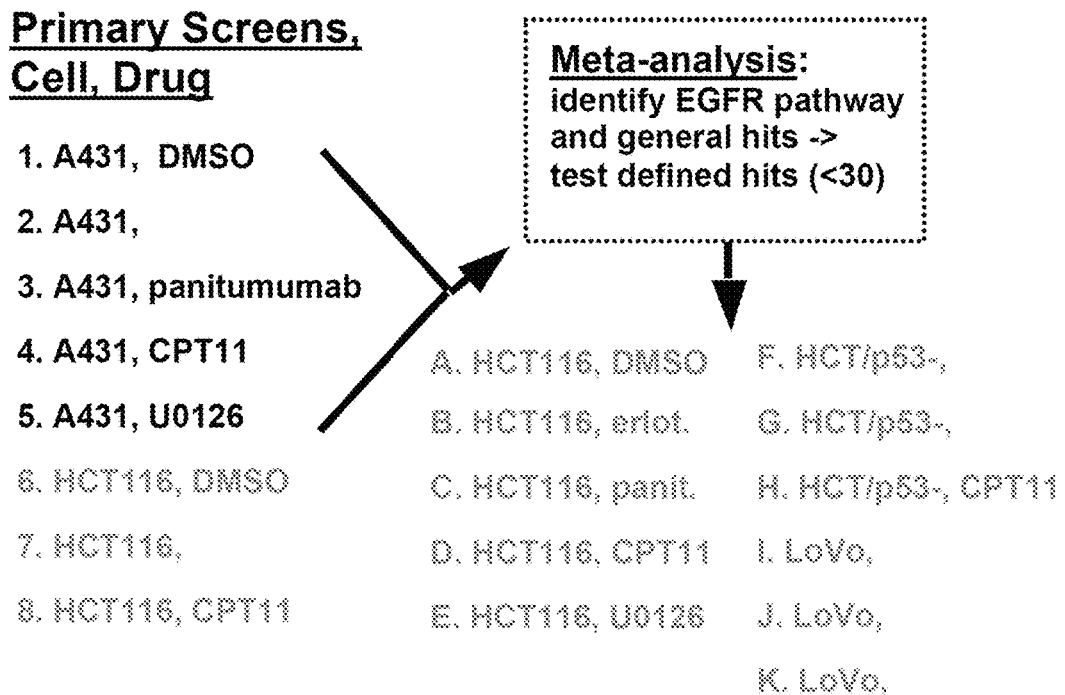
FIG. 4A. Primary screens, exploration of efficacy for validated hits.
Figure 4B:
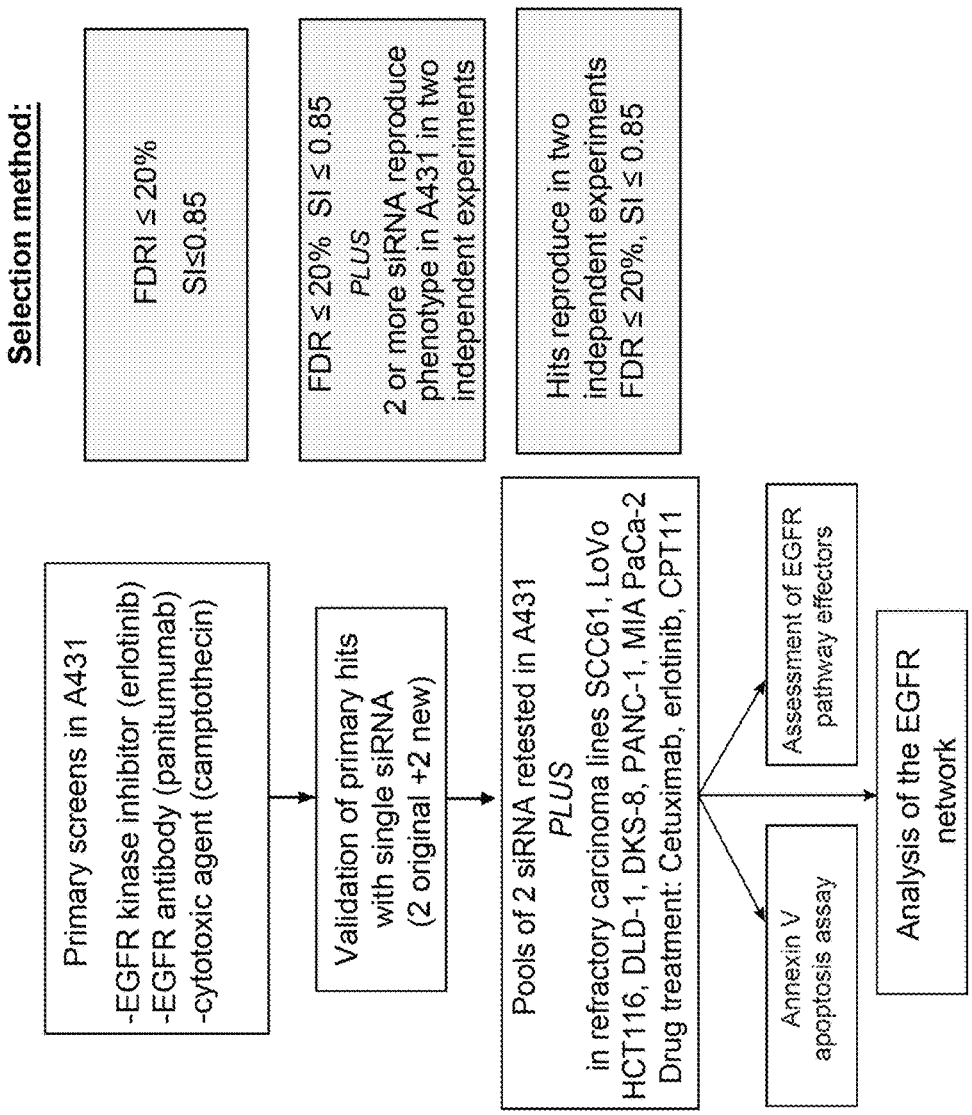
FIG. 4B. Knockdown of 39% (247/638) of genes in the library reduced the viability of DMSO-treated A431 cells by at least 15%, with 7% (45/638) reducing viability more than 30%. 214 primary hits (34% of the library), including 95 strong hits (15%, SI<0.7) sensitized to one or both EGFR-targeting agents. In contrast, 84 primary hits (13%), including 30 strong hits (5%, SI<0.7) were obtained that sensitized to the cytotoxic agent CPT11.

We are using these additional cell lines in two ways. For HCT116, we will repeat interactome library screens essentially as performed in the A431 cell line, using DMSO (vehicle), erlotinib, and CPT11. We will determine whether the overall landscape of hits is similar, or distinct. We anticipate that CPT11 may yield a similar profile in the two lines, while erlotinib may yield a different, extremely restricted, hit map. Hits arising from this screen that also were detected in the A431 line would obviously be of particular interest. Second, for selected, validated hits in the A431 cell line that are of specific interest based on the validation steps described below, we will selectively analyze these hits in HCT116 positive and negative for p53, and in LoVo cells. A summary of our complete set of screens is shown in FIG. 4.

Statistics for Preliminary Selection of Positives.

Positive candidates from the first 5 screens were selected based on standard approaches described in detail in (9) and Swanton et al. (9, 21). Specifically, the Alamar blue fluorescence intensity in the assay wells (R) read after 2 hours of incubation was normalized to the mean siControl (C) on each plate (R/C). The effect of drug treatment on viability was measured based on the normalized viabilities in the drug treated and vehicle wells using Limma (22), Limma borrows strength across genes based on an empirical Bayes approach and identifies statistically significant changes in viability by combining information from a set of gene-specific tests. We utilized the Limma implementation in the Open Source R/Bioconductor Package (available on the world wide web at bioconductor.org) (23), Hits were identified based on statistical significance as well as biological significance. Statistical significance was measured by p-values controlled for the false discovery rate (FDR) using the Benjamini-Hochberg step-up method (24) to account for multiple testing. Hits showing an FDR of less than the desired cut-off were considered statistically significant. The choice of the cut-off itself was flexible. Biological significance was measured by a change of at least 20% in viability relative to vehicle treated cells. Hits identified from each of the above filters were combined and a list of common hits showing greater statistical and biological significance (lower FDR and at least 20% change in viability) were identified.

Figure 5A:
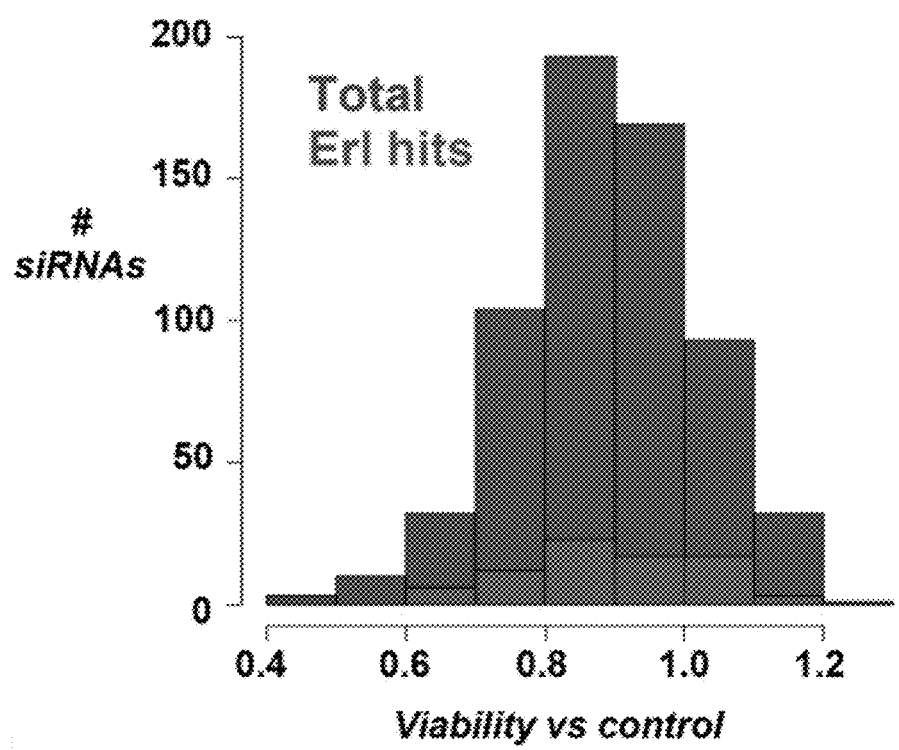
FIGS. 5A-5C. Distribution of hits in relation to effect of siRNA on cells treated with vehicle.

An initial question working with a custom library is whether a custom panel of siRNAs pre-selected to be relevant to EGFR signaling might contain many siRNAs that strongly inhibit cell growth even in the absence of drug treatment. FIG. 5 plots the baseline degree of growth inhibition for each of the siRNAs used in A431 cells treated with DMSO vehicle. From 638 genes, only 145 reduced cell growth more than 20%, 44 more than 30%, and 13 more than 40% (FIG. 5A). This profile contrasted favorably with results observed in the high throughput screening facility with other custom siRNA libraries such as a "cell cycle" library, in which a high percentage of the siRNAs significantly inhibited cell growth, and suggested that inhibition of the EGFR interactome siRNA targets did not induce broad cell cycle arrest or cell death absent drug treatment.

Figure 5B:
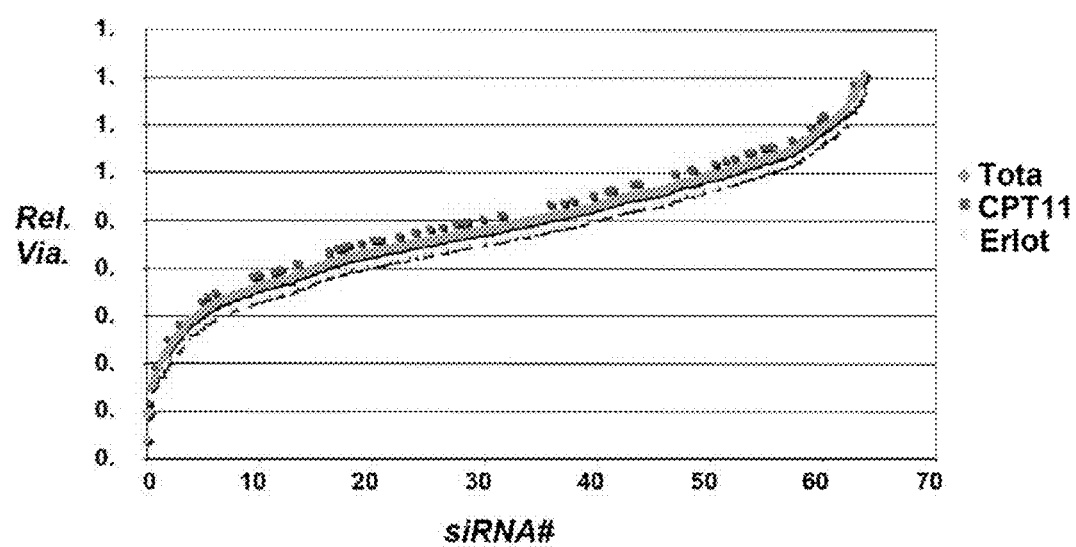
Figure 5C:
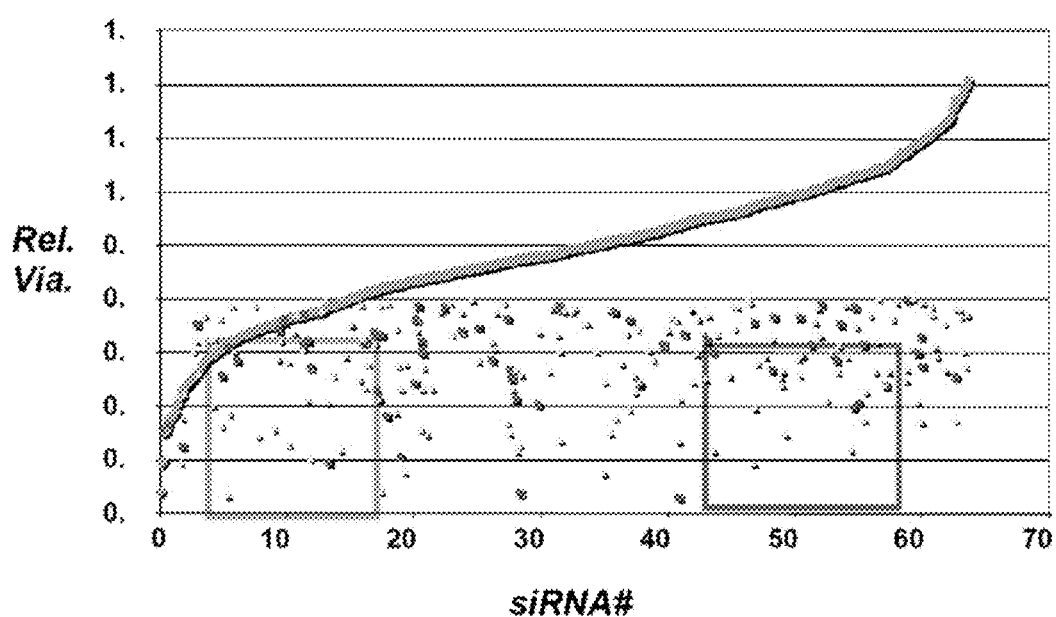

An important fundamental question in relationship of the likelihood of identifying drug sensitizing siRNAs that are useful in predicting a useful clinical strategy is, do the sensitizing siRNAs selectively emerge from the part of the library that intrinsically inhibits cell growth? Or in other words, does sensitization simply reflect the idea that an unhealthy cell is more likely to succumb to drug treatment, or are there specific siRNA-drug interactions? We compared the distribution of siRNAs selected as hits for erlotinib (FIGS. 5A, 5B) or CPT11 (FIG. 5B) versus the ability of the siRNA to reduce cell viability in cells treated only with DMSO (blue). FIG. 5A shows that sensitizing hits were found in bins containing siRNAs intrinsically inducing a 0.6-1.2 relative viability versus control-treated cells. FIG. 5B, which graphically represents all 638 siRNAs aligned from greatest inhibitory effect (left) to least (right) based on behavior with DMSO (blue line): CPT11 (red) and erlotinib (gold) hits are evenly distributed along the gradient. Importantly, FIG. 5C redraws FIG. 5B to indicate the degree of sensitization obtained with each siRNA. Strong hits (indicating those selectively reducing viability to 0.7 or less in the presence of drug versus DMSO) were found among siRNAs that had intrinsic activity in reducing cell growth (e.g., green box) and among those that had no such activity (e.g., purple box). siRNAs in the purple box particularly interesting for therapeutic development, as they possess no intrinsic toxicity, and exhibit specific dependence on drug treatment for efficacy.

Figure 6:
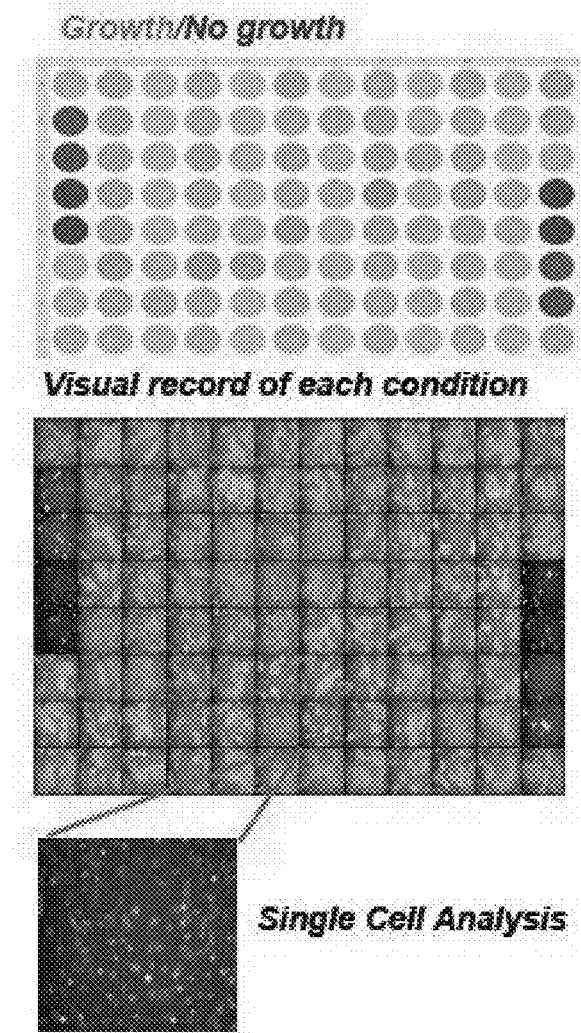
FIG. 6. Muliplexing of Cell Titer. Blue staining for viability (top) with ImageXpress for visualization of cells stained with Hoechst and calcein vital dyes.
Figure 7:
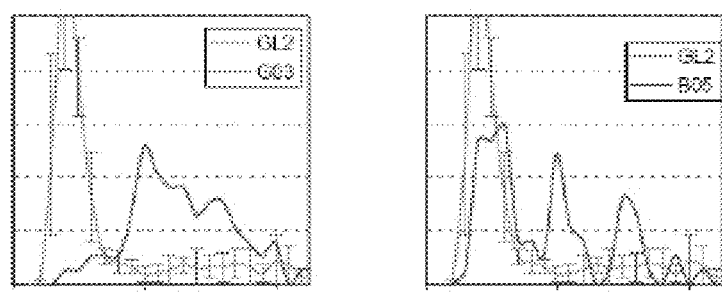
FIG. 7. Examples on ImageXpress cellular profiles. Green line represents trace of profile seen with siRNA negative control, as histogram of values for average nuclear staining with Hoechst. Red lines show generally increased (left) or periodically increased (right) staining, which correlates with DNA condensation, e.g., increased frequency of mitotic or apoptotic cells.

Microscopy-Based Analysis:

In addition to possessing high throughput robotics supporting a platereader, we also employed a Molecular Devices ImageXpress automated microscope. The ImageXpress captures 1-2 fields, representing 100-200 cells, for each individual well of a 96 well microtiter plate (see FIG. 6); time required to obtain readout from 22 plates in a single screen is typically 2-3 hours. The Acuity software used in association with this system is a sophisticated capture/analysis program for the acquired images; in addition, the system exports specified information classes in Excel format, for application of additional analytic approaches. This capacity allows us to record changes in cell spreading and morphology, or staining with specific indicator dyes and antibodies, as additional primary parameters indicating physiological response to an siRNA/drug combination. We have used calcein labeling to paint metabolically active, viable cells, and Hoechst to stain the DNA of all cells. It is clear that a subset of the siRNAs are inducing striking differences in calcein/Hoechst staining suggestive of specific biological responses to drug treatment (e.g., cytokinetic failure; see FIG. 7), yielding a potential hit list that is non-equivalent to the platereader-based hit list. Further analysis of this data is discussed below.

Initial Hits.

Table 2 summarizes the set of hits obtained to date based on screening the library with erlotinib, panitumumab, U0126, and CPT11, so far extracted solely from plate reader data. In each case the SI (sensitization index) value reflects reduction of Alamar blue signal in relation to the same siRNA used in combination with DMSO/vehicle. Taking as initial threshold for hit selection reduction of signal 20% below vehicle, 145 hits (representing a hit rate of 23% of the total library) were obtained with erlotinib, 19 (3%) with panitumumab, 55 (9%) with CPT11, and 7 (1%) with U0126.

Figure 8:
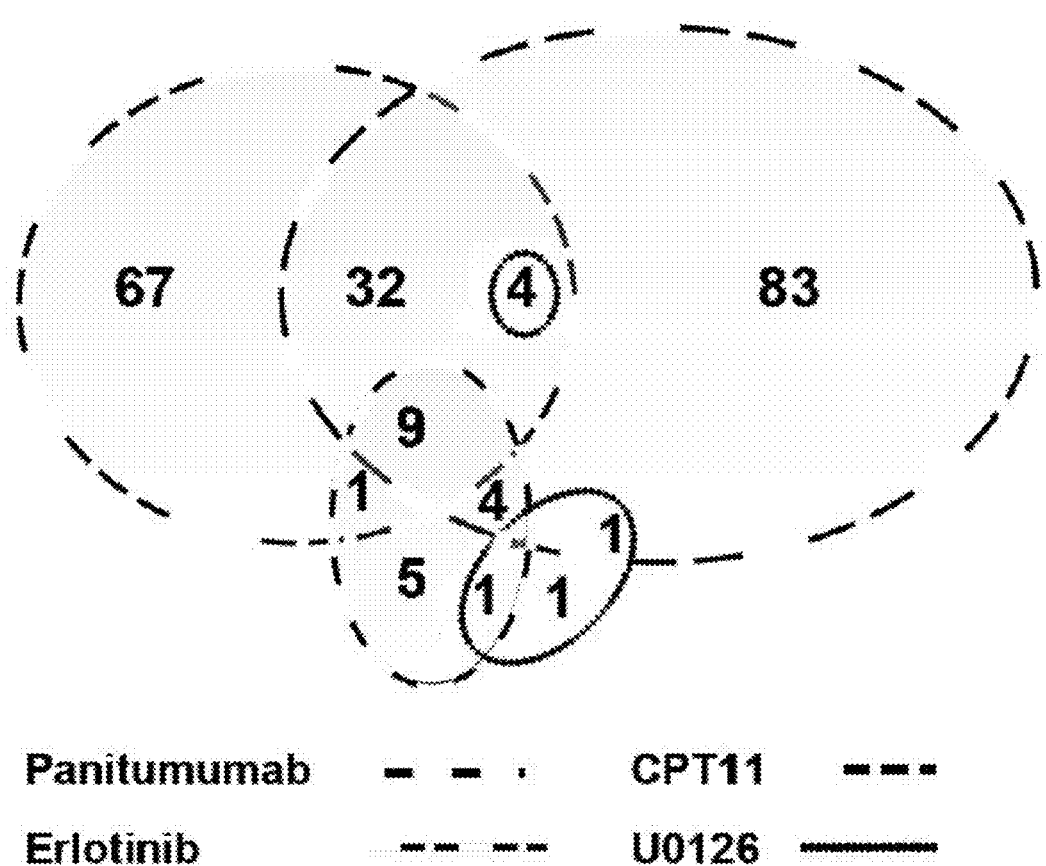
FIG. 8. Sensitization profile of screening hit list. 208 hits, 156 sensitized to one drug, 39 sensitized to two drugs, and 13 to three drugs.

Color-coding indicates a subset of hits that are identified with more than one drug treatment (Table 1; also see Venn Diagram, FIG. 8). In particular, the three classes of hits predicted—common for CPT11 and EGFR-pathway targeting, or specific to each class—were obtained. Hits highlighted in pink were found in common with erlotinib, panitumumab, and CPT11, and are taken to represent general survival factors. Hits highlighted in green were specific to CPT11, while hits highlighted in purple were specific for erlotinib and/or panitumumab. While U0126 yielded many fewer hits overall, all of the hits identified were found to overlap either with the general survival factor group, or the erlotinib/panitumumab group.

Analysis and Conclusions.

Figure 9A:
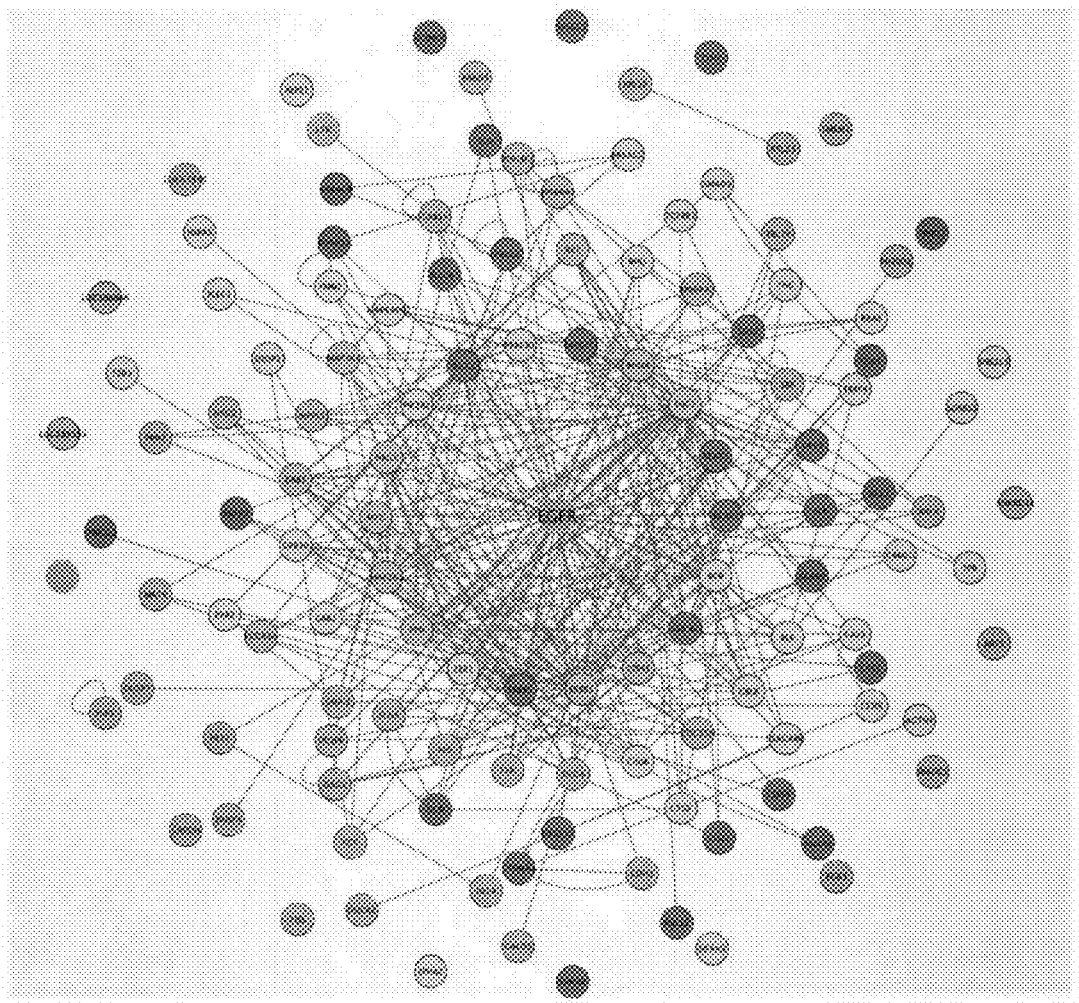
FIG. 9A: Cytoscape mapping of the profile of interactions among the screening hits.
Figure 10:
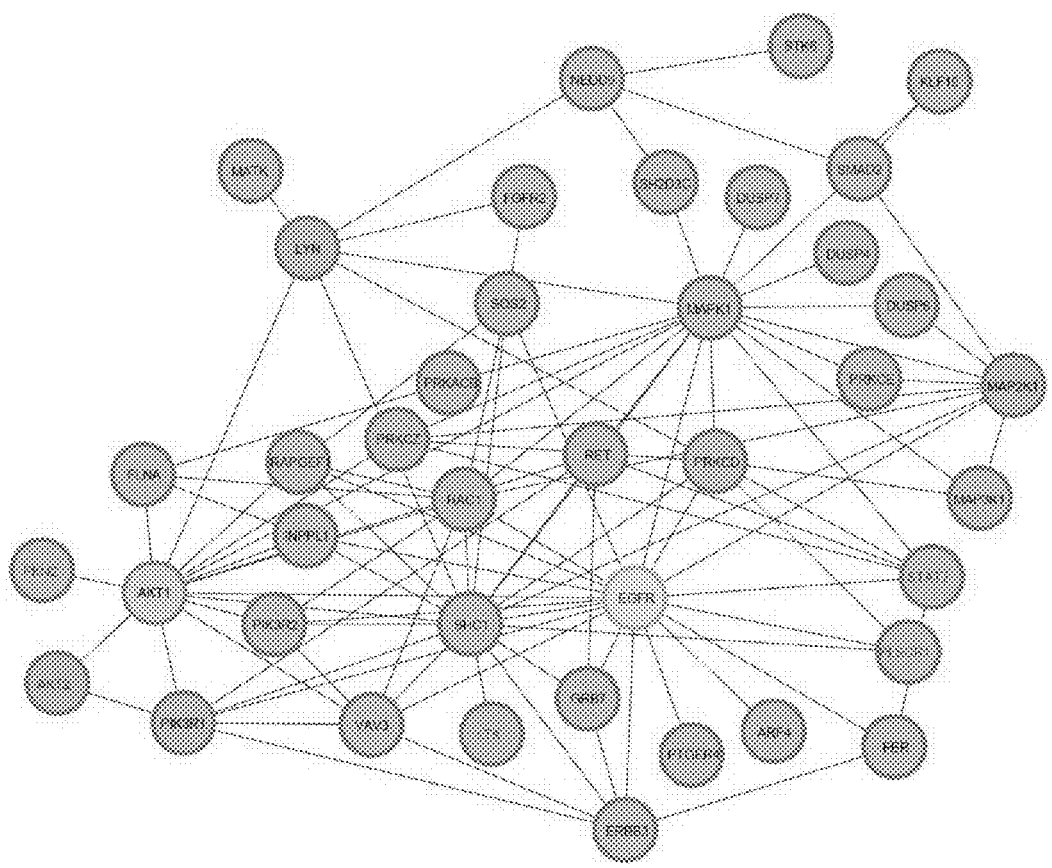
FIG. 10. A network view of connected EGFR interactome components.

We will also perform additional validation experiments described below. However, preliminary consideration of the hit profile obtained to date is suggestive in a number of ways that indicate the clinical relevance of this data. First, erlotinib and panitumumab yielded a large number of overlapping hits. This seems highly unlikely to be a random occurrence. Second, we have used the Cytoscape resource to map the profile of interactions among the screening hits (FIG. 9). A number of the hits that have emerged physically interact with each other, or are known to act in common signaling cascades. As one provocative example, ALK, BCAR1, BCAR3, and CXCL 12 are common components of an integrin-linked general survival pathway (25-27); siRNAs for these genes were identified as strong hits for both erlotinib and CPT11. Third, some siRNAs emerging as strong hits have been previously implicated as highly relevant to EGFR-dependent cell signaling, based mechanistic analyses performed in cell culture, and in some cases demonstrations of resistance factors in tumors. Examples of these include ERBB3 (28,29), PLCG2, and specific protein kinase C family members (30).

We have also identified a set of siRNAs that induce resistance to erlotinib, panitumumab, and CPT11. These include siRNAs that have little or no effect on the viability of cells treated solely with vehicle. However, these siRNAs reduce the ability of panitumumab and/or other agents to decrease cell viability. It appears such genes may target suicide pathways specifically triggered by drug treatment, and as such, these genes may also be valuable for exploitation to improve therapy. Further study of these genes will also inform our understanding of drug resistance mechanisms.

Example 2

Screening Additional Cell Lines for Altered Sensitivity

There is an emerging consensus that a significant degree of the resistance to EGFR-targeting agents is due to activating mutations in K-Ras or B-Raf. Because of the central role of Ras in modulating apoptosis, these mutations may similarly confer resistance to agents such as irenotecan. Following screening and hit validation in the A431 cell line we will perform two classes of screen in colorectal cancer cell lines with mutated K-Ras (HCT116, LoVo) or B-Raf (e.g, WiDr, TCO. First, we will use the same regimen of comparing DMSO, erlotinib, and CPT11 screens as described above for A431 cells, but instead use HCT116 cells to identify a validated sensitization network. Second, we will take all validated hits from the A431 and HCT116 screens, and test them for sensitization in the LoVo and WiDr cell lines.

A relatively small subset of A431-predicted sensitizing siRNAs will be active in conjunction with erlotinib in the resistant cell lines. Among these, siRNAs identified as broadly sensitizing (to erlotinib as well as CPT11), are likely to maintain activity. A higher percentage of the siRNAs identified as sensitizing solely to CPT11 would maintain activity. It also appears that siRNAs targeting genes "upstream" of KRas would be less likely to function in K-Ras mutated lines than siRNAs targeting genes "downstream", or in independent signaling pathways.

Sensitizing siRNAs will be identified for erlotinib and/or CPT11, but they will be very different from those identified with A431 cells. This outcome would initially suggest that some mRNAs for sensitizers well expressed in A431 cells are not present in HCT116 and other model cell lines, and vice versa. This could be immediately tested with qRT-PCR; if so, sensitization strategies will be tailored based on cell lineage. Regardless of outcome, the results of these experiments will facilitate identification of the factors controlling resistance as a factor of drug resistance network function.

Example 3

Identification of the Network Structure of the Validated Hits

The sensitization network construction shown in FIG. 8 will be refined and expanded. We will create a "live", interactive resource, with each hit portrayed as a clickable "node" linked back to full information for the gene, and each interaction among hits as a clickable "edge" linked to full information describing the validation of the interaction. We will systematically compare the networks in the sensitive versus resistant cell line. We will compare the properties of the networks conferring resistance to EGFR-targeting agents, CPT11, or both. We will compare the networks of genes sensitizing to erlotinib, panitumumab, and U0126, to gain insight into the epistatic interactions regulating cell survival following inhibition at different stages of the EGFR-Ras-Raf-MEK1 signaling pathway.

Example 4

Identification of "Complementation Groups" that can be Targeted in Parallel to Achieve Super-Sensitization Complementation groups define sets of genes whose protein products work in a single pathway or multi-protein complex, providing a single chain of input into a biological endpoint. In synthetic lethal analysis, targeting two members of the same complementation group will not enhance the endpoint phenotype, but targeting two members of different complementation groups, which provide parallel input into the biological endpoint, will enhance the final phenotype. The network mapping analysis described above has the potential to identify important "sensitization complementation groups", which we define as small clusters of proteins known to physically interact with each other, or act in proximity on a sub-pathway: the BCAR1-BCAR3-CXCL 12-ALK cluster would define one such group. After segmentation of the hit network into proposed complementation groups, we would determine the consequences for sensitization of simultaneously targeting two siRNAs within the same group (e.g., BCAR1 and BCAR3) versus different groups (e.g., BCAR1 and BCL3). We will thus identify synergistic interactions that can greatly sensitize cells to the effect of treatment with EGFR-targeting agents, CPT11, or potentially both.

Example 5

Extrapolation from siRNA-Based Sensitization to Drug-Based Sensitization

The set of genes included in the EGFR interactome includes many plasma membrane associated receptors and kinases that had already drawn clinical interest, and for which small molecule and/or antibody inhibitory agents already exist. Some of these inhibitory agents have already passed through Phase I/II trials, and are being effectively used in the clinic. First, we will test whether combination of the siRNA-matched drug with erlotinib (and panitumumab, or CPT11, as appropriate) produces a notable synergistic effect using Alamar blue assay to detect reduced viability in A431 and HCT116 cells. We will determine whether the erlotinib-drug combination has a similar mode of action (see Example 6) as the erlotinib-siRNA combination. We will use the A431 and/or HCT116 cell lines to establish xenografts in nude mice, and erlotinib-drug combination in vivo synergy. This analysis provides the means to rapidly identify valuable synergies that would be immediately translatable to the clinic.

Example 6

Elucidation of the Mode of Action of Sensitizer siRNAs

We will first assess if siRNAs directly affect the expression, activation, or localization of the EGFR receptor itself. We will use antibodies to EGFR and phospho(active) EGFR in Western analysis of cell lysates treated with each siRNA, to look for siRNA-dependent loss of signal. We will use antibody to EGFR and the early endosomal marker EEA 1 in immunofluorescence experiments to determine whether siRNAs induce increased internalization of EGFR from the cell surface. As part of microscope-based analysis, we will also determine whether siRNAs specifically alter the morphology (attachment; cytoskeletal integrity) of drug-treated cells. Reciprocally, we will also determine whether EGFR signaling regulates the genes targeted by the sensitizing siRNAs. We will use qRT-PCR to determine whether treatment of quiescent cells with EGFR stimulates expression of the sensitizing genes, and whether treatment of actively growing cells with panitumumab or erlotinib influences expression of these genes. We will also use FACS and/or Guava analysis to measure whether specific siRNAs confer cell cycle arrest and/or apoptosis.

Example 7

Microscope-Based Analysis of Cells Following Identification of Hits Detected by Reduced Alamar Blue Signal A complete database of images of calcein- and Hoechst-stained cells from experiments performed in exact parallel with the Alamar blue values (FIGS. 5 and 6) is being assembled. As noted above, even cursory analysis has indicated that some of the siRNAs are producing unusual patterns suggestive of cytokinetic blocks, early stages of apoptosis, unusual cell morphology, etc, and that some of these hits are nonequivalent to those identified by searching for loss of Alamar blue signal. We will extend this analysis in several ways. First, we will run a series of controls (drug treatments, siRNA treatment) known to induce the specific biological endpoints (cytokinetic block, etc) that we believe are suggested by the data, and compare profiles. We will analyze overall cell population properties using the Acuity software associated with the high throughput microscope, and also use customized analysis developed together with the FCCC Biostatistical facility to quantitate the appearance of sub-groups within the larger profiles.

The congruence of specific endpoint phenotypes (cytokinetic block; reduction in cell spreading; etc) with the overall Alamar blue hit list can be established. We will also validate the hits by a similar strategy to that used above for Alamar blue hits, i.e., regenerating the phenotypes with independent siRNAs, and confirming that degree of mRNA depletion of target correlates with degree of induction of the phenotype. This analysis is extremely likely to result in the addition of new siRNAs to the hit list, i.e., siRNAs that induce phenotypes that are ultimately likely to result in cell death, but which have sufficiently delayed action that moribund cells did not score as positive using Alamar blue-based cutoff values.

Next, we will repeat the network construction analysis described above (Examples 3 and 4). This will be done in two ways: by analyzing the expanded network (Alamar blue hits+microscope hits), and by analyzing networks associated with specific phenotypic endpoints. This can extend definition of sensitization clusters/complementation groups, and may bring more druggable (or already drugged) targets into the groups. It will also illuminate the mechanism by which sensitization is induced. As a hypothetical example, one cluster of closely interacting proteins includes some with strong Alamar blue sensitization to erlotinib, and several members that induce loss of cell area only in cells treated with erlotinib. This might imply the entire group is functionally antagonizing the integrin-dependent cell adhesion machinery, and that antibodies generally antagonizing this process might be of interest for exploring experimental synergies with erlotinib.

Example 8

Treatment of Additional Cancer Types in the Clinic with EGFR-Targeting Agents and/or Irenotecan Besides colorectal cancer, lung cancers, head and neck cancers, and a number of other types of cancer respond to EGFR-targeting agents and/or irenotecan. However, because of differences in cell lineage, these cells will not express an identical complement of proteins as colorectal tumors, implying that their cell signaling/cell survival networks will be non-equivalent. Hence, a subset of the siRNAs that sensitize colorectal tumor cells to EGFR-targeting agents in colorectal cells may not be active in other tumor types, while additional sensitizing siRNAs may be detected in screens of these tumors. We will focus on lung cancer cell lines as a first counter-model to compare with A431 and HCT116 data, and essentially parallel the three Validation Steps outlined above. For the collection of validated hits from A431 and HCT116 screening, we will first use qRT-PCR to determine if the mRNAs are expressed in two erlotinib-sensitive and two K-Ras-mutated, erlotinib resistant lung cancer cell lines. We will then determine what percent of the expressed siRNAs are sensitizing in the lung cancer cell lines. If a significant percentage of A431/HCT116 hits maintain function in lung cancer cell lines, such hits are relevant for improved chemotherapy, particularly if they include siRNAs depleting proteins with existing clinical agents (as discussed in Example 5). If only a very limited number of hits are found to be functional, we will instead repeat the primary screens outlined above, to define the sensitization network of lung cancer tumors. We note this last experiment is of interest in its own right as an inquiry into the basic properties of alternative network construction.

Example 9

Identification of Additional Drugs which Show Promising Experimental Synergies with EGFR-Targeting Agents Although preclinical and clinical analyses are empirically establishing useful synergies between erlotinib or EGFR-targeting antibodies and drugs targeting the mTOR pathway, such as rapamycin or temsirolimus (Costa, 2007; Jimeno, 2007; Buck, 2006, IGF Morgillo, 2006), and other high-value targets, it is currently largely unknown as to which EGFR-dependent signaling pathways contribute to the sensitization. Using the EGFR interactome library, we can rapidly establish this point, using a strategy similar to that outlined for primary screening above to look for a network of sensitizers to selected drugs in the A431 and HCT116 colorectal cancer cell lines. This screen should identify a number of the hits already identified as common sensitizers to erlotinib, panitumumab, and CPT11, but may also identify a sub-network (sensitization complementation group) of hits that is specific to inhibition by the new test drug.

interfering molecules, agents already known to inhibit their function, (e.g., commercially available and clinically safe phosphatase and kinase inhibitors or the small siRNAs interfering molecules described herein.

TABLE A

| Gene Target | Class of inhibitor | Colorectal cancer #cetuximab | HNSCC cetuximab or erlotinib | Lung erlotinib | Pancreas erlotinib or cetuximab | Glioma erlotinib | Breast lapatinib | Other cancers cetuximab, erlotinib, lapatinib |
|---|---|---|---|---|---|---|---|---|
| ANXA6 | Interfering small molecule | 1* | 1 | 1 | | 1 | 1 | |
| ARF4; ARF5 | Ribosyltransferase inhibitor | 1 | 1 | 1 | 1 | 1 | 1 | |
| ASCL2 | Transcription factor inhibitor | 1 | 1 | 1 | 1 | 1 | 1 | Important in ovarian cancer |
| CD59 | Antibody to CD59 | 0 | 1 | 2 | 2 | 0 | 1 | |
| DIXDC1 | Interferring small molecule | 1 | 1 | 1 | 1 | 1 | 1 | |
| DUSP4 | Phosphatase inhibitor | 1 | 1 | 1 | 1 | 1 | 1 | |
| DUSP6 | Phosphatase inhibitor | 2 | 1 | 1 | 1 | 1 | 1 | |
| DUSP7 | Phosphatase inhibitor | 1 | 1 | 1 | 1 | 1 | 1 | |
| FER | Kinase inhibitor | 2 | 1 | 1 | 1 | 1 | 1 | |
| MATK | Kinase inhibitor | 4 | 4 | 4 | 4 | 2 | 1 | |
| NEDD9 | Interfering small molecule | 1 | 1 | 1 | 1 | 1 | 1 | |
| PRIAP19/ SLP1 | Interfering small molecule | 0 | 0 | 1 | 1 | 1 | 1 | Important in ovarian and endometrial cancer |
| PRKACB | Kinase inhibitor | 2 | 3 | 2 | 2 | 4 | 1 | |
| RAPGEF1 | Small molecule inhibitor | 2 | 1 | 1 | 2 | 1 | 1 | |
| SC4MOL | Cholesterol synthesis inhibitor | 1 | 1 | 1 | 1 | 1 | 1 | |
| SH2DC3 | Interfering small molecule | 1 | 1 | 1 | 1 | 1 | 1 | |

*numbers represent expression levels
anti-EGFR agents (cetuximab, erlotinib, and/or lapatinib) to be used in combinations with agents downregulating gene targets listed in column 1

Example 10

Preferred Combinations for the Treatment of Different Cancer Types

The table below provides 16 genes and combinations of agents which should have efficacy for the treatment of the indicated cancer types. Anti-EGFr drugs (cetuximab, an anti-EGFR antibody; erlotinib, lapatinib or any tyrosine kinase inhibitor specific for the EGFR kinase) can be combined with either existing or potentially available inhibitors of the 16 targets presented. In general, cetuximab is used in colorectal, lung, head and neck (HNSCC). Erlotinib is used in lung, pancreas. Potentially, cetuximab or any other anti-EGFR antibody can be approved for lung cancer (NSCLC), and cancer of the pancreas. Lapatinib is preferred for combination treatment of breast, and ovarian cancers. The gene target activity may be inhibited using small Example 11

Generation of Biomarkers that Predict Patient Response to Treatment

One of the most important uses of the information generated from this study will be as a guide to select patients likely to respond to EGFR-centered treatments. Patients with tumors expressing high levels of the mRNAs and proteins targeted by sensitization hits would prove to be resistant to therapy, while patients with low levels of these mRNAs and proteins might be excellent candidates for treatment with the synergistic combination described herein. Additionally, it will be more informative and better exploit the sensitization network that we have identified if we screen tumors for the expression of sets of sensitizing hits, rather than "cherrypicking" a small number of individual hits. Already, hits of clinical relevance have been identified. We will use these genes to generate a screening chip; alternatively, we can generate a Taqman primer set for qRT-PCR. We will then employ a set of at least 10 pre-treatment colorectal tumors from patients who responded to EGFR-targeted therapy, and a matching set of non-responder tumors, and we will systematically compare the expression of the sensitization panel.

Example 12

As described above, we have developed a protein network centered on the highly validated target EGFR, and used siRNA screening to comparatively probe this network for proteins that regulate the effectiveness of both EGFR-targeted and chemotherapeutic agents. This approach identified sub-networks of proteins influencing resistance, with hits enriched among first order protein interactors of the network seeds. Extrapolation from the network structure led to the identification of synergy between EGFR antagonists and drugs targeting PRKC, STAT3, and AURKA, suggesting a direct path to clinical exploitation of study results. Such a focused approach has significant potential to enhance the future coherent design of combination therapies.

A robust network paradigm has critical implications for targeted cancer therapies, predicting that in cells treated with therapies inhibiting an oncogenic node, rescue signaling can be provided by modifying signaling output from any of a number of distinct proteins that are components of a web of interactions centered around the target of inhibition. This concept is reinforced by studies in model organisms demonstrating that quantitatively significant signal-modulating relationships commonly involve proteins that have closely linked functions. In this example, we describe additional regulators of resistance to EGFR-targeted therapies, which can be used to clinical advantage to overcome therapeutic resistance.

Figure 11A:
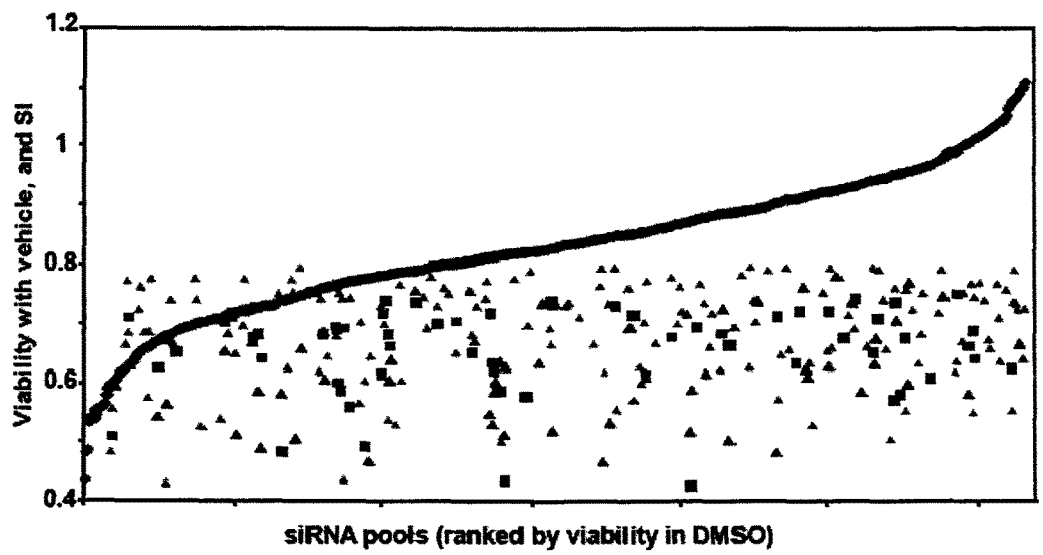
FIG. 11A: Design and screening of a targeted library. Distribution of hits as a factor of overall viability reduction with the siRNA. siRNAs in library are listed in order of intrinsic impact on viability of A431 cells treated with DMSO (gray line). Blue triangles, sensitization index (SI) for primary hits with erlotinib; red triangles, SI for validated hits with erlotinib; green squares, SI for primary hits with CPT11.
Figure 11B:
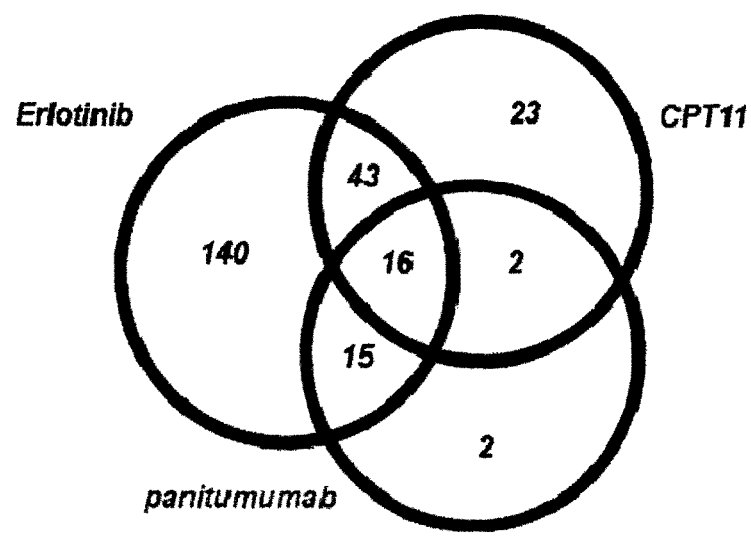
FIG. 11B: Degree of overlap between primary hits obtained for erlotinib, panitumumab, and CPT11.
Figure 11C:
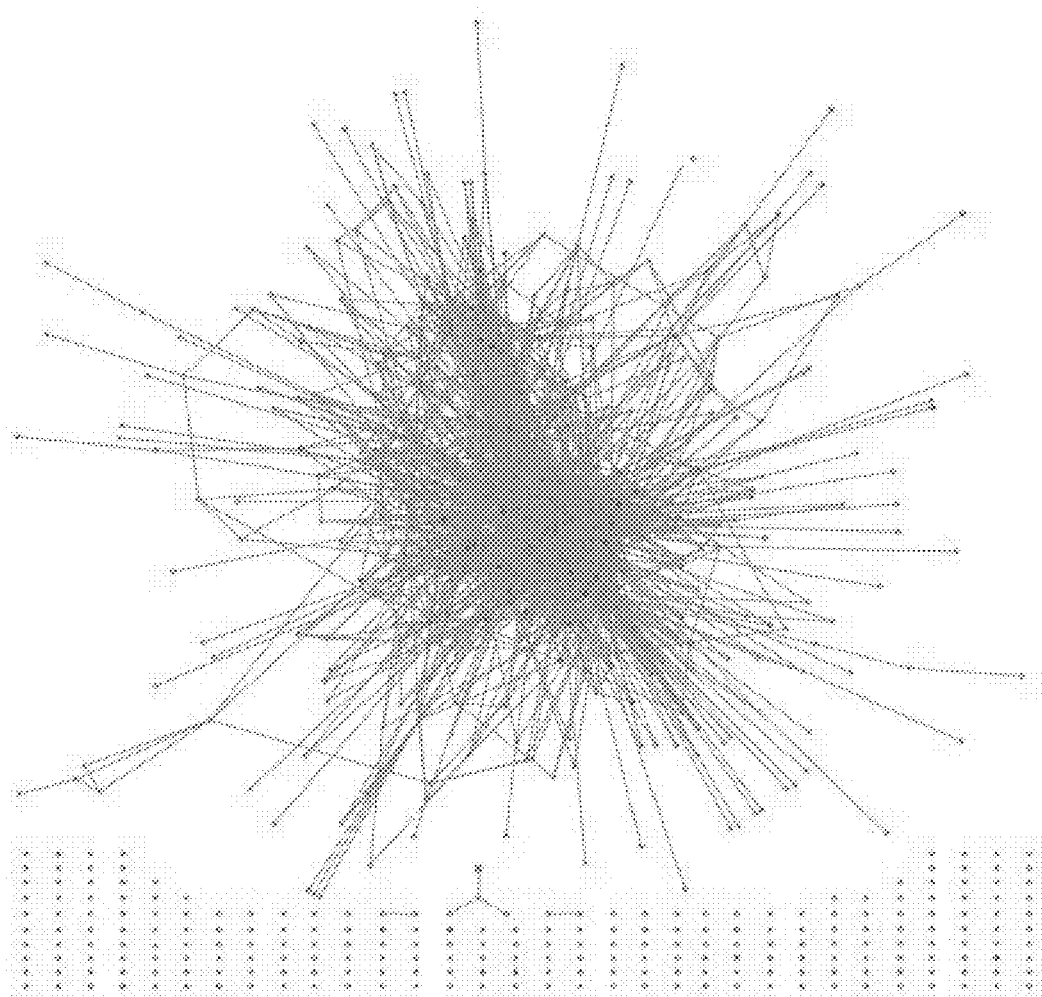
FIG. 11C: Network of validated (red circles) hits sensitizing to EGFR-targeting agents, in the context of the full library. Lines (edges) represent connections based on direct protein-protein interactions or genetic interactions in Drosophila.

As described in Example 1, the A431 cervical adenocarcinoma cell line is highly dependent on EGFR pathway signaling. This cell line was reiteratively screened with the targeted siRNA library used in combination with DMSO (vehicle), or with EGFR-targeting small molecule and antibody inhibitors, or the non-specific cytotoxic agent camptothecin (CPT11) applied at $IC_{25}$-$IC_{35}$ concentrations. Primary hits were defined as siRNAs reducing negative control-normalized viability by at least 15% in the presence of a drug compared to DMSO (defined as the Sensitization Index (SI<0.85), with a false discovery rate (FDR)<20%. The distribution of primary hits was independent of the tendency of a siRNA to affect cell viability in the absence of drug treatment (FIG. 11A). The vast majority of hits obtained with an EGFR-targeting antibody were included within the larger set of EGFR-targeting small molecule hits (FIG. 11B). Subsequent validations confirmed a set of 61 genes (Table B) sensitizing to EGFR-targeting agents in which 2 or more of 4 independent siRNAs recapitulated sensitization to erlotinib. The majority of sensitizing hits (48/61) encoded proteins connected in a physically interacting network (FIG. 11C). The remaining 13 encoded proteins are not known to interact physically with EGFR or its direct partners, but instead are linked to EGFR based on transcriptional response to pathway manipulation.

TABLE B

Validated screen hits.

| Symbol | ID | Gene Description | Origin | Clinical agent |
|---|---|---|---|---|
| ABL1 | 25 | v-abl Abelson murine leukemia viral oncogene homolog 1 | PPI1 | Imatinib, dasatinib |
| AKT2 | 208 | v-akt murine thymoma viral oncogene homolog 2 | PG | Perifosine, triciribine, GSK690693 |
| ANXA6 | 309 | annexin A6 | C, PPI2 | |
| APP | 351 | amyloid beta (A4) precursor protein (peptidase nexin-II, Alzheimer disease) | PPI1 | |
| ARF4 | 378 | ADP-ribosylation factor 4 | PM, PPI1 | |
| ARF5 | 381 | ADP-ribosylation factor 5 | PG | |
| ASCL2 | 430 | achaete-scute complex homolog 2 (*Drosophila*) | PPI2, DG | |
| BCAR1 | 9564 | breast cancer anti-estrogen resistance 1 | PM, C, PPI1 | |
| CALM1 | 801 | calmodulin 1 (phosphorylase kinase, delta) | C PPI1 | phenothiazines |
| CBLC | 23624 | Cas-Br-M (murine) ecotropic retroviral transforming sequence c | PM PPI1 | |
| CCND1 | 595 | cyclin D1 | PM, PPI2 | |
| CD59 | 966 | CD59 molecule, complement regulatory protein | C, PPI2 | Roche, Preclinical |
| CDH3 | 1001 | cadherin 3, type 1, P-cadherin (placental) | PG | |
| CXCL12 | 6387 | chemokine (C-X-C motif) ligand 12 (stromal cell-derived factor 1) | MA | |
| DCN | 1634 | decorin | PPI1 | |
| DDR2 | 4921 | discoidin domain receptor family, member 2 | PPI1 | |
| DIXDC1 | 85458 | DIX domain containing 1 | MA | |
| DLG4 | 1742 | discs, large homolog 4 (*Drosophila*) | PPI1 | |
| DUSP4 | 1846 | dual specificity phosphatase 4 | MA | |
| DUSP6 | 1848 | dual specificity phosphatase 6 | DG | |
| DUSP7 | 1849 | dual specificity phosphatase 7 | DG | |
| EPHA5 | 2044 | EPH receptor A5 | PG | |
| ERBB3 | 2065 | v-erb-b2 erythroblastic leukemia viral oncogene homolog 3 (avian) | PM, PPI1, DG | antibodies, e.g. MM-121 |
| FER | 2241 | fer (fps/fes related) tyrosine kinase (phosphoprotein NCP94) | PPI1 | |
| FGFR2 | 2263 | fibroblast growth factor receptor 2 (bacteria-expressed kinase, keratinocyte | DG | e.g. brivanib, masitinib, TKI258, PHA-739358 |
| FLNA | 2316 | filamin PG, alpha (actin binding protein 280) | C, PPI2 | |
| GRB7 | 2886 | growth factor receptor-bound protein 7 | PM, PPI1 | |
| HSPA9 | 3313 | heat shock 70 kDa protein 9 (mortalin) | C, PPI2 | |
| INPPL1 | 3636 | inositol polyphosphate phosphatase-like 1 | PM, PPI1 | |
| KLF10 | 7071 | Kruppel-like factor 10 | MA | |
| LOC284393 | 284393 | similar to ribosomal protein L10 | PG | |

TABLE B-continued

Validated screen hits.

| Symbol | ID | Gene Description | Origin | Clinical agent |
|---|---|---|---|---|
| LOC63920 | 63920 | transposon-derived Buster3 transposase-like | MA | |
| LTK | 4058 | leukocyte tyrosine kinase | PPI1 | |
| MAP3K1 | 4214 | mitogen-activated protein kinase kinase kinase 1 | PM, PPI2 | |
| MAPK1 | 5594 | mitogen-activated protein kinase 1 | PM, PPI1 | |
| MATK | 4145 | megakaryocyte-associated tyrosine kinase | PM, PPI1 | |
| NEDD9 | 4739 | neural precursor cell expressed, developmentally down-regulated 9 | PPI1 | |
| PIK3R1 | 5295 | phosphoinositide-3-kinase, regulatory subunit 1 (p85 alpha) | PM, PPI1 | e.g. PX-866, BGT226, GDC-0941, XL765 |
| PIK3R2 | 5296 | phosphoinositide-3-kinase, regulatory subunit 2 (p85 beta) | PM, PPI1 | |
| PIN1 | 5300 | protein (peptidylprolyl cis/trans isomerase) NIMA-interacting 1 | PM | |
| PKN2 | 5586 | protein kinase N2 | PM, PPI2 | |
| PLSCR1 | 5359 | phospholipid scramblase 1 | PM, PPI1, MA | |
| PPIA | 5478 | peptidylprolyl isomerase PG (cyclophilin PG) | C, PPI2 | |
| PRKACB | 5567 | protein kinase, cAMP-dependent, catalytic, beta | PG | |
| PRKCD | 5580 | protein kinase C, delta | PM, PPI1 | ruboxistaurin, |
| PRKCE | 5581 | protein kinase C, epsilon | PM, PPI2 | enzastaurin, |
| PRKCZ | 5590 | protein kinase C, zeta | PM, PPI2 | tamoxifen |
| RAC1 | 5879 | ras-related C3 botulinum toxin substrate 1 (rho family, small GTP binding protein | PM, PPI2 | |
| RACGAP1 | 29127 | Rac GTPase activating protein 1 | C, PPI2 | |
| RAPGEF1 | 2889 | Rap guanine nucleotide exchange factor (GEF) 1 | PPI1 | |
| RASA3 | 22821 | RAS p21 protein activator 3 | DG | |
| RET | 5979 | ret proto-oncogene | PPI1, M2 | valdetanib |
| RPS6KA5 | 9252 | ribosomal protein S6 kinase, 90 kDa, polypeptide 5 | PM | ruboxistaurin |
| SC4MOL | 6307 | sterol-C4-methyl oxidase-like | MA | |
| SH2D3C | 10044 | SH2 domain containing 3C | PM, PPI1 | |
| SHC1 | 6464 | SHC (Src homology 2 domain containing) transforming protein 1 | PM, C, PPI1, DG | |
| SMAD2 | 4087 | SMAD family member 2 | PM, PPI1 | peptide 144 targets TGFβ1RIII |
| SOS2 | 6655 | son of sevenless homolog 2 (*Drosophila*) | PM, PPI1, DG | |
| STAT3 | 6774 | signal transducer and activator of transcription 3 (acute-phase response | PM, C, PPI1 | STAT 3 decoy oligo |
| TBL1Y | 90665 | transducin (beta)-like 1Y-linked | DG | |
| VAV3 | 10451 | vav 3 oncogene | PM, C, PPI1 | |

Figure 12A:
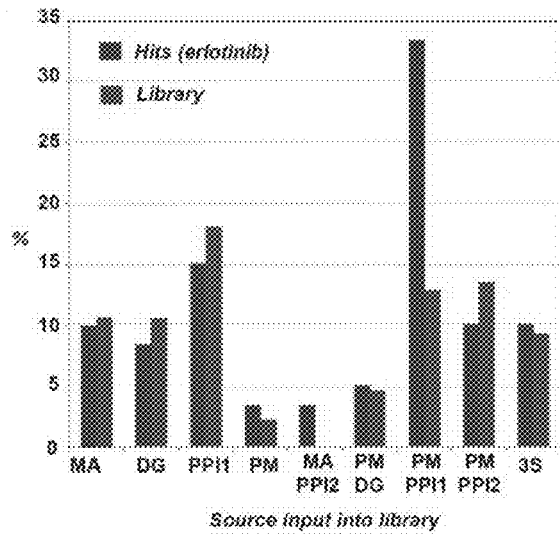
FIG. 12A: Network properties of hits. Hits by source of input in library. MA, microarray indicates transcriptionally responsive to EGFR; DG, Drosophila genetics; PPI1, direct protein interactions with seeds; PM, pathway maps; PPI2, direct protein interactions with a protein within the PPI1 group, or found in a complex with seed proteins; 3S, any 3 sources combined.
Figure 12B:
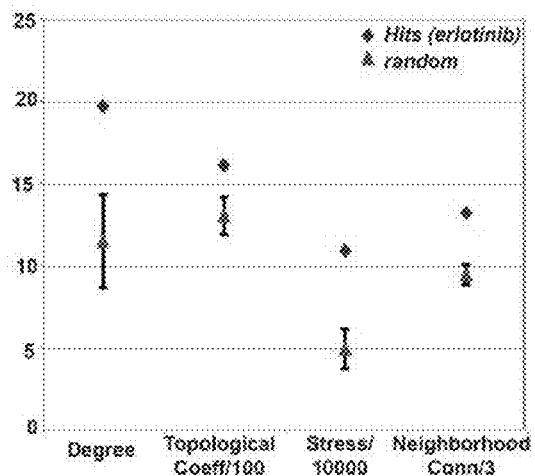
FIG. 12B: Topological analysis of erlotinib hit network identified in A431 cells. Data shown represents difference between properties of the set of 61 validated hits and the average for 20 randomly generated sets of 61 genes from the library. Measures including degree, topological coefficient, stress, and neighborhood connectivity (see Methods) in each case show highly significant enrichment for hits validated with erlotinib, with the error bars for the random set data reflecting a 99% confidence interval.
Figure 12D:
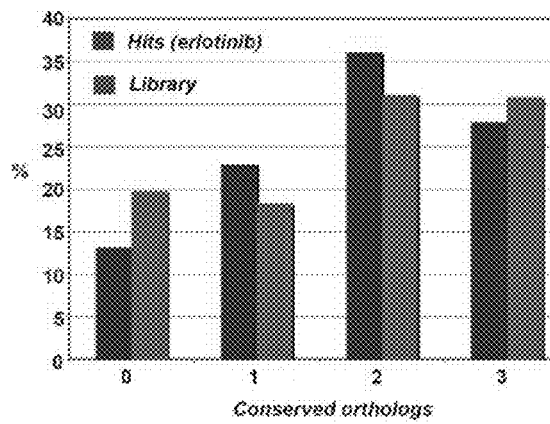
FIG. 12D: Percentage of hits versus library proteins having a recognized ortholog in S. cerevisiae, C. elegans, or D. melanogaster. X axis, the number of species (among listed) having a recognized ortholog.
Figure 12C:
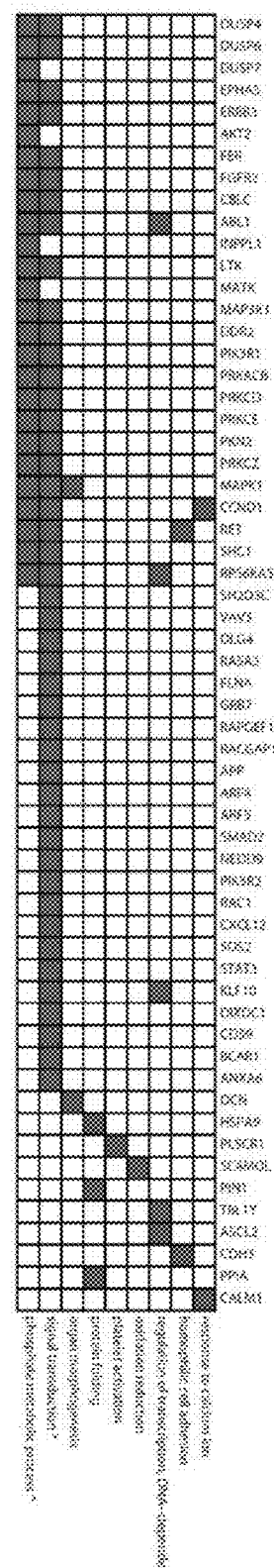
FIG. 12C: Enriched GO classifications identified among hits. Enrichment is highly significant for proteins annotated as involved in phosphate metabolism and signal transduction (as shown by *, p<0.01).

In analyzing the erlotinib-sensitizing hits in comparison to the overall properties of the 638-gene library, there was a highly significant enrichment for genes that were first order PPIs of the seeds, and were also nominated by pathway maps (FIG. 12A). The erlotinib-sensitizing hits were also significantly more likely to have topology parameters distinct from the overall network, suggesting a higher degree of connectivity for these nodes (FIG. 12B). Based on their GO function, erlotinib-sensitizing hits were enriched for proteins classified as involved in phosphate metabolism (kinases or phosphatases) and signal transduction (FIG. 12C) with p value cut-off of 0.01. Validated hits were equally likely to occur among siRNAs that independently reduced cell viability, or had little effect on cell growth in the absence of drug treatment. A weak trend was observed for hits to be evolutionarily conserved, as reflected by the presence one or more defined orthologs in lower eukaryotes than genes in the overall library (FIG. 12D).

Figure 13A:
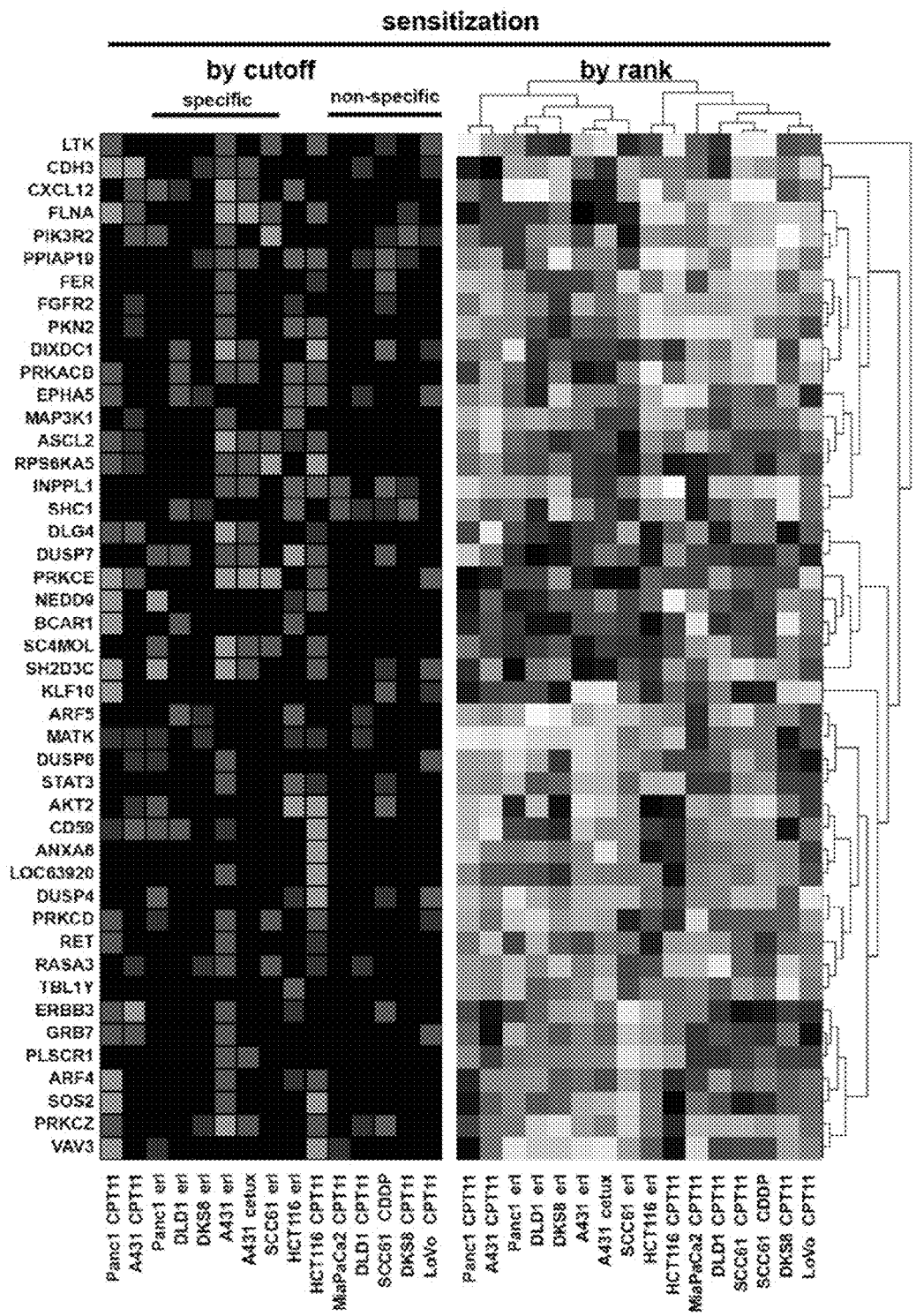
FIG. 13A: Sensitization profile of hits. Left, SI values for erlotinib and CPT11, calculated as (test siRNA)/(GL2) for cells grown in drug, divided by (test siRNA/GL2) for cells grown in DMSO: dim green, SI≤0.85; bright green, SI≤0.7; dim red, SI≥1.15; bright red, SI≥1.3. Right, relative ranking of the efficacy of hits to sensitize cells to drugs indicated: black, most sensitizing; white, least sensitizing. For rank order analysis, cluster analysis was performed to identify genes with similar profiles of sensitization (dendrogram, Y axis), and also to cluster cell lines by similarity of response (dendrogram, X axis): these clustered patterns are used to organize the display of genes selected by threshold. Two cell lines, MIA-Paca2 and LoVo, yielded no reproducible hits sensitizing to erlotinib; BCAR1 and TBL1Y were not tested in LoVo

In additional experiments, we comparatively profiled the efficacy of the hit panel as sensitizers of erlotinib, cetuximab, and CPT11 across a set of cell lines, including A431, the colorectal adenocarcinoma cell lines HCT116, DLD-1, DKS-8, and LoVo, the head and neck squamous cell carcinoma cell line SCC61, and the pancreatic adenocarcinoma cell lines PANC-1 and MIA PaCa-2 (FIG. 13A). In this analysis, cell lines with intrinsic drug resistance mutations (for example, in K-Ras and/or p53) had more noise in sensitization responses, with the result that highly resistant lines (DLD1, DKS-8, LoVo, MIA PaCa-2) yielded far fewer sensitizing hits than A431 by rigorous statistical criteria. To compensate for this difference, we analyzed the data in two ways: first, by conventional threshold analysis (FIG. 13A, left), and second, by assessing the rank order of sensitization phenotype, using relaxed statistical criteria (FIG. 13A, right; see Materials and Methods). The ranking order method mitigates the stochastic "noise" common in resistant tumors, and which we observed in the erlotinib-refractory cell lines.

No gene target sensitized to erlotinib in all tested cell lines. Considering only statistically significant thresholds (FIG. 13A, left), depletion of genes initially identified and validated in A431 most consistently sensitized this cell line to erlotinib, with many in this group also sensitizing A431 cells to cetuximab. Depletion of a further small subset of these genes also consistently sensitized cells to erlotinib in at least two additional cell lines with known resistance mutations. These included SH2D3C, DUSP7, and SC4MOL. Other siRNAs (included RPS6KA5, FLNA, PRKCE, PRKACB, SC4MOL, and ASCL2) sensitized to erlotinib and/or CPT11, in 3-5 cell lines, suggesting a broader action in resistance, but less specificity for EGFR-targeting agents; this overlap may reflect the important role of some EGFR effectors in supporting general survival signaling.

Considering instead sensitization rank (FIG. 13A, right), although all genes detected based on thresholds were again detected as highly sensitizing, a broader pattern of activity was detected for some hits. For example, PRKCE is consistently one of the most sensitizing targets in 11/15 conditions assessed, although it only scored as significantly sensitizing in 6. The broader set of genes now detected as particularly sensitizing to erlotinib and cetuximab based on rank order activity in the majority of the cell lines tested included BCAR1, DUSP7, DLG4, SC4MOL, SH2D3C, and NEDD9, beyond those noted above.

Figure 13B:
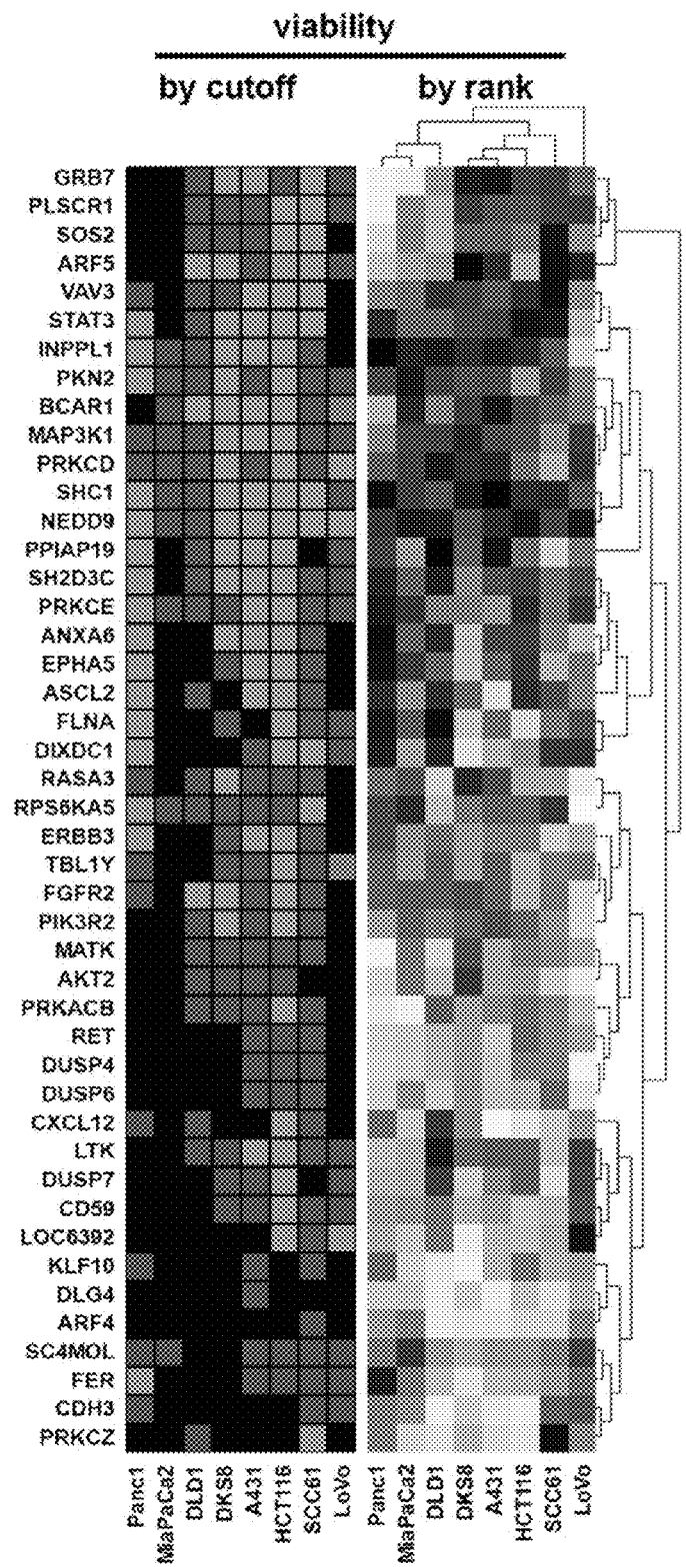
FIG. 13B: Left, siRNA-induced viability reduction below 0.85 (dim green), or 0.7 (bright green) that of control siRNA-treated cells, calculated based on the formula (test siRNA)/(GL2 control siRNA) for cells grown in DMSO. Right, relative ranking of hit efficacy in reducing cell line viability.

As the in vivo effects of inhibiting a selected target will reflect the cumulative sum of intrinsic effect on viability and sensitizing activity, we also established the baseline intrinsic activity of the validated siRNAs in reducing cell growth in DMSO-treated cells (FIG. 13B). Down-modulation of certain genes intrinsically affected cell growth very significantly in multiple cell lines in the presence of vehicle alone. Other effective sensitizers, including DUSP7 and DLG4, exhibited only a minimal effect on viability in the absence of drug treatment. Based on the composite of intrinsic and sensitizing effects, a significant number of the hits (including PRKCE, INPPL1, SH2D3C, SHC1, STAT3, FLNA, and NEDD9) very strongly reduced the growth of multiple tumor cell lines treated with EGFR-targeting agents. 18 of the hits selectively enhanced apoptosis by 2-fold or more in erlotinib-treated versus DMSO treated A431 cells (FIG. 13C), suggesting these genes as desirable targets for cancer therapy.

Figure 14A:
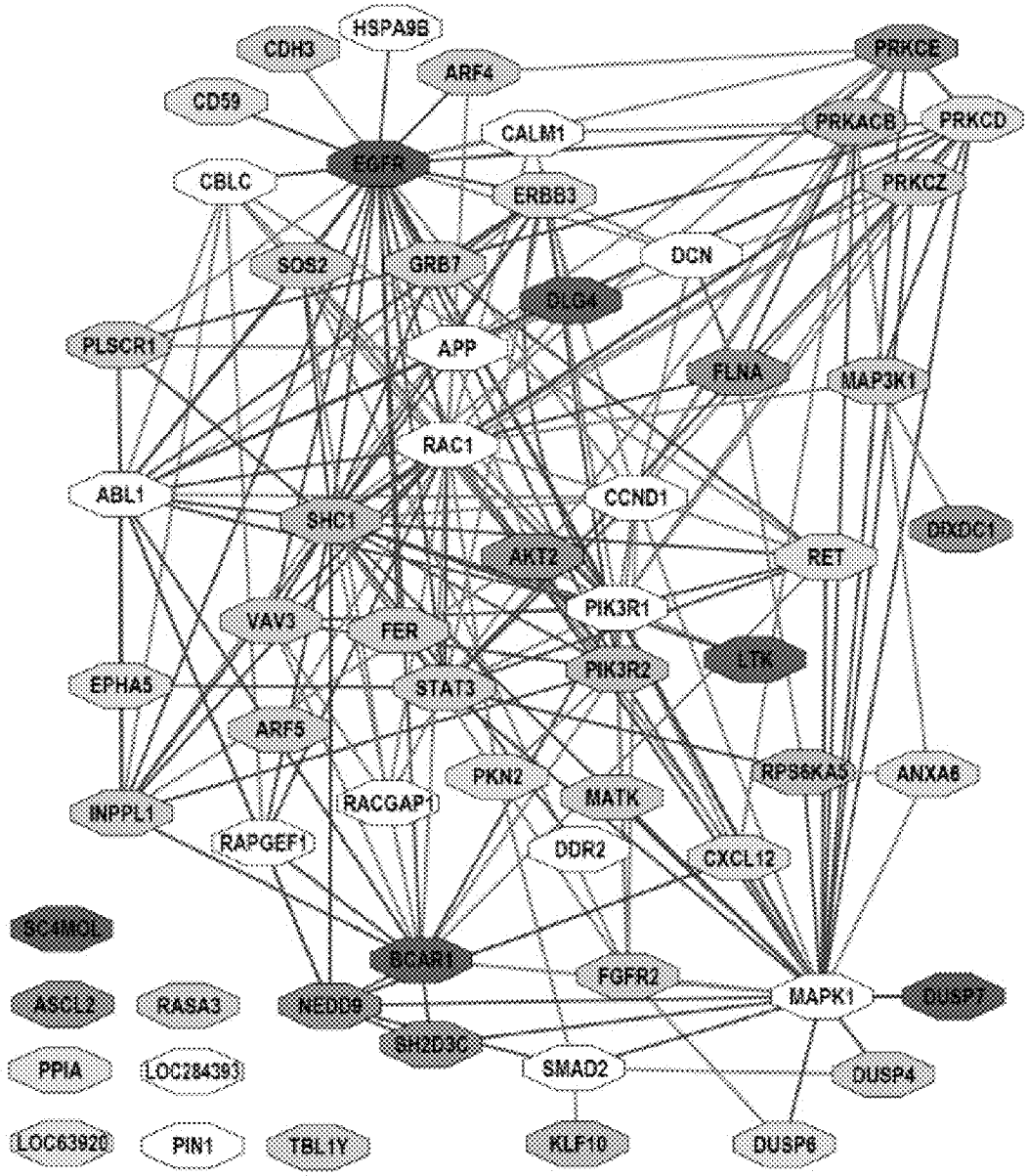
FIG. 14A: Functional classification of hits. Network of validated hits sensitizing to EGFR-targeting agents. Blue lines represent connections based on direct protein-protein interactions or genetic interactions in Drosophila; yellow lines represent connections generated by pathway maps and text mining. Green shadowing on boxes indicates genes that are in the top quartile by rank order of those strongly sensitizing at least 1 (lightest green) to at least 5 (darkest green) cancer cell lines to erlotinib.

These findings supported the idea that a cogently designed network focused around a core cancer target such as EGFR would provide a rich source of genes that modulate resistance to EGFR pathway-targeted agents. In general, a greater effect was seen on the core viability of cell lines containing wt versus mutant Ras, although the stronger hits were typically active in both; in contrast, it was impossible to establish a meaningful correlation between sensitization profile and Ras mutational status, suggesting that sensitizing activity occurred downstream or independently from core Ras signaling outputs. We investigated the relative interactions of the stronger hits within the overall topology of the EGFR signaling network (FIG. 14A). The majority of hits could be placed in a connected sub-network based on direct physical interactions. Notably, the analysis identified 2 separate members of the protein kinase C family as sensitizing in multiple cell lines (PRKCD, and PRKCE), with some of these proteins also directly connecting to the strong sensitizers DLG4 and PRKACB. A second cluster included SH2D3C, BCAR1, and NEDD9, which sensitized preferentially to erlotinib and cetuximab, and were all connected by direct physical interactions. Many of these most sensitizing hits were directly connected to MAPK1, PIK3R, STAT3, SHC1, and EGFR itself, supporting the idea that these proteins modulated core outputs of the central EGFR signaling pathway.

Figure 13C:
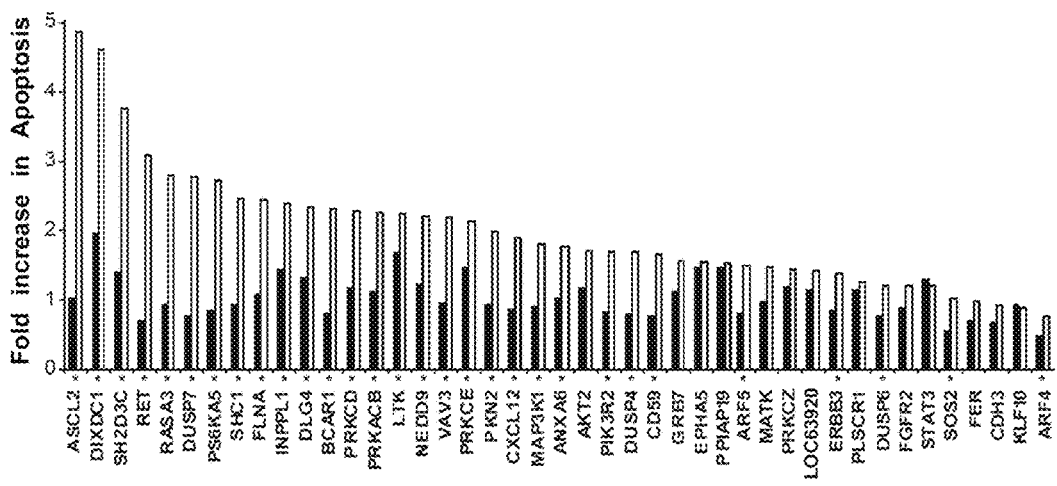
FIG. 13C: Apoptosis was determined by annexin-V labeling and normalized to negative control siRNA. Composite results from two independent experiments are shown as odds ratio columns; black, DMSO treated; white, erlotinib-treated. Asterisks indicate statistically significant (FDR≤0.05) drug-gene interaction in two independent experiments.
Figure 14B:
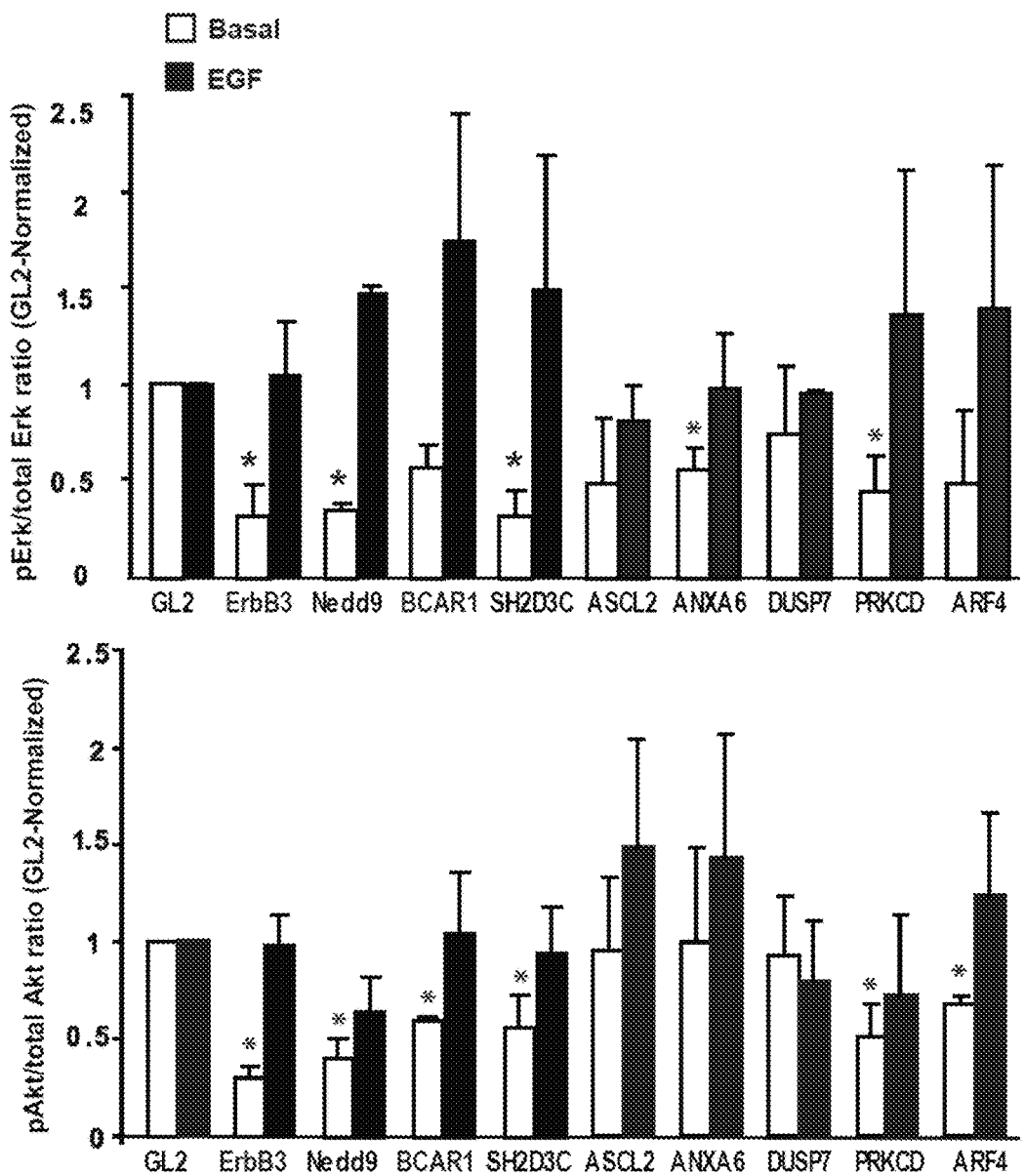
FIG. 14B: Analysis of ERK (top) and AKT (bottom) status in cell lysates from A431 cells following siRNA transfection, under basal medium conditions and following EGF-stimulation. Average results of three independent Western blots are shown as ratios of amounts of phosphorylated and total proteins. Results were normalized to corresponding ratios in GL2 control; error bars are standard deviations. Asterisks indicate statistically significant difference with negative control; t-test p<0.05.
Figure 14C:
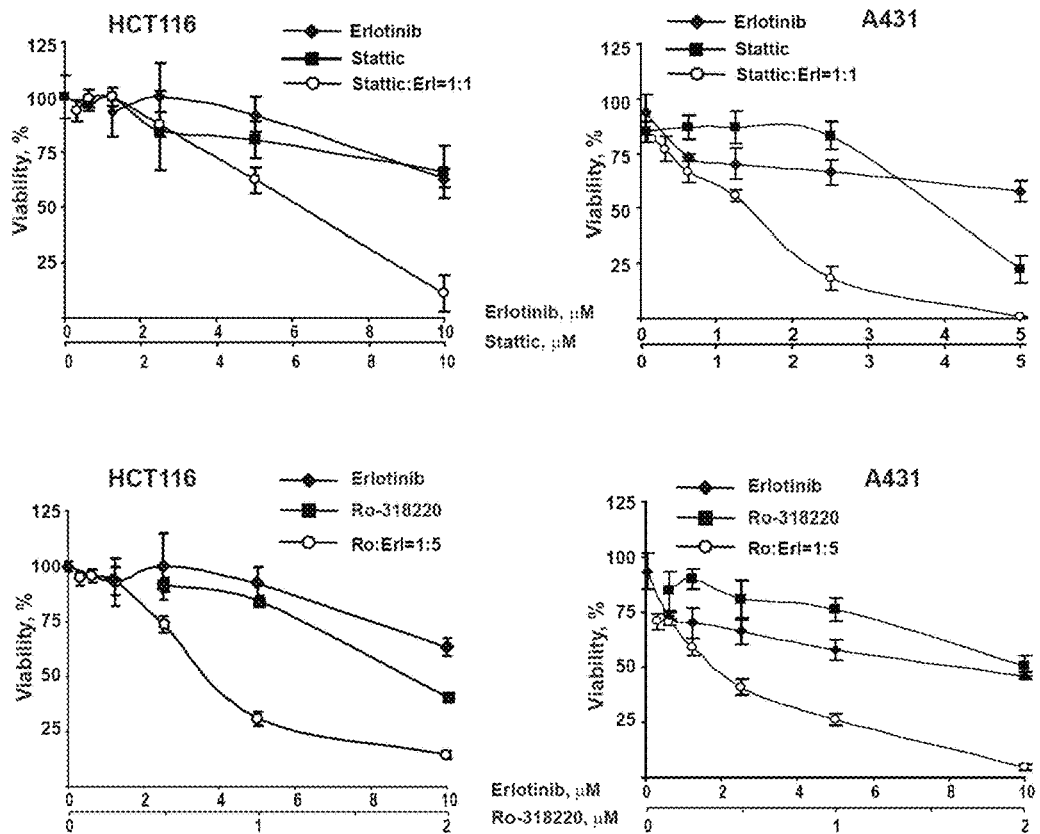
FIG. 14C: Viability curves for erlotinib and Stattic used as single agents, or combined at 1:1 molar ratio in A431 (left) and HCT116 (right) cells, or for erlotinib and Ro-318220 used as single agents, or combined at 1:5 molar ratio in A431 (left) and HCT116 (right) cells.
Figure 15A:
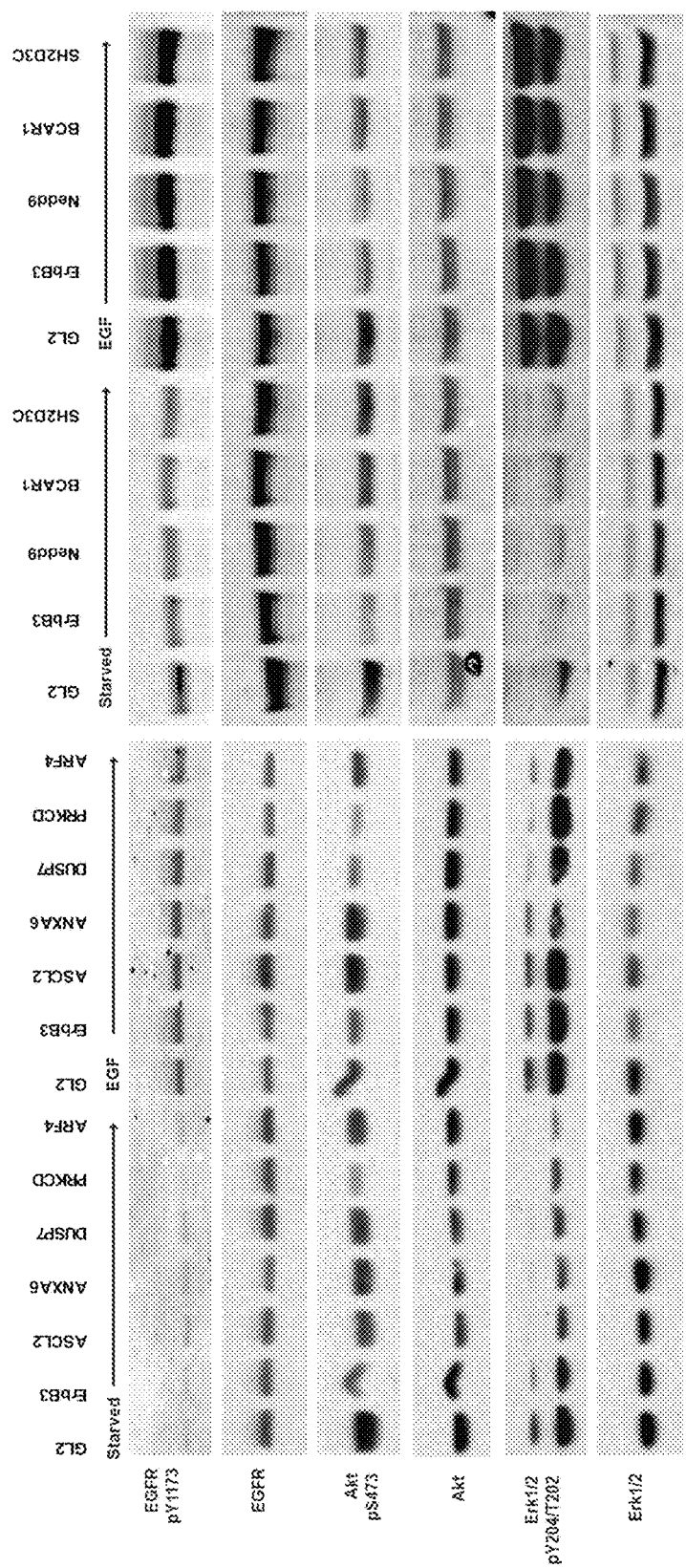
FIG. 15A: Representative Western blots showing status of EGFR pathway members in A431 cells transfected with siRNAs to the indicated genes.

We directly tested the ability of a number of hits to directly modulate both basal and EGF-stimulated activation of the core pathway effectors MAPK1 and AKT (FIGS. 14B and 15A). The inhibition of expression of ERBB3, ANXA6, PRKCD, NEDD9, BCAR1 and SH2D3C in each case reduces basal activation of MAPK1 and AKT, implying collateral input to the canonical EGFR-MAPK-AKT pathway from these target genes. By contrast, a small number of the hits, including TBL1Y, PIN1, SC4MOL, and ASCL2, were not connected by direct protein-protein interactions to the core network, suggesting either a different mode of action, or previously undetected connections. Indeed, upon direct testing, ASCL2 affects neither MAPK1 nor AKT activation, although it potently sensitizes erlotinib-treated cells to apoptosis (FIG. 13C). Interestingly, ASCL2 is a target of Wnt signaling that is up-regulated in a subset of colon carcinomas and has very recently been shown to control the expansion of epithelial stem cells, suggesting a possible mode of activity.

A major goal of this work was to gain insights that could be rapidly translated to the clinic. Although the clinical use of RNAi is a topic of intense current research, small molecules and monoclonal antibodies remain the most broadly applicable therapy platforms. Further, given that most drugs target catalytic enzymes, whereas siRNAs typically reduce protein levels by no more than 80-90%, we hypothesized that combining small molecule inhibitors of siRNA-predicted catalytic hits with erlotinib might enhance sensitization phenotypes over those detected in initial screens. For some sensitizing hits, targeted small molecules exist, including Stattic (a small molecule inhibitor of STAT3 activation and dimerization, enzastaurin and Ro-318220 (both targeting the PRKC family, with members well-represented among the hits.

Figure 14D:
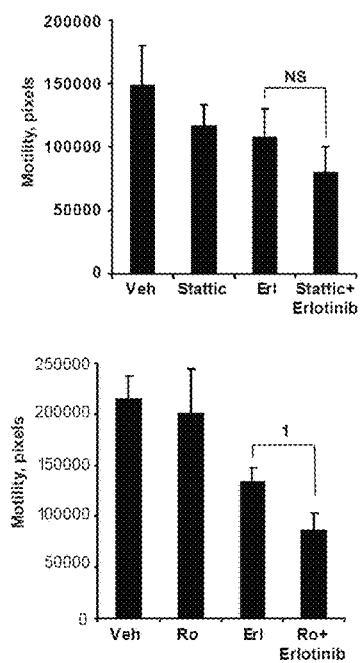
FIG. 14D: Motility was measured by wound healing assay in A431 cells cells treated with 0.5 μM erlotinib alone or in combination with 0.5 μM Stattic (top) or 0.25 μM Ro-318220, and assessed over 18 hours. NS, not significant. *, FDR=3.57*10$^{-5}$.
Figure 15B:
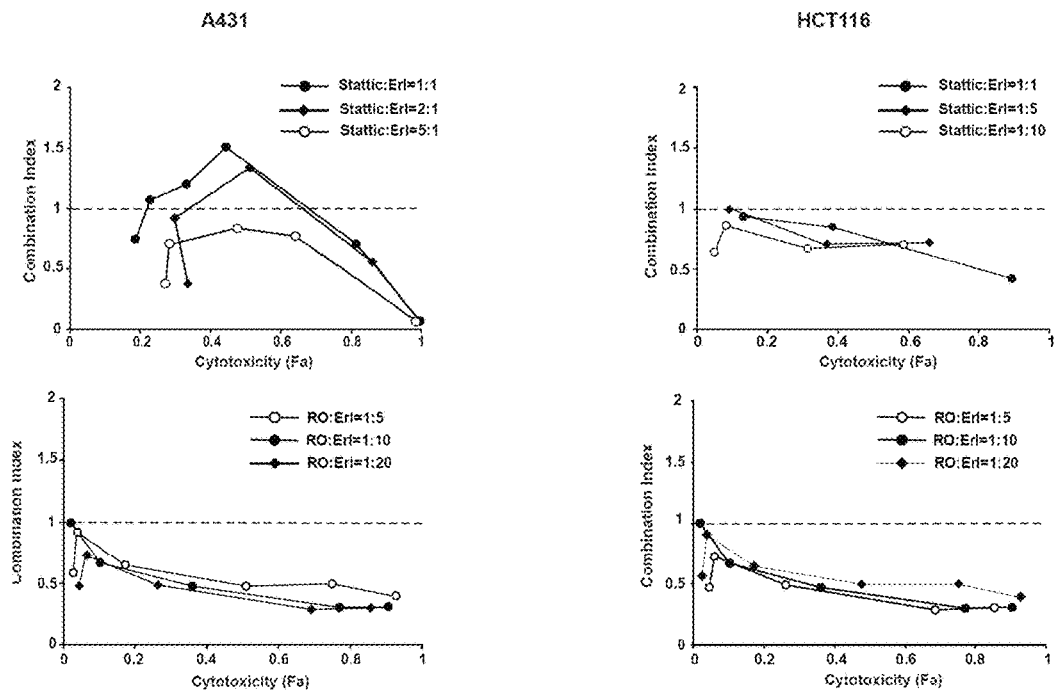
FIG. 15B: Chou Talalay Fa-CI plots obtained for viability of A431 and HCT116 cells treated with protein kinase C inhibitor (Ro, Ro-318220) or STAT3 inhibitor (Stattic) combined with erlotinib at different molar ratios.
Figure 15C:
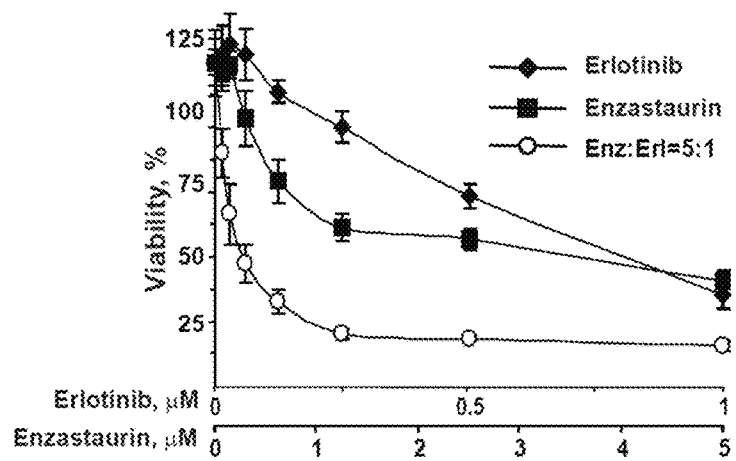
FIG. 15C: Viability curves for erlotinib and enzastaurin used as single agents, or combined at 5:1 (left) or 1:1 (right) molar ratios in A431 cells.
Figure 16A:
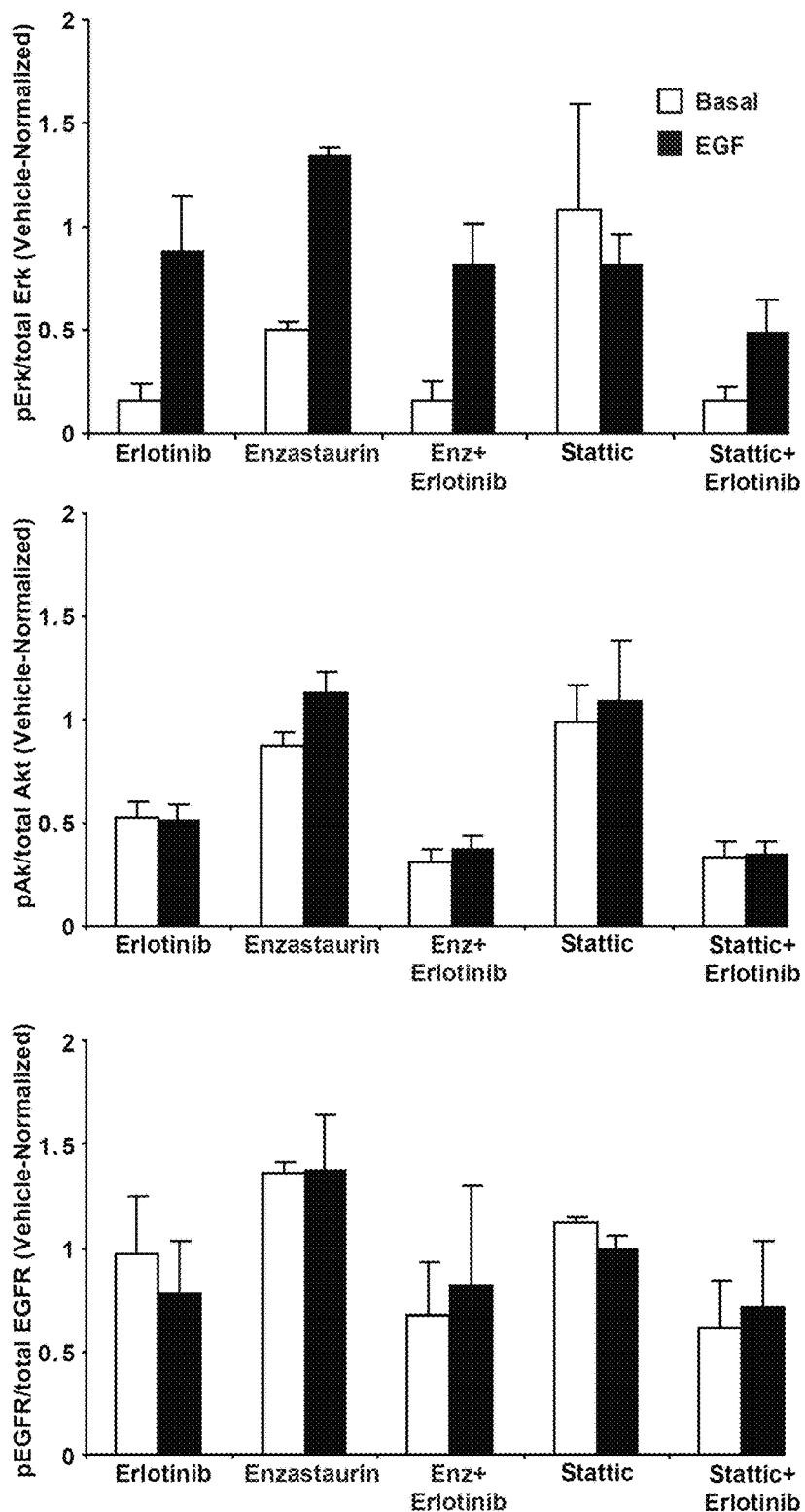
FIGS. 16A-16B. Phosphoprotein changes with signaling inhibitors. Western blot quantitative data of the phosphorylated proteins in A431 lysates obtained under serum starvation (basal) or EGF stimulation. The results represent averages of 3 independently conducted experiments; bars indicate SEM. Data shown calculated from 3 independent biological replicates except for IκB, which was derived from 2 replicates.
Figure 16B:
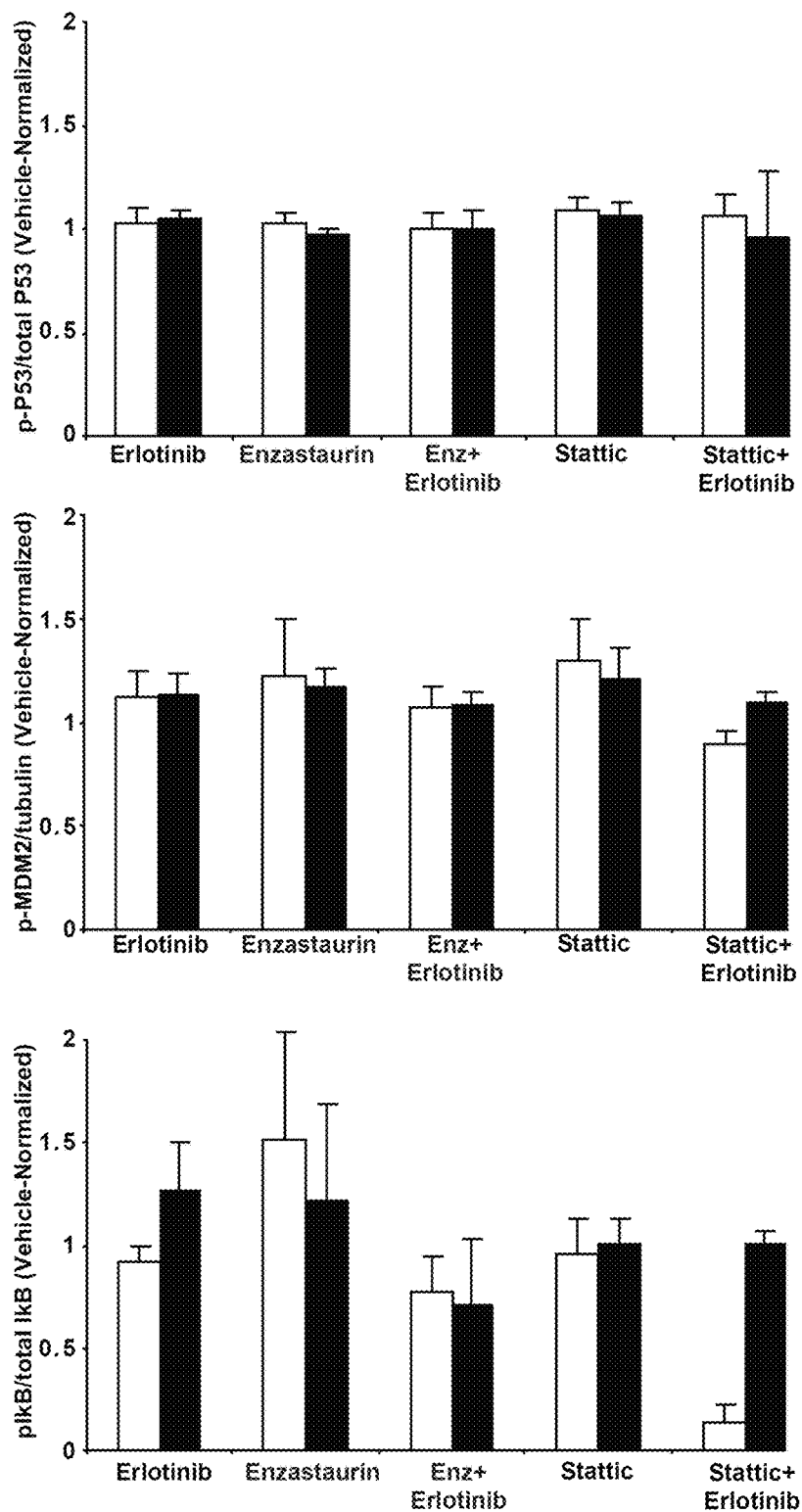

Stattic synergized with erlotinib in inhibiting the growth of both A431 and HCT116 cells (FIGS. 14C and 15B) in keeping with reported dependency of EGFR-driven autocrine growth on STAT3 activation in cancer, but showed no statistically significant synergy in reducing cell motility (FIG. 14D, top). Both Ro-318220 and enzastaurin synergized very significantly with erlotinib in A431 and HCT116 cells (FIGS. 14C and 15C), in experiments employing drugs combined at multiple ratios (1:5, 1:10, 1:20). Combined application of EGFR and Ro-318220 also significantly reduced tumor cell motility (FIG. 14D, bottom). We analyzed the effect of drug combinations on the activation state of a series of benchmark signaling proteins relevant to proliferation and apoptosis, including Akt, Erk, NF-κB, IκB, MDM2, and p53 (FIG. 16). None of these proteins experienced specific activity changes as a consequence of combined application of drugs, with the exception of Akt, which had significantly reduced phosphorylation on $S^{473}$ in cells treated with erlotinib in combination with either static or enzastaurin. Akt-$S^{473}$-phosphorylation has been described as dependent on integrated signaling via PKC, EGFR, and mTOR. This result suggests a potential pathway by which the enzastaurin-erlotinib combination might reduce cell viability.

Figures 17A, 17B:
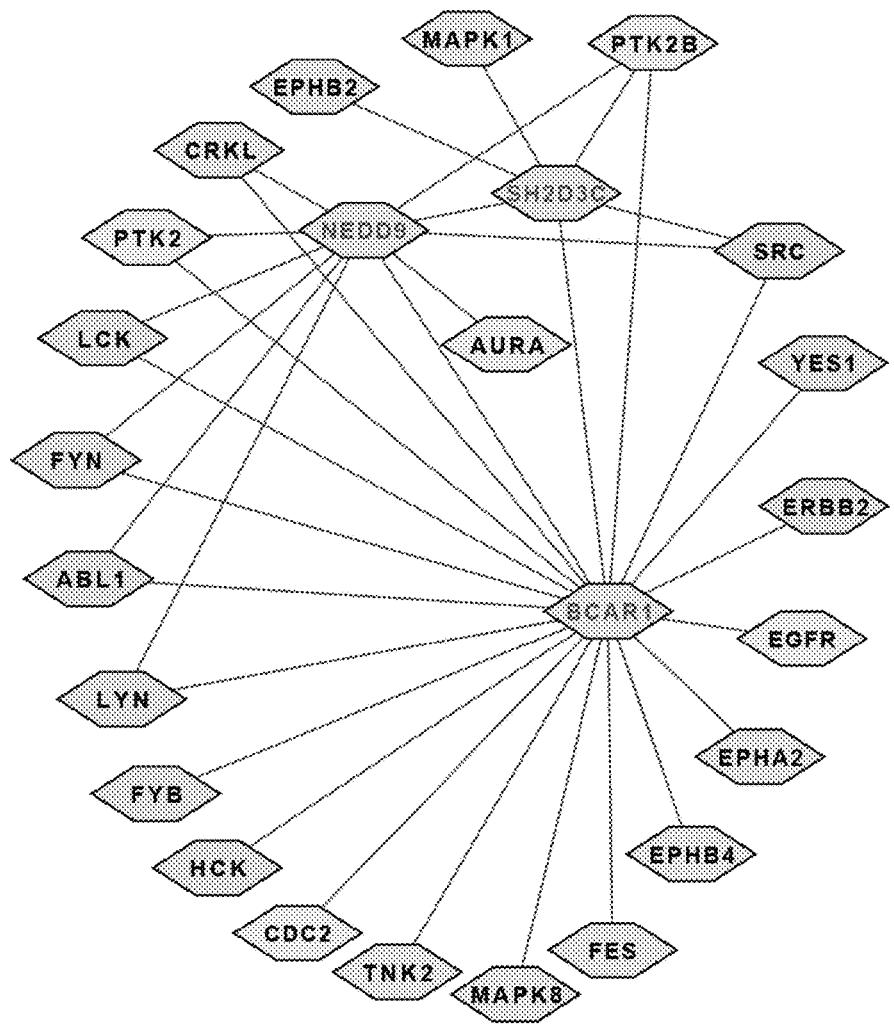
FIG. 17A: Synergy between inhibitors of Aurora-A and of EGFR. Kinases directly associated with the BCAR1-NEDD9-SH2D3C cluster. Kinases with no clinical small molecule inhibitor available are indicated in pink; kinases with small molecule inhibitors are indicated in blue, or in green if inhibitor has previously been tested for synergy with EGFR-targeting agents.
FIG. 17B: Inhibitors of EGFR and inhibitors of Aurora kinase A synergize to reduce viability of cancer cells in vitro. Summary results of drug interactions calculated as Chou-Talalay coefficient of interaction (CI). The results are based on Cell Titer blue viability determinations; similar results were obtained with BrdU (not shown).

The proteins of the consistently sensitizing BCAR1-SH3D2C-NEDD9 cluster have been linked previously to cell survival control in the context of integrin-mediated signaling cascades, suggesting this cluster is of particular interest for therapeutic exploitation. However, these proteins are not catalytic, and have not been targeted by existing small molecule agents. Given the results suggesting the enrichment of sensitizing genes among proteins closely linked to core hits, we hypothesized that small molecules targeting kinases closely linked to this cluster by physical interactions might similarly provide a rich source of synergizing agents for combination with erlotinib. FIG. 17A shows the direct interaction neighborhood around BCAR1, SH3D3C, and NEDD9, which includes 16 kinases. Drugs that are in pre-clinical or clinical development, or approved agents, target 10 of these kinases (either uniquely, or as one member of a protein family), and some of these drugs have indeed been combined productively with EGFR-directed therapeutics (e.g. dasatinib, targeting Src family kinases. Among these, the NEDD9-interacting kinase AURKA (Aurora-A, STK6) was notable because it positively and directly regulates the important EGFR effector Ral, and has been reported to indirectly upregulate AKT. Moreover, well-tolerated drugs targeting Aurora-A are currently undergoing clinical evaluation.

Figure 17C:
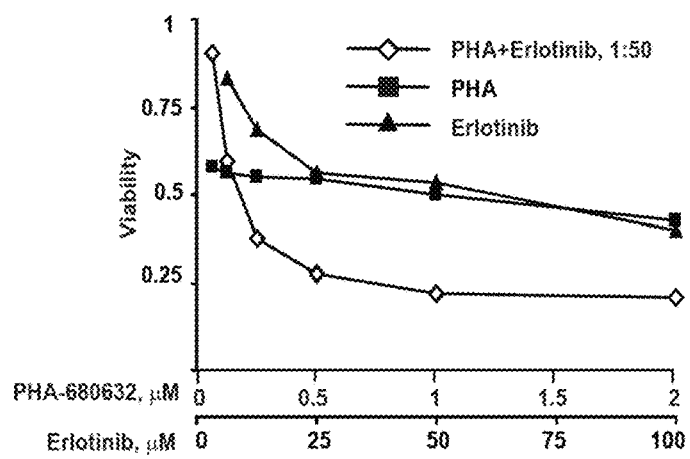
FIG. 17C: Combination of PHA-680632 and erlotinib treatment increases apoptosis in HCT116 cells at 72 hours; *, t-test p=0.001.
Figure 17D:
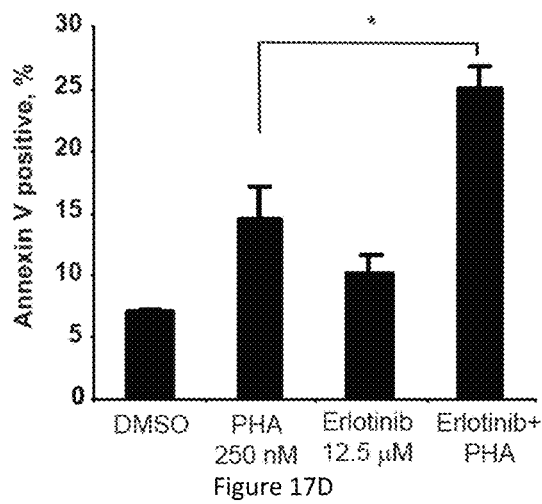
FIG. 17D: Dose-dependent inhibition of HCT116 cell viability by combination of PHA-680632 and erlotinib.
Figure 17E:
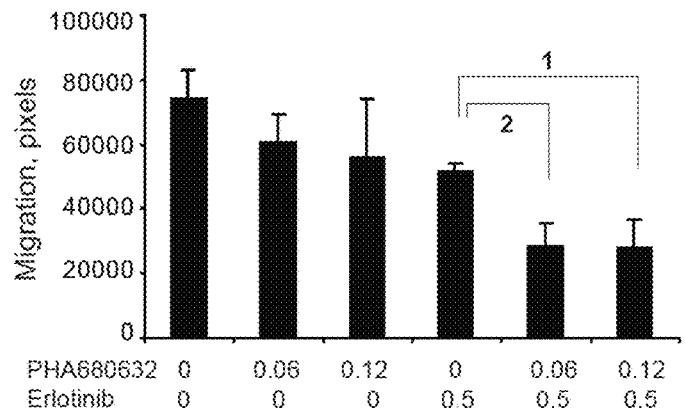
FIG. 17E: Cell motility was measured by wound healing assay in cells treated with drugs at concentrations indicated, and assessed over 18 hours. *FDR is <$10^{-5}$ for (1), (2).
Figure 17F:
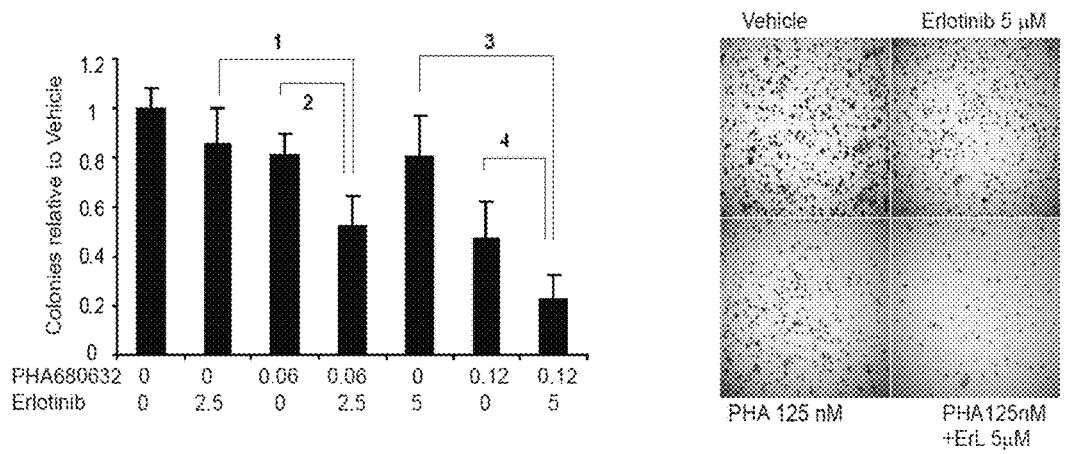
FIG. 17F: Left, relative soft agar colony formation of cells grown for 2-3 weeks in drugs at concentrations indicated. FDR is equal to (1) 0.0003, (2) 0.0006, (3) 0.0003, and (4) 0.004. Right, results from typical experiment.
Figure 17G:
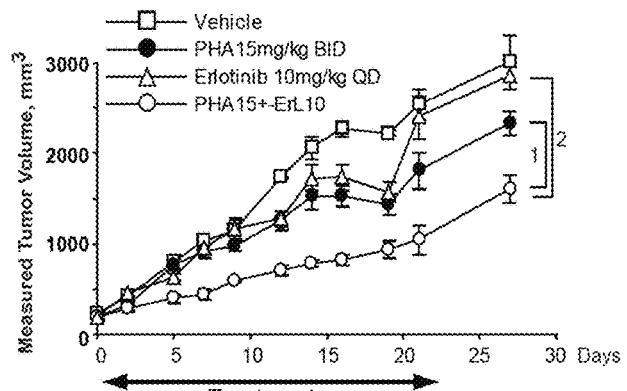
FIG. 17G: Tumor xenografts implanted in SCID mice were treated with drugs as indicated beginning at day 0. P-values are (1) 0.005, (2) 0.008.

The small molecule Aurora-A inhibitors PHA-680632 (Soncini et al. (2006) Clin. Cancer Res. 12:4080) synergized strongly with erlotinib in both A431 and HCT116 cells (FIG. 17B). PHA-680632 also synergized with the EGFR-inhibiting antibody cetuximab (FIG. 17B), while erlotinib also synergized with another Aurora-A inhibitor, C1368 (Tari et al., (2007) Bioorg. Med. Chem. Lett. 17:688) Combination of Aurora-A and EGFR-targeting agents did not merely produce cytostasis, but also cell death, increasing the frequency of apoptosis nearly two-fold (FIGS. 17C, 17D). In addition, combination of these drugs significantly reduced cell motility (FIG. 17E), colony growth in soft agar (FIG. 17F), and the growth of tumor xenografts implanted in SCID mice (FIG. 17G).

Figure 17H:
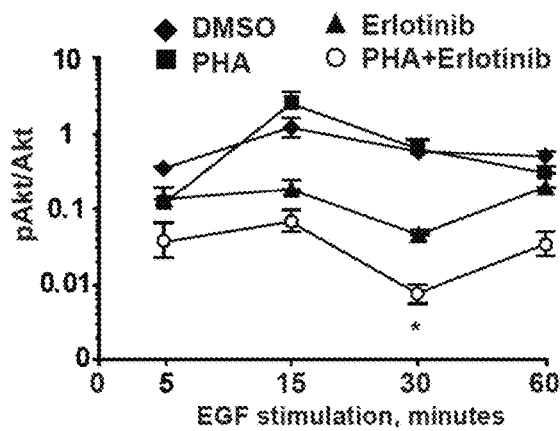
FIG. 17H: Quantitation of 3 independent Western analyses of protein lysates of cells treated with erlotinib and PHA-680632 for 3 hrs followed by EGF stimulation. Error bars represent standard error of the mean (SEM) of three independent experiments; **, t-test p=0.013.
Figure 18:
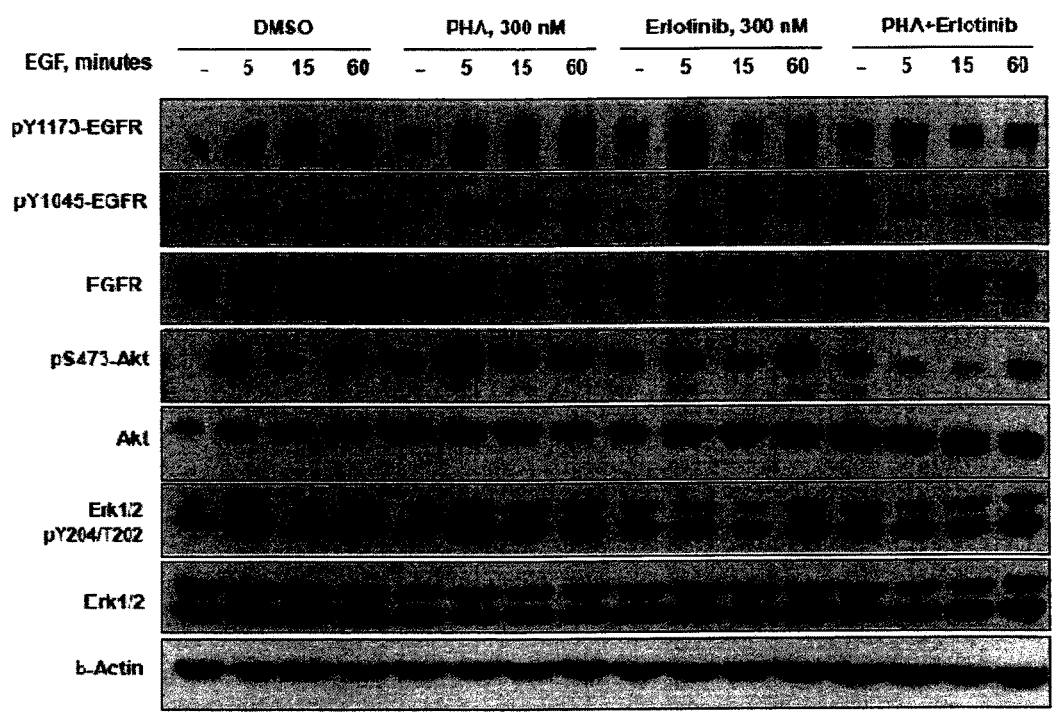
FIG. 18. PHA-680632 and erlotinib combine to reduce AKT phosphorylation. Representative Western blot showing activity of erlotinib and PHA680632 either alone or in combination on serum starved HCT116 cells treated with the indicated inhibitors for 3 hours and stimulated with EGF.

We explored the signaling changes underlying the synergy. Treatment of cells with PHA-680632 alone did not inhibit EGFR expression, autophosphorylation, and activation, and had little effect on ERK1/2 or AKT phosphorylation in response to transient EGF stimulation (FIGS. 17H and 16A). However, in combination with erlotinib treatment, PHA-680632 very significantly reduced $S^{473}$-AKT phosphorylation below levels seen in cells treated with either agent alone, compatible with the reduced survival of cells treated with the drug combination, while not significantly influencing other EGFR-dependent signaling benchmarks (FIGS. 17H, 18).

Figure 19B:
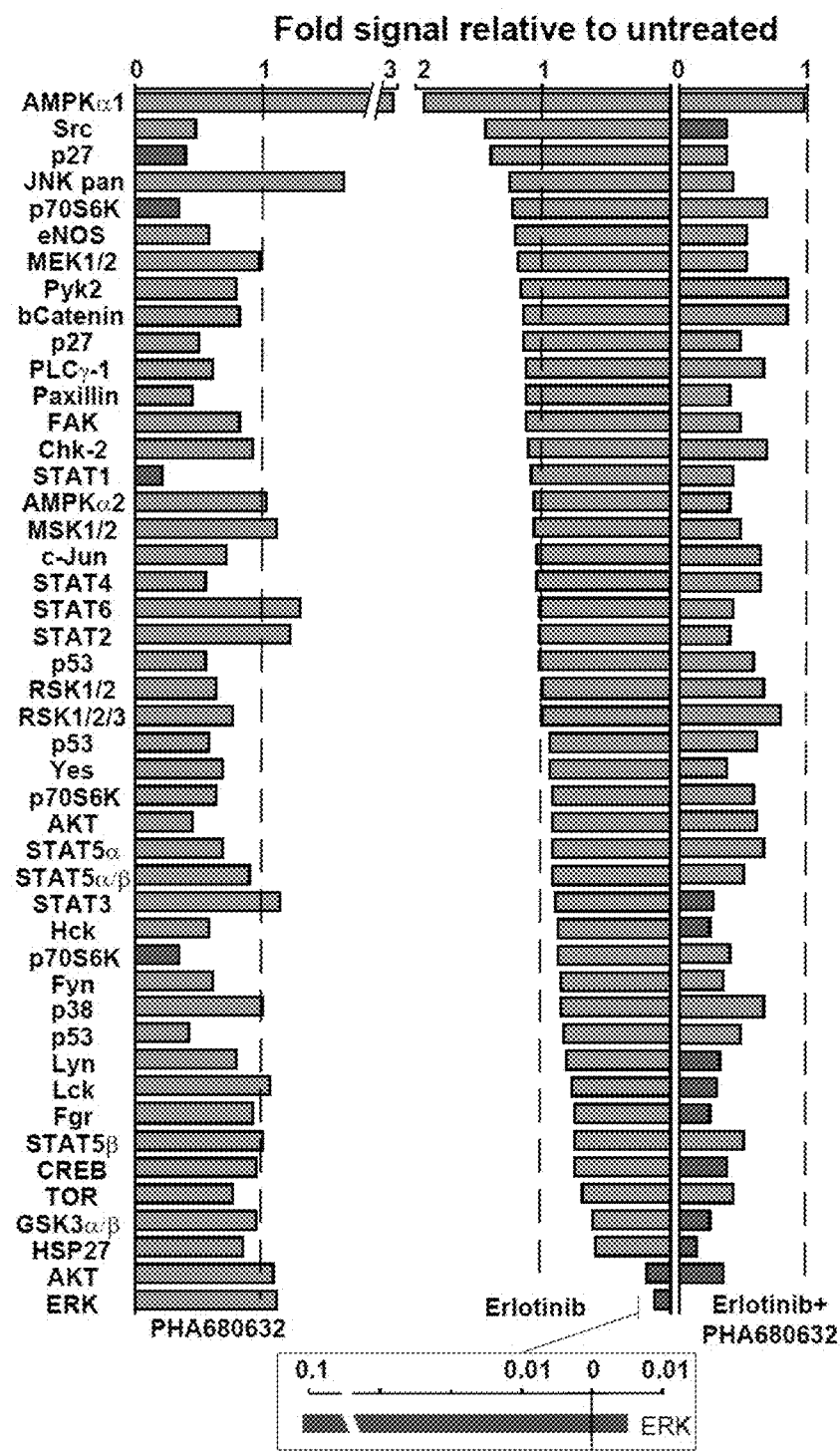

To explore signaling consequences of co-inhibition of Aurora-A and EGFR in greater depth, we next undertook a more comprehensive phospho-proteomic analysis of 46 signaling proteins linked to cell proliferation and survival responses following cell treatment with erlotinib, PHA-680632, or both. Analysis of two independently performed screens (FIG. 19A) established that erlotinib blocked EGF-induced activation of multiple signaling pathways (reducing Akt and ERK below background levels), and PHA-680632 had little effect when used as single agent. In contrast, the combination of drugs led to specific inhibition of a subset of proteins, including the greater inhibition of ERK and Akt detected by candidate analysis, but also inhibition of GSK3β (a known functional partner of Aurora-A), JNK, and the Src family kinase FGR. We performed similar experiments to analyze signaling changes under the steady state growth conditions used to assess synergistic killing of cells (i.e., when the activation state of pathways was not strictly dependent on EGF) (FIG. 19B). Strikingly, this analysis re-identified the same targets for the drug combination as those seen with EGF-dependent signaling (FIG. 19A), but in addition showed significant reduction in activity of STAT3, and a group of Src kinases, including FGR, Hck, Lyn, Src, and Lck. These last hits in particular are intriguing, as the BCAR1-NEDD9-SH2D3C proteins that led us to consider AurA are direct activators and substrates of these same Src family kinases (FIG. 17A). One possibility is that use of AurA inhibitors weakened this resistance cluster in the network.

Figure 20:
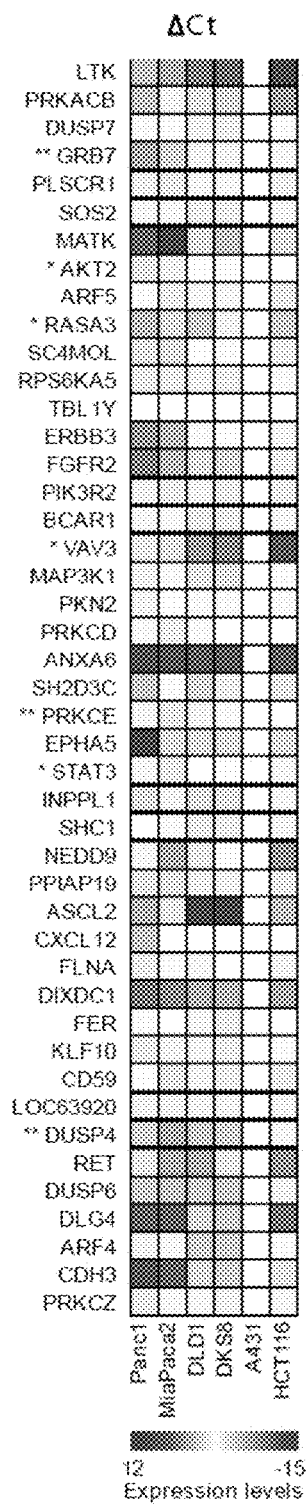
FIG. 20. Expression profile of hits in cell lines. Not all siRNAs were active in all cell lines. The phenomenon of cell line-specific activity could reflect the presence or absence of expression of a targeted mRNA in specific cell lines, or might instead reflect the presence of the mRNA in multiple cell lines, but a requirement for the gene product only in a subset of cell lines. Establishing this point has important implications, as often a criterion for targeting a given protein therapeutically has been the observable high levels of expression of that protein within a tumor. We performed quantitative RT-PCR of the set of validated hits in each of the reference cell lines, and compared relative expression level with intrinsic siRNA sensitivity. Over the entire set of genes, there was no significant correlation between the relative abundance of a targeted mRNA in a cell line and the efficacy of the corresponding siRNA in influencing either sensitization to the drugs used, or cell viability. Shown, relative expression of genes targeted by siRNAs measured for each cell lines using quantitative RT-PCR. ΔCt value is in each case calibrated to A431; e.g., strongest blue requires 12 additional amplification cycles to detect mRNA, indicating it is $2^{12}$-fold less abundant than in A431 cells. Genes with significant correlation (*) or anti-correlation (**) with proliferation ability are indicated; Pearson correlation values are respectively, AKT2, 0.91; RASA3, 0.84; STAT3, 0.81; VAV3, 0.80; GRB7, −0.89; PRKCE, −0.87; DUSP4, −0.81.
Figure 21:
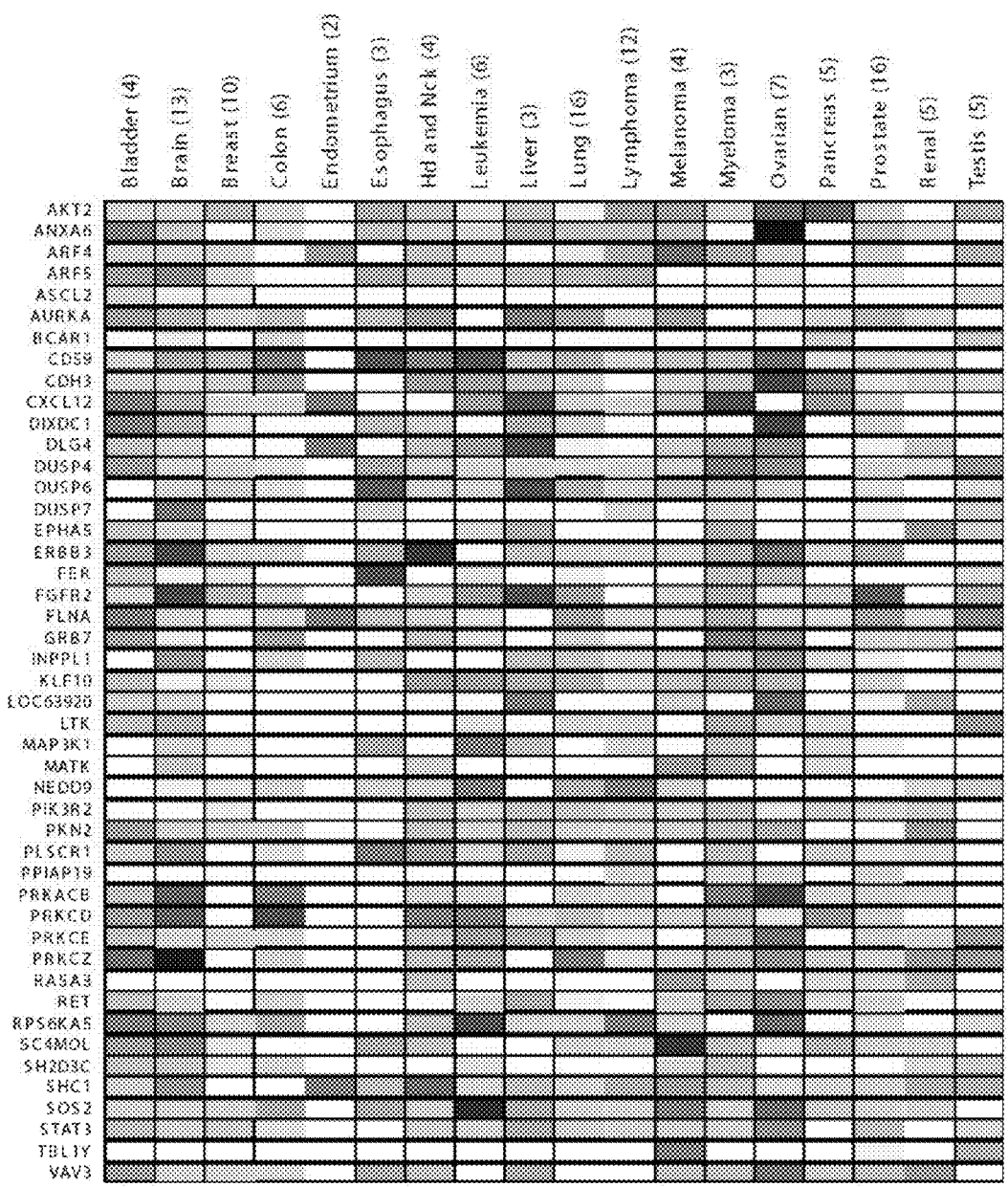
FIG. 21. Expression profile of hits in Oncomine. To identify genes among the hit set that have been reported as up- or down-regulated in cancerous vs. normal tissues (with a p-value equal or less than 0.01), the Oncomine database was searched across all tissue types. Tissues with fewer than two independent analyses available were excluded from analysis. For each gene, the total number of cancer vs. normal samples analyses reporting it to be up- or downregulated was normalized to the total number of analyses for the corresponding tissue type. Data were visualized using MeV: Red, up-regulation; blue, down-regulation. Intense hues represent a value of 1, meaning all of the available cancer vs. normal analyses found comparable up- or down-regulation; less intense hues indicate expression change was found in some but not all independent studies. Yellow indicates the genes found to be both up- and down-regulated in the same tissue type by different data sets. White boxes indicate no significant change in expression was identified in any study.

As described in Example 11, another potential use of this data set is for the nomination of new biomarkers for selecting patient responsiveness. However, extensive analysis of the expression of siRNA targets in cell lines used for functional analysis (FIG. 20) showed no statistically significant correlation between expression level and role in modulating resistance, while analysis of Oncomine profiles (FIG. 21) did not reveal specific trends of altered expression in tumors. Large sequencing projects, have noted including among others the Cancer Gene Census, have noted mutations with some frequency for RET, FLNA, FGFR2, SMAD2, PIK3R1, ABL1, CCND1, and AKT2. See the world wide web at sanger.ac.uk/CGP/. However, most of the genes we identified are not common targets for mutations. These observations have potentially important translational implications, as much effort has gone into analyzing gene expression or mutational status to predict drug resistance. This cumulative lack of a clear pattern of expression or mutation likely reflects the complexity of cancer-associated signaling networks. For many solid tumors, no unique oncogenic driver has been yet identified, but instead, tumor cells undergo multiple, sequential process-oriented oncogenic alterations that together reprogram multiple yet discrete aspects of tumor functionality. In such a scenario, fitness of a cancer cell is determined by the robustness of its signaling network as a whole. The new resistance-mediating genes we have identified should undergo scrutiny as alternative EGFR modulators, joining with proteins such as K-Ras, B-Raf, c-MET, IGF-1, and others.

A major goal of systems-level bioinformatics analyses is to nominate critical nodes to target in combination to enhance therapy in the clinic, with clear successes beginning to emerge from this information-driven strategy (Pritchard et al., (2009) Mol Cancer Ther. 8:2183). Separately, screening of siRNA libraries has emerged as a powerful approach to identify genes that can kill cancer cells, or sensitize them to cytotoxic agents. To date, such screening has typically employed either full genome screens, or screens of small libraries targeting limited groups of proteins, such as the kinome/phosphatome. Interestingly, a genome-wide screen to identify sensitizers to the microtubule-targeting agent paclitaxel identified a number of hits that clustered into coherent groups of genes associated with the proteasome or mitotic spindle (Whitehurst et al., (2007) Nature 446:815), which a priori had been linked to paclitaxel activity based on existing pathway knowledge.

In the current study, we employed bioinformatics design and direct screening, and found that many proteins influencing cellular resistance to EGFR-targeting agents clustered in connection-dense, highly interactive portions of the EGFR signaling network, thus supporting our core hypothesis that these characteristics would enrich for synthetic lethal interactions. These sensitizing protein clusters were useful for predicting the efficacy of combining protein-targeted drugs with EGFR-pathway signaling inhibitors, suggesting the potential of this approach for speeding the translation of results to the clinic. We believe this targeted approach has several advantages in comparison to a full genome screen. Beyond the obvious factors of convenience, speed, and cost, all hits arising from a targeted screen already have at least some defined functional relationships to the signaling pathway being probed, accelerating validation and mechanism testing. Further, the limited size of the library being probed allowed the use of more relaxed statistical criteria in nominating hits for validation than would be necessary in a full genome screen, and allowed us to repeat the primary screen multiple times: given the intrinsic noise in siRNA screening, these are important advantages. Finally, our observation that the single greatest source of enrichment for hits (FIG. 12C) is among the proteins with both direct physical interactions and literature-based pathway connections to the library seeds provides guidance for future library optimization.

We have defined the network structure for EGFR-pathway specific and general drug resistance in several cell lines. Accordingly, the present invention provides a unique resource: a deeply probed, heavily annotated library with a linked live database that provides a "Rosetta Stone" for drug resistance studies. This work can be rapidly translated into improved therapy for cancer patients, as the information is used to design new Phase I trials. Indeed, new combinatorial approaches for the eradication of cancer cells is discloses as are efficacious agents for effecting the same.

REFERENCES

1. Rocha-Lima C M, Soares H P, Raez L E, Singal R. EGFR targeting of solid tumors. Cancer Control 2007; 14:295-304.
2. Ciardiello F, De Vita F. Epidermal growth factor receptor (EGFR) inhibitors in cancer therapy. Prog Drug Res 2005; 63:93-114.
3. Raymond E, Faivre S, Armand J P. Epidermal growth factor receptor tyrosine kinase as a target for anticancer therapy. Drugs 2000; 60:15-23; discussion 41-2.
4. Buchholz T A, Tu X, Ang K K, Esteva F J, Kuerer H M, Pusztai L, Cristofanilli M, Singletary S E, Hortobagyi G N, Sahin A A. Epidermal growth factor receptor expression correlates with poor survival in patients who have breast carcinoma treated with doxorubicin-based neoadjuvant chemotherapy. Cancer 2005; 104:676-81.
5. Chan S K, Hill M E, Gullick W J. The role of the epidermal growth factor receptor in breast cancer. J Mammary Gland Biol Neoplasia 2006; 11:3-11.
6. Cappuzzo F, Toschi L, Finocchiaro G, Ligorio C, Santoro A. Surrogate predictive biomarkers for response to anti-EGFR agents: state of the art and challenges. Int J Biol Markers 2007; 22:S10-23.
7. Jimeno A, Hidalgo M. Pharmacogenomics of epidermal growth factor receptor (EGFR) tyrosine kinase inhibitors. Biochim Biophys Acta 2006; 1766:217-29.
8. Eddy S R. Genetics. Total information awareness for worm genetics. Science 2006; 311:1381-2.
9. Whitehurst A W, Bodemann B O, Cardenas J, Ferguson D, Girard L, Peyton M, Minna J D, Michnoff C, Hao W, Roth M G, Xie X J, White M A. Synthetic lethal screen identification of chemosensitizer loci in cancer cells. Nature 2007; 446:815-9.
10. Skobeleva N, Menon S, Weber L, Golemis E A, Khazak V. In vitro and in vivo synergy of MCP compounds with mitogen-activated protein kinase pathway- and microtubule-targeting inhibitors. Mol Cancer Ther 2007; 6:898-906.
11. Mishra G R, Suresh M, Kumaran K, Kannabiran N, Suresh S, Bala P, Shivakumar K, Anuradha N, Reddy R, Raghavan T M, Menon S, Hanumanthu G, Gupta M, Upendran S, Gupta S, Mahesh M, Jacob B, Mathew P, Chatterjee P, Arun K S, Sharma S, Chandrika K N, Deshpande N, Palvankar K, Raghavnath R, Krishnakanth R, Karathia H, Rekha B, Nayak R, Vishnupriya G, Kumar H G, Nagini M, Kumar G S, Jose R, Deepthi P, Mohan S S, Gandhi T K, Harsha H C, Deshpande K S, Sarker M, Prasad T S, Pandey A. Human protein reference database—2006 update. Nucleic Acids Res 2006; 34:D411-4.
12. Mak H C, Daly M, Gruebel B, Ideker T. CellCircuits: a database of protein network models. Nucleic Acids Res 2007; 35:D538-45.
13. Dimri M, Naramura M, Duan L, Chen J, Ortega-Cava C, Chen G, Goswami R, Fernandes N, Gao Q, Dimri G P, Band V, Band H. Modeling breast cancer-associated c-Src and EGFR overexpression in human MECs: c-Src and EGFR cooperatively promote aberrant threedimensional acinar structure and invasive behavior. Cancer Res 2007; 67:4164-72.
14. Seton-Rogers S E, Brugge J S. ErbB2 and TGF-beta: a cooperative role in mammary tumor progression? Cell Cycle 2004; 3:597-600.
15. O'Neill G M, Fashena S J, Golemis E A. Integrin signaling: a new Cas(t) of characters enters the stage. Trends Cell Biol 2000; 10:111-9.
16. Singh M K, Cowell L, Seo S, O'Neill G M, Golemis E A. Molecular basis for HEF1/NEDD9/Cas-L action as a multifunctional co-ordinator of invasion, apoptosis, and cell cycle. Cell Biochem Biophys 2007 in press.
17. Ji H, Ramsey M R, Hayes D N, Fan C, McNamara K, Kozlowski P, Torrice C, Wu M C, Shimamura T, Perera S A, Liang M C, Cai D, Naumov G N, Bao L, Contreras C M, Li D, Chen L, Krishnamurthy J, Koivunen J, Chirieac L R, Padera R F, Bronson R T, Lindeman N I, Christiani D C, Lin X, Shapiro G I, Janne P A, Johnson B E, Meyerson M, Kwiatkowski D J, Castrillon D H, Bardeesy N, Sharpless N E, Wong K K. LKB1 modulates lung cancer differentiation and metastasis. Nature 2007; 448:807-10.
18. Kim M, Gans J D, Nogueira C, Wang A, Paik J H, Feng B, Brennan C, Hahn W C, Cordon-Cardo C, Wagner S N, Flotte T J, Duncan L M, Granter S R, Chin L. Comparative oncogenomics identifies NEDD9 as a melanoma metastasis gene. Cell 2006; 125:1269-81.
19. O'Neill G M, Seo S, Serebriiskii I G, Lessin S R, Golemis E A. A new central scaffold for metastasis: parsing HEF1/Cas-L/NEDD9. Cancer Res 2007; 67:8975-9.
20. Singh M, Cowell L, Seo S, O'Neill G, Golemis E. Molecular basis for HEF1/NEDD9/Cas-L action as a multifunctional co-ordinator of invasion, apoptosis and cell cycle. Cell Biochem Biophys 2007; 48:54-72.
21. Swanton C, Marani M, Pardo O, Warne P H, Kelly G, Sahai E, Elustondo F, Chang J, Temple J, Ahmed A A, Brenton J D, Downward J, Nicke B. Regulators of mitotic arrest and ceramide metabolism are determinants of sensitivity to Paclitaxel and other chemotherapeutic drugs. Cancer Cell 2007; 11:498-512.
22. Smyth G K. Linear models and empirical bayes methods for assessing differential expression in microarray experiments. Statistical applications in genetics and molecular biology 2004; 3:Article3.
23. Gentleman R C, Carey V J, Bates D M, Bolstad B, Dettling M, Dudoit S, Ellis B, Gautier L, Ge Y, Gentry J, Hornik K, Hothorn T, Huber W, Iacus S, Irizarry R, Leisch F, Li C, Maechler M, Rossini A J, Sawitzki G, Smith C, Smyth G, Tierney L, Yang J Y, Zhang J. Bioconductor: open software development for computational biology and bioinformatics. Genome Biol 2004; 5:R80.
24. Benjamini Y, Hochhberg Y. Controlling the False Discovery Rate: A practical and powerful approach to multiple testing. J Royal Stat Soc B 1995; 57:289-300.

25. Defilippi P, Di Stefano P, Cabodi S. p130Cas: a versatile scaffold in signaling networks. Trends Cell Biol 2006; 16:257-63.
26. Cai D, Iyer A, Felekkis K N, Near R I, Luo Z, Chernoff J, Albanese C, Pestell R G, Lerner A. AND-34/BCAR3, a GDP exchange factor whose overexpression confers antiestrogen resistance, activates Rac, PAK1, and the cyclin D1 promoter. Cancer Res 2003; 63:6802-8.
27. Ambrogio C, Voena C, Manazza A D, Riera L, Piva R, Barberis L, Costa C, Tarone G, Defilippi P, Hirsch E, Boeri Erba E, Mohammed S, Jensen O N, Palestro G, Inghirami G, Chiarle R. p130cas mediates the transforming properties of the anaplastic lymphoma kinase. Blood 2005.
28. Engelman J A, Zejnullahu K, Mitsudomi T, Song Y, Hyland C, Park J O, Lindeman N, Gale C M, Zhao X, Christensen J, Kosaka T, Holmes A J, Rogers A M, Cappuzzo F, Mok T, Lee C, Johnson B E, Cantley L C, Janne P A. MET amplification leads to gefitinib resistance in lung cancer by activating ERBB3 signaling. Science 2007; 316:1039-43.
29. Frolov A, Schuller K, Tzeng C W, Cannon E E, Ku B C, Howard J H, Vickers S M, Heslin M J, Buchsbaum D J, Arnoletti J P. ErbB3 Expression and Dimerization with EGFR Influence Pancreatic Cancer Cell Sensitivity to Erlotinib. Cancer Biol Ther 2007; 6.
30. Valkova C, Maerz S, Imhof D, Liebmann C. Protein kinase Cepsilon may act as EGFinducible scaffold protein for phospholipase Cgamma1. Cell Signal 2007; 19:1830-43.

TABLE 1

| Gene name | Trancriptional change (AG/HRG AG fold) | | Pathways | PPI | Complex | Fly homolog | Paralog | Local expert |
|---|---|---|---|---|---|---|---|---|
| ABHD2 | -2 | -2 | | | | | | |
| ABI1 | | | core | round 2 | | | | |
| ABL1 | | | | round 1 | | | | |
| ACTC | | | | round 2 | complex | | | |
| ACTN4 | 1.5 | 2 | | | complex | | | |
| ACTR3 | | | | round 2 | complex | | | |
| AEBP2 | | | | | | 1 | | |
| AKT1 | | | core | round 2 | | | | |
| AKT2 | | | | | | | paralog | |
| AKT3 | | | | | | | paralog | |
| ALK | | | | round 1 | | | | |
| AMH | | | | round 1 | | | | |
| ANKRD11 | | 1.5 | | round 2 | | | | |
| ANXA2 | | | | round 2 | complex | | | |
| ANXA6 | | | | round 2 | complex | | | |
| AP2A1 | | | five | round 1 | complex | | | |
| AP2A2 | | | | round 1 | | | | |
| APP | | | | round 1 | | | | |
| ARAF | | | core | round 2 | | 3 | | |
| AREG | | | | round 1 | | | | |
| ARF1 | | 1.5 | | round 2 | | | | |
| ARF3 | | | | | | | paralog | |
| ARF4 | | | five | round 1 | | | | |
| ARF5 | | | | | | | paralog | |
| ARG1 | | | | | | | paralog | |
| ARG2 | | | | | | 1 | | |
| ARRDC3 | | -2 | | | | | | |
| ASCL1 | | | | | | 2 | | |
| ASCL2 | | | | round 2 | | 1 | | |
| ATP1B3 | | 2 | | | | | | |
| AVIL | 1.5 | 2 | | round 2 | | | | |
| AXL | | | | round 1 | | | | |
| AZIN1 | | 2 | | | | | | |
| B4GALT1 | 1.5 | 2 | | | | | | |
| BARHL1 | | | | | | 2 | | |
| BARHL2 | | | | | | 1 | | |
| BCAR1 | | | five | round 1 | complex | | | |
| BCAR3 | | | | round 1 | complex | | | |
| BCL10 | | 2 | | | | | | |
| BCL3 | | | | round 1 | | | | |
| BCR | | | | round 1 | | | | |
| BIRC4 | -2 | -2 | | | | | | |
| BLK | | | | | | | paralog | |
| BMP2 | | | | | | 2 | | |
| BMP4 | | | | | | 1 | | |
| BMPR1A | | | | | | 2 | | |
| BMPR1B | | | | round 2 | | 1 | | |
| BRAF | | | five | | | 2 | | |
| BRD4 | | 2 | | | | | | |
| BTC | | | | round 1 | | | | |
| BTRC | | 1.5 | | round 2 | | | | |
| C14orf120 | 1.5 | 2 | | | | | | |
| C20orf119 | | | | | | | paralog | |
| CALCOCO2 | | | | round 1 | | | | |
| CALD1 | | | | round 1 | | | | |
| CALM1 | | | | round 1 | complex | | | |
| CALM2 | | | | round 2 | complex | | | |

TABLE 1-continued

| Gene name | Trancriptional change (AG/HRG AG fold) | Pathways | PPI | Complex | Fly homolog | Paralog | Local expert |
|---|---|---|---|---|---|---|---|
| CALM3 | | | round 2 | complex | | | |
| CAMK2G | | five | round 2 | | | | |
| CAMLG | | | round 1 | | | | |
| CASP1 | | | round 1 | | | | |
| CAV1 | | core | round 1 | complex | | | |
| CAV2 | | core | round 2 | complex | | | |
| CAV3 | | | round 1 | | | | |
| CBL | | core | round 1 | complex | | | |
| CBLB | | five | round 1 | complex | | | |
| CBLC | | five | round 1 | | | | |
| CCND1 | | five | round 2 | | | | |
| CCND2 | | | | | | paralog | |
| CCND3 | | | | | | paralog | |
| CCNE1 | | | round 2 | | 2 | | |
| CCNE2 | | five | | | 1 | | |
| CCR1 | | | | | | paralog | |
| CCR2 | | | | | | paralog | |
| CCR5 | | | round 2 | complex | | | |
| CD22 | | | round 1 | | | | |
| CD247 | | | round 1 | | | | |
| CD2AP | | | round 1 | | | | |
| CD3E | | | round 1 | | | | |
| CD44 | | | round 1 | | | | |
| CD59 | | | round 2 | complex | | | |
| CD82 | | | round 1 | | | | |
| CDC25A | 1.5 | | round 1 | | | | |
| CDC42 | −1.5 | core | round 2 | | | | |
| CDCP1 | | | round 2 | complex | | | |
| CDH1 | | five | round 1 | | | | |
| CDH3 | | | | | | paralog | |
| CDH5 | | | round 1 | | | | |
| CDK2 | | five | round 2 | | | | |
| CEACAM1 | | five | round 1 | | | | |
| CEBPA | | five | round 2 | | | | |
| CEBPB | | five | round 1 | | | | |
| CEBPZ | −2 | | | | | | |
| CHAT | | | round 1 | | | | |
| CHKB | 1.5 | 2 | | | | | |
| CHL1 | | | | | 2 | | |
| CHUK | | five | round 2 | | | | |
| COPS5 | | | | | 1 | | |
| CPSF6 | | 1.5 | round 2 | | | | |
| CREB1 | | core | round 2 | | | | |
| CRK | | five | round 1 | | | | |
| CRKL | | five | round 1 | | | | |
| CSF2RB | | | round 1 | | | | |
| CSF3R | | | round 1 | | | | |
| CSK | | core | round 1 | | | | |
| CSNK2A1 | 1.5 | five | round 2 | | | | |
| CSPG4 | | | round 1 | | | | |
| CTGF | 2 | | | | | | |
| CTNNA1 | −2 | | round 2 | complex | | | |
| CTNNB1 | 2 | five | round 1 | | 1 | | |
| CTNND1 | | five | round 2 | complex | | | |
| CTTN | 2 | | round 2 | complex | | | |
| CUTL1 | 1.5 | | round 2 | | | | |
| CXCL12 | −2 | | | | | | |
| CXorf33 | −2 | −2 | | | | | |
| CXorf56 | −2 | −2 | | | | | |
| CYR61 | 2 | | | | | | |
| DAB2 | 1.5 | | round 2 | | | | |
| DAG1 | | five | round 1 | | | | |
| DCDC2 | −2 | | | | | | |
| DCN | | | round 1 | | | | |
| DDEF1 | | five | round 2 | | | | |
| DDHD1 | 1.5 | 2 | | | | | |
| DDR1 | | | round 1 | | | | |
| DDR2 | | | round 1 | | | | |
| DDX50 | 1.5 | 2 | | | | | |
| DEGS1 | | | round 1 | | | | |
| DIDO1 | 1.5 | 2 | | | | | |
| DIXDC1 | −2 | −2 | | | | | |
| DLG4 | | | round 1 | | | | |
| DLG5 | 1.5 | | round 2 | | | | |
| DLL1 | | | | | 2 | | |
| DLL4 | | | | | 1 | | |
| DNAJA3 | | | round 2 | complex | | | |

TABLE 1-continued

| Gene name | Transcriptional change (AG/HRG AG fold) | Pathways | PPI | Complex | Fly homolog | Paralog | Local expert |
|---|---|---|---|---|---|---|---|
| DNM1 | | | five | round 2 | | | |
| DOCK1 | | | | round 1 | | | |
| DOCK2 | | | | | | paralog | |
| DOCK5 | | | | | | paralog | |
| DOK2 | | | five | round 2 | | | |
| DUSP1 | 2 | | five | | | | |
| DUSP4 | 2 | | | | | | |
| DUSP6 | | | | | 3 | | |
| DUSP7 | | | | | 2 | | |
| DUSP9 | | | | | 1 | | |
| DYNLL1 | | | | round 2 | complex | | |
| DYNLL2 | | | | | | paralog | |
| E2F5 | | | | | 1 | | |
| EBF | | | | | 2 | | |
| EBF3 | | | | | 1 | | |
| EDN1 | 2 | | | | | | |
| EEF1A1 | | | five | round 2 | complex | | |
| EEF1A2 | | | | | | paralog | |
| EFS | | | | round 1 | | | |
| EGF | | core | | round 1 | | | |
| EGFR | | core | | round 1 | complex | 4 | |
| EGR1 | 2 | | | round 2 | | | |
| EGR2 | 2 | | | | | | |
| EGR3 | 2 | | | | | | |
| EIF3S9 | 1.5 | 2 | | | | | |
| EIF4A1 | 2 | | | | complex | | |
| EIF4A2 | | | | | | paralog | |
| EIF4A3 | | | | | | paralog | |
| ELF3 | 2 | 2 | five | round 2 | | | |
| ELK1 | | core | | round 2 | | | |
| EPB41 | | | | | 4 | | |
| EPB41L1 | | | | | 3 | | |
| EPB41L2 | | | | | 2 | | |
| EPB41L3 | | | | | 1 | | |
| EPGN | | | | | | | expert |
| EPHA2 | | | | round 1 | complex | | |
| EPHA3 | | | | | | paralog | |
| EPHA5 | | | | | | paralog | |
| EPHA7 | | | | | | paralog | |
| EPN1 | | | five | round 2 | | | |
| EPOR | | | | round 1 | | | |
| EPPK1 | | | five | round 1 | complex | | |
| EPS15 | | | five | round 1 | | | |
| EPS15L1 | 1.5 | | five | | | | |
| EPS8 | | core | | round 1 | | | |
| ERBB2 | | core | | round 1 | | 3 | |
| ERBB2IP | | | | round 1 | | | |
| ERBB3 | | core | | round 1 | | 2 | |
| ERBB4 | | | | | | | |
| ERBB4 | | | five | round 2 | | 1 | |
| EREG | | | | round 1 | | | |
| ERRFI1 | | | five | round 1 | | | |
| ESR1 | | | | round 1 | | | |
| ETF1 | | | | | 1 | | |
| ETV6 | | | | | 2 | | |
| ETV7 | | | | | 1 | | |
| EXOC4 | 1.5 | 1.5 | | round 2 | | | |
| EYA1 | | | | | 4 | | |
| EYA2 | | | | round 2 | 3 | | |
| EYA3 | | | | | 2 | | |
| EYA4 | | | | | 1 | | |
| FBRS | | 2 | | | | | |
| FCGR3A | | | | round 1 | | | |
| FDFT1 | 1.5 | 2 | | | | | |
| FER | | | | round 1 | | | |
| FES | | | | round 1 | | | |
| FGFR1 | | | | round 1 | 4 | | |
| FGFR2 | | | | | 3 | | |
| FGFR3 | | | | round 2 | 2 | | |
| FGFR4 | | | | | 1 | | |
| FGR | | | | | | paralog | |
| FIGF | | | | | 2 | | |
| FLJ11903 | | 2 | | | | | |
| FLJ20280 | −2 | −2 | | | | | |
| FLNA | | | | round 2 | complex | | |
| FLT1 | | | | round 1 | 3 | | |
| FLT3 | | | | round 1 | | | |

TABLE 1-continued

| Gene name | Trancriptional change (AG/HRG AG fold) | Pathways | PPI | Complex | Fly homolog | Paralog | Local expert |
|---|---|---|---|---|---|---|---|
| FLT4 | | | round 1 | | 2 | | |
| FMN2 | | | | | 1 | | |
| FOS | | 2 | core | | | 1 | |
| FOSB | | 2 | | | | | |
| FOXO1A | | | core | round 2 | | | |
| FRK | | | | | 1 | | |
| FSCN1 | | | round 2 | complex | | | |
| FUS | 1.5 | 2 | | | | | |
| FYN | | | round 1 | | | | |
| FZR1 | | | round 1 | | | | |
| GAB1 | | core | round 1 | | | | |
| GAB2 | | five | round 2 | | | | |
| GAPDH | | | round 2 | complex | | | |
| GFRA1 | −2 | | | | | | |
| GHR | | | round 1 | | | | |
| GIT1 | | five | round 2 | | | | |
| GIT2 | | | | | | paralog | |
| GJA1 | | five | round 2 | | | | |
| GLI2 | | | | | 2 | | |
| GLI3 | | | | | 1 | | |
| GNA12 | | 1.5 | five | | | | |
| GNAI1 | | | five | round 2 | | | |
| GNAI2 | | | round 1 | | | | |
| GNAI3 | | | | | | paralog | |
| GNAO1 | | | | | | paralog | |
| GNB2L1 | | | five | round 2 | | | |
| GRAP | | | | | | paralog | |
| GRAP2 | | | round 1 | | | | |
| GRB10 | | | round 1 | | | | |
| GRB14 | | | five | round 1 | | | |
| GRB2 | | | core | round 1 | complex | | |
| GRB7 | | | core | round 1 | | | |
| GSK3b | | | | | | | expert |
| GSN | | | round 1 | complex | | | |
| HBEGF | | | five | round 1 | | | |
| hCG__1757335 | | | | | | paralog | |
| HCK | | | round 1 | | | | |
| HD | | | five | round 1 | | | |
| HDAC1 | | | five | round 2 | | | |
| HDAC6 | | | | | | | expert |
| HES1 | | 2 | | | | | |
| HGF | | | | | | | expert |
| HIP1 | | | five | round 2 | | | |
| HLA-A | | | round 1 | | | | |
| HNRPA1 | | 1.5 | | complex | | | |
| HNRPK | | | round 2 | complex | | | |
| HRAS | | | core | round 2 | | 2 | |
| HSP90AA1 | | | round 1 | | | | |
| HSP90B1 | | | round 1 | | | | |
| HSPA5 | | | round 2 | complex | | | |
| HSPA8 | | | round 2 | complex | | | |
| HSPA9B | | | round 2 | complex | | | |
| HSPD1 | | | round 2 | complex | | | |
| ID1 | | 2 | | | | | |
| ID2 | | | round 1 | | | | |
| IER2 | | 2 | | | | | |
| IGF1R | 1.5 | 1.5 | | round 1 | | | |
| IKBKB | | | five | round 2 | | | |
| IKBKG | | | five | round 2 | | | |
| IL2 | | | round 1 | | | | |
| IL2RB | | | round 1 | | | | |
| IL2RG | | | round 1 | | | | |
| IL4R | | | round 1 | | | | |
| IL6ST | | | round 1 | | | | |
| ILF3 | | | round 2 | complex | | | |
| INPP5D | | | round 1 | | | | |
| INPPL1 | | core | round 1 | | | | |
| INSR | | | round 1 | | | | |
| INSRR | | | | | | paralog | |
| IQGAP1 | | | round 2 | complex | | | |
| IRS1 | | | round 1 | | | | |
| IRS2 | | | round 1 | | | | |
| ITCH | | | five | round 1 | | | |
| ITGA5 | | | round 1 | | | | |
| ITGB3 | | | round 1 | | | | |
| ITGB4 | | | round 1 | | | | |

TABLE 1-continued

| Gene name | Trancriptional change (AG/HRG AG fold) | Pathways | PPI | Complex | Fly homolog | Paralog | Local expert |
|---|---|---|---|---|---|---|---|
| JAK1 | 1.5 | core | round 2 | | | | |
| JAK2 | | core | round 1 | | | | |
| JUN | 1.5 | core | round 2 | | 3 | | |
| JUNB | 2 | | | | 2 | | |
| JUND | | five | | | 1 | | |
| JUP | | | round 1 | | | | |
| KDR | | | round 1 | | 1 | | |
| KLF10 | 2 | | | | | | |
| KLF6 | 1.5 | 2 | | | | | |
| KRAS | | core | | | | | |
| KRT17 | | five | round 1 | complex | | | |
| KRT18 | | five | round 1 | complex | | | |
| KRT5 | | | round 2 | complex | | | |
| KRT6A | | | round 2 | complex | | | |
| KRT6B | | | | | | paralog | |
| KRT6C | | | | | | paralog | |
| KRT6E | | | | | | paralog | |
| KRT7 | | five | round 1 | complex | | | |
| KRT8 | | five | round 1 | complex | | | |
| KSR2 | | | | | 1 | | |
| L1CAM | | | round 2 | | 1 | | |
| LCK | | | round 1 | | | | |
| LCP2 | | | round 1 | | | | |
| LGALS3 | −2 | −2 | | | | | |
| LIN7A | | | round 2 | | 3 | | |
| LIN7B | | | round 2 | | 2 | | |
| LIN7C | | | | | 1 | | |
| LMNA | | | round 2 | complex | | | |
| LOC284393 | | | | | | paralog | |
| LOC387927 | | | round 1 | | | | |
| LOC389342 | | | | | | paralog | |
| LOC390006 | | | | | | paralog | |
| LOC63920 | | −2 | | | | | |
| LOC642045 | | | | | | paralog | |
| LOC642954 | | | | | | paralog | |
| LOC643751 | | | | | | paralog | |
| LOC643997 | | | | | | paralog | |
| LOC645691 | | | | | | paralog | |
| LOC648695 | | | | | | paralog | |
| LOC650332 | | | | | | paralog | |
| LOC728198 | | | | | | paralog | |
| LOC731173 | | | | | | paralog | |
| LOC731292 | | | | | | paralog | |
| LOC731751 | | | | | | paralog | |
| LRBA | | | | | 2 | | |
| LRP1 | | | round 1 | | | | |
| LRP11 | −2 | −2 | | | | | |
| LRRC4B | | | | | 1 | | |
| LTK | | | round 1 | | | | |
| LYN | | | round 1 | complex | | | |
| MAD1L1 | 2 | 2 | | | | | |
| MAP2K1 | | core | round 2 | | 2 | | |
| MAP2K2 | | core | | | 1 | | |
| MAP2K3 | | core | | | | | |
| MAP2K4 | | core | | | | | |
| MAP2K7 | | core | | | | | |
| MAP3K1 | | core | round 2 | | | | |
| MAP3K11 | | five | round 2 | | | | |
| MAP3K14 | | five | round 1 | | | | |
| MAP3K3 | | five | round 2 | | | | |
| MAP3K4 | | core | | | | | |
| MAP3K5 | 1.5 | | round 2 | | | | |
| MAP4K1 | | | round 1 | | | | |
| MAPK1 | | core | | | | | |
| MAPK10 | | | | | | paralog | |
| MAPK14 | | core | round 2 | | | | |
| MAPK3 | 2 | | | | | | |
| MAPK3 | | core | | | | | |
| MAPK8 | | core | round 2 | | | | |
| MAPK9 | | | | | | paralog | |
| MAPKAPK2 | | | round 1 | | | | |
| MATK | | five | round 1 | | | | |
| MCF2 | | five | round 2 | | | | |
| MDM4 | −2 | | | | | | |
| MET | | | round 1 | | | | |
| MGC14376 | 2 | | | | | | |
| MICAL1 | | | round 1 | | | | |

TABLE 1-continued

| Gene name | Trancriptional change (AG/HRG AG fold) | Pathways | PPI | Complex | Fly homolog | Paralog | Local expert |
|---|---|---|---|---|---|---|---|
| MME | | | round 1 | | | | |
| MRCL3 | 1.5 | 2 | | complex | | | |
| MRLC2 | | | | | | paralog | |
| MST1R | | | round 1 | | | | |
| MUC1 | | five | round 1 | | | | |
| MUC5B | | | | | 1 | | |
| MYC | | core | round 2 | | | | |
| MYH9 | | 1.5 | | complex | | | |
| MYL9 | | | | | | paralog | |
| NBEA | | | | | 1 | | |
| NCK1 | | core | round 1 | | | | |
| NCK2 | | core | round 1 | | | | |
| NDUFA13 | | five | round 2 | | | | |
| NEDD9 | | | round 1 | | | | |
| NFKB1 | 1.5 | five | round 2 | | | | |
| NGFR | | | round 1 | | | | |
| NOTCH2 | | | | | 1 | | |
| NPHP1 | | | round 1 | | | | |
| NPTN | | 2 | | | | | |
| NR4A1 | 1.5 | 2 | | | | | |
| NR4A2 | | 2 | | | | | |
| NRAS | | core | | | 1 | | |
| NRG1 | | | round 1 | | | | |
| NRG2 | | | | | | | expert |
| NTRK1 | | | round 1 | | | | |
| NTRK2 | | | round 1 | | | | |
| NTRK3 | | | round 1 | | | | |
| OVOL1 | | | | | 1 | | |
| PABPC1 | | 1.5 | | complex | | | |
| PABPC3 | | | | | | paralog | |
| PABPC4 | | | | | | paralog | |
| PAFAH1B1 | | | | | 1 | | |
| PAG1 | | | round 1 | | | | |
| PAK1 | | core | round 1 | | | | |
| PAK2 | | | | | | paralog | |
| PAK3 | | | | | | paralog | |
| PAR6 | | | | | | | expert |
| PARD3 | | | | | | | expert |
| PCYT1A | | | | | 2 | | |
| PCYT1B | | | | | 1 | | |
| PDGFRB | | | round 1 | | | | |
| PDLIM7 | | | round 2 | complex | | | |
| PDPK1 | | core | round 2 | | | | |
| PDZK1 | 2 | 1.5 | round 2 | | | | |
| PEBP1 | | five | round 2 | | | | |
| PICK1 | | | round 1 | | | | |
| PIK3C2B | | five | round 1 | | | | |
| PIK3CA | | core | round 2 | | | | |
| PIK3CB | | five | round 2 | | | | |
| PIK3CD | | five | round 2 | | | | |
| PIK3CG | | five | round 2 | | | | |
| PIK3R1 | | core | round 1 | | | | |
| PIK3R2 | | five | round 1 | | | | |
| PIK3R3 | | five | round 2 | | | | |
| Pin1 | | | | | | | expert |
| PIP5K1A | | five | round 2 | | | | |
| PIP5K1B | | five | round 2 | | | | |
| PIP5K2A | | five | round 2 | | | | |
| PIP5K2B | | five | round 2 | | | | |
| PITPNA | | five | round 1 | | 2 | | |
| PITPNB | | | | | 1 | | |
| PKD1 | | | round 1 | | | | |
| PKN2 | | five | round 2 | | | | |
| PLCB1 | | five | round 2 | | | | |
| PLCG1 | | core | round 1 | | 2 | | |
| PLCG2 | | | round 1 | | 1 | | |
| PLD1 | | core | round 2 | | | | |
| PLD1 | | | | | | paralog | |
| PLD2 | | five | round 1 | | | | |
| PLEC1 | | five | round 1 | complex | | | |
| PLSCR1 | 1.5 | five | round 1 | | | | |
| POU3F1 | | | | | 4 | | |
| POU3F2 | | | | | 3 | | |
| POU3F3 | | | | | 2 | | |
| POU3F4 | | | | | 1 | | |
| PPIA | | | round 2 | complex | | | |
| PPP1CB | | five | round 2 | complex | | | |

TABLE 1-continued

| Gene name | Trancriptional change (AG/HRG AG fold) | Pathways | PPI | Complex | Fly homolog | Paralog | Local expert |
|---|---|---|---|---|---|---|---|
| PPP1R10 | 2 | 2 | | | | | |
| PPP2R5A | | | round 1 | | | | |
| PPP4R2 | 2 | | | | | | |
| PRKACA | | | round 1 | | | | |
| PRKACB | | | | | | paralog | |
| PRKACG | | | | | | paralog | |
| PRKAR1A | −1.5 | five | round 1 | | | | |
| PRKCA | | core | round 1 | | | | |
| PRKCB1 | | core | | | | | |
| PRKCD | | five | round 1 | | | | |
| PRKCE | | five | round 2 | | | | |
| PRKCG | | core | | | | | |
| PRKCI | | core | | | | | |
| PRKCQ | | five | round 2 | | | | |
| PRKCZ | | core | round 2 | | | | |
| PRKD1 | | core | round 2 | | | | |
| PRKDC | | | round 2 | complex | | | |
| PRKX | | | | | | paralog | |
| PRMT5 | | | round 2 | complex | | | |
| PRODH | | | | | 1 | | |
| PRSS12 | | | | | 1 | | |
| PSME4 | 2 | | | | | | |
| PTEN | | five | round 2 | | | | |
| PTGER4 | −2 | five | | | | | |
| PTK2 | | five | round 1 | complex | | | |
| PTK2B | | core | round 1 | complex | | | |
| PTK6 | | five | round 1 | | | | |
| PTPN1 | | | round 1 | | | | |
| PTPN11 | | core | round 1 | complex | | | |
| PTPN12 | | five | round 1 | | | | |
| PTPN2 | | | | | | paralog | |
| PTPN6 | | five | round 2 | | | | |
| PTPRF | | | round 1 | | | | |
| PTPRH | | | round 1 | | | | |
| PTPRJ | | | round 1 | | | | |
| PXN | | core | round 1 | complex | | | |
| RAB22A | 2 | | | | | | |
| RAB5A | | core | | | | | |
| RAC1 | | core | round 2 | | | | |
| RAC2 | | | | | | paralog | |
| RAC3 | | | | | | paralog | |
| RACGAP1 | | | round 2 | complex | | | |
| RAF1 | 1.5 | core | round 2 | | 1 | | |
| RALA | | | | | | paralog | |
| RALB | | five | round 2 | | | | |
| RAP1A | 1.5 | | round 2 | | | | |
| RAP1B | | | | | | paralog | |
| RAP2A | | | | | | paralog | |
| RAPGEF1 | | | round 1 | | | | |
| RARA | 1.5 | 2 | round 2 | | | | |
| RARB | | | | | | paralog | |
| RARG | | | | | | paralog | |
| RASA1 | | core | round 1 | | 1 | | |
| RASA2 | | | | | 2 | | |
| RASA3 | | | | | 1 | | |
| RASD1 | 2 | | round 2 | | | | |
| RB1 | | five | round 2 | | | | |
| RBBP4 | | | | | | paralog | |
| RBBP7 | | five | | complex | | | |
| REPS1 | | five | round 1 | | | | |
| RET | 1.5 | | round 1 | | | | |
| RGS16 | | five | round 1 | | | | |
| RGS4 | | five | round 2 | | | | |
| RHO | | | | | 1 | | |
| RHOA | | core | round 2 | | 2 | | |
| RHOB | | | | | | paralog | |
| RHOC | | five | | | 1 | | |
| RHOG | | five | round 2 | | | | |
| RICS | | | round 1 | | | | |
| RIPK1 | | five | round 1 | | | | |
| RLF | 2 | | | | | | |
| ROS1 | | | round 2 | | 1 | | |
| RP11-78J21.1 | | | | | | paralog | |
| RPL10 | 2 | | | complex | | | |
| RPL10L | | | | | | paralog | |
| RPL23 | 1.5 | | | complex | | | |
| RPS6KA1 | | core | | | | | |

TABLE 1-continued

| Gene name | Transcriptional change (AG/HRG AG fold) | Pathways | PPI | Complex | Fly homolog | Paralog | Local expert |
|---|---|---|---|---|---|---|---|
| RPS6KA2 | | core | | | | | |
| RPS6KA3 | | core | | | | | |
| RPS6KA5 | | core | | | | | |
| RRAS | | five | round 2 | | | | |
| RRAS2 | | five | round 2 | | | | |
| RREB1 | 1.5 | 1.5 | | | 1 | | |
| RUNX1 | 1.5 | 1.5 | round 2 | | | | |
| RUVBL2 | | | round 2 | complex | | | |
| RYR1 | | five | round 2 | | | | |
| SAFB2 | | | round 2 | complex | | | |
| SC4MOL | 2 | 2 | | | | | |
| SERPINA3 | | | round 1 | | | | |
| SFN | | | round 2 | complex | | | |
| SH2D3A | | | round 1 | | | | |
| SH2D3C | | five | round 1 | | | | |
| SH3GL3 | | five | round 2 | | | | |
| SH3KBP1 | | five | round 2 | | | | |
| SHC1 | | core | round 1 | complex | 3 | | |
| SHC2 | | | | | 2 | | |
| SHC3 | | five | round 1 | | 1 | | |
| SHCBP1 | | | round 1 | | | | |
| SKIL | 1.5 | | round 2 | | | | |
| SLC35A3 | −2 | | | | | | |
| SLC39A6 | −2 | | | | | | |
| SLPI | 1.5 | | round 2 | | | | |
| SMAD1 | | | round 1 | | | | |
| SMAD2 | | five | round 1 | | | | |
| SMAD3 | | five | round 1 | | | | |
| SMAD9 | | | | | | paralog | |
| SMARCB1 | | | round 2 | | 1 | | |
| SNCA | | five | round 2 | | | | |
| SNF1LK | 2 | | | | | | |
| SNIP | | | round 1 | | | | |
| SNRPD2 | | five | round 1 | complex | | | |
| SNX1 | | | round 1 | | | | |
| SNX2 | | | round 1 | | | | |
| SNX4 | | | round 1 | | | | |
| SNX6 | | | round 1 | | | | |
| SOCS1 | | five | round 1 | | | | |
| SOCS3 | 1.5 | five | round 1 | | | | |
| SORBS3 | | | round 1 | | | | |
| SOS1 | 1.5 | core | round 1 | complex | 2 | | |
| SOS2 | | five | round 1 | | 1 | | |
| SP1 | | five | round 1 | | | | |
| SPECC1 | 1.5 | | | complex | | | |
| SPEN | | | | | 1 | | |
| SPG7 | 1.5 | | round 2 | | | | |
| SPIRE1 | | | | | 1 | | |
| SPRY1 | | | round 2 | | 4 | | |
| SPRY2 | | core | round 2 | | 3 | | |
| SPRY3 | | | | | 2 | | |
| SPRY4 | | | | | 1 | | |
| SPTAN1 | | | round 2 | complex | | | |
| SQLE | 2 | | | | | | |
| SRC | | core | round 1 | | | | |
| SRF | | five | round 2 | | 1 | | |
| SSR3 | −2 | −2 | | | | | |
| STAT1 | | core | round 1 | | | | |
| STAT2 | | five | round 2 | | | | |
| STAT3 | | core | round 1 | complex | | | |
| STAT4 | | | | | | paralog | |
| STAT5A | | core | round 1 | | 3 | | |
| STAT5B | | five | round 1 | | 2 | | |
| STAT6 | | | round 2 | | 1 | | |
| STK3 | | | | | | paralog | |
| STK4 | 2 | | | | | | |
| STUB1 | | | round 1 | | | | |
| TAF9B | −2 | | | | | | |
| TBL1X | | | | | | paralog | |
| TBL1XR1 | | | | | 2 | | |
| TBL1Y | | | | | 1 | | |
| TCF12 | | | | | 3 | | |
| TCF3 | | | round 1 | | 2 | | |
| TCF4 | | | round 2 | | 1 | | |
| TFDP2 | −2 | | | | 1 | | |
| TGFA | | | round 1 | | | | |
| TGFBR1 | 1.5 | | round 2 | | | | |

TABLE 1-continued

| Gene name | Transcriptional change (AG/HRG AG fold) | Pathways | PPI | Complex | Fly homolog | Paralog | Local expert |
|---|---|---|---|---|---|---|---|
| TJP1 | | | round 1 | | | | |
| TLE3 | | | | | 1 | | |
| TLN1 | 1.5 | | round 2 | | | | |
| TMEM1 | 2 | | | | | | |
| TMPO | −2 | | | | | | |
| TNC | | | round 1 | | | | |
| TNK2 | | five | round 1 | | | | |
| TOB1 | | | round 1 | | | | |
| TP53 | | five | round 2 | | | | |
| TPM4 | 2 | | | | | | |
| TPR | | | round 1 | | | | |
| TRAF4 | 1.5 | | round 2 | | | | |
| TRAPPC6A | | | round 1 | | | | |
| TRIM24 | | | round 2 | complex | | | |
| TRIP12 | 1.5 | 2 | | | | | |
| TRIP6 | | | round 1 | | | | |
| TRPM7 | 1.5 | | round 2 | | | | |
| TUBA1B | | | round 2 | complex | | | |
| TUBA2 | | | | | | paralog | |
| TUBA3 | | | | | | paralog | |
| TUBA6 | | | | | | paralog | |
| TXNIP | −2 | | | | | | |
| UBE1L2 | 2 | | | | | | |
| UBE2L3 | | five | round 2 | | | | |
| UQCRFS1 | | | | | 2 | | |
| VAV1 | | core | round 1 | | | | |
| VAV2 | | core | round 1 | complex | | | |
| VAV3 | | core | round 1 | complex | | | |
| VEGFC | | | | | 1 | | |
| WASL | −2 | core | round 2 | | | | |
| WDR1 | 2 | | | complex | | | |
| WWP1 | | | | | | paralog | |
| WWP2 | | | | | | paralog | |
| XRCC5 | 2 | | round 2 | | | | |
| XRCC6 | | | round 1 | complex | | | |
| YES1 | | | round 2 | complex | | | |
| YWHAB | | five | round 2 | | | | |
| YWHAE | | | round 2 | complex | | | |
| YWHAQ | | five | round 2 | complex | | | |
| YWHAZ | | | round 1 | complex | | | |
| ZAP70 | | | round 1 | | | | |
| ZNF259 | | | round 1 | | | | |
| ZNF69 | −2 | | | | | | |
| ZYX | | | round 1 | | | | |

TABLE 2

| | Erlotinib | | Panitumumab | | CPT11 | | U0126 | |
|---|---|---|---|---|---|---|---|---|
| | Gene | Ratio | Gene | Ratio | Gene | Ratio | Gene | Ratio |
| 1 | ALK | 0.57 | ALK | 0.77 | ALK | 0.73 | | |
| 2 | ANXA6 | 0.47 | ANXA6 | 0.78 | ANXA6 | 0.82 | ANXA6 | 0.64 |
| 3 | ASCL2 | 0.52 | | | ASCL2 | 0.82 | | |
| 4 | BCL3 | 0.64 | | | BCL3 | 0.64 | | |
| 5 | CAV2 | 0.56 | | | CAV2 | 0.72 | | |
| 6 | CD22 | 0.70 | | | CD22 | 0.79 | | |
| 7 | CD59 | 0.71 | | | CD59 | 0.82 | | |
| 8 | CDC42 | 0.72 | | | CDC42 | 0.73 | | |
| 9 | CTNNA1 | 0.72 | | | CTNNA1 | 0.69 | | |
| 10 | DCN | 0.71 | | | DCN | 0.71 | | |
| 11 | EPB41L1 | 0.44 | | | EPB41L1 | 0.73 | | |
| 12 | EPHA5 | 0.67 | EPHA5 | 0.59 | EPHA5 | 0.61 | | |
| 13 | ERBB3 | 0.61 | | | ERBB3 | 0.49 | ERBB3 | 0.76 |
| 14 | FGFR2 | 0.73 | | | FGFR2 | 0.72 | | |
| 15 | RAPGEF1 | 0.59 | RAPGEF1 | 0.69 | RAPGEF1 | 0.84 | | |
| 16 | PLCG2 | 0.57 | | | PLCG2 | 0.65 | PLCG2 | 0.68 |
| 17 | PLSCR1 | 0.61 | PLSCR1 | 0.71 | PLSCR1 | 0.72 | | |
| 18 | PRKACB | 0.53 | PRKACB | 0.63 | PRKACB | 0.43 | | |
| 19 | PRKCE | 0.52 | PRKCE | 0.66 | PRKCE | 0.70 | | |
| 20 | SC4MOL | 0.61 | | | SC4MOL | 0.65 | | |
| 21 | CXCL12 | 0.61 | | | CXCL12 | 0.70 | CXCL12* | 0.83 |
| 22 | SLP1 | 0.60 | | | SLP1 | 0.84 | | |
| 23 | SOS2 | 0.69 | | | SOS2 | 0.74 | | |

TABLE 2-continued

| | Erlotinib | | Panitumumab | | CPT11 | | U0126 | |
|---|---|---|---|---|---|---|---|---|
| | Gene | Ratio | Gene | Ratio | Gene | Ratio | Gene | Ratio |
| 24 | STAT3 | 0.56 | | | STAT3 | 0.66 | STAT3* | 0.75 |
| 25 | TLN1 | 0.72 | | | TLN1 | 0.80 | | |
| 26 | PIP5K1B | 0.72 | | | PIP5K1B | 0.75 | | |
| 27 | BCAR3 | 0.58 | | | BCAR3 | 0.52 | | |
| 28 | TRIP12 | 0.63 | | | TRIP12 | 0.50 | | |
| 29 | BCAR1 | 0.67 | | | BCAR1 | 0.80 | | |
| 30 | TOB1 | 0.38 | | | TOB1 | 0.75 | | |
| 31 | VAV3 | 0.66 | | | VAV3 | 0.76 | | |
| 32 | SPECC1 | 0.68 | SPECC1 | 0.73 | SPECC1 | 0.75 | SPECC1 | 0.76 |
| 33 | ARF4 | 0.79 | | | | | | |
| 34 | ARF5 | 0.82 | | | | | | |
| 35 | RHOA | 0.63 | RHOA | 0.67 | | | | |
| 36 | CALD1 | 0.76 | | | | | | |
| 37 | CDC25A | 0.78 | | | | | | |
| 38 | CDH3 | 0.78 | | | | | | |
| 39 | DAG1 | 0.74 | | | | | | |
| 40 | DLG4 | 0.73 | | | | | | |
| 41 | DOCK2 | 0.74 | | | | | | |
| 42 | DUSP4 | 0.71 | | | | | | |
| 43 | DUSP7 | 0.83 | | | | | | |
| 44 | EGR3 | 0.73 | | | | | | |
| 45 | ERBB2 | 0.80 | | | | | | |
| 46 | FCGR3A | 0.52 | | | | | | |
| 47 | FER | 0.63 | | | | | | |
| 48 | FES | 0.66 | | | | | | |
| 49 | FGR | 0.70 | | | | | | |
| 50 | FLNA | 0.48 | | | | | | |
| 51 | FUS | 0.81 | | | | | | |
| 52 | GAPDH | 0.68 | | | | | | |
| 53 | GNAI2 | 0.65 | | | | | GNAI2 | 0.58 |
| 54 | GRB7 | 0.67 | | | | | | |
| 55 | GRB14 | 0.54 | | | | | | |
| 56 | NRG1 | 0.70 | | | | | | |
| 57 | HIP1 | 0.59 | | | | | | |
| 58 | HES1 | 0.66 | | | | | | |
| 59 | INPPL1 | 0.57 | | | | | | |
| 60 | LTK | 0.55 | | | | | LTK | 0.81 |
| 61 | MATK | 0.70 | | | | | | |
| 62 | MAP3K1 | 0.66 | | | | | | |
| 63 | MYC | 0.78 | | | | | | |
| 64 | POU3F2 | 0.65 | POU3F2 | 0.69 | | | | |
| 65 | PKN2 | 0.66 | | | | | | |
| 66 | MAP2K1 | 0.34 | | | | | | |
| 67 | RET | 0.75 | | | | | | |
| 68 | RPL10 | 0.55 | | | | | | |
| 69 | RPS6KA3 | 0.69 | | | | | | |
| 70 | SHC1 | 0.63 | | | | | | |
| 71 | SRF | 0.81 | | | | | | |
| 72 | KLF10 | 0.69 | | | | | | |
| 73 | TMEM1 | 0.77 | | | | | | |
| 74 | RPS6KA5 | 0.62 | | | | | | |
| 75 | RPL23 | 0.69 | | | | | | |
| 76 | NRG2 | 0.69 | | | | | | |
| 77 | SH2D3C | 0.61 | | | | | | |
| 78 | ANKRD11 | 0.74 | | | | | | |
| 79 | DLL4 | 0.75 | | | | | | |
| 80 | PARD3 | 0.72 | | | | | | |
| 81 | LOC63920 | 0.62 | | | | | | |
| 82 | DIXDC1 | 0.81 | | | | | | |
| 83 | TBL1Y | 0.66 | | | | | | |
| 84 | | | | | ACTN4 | 0.83 | | |
| 85 | | | | | BCR | 0.78 | | |
| 86 | | | | | CEACAM1 | 0.61 | | |
| 87 | | | | | BLK | 0.69 | | |
| 88 | | | | | CAMLG | 0.76 | | |
| 89 | | | | | CAV3 | 0.78 | | |
| 90 | | | | | CBLB | 0.60 | | |
| 91 | | | | | CHUK | 0.74 | | |
| 92 | | | | | CCR5 | 0.60 | | |
| 93 | | | | | CTGF | 0.83 | | |
| 94 | | | | | DUSP1 | 0.58 | | |
| 95 | | | | | EPHA7 | 0.73 | | |
| 96 | | | | | ESR1 | 0.76 | | |
| 97 | | | | | EYA2 | 0.81 | | |
| 98 | | | | | GRB10 | 0.76 | | |
| 99 | | | | | HSPA5 | 0.80 | | |

TABLE 2-continued

| | Erlotinib | | Panitumumab | | CPT11 | | U0126 | |
|---|---|---|---|---|---|---|---|---|
| | Gene | Ratio | Gene | Ratio | Gene | Ratio | Gene | Ratio |
| 100 | | | | | TNC | 0.72 | | |
| 101 | | | | | SMAD9 | 0.71 | | |
| 102 | | | | | PIK3R2 | 0.44 | | |
| 103 | | | | | PLEC1 | 0.67 | | |
| 104 | | | | | PRKACG | 0.74 | | |
| 105 | | | | | PRKCB1 | 0.71 | | |
| 106 | | | | | RHO | 0.82 | | |
| 107 | | | | | RRAS | 0.82 | | |
| 108 | | | | | TGFBR1 | 0.77 | | |
| 109 | | | | | TPR | 0.82 | | |
| 110 | | | | | UBE2L3 | 0.76 | | |
| 111 | | | | | MAPKAPK2 | 0.81 | | |
| 112 | | | | | TRAF4 | 0.67 | | |
| 113 | | | | | EIF4A3 | 0.56 | | |
| 114 | | | | | GAB2 | 0.83 | | |
| 115 | | | | | SORBS3 | 0.56 | | |
| 116 | | | | | FZR1 | 0.68 | | |
| 117 | | | | | FMN2 | 0.64 | | |
| 118 | | | | | REPS1 | 0.70 | | |
| 119 | | | | | | | LYN | 0.82 |
| 120 | | | LOC390006 | 0.76 | | | LOC390006 | 0.66 |
| 121 | | | LOC284393 | 0.75 | | | | |

Notes.
False discovery rate set at 5%, except for 2 U0126 hits marked *, where 7.5% was used (statisticians say up to 20% is ok).

TABLE 3

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-1-A | single siRNA, 0.9 nmol | 1 | 12 | SERPINA3 | serpin peptidase inhibitor, clade A (alpha-1 antiproteinase, antitrypsin), member 3 | NM_001085 | AAGGTTCTACTTGAGCAAGAA | SI00715540 | Hs_SERPINA3_4 |
| 900029-1-A | single siRNA, 0.9 nmol | 2 | 207 | AKT1 | v-akt murine thymoma viral oncogene homolog 1 | NM_001014431 NM_001014432 NM_005163 | CACCATGAGCGACGTGCTAT | SI02758406 | Hs_AKT1_11 |
| 900029-1-A | single siRNA, 0.9 nmol | 3 | 331 | BIRC4 | baculoviral IAP repeat-containing 4 | NM_001167 | AAGTGCTTTCACTGTGGAGGA | SI00299446 | Hs_BIRC4_5 |
| 900029-1-A | single siRNA, 0.9 nmol | 4 | 378 | ARF4 | ADP-ribosylation factor 4 | NM_001660 XM_001132763 | ACCAAGGACATGTTTGATAAA | SI00300076 | Hs_ARF4_4 |
| 900029-1-A | single siRNA, 0.9 nmol | 5 | 389 | RHOC | ras homolog gene family, member C | NM_001042678 NM_001042679 NM_175744 | CCCTACTGTCTTTGAGAACTA | SI02663913 | Hs_RHOC_6 |
| 900029-1-A | single siRNA, 0.9 nmol | 6 | 595 | CCND1 | cyclin D1 | NM_053056 | GCCCTCGGTGTCCTACTTCAA | SI02654547 | Hs_CCND1_6 |
| 900029-1-A | single siRNA, 0.9 nmol | 7 | 652 | BMP4 | bone morphogenetic protein 4 | NM_001202 NM_130850 NM_130851 | GCGAGCCATGCAGTTTGATA | SI03105193 | Hs_BMP4_7 |
| 900029-1-A | single siRNA, 0.9 nmol | 8 | 800 | CALD1 | caldesmon 1 | NM_004342 NM_033138 NM_033139 NM_033140 NM_033157 | CGCCAAGAAAGATACGAGATA | SI03193498 | Hs_CALD1_6 |
| 900029-1-A | single siRNA, 0.9 nmol | 9 | 834 | CASP1 | caspase 1, apoptosis-related cysteine peptidase (interleukin 1, beta, convertase) | NM_001223 NM_033292 NM_033293 NM_033294 NM_033295 | TACCTCTTCCCAGGACATTAA | SI02662443 | Hs_CASP1_15 |
| 900029-1-A | single siRNA, 0.9 nmol | 10 | 868 | CBLB | Cas-Br-M (murine) ecotropic retroviral transforming sequence b | NM_170662 | CAGGTGTTGCAGCATCATTGA | SI03072398 | Hs_CBLB_5 |
| 900029-1-A | single siRNA, 0.9 nmol | 11 | 25 | ABL1 | v-abl Abelson murine leukemia viral oncogene homolog 1 | NM_005157 NM_007313 | AACGGCTGATGTGGACTGTCT | SI00299110 | Hs_ABL1_9 |
| 900029-1-A | single siRNA, 0.9 nmol | 12 | 208 | AKT2 | v-akt murine thymoma viral oncogene homolog 2 | NM_001626 | AAGGTACTTCGATGATGAATT | SI00299173 | Hs_AKT2_6 |
| 900029-1-A | single siRNA, 0.9 nmol | 13 | 351 | APP | amyloid beta (A4) precursor protein (peptidase nexin-II, Alzheimer disease) | NM_000484 NM_201413 NM_201414 | CTGGTCTTCAATTACCAAGAA | SI02780288 | Hs_APP_10 |
| 900029-1-A | single siRNA, 0.9 nmol | 14 | 381 | ARF5 | ADP-ribosylation factor 5 | NM_001662 | TTCGGGATCTTCGGAAGAA | SI03242351 | Hs_ARF5_5 |
| 900029-1-A | single siRNA, 0.9 nmol | 15 | 391 | RHOG | ras homolog gene family, member G (rho G) | NM_001665 | CACGCTGCGCTACCTCGAA | SI00702884 | Hs_RHOG_4 |
| 900029-1-A | single siRNA, 0.9 nmol | 16 | 602 | BCL3 | B-cell CLL/lymphoma 3 | NM_005178 | CAACGTGAACGCGCAAATGTA | SI02654554 | Hs_BCL3_5 |
| 900029-1-A | single siRNA, 0.9 nmol | 17 | 657 | BMPR1A | bone morphogenetic protein receptor, type IA | NM_004329 | GCGCAGACATTAAAGGTACA | SI02656629 | Hs_BMPR1A_6 |
| 900029-1-A | single siRNA, 0.9 nmol | 18 | 801 | CALM1 | calmodulin 1 (phosphorylase kinase, delta) | NM_006888 | CTGGTTGTATCTTATTAGCAA | SI02224222 | Hs_CALM1_6 |
| 900029-1-A | single siRNA, 0.9 nmol | 19 | 857 | CAV1 | caveolin 1, caveolae protein, 22kDa | NM_001753 | AAGCAAGTGTACCACGCCCAC | SI00299642 | Hs_CAV1_10 |
| 900029-1-A | single siRNA, 0.9 nmol | 20 | 894 | CCND2 | cyclin D2 | NM_001759 | CAGGGCCGTGCGGACCGCAA | SI03071369 | Hs_CCND2_5 |
| 900029-1-A | single siRNA, 0.9 nmol | 21 | 70 | ACTC1 | actin, alpha, cardiac muscle 1 | NM_005159 | CTGATCGTATGCAGAAGGAA | SI00291389 | Hs_ACTC_3 |
| 900029-1-A | single siRNA, 0.9 nmol | 22 | 238 | ALK1 | anaplastic lymphoma kinase (Ki-1) | NM_004304 | CTGGGCCTGTATACCGGATAA | SI02632854 | Hs_ALK_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-1-A | single siRNA, 0.9 nmol | 23 | 369 | ARAF | v-raf murine sarcoma 3611 viral oncogene homolog | NM_001654 | CCGGGATGGCATGAGTGTCTA | SI00287693 | Hs_ARAF_6 |
| 900029-1-A | single siRNA, 0.9 nmol | 24 | 383 | ARG1 | arginase, liver | NM_000045 | AGCGCCAAGTCCAGAACCATA | SI03043859 | Hs_ARG1_5 |
| 900029-1-A | single siRNA, 0.9 nmol | 25 | 429 | ASCL1 | achaete-scute complex homolog 1 (Drosophila) | NM_004316 | CCAGTTGTACTTCAGCACCAA | SI03075793 | Hs_ASCL1_5 |
| 900029-1-A | single siRNA, 0.9 nmol | 26 | 613 | BCR | breakpoint cluster region | NM_004327 NM_021574 | AAGGTCAACGACCAAAGAGGTG | SI00299425 | Hs_BCR_5 |
| 900029-1-A | single siRNA, 0.9 nmol | 27 | 658 | BMPR1B | bone morphogenetic protein receptor, type IB | NM_001203 | ACGGATATTGTTTCACGATGA | SI00604989 | Hs_BMPR1B_6 |
| 900029-1-A | single siRNA, 0.9 nmol | 28 | 805 | CALM2 | calmodulin 2 (phosphorylase kinase, delta) | NM_001743 | AAGCCCTTCTGCACATCTAAA | SI02758420 | Hs_CALM2_9 |
| 900029-1-A | single siRNA, 0.9 nmol | 29 | 858 | CAV2 | caveolin 2 | NM_001233 NM_198212 | ACCCTAATAAGTGACAAATAA | SI02664389 | Hs_CAV2_10 |
| 900029-1-A | single siRNA, 0.9 nmol | 30 | 896 | CCND3 | cyclin D3 | NM_001760 | CATGCGGAAGATCTGGCTTA | SI03073924 | Hs_CCND3_5 |
| 900029-1-A | single siRNA, 0.9 nmol | 31 | 81 | ACTN4 | actinin, alpha 4 | NM_004924 | CCCGCAAATCATCAACTCCAA | SI02779980 | Hs_ACTN4_6 |
| 900029-1-A | single siRNA, 0.9 nmol | 32 | 268 | AMH | anti-Mullerian hormone | NM_000479 | CCAATAAAGACCAGCAAGCAA | SI02623572 | Hs_AMH_4 |
| 900029-1-A | single siRNA, 0.9 nmol | 33 | 374 | AREG | amphiregulin (schwannoma-derived growth factor) | NM_001657 | ATGATTGACAGTAGTTTATCA | SI03049683 | Hs_AREG_5 |
| 900029-1-A | single siRNA, 0.9 nmol | 34 | 384 | ARG2 | arginase, type II | NM_001172 | AACCTTGTATCTTCTGCAA | SI00301210 | Hs_ARG2_4 |
| 900029-1-A | single siRNA, 0.9 nmol | 35 | 430 | ASCL2 | achaete-scute complex homolog 2 (Drosophila) | NM_005170 | CTCGACTTCTCCAGCTGTTA | SI03091018 | Hs_ASCL2_6 |
| 900029-1-A | single siRNA, 0.9 nmol | 36 | 634 | CEACAM1 | carcinoembryonic antigen-related cell adhesion molecule 1 (biliary glycoprotein) | NM_001024912 NM_001712 | CTCCATCCTCGTTGTTCTTCAA | SI03089632 | Hs_CEACAM1_7 |
| 900029-1-A | single siRNA, 0.9 nmol | 37 | 673 | BRAF | v-raf murine sarcoma viral oncogene homolog B1 | NM_004333 | AACATATAGAGGCCCTATTGG | SI00299488 | Hs_BRAF_1 |
| 900029-1-A | single siRNA, 0.9 nmol | 38 | 808 | CALM3 | calmodulin 3 (phosphorylase kinase, delta) | NM_005184 | CCGCAGAGCTGCGTCACGTAA | SI02659685 | Hs_CALM3_7 |
| 900029-1-A | single siRNA, 0.9 nmol | 39 | 859 | CAV3 | caveolin 3 | NM_001234 NM_033337 | CAGCTTTGAGCGCGTGTGGAA | SI03068730 | Hs_CAV3_9 |
| 900029-1-A | single siRNA, 0.9 nmol | 40 | 898 | CCNE1 | cyclin E1 | NM_001238 NM_057182 | AAGGCAAACGTGACCGTTTTT | SI00299691 | Hs_CCNE1_5 |
| 900029-1-A | single siRNA, 0.9 nmol | 41 | 160 | AP2A1 | adaptor-related protein complex 2, alpha 1 subunit | NM_014203 NM_130787 | CACCGTCATCAATGCCCTCAA | SI02661610 | Hs_AP2A1_6 |
| 900029-1-A | single siRNA, 0.9 nmol | 42 | 302 | ANXA2 | annexin A2 | NM_001002857 NM_001002858 NM_004039 | CACGGCCTGAGCCTCCAGAAA | SI03060855 | Hs_ANXA2_10 |
| 900029-1-A | single siRNA, 0.9 nmol | 43 | 375 | ARF1 | ADP-ribosylation factor 1 | NM_001024226 NM_001024227 NM_001024228 NM_001658 | AGGGAAGACCACGATCCTCTA | SI02757279 | Hs_ARF1_11 |
| 900029-1-A | single siRNA, 0.9 nmol | 44 | 387 | RHOA | ras homolog gene family, member A | NM_001664 | TACCTTATAGTTACTGTGTAA | SI02776907 | Hs_RHOA_8 |
| 900029-1-A | single siRNA, 0.9 nmol | 45 | 483 | ATP1B3 | ATPase, Na+/K+ transporting, beta 3 polypeptide | NM_001679 XM_001133533 XM_001133534 | AAGGATAGATTGTTTCAAA | SI03066614 | Hs_ATP1B3_4 |
| 900029-1-A | single siRNA, 0.9 nmol | 46 | 640 | BLK | B lymphoid tyrosine kinase | NM_001715 | CTGGTAAGCGACTGTCATCAA | SI02626785 | Hs_BLK_5 |
| 930029-1-A | single siRNA, 0.9 nmol | 47 | 685 | BTC | betacellulin | NM_001729 | ATCCATGAGATAGCTATTATA | SI02626820 | Hs_BTC_6 |
| 900029-1-A | single siRNA, 0.9 nmol | 48 | 818 | CAMK2G | calcium/calmodulin-dependent protein kinase (CaM kinase) II gamma | NM_001222 NM_172169 | CTCGGATATGTCGACTTCTGA | SI02758427 | Hs_CAMK2G_7 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-1-A | single siRNA, 0.9 nmol | 49 | 861 | RUNX1 | runt-related transcription factor 1 (acute myeloid leukemia 1; aml1 oncogene) | NM_172170 NM_172171 NM_172172 NM_172173 NM_001001890 | CAGGATACAAGGCAGATCCAA | SI03069766 | Hs_RUNX1_6 |
| 320029-1-A | single siRNA, 0.9 nmol | 50 | 916 | CD3E | CD3e molecule, epsilon (CD3-TCR complex) | NM_000733 | CTCAGTATCCTGGATCTGAAA | SI03088848 | Hs_CD3E_7 |
| 900029-1-A | single siRNA, 0.9 nmol | 51 | 161 | AP2A2 | adaptor-related protein complex 2, alpha 2 subunit | NM_001754 NM_012305 | AGGCTCTTGATGGCTATAGTA | SI03146633 | Hs_AP2A2_5 |
| 900029-1-A | single siRNA, 0.9 nmol | 52 | 309 | ANXA6 | annexin A6 | NM_001155 NM_004033 | CCGACAAACTTTACAAATCCA | SI00297024 | Hs_ANXA6_4 |
| 900029-1-A | single siRNA, 0.9 nmol | 53 | 377 | ARF3 | ADP-ribosylation factor 3 | NM_001659 | CACCTATATGACCAATCCCTA | SI02654477 | Hs_ARF3_5 |
| 900029-1-A | single siRNA, 0.9 nmol | 54 | 388 | RHOB | ras homolog gene family, member B | NM_004040 | CCCGGACTCGCTGGAGAACAT | SI03078257 | Hs_RHOB_6 |
| 900029-1-A | single siRNA, 0.9 nmol | 55 | 558 | AXL | AXL receptor tyrosine kinase | NM_001699 NM_021913 | TCCAAGATTCTAGATGATTAA | SI00605311 | Hs_AXL_10 |
| 900029-1-A | single siRNA, 0.9 nmol | 56 | 650 | BMP2 | bone morphogenetic protein 2 | NM_001200 | CACCGAATTAATATTTATGAA | SI00023373 | Hs_BMP2_4 |
| 900029-1-A | single siRNA, 0.9 nmol | 57 | 780 | DDR1 | discoidin domain receptor family, member 1 | NM_001954 NM_013993 NM_013994 | CAGGAATGATTCCTGAAAGA | SI00605444 | Hs_DDR1_10 |
| 900029-1-A | single siRNA, 0.9 nmol | 58 | 819 | CAMLG | calcium modulating ligand | NM_001745 | AGGGCTGAGTTTGTATTATTA | SI02777110 | Hs_CAMLG_8 |
| 900029-1-A | single siRNA, 0.9 nmol | 59 | 867 | CBL | Cas-Br-M (murine) ecotropic retroviral transforming sequence | NM_005188 | CCGTACTATCTTGTCAAGATA | SI02757321 | Hs_CBL_8 |
| 900029-1-A | single siRNA, 0.9 nmol | 60 | 919 | CD247 | CD247 molecule | NM_000734 NM_198053 | AACGAGCTCAATCTAGGACGA | SI03029397 | Hs_CD247_1 |
| 900029-1-B | single siRNA, 0.9 nmol | 61 | 12 | SERPINA3 | serpin peptidase inhibitor, clade A (alpha-1 antiproteinase, antitrypsin), member 3 | NM_001085 | CCCAAGATACTCATCAGTCAA | SI00715533 | Hs_SERPINA3_3 |
| 900029-1-B | single siRNA, 0.9 nmol | 62 | 207 | AKT1 | v-akt murine thymoma viral oncogene homolog 1 | NM_001014431 NM_001014432 NM_005163 | CACGCTTGGTCCCGAGGCCAA | SI02757244 | Hs_AKT1_10 |
| 900029-1-B | single siRNA, 0.9 nmol | 63 | 331 | BIRC4 | baculoviral IAP repeat-containing 4 | NM_001167 | GGCCGGAATCTTAATATTCGA | SI03105739 | Hs_BIRC4_8 |
| 900029-1-B | single siRNA, 0.9 nmol | 64 | 378 | ARF4 | ADP-ribosylation factor 4 | NM_001660 | CCCATTTGGAATTATTCCTAA | SI03000069 | Hs_ARF4_3 |
| 900029-1-B | single siRNA, 0.9 nmol | 85 | 399 | RHOC | ras homolog gene family, member C | NM_001042678 NM_001042679 NM_175744 | CACCATGCTGCAATCCGAAA | SI02663906 | Hs_RHOC_5 |
| 900029-1-B | single siRNA, 0.9 nmol | 66 | 595 | CCND1 | cyclin D1 | NM_053056 | AACACCAGCTCCTCTGTGCTG | SI02654540 | Hs_CCND1_5 |
| 900029-1-B | single siRNA, 0.9 nmol | 67 | 652 | BMP4 | bone morphogenetic protein 4 | NM_001202 NM_130850 NM_130851 | CAGGAGCATCCCTGAGAACGA | SI03065643 | Hs_BMP4_6 |
| 900029-1-B | single siRNA, 0.9 nmol | 68 | 800 | CALD1 | caldesmon 1 | NM_004342 NM_033138 NM_033139 NM_033140 NM_033157 | ATGGATCAAAGTTTGAATTAA | SI02731232 | Hs_CALD1_5 |
| 900029-1-B | single siRNA, 0.9 nmol | 69 | 834 | CASP1 | caspase 1, apoptosis-related cysteine peptidase (interleukin 1, beta, convertase) | NM_001223 NM_033292 NM_033293 NM_033294 | CTCATTGAACATATGCAAGAA | SI02661932 | Hs_CASP1_14 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-1-B | single siRNA, 0.9 nmol | 70 | 868 | CBLB | Cas-Br-M (murine) ecotropic retroviral transforming sequence b | NM_033295 NM_170662 | ACGGGCAATAGAGACTCTTTAA | SI00156779 | Hs_CBLB_3 |
| 900029-1-B | single siRNA, 0.9 nmol | 71 | 25 | ABL1 | v-abl Abelson murine leukemia viral oncogene homolog 1 | NM_005157 NM_007313 | AACCAAGCCTTTGAAACAATG | SI00299103 | Hs_ABL1_8 |
| 900029-1-B | single siRNA, 0.9 nmol | 72 | 208 | AKT2 | v-akt murine thymoma viral oncogene homolog 2 | NM_001626 | AACAACTTCTCCGTAGCAGAA | SI00299166 | Hs_AKT2_5 |
| 900029-1-B | single siRNA, 0.9 nmol | 73 | 351 | APP | amyloid beta (A4) precursor protein (peptidase nexin-II, Alzheimer disease) | NM_000484 NM_201413 NM_201414 | ACCCAATTAAGTCCTACTTTA | SI00278028 | Hs_APP_9 |
| 900029-1-B | single siRNA, 0.9 nmol | 74 | 381 | ARF5 | ADP-ribosylation factor 5 | NM_001662 | CATCTTTGTGGTGGACAGTAA | SI00300321 | Hs_ARF5_4 |
| 900029-1-B | single siRNA, 0.9 nmol | 75 | 391 | RHOG | ras homolog gene family, member G (rho G) | NM_001665 | GAGAAGGTGAATGTACCCTAA | SI00702877 | Hs_RHOG_3 |
| 900029-1-B | single siRNA, 0.9 nmol | 76 | 602 | BCL3 | B-cell CLL/lymphoma 3 | NM_005178 | CCGGCCCGAGGCGCCTTTACTA | SI00308215 | Hs_BCL3_6 |
| 900029-1-B | single siRNA, 0.9 nmol | 77 | 657 | BMPR1A | bone morphogenetic protein receptor, type IA | NM_004329 | CAGCTACGCCGGACAATAGAA | SI02659622 | Hs_BMPR1A_5 |
| 900329-1-B | single siRNA, 0.9 nmol | 78 | 801 | CALM1 | calmodulin 1 (phosphorylase kinase, delta) | NM_006888 | CGGCAACTTACACACATTGAA | SI02224215 | Hs_CALM1_5 |
| 900029-1-B | single siRNA, 0.9 nmol | 79 | 857 | CAV1 | caveolin 1, caveolae protein, 22kDa | NM_001753 | CACCTTCACTGTGACGAAATA | SI00299614 | Hs_CAV1_6 |
| 900029-1-B | single siRNA, 0.9 nmol | 80 | 894 | CCND2 | cyclin D2 | NM_001759 | AAGAAATAGACTTGCCACCTTA | SI00027853 | Hs_CCND2_4 |
| 900029-1-B | single siRNA, 0.9 nmol | 81 | 70 | ACTC1 | actin, alpha, cardiac muscle 1 | NM_005159 | TCCTAGCACCATGAAGATTAA | SI00291382 | Hs_ACTC_2 |
| 900029-1-B | single siRNA, 0.9 nmol | 82 | 238 | ALK | anaplastic lymphoma kinase (Ki-1) | NM_004304 | CACCTACGTATTTAAGATGAA | SI00263284 | Hs_ALK_5 |
| 900029-1-B | single siRNA, 0.9 nmol | 83 | 369 | ARAF | v-raf murine sarcoma 3611 viral oncogene homolog | NM_001654 | CCGACTCATCAAGGGACGAAA | SI00287686 | Hs_ARAF_5 |
| 900029-1-B | single siRNA, 0.9 nmol | 84 | 383 | ARG1 | arginase, liver | NM_000045 | AAGCATAGAGTTATCCTTCTA | SI00000707 | Hs_ARG1_4 |
| 900029-1-B | single siRNA, 0.9 nmol | 85 | 429 | ASCL1 | achaete-scute complex homolog 1 (Drosophila) | NM_004316 | ACGCGTTATAGTAACTCCCAT | SI00082587 | Hs_ASCL1_3 |
| 900029-1-B | single siRNA, 0.9 nmol | 86 | 613 | BCR | breakpoint cluster region | NM_004327 NM_021574 | CAGCATTCCGCTGACCATCAA | SI00288141 | Hs_BCR_8 |
| 900029-1-B | single siRNA, 0.9 nmol | 87 | 658 | BMPR1B | bone morphogenetic protein receptor, type IB | NM_001203 | AACGAATGTAATAAAGACCTA | SI00604982 | Hs_BMPR1B_5 |
| 900029-1-B | single siRNA, 0.9 nmol | 88 | 805 | CALM2 | calmodulin 2 (phosphorylase kinase, delta) | NM_001743 | GACCTTGTACAGATGTGTTA | SI02758413 | Hs_CALM2_8 |
| 900029-1-B | single siRNA, 0.9 nmol | 89 | 858 | CAV2 | caveolin 2 | NM_001233 NM_198212 | CCGGCTCAACTCGCATCTCAA | SI00299663 | Hs_CAV2_7 |
| 900029-1-B | single siRNA, 0.9 nmol | 90 | 896 | CCND3 | cyclin D3 | NM_001760 | TGGGACAGAATTGGATACATA | SI00027881 | Hs_CCND3_4 |
| 900029-1-B | single siRNA, 0.9 nmol | 91 | 81 | ACTN4 | actinin, alpha 4 | NM_004924 | ACCCAGCATCGTCGGACTACAA | SI02779973 | Hs_ACTN4_5 |
| 900029-1-B | single siRNA, 0.9 nmol | 92 | 268 | AMH | anti-Mullerian hormone | NM_000479 | CAGGGCCATCCGCGGAACTGA | SI02623585 | Hs_AMH_3 |
| 900029-1-B | single siRNA, 0.9 nmol | 93 | 374 | AREG | amphiregulin (schwannoma-derived growth factor) | NM_001657 | ATGGATTTGAGGTTACCTCAA | SI00299936 | Hs_AREG_3 |
| 900029-1-B | single siRNA, 0.9 nmol | 94 | 384 | ARG2 | arginase, type II | NM_001172 | TTGGATAACCTTCCTTCTAAA | SI00301203 | Hs_ARG2_3 |
| 900029-1-B | single siRNA, 0.9 nmol | 95 | 430 | ASCL2 | achaete-scute complex homolog 2 (Drosophila) | NM_005170 | CCGGTGAAGCTGGTGAACTT | SI03081218 | Hs_ASCL2_5 |
| 900029-1-B | single siRNA, 0.9 nmol | 96 | 634 | CEACAM1 | carcinoembryonic antigen-related cell adhesion molecule 1 (biliary glycoprotein) | NM_001024912 NM_001712 | CAAGACGATCATAGTCACTGA | SI03053694 | Hs_CEACAM1_6 |
| 900029-1-B | single siRNA, 0.9 nmol | 97 | 673 | BRAF | v-raf murine sarcoma viral oncogene homolog B1 | NM_004333 | TTGCTTATATGTTAAATTGAA | SI02632966 | Hs_BRAF_5 |
| 900029-1-B | single siRNA, 0.9 nmol | 98 | 806 | CALM3 | calmodulin 3 (phosphorylase kinase, delta) | NM_005184 | CACCAATTGATTGACTGAGAA | SI02622060 | Hs_CALM3_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-1-B | single siRNA, 0.9 nmol | 99 | 859 | CAV3 | caveolin 3 | NM_001234 NM_033337 | TTGCGTTCACTTGTACTGTAA | SI02625665 | Hs_CAV3_7 |
| 900029-1-B | single siRNA, 0.9 nmol | 100 | 896 | CCNE1 | cyclin E1 | NM_001238 NM_057182 | CAAGATTCTTTGACCGGTAT | SI03054037 | Hs_CCNE1_8 |
| 900029-1-B | single siRNA, 0.9 nmol | 101 | 160 | AP2A1 | adaptor-related protein complex 2, alpha 1 subunit | NM_014203 NM_130787 | TTGGATGCTACAGTAAGAAA | SI02661603 | Hs_AP2A1_5 |
| 900029-1-B | single siRNA, 0.9 nmol | 102 | 302 | ANXA2 | annexin A2 | NM_001002857 NM_001002858 NM_004039 | CGGCAAGTCCCTGTACTATTA | SI02632385 | Hs_ANXA2_8 |
| 900029-1-B | single siRNA, 0.9 nmol | 103 | 375 | ARF1 | ADP-ribosylation factor 1 | NM_001024226 NM_001024227 NM_001024228 NM_001658 | CACGATCTCTACAAGCTTAA | SI02757272 | Hs_ARF1_10 |
| 900029-1-B | single siRNA, 0.9 nmol | 104 | 387 | RHOA | ras homolog gene family, member A | NM_001664 | CAAGCTAGACGTGGGAAGAAA | SI02654267 | Hs_RHOA_7 |
| 900029-1-B | single siRNA, 0.9 nmol | 105 | 483 | ATP1B3 | ATPase, Na+/K+ transporting, beta 3 polypeptide | NM_001679 XM_001133533 XM_001133534 | CAGGATGATCGTGACAAGTTT | SI00306607 | Hs_ATP1B3_3 |
| 900029-1-B | single siRNA, 0.9 nmol | 106 | 640 | BLK | B lymphoid tyrosine kinase | NM_001715 | CAACATGAAGGTGGCCATTAA | SI00027055 | Hs_BLK_3 |
| 900029-1-B | single siRNA, 0.9 nmol | 107 | 685 | BTC | betacellulin | NM_001729 | CACCAGAAGTCCTGAAACTAA | SI02626813 | Hs_BTC_5 |
| 900029-1-B | single siRNA, 0.9 nmol | 108 | 818 | CAMK2G | calcium/calmodulin-dependent protein kinase (CaM kinase) II gamma | NM_001222 NM_172169 NM_172170 NM_172171 NM_172172 NM_172173 | CCGATGAGAAACCTCGTGTTA | SI00157402 | Hs_CAMK2G_3 |
| 900029-1-B | single siRNA, 0.9 nmol | 109 | 861 | RUNX1 | runt-related transcription factor 1 (acute myeloid leukemia 1; aml1 oncogene) | NM_001001890 NM_001754 | CAGGTCGTTCTTATCTAGAGA | SI00027769 | Hs_RUNX1_4 |
| 900029-1-B | single siRNA, 0.9 nmol | 110 | 916 | CD3E | CD3e molecule, epsilon (CD3-TCR complex) | NM_000733 | CACAATTGTCATAGTGACAT | SI03055598 | Hs_CD3E_6 |
| 900029-1-B | single siRNA, 0.9 nmol | 111 | 161 | AP2A2 | adaptor-related protein complex 2, alpha 2 subunit | NM_012305 | TCGGATATCCGCAACTGTAAA | SI00297444 | Hs_AP2A2_4 |
| 900029-1-B | single siRNA, 0.9 nmol | 112 | 309 | ANXA6 | annexin A6 | NM_001155 NM_004033 | AAGGCTCTTCAAGGCTATGAA | SI00297017 | Hs_ANXA6_3 |
| 900029-1-B | single siRNA, 0.9 nmol | 113 | 377 | ARF3 | ADP-ribosylation factor 3 | NM_001659 | TTTCCAATTTACTGGATTTAAA | SI00300020 | Hs_ARF3_4 |
| 900029-1-B | single siRNA, 0.9 nmol | 114 | 388 | RHOB | ras homolog gene family, member B | NM_004040 | ACAAGGCATTCTCTAAAGCTA | SI03037531 | Hs_RHOB_5 |
| 900029-1-B | single siRNA, 0.9 nmol | 115 | 558 | AXL | AXL receptor tyrosine kinase | NM_001699 NM_021913 | CCCGTGTTCTAAGATGTGATA | SI00605304 | Hs_AXL_9 |
| 900029-1-B | single siRNA, 0.9 nmol | 116 | 650 | BMP2 | bone morphogenetic protein 2 | NM_001200 | CTCAGCATGTTCGGCCTGAAA | SI00023366 | Hs_BMP2_3 |
| 900029-1-B | single siRNA, 0.9 nmol | 117 | 780 | DDR1 | discoidin domain receptor family, member 1 | NM_001954 NM_013993 NM_013994 | ACGGTGTGAATCACACATCCA | SI00605437 | Hs_DDR1_9 |
| 900029-1-B | single siRNA, 0.9 nmol | 118 | 819 | CAMLG | calcium modulating ligand | NM_001745 | ATCGATCAATGGATACCTATA | SI02777103 | Hs_CAMLG_7 |
| 900029-1-B | single siRNA, 0.9 nmol | 119 | 867 | CBL | Cas-Br-M (murine) ecotropic retroviral transforming sequence | NM_005188 | CCCGCCGAACTCTCAGATA | SI02662471 | Hs_CBL_7 |
| 900029-1-B | single siRNA, 0.9 nmol | 120 | 919 | CD247 | CD247 molecule | NM_000734 NM_198053 | CAGGAAGGCCTGTACAATGAA | SI00014462 | Hs_CD3Z_4 |
| 900029-2-A | single siRNA, 0.9 nmol | 121 | 933 | CD22 | CD22 molecule | NM_001771 | AAGCAGAATACATTCACGCTA | SI03032820 | Hs_CD22_7 |
| 900029-2-A | single siRNA, 0.9 nmol | 122 | 999 | CDH1 | cadherin 1, type 1, E-cadherin | NM_004360 | TCGGCCTGAAGTGACTCGTAA | SI02654029 | Hs_CDH1_13 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-A | single siRNA, 0.9 nmol | 123 | 1103 | CHAT | choline acetyltransferase (epithelial) | NM_020549 NM_020984 NM_020985 NM_020986 | CACGGAGATGTTCTGCTGCTA | SI00127022 | Hs_CHAT_4 |
| 900029-2-A | single siRNA, 0.9 nmol | 124 | 1316 | KLF6 | Kruppel-like factor 6 | NM_001008490 NM_001300 | CAGGAAGATCTGTGGACCAAA | SI03068968 | Hs_KLF6_5 |
| 900029-2-A | single siRNA, 0.9 nmol | 125 | 1441 | CSF3R | colony stimulating factor 3 receptor (granulocyte) | NM_000760 NM_156038 NM_156039 NM_172313 | CCAGGCGATCTGCATACTTTA | SI00156723 | Hs_CSF3R_5 |
| 900029-2-A | single siRNA, 0.9 nmol | 126 | 1499 | CTNNB1 | catenin (cadherin-associated protein), beta 1, 88 kDa | NM_001904 XM_001133660 XM_001133664 XM_001133673 | CTCGGGATGTTCACAACCGAA | SI02662478 | Hs_CTNNB1_5 |
| 900029-2-A | single siRNA, 0.9 nmol | 127 | 1742 | DLG4 | discs, large homolog 4 (Drosophila) | NM_001365 | CAGGATATGAGTTGCAGGTGA | SI02626106 | Hs_DLG4_6 |
| 900029-2-A | single siRNA, 0.9 nmol | 128 | 1846 | DUSP4 | dual specificity phosphatase 4 | NM_001394 NM_057158 | AAGGACTCCGATACATAATA | SI03132227 | Hs_DUSP4_5 |
| 900029-2-A | single siRNA, 0.9 nmol | 129 | 1906 | EDN1 | endothelin 1 | NM_001955 | CAGGTCGGAGACCATGAGAAA | SI02627380 | Hs_EDN1_6 |
| 900029-2-A | single siRNA, 0.9 nmol | 130 | 1959 | EGR2 | early growth response 2 (Krox-20 homolog, Drosophila) | NM_000399 | GAGCGAGAGCAATTGATTAA | SI00008792 | Hs_EGR2_4 |
| 900029-2-A | single siRNA, 0.9 nmol | 131 | 960 | CD44 | CD44 molecule (Indian blood group) | NM_000610 NM_001001389 NM_001001390 NM_001001391 | AACTCCATCTGTGCAGCAAAC | SI00299705 | Hs_CD44_5 |
| 900029-2-A | single siRNA, 0.9 nmol | 132 | 1001 | CDH3 | cadherin 3, type 1, P-cadherin (placental) | NM_001793 | AAGCCTCTTTACCTGCCCTAAA | SI02663941 | Hs_CDH3_6 |
| 900029-2-A | single siRNA, 0.9 nmol | 133 | 1120 | CHKB | choline kinase beta | NM_005198 NM_152253 | GACCATGAGCCGTACCTAAA | SI03101511 | Hs_CHKB_5 |
| 900029-2-A | single siRNA, 0.9 nmol | 134 | 1385 | CREB1 | cAMP responsive element binding protein 1 | NM_004379 | AAGCCCAGCACAGATTGCCA | SI00299908 | Hs_CREB1_7 |
| 900029-2-A | single siRNA, 0.9 nmol | 135 | 1445 | CSK | c-src tyrosine kinase | NM_134442 NM_004383 | AAGTACAACTTCCACGGCACT | SI00299943 | Hs_CSK_1 |
| 900029-2-A | single siRNA, 0.9 nmol | 136 | 1500 | CTNND1 | catenin (cadherin-associated protein), delta 1 | NM_001331 XM_001126721 XM_001126756 XM_001126767 XM_001126781 XM_001126793 XM_001126823 | CTGGTGTTGATCAACAATCA | SI02626001 | Hs_CTNND1_5 |
| 900029-2-A | single siRNA, 0.9 nmol | 137 | 1759 | DNM1 | dynamin 1 | NM_001005336 NM_004408 | CAGGTCATGCTTCTCATCGAT | SI03071894 | Hs_DNM1_5 |
| 900029-2-A | single siRNA, 0.9 nmol | 138 | 1848 | DUSP6 | dual specificity phosphatase 6 | NM_001946 NM_022652 | GTCGGAAATGGCGATCAGCAA | SI03106404 | Hs_DUSP6_6 |
| 900029-2-A | single siRNA, 0.9 nmol | 139 | 1915 | EEF1A1 | eukaryotic translation elongation factor 1 alpha 1 | NM_001402 | CAGAATAGGAACAAGGTTCTA | SI03063235 | Hs_EEF1A1_8 |
| 900029-2-A | single siRNA, 0.9 nmol | 140 | 1960 | EGR3 | early growth response 3 | NM_004430 XM_001130047 | CGGCAACAAGACCGTGACCTA | SI03195766 | Hs_EGR3_6 |
| 900029-2-A | single siRNA, 0.9 nmol | 141 | 966 | CD59 | CD59 molecule, complement regulatory | NM_000611 | TAGGTGTGACTTGAACTAGAT | SI03112200 | Hs_CD59_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-A | single siRNA, 0.9 nmol | 142 | 1003 | CDH5 | cadherin 5, type 2, VE-cadherin (vascular epithelium) | NM_203329 NM_203330 NM_203331 | CAAGGACATAACACCACGAAA | SI00028497Hs | CDH5 4 |
| 900029-2-A | single siRNA, 0.9 nmol | 143 | 1147 | CHUK | conserved helix-loop-helix ubiquitous kinase | NM_001278 | AAGCAGAAGATTATTGATCTA | SI02654659Hs | CHUK 8 |
| 900029-2-A | single siRNA, 0.9 nmol | 144 | 1398 | CRK | v-crk sarcoma virus CT10 oncogene homolog (avian) | NM_005206 NM_016823 | AATCCGGACAAGCCTGAAGA | SI00299929Hs | CRK 5 |
| 900029-2-A | single siRNA, 0.9 nmol | 145 | 1457 | CSNK2A1 | casein kinase 2, alpha 1 polypeptide | NM_001895 NM_177559 NM_177560 | CTGGTCGCTTACATCACTTTA | SI02660504Hs | CSNK2A1 10 |
| 900029-2-A | single siRNA, 0.9 nmol | 146 | 1523 | CUTL1 | cut-like 1, CCAAT displacement protein (Drosophila) | NM_001913 NM_181500 NM_181552 | AACAGATTATTGACCTGAA | SI02660994Hs | CUTL1 6 |
| 900029-2-A | single siRNA, 0.9 nmol | 147 | 1793 | DOCK1 | dedicator of cytokinesis 1 | NM_001380 | AACGAGGTCCAGCGATTTGAA | SI00372526Hs | DOCK1 4 |
| 900029-2-A | single siRNA, 0.9 nmol | 148 | 1849 | DUSP7 | dual specificity phosphatase 7 | NM_001947 | CAAGGTGGTTCAACAAGTTT | SI02658663Hs | DUSP7 7 |
| 900029-2-A | single siRNA, 0.9 nmol | 149 | 1917 | EEF1A2 | eukaryotic translation elongation factor 1 alpha 2 | NM_001958 | CTGGAAGTTCGAGACCACCAA | SI02262492Hs | EEF1A2 7 |
| 900029-2-A | single siRNA, 0.9 nmol | 150 | 1969 | EPHA2 | EPH receptor A2 | NM_004431 | TCGGACAGACATATAGGATAT | SI02223515Hs | EPHA2 8 |
| 900029-2-A | single siRNA, 0.9 nmol | 151 | 987 | LRBA | LPS-responsive vesicle trafficking, beach and anchor containing | NM_006726 | CCGGCGACGATTTGTGCGTAA | SI03190880Hs | LRBA_5 |
| 900029-2-A | single siRNA, 0.9 nmol | 152 | 1017 | CDK2 | cyclin-dependent kinase 2 | NM_001798 NM_052827 | AAGATGGACGGAGCTTGTTAT | SI02654638Hs | CDK2 12 |
| 900029-2-A | single siRNA, 0.9 nmol | 153 | 1230 | CCR1 | chemokine (C-C motif) receptor 1 | NM_001295 | GACGGAAGAGTTGAGACCTAA | SI02625889Hs | CCR1 6 |
| 900029-2-A | single siRNA, 0.9 nmol | 154 | 1399 | CRKL | v-crk sarcoma virus CT10 oncogene homolog (avian)-like | NM_005207 | TAGTTTATCATTAACCACTTA | SI02634688Hs | CRKL_6 |
| 900029-2-A | single siRNA, 0.9 nmol | 155 | 1464 | CSPG4 | chondroitin sulfate proteoglycan 4 | NM_001897 | TACGCTGGGAATATTCTGTAT | SI00355446Hs | CSPG4 4 |
| 900029-2-A | single siRNA, 0.9 nmol | 156 | 1601 | DAB2 | disabled homolog 2, mitogen-responsive phosphoprotein (Drosophila) | NM_001343 | TAGAGCATGAACATCCAGTAA | SI02780386Hs | DAB2_6 |
| 900029-2-A | single siRNA, 0.9 nmol | 157 | 1794 | DOCK2 | dedicator of cytokinesis 2 | NM_004946 | CCCGGTTACAGCTGAGAATGA | SI03070350Hs | DOCK2 4 |
| 900029-2-A | single siRNA, 0.9 nmol | 158 | 1852 | DUSP9 | dual specificity phosphatase 9 | NM_001395 | CTGAATAACAGTTATTTAA | SI02665572Hs | DUSP9 5 |
| 900029-2-A | single siRNA, 0.9 nmol | 159 | 1950 | EGF | epidermal growth factor (beta-urogastrone) | NM_001963 | GCCGGTTGTTCCTCACCCGATA | SI03105613Hs | EGF 5 |
| 900029-2-A | single siRNA, 0.9 nmol | 160 | 1973 | EIF4A1 | eukaryotic translation initiation factor 4A, isoform 1 | NM_001416 | ACCAGACCTGATTATGAGGGA | SI02655849Hs | EIF4A1 6 |
| 900029-2-A | single siRNA, 0.9 nmol | 161 | 993 | CDC25A | cell division cycle 25 homolog A (S. pombe) | NM_001789 NM_201567 | AAGGGTTATCTCTTTCATACA | SI02653273Hs | CDC25A 9 |
| 900029-2-A | single siRNA, 0.9 nmol | 162 | 1050 | CEBPA | CCAAT/enhancer binding protein (C/EBP), alpha | NM_004364 | CCCGACTTGGTCGTCATCTAAGA | SI03081806Hs | CEBPA 6 |
| 900029-2-A | single siRNA, 0.9 nmol | 163 | 1231 | CCR2 | chemokine (C-C motif) receptor 2 | NM_000647 NM_000648 | CTGGTCGTCCTCATCTTAATA | SI03099677Hs | CCR2 6 |
| 900029-2-A | single siRNA, 0.9 nmol | 164 | 1432 | MAPK14 | mitogen-activated protein kinase 14 | NM_001315 NM_139012 | CTCAGTGATACGTACAGCCAA | SI00605164Hs | MAPK14 7 |
| 900029-2-A | single siRNA, 0.9 nmol | 165 | 1490 | CTGF | connective tissue growth factor | NM_001901 | AAAGATTCCCACCCAATTCAA | SI00029694Hs | CTGF 4 |
| 900029-2-A | single siRNA, 0.9 nmol | 166 | 1605 | DAG1 | dystroglycan 1 (dystrophin-associated glycoprotein 1) | NM_004393 | CAAGAAGATTGCTTGGTAAA | SI02633176Hs | DAG1 7 |
| 900029-2-A | single siRNA, 0.9 nmol | 167 | 1839 | HBEGF | heparin-binding EGF-like growth factor | NM_001945 | TCCCATAATTGCTTGCCAAA | SI03114195Hs | HBEGF 7 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-A | single siRNA, 0.9 nmol | 168 | 1875 | E2F5 | E2F transcription factor 5, p130-binding | NM_001951 | GACGGCGTTCTGATCTCAAA | SI03102141 | Hs_E2F5_7 |
| 900029-2-A | single siRNA, 0.9 nmol | 169 | 1956 | EGFR | epidermal growth factor receptor (erythroblastic leukemia viral (v-erb-b) oncogene homolog, avian) | NM_005228 NM_201282 NM_201283 NM_201284 | CAGGAACTGGATATTCTGAAA | SI02663983 | Hs_EGFR_12 |
| 900029-2-A | single siRNA, 0.9 nmol | 170 | 1974 | EIF4A2 | eukaryotic translation initiation factor 4A, isoform 2 | NM_001967 | TGCCATATTGCACATGTCTTA | SI03236051 | Hs_EIF4A2_6 |
| 900029-2-A | single siRNA, 0.9 nmol | 171 | 998 | CDC42 | cell division cycle 42 (GTP binding protein, 25 kDa) | NM_001039802 NM_001791 NM_044472 | CATCAGATTTGAAATATTAA | SI02757328 | Hs_CDC42_7 |
| 900029-2-A | single siRNA, 0.9 nmol | 172 | 1051 | CEBPB | CCAAT/enhancer binding protein (C/EBP), beta | NM_005194 | CGGGCCCTGAGTAATCGCTTA | SI02777292 | Hs_CEBPB_5 |
| 900029-2-A | single siRNA, 0.9 nmol | 173 | 1234 | CCR5 | chemokine (C-C motif) receptor 5 | NM_000579 | AAGATGGATTATCAAGTGTCA | SI00012180 | Hs_CCR5_2 |
| 900029-2-A | single siRNA, 0.9 nmol | 174 | 1439 | CSF2RB | colony stimulating factor 2 receptor, beta, low-affinity (granulocyte-macrophage) | NM_000395 | AAGGACAGCCCTGTGGCTATA | SI03034381 | Hs_CSF2RB_6 |
| 900029-2-A | single siRNA, 0.9 nmol | 175 | 1495 | CTNNA1 | catenin (cadherin-associated protein), alpha 1, 102 kDa | NM_001903 | CACCCCTGATGTCGCAGCCTAT | SI02757377 | Hs_CTNNA1_9 |
| 900029-2-A | single siRNA, 0.9 nmol | 176 | 1634 | DCN | decorin | NM_001920 NM_133503 NM_133504 NM_133505 NM_133506 NM_133507 | AAGTAGATACTGGAAACCTA | SI02647960 | Hs_DCN_9 |
| 900029-2-B | single siRNA, 0.9 nmol | 177 | 1843 | DUSP1 | dual specificity phosphatase 1 | NM_004417 | CTGGTTCAACGAGGCCATTGA | SI03100048 | Hs_DUSP1_5 |
| 900029-2-B | single siRNA, 0.9 nmol | 178 | 1879 | EBF1 | early B-cell factor 1 | NM_024007 | TACAAGGACACTATAAATAA | SI03075746 | Hs_EBF_4 |
| 900029-2-B | single siRNA, 0.9 nmol | 179 | 1958 | EGR1 | early growth response 1 | NM_001964 | CCCGTCGTGGCCACCACTA | SI03078950 | Hs_EGR1_7 |
| 900029-2-B | single siRNA, 0.9 nmol | 180 | 1999 | ELF3 | E74-like factor 3 (ets domain transcription factor, epithelial-specific) | NM_004433 | TCAGATGTACATAGAGATCTA | SI03078462 | Hs_ELF3_4 |
| 900029-2-B | single siRNA, 0.9 nmol | 181 | 933 | CD22 | CD22 molecule | NM_001771 | CACGAATATTATGCCCAGTTT | SI02627016 | Hs_CD22_6 |
| 900029-2-B | single siRNA, 0.9 nmol | 182 | 999 | CDH1 | cadherin 1, type 1, E-cadherin (epithelial) | NM_004360 | CTAGGTATTGTCTACTCTGAA | SI02653546 | Hs_CDH1_12 |
| 900029-2-B | single siRNA, 0.9 nmol | 183 | 1103 | CHAT | choline acetyltransferase | NM_020549 NM_020984 NM_020985 NM_020986 | CCCGAGATGTTCATGGATGAA | SI00127015 | Hs_CHAT_3 |
| 900029-2-B | single siRNA, 0.9 nmol | 184 | 1316 | KLF6 | Kruppel-like factor 6 | NM_001008490 NM_001300 | CACGGCCAAGTTTACCTCCGA | SI00025095 | Hs_KLF6_4 |
| 900029-2-B | single siRNA, 0.9 nmol | 185 | 1441 | CSF3R | colony stimulating factor 3 receptor (granulocyte) | NM_000760 NM_156038 NM_156039 NM_172313 | TCCTATAACTTCAGTATTGTA | SI00015022 | Hs_CSF3R_4 |
| 900029-2-B | single siRNA, 0.9 nmol | 186 | 1499 | CTNNB1 | catenin (cadherin-associated protein), beta 1, 88 kDa | NM_001904 | TAAGAATTGAGTAGTAATGTGTA | SI00029750 | Hs_CTNNB1_4 |
| 900029-2-B | single siRNA, 0.9 nmol | 187 | 1742 | DLG4 | discs, large homolog 4 (Drosophila) | NM_001365 | GACGAGAGTGGTCAAGTTAA | SI02626099 | Hs_DLG4_5 |
| 900029-2-B | single siRNA, 0.9 nmol | 188 | 1846 | DUSP4 | dual specificity phosphatase 4 | NM_001394 NM_057158 | TACCCAGAATTCTGTTCTAA | SI00374934 | Hs_DUSP4_4 |
| 900029-2-B | single siRNA, 0.9 nmol | 189 | 1906 | EDN1 | endothelin 1 | NM_001955 | ACCGAGCACATTGGTGACAGA | SI02627373 | Hs_EDN1_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-B | single siRNA, 0.9 nmol | 190 | 1959 | EGR2 | early growth response 2 (Krox-20 homolog, Drosophila) | NM_000399 | TCCACTCTCTACAATCCGTAA | SI00008785 | Hs_EGR2_3 |
| 900029-2-B | single siRNA, 0.9 nmol | 191 | 960 | CD44 | CD44 molecule (Indian blood group) | NM_000610 NM_001001389 NM_001001390 NM_001001391 NM_001001392 | CTGGCGCAGATCGATTTGAAT | SI03098123 | Hs_CD44_10 |
| 900029-2-B | single siRNA, 0.9 nmol | 192 | 1001 | CDH3 | cadherin 3, type 1, P-cadherin (placental) | NM_001793 | CAGATGAAATCGGCAACTTTA | SI02663934 | Hs_CDH3_5 |
| 900029-2-B | single siRNA, 0.9 nmol | 193 | 1120 | CHKB | choline kinase beta | NM_005198 NM_152253 | CTGGTAGAAGTCAGTCCGTAT | SI02634639 | Hs_CHKB_4 |
| 900029-2-B | single siRNA, 0.9 nmol | 194 | 1385 | CREB1 | cAMP responsive element binding protein 1 | NM_004379 NM_134442 | AACTGATTCCCAAAAGCCAAG | SI00299901 | Hs_CREB1_6 |
| 900029-2-B | single siRNA, 0.9 nmol | 195 | 1445 | CSK | c-src tyrosine kinase | NM_004383 | TACGCGCCTCATTAAACCAAA | SI00288169 | Hs_CSK_3 |
| 900029-2-B | single siRNA, 0.9 nmol | 196 | 1500 | CTNND1 | catenin (cadherin-associated protein), delta 1 | NM_001331 XM_001126721 XM_001126756 XM_001126767 XM_001126781 XM_001126793 XM_001126823 | AAGGGTTAAGATCTATGGAA | SI00025396 | Hs_CTNND1_4 |
| 900029-2-B | single siRNA, 0.9 nmol | 197 | 1759 | DNM1 | dynamin 1 | NM_001005338 NM_004408 | GAGGAATGTCTACAAGGATTA | SI00063392 | Hs_DNM1_3 |
| 900029-2-B | single siRNA, 0.9 nmol | 198 | 1848 | DUSP6 | dual specificity phosphatase 6 | NM_001946 NM_022652 | TACGGACACTATTATCACTAA | SI02627338 | Hs_DUSP6_5 |
| 900029-2-B | single siRNA, 0.9 nmol | 199 | 1915 | EEF1A1 | eukaryotic translation elongation factor 1 alpha 1 | NM_C01402 | CACCCGAGACATTAGGTGAAA | SI03058230 | Hs_EEF1A1_7 |
| 900029-2-B | single siRNA, 0.9 nmol | 200 | 1960 | EGR3 | early growth response 3 | NM_004430 XM_001130047 | CAGCGACTCGGTAGTCCATTA | SI03171623 | Hs_EGR3_5 |
| 900029-2-B | single siRNA, 0.9 nmol | 201 | 966 | CD59 | CD59 molecule, complement regulatory protein | NM_000611 NM_203329 NM_203330 NM_203331 | CAAAGTCTGGGTTACAAGTGTA | SI03052616 | Hs_CD59_5 |
| 900029-2-B | single siRNA, 0.9 nmol | 202 | 1003 | CDH5 | cadherin 5, type 2, VE-cadherin (vascular epithelium) | NM_001795 | ACCACGAAACGTGAAGTTCAA | SI00028490 | Hs_CDH5_3 |
| 900029-2-B | single siRNA, 0.9 nmol | 203 | 1147 | CHUK | conserved helix-loop-helix ubiquitous kinase | NM_001278 | TTCCATAAGCTTGGTGACAAA | SI00605122 | Hs_CHUK_6 |
| 900029-2-B | single siRNA, 0.9 nmol | 204 | 1398 | CRK | v-crk sarcoma virus CT10 oncogene homolog (avain) | NM_005206 NM_016823 | CAGGATGTACCGAGCACTTTA | SI00073780 | Hs_CRK_1 |
| 900029-2-B | single siRNA, 0.9 nmol | 205 | 1457 | CSNK2A1 | casein kinase 2, alpha 1 polypeptide | NM_001895 NM_177559 NM_177560 | TCCATTGAAGCTGAAATGGTA | SI02660497 | Hs_CSNK2A1_9 |
| 900029-2-B | single siRNA, 0.9 nmol | 206 | 1523 | CUTL1 | cut-like 1, CCAAT displacement protein (Drosophila) | NM_001913 NM_181500 NM_181552 | CAGCGCCTGCACGATATTGAA | SI00357070 | Hs_CUTL1_4 |
| 900029-2-B | single siRNA, 0.9 nmol | 207 | 1793 | DOCK1 | dedicator of cytokinesis 1 | NM_001380 | CCGAGGTTACACGTTACGAAA | SI00372519 | Hs_DOCK1_3 |
| 900029-2-B | single siRNA, 0.9 nmol | 208 | 1849 | DUSP7 | dual specificity phosphatase 7 | NM_001947 | TACGACTTTGTCAAGAGGAAA | SI02658656 | Hs_DUSP7_6 |
| 900029-2-B | single siRNA, 0.9 nmol | 209 | 1917 | EEF1A2 | eukaryotic translation elongation factor 1 alpha 2 | NM_001958 | CAAGGAGAAGACCCACATCAA | SI02661967 | Hs_EEF1A2_6 |

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-B | single siRNA, 0.9 nmol | 210 | 1969 | EPHA2 | EPH receptor A2 | NM_004431 | CAGCGCCAAGTAAACAGGTA | SI02223508 | Hs_EPHA2_7 |
| 900029-2-B | single siRNA, 0.9 nmol | 211 | 987 | LRBA | LPS-responsive vesicle trafficking, beach and anchor containing | NM_006726 | CAGGCCATTCTTAATTACCTA | SI00623224 | Hs_LRBA_4 |
| 900029-2-B | single siRNA, 0.9 nmol | 212 | 1017 | CDK2 | cyclin-dependent kinase 2 | NM_001798 NM_052827 | AACTTGCCTTAAACACTCACC | SI02654631 | Hs_CDK2_11 |
| 900029-2-B | single siRNA, 0.9 nmol | 213 | 1230 | CCR1 | chemokine (C-C motif) receptor 1 | NM_001295 | CTGGATCGACTACAAGTTGAA | SI02625882 | Hs_CCR1_5 |
| 900029-2-B | single siRNA, 0.9 nmol | 214 | 1399 | CRKL | v-crk sarcoma virus CT10 oncogene homolog (avian)-like | NM_005207 | CAGGTTGTTTATATATTAATCCT | SI00073829 | Hs_CRKL_4 |
| 900029-2-B | single siRNA, 0.9 nmol | 215 | 1464 | CSPG4 | chondroitin sulfate proteoglycan 4 | NM_001897 | CACGGTTGAGGGATGTAAATGA | SI00355439 | Hs_CSPG4_3 |
| 900029-2-B | single siRNA, 0.9 nmol | 216 | 1601 | DAB2 | disabled homolog 2, mitogen-responsive phosphoprotein (Drosophila) | NM_001343 | AAGGTTGCCCTTAGTAGTCAA | SI02780316 | Hs_DAB2_5 |
| 900029-2-B | single siRNA, 0.9 nmol | 217 | 1794 | DOCK2 | dedicator of cytokinesis 2 | NM_004946 | CAGGTCTATGCTGCGCTCATA | SI00070343 | Hs_DOCK2_3 |
| 900029-2-B | single siRNA, 0.9 nmol | 218 | 1852 | DUSP9 | dual specificity phosphatase 9 | NM_001395 | CCGGGATTCCGCCAATTTGGA | SI03191349 | Hs_DUSP9_6 |
| 900029-2-B | single siRNA, 0.9 nmol | 219 | 1950 | EGF | epidermal growth factor (beta-urogastrone) | NM_001963 | TACGACTAATCACCTACTCAA | SI00030681 | Hs_EGF_4 |
| 900029-2-B | single siRNA, 0.9 nmol | 220 | 1973 | EIF4A1 | eukaryotic translation initiation factor 4A, isoform 1 | NM_001416 | AGGGATGGACATCTTGTCATT | SI02655842 | Hs_EIF4A1_5 |
| 900029-2-B | single siRNA, 0.9 nmol | 221 | 993 | CDC25A | cell division cycle 25 homolog A (S. pombe) | NM_001789 NM_201567 | CTGCCAAATAGCAAAGACAA | SI02225545 | Hs_CDC25A_6 |
| 900029-2-B | single siRNA, 0.9 nmol | 222 | 1050 | CEBPA | CCAAT/enhancer binding protein (C/EBP), alpha | NM_0043464 | CCCGGCAACTCTAGTATTTAG | SI03078425 | Hs_CEBPA_5 |
| 900029-2-B | single siRNA, 0.9 nmol | 223 | 1231 | CCR2 | chemokine (C-C motif) receptor 2 | NM_000647 NM_000648 | AGGGCTGTATCACATCGGTTA | SI03046036 | Hs_CCR2_5 |
| 900029-2-B | single siRNA, 0.9 nmol | 224 | 1432 | MAPK14 | mitogen-activated protein kinase 14 | NM_001315 NM_139012 NM_139013 | CAGAGAACTGCGTTACTTAA | SI03605157 | Hs_MAPK14_6 |
| 900029-2-B | single siRNA, 0.9 nmol | 225 | 1490 | CTGF | connective tissue growth factor | NM_001901 | CTGATGTCTTCAAAGCATGAAA | SI00029687 | Hs_CTGF_3 |
| 900029-2-B | single siRNA, 0.9 nmol | 226 | 1605 | DAG1 | dystroglycan 1 (dystrophin-associated glycoprotein 1) | NM_004393 | AAGGGTGTGCATTACATTTCA | SI02633169 | Hs_DAG1_6 |
| 900029-2-B | single siRNA, 0.9 nmol | 227 | 1839 | HBEGF | heparin-binding EGF-like growth factor | NM_001945 | GTGCTGCTGATTTGATGAGTAA | SI03106726 | Hs_HBEGF_6 |
| 900029-2-B | single siRNA, 0.9 nmol | 228 | 1875 | E2F5 | E2F transcription factor 5, p130-binding | NM_001951 | CTGGAGGTACCCATTCCAGAA | SI03097276 | Hs_E2F5_6 |
| 900029-2-B | single siRNA, 0.9 nmol | 229 | 1956 | EGFR | epidermal growth factor receptor (erythroblastic leukemia viral (v-erb-b) oncogene homolog, avian) | NM_005228 NM_201282 NM_201283 NM_201284 | ATAGGTATTGGTGAATTTAAA | SI02660147 | Hs_EGFR_11 |
| 900029-2-B | single siRNA, 0.9 nmol | 230 | 1974 | EIF4A2 | eukaryotic translation initiation factor 4A, isoform 2 | NM_001967 | AAAGATAAGTGCTGTATAA | SI02655877 | Hs_EIF4A2_5 |
| 900029-2-B | single siRNA, 0.9 nmol | 231 | 998 | CDC42 | cell division cycle 42 (GTP binding protein, 25 kDa) | NM_044472 | TACAATTGTGGTTACCTTCAA | SI03107965 | Hs_CDC42_14 |
| 900029-2-B | single siRNA, 0.9 nmol | 232 | 1051 | CEBPB | CCAAT/enhancer binding protein (C/EBP), beta | NM_005194 | CACCCTGCGGAACTTGTTCAA | SI03058062 | Hs_CEBPB_7 |
| 900029-2-B | single siRNA, 0.9 nmol | 233 | 1234 | CCR5 | chemokine (C-C motif) receptor 5 | NM_000579 | AAGGGACATATTCATTTGGAA | SI00012194 | Hs_CCR5_4 |
| 900029-2-B | single siRNA, 0.9 nmol | 234 | 1439 | CSF2RB | colony stimulating factor 2 receptor, beta, low-affinity (granulocyte-macrophage) | NM_000395 | AAGCATGCTCTGTGATCCACCA | SI03033079 | Hs_CSF2RB_5 |
| 900029-2-B | single siRNA, 0.9 nmol | 235 | 1495 | CTNNA1 | catenin (cadherin-associated protein), alpha 1, 102 kDa | NM_001903 | GCGAATTGTGGCAGAGTGTAA | SI02663962 | Hs_CTNNA1_8 |
| 900029-2-B | single siRNA, 0.9 nmol | 236 | 1634 | DCN | decorin | NM_001920 | TACGTGCCTCTGCCATTCAA | SI00150290 | Hs_DCN_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-2-B | single siRNA, 0.9 nmol | 237 | 1843 | DUSP1 | dual specificity phosphatase 1 | NM_133503 NM_133504 NM_133505 NM_133506 NM_133507 | CAGTTGTATGTTTGCTGATTA | SI00374822 | Hs_DUSP1_4 |
| 900029-2-B | single siRNA, 0.9 nmol | 238 | 1879 | EBF1 | early B-cell factor 1 | NM_004417 | AGGGTGTTGGTTAAAGTTGTA | SI00375739 | Hs_EBF_3 |
| 900029-2-B | single siRNA, 0.9 nmol | 239 | 1958 | EGR1 | early growth response 1 | NM_024007 NM_001964 | CAGGACAATTGAAATTTGCTA | SI00369108 | Hs_EGR1_6 |
| 900029-2-B | single siRNA, 0.9 nmol | 240 | 1999 | ELF3 | E74-like factor 3 (ets domain transcription factor, epithelial-specific) | NM_004433 | CAGACTTGACAATCATTAAA | SI00378455 | Hs_ELF3_3 |
| 900029-3-A | single siRNA, 0.9 nmol | 241 | 2002 | ELK1 | ELK1, member of ETS oncogene family | NM_005229 NM_004439 | AGGGAGTCATCTTCTTCCTATA | SI02662506 | Hs_ELK1_7 |
| 900029-3-A | single siRNA, 0.9 nmol | 242 | 2044 | EPHA5 | EPH receptor A5 | NM_182472 | ACCAGTTGGATCTCCAATGAA | SI02223536 | Hs_EPHA5_5 |
| 900029-3-A | single siRNA, 0.9 nmol | 243 | 2065 | ERBB3 | v-erb-b2 erythroblastic leukemia viral oncogene homolog 3 (avian) | NM_001982 | CCCAGTGAGAAGGCTAACAAA | SI02660252 | Hs_ERBB3_7 |
| 900029-3-A | single siRNA, 0.9 nmol | 244 | 2120 | ETV6 | ets variant gene 6 (TEL oncogene) | NM_001987 | TAGCATTAAGCAGGAACCAAT | SI03111038 | Hs_ETV6_5 |
| 900029-3-A | single siRNA, 0.9 nmol | 245 | 2222 | FDFT1 | farnesyl-diphosphate farnesyltransferase 1 | NM_004462 | CTGGCGGTTCATGGAGAGCAA | SI03098221 | Hs_FDFT1_8 |
| 900029-3-A | single siRNA, 0.9 nmol | 246 | 2264 | FGFR4 | fibroblast growth factor receptor 4 | NM_002011 NM_022963 | CAGGCTCTTCCGCAAGTCAA | SI02865306 | Hs_FGFR4_6 |
| 900029-3-A | single siRNA, 0.9 nmol | 247 | 2322 | FLT3 | fms-related tyrosine kinase 3 | NM_004119 | TACGTTGGATTTCAGAGAATAT | SI02659615 | Hs_FLT3_7 |
| 900029-3-A | single siRNA, 0.9 nmol | 248 | 2534 | FYN | FYN oncogene related to SRC, FGR, YES | NM_002037 | AAGAAGCAGGATGTCGATCTA | SI02659545 | Hs_FYN_8 |
| 900029-3-A | single siRNA, 0.9 nmol | 249 | 2690 | GHR | growth hormone receptor | NM_000163 | CAGGTGAGCGACATTACACCA | SI03072104 | Hs_GHR_6 |
| 900029-3-A | single siRNA, 0.9 nmol | 250 | 2771 | GNA12 | guanine nucleotide binding protein (G protein), alpha inhibiting activity polypeptide 2 | NM_002070 | CCGGGCGTTGTCTACAGCAA | SI02780981 | Hs_GNAI2_6 |
| 900029-3-A | single siRNA, 0.9 nmol | 251 | 2017 | CTTN | cortactin | NM_005231 NM_138565 | ATGCAACTTATTGTATCTGAA | SI02662485 | Hs_CTTN_6 |
| 900029-3-A | single siRNA, 0.9 nmol | 252 | 2045 | EPHA7 | EPH receptor A7 | NM_001042599 NM_034440 | CAGGGTCCGAAGGAAGTACTA | SI02223550 | Hs_EPHA7_6 |
| 900029-3-A | single siRNA, 0.9 nmol | 253 | 2066 | ERBB4 | v-erb-a erythroblastic leukemia viral oncogene homolog 4 (avian) | NM_005235 | TCGGGATTTGGCAGCCCGTAA | SI02223900 | Hs_ERBB4_6 |
| 900029-3-A | single siRNA, 0.9 nmol | 254 | 2138 | EYA1 | eyes absent homolog 1 (Drosophila) | NM_000503 NM_172058 NM_172059 NM_172060 | CTTCACCGTATCCAGCACATTA | SI03084047 | Hs_EYA1_10 |
| 900029-3-A | single siRNA, 0.9 nmol | 255 | 2241 | FER | fer (fps/fes related) tyrosine kinase (phosphoprotein NCP94) | NM_005246 | CAGAACAACTTAGTAGGATAA | SI02622067 | Hs_FER_6 |
| 900029-3-A | single siRNA, 0.9 nmol | 256 | 2288 | FGR | Gardner-Rasheed feline sarcoma viral (v-fgr) oncogene homolog | NM_001042729 NM_001042747 | CACCACCACGGGTTCAGTTCAA | SI03057047 | Hs_FGR_6 |
| 900029-3-A | single siRNA, 0.9 nmol | 257 | 2324 | FLT4 | fms-related tyrosine kinase 4 | NM_002020 NM_182925 | CACGCTCTTTGGTCAACAGGAA | SI02225454 | Hs_FLT4_9 |
| 900029-3-A | single siRNA, 0.9 nmol | 258 | 2547 | XRCC6 | X-ray repair complementing defective repair in Chinese hamster cells 6 (Ku autoantigen, 70 kDa) | NM_001469 | ACCGAGGCGATGAAGAAGCA | SI03039855 | Hs_XRCC6_4 |
| 900029-3-A | single siRNA, 0.9 nmol | 259 | 2697 | GJA1 | gap junction protein, alpha 1, 43 kDa | NM_000165 | ATGCTTAGAGTGGACTATTAA | SI02780491 | Hs_GJA1_5 |
| 900029-3-A | single siRNA, 0.9 nmol | 260 | 2773 | GNA13 | guanine nucleotide binding protein (G protein), alpha inhibiting activity | NM_006496 | CAGATGATGCCCGGCAATTAT | SI03064803 | Hs_GNAI3_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-3-A | single siRNA, 0.9 nmol | 261 | 2035 | EPB41 | erythrocyte membrane protein band 4.1 (elliptocytosis 1, RH-linked) | NM_004437 NM_203342 NM_203343 | GAAGGAGTAGATATCATCCTA | SI03101084 | Hs_EPB41_6 |
| 900029-3-A | single siRNA, 0.9 nmol | 262 | 2057 | EPOR | erythropoietin receptor | NM_000121 | CAGATGATCAGGATCCAATA | SI02780400 | Hs_EPOR_6 |
| 900029-3-A | single siRNA, 0.9 nmol | 263 | 2069 | EREG | epiregulin | NM_001432 | CAGGAATATTAAGTTCTATAA | SI03019937 | Hs_EREG_7 |
| 900029-3-A | single siRNA, 0.9 nmol | 264 | 2139 | EYA2 | eyes absent homolog 2 (Drosophola) | NM_005244 NM_172110 NM_172111 NM_172112 NM_172113 | TGGGTGCTTTGTGATGATAA | SI00382214 | Hs_EYA2_4 |
| 900029-3-A | single siRNA, 0.9 nmol | 265 | 2242 | FES | feline sarcoma oncogene | NM_002005 | CAGCCTGAGGCTGAGTACCAA | SI02659496 | Hs_FES_6 |
| 900029-3-A | single siRNA, 0.9 nmol | 266 | 2277 | FIGF | c-fos induced growth factor (vascular endothelial growth factor D) | NM_004469 | TTCTATGACATTGAAACACTA | SI02633358 | Hs_FIGF_6 |
| 900029-3-A | single siRNA, 0.9 nmol | 267 | 2353 | FOS | v-fos FBJ murine osteosarcoma viral oncogene homolog | NM_005252 | TGGGTTCATTATTGGAATTAA | SI02781464 | Hs_FOS_6 |
| 900029-3-A | single siRNA, 0.9 nmol | 268 | 2549 | GAB1 | GRB2-associated binding protein 1 | NM_002039 NM_207123 | TAGATGCTGGATTGACATTTA | SI02654736 | Hs_GAB1_6 |
| 900029-3-A | single siRNA, 0.9 nmol | 269 | 2736 | GLI2 | GLI-Kruppel family member GLI2 | NM_005270 NM_030379 NM_030380 | TACCCGGGCTACAGTCCGCAA | SI03110847 | Hs_GLI2_9 |
| 900029-3-A | single siRNA, 0.9 nmol | 270 | 2775 | GNAO1 | guanine nucleotide binding protein (G protein), alpha activating activity polypeptide O | NM_020988 NM_138736 | CCGGGAGTATCAACTCAACGA | SI03082506 | Hs_GNAO1_8 |
| 900029-3-A | single siRNA, 0.9 nmol | 271 | 2036 | EPB41L1 | erythrocyte membrane protein band, 4.1-like 1 | NM_012156 NM_177996 | CACGTTACAGTTAGCAGACGA | SI02639014 | Hs_EPB41L1_7 |
| 900029-3-A | single siRNA, 0.9 nmol | 272 | 2059 | EPS8 | epidermal growth factor receptor pathway substrate 8 | NM_004447 | TACCTTTGTCCTGGATCGGAA | SI03109302 | Hs_EPS8_5 |
| 900029-3-A | single siRNA, 0.9 nmol | 273 | 2070 | EYA4 | eyes absent homolog 4 (Drosophila) | NM_004100 NM_172103 NM_172104 NM_172105 | CAGCTTTAGCAAAGAACTCTT | SI00059717 | Hs_EYA4_4 |
| 900029-3-A | single siRNA, 0.9 nmol | 274 | 2140 | EYA3 | eyes absent homolog 3 (Drosophila) | NM_001990 NM_172098 | CAGACTCAATACCAGACACTA | SI03167612 | Hs_EYA3_5 |
| 900029-3-A | single siRNA, 0.9 nmol | 275 | 2260 | FGFR1 | fibroblast growth factor receptor 1 (fms-related tyrosine kisane 2, Pfeiffer syndrome) | NM_000604 NM_015850 NM_023109 NM_023110 NM_023111 | CCCGGCCCTCCTATGCTTGCCTAA | SI02224684 | Hs_FGFR1_7 |
| 900029-3-A | single siRNA, 0.9 nmol | 276 | 2308 | FOXO1 | forkhead box O1 | NM_002015 | CCCGAGTTTAGTAACACGTGCA | SI02781450 | Hs_FOXO1A_7 |
| 900029-3-A | single siRNA, 0.9 nmol | 277 | 2354 | FOSB | FBJ murine osteosarcoma viral oncogene homolog B | NM_006732 | TTCCTGGTTTCCAAAAGCAA | SI00091378 | Hs_FOSB_4 |
| 900029-3-A | single siRNA, 0.9 nmol | 278 | 2597 | GAPDH | glyceraldehyde-3-phosphate dehydrogenase | NM_002046 | AAGGTCGGAGTCAACGGATTT | SI03571113 | Hs_GAPDH_3 |
| 900029-3-A | single siRNA, 0.9 nmol | 279 | 2737 | GLI3 | GLI-Kruppel family member GLI3 (Greig cephalopolysyndactyly syndrome) | NM_000168 | CTGACCGATGGAGGTAGTATA | SI00000351 | Hs_GLI3_4 |
| 900029-3-A | single siRNA, 0.9 nmol | 280 | 2810 | SFN | stratifin | NM_006142 | CCGGAGAAGGTTGGAGACTGA | SI02653679 | Hs_SFN_6 |
| 900029-3-A | single siRNA, 0.9 nmol | 281 | 2037 | EPB41L2 | erythrocyte membrane protein band 4.1-like 2 | NM_001431 | TCCATGCATTAATATATTA | SI00380254 | Hs_EPB41L2_4 |
| 900029-3-A | single siRNA, 0.9 nmol | 282 | 2060 | EPS15 | epidermal growth factor receptor | NM_001981 | TACATCGTAGAAACGTTGAA | SI03108350 | Hs_EPS15_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-3-A | single siRNA, 0.9 nmol | 283 | 2099 | ESR1 | pathway substrate 15 estrogen receptor 1 | NM_000125 | GAGACTTGAATTAATAAGTGA | SI02781401 | Hs_ESR1_8 |
| 900029-3-A | single siRNA, 0.9 nmol | 284 | 2185 | PTK2B | PTK2B protein tyrosine kinase 2 beta | NM_004103 NM_173174 NM_173175 NM_173176 | CAGGAGAACTTAAGCCCAAA | SI02225328 | Hs_PTK2B_14 |
| 900029-3-A | single siRNA, 0.9 nmol | 285 | 2261 | FGFR3 | fibroblast growth factor receptor 3 (achondroplasia, thanatophoric dwarfism) | NM_000142 NM_022965 | CCGATGTTATTAGATGTTACA | SI00604779 | Hs_FGFR3_6 |
| 900029-3-A | single siRNA, 0.9 nmol | 288 | 2318 | FLNA | filamin A, alpha (actin binding protein 280) | NM_001456 | GTGGAAGAAGATCCAGCAGAA | SI02654722 | Hs_FLNA_5 |
| 900029-3-A | single siRNA, 0.9 nmol | 287 | 2444 | FRK | fyn-related kinase | NM_002031 | CTGGGAGTACCTAGAACCCTA | SI00287427 | Hs_FRK_6 |
| 900029-3-A | single siRNA, 0.9 nmol | 288 | 2674 | GFRA1 | GDNF family receptor alpha 1 | NM_005264 NM_145793 | TCCGTGCTTCCAGCCACATAA | SI03117205 | Hs_GFRA1_7 |
| 900029-3-A | single siRNA, 0.9 nmol | 289 | 2768 | GNA12 | guanine nucleotide binding protein (G protein) alpha 12 | NM_007353 | CGGCCGCCAGTTCGACCAGAA | SI03086195 | Hs_GNA12_5 |
| 900029-3-A | single siRNA, 0.9 nmol | 290 | 2885 | GRB2 | growth factor receptor-bound protein 2 | NM_002086 NM_203506 | CAAGAACTACATAGAAATGAA | SI02654750 | Hs_GRB2_8 |
| 900029-3-A | single siRNA, 0.9 nmol | 291 | 2042 | EPHA3 | EPH receptor A3 | NM_005233 | TTGGATAGTTTCCTACGTAAA | SI00287553 | Hs_EPHA3_6 |
| 900029-3-A | single siRNA, 0.9 nmol | 292 | 2064 | ERBB2 | v-erb-b2 erythroblastic leukemia viral oncogene homolog 2, neuro/glioblastoma derived oncogene homolog (avian) | NM_001005862 NM_004448 | CACGTTTGAGTCCATGCCCAA | SI02223578 | Hs_ERBB2_15 |
| 900029-3-A | single eiRNA, 0.9 nmol | 293 | 2107 | ETF1 | eukaryotic translation termination factor 1 | NM_004730 | TTGGAACTGCATCTAACATTA | SI03244416 | Hs_ETF1_5 |
| 900029-3-A | single siRNA, 0.9 nmol | 294 | 2214 | FCGR3A | Fc fragment of IgG, low affinity IIIa, receptor (CD16a) | NM_000569 | CTGGAAGGACCATAAATTTAA | SI03209913 | Hs_FCGR3A_5 |
| 900029-3-A | single siRNA, 0.9 nmol | 295 | 2263 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | NM_000141 NM_022969 NM_022970 NM_022972 NM_022975 NM_023028 NM_023029 NM_023030 NM_023031 | CAGCATATGTGTAAAGATTTA | SI02665299 | Hs_FGFR2_7 |
| 900029-3-A | single siRNA, 0.9 nmol | 296 | 2321 | FLT1 | fms-related tyrosine kinase 1 (vascular endothelial growth factor/vascular permeability factor receptor) | NM_002019 | CACTACTAGTATTAGCAAGCAA | SI02627576 | Hs_FLT1_6 |
| 900029-3-A | single siRNA, 0.9 nmol | 297 | 2521 | FUS | fusion (involved in t(12;16) in malignant liposarcoma) | NM_001010850 NM_004960 | AAGATCAATCCTCCATGAGTA | SI03032225 | Hs_FUS_5 |
| 900029-3-A | single siRNA, 0.9 nmol | 298 | 2683 | B4GALT1 | UDP-Gal:betaGlcNAc beta 1,4-galactosyltransferase, polypeptide 1 | NM_001497 | GGCGGGAGCACTATATTCAA | SI03105907 | Hs_B4GALT1_6 |
| 900029-3-A | single siRNA, 0.9 nmol | 299 | 2770 | GNAI1 | guanine nudeotide binding protein (G protein), alpha inhibiting activity polypeptide 1 | NM_002069 | TACGACCTGGTTCTAGCTGAA | SI03109414 | Hs_GNAI1_6 |
| 900029-3-A | single siRNA, 0.9 nmol | 300 | 2886 | GRB7 | growth factor receptor-bound protein 7 | NM_001030002 NM_005310 | CTGGATCTGTCTCCACCTCAT | SI03097598 | Hs_GRB7_7 |
| 900329-3-B | single siRNA, 0.9 nmol | 301 | 2002 | ELK1 | ELK1, member of ETS oncogene family | NM_005229 | CTGCTGAGAGAGCAAGGCAAT | SI00300146 | Hs_ELK1_5 |
| 900029-3-B | single siRNA, 0.9 nmol | 302 | 2044 | EPHA5 | EPH receptor A5 | NM_004439 NM_182472 | CCCGGCAGTATGTGTCTGTAA | SI00287511 | Hs_EPHA5_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900329-3-B | single siRNA, 0.9 nmol | 303 | 2065 | ERBB3 | v-erb-b2 erythroblastic leukemia viral oncogene homolog 3 (avian) | NM_001005915 | CTTCGTCATGTTGAACTATAAA | SI02660245 | Hs_ERBB3_6 |
| 900029-3-B | single siRNA, 0.9 nmol | 304 | 2120 | ETV6 | ets variant gene 6 (TEL oncogene) | NM_001987 | GCGCCACTACTACAAACTAAA | SI00030996 | Hs_ETV6_3 |
| 900029-3-B | single siRNA, 0.9 nmol | 306 | 2222 | FDFT1 | farnesyl-diphosphate farnesyltransferase 1 | NM_004462 | TTGAATGTTCGTAATAGTAGA | SI02633330 | Hs_FDFT1_6 |
| 900029-3-B | single siRNA, 0.9 nmol | 306 | 2264 | FGFR4 | fibroblast growth factor receptor 4 | NM_002011 NM_022963 NM_213647 | CCGCCTGACCTTCGGACCCTA | SI02659979 | Hs_FGFR4_5 |
| 900029-3-B | single siRNA, 0.9 nmol | 307 | 2322 | FLT3 | fms-related tyrosine kinase 3 | NM_004119 | ACCAATTCAAGTGAAGATTAT | SI00059878 | Hs_FLT3_3 |
| 900029-3-B | single siRNA, 0.9 nmol | 308 | 2534 | FYN | FYN oncogene related to SRC, FGR, YES | NM_002037 NM_153047 NM_153048 | GTGGCCCTTATGACTATGAA | SI02654729 | Hs_FYN_7 |
| 900029-3-B | single siRNA, 0.9 nmol | 309 | 2690 | GHR | growth hormone receptor | NM_000163 | AAGTGTTAATCCAGGCCTAAA | SI03037090 | Hs_GHR_5 |
| 90+329-3-B | single siRNA, 0.9 nmol | 310 | 2771 | GNA12 | guanine nucleotide binding protein (G protein), alpha inhibiting activity polypeptide 2 | NM_002070 | CAGCCCAAGTCCAAATGTTTA | SI02780505 | Hs_GNAI2_5 |
| 900029-3-B | single siRNA, 0.9 nmol | 311 | 2017 | CTTN | cortactin | NM_005231 NM_138565 | CACCAGGAGCATATCAACATA | SI02661960 | Hs_CTTN_5 |
| 900029-3-B | single siRNA, 0.9 nmol | 312 | 2045 | EPHA7 | EPH receptor A7 | NM_004440 | ACCAGTCATGATAGTAATAGA | SI02223543 | Hs_EPHA7_5 |
| 900029-3-B | single siRNA, 0.9 nmol | 313 | 2066 | ERBB4 | v-erb-a erythroblastic leukemia viral oncogene homolog 4 (avian) | NM_001042599 NM_005235 | CTACGTGTTAGTGGCTCTTAA | SI02223893 | Hs_ERBB4_5 |
| 900029-3-B | single siRNA, 0.9 nmol | 314 | 2138 | EYA1 | eyes absent homolog 1 (Drosophila) | NM_000503 NM_172058 NM_172059 NM_172060 | AGCCGACGACCGGTCTTTAAACAA | SI03043334 | Hs_EYA1_9 |
| 900029-3-B | single siRNA, 0.9 nmol | 315 | 2241 | FER | fer (fps/fes related) tyrosine kinase (phosphoprotein NCP94) | NM_005246 | CAGATAGATCCTAGTACAGAA | SI00287756 | Hs_FER_5 |
| 900029-3-B | single siRNA, 0.9 nmol | 316 | 2268 | FGR | Gardner-Rasheed feline sarcoma viral (v-fgr) oncogene homolog | NM_001042729 NM_001042747 | CACGTGGAACGGCAGCACTAA | SI02634807 | Hs_FGR_5 |
| 900029-3-B | single siRNA, 0.9 nmol | 317 | 2324 | FLT4 | fms-related tyrosine kinase 4 | NM_002020 NM_182925 | CACCGTGTGGGCTGAGTTTAA | SI02225447 | Hs_FLT4_8 |
| 900029-3-B | single siRNA, 0.9 nmol | 318 | 2547 | XRCC6 | X-ray repair complementing defective repair in Chinese hamster cells 6 (Ku autoantigen, 70 kDa) | NM_001469 | AAGCTCTATCGGGAAACAAAT | SI03033884 | Hs_XRCC6_3 |
| 900029-3-B | single siRNA, 0.9 nmol | 319 | 2697 | GJA1 | gap junction protein, alpha 1, 43 kDa | NM_000165 | CAGGGAATCAAGCACATGCTTA | SI00035507 | Hs_GJA1_4 |
| 900029-3-B | single siRNA, 0.9 nmol | 320 | 2773 | GNA13 | guanine nucleotide binding protein (G protein), alpha inhibiting activity polypeptide 3 | NM_006496 | AAAGTGTGATTCGATCGTCAA | SI00088956 | Hs_GNAI3_4 |
| 900029-3-B | single siRNA, 0.9 nmol | 321 | 2035 | EPB41 | erythrocyte membrane protein band 4.1 (elliptocytosis 1, RH-linked) | NM_004437 NM_203342 NM_203343 | TTCGAGCGTACAGCAAGTAAA | SI03022698 | Hs_EPB41_5 |
| 900029-3-B | single siRNA, 0.9 nmol | 322 | 2057 | EPOR | erythropoietin receptor | NM_000121 | CCAGTGCAGAGACTTCAAGACTTA | SI02780351 | Hs_EPOR_5 |
| 900029-3-B | single siRNA, 0.9 nmol | 323 | 2069 | EREG | epiregulin | NM_001432 | CACCATGTATCATATATTAA | SI02655863 | Hs_EREG_5 |
| 900029-3-B | single siRNA, 0.9 nmol | 324 | 2139 | EYA2 | eyes absent homolog 2 (Drosophila) | NM_005244 NM_172110 NM_172111 NM_172112 NM_172113 | AAGGCAGTTCAAGCTGTTGAA | SI00382207 | Hs_EYA2_3 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-3-B | 0.9 nmol single siRNA, | 325 | 2242 | FES | feline sarcoma oncogene | NM_002005 | AAGGCCAAGTTTCTACAGGAA | SI02659489 | Hs_FES_5 |
| 900029-3-B | 0.9 nmol single siRNA, | 326 | 2277 | FIGF | c-fos induced growth factor (vascular endothelial growth factor D) | NM_004469 | CAGGTTGTAAGTGCTTGCCAA | SI02633351 | Hs_FIGF_5 |
| 900029-3-B | 0.9 nmol single siRNA, | 327 | 2353 | FOS | v-fos FBJ murine osteosarcoma viral oncogene homolog | NM_005252 | GACCAATATTATACTAAGAAA | SI02781429 | Hs_FOS_5 |
| 900029-3-B | 0.9 nmol single siRNA, | 328 | 2549 | GAB1 | GRB2-associated binding protein 1 | NM_002039 NM_207123 | CCCGACCAGATTCAGTGCATA | SI03077403 | Hs_GAB1_7 |
| 900029-3-B | 0.9 nmol single siRNA, | 329 | 2736 | GLI2 | GLI-Kruppel family member GLI2 | NM_005270 | CTCGCTAGTGGCCTACATCAA | SI03091445 | Hs_GLI2_8 |
| 900029-3-B | 0.9 nmol single siRNA, | 330 | 2775 | GNAO1 | guanine nucleotide binding protein (G protein), alpha activating activity polypeptide O | NM_020988 NM_138736 | ATGGACACTTTGGGCATCGAA | SI03050523 | Hs_GNAO1_7 |
| 900029-3-B | 0.9 nmol single siRNA, | 331 | 2036 | EPB41L1 | erythrocyte membrane protein band 4.1-like 1 | NM_012156 NM_177996 | CAGAGTCTCCGCTATGGATAA | SI00160489 | Hs_EPB41L1_5 |
| 900029-3-B | 0.9 nmol single siRNA, | 332 | 2059 | EPS8 | epidermal growth factor receptor pathway substrate 8 | NM_004447 | CAGGTGGATGTTAGAAGTCGA | SI00380751 | Hs_EPS8_3 |
| 900029-3-B | 0.9 nmol single siRNA, | 333 | 2070 | EYA4 | eyes absent homolog 4 (Drosophila) | NM_004100 NM_172103 NM_172104 NM_172105 | CTGGGTCAGTAATTACAAGTA | SI00059710 | Hs_EYA4_3 |
| 900029-3-B | 0.9 nmol single siRNA, | 334 | 2140 | EYA3 | eyes absent homolog 3 (Drosophila) | NM_001990 NM_172098 | CAGTCACATAAGTATAATAAA | SI00382242 | Hs_EYA3_4 |
| 900029-3-B | 0.9 nmol single siRNA, | 335 | 2260 | FGFR1 | fibroblast growth factor receptor 1 (fms-related tyrosine kinase 2, Pfeiffer syndrome) | NM_000604 NM_015850 NM_023105 NM_023106 NM_023109 NM_023110 NM_023111 | CAGAGATTTACCCATCGGGTA | SI02224677 | Hs_FGFR1_6 |
| 900029-3-B | 0.9 nmol single siRNA, | 336 | 2308 | FOXO1 | forkhead box O1 | NM_002015 | AACCAAGTAGCCTGTTATCAA | SI02781415 | Hs_FOXO1A_6 |
| 900029-3-B | 0.9 nmol single siRNA, | 337 | 2354 | FOSB | FBJ murine osteosarcoma viral oncogene homolog B | NM_006732 | AAGGGTGCGCCGGAACGAAA | SI00091371 | Hs_FOSB_3 |
| 900029-3-B | 0.9 nmol single siRNA, | 338 | 2597 | GAPDH | glyceraldehyde-3-phosphate dehydrogenase | NM_002046 | CCGAGCCACATCGCTCAGACA | SI02653266 | Hs_GAPD_5 |
| 900029-3-B | 0.9 nmol single siRNA, | 339 | 2737 | GLI3 | GLI-Kruppel family member GLI3 (Greig cephalopolysyndactyly syndrome) | NM_000168 | CCGCCTTATCTAGTAGCCCTA | SI00003584 | Hs_GLI3_3 |
| 900029-3-B | 0.9 nmol single siRNA, | 340 | 2810 | SFN | stratifin | NM_006142 | ACCATGTTTCCTCTCAATAAA | SI02653637 | Hs_SFN_5 |
| 900029-3-B | 0.9 nmol single siRNA, | 341 | 2037 | EPB41L2 | erythrocyte membrane protein band 4.1-like 2 | NM_001431 | CAGGCTAAGGGTGATGCTGAA | SI00380247 | Hs_EPB41L2_3 |
| 900029-3-B | 0.9 nmol single siRNA, | 342 | 2060 | EPS15 | epidermal growth factor receptor pathway substrate 15 | NM_001981 | TAGCCTATAAATAAATTCCAA | SI02627457 | Hs_EPS15_7 |
| 900029-3-B | 0.9 nmol single siRNA, | 343 | 2099 | ESR1 | estrogen receptor 1 | NM_000125 | TCCGAGTATGATCCTACCAGA | SI03114979 | Hs_ESR1_11 |
| 900029-3-B | 0.9 nmol single siRNA, | 344 | 2185 | PTK2B | PTK2B protein tyrosine kinase 2 beta | NM_004103 | AAGCTGATCGGCATCATTGAA | SI02225321 | Hs_PTK2B_13 |
| 900029-3-B | 0.9 nmol single siRNA, | 345 | 2261 | FGFR3 | fibroblast growth factor receptor 3 (achondroplasia, thanatophoric dwarfism) | NM_000142 NM_022965 | ACCCTACGTTACCGTGCTCAA | SI00604772 | Hs_FGFR3_5 |
| 900029-3-B | 0.9 nmol single siRNA, | 346 | 2316 | FLNA | filamin A, alpha (actin binding protein 280) | NM_001456 | CACCCATGGAGTAGTGAACAA | SI02655912 | Hs_FLNA_7 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-3-B | single siRNA, 0.9 nmol | 347 | 2444 | FRK | fyn-related kinase | NM_002031 | CAGGACAGTCAAGGTGATATA | SI00287420 | Hs_FRK_5 |
| 900029-3-B | single siRNA, 0.9 nmol | 348 | 2674 | GFRA1 | GDNF family receptor alpha 1 | NM_005264 NM_145793 | AAGGCAGTGCGTGGCGGGCAA | SI03035256 | Hs_GFRA1_6 |
| 900029-3-B | single siRNA, 0.9 nmol | 349 | 2768 | GNA12 | guanine nucleotide binding protein (G protein) alpha 12 | NM_007353 | GTCCGTTTAACTCGATAGAAA | SI00096572 | Hs_GNA12_4 |
| 900029-3-B | single siRNA, 0.9 nmol | 350 | 2885 | GRB2 | growth factor receptor-bound protein 2 | NM_002086 | AAGTTTGGAAACGATGTGCAG | SI00300328 | Hs_GRB2_5 |
| 900029-3-B | single siRNA, 0.9 nmol | 351 | 2042 | EPHA3 | EPH receptor A3 | NM_005233 | TCGGATATGATTGTTTCTCAA | SI00287546 | Hs_EPHA3_5 |
| 900029-3-B | single siRNA, 0.9 nmol | 352 | 2064 | ERBB2 | v-erb-b2 erythroblastic leukemia viral oncogene homolog 2, neuro/glioblastoma derived oncogene homolog (avian) | NM_001005862 NM_004448 | AACAAAGAAATCTTAGACGAA | SI02223571 | Hs_ERBB2_14 |
| 900029-3-B | single siRNA, 0.9 nmol | 353 | 2107 | ETF1 | eukaryotic translation termination factor 1 | NM_004730 | AGGGAGTATGTCTTAAATGTA | SI00381346 | Hs_ETF1_4 |
| 900029-3-B | single siRNA, 0.9 nmol | 354 | 2214 | FCGR3A | Fc fragment of IgG, low affinity IIIa, receptor (CD16a) | NM_000569 | CAAGTTGCTAAGTGAACAGAA | SI00386099 | Hs_FCGR3A_3 |
| 900029-3-B | single siRNA, 0.9 nmol | 355 | 2263 | FGFR2 | fibroblast growth factor receptor 2 (bacteria-expressed kinase, keratinocyte growth factor receptor, craniofacial dysostosis 1, Crouzon syndrome, Pfeiffer syndrome, Jackson-Weiss syndrome) | NM_000141 NM_022969 NM_022970 NM_022971 NM_022972 NM_022973 NM_022974 NM_022975 NM_022976 NM_023028 NM_023029 NM_023030 NM_023031 | TTAGTTGGAGGATACCACCATTA | SI02623047 | Hs_FGFR2_6 |
| 900029-3-B | single siRNA, 0.9 nmol | 356 | 2321 | FLT | fms-related tyrosine kinase 1 (vascular endothelial growth factor/vascular permeability factor receptor) | NM_002019 | ACCGCATATGGTATCCCTCAA | SI02627569 | Hs_FLT1_5 |
| 900029-3-B | single siRNA, 0.9 nmol | 357 | 2521 | FUS | fusion (involved in t(12;16) in malignant liposarcoma) | NM_001010850 NM_004960 | ACAGGATAATTCAGACAACAA | SI00070518 | Hs_FUS_4 |
| 900029-3-B | single siRNA, 0.9 nmol | 358 | 2683 | B4GALT1 | UDP-Gal:betaGlcNAc beta 1,4-galactosyltransferase, polypeptide 1 | NM_001497 | CAGAGGTTTGACCGAATTGCA | SI03064250 | Hs_B4GALT1_5 |
| 900029-3-B | single siRNA, 0.9 nmol | 359 | 2770 | GNAI1 | guanine nucleotide binding protein (G protein), alpha inhibiting activity polypeptide 1 | NM_002069 | CGGGCCGATGATGCACGCCAA | SI03087140 | Hs_GNAI1_5 |
| 900029-3-B | single siRNA, 0.9 nmol | 360 | 2886 | GRB7 | growth factor receptor-bound protein 7 | NM_001030002 NM_005310 | CCTGCAGAAAGTGAAGCATTA | SI03083381 | Hs_GRB7_6 |
| 900029-3-B | single siRNA, 0.9 nmol | 361 | 2887 | GRB10 | growth factor receptor-bound protein 10 | NM_001001549 NM_001001550 NM_001001555 NM_005311 | CTAGATGACGGGAACACCAAA | SI02780526 | Hs_GRB10_6 |
| 900029-4-A | single siRNA, 0.9 nmol | 362 | 3064 | HD | huntingtin (Huntington disease) | NM_002111 | CCCGCTGACATTTCCGTTGTA | SI02662555 | Hs_HD_7 |
| 900029-4-A | single siRNA, 0.9 nmol | 363 | 3164 | NR4A1 | nuclear receptor subfamily 4, group A, member 1 | NM_002135 NM_173157 NM_173158 | CTTCCAGTGCTCTGACTACTA | SI03089576 | Hs_NR4A1_6 |
| 900029-4-A | single siRNA, 0.9 nmol | 364 | 3312 | HSPA8 | heat shock 70 kDa protein 8 | NM_006597 NM_153201 | AGGAAATAACATTGCACTTTA | SI03145317 | Hs_HSPA8_9 |

TABLE 3-continued

| SEQ ID NO: | Plate Id | Plate Name | Entrez Gene Id | NCBI gene symbol | Gene Description | mRNA Accessions | siRNA Target Sequence | Product Id | Product Name |
|---|---|---|---|---|---|---|---|---|---|
| 365 | 900029-4-A | single siRNA, 0.9 nmol | 3398 | ID2 | inhibitor of DNA binding 2, dominant negative helix-loop-helix protein | NM_002166 | TTGGACTGTGATATTCGTTAT | SI03244805 | Hs_ID2_6 |
| 366 | 900029-4-A | single siRNA, 0.9 nmol | 3561 | IL2RG | interleukin 2 receptor, gamma (severe combined immunodeficiency) | NM_000206 | AAGAACTCGGATAATGATAAA | SI00004486 | Hs_IL24G_4 |
| 367 | 900029-4-A | single siRNA, 0.9 nmol | 3643 | INSR | insulin receptor | NM_000208 NM_001079817 | TCCGGGTACCGCGAAGGGCAA | SI03115434 | Hs_INSR_6 |
| 368 | 900029-4-A | single siRNA, 0.9 nmol | 3716 | JAK1 | Janus kinase 1 (a protein tyrosine kinase) | NM_002227 | CACGGATAACATCAGCTTCAT | SI00605521 | Hs_JAK1_6 |
| 369 | 900029-4-A | single siRNA, 0.9 nmol | 3732 | CD82 | CD82 molecule | NM_001024844 NM_002231 | CGGCTGGGTCAGCTTCTACAA | SI03086650 | Hs_CD82_4 |
| 370 | 900029-4-A | single siRNA, 0.9 nmol | 3855 | KRT7 | keratin 7 | NM_005556 | CCGCGAGTCACCATTAACCA | SI00465073 | Hs_KRT7_4 |
| 371 | 900029-4-A | single siRNA, 0.9 nmol | 2888 | GR814 | growth factor receptor-bound protein 14 | NM_004490 XM_001131269 | CAGACCTATTTCCCAAAGCAA | SI00430717 | Hs_GRB14_4 |
| 372 | 900029-4-A | single siRNA, 0.9 nmol | 3065 | HDAC1 | histone deacetylase 1 | NM_004964 | CACCCGGAGGAAAGTCTGTTA | SI02663472 | Hs_HDAC1_6 |
| 373 | 900029-4-A | single siRNA, 0.9 nmol | 3178 | HNRPA1 | heterogeneous nuclear ribonucleoprotein A1 | NM_002136 NM_031157 | AATCATGACTGACCGAGCAG | SI00300419 | Hs_HNRPA1_1 |
| 374 | 900029-4-A | single siRNA, 0.9 nmol | 3313 | HSPA9 | heat shock 70 kDa protein 9 (mortalin) | NM_004134 | AATTGTATTCTCCGAGTCAGA | SI02654813 | Hs_HSPA9B_5 |
| 375 | 900029-4-A | single siRNA, 0.9 nmol | 3480 | IGF1R | insulin-like growth factor 1 receptor | NM_000875 | CTGGACTCAGTACGCCCGTTTA | SI03096926 | Hs_IGF1R_8 |
| 376 | 900029-4-A | single siRNA, 0.9 nmol | 3566 | IL4R | interleukin 4 receptor | NM_000418 NM_001008699 | CACGTGTATCCCTGAGAACAA | SI03061765 | Hs_IL4R_6 |
| 377 | 900029-4-A | single siRNA, 0.9 nmol | 3645 | INSRR | insulin receptor-related receptor | NM_014215 | CAAGATCTACTTCGCTTCAA | SI00103642 | Hs_INSRR_4 |
| 378 | 900029-4-A | single siRNA, 0.9 nmol | 3717 | JAK2 | Janus kinase 2 (a protein tyrosine kinase) | NM_004972 | CTGCCTTACGATGACAGAAAT | SI02659664 | Hs_JAK2_8 |
| 379 | 900029-4-A | single siRNA, 0.9 nmol | 3791 | KDR | kinase insert domain receptor (a type III receptor tyrosine kinase) | NM_002253 | AAGGCTAATACAACTCTTCAA | SI00605535 | Hs_KDR_6 |
| 380 | 900029-4-A | single siRNA, 0.9 nmol | 3856 | KRT8 | keratin 8 | NM_002273 | CCTGAGAGTCTTCCTCACCAA | SI03083304 | Hs_KRT8_8 |
| 381 | 900029-4-A | single siRNA, 0.9 nmol | 2889 | RAPGEF1 | Rap guanine nucleotide exchange factor (GEF) 1 | NM_005312 NM_198679 | CTGGGTCCGGTCCATAATCAT | SI03099194 | Hs_RAPGEF1_7 |
| 382 | 900029-4-A | single siRNA, 0.9 nmol | 3082 | HGF | hepatocyte growth factor (hepapoietin A; scatter factor) | NM_000601 NM_001010931 NM_001010932 NM_001010933 NM_001010934 | TAGCATGTCAAGTGGAGTGAA | SI03111031 | Hs_HGF_9 |
| 383 | 900029-4-A | single siRNA, 0.9 nmol | 3190 | HNRPK | heterogeneous nuclear ribonucleoprotein K | NM_002140 NM_031262 NM_031263 | AATCTGATGCTGTGGAATGCT | SI03030468 | Hs_HNRPK_1 |
| 384 | 900029-4-A | single siRNA, 0.9 nmol | 3320 | HSP90AA1 | heat shock protein 90 kDa alpha (cytosolic), class A member 1 | NM_001017963 NM_005348 | TGCACTGTAAGACGTATGATCCA | SI03117814 | Hs_HSP90AA1_2 |
| 385 | 900029-4-A | single siRNA, 0.9 nmol | 3491 | CYR61 | cysteine-rich, angiogenic inducer, 61 | NM_001554 | CAAGAACGTCATGATGATCCA | SI03053477 | Hs_CYR61_8 |
| 386 | 900029-4-A | single siRNA, 0.9 nmol | 3572 | IL6ST | interleukin 6 signal transducer (gp130, oncostatin M receptor) | NM_002184 NM_175767 | ATGGACCAACCCAAGTATTAA | SI03050544 | Hs_IL6ST_5 |
| 387 | 900029-4-A | single siRNA, 0.9 nmol | 3667 | IRS1 | insulin receptor substrate 1 | NM_005544 | ACAATAGGCCATGTTAATTAA | SI00078652 | Hs_IRS1_4 |
| 388 | 900029-4-A | single siRNA, 0.9 nmol | 3725 | JUN | jun oncogene | NM_002228 | AAGAACTGACAGATGACGAG | SI00300580 | Hs_JUN_5 |
| 389 | 900029-4-A | single siRNA, 0.9 nmol | 3845 | KRAS | v-Ki-ras2 Kirsten rat sarcoma viral oncogene homolog | NM_004985 NM_033360 | AAGGAGAATTAATAAAGATA | SI02662051 | Hs_KRAS2_8 |
| 390 | 900029-4-A | single siRNA, 0.9 nmol | 3872 | KRT17 | keratin 17 | NM_000422 | TCCTTGCCTGATGACAATAAA | SI03233307 | Hs_KRT17_5 |
| 391 | 900029-4-A | single siRNA, 0.9 nmol | 2932 | GSK3B | glycogen synthase kinase 3 beta | NM_002093 | CTGCATTTATCGTTAACCTAA | SI00605479 | Hs_GSK3B_8 |
| 392 | 900029-4-A | single siRNA, 0.9 nmol | 3084 | NRG1 | neuregulin 1 | NM_004495 | TGGCTGATTCTGAGAGTATA | SI03120530 | Hs_NRG1_11 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-4-A | single siRNA, 0.9 nmol | 393 | 3265 | HRAS | v-Ha-ras Harvey rat sarcoma viral oncogene homolog | NM_013956 NM_013957 NM_013958 NM_013960 NM_013961 NM_013962 NM_013964 NM_005343 | AGGAGCGATGACGGAATATAA | SI02662576 | Hs_HRAS_8 |
| 900029-4-A | single siRNA, 0.9 nmol | 394 | 3329 | HSPD1 | heat shock 60 kDa protein 1 (chaperonin) | NM_176795 NM_002156 | CAGGGTTTGGTGACAATAGAA | SI02654162 | Hs_HSPD1_8 |
| 900029-4-A | single siRNA, 0.9 nmol | 395 | 3551 | IKBKB | inhibitor of kappa light polypeptide gene enhancer in B-cells, kinase beta | NM_199440 NM_001556 | CTGGAGAAGTACAGCGAGCAA | SI02777376 | Hs_IKBKB_9 |
| 900029-4-A | single siRNA, 0.9 nmol | 396 | 3609 | ILF3 | interleukin enhancer binding factor 3, 90 kDa | NM_004516 NM_012218 NM_153464 | CTCGCCCTTGATGCCAACAAA | SI03091361 | Hs_ILF3_12 |
| 900029-4-A | single siRNA, 0.9 nmol | 397 | 3678 | ITGA5 | integrin, alpha 5 (fibronectin receptor, alpha polypeptide) | NM_002205 | AATCCTTAATGGCTCAGACAT | SI02654841 | Hs_ITGA5_5 |
| 900029-4-A | single siRNA, 0.9 nmol | 398 | 3726 | JUNB | jun B proto-oncogene | NM_002229 | CCCGACGACCACCATCAGCTA | SI03077445 | Hs_JUNB_5 |
| 900029-4-A | single siRNA, 0.9 nmol | 399 | 3852 | KRT5 | keratin 5 (epidermolysis bullosa simplex, Dowling-Meara/Kobner/Weber-Cockayne types) | NM_000424 | ACGCATGTCTCTGACACCTCA | SI03140788 | Hs_KRT5_6 |
| 900029-4-A | single siRNA, 0.9 nmol | 400 | 3875 | KRT18 | keratin 18 | NM_000224 NM_199187 | CCCCCGGATAGTCGATGGCAA | SI02653658 | Hs_KRT18_3 |
| 900029-4-A | single siRNA, 0.9 nmol | 401 | 2934 | GSN | gelsolin (amyloidosis, Finnish type) | NM_000177 NM_198252 | CAGCTACATCATTCTGTACAA | SI02664046 | Hs_GSN_6 |
| 900029-4-A | single siRNA, 0.9 nmol | 402 | 3092 | HIP1 | huntingtin interacting protein 1 | NM_005338 | CAGGTTAGGGTGCTAGAGCTA | SI00075859 | Hs_HIP1_4 |
| 900029-4-A | single siRNA, 0.9 nmol | 403 | 3280 | HES1 | hairy and enhancer of split 1, (Drosophila) | NM_005524 | CCAGATCAATGCCATGACCTA | SI03075016 | Hs_HES1_5 |
| 900029-4-A | single siRNA, 0, 9 nmol | 404 | 3371 | TNC | tenascin C (hexabrachion) | NM_002160 | CACGCCTTATAGAGTCTCCAT | SI03060232 | Hs_TNC_6 |
| 900029-4-A | single siRNA, 0.9 nmol | 405 | 3558 | IL2 | interleukin 2 | NM_000586 | GTGCACCTACTTCAAGTTCTA | SI03106600 | Hs_IL2_5 |
| 900029-4-A | single siRNA, 0.9 nmol | 406 | 3635 | INPP5D | inositol polyphosphate-5-phosphatase, 145 kDa | NM_001017915 NM_005541 | AACCTCCTTAGGGTTCGTCAA | SI03029005 | Hs_INPP5D_5 |
| 900029-4-A | single siRNA, 0.9 nmol | 407 | 3690 | ITGB3 | integrin, beta 3 (platelet glycoprotein IIIa, antigen CD61) | NM_000212 | CACGTGTGGCCTGTTCTTCTA | SI02623159 | Hs_ITGB3_5 |
| 900029-4-A | single siRNA, 0.9 nmol | 408 | 3727 | JUND | jun D proto-oncogene | NM_005354 | CGCGGCCGGCAGCATGATGAA | SI03085201 | Hs_JUND_6 |
| 900029-4-A | single siRNA, 0.9 nmol | 409 | 3853 | KRT6A | keratin 6A | NM_058242 | TTCACTCTTTGCAATTGCTAA | SI03240776 | Hs_KRT6C_7 |
| 900029-4-A | single siRNA, 0.9 nmol | 410 | 3897 | L1CAM | L1 cell adhesion molecule | NM_000425 NM_024003 | CACCCTCAAGCTGTCGCCCTA | SI00009296 | Hs_L1CAM_4 |
| 900029-4-A | single siRNA, 0.9 nmol | 411 | 3055 | HCK | hemopoietic cell kinase | NM_002110 | CCGGGATAGCGAGACCACTAA | SI02665327 | Hs_HCK_8 |
| 900029-4-A | single siRNA, 0.9 nmol | 412 | 3105 | HLA-A | major histocompatibility complex, class I, A | NM_002116 | TGCCGTGATGTGGAGGAGGAA | SI03236338 | Hs_HLA-A_5 |
| 900029-4-A | single siRNA, 0.9 nmol | 413 | 3309 | HSPA5 | heat shock 70 kDa protein 5 (glucose-regulated protein, 78 kDa) | NM_005347 | TGGGATAAGGAAACACTTCTA | SI02781016 | Hs_HSPA5_7 |
| 900029-4-A | single siRNA, 0.9 nmol | 414 | 3397 | ID1 | inhibitor of DNA binding 1, dominant negative helix-loop-helix protein | NM_002165 NM_181353 | CCAGTCGCCAAGAATCATGAA | SI03075653 | Hs_ID1_7 |
| 900029-4-A | single siRNA, 0.9 nmol | 415 | 3580 | IL2RB | interleukin 2 receptor, beta | NM_000878 | CTGCCAGGTGTACTTTACTTA | SI03094714 | Hs_IL2RB_6 |

TABLE 3-continued

| SEQ ID NO: | Plate Id | Plate Name | Entrez Gene Id | NCBI gene symbol | Gene Description | mRNA Accessions | siRNA Target Sequence | Product Id | Product Name |
|---|---|---|---|---|---|---|---|---|---|
| 416 | 900029-4-A | single siRNA, 0.9 nmol | 3636 | INPPL1 | inositol polyphosphate phosphatase-like 1 | NM_001567 | ACCCAAGAACAGCTTCAATAA | SI00447825 | Hs_INPPL1_4 |
| 417 | 900029-4-A | single siRNA, 0.9 nmol | 3691 | ITGB4 | integrin, beta 4 | NM_000213 NM_001005619 NM_001005731 | AACGATGACAACCGACCTATT | SI02664109 | Hs_ITGB4_6 |
| 418 | 900029-4-A | single siRNA, 0.9 nmol | 3728 | JUP | junction plakoglobin | NM_002203 NM_021991 | CCGCACTTCCGAGGACAAGAA | SI00034741 | Hs_JUP_4 |
| 419 | 900029-4-A | single siRNA, 0.9 nmol | 3854 | KRT6B | keratin 6B | NM_005555 | CTCTCTTTAATTGCTAACCAT | SI00464933 | Hs_KRT6B_4 |
| 420 | 900029-4-A | single siRNA, 0, 9 nmol | 3932 | LCK | lymphocyte-specific protein tyrosine kinase | NM_001042771 | AGGCATCAAGTTGACCATCAA | SI02635066 | Hs_LCK_5 |
| 421 | 900029-4-B | single siRNA, 0.9 nmol | 2887 | GRB10 | growth factor receptor-bound protein 10 | NM_005356 NM_001001549 NM_001001550 NM_001001555 | CCGCCGCAAAGCAGGATGTTA | SI03080868 | Hs_GRB10_7 |
| 422 | 900029-4-B | single siRNA, 0.9 nmol | 3064 | HD | huntingtin (Huntington disease) | NM_005311 NM_002111 | CACACGCTAACTACAAGGTCA | SI03055696 | Hs_HD_9 |
| 423 | 900029-4-B | single siRNA, 0.9 nmol | 3164 | NR4A1 | nuclear receptor subfamily 4, group A, member 1 | NM_002135 NM_173158 | CACAGGAGAGTTTGACACCTT AACACTGTATTGTAAGTGGAA | SI03056221 SI03123218 | Hs_NR4A1_5 Hs_HSPAB_8 |
| 424 | 900029-4-B | single siRNA, 0.9 nmol | 3312 | HSPA8 | heat shock 70 kDa protein 8 | NM_006597 NM_153201 | AAAGTTTAGTTGTAAACTTAA | SI03122518 | Hs_ID2_5 |
| 425 | 900029-4-B | single siRNA, 0.9 nmol | 3398 | ID2 | inhibitor of DNA binding 2, dominant negative helix-loop-helix protein | NM_002166 | CACGACAATTCTGACGCCCAA | SI00004459 | Hs_IL2RG_3 |
| 426 | 900029-4-B | single siRNA, 0.9 nmol | 3561 | IL2RG | interleukin 2 receptor, gamma (severe combined immunodeficiency) | NM_000206 | TTGGACGGTGGTAGACATTGA | SI03024581 | Hs_INSR_5 |
| 427 | 900029-4-B | single siRNA, 0.9 nmol | 3643 | INSR | insulin receptor | NM_000208 NM_001079817 | ACCGGATGAGGTTCTATTTCA | SI00605514 | Hs_JAK1_5 |
| 428 | 900029-4-B | single siRNA, 0.9 nmol | 3716 | JAK1 | Janus kinase 1 (a protein tyrosine kinase) | NM_002227 | CGCAGGTGGGCTGGACTTCTA | SI03084123 | Hs_CD82_3 |
| 429 | 900029-4-B | single siRNA, 0.9 nmol | 3732 | CD82 | CD82 molecule | NM_001024844 NM_002231 | TGCCCTGAATGATGAGATCAA AAGAATGTATTTCACCTGCAA | SI00485066 SI00430710 | Hs_KRT7_3 Hs_GRB14_3 |
| 430 431 | 900029-4-B 900029-4-B | single siRNA, 0.9 nmol single siRNA, 0.9 nmol | 3855 2888 | KRT7 GRB14 | keratin 7 growth factor receptor-bound protein 14 | NM_005556 NM_004490 XM_001131269 XM_001131281 | CCCGTTCTTAACTTTGAACCA | SI02634149 | Hs_HDAC1_5 |
| 432 | 900029-4-B | single siRNA, 0.9 nmol | 3065 | HDAC1 | histone deacetylase 1 | NM_004964 NM_032136 | CTCTTAAGCCATCTTGGTAAA | SI03205657 | Hs_HNRPA1_10 |
| 433 | 900029-4-B | single siRNA, 0.9 nmol | 3178 | HNRPA1 | heterogeneous nuclear ribonucleoprotein A1 | NM_031157 | AAGAGACTTCCTGAGCAGAGA | SI03128496 | Hs_HSPA9B_6 |
| 434 | 900029-4-B | single siRNA, 0.9 nmol | 3313 | HSPA9 | heat shock 70 kDa protein 9 (mortalin) | NM_004134 | TCGAAGAATCGCATCATCATA | SI02624552 | Hs_IGF1R_7 |
| 435 | 900029-4-B | single siRNA, 0.9 nmol | 3480 | IGF1R | insulin-like growth factor 1 receptor | NM_000875 | AAGCCCAGCGAGCATGTGAAA | SI03033177 | Hs_IL4R_5 |
| 436 | 900029-4-B | single siRNA, 0.9 nmol | 3566 | IL4R | interleukin 4 receptor | NM_000418 NM_001008699 | CAGCTCGGATTTCGAGATCCA | SI00103635 | Hs_INSRR_3 |
| 437 | 900029-4-B | single siRNA, 0.9 nmol | 3645 | INSRR | insulin receptor-related receptor | NM_014215 | AGCCATCATACGAGATCTTAA | SI02659657 | Hs_JAK2_7 |
| 438 | 900029-4-B | single siRNA, 0.9 nmol | 3717 | JAK2 | Janus kinase 2 (a protein tyrosine kinase) | NM_004972 | AACGCTGACATGTACGGTCTA | SI00605528 | Hs_KDR_5 |
| 439 | 900029-4-B | single siRNA, 0.9 nmol | 3791 | KDR | kinase insert domain receptor (a type III receptor tyrosine kinase) | NM_002253 | CACCGCAGTTACGGTCAACCA | SI03058356 | Hs_KRT8_7 |
| 440 | 900029-4-B | single siRNA, 0.9 nmol | 3856 | KRT8 | keratin 8 | NM_002273 | | | |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-4-B | single siRNA, 0.9 nmol | 441 | 2889 | RAPGEF1 | Rap guanine nucleotide exchange factor (GEF) 1 | NM_005312 NM_198679 | CAGGAAAGATTGGTGTTGTA | SI02634989Hs_RAPGEF1_5 | |
| 900029-4-B | single siRNA, 0.9 nmol | 442 | 3082 | HGF | hepatocyte growth factor (hepapoietin A; scatter factor) | NM_000601 NM_001010931 NM_001010932 NM_001010933 NM_001010934 | CTGGAGTTCCATGATACCACA | SI03097395Hs_HGF_8 | |
| 900029-4-B | single siRNA, 0.9 nmol | 443 | 3190 | HNRPK | heterogeneous nuclear ribonucleoprotein K | NM_002140 NM_031262 NM_031263 | TTCCATTGTATGCAAATTGAA | SI02650844Hs_HNRPK_5 | |
| 900029-4-B | single siRNA, 0.9 nmol | 444 | 3320 | HSP90AA1 | heat shock protein 90 kDa alpha (cytosolic), class A member 1 | NM_001017963 NM_005348 | AACCCTGACCATTCCATTATT | SI03028606Hs_HSP90AA1_1 | |
| 900029-4-B | single siRNA, 0.9 nmol | 445 | 3491 | CYR61 | cysteine-rich, angiogenic inducer, 61 | NM_001554 | AACCCTTTACAAGGCCAGAAA | SI03028855Hs_CYR61_7 | |
| 900029-4-B | single siRNA, 0.9 nmol | 446 | 3572 | IL6ST | interleukin 6 signal transducer (gp 130, oncostatin M receptor) | NM_002184 NM_175767 | CACATTGTACATGGTACGAAT | SI00033740Hs_IL6ST_4 | |
| 900029-4-B | single siRNA, 0.9 nmol | 447 | 3667 | IRS1 | insulin receptor substrate 1 | NM_005544 | CCGTATCGTTTCGCATGGAA | SI00078645Hs_IRS1_3 | |
| 900029-4-B | single siRNA, 0.9 nmol | 448 | 3725 | JUN | jun oncogene | NM_002228 | CCCGAGCTGGAGCGCCTGATA | SI03077599Hs_JUN_7 | |
| 900029-4-B | single siRNA, 0.9 nmol | 449 | 3845 | KRAS | v-Ki-ras2 Kirsten rat sarcoma viral oncogene homolog | NM_004985 NM_033360 | GTGGACGAATATGATCCAACA | SI03106824Hs_KRAS_2 | |
| 900029-4-B | single siRNA, 0.9 nmol | 450 | 3872 | KRT17 | keratin 17 | NM_000422 | CACCGTGACAATGCCAACAT | SI00464513Hs_KRT17_4 | |
| 900029-4-B | single siRNA, 0.9 nmol | 451 | 2932 | GSK3B | glycogen synthase kinase 3 beta | NM_002093 | AACACTGTCACGTTTGGAAA | SI00060472Hs_GSK3B_7 | |
| 900029-4-B | single siRNA, 0.9 nmol | 452 | 3084 | NRG1 | neuregulin 1 | NM_004495 NM_013956 NM_013957 NM_013958 NM_013960 NM_013961 NM_013964 | TCGGCTGCCAGGTTCCAAACTA | SI03116974Hs_NRG1_10 | |
| 900029-4-B | single siRNA, 0.9 nmol | 453 | 3265 | HRAS | v-Ha-ras Harvey rat sarcoma viral oncogene homolog | NM_005343 NM_176795 | CACAGATGGGATCACAGTAAA | SI02662030Hs_HRAS_7 | |
| 900029-4-B | single siRNA, 0.9 nmol | 454 | 3329 | HSPD1 | heat shock 60 kDa protein 1 (chaperonin) | NM_002156 NM_199440 | CACCACCAGATGAGAAGTTAA | SI02653007Hs_HSPD1_7 | |
| 900029-4-B | single siRNA, 0.9 nmol | 455 | 3551 | IKBKB | inhibitor of kappa light polypeptide gene enhancer in B-cells, kinase beta | NM_001556 | AAACCGAGTTGGGATCACAT | SI00300545Hs_IKKB2_1 | |
| 900029-4-B | single siRNA, 0.9 nmol | 456 | 3609 | ILF3 | interleukin enhancer binding factor 3, 90 kDa | NM_004516 NM_012218 NM_153464 | CACAACCGCCCTCCTGGACAA | SI03055297Hs_ILF3_11 | |
| 900029-4-B | single siRNA, 0.9 nmol | 457 | 3678 | ITGA5 | integrin, alpha 5 (fibronectin receptor, alpha polypeptide) | NM_002205 | CAGGGTCTACGTCTACCTGCA | SI03071572Hs_ITGA5_7 | |
| 900029-4-B | single siRNA, 0.9 nmol | 458 | 3726 | JUNB | jun B proto-oncogene | NM_002229 | AAACACGCACTTAGTCTCTAA | SI00034713Hs_JUNB_4 | |
| 900029-4-B | single siRNA, 0.9 nmol | 459 | 3852 | KRT5 | keratin 5 (epidermolysis bullosa simplex, Dowling-Meara/Kobner/Weber-Cockayne types) | NM_000424 | AAGCCGAGTCCTGGTATCAGA | SI03130414Hs_KRT5_5 | |
| 900029-4-B | single siRNA, 0.9 nmol | 460 | 3875 | KRT18 | keratin 18 | NM_000224 NM_199187 | TCGCTCCACCTTCTCCACCAA | SI03234091Hs_KRT18_10 | |
| 900029-4-B | single siRNA, 0.9 nmol | 461 | 2934 | GSN | gelsolin (amyloidosis, Finnish type) | NM_000177 NM_198252 | AACGATGCCTTTGTTCTGAAA | SI02664039Hs_GSN_5 | |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-4-B | single siRNA, 0.9 nmol | 462 | 3092 | HIP1 | huntingtin interacting protein 1 | NM_005338 | CACAACAATGGGTATCCTTAA | SI00075852 | Hs_HIP1_3 |
| 900029-4-B | single siRNA, 0.9 nmol | 463 | 3280 | HES1 | hairy and enhancer of split 1, (Drosophila) | NM_005524 | AAAGACGAAGAGCAAGAATAA | SI00078344 | Hs_HES1_4 |
| 900029-4-B | single siRNA, 0.9 nmol | 464 | 3371 | TNC | tenascin C (hexabrachion) | NM_002160 | CACGATGGCTTTGCAGGCGAT | SI03105987 | Hs_TNC_5 |
| 900029-4-B | single siRNA, 0.9 nmol | 465 | 3558 | IL2 | interleukin 2 | NM_000586 | CTGGAGGAAGTGCTAAATTTA | SI00012271 | Hs_IL2_3 |
| 900029-4-B | single siRNA, 0.9 nmol | 466 | 3635 | INPP5D | inositol polyphosphate-5-phosphatase, 145 kDa | NM_001017915 NM_005541 | CCCGGACTGTTGACAGCCAA | SI00078589 | Hs_INPP5D_3 |
| 900029-4-B | single siRNA, 0.9 nmol | 467 | 3690 | ITGB3 | integrin, beta 3 (platelet glycoprotein IIIa, antigen CD61) | NM_000212 | CAAGCTGAACCTAATAGCCAT | SI00004606 | Hs_ITGB3_4 |
| 900029-4-B | single siRNA, 0.9 nmol | 468 | 3727 | JUND | jun D proto-oncogene | NM_005354 | CCCGCCGTTGTCGCCCATCGA | SI03077956 | Hs_JUND_5 |
| 900029-4-B | single siRNA, 0.9 nmol | 469 | 3853 | KRT6A | keratin 6A | NM_005554 NM_058242 | CTGGAGCTTCACTGTTACTAA | SI03210725 | Hs_KRT6C_6 |
| 900029-4-B | single siRNA, 0.9 nmol | 470 | 3897 | L1CAM | L1 cell adhesion molecule | NM_000425 NM_024003 | CCGCGGATACAATGTGACGTA | SI00009289 | Hs_L1CAM_3 |
| 900029-4-B | single siRNA, 0.9 nmol | 471 | 3055 | HCK | hemopoietic cell kinase | NM_002110 | CGGCAGGAGATACCGTGAAA | SI02665320 | Hs_HCK_7 |
| 900029-4-B | single siRNA, 0.9 nmol | 472 | 3105 | HLA-A | major histocompatibility complex, class I, A | NM_002116 | TAGAACCTTAGTATAAATTTA | SI00438641 | Hs_HLA-A_4 |
| 900029-4-B | single siRNA, 0.9 nmol | 473 | 3309 | HSPA5 | heat shock 70 kDa protein 5 (glucose-regulated protein, 78 kDa) | NM_005347 | TAGGGTGTGTGTTCACCTTCA | SI02780554 | Hs_HSPA5_6 |
| 900029-4-B | single siRNA, 0.9 nmol | 474 | 3397 | ID1 | inhibitor of DNA binding 1, dominant negative helix-loop-helix protein | NM_002165 NM_181353 | CAGTTGGAGCTGAACTCCGAA | SI03073525 | Hs_ID1_6 |
| 900029-4-B | single siRNA, 0.9 nmol | 475 | 3560 | IL2RB | interleukin 2 receptor, beta | NM_000878 | ACAGACGGCGGTGGAACCAAA | SI03037664 | Hs_IL2RB_5 |
| 900029-4-B | single siRNA, 0.9 nmol | 476 | 3636 | INPPL1 | inositol polyphosphate phosphatase-like 1 | NM_001567 | CAAGTTCTTCATCGAGTTCTA | SI00447818 | Hs_INPPL1_3 |
| 900029-4-B | single siRNA, 0.9 nmol | 477 | 3691 | ITGB4 | integrin, beta 4 | NM_000213 NM_001005619 NM_001005731 | GTGGATGAGTTCCGGATAAA | SI02664102 | Hs_ITGB4_5 |
| 900029-4-B | single siRNA, 0.9 nmol | 478 | 3728 | JUP | junction plakoglobin | NM_002230 NM_021991 | AACCATCGGCTTGATCAGGAA | SI00034734 | Hs_JUP_3 |
| 900029-4-B | single siRNA, 0.9 nmol | 479 | 3854 | KRT6B | keratin 6B | NM_005555 | TCAGGAGTTCTCATCTGACAA | SI00464926 | Hs_KRT6B_3 |
| 900029-4-B | single siRNA, 0.9 nmol | 480 | 3932 | LCK | lymphocyte-specific protein tyrosine kinase | NM_001042771 NM_005356 | CTACGGGACATTCACCATCAA | SI00076013 | Hs_LCK_4 |
| 900029-4-B | single siRNA, 0.9 nmol | 481 | 3937 | LCP2 | lymphocyte cytosolic protein 2 (SH2 domain containing leukocyte protein of 76 kDa) | NM_005565 | CCCGGGTGCCGATTCTCAGTAA | SI02656185 | Hs_LCP2_8 |
| 900029-5-A | single siRNA, 0.9 nmol | 482 | 4086 | SMAD1 | SMAD family member 1 | NM_001003688 NM_005900 | CTGGTGCTCTATTGTCTACTA | SI03099824 | Hs_SMAD1_9 |
| 900029-5-A | single siRNA, 0.9 nmol | 483 | 4194 | MDM4 | Mdm4, transformed 3T3 cell double minute 4, p53 binding protein (mouse) | NM_002393 | GACCACGAGACGGGAACATTA | SI03101476 | Hs_MDM4_5 |
| 900029-5-A | single siRNA, 0.9 nmol | 484 | 4296 | MAP3K11 | mitogen-activated protein kinase kinase kinase 11 | NM_002419 | CCCGACTCTGAGGAGACTCAA | SI02659552 | Hs_MAP3K11_6 |
| 900029-5-A | single siRNA, 0.9 nmol | 485 | 4690 | NCK1 | NCK adaptor protein 1 | NM_006153 | ACCGTTATGCAGAATAATCCA | SI02654918 | Hs_NCK1_5 |
| 900029-5-A | single siRNA, 0.9 nmol | 486 | 4893 | NRAS | neuroblastoma RAS viral (v-ras) oncogene homolog | NM_002524 | CTGAGATACGTCTGTGACTTA | SI02662632 | Hs_NRAS_6 |
| 900029-5-A | single siRNA, 0.9 nmol | 487 | 5017 | OVOL1 | ovo-like 1 (Drosophila) | NM_004561 XM_001129344 | CAAGGCTGCCTTCAATTAGAA | SI00065261 | Hs_OVOL1_4 |
| 900029-5-A | single siRNA, 0.9 nmol | 488 | 5063 | PAK3 | p21 (CDKN1A)-activated kinase 3 | NM_002578 | TTTCCAGTACTTTGTACAGGAA | SI00287434 | Hs_PAK3_5 |
| 900029-5-A | single siRNA, 0.9 nmol | 489 | 5290 | PIK3CA | phosphoinositide-3-kinase, catalytic, alpha polypeptide | NM_006218 | CTCCGTGAGGCTACATTAATA | SI02665369 | Hs_PIK3CA_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-A | single siRNA, 0.9 nmol | 490 | 5300 | PIN1 | protein (peptidylprolyl cis/trans isomerase) NIMA-interacting 1 | NM_006221 | CAGTATTTATTGTTCCCACAA | SI02662667 | Hs_PIN1_6 |
| 900029-5-A | single siRNA, 0.9 nmol | 491 | 3958 | LGALS3 | lectin, galactoside-binding, soluble, 3 | NM_002306 NM_194327 NR_003225 | CAATACAAAGCTGGATAATAA | SI02731183 | Hs_LGALS3_6 |
| 900029-5-A | single siRNA, 0.9 nmol | 492 | 4087 | SMAD2 | SMAD family member 2 | NM_001003652 NM_005901 | CAGGTAATGTATCATGATCCA | SI02757496 | Hs_SMAD2_6 |
| 900029-5-A | single siRNA, 0.9 nmol | 493 | 4214 | PAAP3K1 | mitogen-activated protein kinase kinase kinase 1 | XM_001128827 XM_042066 | CTCCGGGTGTTTCAACTAGAA | SI02659965 | Hs_MAP3K1_11 |
| 900029-5-A | single siRNA, 0.9 nmol | 494 | 4311 | MME | membrane metallo-endopeptidase | NM_000902 NM_007287 NM_007288 NM_007289 | AGGTGTGTGTGAACCTATA | SI03046302 | Hs_MME_5 |
| 900029-5-A | single siRNA, 0.9 nmol | 495 | 4739 | NEDD9 | neural precursor cell expressed, developmentally down-regulated 9 | NM_006403 NM_182966 | CCTGACCCTCATAGAGCAGAA | SI03192406 | Hs_NEDD9_6 |
| 900029-5-A | single siRNA, 0.9 nmol | 496 | 4914 | NTRK1 | neurotrophic tyrosine kinase, receptor, type 1 | NM_001007204 NM_001007792 NM_001012331 NM_002529 | CTGGGAGTGGTTAGCCGGAAT | SI03098697 | Hs_NTRK1_6 |
| 900029-5-A | single siRNA, 0.9 nmol | 497 | 5037 | PEBP1 | phosphatidylethanolamine binding protein 1 | NM_002567 | CAGGTCTACAGTGATGAGCA | SI03246376 | Hs_PEBP1_2 |
| 900029-5-A | single siRNA, 0.9 nmol | 498 | 5130 | PCYT1A | phosphate cytidylyltransferase 1, choline, alpha | NM_005017 | AAGCGCCACCTCAGAAGATAA | SI00681016 | Hs_PCYT1A_4 |
| 900029-5-A | single siRNA, 0.9 nmol | 499 | 5291 | PIK3CB | phosphoinositide-3-kinase, catalytic, beta polypeptide | NM_006219 | TCGGGAAGCTACCATTTCTTA | SI02622221 | Hs_PIK3CB_6 |
| 900029-5-A | single siRNA, 0.9 nmol | 500 | 5305 | PIP5K2A | phosphatidylinositol-4-phosphate 5-kinase, type II, alpha | NM_005028 | CTGCCCGATGGTCTTCCGTAA | SI02223830 | Hs_PIP5K2A_6 |
| 900029-5-A | single siRNA, 0.9 nmol | 501 | 4000 | LMNA | lamin A/C | NM_005572 NM_170707 NM_170708 | CCAGGAGCTTCTGGACATCAA | SI02662597 | Hs_LMNA_14 |
| 900029-5-A | single siRNA, 0.9 nmol | 502 | 4088 | SMAD3 | SMAD family member 3 | NM_005902 | ATGGTGCGAGAAGGCGGTCAA | SI03052126 | Hs_SMAD3_5 |
| 900029-5-A | single siRNA, 0.9 nmol | 503 | 4215 | MAP3K3 | mitogen-activated protein kinase kinase kinase 3 | NM_002401 NM_203351 | CCACGTGTCTGTGCACCACAA | SI00605619 | Hs_MAP3K3_6 |
| 900029-5-A | single siRNA, 0.9 nmol | 504 | 4486 | MST1R | macrophage stimulating 1 receptor (c-met-related tyrosine kinase) | NM_002447 | CAGGTCTGCGTAGATGGTGAA | SI02758539 | Hs_MST1R_7 |
| 900029-5-A | single siRNA, 0.9 nmol | 505 | 4790 | NFKB1 | nuclear factor of kappa light polypeptide gene enhancer in B-cells 1 (p105) | NM_003998 | GACGCCATCTATGACAGTAAA | SI02662618 | Hs_NFKB1_10 |
| 900029-5-A | single siRNA, 0.9 nmol | 506 | 4915 | NTRK2 | neurotrophic tyrosine kinase, receptor, type 2 | NM_001007097 NM_001018064 NM_001018065 NM_001018066 NM_006180 | GGGCTCCTTAAGGATAACTAA | SI03106173 | Hs_NTRK2_7 |
| 900029-6-A | single siRNA, 0.9 nmol | 507 | 5042 | PABPC3 | poly(A) binding protein, cytoplasmic 3 | NM_030979 | CACGGTTCCACGTATAAATA | SI03164812 | Hs_PABPC3_5 |
| 900029-5-A | single siRNA, 0.9 nmol | 508 | 5159 | PDGFRB | platelet-derived growth factor receptor, beta polypeptide | NM_002609 | CTGCCGAGCAACTTTGATCAA | SI00605745 | Hs_PDGFRB_6 |
| 900029-5-A | single siRNA, 0.9 nmol | 509 | 5293 | PIK3CD | phosphoinositide-3-kinase, catalytic, delta polypeptide | NM_005026 | CGCCGTGATCGAGAAAGCCAA | SI02223816 | Hs_PIK3CD_6 |
| 900029-5-A | single siRNA, 0.9 nmol | 510 | 5306 | PITPNA | phosphatidylinositol transfer protein, alpha | NM_006224 | CTGCACAATATGAGCATGCAA | SI03019436 | Hs_PITPNA_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-A | single siRNA, 0.9 nmol | 511 | 4035 | LRP1 | low density lipoprotein-related protein 1 (alpha-2-macroglobulin receptor) | NM_002332 | TACGACCGCATCGAGACGATA | SI03109400 | Hs_LRP1_5 |
| 900029-5-A | single siRNA, 0.9 nmol | 512 | 4093 | SMAD9 | SMAD family member 9 | NM_005905 NM_005922 | CTGGTGCTCGGTCGCCTACTA | SI03213382 | Hs_SMAD9_5 |
| 900029-5-A | single siRNA, 0.9 nmol | 513 | 4216 | MAP3K4 | mitogen-activated protein kinase kinase kinase 4 | NM_006724 | CTCAAGCATCGCATAGTTAA | SI02224012 | Hs_MAP3K4_6 |
| 900029-5-A | single siRNA, 0.9 nmol | 514 | 4582 | MUC1 | mucin 1, cell surface associated | NM_001018016 NM_001018017 NM_001044390 NM_001044391 NM_001044392 NM_001044393 NM_002456 NM_182741 | CAGCAGCCTCTCTTACACAAA | SI02780673 | Hs_MUC1_7 |
| 900029-5-A | single siRNA, 0.9 nmol | 515 | 4804 | NGFR | nerve growth factor receptor (TNFR superfamily, member 16) | NM_002507 | CCCAGCACATAGACTCCTTTA | SI03080119 | Hs_NGFR_7 |
| 900029-5-A | single siRNA, 0.9 nmol | 516 | 4916 | NTRK3 | neurotrophic tyrosine kinase, receptor, type 3 | NM_001007155 NM_001012338 NM_002530 | CTGGTTGGAGCCGAATCTGCTA | SI00605689 | Hs_NTRK3_10 |
| 900029-5-A | single siRNA, 0.9 nmol | 517 | 5048 | PAFAH1B1 | platelet-activating factor acetylhydrolase, isoform Ib, alpha subunit 45 kDa | NM_000430 | ATGCGCATGAACACTTTGTTA | SI03152576 | Hs_PAFAH1B1_5 |
| 900029-5-A | single siRNA, 0.9 nmol | 518 | 5170 | PDPK1 | 3-phosphoinositide dependent protein kinase-1 | NM_002613 NM_031268 NM_001130789 | CACGCCTAACAGGACGTATTA | SI00605787 | Hs_PDPK1_9 |
| 900029-5-A | single siRNA, 0.9 nmol | 519 | 5294 | PIK3CG | phosphoinositide-3-kinase, catalytic, gamma polypeptide | NM_002649 | CACCTTTACTCTATAACTCAA | SI00605843 | Hs_PIK3CG_6 |
| 900029-5-A | single siRNA, 0.9 nmol | 520 | 5310 | PKD1 | polycystic kidney disease 1 (autosomal dominant) | NM_000296 NM_001009944 | TCCGTCTTTGGCAAGACATTA | SI03115560 | Hs_PKD1_6 |
| 900029-5-A | single siRNA, 0.9 nmol | 521 | 4058 | LTK | leukocyte tyrosine kinase | NM_002344 NM_206961 | CCTGCAGATGCTTCTAATAAA | SI00605563 | Hs_LTK_6 |
| 900029-5-A | single siRNA, 0.9 nmol | 522 | 4145 | MATK | megakaryocyte-associated tyrosine kinase | NM_002378 NM_139354 NM_139355 | GACGGATTCTAAGGACTCTAA | SI00605605 | Hs_MATK_10 |
| 900029-5-A | single siRNA, 0.9 nmol | 523 | 4217 | MAP3K5 | mitogen-activated protein kinase kinase kinase 5 | NM_005923 | AACGAAGCGAGCCAAGGGCAA | SI00265890 | Hs_MAP3K5_7 |
| 900029-5-A | single siRNA, 0.9 nmol | 524 | 4609 | MYC | v-myc myelocytomatosis viral oncogene homolog (avian) | NM_002467 | CTCGGTGCAGCCCTATTTCTA | SI00262611 | Hs_MYC_7 |
| 900029-5-A | single siRNA, 0.9 nmol | 525 | 4853 | NOTCH2 | Notch homolog 2 (Drosophila) | NM_024408 XM_001133349 | CAGCGGTGTACCATTGACATT | SI03067526 | Hs_NOTCH2_5 |
| 900029-5-A | single siRNA, 0.9 nmol | 526 | 4921 | DDR2 | discoidin domain receptor family, member 2 | NM_001014796 NM_006182 | CACCCACAACCTATGATCCAA | SI03649499 | Hs_DDR2_6 |
| 900029-5-A | single siRNA, 0.9 nmol | 527 | 5058 | PAK1 | p21/Cdc42/Rac1-activated kinase 1 (STE20 homolog, yeast) | NM_002576 | TTGAAGAGAACTGCAACTGAA | SI00605703 | Hs_PAK1_9 |
| 900029-5-A | single siRNA, 0.9 nmol | 528 | 5174 | PDZK1 | PDZ domain containing 1 | NM_002614 | AAGGCCTATGATTATTCCAA | SI00681800 | Hs_PDZK1_4 |
| 900029-5-A | single siRNA, 0.9 nmol | 529 | 5295 | PIK3R1 | phosphoinositide-3-kinase, regulatory subunit 1 (p85 alpha) | NM_181504 NM_181523 NM_181524 | TAGCTGGTTATGAACTAGTAA | SI02225412 | Hs_PIK3R1_6 |
| 900029-5-A | single siRNA, 0.9 nmol | 530 | 5335 | PLCG1 | phospholipase C, gamma 1 | NM_002660 | CAAGTCTTCTTGACAGACAA | SI00041195 | Hs_PLCG1_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-A | single siRNA, 0.9 nmol | 531 | 4067 | LYN | v-yes-1 Yamaguchi sarcoma viral related oncogene homolog | NM_182811 NM_002350 | CGGGAAATATGGGATGTATAA | SI00605577 | Hs_LYN_13 |
| 903329-5-A | single siRNA, 0.9 nmol | 532 | 4168 | MCF2 | MCF.2 cell line derived transforming sequence | NM_005369 | GAGGTGCAATGAGCTACGTTA | SI03104227 | Hs_MCF2_6 |
| 900029-5-A | single siRNA, 0.9 nmol | 533 | 4233 | MET | met proto-oncogene (hepatocyte growth factor receptor) | NM_000245 | CAACACCCATCCAGAATGTCA | SI02654897 | Hs_MET_10 |
| 900029-5-A | single siRNA, 0.9 nmol | 534 | 4627 | MYH9 | myosin, heavy chain 9, non-muscle | NM_002473 NM_000272 | CAGGAGCAGCTCCAGGCAGAA | SI02654911 | Hs_MYH9_6 |
| 900029-5-A | single siRNA, 0.9 nmol | 535 | 4867 | NPHP1 | nephronophthisis 1 (juvenile) | NM_207181 | CCAGTTAAAGCAGGCAATAGA | SI03075772 | Hs_NPHP1_7 |
| 900029-5-A | single siRNA, 0.9 nmol | 536 | 4929 | NR4A2 | nuclear receptor subfamily 4, group A, member 2 | NM_006186 NM_173171 NM_173172 NM_173173 | TACGACACTGTCCACCTTTAA | SI00085330 | Hs_NR4A2_4 |
| 900029-5-A | single siRNA, 0.9 nmol | 537 | 5062 | PAK2 | p21 (CDKN1A)-activated kinase 2 | NM_002577 XM_001126110 | CCGGATCATACGAAATCAATT | SI00605717 | Hs_PAK2_9 |
| 900029-5-A | single siRNA, 0.9 nmol | 538 | 5287 | PIK3C2B | phosphoinositide-3-kinase, class 2, beta polypeptide | NM_002646 | CACTGTAGACTTGCTTATCTA | SI02660070 | Hs_PIK3C2B_6 |
| 900029-5-A | single siRNA, 0.9 nmol | 539 | 5296 | PIK3R2 | phosphoinositide-3-kinase, regulatory subunit 2 (p85 beta) | NM_005027 | TTGGTACGTGGGCAAGATCAA | SI00287539 | Hs_PIK3R2_6 |
| 900029-5-A | single siRNA, 0.9 nmol | 540 | 5336 | PLCG2 | phospholipase C, gamma 2 (phosphatidyl-inositol-specific) | NM_002661 | GACGACGGTTGTGAATGATAA | SI02626281 | Hs_PLCG2_5 |
| 900029-5-A | single siRNA, 0.9 nmol | 541 | 3937 | LCP2 | lymphocyte cytosolic protein 2 (SH2 domain containing leukocyte protein of 76 kDa) | NM_005565 | AAGCTGCTCTTAGAAAGATAA | SI02656178 | Hs_LCP2_7 |
| 900029-5-B | single siRNA, 0.9 nmol | 542 | 4066 | SMAD1 | SMAD family member 1 | NM_001003688 NM_005900 | CTCCCAATAGCAGTTACCCAA | SI03089716 | Hs_SMAD1_8 |
| 900029-5-B | single siRNA, 0.9 nmol | 543 | 4194 | MDM4 | Mdm4, transformed 3T3 cell double minute 4, p53 binding protein (mouse) | NM_032393 | GACCTAAAGATGCGTATATAA | SI00037163 | Hs_MDM4_4 |
| 900029-5-B | single siRNA, 0.9 nmol | 544 | 4296 | MAP3K11 | mitogen-activated protein kinase kinase kinase 11 | NM_002419 | CCGGAGAGAAACGTCTTCGA | SI00605626 | Hs_MAP3K11_5 |
| 900029-5-B | single siRNA, 0.9 nmol | 545 | 4690 | NCK1 | NCK adaptor protein 1 | NM_006153 | AGCAGTGCTCAATAACCTAAA | SI03042767 | Hs_NCK1_6 |
| 900029-5-B | single siRNA, 0.9 nmol | 546 | 4893 | NRAS | neuroblastoma RAS viral (v-ras) oncogene homolog | NM_002524 | AACCTGTTTGTTGGACATACT | SI03030993 | Hs_NRAS_5 |
| 900029-5-B | single siRNA, 0.9 nmol | 547 | 5017 | OVOL1 | ovo-like 1 (Drosophila) | NM_004561 | CCCGGCGTTCCTGGTGAAGAA | SI00065254 | Hs_OVOL1_3 |
| 900029-5-B | single siRNA, 0.9 nmol | 548 | 5063 | PAK3 | p21 (CDKN1A)-activated kinase 3 | NM_002578 | CAAGAAGAATTAATTATTAA | SI02628983 | Hs_PAK3_6 |
| 900029-5-B | single siRNA, 0.9 nmol | 549 | 5290 | PIK3CA | phosphoinositide-3-kinase, catalytic, alpha polypeptide | NM_006218 | CTGAGTCAGTATAAGTATATA | SI02622207 | Hs_PIK3CA_5 |
| 900029-5-B | single siRNA, 0.9 nmol | 550 | 5300 | PIN1 | protein (peptidylprolyl cis/trans isomerase) NIMA-interacting 1 | NM_006221 | GACCGCCAGATTCTCCCTTAA | SI02662128 | Hs_PIN1_5 |
| 900029-5-B | single siRNA, 0.9 nmol | 551 | 3958 | LGALS3 | lectin, galactoside-binding, soluble, 3 | NM_002306 NM_194327 NR_003225 | ATCGTTATCTGGGTCTGGAA | SI02707292 | Hs_LGALS3_5 |
| 900029-5-B | single siRNA, 0.9 nmol | 552 | 4067 | SMAD2 | SMAD family member 2 | NM_001003652 NM_005901 | AAGCCGTTCTATCAGCTAACTA | SI03033275 | Hs_SMAD2_8 |
| 900029-5-B | single siRNA, 0.9 nmol | 553 | 4214 | MAP3K1 | mitogen-activated protein kinase kinase kinase 1 | XM_001128827 XM_042066 | CACGCATGTCAAATTCCATA | SI02659958 | Hs_MAP3K1_10 |
| 900029-5-B | single siRNA, 0.9 nmol | 554 | 4311 | MME | membrane metallo-endopeptidase | NM_000902 NM_007287 | CACCGTTACAAGTATATACTTAT | SI00018130 | Hs_MME_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-B | single siRNA, 0.9 nmol | 555 | 4739 | NEDD9 | neural precursor cell expressed, developmentally down-regulated 9 | NM_007288 NM_007289 | CAGAAGCTCTATCAAGTGCCA | SI03166898 | Hs_NEDD9_5 |
| 900029-5-B | single siRNA, 0.9 nmol | 556 | 4914 | NTRK1 | neurotrophic tyrosine kinase, receptor, type 1 | NM_006403 NM_182966 NM_001007792 NM_001012331 NM_002529 | CACATCATCGAGAACCCACAA | SI02628836 | Hs_NTRK1_5 |
| 900029-5-B | single siRNA, 0.9 nmol | 557 | 5037 | PEBP1 | phosphatidylethanolamine binding protein 1 | NM_002567 | CCGCTATGTCTGGCTGGTTTA | SI03189739 | Hs_PEBP1_1 |
| 900029-5-B | single siRNA, 0.9 nmol | 558 | 5130 | PCYT1A | phosphate cytidylyltransferase 1, choline, alpha | NM_005017 | CAGCTTTATCAACGAGAAGAA | SI00681009 | Hs_PCYT1A_3 |
| 900029-5-B | single siRNA, 0.9 nmol | 559 | 5291 | PIK3CB | phosphoinositide-3-kinase, catalytic, beta polypeptide | NM_006219 | CCCTTCGATAAGATTATTGAA | SI02622214 | Hs_PIK3C13_5 |
| 030029-5-B | single siRNA, 0.9 nmol | 560 | 5305 | PIP5K2A | phosphatidylinositol-4-phosphate 5-kinase, type II, alpha | NM_005028 | ATGGAATTAAGTGCCATGAAA | SI02223823 | Hs_PIP5K2A_5 |
| 900029-5-B | single siRNA, 0.9 nmol | 561 | 4000 | LMNA | lamin A/C | NM_005572 NM_170707 NM_170708 | AACTGGACTTCCAGAAGAACA | SI02654862 | Hs_LMNA_13 |
| 900029-5-B | single siRNA, 0.9 nmol | 562 | 4088 | SMAD3 | SMAD family member 3 | NM_005902 | AAGGAGCACCTTGACAGACTT | SI00082502 | Hs_SMAD3_4 |
| 900029-5-B | single siRNA, 0.9 nmol | 563 | 4215 | MAP3K3 | mitogen-activated protein kinase kinase kinase 3 | NM_002401 NM_203351 | CAGGAATACTCAGATCGGGAA | SI00605612 | Hs_MAP3K3_5 |
| 900029-5-B | single siRNA, 0.9 nmol | 564 | 4486 | MST1R | macrophage stimulating 1 receptor (c-met-related tyrosine kinase) | NM_002447 | TCCCGGTGACACAGACACAAA | SI02758532 | Hs_MST1R_6 |
| 900029-5-B | single siRNA, 0.9 nmol | 565 | 4790 | NFKB1 | nuclear factor of kappa light polypeptide gene enhancer in B-cells 1 (p105) | NM_003998 | CTGGGTATACTTCATGTGACA | SI00262093 | Hs_NFKB1_9 |
| 900029-5-B | single siRNA, 0.9 nmol | 566 | 4915 | NTRK2 | neurotrophic tyrosine kinase, receptor, type 2 | NM_001007097 NM_001018064 NM_001018065 NM_001018066 NM_006180 | CAGCGCTTCAGTGGTTCTATA | SI03067246 | Hs_NTRK2_6 |
| 900029-5-B | single siRNA, 0.9 nmol | 567 | 5042 | PABPC3 | poly(A) binding protein, cytoplasmic 3 | NM_030979 | CTCCAACTACGCGTATGTGAA | SI00676697 | Hs_PABPC3_3 |
| 900029-5-B | single siRNA, 0.9 nmol | 568 | 5159 | PDGFRB | platelet-derived growth factor receptor, beta polypeptide | NM_002609 | CCGAGCAACTTTGATCAACGA | SI00605738 | Hs_PDGFRB_5 |
| 900029-5-B | single siRNA, 0.9 nmol | 569 | 5293 | PIK3CD | phosphoinositide-3-kinase, catalytic, delta polypeptide | NM_005026 | CCGGTCACGCATGAAGGCAAA | SI02223809 | Hs_PIK3CD_5 |
| 900029-5-B | single siRNA, 0.9 nmol | 570 | 5306 | PITPNA | phosphatidylinositol transfer protein, alpha | NM_006224 | AAGGATGGAAGAAGAGACGAA | SI00685188 | Hs_PITPNA_4 |
| 900029-5-B | single siRNA, 0.9 nmol | 571 | 4035 | LRP1 | low density lipoprotein-related protein 1 (alpha-2-macroglobulin receptor) | NM_002332 | CTGGCTATTGACTTCCCTGAA | SI00036204 | Hs_LRP1_3 |
| 900029-5-B | single siRNA, 0.9 nmol | 572 | 4093 | SMAD9 | SMAD family member 9 | NM_005905 | CAGATGAAACAAAGCAGTGAA | SI00726572 | Hs_SMAD9_4 |
| 900029-5-B | single siRNA, 0.9 nmol | 573 | 4216 | MAP3K4 | mitogen-activated protein kinase kinase kinase 4 | NM_005922 NM_006724 | CACCAATCCCTGAAAGATTAA | SI02224005 | Hs_MAP3K4_5 |
| 900029-5-B | single siRNA, 0.9 nmol | 574 | 4582 | MUC1 | mucin 1, cell surface associated | NM_001018016 NM_001018017 NM_001018021 NM_001044390 NM_001044393 | CTGGCCATTGTCTATCTTCATT | SI03097927 | Hs_MUC1_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-B | single siRNA, 0.9 nmol | 575 | 4804 | NGFR | nerve growth factor receptor (TNFR superfamily, member 16) | NM_002456 NM_182741 NM_002507 | CACAGCGTGAGTGCTGCAAA | SI03056151 | Hs_NGFR_6 |
| 900029-5-B | single siRNA, 0.9 nmol | 576 | 4916 | NTRK3 | neurotrophic tyrosine kinase, receptor, type 3 | NM_001007155 NM_001007156 NM_001012338 NM_002530 | CACGGATAACTTATCTTGTT | SI03605682 | Hs_NTRK3_9 |
| 900029-5-B | single siRNA, 0.9 nmol | 577 | 5048 | PAFAH1B1 | platelet-activating factor acetylhydrolase, isoform Ib, alpha subunit 45 kDa | NM_000430 | CAGAATTTCTGAACCATCTA | SI00677012 | Hs_PAFAH1B1_4 |
| 900029-5-B | single siRNA, 0.9 nmol | 578 | 5170 | PDPK1 | 3-phosphoinositide dependent protein kinase-1 | NM_002613 NM_031268 XM_001130789 | AAGCGGTTAGGCTGTGAGGAA | SI00605780 | Hs_PDPK1_8 |
| 900029-5-B | single siRNA, 0.9 nmol | 579 | 5294 | PIK3CG | phosphoinositide-3-kinase, catalytic, gamma polypeptide | NM_002649 | ATCGAAGTTTGCAGAGACAAA | SI00605836 | Hs_PIK3CG_5 |
| 900029-5-B | single siRNA, 0.9 nmol | 580 | 5310 | PKD1 | polycystic kidney disease 1 (autosomal dominant) | NM_000296 NM_001009944 | TCCGGAGGTCACCCACGCTTA | SI03115287 | Hs_PKD1_5 |
| 900029-5-B | single siRNA, 0.9 nmol | 581 | 4058 | LTK | leukocyte tyrosine kinase | NM_002344 NM_206961 | ACAGATCTTTGGAGTGCCTAA | SI00605556 | Hs_LTK_5 |
| 900029-5-B | single siRNA, 0.9 nmol | 582 | 4145 | MATK | megakaryocyte-associated tyrosine kinase | NM_002378 NM_139354 NM_139355 | ACGGATTCTAAGGACTCTAAA | SI00605598 | Hs_MATK_9 |
| 900029-5-B | single siRNA, 0.9 nmol | 583 | 4217 | MAP3K5 | mitogen-activated protein kinase kinase kinase 5 | NM_005923 | CCCGGAATCTATACTCAATGA | SI02224026 | Hs_MAP3K5_6 |
| 900029-5-B | single siRNA, 0.9 nmol | 584 | 4609 | MYC | v-myc myelocytomatosis viral oncogene homolog (avian) | NM_002467 | GATCCCGAGTTGGAAAACAA | SI00300902 | Hs_MYC_5 |
| 900029-5-B | single siRNA, 0.9 nmol | 585 | 4853 | NOTCH2 | Notch homolog 2 (Drosophila) | NM_024408 XM_001133349 | TTAGATGATAATGGACAACTA | SI00136206 | Hs_NOTCH2_3 |
| 900029-5-B | single siRNA, 0.9 nmol | 586 | 4921 | DDR2 | discoidin domain receptor family, member 2 | NM_001014796 NM_006182 | AAAGAAGCGTTTCACACACAA | SI03649492 | Hs_DDR2_5 |
| 900029-5-B | single siRNA, 0.9 nmol | 587 | 5058 | PAK1 | p21/Cdc42/Rac1-activated kinase 1 (STE20 homolog, yeast) | NM_002576 | TCCACTGATTGCTGCAGCTAA | SI00605696 | Hs_PAK1_8 |
| 900029-5-B | single siRNA, 0.9 nmol | 588 | 5174 | PDZK1 | PDZ domain containing 1 | NM_002614 XM_001126677 XM_001126710 XM_001126720 | ATGACTGATATTACACCTCAA | SI00681793 | Hs_PDZK1_3 |
| 900029-5-B | single siRNA, 0.9 nmol | 599 | 5295 | PIK3R1 | phosphoinositide-3-kinase, regulatory subunit 1 (p85 alpha) | NM_181504 NM_181523 NM_181524 | CAGCATTAAACCAGACGACCTTAT | SI02225405 | Hs_PIK3R1_5 |
| 900029-5-B | single siRNA, 0.9 nmol | 590 | 5335 | PLCG1 | phospholipase C, gamma 1 | NM_002660 NM_182811 | CACGCTCCTCTTTCTGCCGGAA | SI00041188 | Hs_PLCG1_3 |
| 900029-5-B | single siRNA, 0.9 nmol | 591 | 4067 | LYN | v-yes-1 Yamaguchi sarcoma viral related oncogene homolog | NM_002350 | CCCGGACGACTTGTCTTTCAA | SI00605570 | Hs_LYN_12 |
| 900029-5-B | single siRNA, 0.9 nmol | 592 | 4168 | MCF2 | MCF.2 cell line derived transforming sequence | NM_005369 | CAGCGTTTGGATAGGGCACAA | SI03067862 | Hs_MCF2_5 |
| 900029-5-B | single siRNA, 0.9 nmol | 593 | 4233 | MET | met proto-oncogene (hepatocyte growth factor receptor) | NM_000245 | CCGCCCGTGATGATGAATATCGAA | SI00604821 | Hs_MET_9 |
| 900029-5-B | single siRNA, 0.9 nmol | 594 | 4627 | MYH9 | myosin, heavy chain 9, non-muscle | NM_002473 | AACCGGGACGAAGCCATCAAA | SI00033860 | Hs_MYH9_3 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-5-B | single siRNA, 0.9 nmol | 595 | 4867 | NPHP1 | nephronophthisis 1 (juvenile) | NM_000272 NM_207181 | CAGGGCCTTGCTGTGACAATA | SI03071397 | Hs NPHP1 6 |
| 900029-5-B | single siRNA, 0.9 nmol | 596 | 4929 | NR4A2 | nuclear receptor subfamily 4, group A, member 2 | NM_006186 NM_173171 NM_173172 NM_173173 | CTGGATTAGAACATGGACTA | SI00065323 | Hs NR4A2 3 |
| 900029-5-B | single siRNA, 0.9 nmol | 597 | 5062 | PAK2 | p21 (CDKN1A)-activated kinase 2 | NM_002577 XM_001126110 | CCGCGACCGGATCATACGAAA | SI00605710 | Hs PAK2 8 |
| 900029-5-B | single siRNA, 0.9 nmol | 598 | 5287 | PIK3C2B | phosphoinositide-3-kinase, class 2, beta polypeptide | NM_002646 | GAGGGAGAGCTAAACGGTTA | SI02660063 | Hs PIK3C2B 5 |
| 900029-5-B | single siRNA, 0.9 nmol | 599 | 5296 | PIK3R2 | phosphoinositide-3-kinase, regulatory subunit 2 (p85 beta) | NM_005027 | CCGCGAGTGACCAGCTTTA | SI00287532 | Hs PIK3R2 5 |
| 900029-5-B | single siRNA, 0.9 nmol | 600 | 5336 | PLCG2 | phospholipase C, gamma 2 (phosphatidyl-inositol-specific) | NM_002661 | GGGCGGGACCCTGAAATACTA | SI03106138 | Hs PLCG2 7 |
| 900029-5-B | single siRNA, 0.9 nmol | 601 | 5337 | PLD1 | phospholipase D1, phosphatidylcholine-specific | NM_002662 | TCCGAATTGATATCTTTCAA | SI03232152 | Hs PLD1 5 |
| 900029-5-B | single siRNA, 0.9 nmol | 602 | 5455 | POU3F3 | POU domain, class 3, transcription factor 3 | NM_006236 | CACGCCCAGAGCTGGCCAGCA | SI00690284 | Hs POU3F3 4 |
| 900029-5-B | single siRNA, 0.9 nmol | 603 | 5566 | PRKACA | protein kinase, cAMP-dependent, catalytic, alpha | NM_002730 NM_207518 | CAGAAGGTGGTGAAACTGAAA | SI00605864 | Hs PRKACA 6 |
| 900029-5-B | single siRNA, 0.9 nmol | 604 | 5580 | PRKCD | protein kinase C, delta | NM_006254 NM_212539 | CAGCAGCAAGTGCAAACATCAA | SI02660539 | Hs PRKCD 11 |
| 900029-6-A | single siRNA, 0.9 nmol | 605 | 5588 | PRKCQ | protein kinase C, theta | NM_002657 | CACAAGAAGTGTATTGATAAA | SI03571148 | Hs PRKCQ 12 |
| 900029-6-A | single siRNA, 0.9 nmol | 606 | 5601 | MAPK9 | mitogen-activated protein kinase 9 | NM_002752 NM_139068 NM_139069 NM_139070 | ATCGTGAACTTGTCCTCTTAA | SI02222920 | Hs MAPK9 7 |
| 900029-6-A | single siRNA, 0.9 nmol | 607 | 5613 | PRKX | protein kinase, X-linked | NM_005044 | TTGGAATACTCTAAGAGAATA | SI02223858 | Hs PRKX 6 |
| 900029-6-A | single siRNA, 0.9 nmol | 608 | 5770 | PTPN1 | protein tyrosine phosphatase, non-receptor type 1 | NM_002827 | ACGGACGTTGGTTCTGCACTA | SI00043827 | Hs PTPN1 4 |
| 900029-6-A | single siRNA, 0.9 nmol | 609 | 5794 | PTPRH | protein tyrosine phosphatase, receptor type, H | NM_002842 | CACGACCATCTGGGACGGAAT | SI03059588 | Hs PTPRH 6 |
| 900029-8-A | single siRNA, 0.9 nmol | 610 | 5881 | RAC3 | ras-related C3 botulinum toxin substrate 3 (rho family, small GTP binding protein Rac3) | NM_005052 | GACATGCTTGCTGATCAGCTA | SI02634310 | Hs RAC3 5 |
| 900029-6-A | single siRNA, 0.9 nmol | 611 | 5338 | PLD2 | phospholipase D2 | NM_002663 | CAGCAAGTGCTCATCCGCAGA | SI03065335 | Hs PLD2 6 |
| 900029-6-A | single siRNA, 0.9 nmol | 612 | 5458 | POU3F4 | POU domain, class 3, transcription factor 4 | NM_000307 | CCCGACCAGCATTGACAAGAT | SI03077410 | Hs POU3F4 7 |
| 900029-6-A | single siRNA, 0.9 nmol | 613 | 5567 | PRKAC8 | protein kinase, cAMP-dependent, catalytic, beta | NM_002731 NM_182948 | CTGACCAATCAAGTACACTA | SI02225468 | Hs PRKACB 10 |
| 900029-6-A | single siRNA, 0.9 nmol | 614 | 5581 | PRKCE | protein kinase C, epsilon | NM_005400 | CACGGAAACACCCGTACCTTA | SI02622088 | Hs PRKCE 6 |
| 900029-6-A | single siRNA, 0.9 nmol | 615 | 5590 | PRKCZ | protein kinase C, zeta | NM_001033581 NM_001033582 NM_002744 | GACCAAATTTACGCCATGAAA | SI00605976 | Hs PRKCZ 6 |
| 900029-6-A | single siRNA, 0.9 nmol | 616 | 5602 | MAPK10 | mitogen-activated protein kinase 10 | NM_002753 NM_138980 NM_138981 NM_138982 | TCCGAGCACAATAAACTCAAA | SI02222934 | Hs MAPK10 6 |
| 900029-6-A | single siRNA, 0.9 nmol | 617 | 5625 | PRODH | proline dehydrogenase (oxidase) 1 | NM_016335 | CCGCACCTACTTCTACGCCAA | SI03080518 | Hs PRODH 5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-6-A | single siRNA, 0.9 nmol | 618 | 5771 | PTPN2 | protein tyrosine phosphatase, non-receptor type 2 | NM_002828 NM_080422 NM_080423 | CACAAAGAGTTACATCTTAA | SI02759239 | Hs_PTPN2_10 |
| 900029-6-A | single siRNA, 0.9 nmol | 619 | 5795 | PTPRJ | protein tyrosine phosphatase, receptor type, J | NM_002843 | TCCGAGTATGTCTACCATTA | SI02658817 | Hs_PTPRJ_6 |
| 900029-6-A | single siRNA, 0.9 nmol | 620 | 5894 | RAF1 | v-raf-1 murine leukemia viral oncogene homolog 1 | NM_002880 | TGGGAAATAGAAGCCAGTGAA | SI02223039 | Hs_RAF1_7 |
| 900029-6-A | single siRNA, 0.9 nmol | 621 | 5339 | PLEC1 | plectin 1, intermediate filament binding protein 500 kDa | NM_000445 NM_201378 NM_201379 NM_201380 NM_201381 NM_201382 NM_201383 NM_201384 | CCAGACTAATATATTAATAATA | SI02662142 | Hs_PLEC1_9 |
| 900029-6-A | single siRNA, 0.9 nmol | 622 | 5478 | PPIA | peptidylprolyl isomerase A (cyclophilin A) | NM_021130 NM_203430 NM_203431 | TTCAAGATGACTAATGTCAAA | SI00690921 | Hs_PPIA_3 |
| 900029-6-A | single siRNA, 0.9 nmol | 623 | 5568 | PRKACG | protein kinase, cAMP-dependent, catalytic, gamma | NM_002732 | CTGGATGCCATCTATGAGAA | SI00605878 | Hs_PRKACG_6 |
| 900029-6-A | single siRNA, 0.9 nmol | 624 | 5582 | PRKCG | protein kinase C, gamma | NM_002739 | CTACGCCATCAAGATCTTGAA | SI03087763 | Hs_PRKCG_6 |
| 900029-8-A | single siRNA, 0.9 nmol | 625 | 5591 | PRKDC | protein kinase, DNA-activated, catalytic polypeptide | NM_001081640 NM_006904 | GACCCTGTTGACAGTACTTTA | SI02663633 | Hs_PRKDC_8 |
| 900029-6-A | single siRNA, 0.9 nmol | 626 | 5604 | MAP2K1 | mitogen-activated protein kinase kinase 1 | NM_002755 | CTGGATCAAGTCCTGAAGAAA | SI02222962 | Hs_MAP2K1_8 |
| 900029-6-A | single siRNA, 0.9 nmol | 627 | 5728 | PTEN | phosphatase and tensin homolog (mutated in multiple advanced cancers 1) | NM_000314 | AAGGCGTATACAGGAACAATA | SI00301504 | Hs_PTEN_6 |
| 900029-6-A | single siRNA, 0.9 nmol | 628 | 5777 | PTPN6 | protein tyrosine phosphatase, non-receptor type 6 | NM_002831 NM_080548 NM_080549 | TAGGCCCTGATGAGAACGCTA | SI02658733 | Hs_PTPN6_6 |
| 900029-6-A | single siRNA, 0.9 nmol | 629 | 5829 | PXN | paxillin | NM_002859 | TCCGACTTTGATAGATTTCTA | SI02757601 | Hs_PXN_7 |
| 900029-6-A | single siRNA, 0.9 nmol | 630 | 5898 | RALA | v-ral simian leukemia viral oncogene homolog A (ras related) | NM_005402 | CGCGGTGCAGATTCTTCTTAA | SI02662835 | Hs_RALA_7 |
| 900029-6-A | single siRNA, 0.9 nmol | 631 | 5359 | PLSCR1 | phospholipid scramblase 1 | NM_21105 | CCAGTGTATAATCAGCCAGTA | SI03075751 | Hs_PLSCR1_6 |
| 900029-6-A | single siRNA, 0.9 nmol | 632 | 5500 | PPP1CB | protein phosphatase 1, catalytic subunit, beta isoform | NM_002709 NM_206876 NM_206877 | CACTATTGGATGTGATTCTAA | SI02759204 | Hs_PPP1CB_6 |
| 900029-6-A | single siRNA, 0.9 nmol | 633 | 5573 | PRKAR1A | protein kinase, cAMP-dependent, regulatory, type I, alpha (tissue specific extinguisher 1) | NM_002734 NM_212471 NM_212472 | CTGGACCGACCTAGATTTGAA | SI00605996 | Hs_PRKAR1A_8 |
| 900029-6-A | single siRNA, 0.9 nmol | 634 | 5584 | PRKCI | protein kinase C, iota | NM_002740 | GTGCCGGTACATTTACTTAAA | SI02660105 | Hs_PRKCI_11 |
| 900029-6-A | single siRNA, 0.9 nmol | 635 | 5594 | MAPK1 | mitogen-activated protein kinase 1 | NM_002745 | ATCATGGTAGTCACTAACATA | SI00605990 | Hs_MAPK1_13 |
| 900029-6-A | single siRNA, 0.9 nmol | 636 | 5605 | MAP2K2 | mitogen-activated protein kinase kinase 2 | NM_030662 | CCGGCCTGCCATGGCCATCTT | SI02225097 | Hs_MAP2K2_6 |
| 900029-6-A | single siRNA, 0.9 nmol | 637 | 5734 | PTGER4 | prostaglandin E receptor 4 (subtype EP4) | NM_000958 | AGCTCTATTCCAATAAACTA | SI02624699 | Hs_PTGER4_6 |
| 900029-6-A | single siRNA, 0.9 nmol | 638 | 5781 | PTPN11 | protein tyrosine phosphatase, non-receptor type 11 (Noonan syndrome 1) | NM_002834 | CCGCTCATGACTATACGCTAA | SI02225909 | Hs_PTPN11_7 |
| 900029-6-A | single siRNA, 0.9 nmol | 639 | 5868 | RAB5A | RAB5A, member RAS oncogene family | NM_004162 | AACCCAAACTGTATGTCTTGA | SI02655037 | Hs_RAB5A_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-6-A | single siRNA, 0.9 nmol | 640 | 5899 | RALB | v-ral simian leukemia viral oncogene homolog B (ras related; GTP binding protein) | NM_002881 | TGACGAGTTTGTAGAAGACTA | SI03117492 | Hs_RALB_7 |
| 900029-6-A | single siRNA, 0.9 nmol | 641 | 5453 | POU3F1 | POU domain, class 3, transcription factor 1 | NM_002699 | CCGCCCGCGCCCTTAATTTAA | SI03069228 | Hs_POU3F1_4 |
| 900029-6-A | single siRNA, 0.9 nmol | 642 | 5514 | PPP1R10 | protein phosphatase 1, regulatory (inhibitor) subunit 10 | NM_002714 | CTCAAACGTCAGAGCAACGTA | SI03308411 | Hs_PPP1R10_6 |
| 900029-6-A | single siRNA, 0.9 nmol | 643 | 5578 | PRKCA | protein kinase C, alpha | NM_002737 | TACAAGTTGCTTAACCAAGAA | SI00605934 | Hs_PRKCA_7 |
| 900029-6-A | single siRNA, 0.9 nmol | 644 | 5586 | PKN2 | protein kinase N2 | NM_006256 | CACGTCAAAGTATGATATCTA | SI02224096 | Hs_PKN2_6 |
| 900029-6-A | single siRNA, 0.9 nmol | 645 | 5595 | MAPK3 | mitogen-activated protein kinase 3 | NM_001040056 NM_002746 | CTCCCTGACCCGTCTAATATA | SI00606004 | Hs_MAPK3_7 |
| 900029-6-A | single siRNA, 0.9 nmol | 646 | 5606 | MAP2K3 | mitogen-activated protein kinase kinase 3 | NM_002756 NM_145109 NM_145110 | CCCGGGCCACCGTGAACTCACA | SI02222976 | Hs_MAP2K3_6 |
| 900029-6-A | single siRNA, 0.9 nmol | 647 | 5747 | PTK2 | PTK2 protein tyrosine kinase 2 | NM_005607 | CCGGTCGAATGATAAGGTGTA | SI02622130 | Hs_PTK2_10 |
| 900029-6-A | single siRNA, 0.9 nmol | 648 | 5782 | PTPN12 | protein tyrosine phosphatase, non-receptor type 12 | NM_002835 | AAGCTTAATGAGGAAATATCA | SI02658768 | Hs_PTPN12_8 |
| 900029-6-A | single siRNA, 0.9 nmol | 649 | 5879 | RAC1 | ras-related C3 botulinum toxin substrate 1 (rho family, small GTP binding protein Rac1) | NM_006908 NM_018890 NM_198829 | ATGCATTTCCTGGAGAATATA | SI02655051 | Hs_RAC1_6 |
| 900029-6-A | single siRNA, 0.9 nmol | 650 | 5906 | RAP1A | RAP1A, member of RAS oncogene family | NM_001010935 NM_002884 | CAGGGGCCAGAATTTAGCAAGA | SI02662296 | Hs_RAP1A_6 |
| 900029-6-A | single siRNA, 0.9 nmol | 651 | 5454 | POU3F2 | POU domain, class 3, transcription factor 2 | NM_005604 | TACCCGCTTTATCGAAGGCAA | SI03224683 | Hs_POU3F2_6 |
| 900029-6-A | single siRNA, 0.9 nmol | 652 | 5525 | PPP2R5A | protein phosphatase 2, regulatory subunit B', alpha isoform | NM_006243 | CAGCGTATTCTGATATAGTAA | SI02225846 | Hs_PPP2R5A_6 |
| 900029-6-A | single siRNA, 0.9 nmol | 653 | 5579 | PRKCB1 | protein kinase C, beta 1 | NM_002738 NM_212535 | CCGGATGAAACTGACCGATTT | SI00605948 | Hs_PRKCB1_6 |
| 900029-6-A | single siRNA, 0.9 nmol | 654 | 5587 | PRKD1 | protein kinase D1 | NM_002742 | AAGCGGCACATTCCCATTTAA | SI00301350 | Hs_PRKCM_2 |
| 900029-6-A | single siRNA, 0.9 nmol | 655 | 5599 | MAPK8 | mitogen-activated protein kinase 8 | NM_002750 NM_139046 NM_139047 NM_139049 | ATGATGTGTCTTCAATGTCAA | SI02758851 | Hs_MAPK8_15 |
| 900029-6-A | single siRNA, 0.9 nmol | 656 | 5609 | MAP2K7 | mitogen-activated protein kinase kinase 7 | NM_145185 | CAGGAAGAGACCAAAGTATAA | SI02660588 | Hs_MAP2K7_9 |
| 900029-6-A | single siRNA, 0.9 nmol | 657 | 5753 | PTK6 | PTK6 protein tyrosine kinase 6 | NM_005975 | CTCCGCGACTCTGATGAGAAA | SI03090024 | Hs_PTK6_5 |
| 900029-6-A | single siRNA, 0.9 nmol | 658 | 5792 | PTPRF | protein tyrosine phosphatase, receptor type, F | NM_002840 NM_130440 | CATCGTGTTTGCAAAGGTTAA | SI02658796 | Hs_PTPRF_6 |
| 900029-6-A | single siRNA, 0.9 nmol | 659 | 5880 | RAC2 | ras-related C3 botulinum toxin substrate 2 (rho family, small GTP binding protein Rac2) | NM_002872 | AACTATTCAGCCAATGTGATG | SI02655058 | Hs_RAC2_5 |
| 900329-6-A | single siRNA, 0.9 nmol | 660 | 5908 | RAP1B | RAP1B, member of RAS oncogene family | NM_001010942 NM_015646 | CAGTATATAATGTCTTAGATTAA | SI02662849 | Hs_RAP1B_7 |
| 900029-6-B | single siRNA, 0.9 nmol | 661 | 5337 | PLD1 | phospholipase D1, phosphatidylcholine-specific | NM_002662 | ATGGGATATTTGATTACTAA | SI00686357 | Hs_PLD1_3 |
| 900029-6-B | single siRNA, 0.9 nmol | 662 | 5455 | POU3F3 | POU domain, class 3, transcription factor 3 | NM_006236 | CGGCTCTATTGTGCACTCGGA | SI03069277 | Hs_POU3F3_3 |
| 900029-6-B | single siRNA, 0.9 nmol | 663 | 5566 | PRKACA | protein kinase, cAMP-dependent, | NM_002730 | CAAGGACAACTCAAACTTATA | SI00605587 | H5_PRKACA_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-6-B | single siRNA, 0.9 nmol | 664 | 5580 | PRKCD | protein kinase C, delta | NM_207518 NM_006254 NM_212539 | AACTCTACCGTGCCACGTTTT | SI00301329 | Hs_PRKCD_7 |
| 900029-6-B | single siRNA, 0.9 nmol | 665 | 5588 | PRKCQ | protein kinase C, theta | NM_006257 | AACCATAGTTATTACTTGAA | SI02758623 | Hs_PRKCQ_8 |
| 900029-6-B | single siRNA, 0.9 nmol | 666 | 5601 | MAPK9 | mitogen-activated protein kinase 9 | NM_002752 NM_139068 NM_139069 NM_139070 | AAAGTCGATTTATGTGTATTA | SI02222913 | Hs_MAPK9_6 |
| 900029-6-B | single siRNA, 0.9 nmol | 667 | 5613 | PRKX | protein kinase, X-linked | NM_005044 | CGGATGGGATTCACTTAAGAA | SI02223851 | Hs_PRKX_5 |
| 900029-6-B | single siRNA, 0.9 nmol | 668 | 5770 | PTPN1 | protein tyrosine phosphatase, non-receptor type 1 | NM_002827 | CAGGAATAGGCATTTGCCTAA | SI00043820 | Hs_PTPN1_3 |
| 900029-6-B | single siRNA, 0.9 nmol | 669 | 5794 | PTPRH | protein tyrosine phosphatase, receptor type, H | NM_002842 | ATCACCGTGGATAGACTTGAA | SI03046904 | Hs_PTPRH_5 |
| 900029-6-B | single siRNA, 0.9 nmol | 670 | 5881 | RAC3 | ras-related C3 botulinum toxin substrate 3 (rho family, small GTP binding protein Rac3) | NM_005052 | CCCGGAGATTGGCTCTGTGAA | SI00071890 | Hs_RAC3_4 |
| 900029-6-B | single siRNA, 0.9 nmol | 671 | 5338 | PLD2 | phospholipase D2 | NM_002663 | TGGGCGACGGTTCTGAACAA | SI03020857 | Hs_PLD2_5 |
| 900029-6-B | single siRNA, 0.9 nmol | 672 | 5456 | POU3F4 | POU domain, class 3, transcription factor 4 | NM_000307 | CAGAAACTTCTCCAAAGTGAT | SI03062675 | Hs_POU3F4_6 |
| 900029-6-B | single siRNA, 0.9 nmol | 673 | 5567 | PRKACB | protein kinase, cAMP-dependent, catalytic, beta | NM_002731 NM_182948 | CAGCCTGTGTAGTGTGACAAA | SI02225461 | Hs_PRKACB_9 |
| 900029-6-B | single siRNA, 0.9 nmol | 674 | 5581 | PRKCE | protein kinase C, epsilon | NM_005400 | CCCGACCATGGTAGTGTTCAA | SI00287784 | Hs_PRKCE_5 |
| 900029-6-B | single siRNA, 0.9 nmol | 675 | 5590 | PRKCZ | protein kinase C, zeta | NM_001033581 NM_001033582 | CGGAAGCATGACCAGCATTAAA | SI00605969 | Hs_PRKCZ_5 |
| 900029-6-B | single siRNA, 0.9 nmol | 676 | 5602 | MAPK10 | mitogen-activated protein kinase 10 | NM_002753 NM_138980 NM_138981 NM_138982 | CCGCATGTGTCTGTATTCATA | SI02222927 | Hs_MAPK10_5 |
| 900029-6-B | single siRNA, 0.9 nmol | 677 | 5625 | PRODH | proline dehydrogenase (oxidase) 1 | NM_016335 | CTTGGCATTTGTCAGGAATATA | SI00115451 | Hs_PRODH_3 |
| 900029-6-B | single siRNA, 0.9 nmol | 678 | 5771 | PTPN2 | protein tyrosine phosphatase, non-receptor type 2 | NM_002828 NM_080422 NM_080423 | CCGCTGTACTTGGAAATTCGA | SI02225895 | Hs_PTPN2_9 |
| 900029-6-B | single siRNA, 0.9 nmol | 679 | 5795 | PTPRJ | protein tyrosine phosphatase, receptor type, J | NM_002843 | TCGGGTAGAAATAACCACCAA | SI02658810 | Hs_PTPRJ_5 |
| 900029-6-B | single siRNA, 0.9 nmol | 680 | 5894 | RAF1 | v-raf-1 murine leukemia viral oncogene homolog 1 | NM_002880 | CAGATCTTAGTAAGCTATATA | SI02223032 | Hs_RAF1_6 |
| 900029-6-B | single siRNA, 0.9 nmol | 681 | 5339 | PLEC1 | plectin 1, intermediate filament binding protein 500 kDa | NM_000445 NM_201378 NM_201379 NM_201380 NM_201381 NM_201382 NM_201383 NM_201384 | CCGCCAGGTGAAGCTGGTGAA | SI02654988 | Hs_PLEC1_8 |
| 900029-6-B | single siRNA, 0.9 nmol | 682 | 5478 | PPIA | peptidylprolyl isomerase A (cyclophilin A) | NM_021130 NM_203430 NM_203431 | CAGTAATGGGTTACTTCTGAA | SI00690914 | Hs_PPIA_2 |
| 900029-6-B | single siRNA, 0.9 nmol | 683 | 5568 | PRKACG | protein kinase, cAMP-dependent, | NM_002732 | AACCAGCTGGATCGCCATCTA | SI00605871 | Hs_PRKACG_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-6-B | single siRNA, 0.9 nmol | 684 | 5582 | PRKCG | protein kinase C, gamma | NM_002739 | CCCGGAGATCATTGCCTACCA | SI03078306 | Hs_PRKCG_5 |
| 900029-6-B | single siRNA, 0.9 nmol | 685 | 5591 | PRKDC | protein kinase, DNA-activated, catalytic polypeptide | NM_001081640 NM_006904 | TTCGGCTAACTCGCCAGTTTA | SI02224236 | Hs_PRKDC_6 |
| 900029-6-B | single siRNA, 0.9 nmol | 686 | 5604 | MAP2K1 | mitogen-activated protein kinase kinase 1 | NM_032755 | CTGGAAGAATTCTGACCAAA | SI02222955 | Hs_MAP2K1_7 |
| 900029-6-B | single siRNA, 0.9 nmol | 687 | 5728 | PTEN | phosphatase and tensin homolog (mutated in multiple advanced cancers 1) | NM_000314 | TCGACTTAGACTTGACCTATA | SI03116092 | Hs_PTEN_9 |
| 900029-6-B | single siRNA, 0.9 nmol | 688 | 5777 | PTPN6 | protein tyrosine phosphatase, non-receptor type 6 | NM_002831 NM_080548 NM_080549 | CCCGAACAAATCGTCCCATA | SI02658726 | Hs_PTPN6_5 |
| 900029-6-B | single siRNA, 0.9 nmol | 689 | 5829 | PXN | paxillin | NM_002859 | CCCACTGAAACTGGAACCCTT | SI02757594 | Hs_PXN_6 |
| 900029-6-B | single siRNA, 0.9 nmol | 690 | 5898 | RALA | v-ral simian leukemia viral oncogene homolog A (ras related) | NM_005402 | TAGGAACTCACTCTTTAGATA | SI00076608 | Hs_RALA_3 |
| 900029-6-B | single siRNA, 0.9 nmol | 691 | 5359 | PLSCR1 | phospholipid scramblase 1 | NM_021105 | CAGCGCCACAGCCTCCATTAA | SI03067043 | Hs_PLSCR1_5 |
| 900029-6-B | single siRNA, 0.9 nmol | 692 | 5500 | PPP1CB | protein phosphatase 1, catalytic subunit, beta isoform | NM_002709 NM_206876 | TACGAGGATGTCCTCCAGGAA | SI02225762 | Hs_PPP1CB_5 |
| 930029-6-B | single siRNA, 0.9 nmol | 693 | 5573 | PRKAR1A | protein kinase, cAMP-dependent, regulatory, type I, alpha (tissue specific extinguisher 1) | NM_002734 NM_212471 NM_212472 | CAGCTAGTGCCAAATAATTGA | SI00605899 | Hs_PRKAR1A_7 |
| 900029-6-B | single siRNA, 0.9 nmol | 694 | 5584 | PRKCI | protein kinase C, iota | NM_002740 | CAGAGATTGTTCTTTGTTATAGA | SI02660098 | Hs_PRKCI_10 |
| 900029-6-B | single siRNA, 0.9 nmol | 695 | 5594 | MAPK1 | mitogen-activated protein kinase 1 | NM_002745 | AACACTTGTCAAGAAGCGTTA | SI00605983 | Hs_MAPK1_12 |
| 900029-6-B | single siRNA, 0.9 nmol | 696 | 5605 | MAP2K2 | mitogen-activated protein kinase kinase 2 | NM_030662 | CAGCATTTGCATGGAACACAT | SI02225090 | Hs_MAP2K2_5 |
| 900029-6-B | single siRNA, 0.9 nmol | 697 | 5734 | PTGER4 | prostaglandin E receptor 4 (subtype EP4) | NM_000958 | ACCCATAATTGAAGTGTATAA | SI02264692 | Hs_PTGER4_5 |
| 900029-6-B | single siRNA, 0.9 nmol | 698 | 5781 | PTPN11 | protein tyrosine phosphatase, non-receptor type 11 (Noonan syndrome 1) | NM_002834 | CAGAAGCACAGTACCGATTTA | SI02225902 | Hs_PTPN11_6 |
| 900029-6-B | single siRNA, 0.9 nmol | 699 | 5866 | RAB5A | RAB5A, member RAS oncogene family | NM_004162 | ATTCATGAGACATCCGCTAA | SI00301588 | Hs_RAB5A_5 |
| 900029-6-B | single siRNA, 0.9 nmol | 700 | 5899 | RALB | v-ral simian leukemia viral oncogene homolog B (ras related; GTP binding protein) | NM_002881 | CAAGGTGTTCTTTGACCTAAT | SI03054793 | Hs_RALB_6 |
| 900029-6-B | single siRNA, 0.9 nmol | 701 | 5453 | POU3F1 | POU domain, class 3, transcription factor 1 | NM_002699 | CCCGCCCATGGACGATGTATA | SI00690221 | Hs_POU3F1_3 |
| 900029-6-B | single siRNA, 0.9 nmol | 702 | 5514 | PPP1R10 | protein phosphatase 1, regulatory (inhibitor) subunit 10 | NM_002714 | AAGCAATAGTCAGGAGCGATA | SI03032666 | Hs_PPP1R10_5 |
| 900029-6-B | single siRNA, 0.9 nmol | 703 | 5578 | PRKCA | protein kinase C, alpha | NM_002737 | CGCAGTGAATGAGTCCTTTA | SI00605927 | Hs_PRKCA_6 |
| 900029-6-B | single siRNA, 0.9 nmol | 704 | 5586 | PKN2 | protein kinase N2 | NM_006256 | AAAGTATGATATCTACGCAAA | SI02224089 | Hs_PKN2_5 |
| 900029-6-B | single siRNA, 0.9 nmol | 705 | 5595 | MAPK3 | mitogen-activated protein kinase 3 | NM_001040056 NM_002746 | CCCGTCTAATATATATAAATATA | SI00605997 | Hs_MAPK3_6 |
| 900029-6-B | single siRNA, 0.9 nmol | 706 | 5606 | MAP2K3 | mitogen-activated protein kinase kinase 3 | NM_002756 NM_145109 NM_145110 XM_001130488 | ACGGATATCCTGCATGTCCAA | SI02222969 | Hs_MAP2K3_5 |
| 900029-6-B | single siRNA, 0.9 nmol | 707 | 5747 | PTK2 | PTK2 protein tyrosine kinase 2 | NM_005607 | AATCACACACCAAATTCGAGT | SI00301532 | Hs_PTK2_9 |
| 900029-6-B | single siRNA, 0.9 nmol | 708 | 5782 | PTPN12 | protein tyrosine phosphatase, non-receptor type 12 | NM_153831 | TTGCAGGTTATCAGAGATCAA | SI02658761 | Hs_PTPN12_7 |
| 900029-6-B | single siRNA, 0.9 nmol | 709 | 5879 | RAC1 | ras-related C3 botulinum toxin substrate 1 (rho family, small GTP binding protein) | NM_006908 NM_018890 | CAGCACGTGTCCCGACATAA | SI03066531 | Hs_RAC1_10 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-6-B | single siRNA, 0.9 nmol | 710 | 5906 | RAP1A | protein Rac1) RAP1A, member of RAS oncogene family | NM_198829 NM_001010935 | CCCAACGATAGAAGAGATTCCTA | SI03075961 | Hs_RAP1A_8 |
| 900029-6-B | single siRNA, 0.9 nmol | 711 | 5454 | POU3F2 | POU domain, class 3, transcription factor 2 | NM_005604 | CCGCAGCGTCTAACCACTACA | SI03188626 | Hs_POU3F2_5 |
| 900029-6-B | single siRNA, 0.9 nmol | 712 | 5525 | PPP2R5A | protein phosphatase 2, regulatory subunit B', alpha isoform | NM_006243 | CTGTATCATGGCCATAGTATA | SI02225839 | Hs_PPP2R5A_5 |
| 900029-6-B | single siRNA, 0.9 nmol | 713 | 5579 | PRKCB1 | protein kinase C, beta 1 | NM_002738 | CAAGAGCTAAGTAGATGTGTA | SI00605941 | Hs_PRKCB1_5 |
| 900029-6-B | single siRNA, 0.9 nmol | 714 | 5587 | PRKD1 | protein kinase D1 | NM_002742 | TCGATTATTCCAGTGTTCTA | SI00042378 | Hs_PRKD1_3 |
| 900029-6-B | single siRNA, 0.9 nmol | 715 | 5599 | MAPK8 | mitogen-activated protein kinase 8 | NM_002750 NM_139046 NM_139047 | ATGAAATGTTAATCACAAA | SI02758644 | Hs_MAPK8_14 |
| 900029-6-B | single siRNA, 0.9 nmol | 716 | 5809 | MAP2K7 | mitogen-activated protein kinase kinase 7 | NM_145185 | AAAGATGACAGTGGCGATTGT | SI03007720 | Hs_MAP2K7_1 |
| 900029-6-B | single siRNA, 0.9 nmol | 717 | 5753 | PTK6 | PTK6 protein tyrosine kinase 6 | NM_005975 | ACCGCTGTGCTCCTCCTCTTA | SI00083314 | Hs_PTK6_3 |
| 900029-6-B | single siRNA, 0.9 nmol | 718 | 5792 | PTPRF | protein tyrosine phosphatase, receptor type, F | NM_002840 NM_130440 | CAGCGCTATCTAGATAGGTAA | SI02658789 | Hs_PTPRF_5 |
| 900029-6-B | single siRNA, 0.9 nmol | 719 | 5880 | RAC2 | ras-related C3 botulinum toxin substrate 2 (rho family, small GTP binding protein Rac2) | NM_002872 | CAATGTGATGGTGGACAGCAA | SI00004947 | Hs_RAC2_4 |
| 900029-6-B | single siRNA, 0.9 nmol | 720 | 5908 | RAP1B | RAP1B, member of RAS oncogene family | NM_001010942 NM_015646 | GACGAGTACTGTGGATGTGAA | SI02662303 | Hs_RAP1B_6 |
| 900029-6-B | single siRNA, 0.9 nmol | 721 | 5911 | RAP2A | RAP2A, member of RAS oncogene family | NM_021033 | CCAGTGTATTCCGTCAAGTAA | SI02663087 | Hs_RAP2A_6 |
| 900029-6-B | single siRNA, 0.9 nmol | 722 | 5925 | RB1 | retinoblastoma 1 (including osteosarcoma) | NM_000321 | CAGGGTTGTGTCGAAATTGGA | SI02653993 | Hs_RB1_8 |
| 900029-6-B | single siRNA, 0.9 nmol | 723 | 6010 | RHO | rhodopsin (opsin 2, rod pigment) (retinitis pigmentosa 4, autosomal dominant) | NM_000539 | CAGCTTAGGATAAGTGTCTA | SI03068855 | Hs_RHO_5 |
| 900029-6-B | single siRNA, 0.9 nmol | 724 | 6197 | RPS6KA3 | ribosomal protein S6 kinase, 90 kDa, polypeptide 3 | NM_004586 | TCCAAACATTATCACTCTAAA | SI00288197 | Hs_RPS6KA3_6 |
| 900029-6-B | single siRNA, 0.9 nmol | 725 | 6416 | MAP2K4 | mitogen-activated protein kinase kinase 4 | NM_003010 | TTGGACAGGAGCTTATGGTT | SI02655079 | Hs_MAP2K4_10 |
| 900029-6-B | single siRNA, 0.9 nmol | 726 | 6622 | SNCA | synuclein, alpha (non A4 component of amyloid precursor) | NM_000345 NM_007308 | ATGGATGTATTCATGAAAGGA | SI03051209 | Hs_SNCA_6 |
| 900329-7-A | single siRNA, 0.9 nmol | 727 | 6655 | SOS2 | son of sevenless homolog 2 (Drosophila) | NM_006939 | AAGCATTTGATCTTATGAAA | SI00729344 | Hs_SOS2_4 |
| 900329-7-A | single siRNA, 0.9 nmol | 728 | 6722 | SRF | serum response factor (c-fos serum response element-binding transcription factor) | NM_003131 | CAAGATGAGTTCATCGACAA | SI02757622 | Hs_SRF_5 |
| 900029-7-A | single siRNA, 0.9 nmol | 729 | 6776 | STAT5A | signal transducer and activator of transcription 5A | NM_033152 | AGGCACGTGGAGGAACTCTTA | SI03045014 | Hs_STAT5A_5 |
| 900029-7-A | single siRNA, 0.9 nmol | 730 | 6907 | TBL1X | transducin (beta)-like 1X-linked | NM_005647 | CCCGCATGTCACTTAGTCTAA | SI00740432 | Hs_TBL1X_4 |
| 900029-7-A | single siRNA, 0.9 nmol | 731 | 5914 | RARA | retinoic acid receptor, alpha | NM_000964 NM_001024809 NM_001033603 | CAGGAAATGTTGGAGAACTCA | SI03068821 | Hs_RARA_6 |
| 900029-7-A | single siRNA, 0.9 nmol | 732 | 5928 | RBBP4 | retinoblastoma binding protein 4 | NM_005610 | CAGCTATCCCTCTATATAATA | SI02653420 | Hs_RBBP4_8 |
| 900029-7-A | single siRNA, 0.9 nmol | 733 | 6018 | RLF | rearranged L-myc fusion | NM_012421 | CACCTTAGGATTCATTATAAA | SI00703752 | Hs_RLF_4 |
| 900029-7-A | single siRNA, 0.9 nmol | 734 | 6237 | RRAS | related RAS viral (r-ras) oncogene homolog | NM_006270 | CTCGGCCAAACTGCGTCTCAA | SI02663115 | Hs_RRAS_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-7-A | 0.9 nmol single siRNA, | 735 | 6457 | SH3GL3 | SH3-domain GRB2-like 3 | NM_003027 | CAAGGAGAATTAGGATTTAAA | SI00717388 | Hs_SH3GL3_4 |
| 900029-7-A | 0.9 nmol single siRNA, | 736 | 6624 | FSCN1 | fascin homolog 1, actin-bundling protein (strongylocentrotus purpuratus) | NM_003088 | CTGAGCCTTATTTCTCTGGAA | SI00421813 | Hs_FSCN1_4 |
| 900029-7-A | 0.9 nmol single siRNA, | 737 | 6667 | SP1 | Sp1 transcription factor | NM_138473 | CAGGTCGTTGGCAGACTCTA | SI03071887 | Hs_SP1_8 |
| 900029-7-A | 0.9 nmol single siRNA, | 738 | 6747 | SSR3 | signal sequence receptor, gamma (translocon-associated protein gamma) | NM_007107 | CTCCGCCTCTTCTTCCGAAA | SI03090031 | Hs_SSR3_10 |
| 900029-7-A | 0.9 nmol single siRNA, | 739 | 6777 | STAT5B | signal transducer and activator of transcription 5B | NM_012448 | ATGGGACTCAGTAGATCTTGA | SI03051678 | Hs_STAT5B_5 |
| 900029-7-A | 0.9 nmol single siRNA, | 740 | 6925 | TCF4 | transcription factor 4 | NM_003199 | GACACAAGAAGAAGATATCAAA | SI03101805 | Hs_TCF4_5 |
| 900029-7-A | 0.9 nmol single siRNA, | 741 | 5915 | RARB | retinoic acid receptor, beta | NM_000965 NM_016152 | GAGCGTGTAATTACCTTGAA | SI00019411 | Hs_RARB_4 |
| 900029-7-A | 0.9 nmol single siRNA, | 742 | 5931 | RBBP7 | retinoblastoma binding protein 7 | NM_002893 XM_001128441 | CCCACGCAAGATGGCGACTAA | SI02664466 | Hs_RBBP7_6 |
| 900029-7-A | 0.9 nmol single siRNA, | 743 | 6096 | ROS1 | v-ros UR2 sarcoma virus oncogene homolog 1 (avian) | NM_002944 | ACCGAGAAGGGTTAAACTATA | SI02223053 | Hs_ROS1_6 |
| 900029-7-A | 0.9 nmol single siRNA, | 744 | 6239 | RREB1 | ras responsive element binding protein 1 | NM_001003698 NM_001003699 NM_002955 | CGGAGGTCATCAGCGAGCAA | SI03195605 | Hs_RREB1_6 |
| 900029-7-A | 0.9 nmol single siRNA, | 745 | 6464 | SHC1 | SHC (Src homology 2 domain containing) transforming protein 1 | NM_003029 NM_183001 | CTGAAATTTGCTGGAATGCCA | SI02655100 | Hs_SHC1_11 |
| 900029-7-A | 0.9 nmol single siRNA, | 746 | 6633 | SNRPD2 | small nuclear ribonucleoprotein D2 polypeptide 16.5 kDa | NM_004597 NM_177542 | TGCCATTGGTGTTGAGAATAA | SI03236156 | Hs_SNRPD2_5 |
| 900029-7-A | 0.9 nmol single siRNA, | 747 | 6687 | SPG7 | spastic paraplegia 7 (pure and complicated autosomal recessive) | NM_003119 NM_199367 | AAGGTTGAAGCAGAAGAATAA | SI03019695 | Hs_SPG7_5 |
| 900029-7-A | 0.9 nmol single siRNA, | 748 | 6772 | STAT1 | signal transducer and activator of transcription 1, 91 kDa | NM_007315 NM_139266 | CCAGATGTCTATGATCATTA | SI02662884 | Hs_STAT1_7 |
| 900029-7-A | 0.9 nmol single siRNA, | 749 | 6778 | STAT6 | signal transducer and activator of transcription 6, interleukin-4 induced | NM_003153 | ACGGATAGGCAGGAACATACA | SI02662905 | Hs_STAT6_5 |
| 900029-7-A | 0.9 nmol single siRNA, | 750 | 6929 | TCF3 | transcription factor 3 (E2A immunoglobulin enhancer binding factors E12/E47) | NM_003200 | GAGCGGAACCTGAATCCCAAA | SI03103086 | Hs_TCF3_5 |
| 900029-7-A | 0.9 nmol single siRNA, | 751 | 5916 | RARG | retinoic acid receptor, gamma | NM_001042728 XM_940838 NM_000323 NM_020629 NM_020630 NM_020975 | TCCTGTTTCGCCGGACTTGAA | SI04025616 | Hs_RARG_9 |
| 900029-7-A | 0.9 nmol single siRNA, | 752 | 5979 | RET | ret proto-oncogene | NM_020630 NM_020975 NM_006013 NM_000540 NM_001042723 | TAGGCTCGTTCTCAACCGGAA | SI02224992 | Hs_RET_10 |
| 900029-7-A | 0.9 nmol single siRNA, | 753 | 6134 | RPL10 | ribosomal protein L10 | NM_006013 | CAGCAAAGCCTTGCAATCCCA | SI02636473 | Hs_RPL10_5 |
| 900029-7-A | 0.9 nmol single siRNA, | 754 | 6261 | RYR1 | ryanodine receptor 1 (skeletal) | NM_000540 NM_001042723 | CCGCTATGGCCTTCCTCATAAA | SI00011494 | Hs_RYR1_4 |
| 900029-7-A | 0.9 nmol single siRNA, | 755 | 6498 | SKIL | SKI-like oncogene | NM_005414 NM_003099 | TTGGTTCAGGGCTCAACTAAA | SI00076776 | Hs_SKIL_4 |
| 900029-7-A | 0.9 nmol single siRNA, | 756 | 6642 | SNX1 | sorting nexin 1 | NM_148955 NM_152826 | GAGGGCCGCTTTAGAAGGTA | SI03104003 | Hs_SNX1_7 |
| 900029-7-A | 0.9 nmol single siRNA, | 757 | 6709 | SPTAN1 | spectrin, alpha, non-erythrocytic 1 (alpha-fodrin) | NM_003127 | AACGCTTCCTTGCTGACTTCC | SI00301861 | Hs_SPTAN1_5 |
| 900029-7-A | 0.9 nmol single siRNA, | 758 | 6773 | STAT2 | signal transducer and activator of transcription 2, 113 kDa | NM_005419 | AACGTTCAGGTGGTTCAGGAA | SI02662891 | Hs_STAT2_7 |
| 900029-7-A | 0.9 nmol single siRNA, | 759 | 6788 | STK3 | serine/threonine kinase 3 (STE20 | NM_006281 | CGGCGCCTAAGAGTAAACTAA | SI02622263 | Hs_STK3_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-7-A | single siRNA, 0.9 nmol | 760 | 6938 | TCF12 | transcription factor 12 (HTF4, helix-loop-helix transcription factors 4) | NM_003205 NM_207036 NM_207037 NM_207038 | ATGGTTGGAACTCATCGGAA | SI03052231 | Hs_TCF12_6 |
| 900029-7-A | single siRNA, 0.9 nmol | 761 | 5921 | RASA1 | RAS p21 protein activator (GTPase activating protein) 1 | NM_002890 NM_022650 | CAGACCTAATAGTTATTACA | SI00045367 | Hs_RASA1_4 |
| 900029-7-A | single siRNA, 0.9 nmol | 762 | 5999 | RGS4 | regulator of G-protein signalling 4 | NM_005613 | CTGGTCCCTCAGTGTGCCTAA | SI03099600 | Hs_RGS4_11 |
| 900029-7-A | single siRNA, 0.9 nmol | 763 | 6195 | RPS6KA1 | ribosomal protein S6 kinase, 90 kDa, polypeptide 1 | NM_001006665 NM_002953 | TGCCACGTACTCCGCACTCAA | SI02223067 | Hs_RPS6KA1_10 |
| 900029-7-A | single siRNA, 0.9 nmol | 764 | 6307 | SC4MOL | sterol-C4-methyl oxidase-like | NM_001017369 NM_006745 | TTGAAGATACTTGGCACTATT | SI03243149 | Hs_SC4MOL_8 |
| 900029-7-A | single siRNA, 0.9 nmol | 765 | 6590 | SLPI | secretory leukocyte peptidase inhibitor | NM_003064 | AAGGCTCTGGAAAGTCCTTCA | SI00726404 | Hs_SLPI_4 |
| 900029-7-A | single siRNA, 0.9 nmol | 766 | 6643 | SNX2 | sorting nexin 2 | NM_003100 | AAGTGCTGTCTAAGGTAGA | SI03135454 | Hs_SNX2_5 |
| 900029-7-A | single siRNA, 0.9 nmol | 767 | 6713 | SQLE | squalene epoxidase | NM_003129 | TGGGAGACGCATATAATATGA | SI03120894 | Hs_SQLE_6 |
| 900029.7-A | single siRNA, 0.9 nmol | 768 | 6774 | STAT3 | signal transducer and activator of transcription 3 (acute-phase response factor) | NM_003150 NM_139276 NM_213662 | CAGGCTGTAATTTATTATAAT | SI02662898 | Hs_STAT3_8 |
| 900029-7-A | single siRNA, 0.9 nmol | 769 | 6789 | STK4 | serine/threonine kinase 4 | NM_006282 | CACCATTTGCTGTCGAATTA | SI02622277 | Hs_STK4_6 |
| 900029-7-A | single siRNA, 0.9 nmol | 770 | 7029 | TFDP2 | transcription factor Dp-2 (E2F dimerization partner 2) | NM_006286 | CATGATGACATAGAAGTACTA | SI03073868 | Hs_TFDP2_6 |
| 900029-7-A | single siRNA, 0.9 nmol | 771 | 5922 | RASA2 | RAS p21 protein activator 2 | NM_006506 | CCGCAGTTTAATGAAATCTTT | SI00698740 | Hs_RASA2_4 |
| 900029-7-A | single siRNA, 0.9 nmol | 772 | 6004 | RGS16 | regulator of G-protein signalling 16 | NM_002928 | CAGGACCATGGCACCCTTAGA | SI03069178 | Hs_RGS16_7 |
| 900029-7-A | single siRNA, 0.9 nmol | 773 | 6196 | RPS6KA2 | ribosomal protein S6 kinase, 90 kDa, polypeptide 2 | NM_001008932 NM_021135 | CCCGAGTCCTGAAGCGTCAA | SI02225006 | Hs_RPS6KA2_10 |
| 900029-7-A | single siRNA, 0.9 nmol | 774 | 6387 | CXCL12 | chemokine (C-X-C motif) ligand 12 (stromal cell-derived factor 1) | NM_000609 NM_001033886 NM_199168 | GTGCATTGACCCGAAGCTAAA | SI03649149 | Hs_CXCL12_11 |
| 900029-7-A | single siRNA, 0.9 nmol | 775 | 6598 | SMARCB1 | SWI/SNF related, matrix associated, actin dependent regulator of chromatin, subfamily b, member 1 | NM_001007468 NM_003073 | CTCCACAACCATCAACAGGAA | SI00726824 | Hs_SMARCB1_4 |
| 900029-7-A | single siRNA, 0.9 nmol | 776 | 6654 | SOS1 | son of sevenless homolog 1 (Drosophila) | NM_005633 | AAGGAGGTCCTAGGTTATAAA | SI02655121 | Hs_SOS1_5 |
| 900029-7-A | single siRNA, 0.9 nmol | 777 | 6714 | SRC | v-src sarcoma (Schmidt-Ruppin A-2) viral oncogene homolog (avian) | NM_005417 NM_198291 | CTCCATGTGCGTCCATATTTA | SI02664151 | Hs_SRC_10 |
| 900029-7-A | single siRNA, 0.9 nmol | 778 | 6775 | STAT4 | signal transducer and activator of transcription 4 | NM_003151 | TCAGAGGCCGTTGGTACTTAA | SI00048412 | Hs_STAT4_4 |
| 900029-7-A | single siRNA, 0.9 nmol | 779 | 6790 | AURKA | aurora kinase A | NM_003600 NM_198433 NM_198434 NM_198435 NM_198436 NM_198437 | CACCTTCGGCATCCTAATATT | SI02223305 | Hs_STK6_5 |
| 900029-7-B | single siRNA, 0.9 nmol | 780 | 7039 | TGFA | transforming growth factor, alpha | NM_003236 | CTGGCTGTCCTTATCATCACA | SI03098403 | Hs_TGFA_5 |
| 900029-7-B | single siRNA, 0.9 nmol | 781 | 5911 | RAP2A | RAP2A, member of RAS oncogene family | NM_021033 | ACCGGCACCTTCATCGAGAAA | SI03040198 | Hs_RAP2A_7 |
| 900029-7-B | single siRNA, 0.9 nmol | 782 | 5925 | RB1 | retinoblastoma 1 (including osteosarcoma) | NM_000321 | CGCGTGTAAATTCTACTGCAA | SI02653819 | Hs_RB1_7 |
| 900029-7-B | single siRNA, 0.9 nmol | 783 | 6010 | RHO | rhodopsin (opsin 2, rod pigment) (retinitus pigmentosa 4, autosomal | NM_000539 | CCACATTTAATTAACAGCTGA | SI00011466 | Hs_RHO_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-7-B | single siRNA, 0.9 nmol | 784 | 6197 | RPS6KA3 | ribosomal protein S6 kinase, 90 kDa, polypeptide 3 | NM_004596 | AGCGCTGAGAATGGACAGCAA | SI00288190 | Hs_RPS6KA3_5 |
| 900029-7-B | single siRNA, 0.9 nmol | 785 | 6416 | MAP2K4 | mitogen-activated protein kinase kinase 4 | NM_003010 | AGGGTGTATAGTGTTCACAAA | SI02223102 | Hs_MAP2K4_8 |
| 900029-7-B | single siRNA, 0.9 nmol | 786 | 6622 | SNCA | synuclein, alpha (non A4 component of amyloid precursor) | NM_000345 NM_007308 | AAAGAGGSTGTTCTCTATGTA | SI03026478 | Hs_SNCA_5 |
| 900029-7-B | single siRNA, 0.9 nmol | 787 | 6655 | SOS2 | son of sevenless homolog 2 (Drosophila) | NM_006939 | CAGCATAATATATTGCTGCTAA | SI00729937 | Hs_SOS2_3 |
| 900029-7-B | single siRNA, 0.9 nmol | 788 | 6722 | SRF | serum response factor (c-fos serum response element-binding transcription factor) | NM_003131 | AAGGAGCGGCCTCGCCATAAA | SI03034731 | Hs_SRF_7 |
| 900029-7-B | single siRNA, 0.9 nmol | 789 | 6776 | STAT5A | signal transducer and activator of transcription 5A | NM_003152 | TTCGAAGTTAGGAGGACTCAA | SI00048440 | Hs_STAT5A_4 |
| 900029-7-B | single siRNA, 0.9 nmol | 790 | 6907 | TBL1X | transducin (beta)-like 1X-linked | NM_005647 | TAGAGTCATCCCTGTAATCAA | SI00740425 | Hs_TBL1X_3 |
| 900329-7-B | single siRNA, 0.9 nmol | 791 | 5914 | RARA | retinoic acid receptor, alpha | NM_000964 NM_001024809 NM_001033603 | CACTGAGATCTACTGGATAAA | SI03062318 | Hs_RARA_5 |
| 900029-7-B | single siRNA, 0.9 nmol | 792 | 5928 | RBBP4 | retinoblastoma binding protein 4 | NM_005610 | AAGACTCCTTCCAGTGATGTT | SI00301658 | Hs_RBBP4_5 |
| 900029-7-B | single siRNA, 0.9 nmol | 793 | 6018 | RLF | rearranged L-myc fusion | NM_012421 | AAGGATGAATGATAGTTCTGAA | SI00703745 | Hs_RLF_3 |
| 900029-7-B | single siRNA, 0.9 nmol | 794 | 6237 | RRAS | related RAS viral (r-ras) oncogene homolog | NM_006270 | CCCGGGTCACTGCTGTATATAA | SI02263108 | Hs_RRAS_5 |
| 900029-7-B | single siRNA, 0.9 nmol | 795 | 6457 | SH3GL3 | SH3-domain GRB2-like 3 | NM_003027 | CGCCTGGATTACGATTATAAA | SI00717381 | Hs_SH3GL3_3 |
| 900029-7-B | single siRNA, 0.9 nmol | 796 | 6624 | FSCN1 | fascin homolog 1, actin-bundling protein (strongylocentrotus purpuratus) | NM_003088 | CAGCTGCTACTTTGACATCGA | SI00421806 | Hs_FSCN1_3 |
| 900029-7-B | single siRNA, 0.9 nmol | 797 | 6667 | SP1 | Sp1 transcription factor | NM_138473 | ATGCCTAATATTCAGTATCAA | SI03050054 | Hs_SP1_7 |
| 900029-7-B | single siRNA, 0.9 nmol | 798 | 6747 | SSR3 | signal sequence receptor, gamma (translocon-associated protein gamma) | NM_007107 | CAGCCGCAATCTCTCGGCCAA | SI03066371 | Hs_SSR3_9 |
| 900029-7-B | single siRNA, 0.9 nmol | 799 | 6777 | STAT5B | signal transducer and activator of transcription 5B | NM_012448 | GCCACCCTAATTTGACATCAA | SI00100415 | Hs_STAT5B_4 |
| 900029-7-B | single siRNA, 0.9 nmol | 800 | 6925 | TCF4 | transcription factor 4 | NM_003199 | AGCCGAATTGAAGATCTTTA | SI00048965 | Hs_TCF4_4 |
| 900029-7-B | single siRNA, 0.9 nmol | 801 | 5915 | RARB | retinoic acid receptor, beta | NM_000965 NM_016152 | CTGCCAGTTCAGTAATCAAA | SI00019404 | Hs_RARB_3 |
| 900029-7-B | single siRNA, 0.9 nmol | 802 | 5931 | RBBP7 | retinoblastoma binding protein 7 | NM_002893 XM_001128430 XM_001128441 | GCCGATAAGACCCTAGCTTTA | SI02664459 | Hs_RBBP7_5 |
| 900029-7-B | single siRNA, 0.9 nmol | 803 | 6098 | ROS1 | v-ros UR2 sarcoma virus oncogene homolog 1 (avian) | NM_002944 | AAGGTAATTGCTCTAACTTTA | SI02223046 | Hs_ROS1_5 |
| 900029-7-B | single siRNA, 0.9 nmol | 804 | 6239 | RREB1 | ras responsive element binding protein 1 | NM_001003698 NM_001003699 NM_002955 | AACGCGCTTGTCCACAACAA | SI03125843 | Hs_RREB1_5 |
| 900029-7-B | single siRNA, 0.9 nmol | 805 | 6464 | SHC1 | SHC (Src homology 2 domain containing) transforming protein 1 | NM_003029 NM_183001 | AAGAGCCACCTGACCATCAGT | SI00301791 | Hs_SHC1_9 |
| 900029-7-B | single siRNA, 0.9 nmol | 806 | 6633 | SNRPD2 | small nuclear ribonucleoprotein D2 polypeptide 16.5 kDa | NM_004597 NM_177542 | CCGCAACAATAAGAAACTCCT | SI00728385 | Hs_SNRPD2_3 |
| 900029-7-B | single siRNA, 0.9 nmol | 807 | 6687 | SPG7 | spastic paraplegia 7 (pure and complicated autosomal recessive) | NM_003119 NM_199367 | GAGCGACGTGGTGGAAGTCTA | SI03217753 | Hs_SPG7_7 |
| 900029-7-B | single siRNA, 0.9 nmol | 808 | 6772 | STAT1 | signal transducer and activator of transcription 1, 91 kDa | NM_007315 NM_139266 | CAGAAAGAGCTTGACAGTAAA | SI02662324 | Hs_STAT1_6 |
| 900029-7-B | single siRNA, 0.9 nmol | 809 | 6778 | STAT6 | signal transducer and activator of | NM_003153 | CAGCGGCTCTATGTCGACTTT | SI03067414 | Hs_STAT6_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-7-B | single siRNA, 0.9 nmol | 810 | 6929 | TCF3 | transcription 6, interleukin-4 induced transcription factor 3 (E2A immunoglobulin enhancer binding factors E12/E47) | NM_003200 | CTGGATGATTGGACTTTAAA | SI00048893 | Hs_TCF3_4 |
| 900029-7-B | single siRNA, 0.9 nmol | 811 | 5916 | RARG | retinoic acid receptor, gamma | NM_001042728 XM_940838 NM_000323 NM_020629 NM_020630 NM_020975 | TACGACTGTATGAAACGTTT | SI04025609 | Hs_RARG_8 |
| 900029-7-B | single siRNA, 0.9 nmol | 812 | 5979 | RET | ret proto-oncogene | NM_020630 NM_020975 | CCGCTGGTGGACTGTAATAAT | SI02224985 | Hs_RET_9 |
| 900029-7-B | single siRNA, 0.9 nmol | 813 | 6134 | RPL10 | ribosomal protein L10 | NM_006013 | CAGAAACAGGTTGACACTCA | SI00083685 | Hs_RPL10_2 |
| 900029-7-B | single siRNA, 0.9 nmol | 814 | 6261 | RYR1 | ryanodine receptor 1 (skeletal) | NM_000540 NM_001042723 | CTGGGAATGGACCATAGAGAA | SI00011487 | Hs_RYR1_3 |
| 900029-7-B | single siRNA, 0.9 nmol | 815 | 6498 | SKIL | SKI-like oncogene | NM_005414 NM_003099 | AGGCAAGTAAGTCCATATCAA | SI00076769 | Hs_SKIL_3 |
| 900029-7-B | single siRNA, 0.9 nmol | 816 | 6642 | SNX1 | sorting nexin 1 | NM_148955 NM_152826 | CTGGGTCTTTATGAGAAGCTT | SI02630250 | Hs_SNX1_6 |
| 900029-7-B | single siRNA, 0.9 nmol | 817 | 6709 | SPTAN1 | spectrin, alpha, non-eythrocytic 1 (alpha-fodrin) | NM_003127 | CCGGCTGCGTACGTGAAGAAA | SI00048069 | Hs_SPTAN1_4 |
| 900029-7-B | single siRNA, 0.9 nmol | 818 | 6773 | STAT2 | signal transducer and activator of transcription 2, 113 kDa | NM_005419 | TAGGCCGATTAACTACCCTAA | SI02662331 | Hs_STAT2_6 |
| 900029-7-B | single siRNA, 0.9 nmol | 819 | 6788 | STK3 | serine/threonine kinase 3 (STE20 homolog, yeast) | NM_006281 | CCGGCGCTAAGAGTAAACTA | SI02622256 | Hs_STK3_5 |
| 900029-7-B | single siRNA, 0.9 nmol | 820 | 6938 | TCF12 | transcription factor 12 (HTF4, helix-loop-helix transcription factors 4) | NM_003205 NM_207036 NM_207037 NM_207038 NM_207040 | AACCGTGAATCTCCTAGTTAT | SI03028893 | Hs_TCF12_5 |
| 900020-7-B | single siRNA, 0.9 nmol | 821 | 5921 | RASA1 | RAS p21 protein activator (GTPase activating protein) 1 | NM_002890 NM_022650 | ACGGACCTGTCCCGTGATTA | SI00045360 | Hs_RASA1_3 |
| 900029-7-B | single siRNA, 0.9 nmol | 822 | 5999 | RGS4 | regulator of G-protein signalling 4 | NM_005613 | CTGGATTCTTGCACCAGGGAA | SI03097766 | Hs_RGS4_10 |
| 900049-7-B | single siRNA, 0.9 nmol | 823 | 6195 | RPS6KA1 | ribosomal protein S6 kinase, 90 kDa, polypeptide 1 | NM_001006665 NM_002953 | CCCAACATCATCACTCTGAAA | SI02223060 | Hs_RPS6KA1_9 |
| 900029-7-B | single siRNA, 0.9 nmol | 824 | 6307 | SC4MOL | sterol-C4-methyl oxidase-like | NM_001017369 NM_006745 | CTCTCAGTATATGCCTATAA | SI03205398 | Hs_SC4MOL_7 |
| 900029-7-B | single siRNA, 0.9 nmol | 825 | 6590 | SLPI | secretory leukocyte peptidase inhibitor | NM_003064 | CAGTGCCTTAGATACAAGAAA | SI00726397 | Hs_SLPI_3 |
| 900029-7-B | single siRNA, 0.9 nmol | 826 | 6643 | SNX2 | sorting nexin 2 | NM_003100 | CTGATCAGCAACTTAGGAGAA | SI00728840 | Hs_SNX2_4 |
| 900029-7-B | single siRNA, 0.9 nmol | 827 | 6713 | SQLE | squalene epoxidase | NM_003129 | CTCGAGTACTTGTTGACATTA | SI03091123 | Hs_SQLE_5 |
| 900029-7-B | single siRNA, 0.9 nmol | 828 | 6774 | STAT3 | signal transducer and activator of transcription 3 (acute-phase response factor) | NM_003150 NM_139276 NM_213662 | CAGCCTCTCTGCAGAATTCAA | SI02662338 | Hs_STAT3_7 |
| 900029-7-B | single siRNA, 0.9 nmol | 829 | 6789 | STK4 | serine/threonine kinase 4 | NM_006282 | AGGATTCATAGCATCACTATA | SI02622270 | Hs_STK4_5 |
| 900029-7-B | single siRNA, 0.9 nmol | 830 | 7029 | TFDP2 | transcription factor Dp-2 (E2F dimerization partner 2) | NM_006286 | CAGAGGCGGATAGAACCGATA | SI00086954 | Hs_TFDP2_4 |
| 900029-7-B | single siRNA, 0.9 nmol | 831 | 5922 | RASA2 | RAS p21 protein activator 2 | NM_006506 | CTACCTGAAAGTAACATTAAA | SI00698733 | Hs_RASA2_3 |
| 900029-7-B | single siRNA, 0.9 nmol | 832 | 6004 | RGS16 | regulator of G-protein signalling 16 | NM_002928 | CAGACTGTTCTGGCACGGAA | SI03063760 | Hs_RGS16_6 |
| 900029-7-B | single siRNA, 0.9 nmol | 833 | 6196 | RPS6KA2 | ribosomal protein S6 kinase, 90 kDa, polypeptide 2 | NM_001006932 NM_021135 | CCGAGTGAGATCGAAGATGAA | SI02224999 | Hs_RPS6KA2_9 |
| 900029-7-B | single siRNA, 0.9 nmol | 834 | 6387 | CXCL12 | chemokine (C-X-C motif) ligand 12 | NM_000609 | CTGAAGAACAACAACAGACAA | SI03649100 | Hs_CXCL12_10 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-7-B | single siRNA, 0.9 nmol | 835 | 6598 | SMARCB1 | SWI/SNF related, matrix associated, actin dependent regulator of chromatin, subfamily b, member 1 (stromal cell-derived factor 1) | NM_001033886 NM_199168 NM_001007468 NM_003073 | ACCAGAGAAGTTGCCCTGAA | SI00726817 | Hs_SMARCB1_3 |
| 900029-7-B | single siRNA, 0.9 nmol | 836 | 6654 | SOS1 | son of sevenless homolog 1 (Drosophila) | NM_005633 | TGGGTTGAATCCATCACTAAA | SI00079807 | Hs_SOS1_3 |
| 900029-7-B | single siRNA, 0.9 nmol | 837 | 6714 | SRC | v-src sarcoma (Schmidt-Ruppin A-2) viral oncogene homolog (avian) | NM_005417 NM_198291 | CGGCTTGTGGGTGATGTTTGA | SI02223928 | Hs_SRC_7 |
| 900029-7-B | single siRNA, 0.9 nmol | 838 | 6775 | STAT4 | signal transducer and activator of transcription 4 | NM_003151 | TGGAATCAAGTCCAACAGTTA | SI00048405 | Hs_STAT4_3 |
| 900029-7-B | single siRNA, 0.9 nmol | 839 | 6790 | AURKA | aurora kinase A | NM_003600 NM_198433 NM_198434 NM_198435 NM_198436 NM_198437 | TCCCAGCGCATTCCTTTGCAA | SI03114111 | Hs_AURKA_1 |
| 900029-7-B | single siRNA, 0.9 nmol | 840 | 7039 | TGFA | transforming growth factor, alpha | NM_003236 | AAGCCGTAAATGCCTCAATA | SI00049448 | Hs_TGFA_4 |
| 900029-8-A | single siRNA, 0.9 nmol | 841 | 7046 | TGFBR1 | transforming growth factor, beta receptor I (activin A receptor type II-like kinase, 53 kDa) | NM_004612 | CTGCCTTATTATGATCTTGTA | SI02664158 | Hs_TGFBR1_9 |
| 900029-8-A | single siRNA, 0.9 nmol | 842 | 7112 | TMPO | thymopoietin | NM_001032283 NM_001032284 NM_003276 | CCCAGACAAGAAGATAAAGAT | SI03183061 | Hs_TMPO_6 |
| 900029-8-A | single siRNA, 0.9 nmol | 843 | 7278 | TUBA3C | tubulin, alpha 3c | NM_006001 | TGGATTTAAGGTGGGCATTAA | SI03119858 | Hs_TUBA2_8 |
| 900029-8-A | single siRNA, 0.9 nmol | 844 | 7520 | XRCC5 | X-ray repair complementing defective repair in Chinese hamster cells 5 (double-strand-break rejoining; Ku autoantigen, 80 kDa) | NM_021141 | AAGCGAGTAACCAGCTCATAA | SI02663773 | Hs_XRCC5_7 |
| 900029-8-A | single siRNA, 0.9 nmol | 845 | 7620 | ZNF69 | zinc finger protein 69 | NM_021915 | TTTGGCCATGTTTATGATTGA | SI03245186 | Hs_ZNF69_8 |
| 900029-8-A | single siRNA, 0.9 nmol | 846 | 8396 | PIP5K2B | phosphatidylinositol-4-phosphate 5-kinase, type II, beta | NM_003559 | CACGATCAATGAGCTGAGCAA | SI02660133 | Hs_PIP5K2B_9 |
| 900029-8-A | single siRNA, 0.9 nmol | 847 | 8560 | DEGS1 | degenerative spermatocyte homolog 1, lipid desaturase (Drosophila) | NM_138687 NM_003676 | TACGTATCTGGAAGTTATCAA | SI03109946 | Hs_DEGS1_8 |
| 900029-8-A | single siRNA, 0.9 nmol | 848 | 8737 | RIPK1 | receptor (TNFRSF)-interacting serine-threonine kinase 1 | NM_144780 NM_003804 | CCCACATTTCCTTGGCATTGAA | SI02621983 | Hs_RIPK1_6 |
| 900029-8-A | single siRNA, 0.9 nmol | 849 | 8915 | BCL10 | B-cell CLL/lymphoma 10 | NM_003921 | CTTGTCGAACATCAAGTAGAA | SI03100958 | Hs_BCL10_8 |
| 900029-8-A | single siRNA, 0.9 nmol | 850 | 9093 | DNAJA3 | DnaJ (Hsp40) homolog, subfamily A, member 3 | NM_005147 | ATGATTCTGTATTAATGTAAA | SI00370678 | Hs_DNAJA3_4 |
| 900029-8-A | single siRNA, 0.9 nmol | 851 | 7071 | KLF10 | Kruppel-like factor 10 | NM_001032282 NM_005655 | CCGGCGGTTCATGAGGAGTGA | SI03082268 | Hs_KLF10_9 |
| 900329-8-A | single siRNA, 0.9 nmol | 852 | 7157 | TP53 | tumor protein p53 (Li-Fraumeni syndrome) | NM_000546 | AAGGAAATTTGCGTGTGGAGT | SI02655170 | Hs_TP53_9 |
| 900029-8-A | single siRNA, 0.9 nmol | 853 | 7332 | UBE2L3 | ubiquitin-conjugating enzyme E2L 3 | NM_003347 NM_198157 | CCGCACTAGTAGAAGAATCCAT | SI03188563 | Hs_UBE2L3_5 |
| 900029-8-A | single siRNA, 0.9 nmol | 854 | 7525 | YES1 | v-yes-1 Yamaguchi sarcoma viral oncogene homolog 1 | NM_005433 | GAGGCTCCTGCTTATTTATAA | SI02223942 | Hs_YES1_7 |
| 900029-8-A | single siRNA, 0.9 nmol | 855 | 7791 | ZYX | zyxin | NM_001010972 NM_003461 | AAGGTGAGCAGTATTGATTG | SI00302225 | Hs_ZYX_1 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-8-A | single siRNA, 0.9 nmol | 856 | 8412 | BCAR3 | breast cancer anti-estrogen resistance 3 | NM_003567 | CCGGAACTCTGCGTCAACTA | SI03081603 | Hs BCAR3 6 |
| 900029-8-A | single siRNA, 0.9 nmol | 857 | 8651 | SOCS1 | suppressor of cytokine signaling 1 | NM_003745 | TACCCAGTATCTTTGCACAAA | SI03108812 | Hs SOCS1 6 |
| 900029-8-A | single siRNA, 0.9 nmol | 858 | 8761 | PABPC4 | poly(A) binding protein, cytoplasmic 4 (inducible form) | NM_003819 | AACTTGATGTGATTAAGGGA | SI00301035 | Hs PABPC4 1 |
| 900029-8-A | single siRNA, 0.9 nmol | 859 | 8945 | BTRC | beta-transducin repeat containing | NM_003939 NM_033637 | CAGGATAGCAACAACAGTAA | SI02632322 | Hs BTRC 10 |
| 900029-8-A | single siRNA, 0.9 nmol | 860 | 9134 | CCNE2 | cyclin E2 | NM_004702 NM_057735 NM_057749 | CTCCAAGTTGATGCTCTTAAA | SI02653238 | Hs CCNE2 8 |
| 900029-8-A | single siRNA, 0.9 nmol | 861 | 7082 | TJP1 | tight junction protein 1 (zona occludens 1) | NM_003257 NM_175610 | CCAGTATCTGATAATGAAGAA | SI02655149 | Hs TJP1 7 |
| 900029-8-A | single siRNA, 0.9 nmol | 862 | 7171 | TPM4 | tropomyosin 4 | NM_003290 | CTGGCCCAACTTCATTTCCAT | SI03211551 | Hs TPM4 5 |
| 900029-8-A | single siRNA, 0.9 nmol | 863 | 7386 | UQCRFS1 | ubiquinol-cytochrome c reductase, Rieske iron-sulfur polypeptide 1 | NM_006003 | TAGATAGTACGAAGTCTTCAA | SI03227154 | Hs_UQCRFS1_6 |
| 900029-8-A | single siRNA, 0.9 nmol | 864 | 7529 | YWHAB | tyrosine 3-monooxygenase/tryptophan 5-monooxygenase activation protein, beta polypeptide | NM_003404 NM_139323 | AAAGAGTACCGTGAGAAGATA | SI03026499 | Hs_YWHAB_6 |
| 900029-8-A | single siRNA, 0.9 nmol | 865 | 7846 | TUBA1A | tubulin, alpha 1a | NM_006009 | AAGTTGTGGTCTGATCAGTTA | SI03037251 | Hs TUBA3 5 |
| 900029-8-A | single siRNA, 0.9 nmol | 866 | 8440 | NCK2 | NCK adaptor protein 2 | NM_001004720 NM_001004722 | GACGGGCTATGTACCGTCCAA | SI03102190 | Hs NCK2 11 |
| 900029-8-A | single siRNA, 0.9 nmol | 867 | 8655 | DYNLL1 | dynein, light chain, LC8-type 1 | NM_003746 NM_001037494 NM_001037495 | CAGAATAGCCTACATTTGTAT | SI03167052 | Hs DYNLL1 3 |
| 900029-8-A | single siRNA, 0.9 nmol | 868 | 8805 | TRIM24 | tripartite motif-containing 24 | NM_003852 NM_015905 | CAGAACGGTCCAGTCACCAAA | SI03062899 | Hs TRIM24 1 |
| 900029-8-A | single siRNA, 0.9 nmol | 869 | 8976 | WASL | Wiskott-Aldrich syndrome-like | NM_003941 | AACCTTAATGTAATTTACTTA | SI02757692 | Hs WASL 7 |
| 900029-8-A | single siRNA, 0.9 nmol | 870 | 9231 | DLG5 | discs, large homolog 5 (Drosophila) | NM_004747 | CTGTGGCATATTTGTCACTAA | SI00067879 | Hs DLG5 4 |
| 900029-8-A | single siRNA, 0.9 nmol | 871 | 7090 | TLE3 | transducin-like enhancer of split 3 (E(sp1) homolog, Drosophila) | NM_005078 | CACCATGAACTCGATCACAGA | SI00745696 | Hs_TLE3_4 |
| 900029-8-A | single siRNA, 0.9 nmol | 872 | 7175 | TPR | translocated promoter region (to activated MET oncogene) | NM_003292 | CAGCGTGATATGTACCGTATT | SI03172260 | Hs_TPR_5 |
| 900029-8-A | single siRNA, 0.9 nmol | 873 | 7409 | VAV1 | vav 1 oncogene | NM_005428 | CAAGGAGAGGTTCCTCGTCTA | SI03054401 | Hs VAV1 5 |
| 900029-8-A | single siRNA, 0.9 nmol | 874 | 7531 | YWHAE | tyrosine 3-monooxygenase/tryptophan 5-monooxygenase activation protein, epsilon polypeptide | NM_006761 | ACCATTAGCAAATGGAAATTA | SI03038868 | Hs_YWHAE_8 |
| 900029-8-A | single siRNA, 0.9 nmol | 875 | 8379 | MAD1L1 | MAD1 mitotic arrest deficient-like 1 (yeast) | NM_001013836 NM_001013837 NM_003550 | CACGCTCAGGTTGAAGGTCGA | SI03060365 | Hs MAD1L1 7 |
| 900329-8-A | single siRNA, 0.9 nmol | 876 | 8492 | PRSS12 | protease, serine, 12 (neurotrypsin, motopsin) | NM_003619 | CTTCAGTGTAGTGGAAGTGATA | SI00053830 | Hs PRSS12 4 |
| 900029-8-A | single siRNA, 0.9 nmol | 877 | 8660 | IRS2 | insulin receptor substrate 2 | NM_003749 | CAGTGTATTGACGCATATTTA | SI02662583 | Hs IRS2 6 |
| 900029-8-A | single siRNA, 0.9 nmol | 878 | 8825 | LIN7A | lin-7 homolog A (C. elegans) | NM_004664 | CCCATTATATCTCTCCGCATA | SI00066822 | Hs LIN7A 3 |
| 900029-8-A | single siRNA, 0.9 nmol | 879 | 9020 | MAP3K14 | mitogen-activated protein kinase kinase kinase 14 | NM_003954 | TACCTAGTGCATGCTCTGCAA | SI02632343 | Hs MAP3K14 6 |
| 900029-8-A | single siRNA, 0.9 nmol | 880 | 9252 | RPS6KA5 | ribosomal protein S6 kinase, 90 kDa, polypeptide 5 | NM_182398 | CTGGATCTCTTACGTAATTCA | SI02225440 | Hs RPS6KA5 9 |
| 900029-8-A | single siRNA, 0.9 nmol | 881 | 7094 | TLN1 | talin 1 | NM_006289 | AACAGAGACCCCTGAAGATCC | SI00301931 | Hs TLN1 5 |
| 900329-8-A | single siRNA, 0.9 nmol | 882 | 7184 | HSP90B1 | heat shock protein 90 kDa beta (Grp94), | NM_003299 | TCGCCTCCAGTTTGAACATTGA | SI02663738 | Hs TRA1 9 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900020-8-A | single siRNA, 0.9 nmol | 883 | 7410 | VAV2 | vav 2 oncogene | NM_003371 | CTGAAAGTCTGCCACGATAAA | SI02662947 | Hs_VAV2_6 |
| 900029-8-A | single siRNA, 0.9 nmol | 884 | 7534 | YWHAZ | tyrosine 3-monooxygenase/tryptophan 5-monooxygenase activation protein, zeta polypeptide | NM_003406 NM_145690 | CAATCCAAGCATATAATTGTTAA | SI03158295 | Hs_YWHAZ_5 |
| 900029-8-A | single siRNA, 0.9 nmol | 885 | 8394 | PIP5K1A | phosphatidylinositol-4-phosphate 5-kinase, type I, alpha | NM_003557 | CCCTGCCTTGATAATATGTTA | SI02223263 | Hs_PIP5K1A_6 |
| 900029-8-A | single siRNA, 0.9 nmol | 886 | 8503 | PIK3R3 | phosphoinositide-3-kinase, regulatory subunit 3 (p55, gamma) | NM_003629 | ATGAATTATGATAAATTGAAA | SI02777446 | Hs_PIK3R3_9 |
| 900029-8-A | single siRNA, 0.9 nmol | 887 | 8662 | EIF3S9 | eukaryotic translation initiation factor 3, subunit 9 eta, 116 kDa | NM_001037283 NM_003751 NM_182712 | CCGCACTTCCATATTCTGGAA | SI00377846 | Hs_EIF3S9_4 |
| 900029-8-A | single siRNA, 0.9 nmol | 888 | 8826 | IQGAP1 | IQ motif containing GTPase activating protein 1 | NM_003870 | AAGGAGACGTCAGAACGTGGC | SI02655268 | Hs_IQGAP1_5 |
| 900029-8-A | single siRNA, 0.9 nmol | 889 | 9021 | SOCS3 | suppressor of cytokine signaling 3 | NM_003955 | TCGGAGTTCCTGGACCAGTA | SI00058345 | Hs_SOCS3_1 |
| 900029-8-A | single siRNA, 0.9 nmol | 890 | 9260 | PDLIM7 | PDZ and LIM domain 7 (enigma) | NM_005451 NM_203352 NM_213636 | CTGAGCATCGATGGCGAGAAT | SI03093405 | Hs_PDLIM7_10 |
| 900029-8-A | single siRNA, 0.9 nmol | 891 | 7109 | TMEM1 | transmembrane protein 1 | NM_001001723 NM_003274 | TCCGAAGATGATTCACCTAGA | SI03114860 | Hs_TMEM1_8 |
| 900029-8-A | single siRNA, 0.9 nmol | 892 | 7205 | TRIP6 | thyroid hormone receptor interactor 6 | NM_003302 | CAGGAGGAGACTGTGAGAATT | SI03069654 | Hs_TRIP6_5 |
| 900029-8-A | single siRNA, 0.9 nmol | 893 | 7424 | VEGFC | vascular endothelial growth factor C | NM_005429 | TTGCTGCAGCACATTATAATA | SI02664221 | Hs_VEGFC_6 |
| 900029-8-A | single siRNA, 0.9 nmol | 894 | 7535 | ZAP70 | zeta-chain (TCR) associated protein kinase 70 kDa | NM_001079 NM_207519 | CACGGAGAGATGATGCCGA | SI03060540 | Hs_ZAP70_6 |
| 900029-8-A | single siRNA, 0.9 nmol | 895 | 8395 | PIP5K1B | phosphatidylinositol-4-phosphate 5-kinase, type I, beta | NM_001031687 NM_003558 | AAGGGTTACCTTCCAGTTCAA | SI03571155 | Hs_PIP5K1B_7 |
| 900029-8-A | single siRNA, 0.9 nmol | 896 | 8517 | IKBKG | inhibitor of kappa light polypeptide gene enhancer in B-cells, kinase gamma | NM_003639 | TTCGGAAATGCCTCACATATA | SI02223340 | Hs_IKBKG_6 |
| 900029-8-A | single siRNA, 0.9 nmol | 897 | 8723 | SNX4 | sorting nexin 4 | NM_003794 | TGGCGGCGATATAGTGAATT | SI03120376 | Hs_SNX4_10 |
| 900029-8-A | single siRNA, 0.9 nmol | 898 | 8882 | ZNF259 | zinc finger protein 259 | NM_003904 | TAGGAGGAAACCCAGAAATGA | SI03228267 | Hs_ZNF259_8 |
| 900029-8-A | single siRNA, 0.9 nmol | 899 | 9046 | DOK2 | docking protein 2, 56 kDa | NM_003974 NM_201349 | GAGTATGACAATGTTGTACTA | SI03104346 | Hs_DOK2_6 |
| 900029-8-A | single siRNA, 0.9 nmol | 900 | 9261 | MAPKAPK2 | mitogen-activated protein kinase-activated protein kinase 2 | NM_004759 NM_032960 | CTACGAGCAGATCAAGATAAA | SI02223697 | Hs_MAPKAPK2_5 |
| 900029-8-B | single siRNA, 0.9 nmol | 901 | 7046 | TGFBR1 | transforming growth factor, beta receptor I (activin A receptor type II-like kinase, 53 kDa) | NM_004612 | TGGGATTGTACTATACCAGTA | SI02223634 | Hs_TGFBR1_7 |
| 900029-8-B | single siRNA, 0.9 nmol | 902 | 7112 | TMPO | thymopoietin | NM_001032283 NM_001032284 NM_003276 | TAGATGTAACAGAGCTCACTA | SI03227217 | Hs_TMPO_9 |
| 900029-8-B | single siRNA, 0.9 nmol | 903 | 7278 | TUBA3C | tubulin, alpha 3c | NM_006001 NM_079836 | CAGCTGATCACCGGGAAGGAA | SI03068296 | Hs_TUBA2_7 |
| 900029-8-B | single siRNA, 0.9 nmol | 904 | 7520 | XRCC5 | X-ray repair complementing defective repair in Chinese hamster cells 5 (double-strand-break rejoining; Ku autoantigen, 80 kDa) | NM_021141 | AAGCATAAACTATGAGTGTTTA | SI02663766 | Hs_XRCC5_6 |
| 900029-8-B | single siRNA, 0.9 nmol | 905 | 7620 | ZNF69 | zinc finger protein 69 | NM_021915 | TACCAACAGTTATCTCATGTA | SI03222417 | Hs_ZNF69_7 |
| 900029-8-B | single siRNA, 0.9 nmol | 906 | 8396 | PIP5K2B | phosphatidylinositol-4-phosphate 5- | NM_003559 | GCGGAGATGCAACACATCTTA | SI02660126 | Hs_PIP5K2B_8 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-8-B | single siRNA, 0.9 nmol | 907 | 8560 | DEGS1 | degenerative spermatocyte homolog 1, lipid desaturase (Drosophila) | NM_138687 NM_003676 | ATGCGTTTGGCAGTTGCATTA | SI03050201 | Hs_DEGS1_7 |
| 900029-8-B | single siRNA, 0.9 nmol | 908 | 8737 | RIPK1 | receptor (TNFRSF)-interacting serine-threonine kinase 1 | NM_144780 NM_003804 | TACCACTAGTCTGACGGATAA | SI00288092 | Hs_RIPK1_5 |
| 900029-8-B | single siRNA, 0.9 nmol | 909 | 8915 | BCL10 | B-cell CLL/lymphoma 10 | NM_003921 | CAGAAGGAGAATCCAGCACGA | SI03063144 | Hs_BCL10_7 |
| 900029-8-B | single siRNA, 0.9 nmol | 910 | 9093 | DNAJA3 | DnaJ (Hsp40) homolog, subfamily A, member 3 | NM_005147 | TCCGACCTCTTATTTCTATA | SI00370671 | Hs_DNAJA3_3 |
| 900029-8-B | single siRNA, 0.9 nmol | 911 | 7071 | KLF10 | Kruppel-like factor 10 | NM_001032282 NM_005655 | AGCCCGTTGTGCAGAGTTCAA | SI03043236 | Hs_KLF10_8 |
| 900029-8-B | single siRNA, 0.9 nmol | 912 | 7157 | TP53 | tumor protein p53 (Li-Fraumeni syndrome) | NM_000546 | CAGAGTGCATTGTGAGGGTTA | SI00011655 | Hs_TP53_3 |
| 900029-8-B | single siRNA, 0.9 nmol | 913 | 7332 | UBE2L3 | ubiquitin-conjugating enzyme E2L 3 | NM_003347 NM_198157 | CACACTCCAGTTTGTAATAAA | SI00754649 | Hs_UBE2L3_3 |
| 900029-8-B | single siRNA, 0.9 nmol | 914 | 7525 | YES1 | v-yes-1 Yamaguchi sarcoma viral oncogene homolog 1 | NM_005433 | CCAGCCTACATTCACTTCTAA | SI02223935 | Hs_YES1_6 |
| 900029-8-B | single siRNA, 0.9 nmol | 915 | 7791 | ZYX | zyxin | NM_001010972 NM_003461 | ACCAAGAATGATCCTTTCAAA | SI02651334 | Hs_ZYX_5 |
| 900029-8-B | single siRNA, 0.9 nmol | 916 | 8412 | BCAR3 | breast cancer anti-estrogen resistance 3 | NM_003567 | CCGAGCGCCACTCAGCTGAGTAA | SI03080196 | Hs_BCAR3_5 |
| 900029-8-B | single siRNA, 0.9 nmol | 917 | 8651 | SOCS1 | suppressor of cytokine signaling 1 | NM_003745 | TAAAGTCAGTTTAGGTAATAA | SI03107342 | Hs_SOCS1_5 |
| 900029-8-B | single siRNA, 0.9 nmol | 918 | 8761 | PABPC4 | poly(A) binding protein, cytoplasmic 4 (inducible form) | NM_003819 | ACGGAAATTTGAACAGTTGAA | SI02651474 | Hs_PABPC4_7 |
| 900029-8-B | single siRNA, 0.9 nmol | 919 | 8945 | BTRC | beta-transducin repeat containing | NM_003939 NM_033637 | CACGTTGATTCACCATTGTGA | SI03061807 | Hs_BTRC_11 |
| 900029-8-B | single siRNA, 0.9 nmol | 920 | 9134 | CCNE2 | cyclin E2 | NM_004702 NM_057735 NM_057749 | AAGAAGAGTATTAAATATATA | SI02653035 | Hs_CCNE2_7 |
| 900029-8-B | single siRNA, 0.9 nmol | 921 | 7082 | TJP1 | tight junction protein 1 (zona occludens 1) | NM_003257 NM_175610 | AAGGATCCATATCCGAGGAA | SI03034983 | Hs_TJP1_8 |
| 900029-8-B | single siRNA, 0.9 nmol | 922 | 7171 | TPM4 | tropomyosin 4 | NM_003290 | TTGCATATTTCCTTCATTCTA | SI00750148 | Hs_TPM4_4 |
| 900029-8-B | single siRNA, 0.9 nmol | 923 | 7386 | UQCRFS1 | ubiquinol-cytochrome c reductase, Rieske iron-sulfur polypeptide 1 | NM_006003 | ATGCTCAGTCATCACACGCGAA | SI03152765 | Hs_UQCRFS1_5 |
| 900029-8-B | single siRNA, 0.9 nmol | 924 | 7529 | YWHAB | tyrosine 3-monooxygenase/tryptophan 5-monooxygenase activation protein, beta polypeptide | NM_033404 NM_139323 | CAGCAATATGTTCACTATGTT | SI02631104 | Hs_YWHAB_5 |
| 900029-8-B | single siRNA, 0.9 nmol | 925 | 7846 | TUBA1A | tubulin, alpha 1a | NM_006009 | TCCAACCTATACTAACCTGAA | SI00753305 | Hs_TUBA3_3 |
| 900029-8-B | single siRNA, 0.9 nmol | 926 | 8440 | NCK2 | NCK adaptor protein 2 | NM_001004720 NM_001004722 | GACACTAATACAGATGATTAA | SI02624993 | Hs_NCK2_9 |
| 900029-8-B | single siRNA, 0.9 nmol | 927 | 8655 | DYNLL1 | dynein, light chain, LC8-type 1 | NM_003581 NM_001037494 NM_001037495 | CACACCCAGTGATCCATCCAA | SI03158939 | Hs_DYNLL1_2 |
| 900029-8-B | single siRNA, 0.9 nmol | 928 | 8805 | TRIM24 | tripartite motif-containing 24 | NM_003852 NM_015905 | CCGAGACTTATCTAAACCAGA | SI00056805 | Hs_TIF1_4 |
| 900029-8-B | single siRNA, 0.9 nmol | 929 | 8976 | WASL | Wiskott-Aldrich syndrome-like | NM_003941 | CAGATACGACAGGGTATCCAA | SI02664263 | Hs_WASL_6 |
| 900029-8-B | single siRNA, 0.9 nmol | 930 | 9231 | DLG5 | discs, large homolog 5 (Drosophila) | NM_004747 | TTGCTCGTTTGTCGACTATAA | SI00067872 | Hs_DLG5_5 |
| 900029-8-B | single siRNA, 0.9 nmol | 931 | 7090 | TLE3 | transducin-like enhancer of split 3 (E(sp1) homolog, Drosophila) | NM_005078 | CCCGGGCAGCCGGGATTTAAA | SI00745689 | Hs_TLE3_3 |
| 900029-8-B | single siRNA, 0.9 nmol | 932 | 7175 | TPR | translocated promoter region (to activated MET oncogene) | NM_003292 | GAGGGTGAAGAGTAGTAATGAA | SI00750232 | Hs_TPR_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-8-B | 0.9 nmol single siRNA, | 933 | 7409 | VAV1 | vav 1 oncogene | NM_005428 | GTCGAGGTCAAGCAGCATTAAA | SI00077021 | Hs_VAV1_4 |
| 900029-8-B | 0.9 nmol single siRNA, | 934 | 7531 | YWHAE | tyrosine 3-monooxygenase/tryptophan 5-monooxygenase activation protein, epsilon polypeptide | NM_006761 | AAGCATCTAAGAGAGAGGTTA | SI03033023 | Hs_YWHAE_7 |
| 900029-8-B | 0.9 nmol single siRNA, | 935 | 8379 | MAD1L1 | MAD1 mitotic arrest deficient-like 1 (yeast) | NM_001013836 NM_001013837 NM_003550 | CACGAGCAGCAGATTAAGGAT | SI03059791 | Hs_MAD1L1_6 |
| 900029-8-B | 0.9 nmol single siRNA, | 936 | 8492 | PRSS12 | protease, serine, 12 (neurotrypsin, motopsin) | NM_003619 | AAGCGGATCATTGGTGGGAAA | SI00053823 | Hs_PRSS12_3 |
| 900029-8-B | 0.9 nmol single siRNA, | 937 | 8660 | IRS2 | insulin receptor substrate 2 | NM_003749 | TCGCTATAGAATAATGCATTA | SI02662037 | Hs_IRS2_5 |
| 900029-8-B | 0.9 nmol single siRNA, | 938 | 8825 | LIN7A | lin-7 homolog A (C. elegans) | NM_004664 | TTCGAGAGGTGTATCAATATA | SI00066815 | Hs_LIN7A_2 |
| 900029-8-B | 0.9 nmol single siRNA, | 939 | 9020 | MAP3K14 | mitogen-activated protein kinase kinase kinase 14 | NM_003954 | CACATGCATGTGACTCCTCAA | SI02632336 | Hs_MAP3K14_5 |
| 900029-8-B | 0.9 nmol single siRNA, | 940 | 9252 | RPS6KA5 | ribosomal protein S6 kinase, 90 kDa, polypeptide 5 | NM_004755 NM_182398 | AAGCCAGTCATTCGAGATGAA | SI02225433 | Hs_RPS6KA5_8 |
| 900029-8-B | 0.9 nmol single siRNA, | 941 | 7094 | TLN1 | talin 1 | NM_006289 | TGGGAAAGCTTTGGACTACTA | SI00086982 | Hs_TLN1_4 |
| 900029-8-B | 0.9 nmol single siRNA, | 942 | 7184 | HSP90B1 | heat shock protein 90 kDa beta (rp94), member 1 | NM_003299 | AAGTTGATGTGGATGGTACAT | SI02655177 | Hs_TRA1_8 |
| 900029-8-B | 0.9 nmol single siRNA, | 943 | 7410 | VAV2 | vav 2 oncogene | NM_003371 | TTGGCGATGTACATCAATGAA | SI02662380 | Hs_VAV2_5 |
| 900029-8-B | 0.9 nmol single siRNA, | 944 | 7534 | YWHAZ | tyrosine 3-monooxygenase/tryptophan 5-monooxygenase activation protein, zeta polypeptide | NM_003406 NM_145690 | CAGGTTTATGTTACTTCTATT | SI00764813 | Hs_YWHAZ_3 |
| 900029-8-B | 0.9 nmol single siRNA, | 945 | 8394 | PIP5K1A | phosphatidylinositol-4-phosphate 5-kinase, type I, alpha | NM_003557 | CAGCCTCTTGATGTCAATCCA | SI02223256 | Hs_PIP5K1A_5 |
| 900029-8-B | 0.9 nmol single siRNA, | 946 | 8503 | PIK3R3 | phosphoinositide-3-kinase, regulatory subunit 3 (p55, gamma) | NM_003629 | CAGGGCTGTAGTATTCAGTAA | SI02777439 | Hs_PIK3R3_8 |
| 900029-8-B | 0.9 nmol single siRNA, | 947 | 8662 | EIF3S9 | eukaryotic translation initiation factor 3, subunit 9 eta,116 kDa | NM_001037283 NM_003751 NM_182712 | CAGGTTGAACATGGAAATAAA | SI03077839 | Hs_EIF3S9_3 |
| 900029-8-B | 0.9 nmol single siRNA, | 948 | 8826 | IQGAP1 | IQ motif containing GTPase activating protein 1 | NM_003870 | TCCTATGTTGTGGTCCGAAA | SI03115770 | Hs_IQGAP1_6 |
| 900029-8-B | 0.9 nmol single siRNA, | 949 | 9021 | SOCS3 | suppressor of cytokine signaling 3 | NM_003955 | CAGAAGAGCCTATTACATCTA | SI03062997 | Hs_SOCS3_7 |
| 900029-8-B | 0.9 nmol single siRNA, | 950 | 9260 | PDLIM7 | PDZ and LIM domain 7 (enigma) | NM_005451 NM_203352 NM_203353 | AGGCACCCAGTTCATGCAAGA | SI03044979 | Hs_PDLIM7_9 |
| 900029-8-B | 0.9 nmol single siRNA, | 951 | 7109 | TMEM1 | transmembrane protein 1 | NM_001001723 NM_003274 | CTGGTTAATAGTCGATAGTTGA | SI03099999 | Hs_TMEM1_7 |
| 900029-8-B | 0.9 nmol single siRNA, | 952 | 7205 | TRIP6 | thyroid hormone receptor interactor 6 | NM_003302 | TGGGCTGCTTGTCTATGTTCTA | SI02630866 | Hs_TRIP6_4 |
| 900029-8-B | 0.9 nmol single siRNA, | 953 | 7424 | VEGFC | vascular endothelial growth factor C | NM_005429 | CACGGCTTATGCAAGCAAAGA | SI03060939 | Hs_VEGFC_7 |
| 900029-8-B | 0.9 nmol single siRNA, | 954 | 7535 | ZAP70 | zeta-chain (TCR) associated protein kinase 70 kDa | NM_011079 NM_207519 | CCGCAACCTCCTGCTGGTTAA | SI00021672 | Hs_ZAP70_3 |
| 900029-8-B | 0.9 nmol single siRNA, | 955 | 8395 | PIP5K1B | phosphatidylinositol-4-phosphate 5-kinase, type I, beta | NM_003558 | TACACTCTATTCAAACAGCAA | SI02660273 | Hs_PIP5K1B_5 |
| 900029-8-B | 0.9 nmol single siRNA, | 956 | 8517 | IKBKG | inhibitor of kappa light polypeptide gene enhancer in B-cells, kinase gamma | NM_003639 | CTCCTCTAGTTCAGAGACATA | SI02923333 | Hs_IKBKG_5 |
| 900029-8-B | 0.9 nmol single siRNA, | 957 | 8723 | SNX4 | sorting nexin 4 | NM_003794 | AGGACGGATTGGTTTAGAA | SI03045168 | Hs_SNX4_9 |
| 900029-8-B | 0.9 nmol single siRNA, | 958 | 8882 | ZNF259 | zinc finger protein 259 | NM_003904 | CAGCTTGTGATGCAAGTGTGA | SI03173311 | Hs_ZNF259_7 |
| 900029-8-B | 0.9 nmol single siRNA, | 959 | 9046 | DOK2 | docking protein 2, 56 kDa | NM_003974 | TTGGGCTGCTTGCTTGCTATGCAA | SI03025344 | Hs_DOK2_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-8-B | single siRNA, 0.9 nmol | 960 | 9261 | MAPKAPK2 | mitogen-activated protein kinase-activated protein kinase 2 | NM_201349 NM_004759 | CGCCATCATCGATGACTACAA | SI00288246 | Hs_MAPKAPK2_6 |
| 900029-9-A | single siRNA, 0.9 nmol | 961 | 9320 | TRIP12 | thyroid hormone receptor interactor 12 | NM_032960 NM_004238 | CAGATGTTTCATCATTTGAAA | SI04023145 | Hs_TRIP12_8 |
| 900029-9-A | single siRNA, 0.9 nmol | 962 | 9564 | BCAR1 | breast cancer anti-estrogen resistance 1 | NM_014567 NM_014776 | AAGCAGTTGAACGACTGGAA | SI02757741 | Hs_BCAR1_6 |
| 900029-9-A | single siRNA, 0.9 nmol | 963 | 9615 | GIT2 | G protein-coupled receptor kinase interactor 2 | NM_057169 NM_057170 NM_139201 | CCCGTTGATTATGCAAGCAA | SI02660420 | Hs_GIT2_6 |
| 900029-9-A | single siRNA, 0.9 nmol | 964 | 10044 | SH2D3C | SH2 domain containing 3C | NM_005489 NM_170600 | TAGGATACTGGGCGTTACCAA | SI03111717 | Hs_SH2D3C_6 |
| 900029-9-A | single siRNA, 0.9 nmol | 965 | 10188 | TNK2 | tyrosine kinase, non-receptor, 2 | NM_001010938 NM_005781 | CGGCAGTCAGATCCTGCATAA | SI02622151 | Hs_TNK2_6 |
| 900029-9-A | single siRNA, 0.9 nmol | 966 | 10278 | EFS | embryonal Fyn-associated substrate | NM_032459 NM_005864 | CAGCACTGCCACTGTTAGCTGA | SI03169929 | Hs_EFS_6 |
| 900029-9-A | single siRNA, 0.9 nmol | 967 | 10627 | MRCL3 | myosin regulatory light chain MRCL3 | NM_006471 | CGGGACTTTCTATTAATATCA | SI00647976 | Hs_MRCL3_4 |
| 900029-9-A | single siRNA, 0.9 nmol | 968 | 10971 | YWHAQ | tyrosine 3-monooxygenase/tryptophan 5-monooxygenase activation protein, theta polypeptide | NM_006826 | TCGGGAGAAAGTGGAGTCCGA | SI03117030 | Hs_YWHAQ_8 |
| 900029-9-A | single siRNA, 0.9 nmol | 969 | 11083 | DIDO1 | death inducer-obliterator 1 | NM_022105 NM_033081 NM_080796 NM_080797 | TAGCGAAGACCAAGGATAAA | SI03111185 | Hs_DIDO1_2 |
| 900029-9-A | single siRNA, 0.9 nmol | 970 | 23198 | PSME4 | proteasome (prosome, macropain) activator subunit 4 | NM_014614 | TAGGATTAAATTGGTTTCCTA | SI00695128 | Hs_PSME4_4 |
| 900029-9-A | single siRNA, 0.9 nmol | 971 | 9349 | RPL23 | ribosomal protein L23 | NM_000978 | TCCCAGTGTCCTTTGAATCGA | SI03231389 | Hs_RPL23_7 |
| 900029-9-A | single siRNA, 0.9 nmol | 972 | 9592 | IER2 | immediate early response 2 | NM_004907 | CGCCGTCGAGTCGCCATGGAA | SI03194079 | Hs_IER2_6 |
| 900029-9-A | single siRNA, 0.9 nmol | 973 | 9846 | GAB2 | GRB2-associated binding protein 2 | NM_012296 NM_080491 | CACTTGGCTACCCATCAACAA | SI03062570 | Hs_GAB2_8 |
| 900029-9-A | single siRNA, 0.9 anal | 974 | 10045 | SH2D3A | SH2 domain containing 3A | NM_005490 | GCCGTGATTTCTAGCAGTTGA | SI03105074 | Hs_SH2D3A_7 |
| 900029-9-A | single siRNA, 0.9 nmol | 975 | 10241 | CALCOCO2 | calcium binding and coiled-coil domain 2 | NM_005831 | CAGGGACTAACAAATGGAAA | SI00656040 | Hs_NDP52_4 |
| 900029-9-A | single siRNA, 0.9 nmol | 976 | 10376 | TUBA1B | tubulin, alpha 1b | NM_006082 | CAGCTTAACTGACAGACGTTA | SI02636634 | Hs_K-ALPHA-1_6 |
| 900029-9-A | single siRNA, 0.9 nmol | 977 | 10628 | TXNIP | thioredoxin interacting protein | NM_006472 | AAGAGCCAATTAACAACTA | SI03648827 | Hs_TXNIP_8 |
| 900029-9-A | single siRNA, 0.9 nmol | 978 | 10987 | COPS5 | COP9 constitutive photomorphogenic homolog subunit 5 (Arabidopsis) | NM_006837 | CTGGACTAAGGATCACCATTA | SI03096905 | Hs_COPS5_7 |
| 900029-9-A | single siRNA, 0.9 nmol | 979 | 11184 | MAP4K1 | mitogen-activated protein kinase kinase kinase kinase 1 | NM_001042600 NM_007181 | TACGTGGGTGTACTCCATCAA | SI02224257 | Hs_MAP4K1_6 |
| 900029-9-A | single siRNA, 0.9 nmol | 980 | 23236 | PLCB1 | phospholipase C, beta 1 (phosphoinositide-specific) | NM_015192 NM_182734 | CAGAGATGAATGGATCTGTAAA | SI02781184 | Hs_PLCB1_6 |
| 900029-9-A | single siRNA, 0.9 nmol | 981 | 9402 | GRAP2 | GRB2-related adaptor protein 2 | NM_004810 | CACAGTTAATGGATCTGTAAA | SI00068705 | Hs_GRAP2_4 |
| 900029-9-A | single siRNA, 0.9 nmol | 982 | 9618 | TRAF4 | TNF receptor-associated factor 4 | NM_004295 NM_145751 | CCGAGCTGGAAGTACAAGTA | SI02665159 | Hs_TRAF4_8 |
| 900029-9-A | single siRNA, 0.9 nmol | 983 | 9948 | WDR1 | WD repeat domain 1 | NM_005112 NM_017491 | AAAGTGCCTCATCCTAAGGAA | SI03122448 | Hs_WDR1_5 |
| 900329-9-A | single siRNA, 0.9 nmol | 984 | 10096 | ACTR3 | ARP3 actin-related protein 3 homolog (yeast) | NM_005721 | ATCGATGTTGGTTATGAGAGA | SI02664305 | Hs_ACTR3_8 |
| 900029-9-A | single siRNA, 0.9 nmol | 985 | 10251 | SPRY3 | sprouty homolog 3 (Drosophila) | NM_005840 | CTGAAGGAGAAGCTGAGCAA | SI03206063 | Hs_SPRY3_5 |
| 900029-9-A | single siRNA, 0.9 nmol | 986 | 10398 | MYL9 | myosin, light chain 9, regulatory | NM_006097 | CACATCCAATGTCTTCGCAAT | SI03159926 | Hs_MYL9_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-9-A | single siRNA, 0.9 nmol | 987 | 10677 | AVIL | advillin | NM_181526 | CAGGAAATAATTTATCCACCA | SI00308490 | Hs_AVIL_4 |
| 900029-9-A | single siRNA, 0.9 nmol | 988 | 11052 | CPSF6 | cleavage and polyadenylation specific factor 6, 68 kDa | NM_006576 | ACCGTCATGACGATTATTACA | SI03139563 | Hs_CPSF6_5 |
| 900029-9-A | single siRNA, 0.9 nmol | 989 | 22800 | RRAS2 | related RAS viral (r-ras) oncogene homolog 2 | NM_012250 | AACAGTTAGCACGGCAGCTTA | SI02662870 | Hs_RRAS2_6 |
| 900029-9-A | single siRNA, 0.9 nmol | 990 | 23443 | SLC35A3 | solute carrier family 35 (UDP-N-acetylglucosamine (UDP-GlcNAc) transporter), member A3 | NM_012243 | TCCCACTAAAGCATAGTTGTA | SI03231270 | Hs_SLC35A3_5 |
| 900029-9-A | single siRNA, 0.9 nmol | 991 | 9463 | PICK1 | protein interacting with PRKCA 1 | NM_001039583 NM_001039584 NM_012407 | CACCTCGCGCGGCCTTTATTTA | SI02660350 | Hs_PRKCABP_7 |
| 900029-9-A | single siRNA, 0.9 nmol | 992 | 9667 | SAFB2 | scaffold attachment factor B2 | NM_014649 | GCGGACGGTCGTGATGATAA | SI03220441 | Hs_SAFB2_5 |
| 900029-9-A | single siRNA, 0.9 nmol | 993 | 10000 | AKT3 | v-akt murine thymoma viral oncogene homolog 3 (protein kinase B, gamma) | NM_005465 NM_181690 | ACCAGAGTGTTAGAAGATAA | SI02757762 | Hs_AKT3_12 |
| 900029-9-A | single siRNA, 0.9 nmol | 994 | 10140 | TOB1 | transducer of ERBB2, 1 | NM_005749 | CCAGCCTTGTTATGGCTAACTA | SI02663248 | Hs_TOB1_7 |
| 900029-9-A | single siRNA, 0.9 nmol | 995 | 10252 | SPRY1 | sprouty homolog 1, antagonist of FGF signaling (Drosophila) | NM_005841 NM_199327 | AAGCATGAAAGGACTCATGAA | SI0303030 | Hs_SPRY1_8 |
| 900029-9-A | single siRNA, 0.9 nmol | 996 | 10399 | GNB2L1 | guanine nucleotide binding protein (G protein), beta polypeptide 2-like 1 | NM_006098 | ACCAGGATGAGACCAACTAT | SI03038851 | Hs_GNB2L1_7 |
| 900029-9-A | single siRNA, 0.9 nmol | 997 | 10750 | GRAP | GRB2-related adaptor protein | NM_006613 XM_001132900 | TGGCTTCTTCCCACGGAGTTA | SI03238564 | Hs_GRAP_8 |
| 900029-9-A | single siRNA, 0.9 nmol | 998 | 11057 | ABHD2 | abhydrolase domain containing 2 | NM_007011 NM_152924 | TTCGTTGACTACGCCCAGAAA | SI03242806 | Hs_ABHD2_6 |
| 900029-9-A | single siRNA, 0.9 nmol | 999 | 22821 | RASA3 | RAS p21 protein activator 3 | NM_007368 | AACCTGAAGTTTGGAGATGAA | SI00698768 | Hs_RASA3_4 |
| 900029-9-A | single siRNA, 0.9 nmol | 1000 | 23476 | BRD4 | bromodomain containing 4 | NM_014299 NM_058243 | TGGCGTTTCCACGGTACCAAA | SI03238361 | Hs_BRD4_7 |
| 900029-9-A | single siRNA, 0.9 nmol | 1001 | 9468 | PCYT1B | phosphate cytidylyltransferase 1, choline, beta | NM_004845 | CTCAACTCGTTTATAAATAAA | SI00681044 | Hs_PCYT1B_4 |
| 900029-9-A | single siRNA, 0.9 nmol | 1002 | 9743 | RICS | Rho GTPase-activating protein | NM_014715 NM_001012750 NM_001012751 NM_001012752 | CCTGATGAATCTACTGCTAAA | SI00107702 | Hs_RICS_4 |
| 900029-9-A | single siRNA, 0.9 nmol | 1003 | 10006 | ABI1 | abl-interactor 1 | NM_005470 | CTAGTGTTGCTTATCAAATAA | SI02655338 | Hs_ABI1_5 |
| 900029-9-A | single siRNA, 0.9 nmol | 1004 | 10153 | CEBPZ | CCAAT/enhancer binding protein zeta | NM_005760 | TGGATCGATTGTTATACCGAA | SI03237710 | Hs_CEBPZ_7 |
| 900028-9-A | single siRNA, 0.9 nmol | 1005 | 10253 | SPRY2 | sprouty homolog 2 (Drosophila) | NM_005842 | CAGGTCCATTCTTCTGCCACA | SI03071943 | Hs_SPRY2_7 |
| 900029-9-A | single siRNA, 0.9 nmol | 1006 | 10419 | PRMT5 | protein arginine methyltransferase 5 | NM_001039619 NM_006109 | AAGAGGGAGTTCATTCAGGAA | SI02657067 | Hs_SKB1_6 |
| 900029-9-A | single siRNA, 0.9 nmol | 1007 | 10752 | CHL1 | cell adhesion molecule with homology to L1CAM (close homolog of L1) | NM_006614 | ACCCAAGAAATGATTATAAG | SI03138058 | Hs_CHL1_5 |
| 900029-9-A | single siRNA, 0.9 nmol | 1008 | 11059 | WWP1 | WW domain containing E3 ubiquitin protein ligase 1 | NM_007013 | CAGTTCTATTTAACTGAATTA | SI03179001 | Hs_WWP1_5 |
| 900029-9-A | single siRNA, 0.9 nmol | 1009 | 23013 | SPEN | spen homolog, transcriptional regulator (Drosophila) | NM_015001 | CCCGATCACGCCGCAAGCGAA | SI03077697 | Hs_SPEN_8 |
| 900029-9-A | single siRNA, 0.9 nmol | 1010 | 23607 | CD2AP | CD2-associated protein | NM_012120 | TAGCAAGTCTTGTACAACGAA | SI03110884 | Hs_CD2AP_8 |
| 900029-9-A | single siRNA, 0.9 nmol | 1011 | 9542 | NRG2 | neuregulin 2 | NM_004883 NM_013981 NM_013982 NM_013983 | CAGCCTCCAAGTCAGTGCAGGA | SI03066483 | Hs_NRG2_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-9-A | 0.9 nmol single siRNA, | nmol1012 | 9775 | EIF4A3 | eukaryotic translation initiation factor 4A, isoform 3 | NM_013984 NM_013985 NM_014740 | CCGCATCTTGGTGAAACGTGA | SI02663794 | Hs_DDX48_5 |
| 900029-9-A | 0.9 nmol single siRNA, | nmol1013 | 10013 | HDAC6 | histone deacetylase 6 | NM_006044 | CACTTCGAAGCGAAATATTAA | SI02757769 | Hs_HDAC6_6 |
| 900029-9-A | 0.9 nmol single siRNA, | nmol1014 | 10174 | SORBS3 | sorbin and SH3 domain containing 3 | NM_001018003 NM_005775 | TACGTGCAGGTGTCTCGTGAA | SI03225971 | Hs_SORBS3_4 |
| 900029-9-A | 0.9 nmol single siRNA, | nmol1015 | 10273 | STUB1 | STIP1 homology and U-box containing protein 1 | NM_005861 | TACGCGAACGCCCACCCTTAA | SI03109659 | Hs_STUB1_5 |
| 900029-9-A | 0.9 nmol single siRNA, | nmol1016 | 10451 | VAV3 | vav 3 oncogene | NM_006113 | CACGACTTTCTCGAACACCTA | SI02781233 | Hs_VAV3_5 |
| 900029-9-A | 0.9 nmol single siRNA, | nmol1017 | 10856 | RUVBL2 | RuvB-like 2 (E. coli) | NM_006666 | CCAGAGCCTTCCTCTTCAA | SI00709268 | Hs_RUVBL2_4 |
| 900029-9-A | 0.9 nmol single siRNA, | nmol1018 | 11060 | WWP2 | WW domain containing E3 ubiquitin protein ligase 2 | NM_007014 NM_199424 | TACCCGACCACCACCTTTAA | SI03108826 | Hs_WWP2_9 |
| 900029-9-A | 0.9 nmol single siRNA, | nmol1019 | 23136 | EPB41L3 | erythrocyte membrane protein band 4.1-like 3 | NM_012307 | CTGCACGTCATAACCAACAA | SI03207491 | Hs_EPB41L3_5 |
| 900029-9-A | 0.9 nmol single siRNA, | nmol1020 | 23624 | CBLC | Cas-Br-M (murine) ecotropic retroviral transforming sequence c | NM_012116 | CTCACCTATGATGAGGTCCAA | SI03088414 | Hs_CBLC_6 |
| 900029-9-B | 0.9 nmol single siRNA, | nmol1021 | 9320 | TRIP12 | thyroid hormone receptor interactor 12 | NM_004238 | CAGTGCTAGTCCAGATACAA | SI03073182 | Hs_TRIP12_7 |
| 900029-9-B | 0.9 nmol single siRNA, | nmol1022 | 9564 | BCAR1 | breast cancer anti-estrogen resistance 1 | NM_014567 | CTGGATGGAGGACTATGACTA | SI02757734 | Hs_BCAR1_5 |
| 900029-9-B | 0.9 nmol single siRNA, | nmol1023 | 9815 | GIT2 | G protein-coupled receptor kinase interactor 2 | NM_014776 NM_057169 NM_057170 NM_139201 | CAGCGTTGAGAGTCAAGACAA | SI02660413 | Hs_GIT2_5 |
| 900029-9-B | 0.9 nmol single siRNA, | nmol1024 | 10044 | SH2D3C | SH2 domain containing 3C | NM_005489 NM_170600 | CCGGCGCTATGAGAAGTTCGA | SI03082198 | Hs_SH2D3C_5 |
| 900029-9-B | 0.9 nmol single siRNA, | nmol1025 | 10186 | TNK2 | tyrosine kinase, non-receptor, 2 | NM_001010938 NM_005781 | ACGCAAGTCGTGATGAGTAA | SI02622144 | Hs_TNK2_5 |
| 900029-9-B | 0.9 nmol single siRNA, | nmol1026 | 10278 | EFS | embryonal Fyn-associated substrate | NM_005864 NM_032459 | ACGAGCGTCAGCTTACTCAA | SI03140431 | Hs_EFS_5 |
| 900029-9-B | 0.9 nmol single siRNA, | nmol1027 | 10627 | MRCL3 | myosin regulatory light chain MRCL3 | NM_006471 | TTGGGCATATGTATCTTTATA | SI00647969 | Hs_MRCL3_3 |
| 900029-9-B | 0.9 nmol single siRNA, | nmol1028 | 10971 | YWHAQ | tyrosine 3-monooxygenase/tryptophan 5-monooxygenase activation protein, theta polypeptide | NM_006826 | CTCATGAAGGCAGTGACCGA | SI03094581 | Hs_YWHAQ_7 |
| 900029-9-B | 0.9 nmol single siRNA, | nmol1029 | 11083 | DIDO1 | death inducer-obliterator 1 | NM_022105 NM_033081 NM_080796 NM_080797 | CCGACTCGGTGTACTGCAGTA | SI03080042 | Hs_DIDO1_1 |
| 900029-9-B | 0.9 nmol single siRNA, | nmol1030 | 23198 | PSME4 | proteasome (prosome, macropain) activator subunit 4 | NM_014614 | CACGTGTAGTTCTTTATTATA | SI00695121 | Hs_PSME4_3 |
| 900029-9-B | 0.9 nmol single siRNA, | nmol1031 | 9349 | RPL23 | ribosomal protein L23 | NM_000978 | GGCGTTAAAGTTCATATCCCA | SI03221211 | Hs_RPL23_6 |
| 900029-9-B | 0.9 nmol single siRNA, | nmol1032 | 9592 | IER2 | immediate early response 2 | NM_004907 | AGCAAGAAAGCCCGTCTGGAA | SI03143000 | Hs_IER2_5 |
| 900029-9-B | 0.9 nmol single siRNA, | nmol1033 | 9846 | GAB2 | GRB2-associated binding protein 2 | NM_012296 NM_080491 | CACCAATTCTGAAGACACTA | SI02639301 | Hs_GAB2_6 |
| 900029-9-B | 0.9 nmol single siRNA, | nmol1034 | 10045 | SH2D3A | SH2 domain containing 3A | NM_005490 | CAGGTGCCACAGGATGAGAA | SI03072167 | Hs_SH2D3A_6 |
| 900029-9-B | 0.9 nmol single siRNA, | nmol1035 | 10241 | CALCOCO2 | calcium binding and coiled-coil domain 2 | NM_005831 | CAGCAGGAAGTCAATTCAAA | SI00656033 | Hs_NDP52_3 |
| 900029-9-B | 0.9 nmol single siRNA, | nmol1036 | 10376 | TUBA1B | tubulin, alpha 1b | NM_006082 | CCCGCCCTAGTGCGTTACTTA | SI02636627 | Hs_K-ALPHA-1_5 |
| 903291-9-B | 0.9 nmol single siRNA, | nmol1037 | 10628 | TXNIP | thioredoxin interacting protein | NM_006472 | TGCAACATCCTTCGAGTTGAA | SI03117723 | Hs_TXNIP_7 |
| 900029-9-B | 0.9 nmol single siRNA, | nmol1038 | 10987 | COPS5 | COP9 constitutive photomorphogenic | NM_006837 | ATGCAATGGGGTGTATCATA | SI03049774 | Hs_COPS5_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-9-B | single siRNA, 0.9 nmol | 1039 | 11184 | MAP4K1 | mitogen-activated protein kinase kinase kinase kinase 1 | NM_001042600 NM_007181 | CTGACTAAGAGTCCCAAGAAA | SI02224250 | Hs_MAP4K1_5 |
| 900029-9-B | single siRNA, 0.9 nmol | 1040 | 23236 | PLCB1 | phospholipase C, beta 1 (phosphoinositide-specific) | NM_015192 NM_182734 | TCGAGATTACATGGATGTTAA | SI02780939 | Hs_PLCB1_5 |
| 900029-9-B | single siRNA, 0.9 nmol | 1041 | 9402 | GRAP2 | GRB2-related adaptor protein 2 | NM_004810 | CTGGTAATTAGTTGATGATCAAA | SI00068698 | Hs_GRAP2_3 |
| 900029-9-B | single siRNA, 0.9 nmol | 1042 | 9618 | TRAF4 | TNF receptor-associated factor 4 | NM_004295 NM_145751 | CTGCAGGAGTTCCTCAGTGAA | SI02665152 | Hs_TRAF4_7 |
| 900029-9-B | single siRNA, 0.9 nmol | 1043 | 9948 | WDR1 | WD repeat domain 1 | NM_005112 NM_017491 | CAGTAACAGTTTGCACATGAA | SI00761712 | Hs_WDR1_4 |
| 900029-9-B | single siRNA, 0.9 nmol | 1044 | 10096 | ACTR3 | ARP3 actin-related protein 3 homolog (yeast) | NM_005721 | CCGGCTGAAATTAAGTGAGGA | SI02664298 | Hs_ACTR3_7 |
| 900029-9-B | single siRNA, 0.9 nmol | 1045 | 10251 | SPRY3 | sprouty homolog 3 (Drosophila) | NM_005840 NM_006097 | CAGGGTAGTATGAGTAAGGAA | SI00732620 | Hs_SPRY3_4 |
| 900029-9-B | single siRNA, 0.9 nmol | 1046 | 10398 | MYL9 | myosin, light chain 9, regulatory | NM_181526 | CGCCAAGGATAAAGACGACTA | SI00653072 | Hs_MYL9_4 |
| 900029-9-B | single siRNA, 0.9 nmol | 1047 | 10677 | AVIL | advillin | NM_006576 | CTGGACCAAAGTGGAACCAAA | SI00308483 | Hs_AVIL_3 |
| 900029-9-B | single siRNA, 0.9 nmol | 1048 | 11052 | CPSF6 | cleavage and polyadenylation specific factor 6, 68 kDa | NM_007007 | TAGATGTAGTGTTGTAATAAA | SI00355227 | Hs_CPSF6_3 |
| 900029-9-B | single siRNA, 0.9 nmol | 1049 | 22800 | RRAS2 | related RAS viral (r-ras) oncogene homolog 2 | NM_012250 | TAGTCCTTTCTGAAGCTAA | SI03112340 | Hs_RRAS2_9 |
| 900029-9-B | single siRNA, 0.9 nmol | 1050 | 23443 | SLC35A3 | solute carrier family 35 (UDP-N-acetylglucosamine (UDP-GlcNAc) transporter), member A3 | NM_012243 | GAGAATAAATATCAAATCTAA | SI00723464 | Hs_SLC35A3_4 |
| 900029-9-B | single siRNA, 0.9 nmol | 1051 | 9463 | PICK1 | protein interacting with PRKCA 1 | NM_001039583 NM_001039584 NM_012407 | TCGCCTCACCATCAAGAAGTA | SI00287574 | Hs_PRKCABP_5 |
| 900029-9-B | single siRNA, 0.9 nmol | 1052 | 9667 | SAFB2 | scaffold attachment factor B2 | NM_014649 | CCGGACCTACACAAATCGGTCTA | SI00710080 | Hs_SAFB2_4 |
| 900023-9-B | single siRNA, 0.9 nmol | 1053 | 10000 | AKT3 | v-akt murine thymoma viral oncogene homolog 3 (protein kinase B, gamma) | NM_181690 | CAGCAGGCACGTTAACTCGAA | SI02622494 | Hs_AKT3_8 |
| 900029-9-B | single siRNA, 0.9 nmol | 1054 | 10140 | TOB1 | transducer of ERBB2, 1 | NM_005749 | ACCAAGTTCGGCTCTACCAAA | SI03038322 | Hs_TOB1_8 |
| 900029-9-B | single siRNA, 0.9 nmol | 1055 | 10252 | SPRY1 | sprouty homolog 1, antagonist of FGF signaling (Drosophila) | NM_005841 NM_199327 | TTGGATAGCCGTCAGAGATTA | SI03024805 | Hs_SPRY1_7 |
| 900029-9-B | single siRNA, 0.9 nmol | 1056 | 10399 | GNB2L1 | guanine nucleotide binding protein (G protein), beta polypeptide 2-like 1 | NM_006098 | TTGGCACACGCTAGAAGTTA | SI02636662 | Hs_GNB2L1_5 |
| 900029-9-B | single siRNA, 0.9 nmol | 1057 | 10750 | GRAP | GRB2-related adaptor protein | NM_006613 XM_001132900 | CCCGCCGTGGCGGACCATTGA | SI03189088 | Hs_GRAP_7 |
| 900029-9-B | single siRNA, 0.9 nmol | 1058 | 11057 | ABHD2 | abhydrolase domain containing 2 | NM_007011 NM_152924 | ACCATCCCTTGGTGCATGAAA | SI03140557 | Hs_ABHD2_5 |
| 900029-9-B | single siRNA, 0.9 nmol | 1059 | 22821 | RASA3 | RAS p21 protein activator 3 | NM_007368 | TAGGAACTTTCTTGTCACCAAA | SI00698761 | Hs_RASA3_3 |
| 900029-9-B | single siRNA, 0.9 nmol | 1060 | 23476 | BRD4 | bromodomain containing 4 | NM_014299 NM_058243 | CCGGCCTGTGAAACCTCCAAA | SI03190845 | Hs_BRD4_6 |
| 900029-9-B | single siRNA, 0.9 nmol | 1061 | 9468 | PCYT1B | phosphate cytidylyltransferase 1, choline, beta | NM_004845 | CCGGGTGTATCCCATGTGCAA | SI00681037 | Hs_PCYT1B_3 |
| 900029-9-B | single siRNA, 0.9 nmol | 1062 | 9743 | RICS | Rho GTPase-activating protein | NM_014715 | TAGGCAGTTCTGTGAGTCAAA | SI00107695 | Hs_RICS_3 |
| 900029-9-B | single siRNA, 0.9 nmol | 1063 | 10006 | ABI1 | abl-interactor 1 | NM_001012750 NM_001012751 NM_001012752 NM_005470 | GAGGGCGCTGATCGAGAGTTA | SI03218754 | Hs_ABI1_6 |
| 900029-9-B | single siRNA, 0.9 nmol | 1064 | 10153 | CEBPZ | CCAAT/enhancer binding protein zeta | NM_005760 | CAGTACCACCGAAAGTAAA | SI03178007 | Hs_CEBPZ_6 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-9-B | 0.9 single siRNA, | nmol1065 | 10253 | SPRY2 | sprouty homolog 2 (Drosophila) | NM_005842 | AACCAACATAGCATCATTAAT | SI02636151 | Hs_SPRY2_6 |
| 900029-9-B | 0.9 single siRNA, | nmol1066 | 10419 | PRMT5 | protein arginine methyltransferase 5 | NM_001039619 NM_006109 | TGGGCAAGGATTATAATTAA | SI02657060 | Hs_SKB1_5 |
| 900029-9-B | 0.9 single siRNA, | nmol1067 | 10752 | CHL1 | cell adhesion molecule with homology to L1CAM (close homolog of L1) | NM_006614 | CCCAGAGATGGTCATATTTAA | SI02345954 | Hs_CHL1_4 |
| 900029-9-B | 0.9 single siRNA, | nmol1068 | 11059 | WWP1 | WW domain containing E3 ubiquitin protein ligase 1 | NM_007013 | AAGGATTCATTGAGCAGCATA | SI00763784 | Hs_WWP1_4 |
| 900029-9-B | 0.9 single siRNA, | nmol1069 | 23013 | SPEN | span homolog, transcriptional regulator (Drosophila) | NM_015001 | CAGAACTGCCTTTGCACTAAA | SI02641128 | Hs_SPEN_7 |
| 900029-9-B | 0.9 single siRNA, | nmol1070 | 23607 | CD2AP | CD2-associated protein | NM_012120 | AAGCGTCAGTGTAAAGTTCTT | SI03033681 | Hs_CD2AP_7 |
| 900029-9-B | 0.9 single siRNA, | nmol1071 | 9542 | NRG2 | neuregulin 2 | NM_004883 NM_013981 NM_013982 NM_013983 NM_013984 NM_013985 | CAGAAAGAACTACGACTACA | SI03082682 | Hs_NRG2_5 |
| 900029-9-B | 0.9 single siRNA, | nmol1072 | 9775 | EIF4A3 | eukaryotic translation initiation factor 4A, isoform 3 | NM_014740 | ATGATTCGTCGCAGAAGCCTA | SI03049676 | Hs_DDX48_6 |
| 900029-9-B | 0.9 single siRNA, | nmol1073 | 10013 | HDAC6 | histone deacetylase 6 | NM_006044 | CACCGTCAACGTGGCATGGAA | SI02663808 | Hs_HDAC6_5 |
| 900029-9-B | 0.9 single siRNA, | nmol1074 | 10174 | SORBS3 | sorbin and SH3 domain containing 3 | NM_001018003 | CGGAACGTTCCCTGGAAATTA | SI03195248 | Hs_SORBS3_3 |
| 900029-9-B | 0.9 single siRNA, | nmol1075 | 10273 | STUB1 | STIP1 homology and U-box containing protein 1 | NM_005861 | CCCGAGCGCGAGGAGACTCAA | SI00081977 | Hs_STUB1_3 |
| 900029-9-B | 0.9 single siRNA, | nmol1076 | 10451 | VAV3 | vav 3 oncogene | NM_001079874 NM_006113 | ATGGACTGCGAAGAACTCCTA | SI03050733 | Hs_VAV3_6 |
| 900029-9-B | 0.9 single siRNA, | nmol1077 | 10856 | RUVBL2 | RuvB-like 2 (E. coli) | NM_006666 | AACCGTTACAGCCACCAACCAA | SI00709261 | Hs_RUVBL2_3 |
| 900029-9-B | 0.9 single siRNA, | nmol1078 | 11060 | WWP2 | WW domain containing E3 ubiquitin protein ligase 2 | NM_007014 NM_199424 | CTGCGTACTTTGACGAGAAA | SI03095344 | Hs_WWP2_8 |
| 900029-9-B | 0.9 single siRNA, | nmol1079 | 23136 | EPB41L3 | erythrocyte membrane protein band 4.1-like 3 | NM_012307 | TAACCTTATATTTACAATAAA | SI03080282 | Hs_EPB41L3_4 |
| 900029-9-B | 0.9 single siRNA, | nmol1080 | 23624 | CBLC | Cas-Br-M (murine) ecotropic retroviral transforming sequence c | NM_012116 | ATGGCCAACACTCCTCAAGAA | SI03051349 | Hs_CBLC_5 |
| 900329-10-A | 0.9 single siRNA, | nmol1081 | 23760 | PITPNB | phosphatidylinositol transfer protein, beta | NM_012399 | CACGTCGGCTGCTGATGTCTA | SI03165050 | Hs_PITPNB_8 |
| 900029-10-A | 0.9 single siRNA, | nmol1082 | 27020 | NPTN | neuroplastin | NM_012428 NM_017455 | CAGACTCGATATGGCGCAAGA | SI03063739 | Hs_NPTN_1 |
| 900029-10-A | 0.9 single siRNA, | nmol1083 | 30011 | SH3KBP1 | SH3-domain kinase binding protein 1 | NM_001024666 NM_031892 | TAGCTTATATATGACGGTATA | SI00287903 | Hs_SH3KBP1_6 |
| 900029-10-A | 0.9 single siRNA, | nmol1084 | 51513 | ETV7 | ets variant gene 7 (TEL2 oncogene) | NM_016135 | CAGCTGTCTCCTTGATACCCGA | SI03068887 | Hs_ETV7_6 |
| 900029-10-A | 0.9 single siRNA, | nmol1085 | 54567 | DLL4 | delta-like 4 (Drosophila) | NM_019074 | CCGGGTCATCGCAGTGACAA | SI03082653 | Hs_DLL4_6 |
| 900029-10-A | 0.9 single siRNA, | nmol1086 | 55914 | ERBB2IP | erbb2 interacting protein | NM_001006600 NM_018695 | CAAGATGTTATCAATTGGTTA | SI02778195 | Hs_ERBB2IP_11 |
| 900029-10-A | 0.9 single siRNA, | nmol1087 | 57561 | ARRDC3 | arrestin domain containing 3 | NM_020801 | CAGAATTACACTGAAGAAGTA | SI03167220 | Hs_ARRDC3_5 |
| 900029-10-A | 0.9 single siRNA, | nmol1088 | 64130 | LIN7B | lin-7 homolog B (C. elegans) | NM_022165 | CTCGAGGTTGAAACCACAGAT | SI03091116 | Hs_LIN7B_7 |
| 900329-10-A | 0.9 single siRNA, | nmol1089 | 79718 | TBL1XR1 | transducin (beta)-like 1X-linked receptor 1 | NM_024665 | AAGGAGCTATCTGTTTATGTA | SI00136808 | Hs_TBL1XR1_1 |
| 900029-10-A | 0.9 single siRNA, | nmol1090 | 80821 | DDHD1 | DDHD domain containing 1 | NM_030637 | CTTGACAAAGTACGAGGTTAA | SI03206238 | Hs_DDHD1_5 |
| 900029-10-A | 0.9 single siRNA, | nmol1091 | 25759 | SHC2 | SHC (Src homology 2 domain containing) transforming protein 2 | XM_001129272 XM_939572 | TTCCGATCGGTTTGTAATTAA | SI02825263 | Hs_SHC2_7 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-10-A | single siRNA, 0.9 nmol | 1092 | 28514 | DLL1 | delta-like 1 (Drosophila) | NM_005618 | AAGGATGAGTGCGTCATAGCA | SI03113836 | Hs_DLL1_5 |
| 900029-10-A | single siRNA, 0.9 nmol | 1093 | 50807 | DDEF1 | development and differentiation enhancing factor 1 | NM_018482 | CACCTTGGATTCTTTGTTAAA | SI00360596 | Hs_DDEF1_4 |
| 900029-10-A | single siRNA, 0.9 nmol | 1094 | 51582 | AZIN1 | antizyme inhibitor 1 | NM_015878 NM_148174 | ACACTCGCAGTTAATATCATA | SI03037622 | Hs_AZIN1_1 |
| 900029-10-A | single siRNA, 0.9 nmol | 1095 | 54822 | TRPM7 | transient receptor potential cation channel, subfamily M, member 7 | NM_017672 | CTGCTAGCGTATATTCATAAA | SI03095806 | Hs_TRPM7_8 |
| 900029-10-A | single siRNA, 0.9 nmol | 1096 | 56288 | PARD3 | par-3 partitioning defective 3 homolog (C. elegans) | NM_019619 | TAGGTATAGCTGACGAGACTA | SI03228932 | Hs_PARD3_6 |
| 900029-10-A | single siRNA, 0.9 nmol | 1097 | 58513 | EPS15L1 | epidermal growth factor receptor pathway substrate 15-like 1 | NM_021235 | TACCTCCGATCCATTCACGAA | SI03109176 | Hs_EPS15L1_7 |
| 900029-10-A | single siRNA, 0.9 nmol | 1098 | 64319 | FBRS | fibrosin | NM_022452 | CCAAGGAATCTGCGGGTAA | SI03179960 | Hs_FBS1_5 |
| 900029-10-A | single siRNA, 0.9 nmol | 1099 | 79801 | SHCBP1 | SHC SH2-domain binding protein 1 | NM_024745 | CAAGATATCCATGGTGAATAA | SI00717864 | Hs_SHCBP1_4 |
| 900029-10-A | single siRNA, 0.9 nmol | 1100 | 81848 | SPRY4 | sprouty homolog 4 (Drosophila) | NM_030964 | CACGAACAGCGTCATCTGCAA | SI00732648 | Hs_SPRY4_4 |
| 900029-10-A | single siRNA, 0.9 nmol | 1101 | 25800 | SLC39A6 | solute carrier family 39 (zinc transporter), member 6 | NM_012319 | CACGAGCATCACTCTGACCAT | SI03059805 | Hs_SLC39A6_8 |
| 900329-10-A | single siRNA, 0.9 nmol | 1102 | 28964 | GIT1 | G protein-coupled receptor kinase interactor 1 | NM_014030 | GCCGCTGGAGGATGTCCCGAAA | SI02622340 | Hs_GIT1_6 |
| 900029-10-A | single siRNA, 0.9 nmol | 1103 | 50855 | PARD6A | par-6 partitioning defective 6 homolog alpha (C. elegans) | NM_001037281 NM_016948 | CCAGGTTTCCTCCAGTCATAGA | SI02664340 | Hs_PARD6A_5 |
| 900029-10-A | single siRNA, 0.9 nmol | 1104 | 51616 | TAF9B | TAF9B RNA polymerase II, TATA box binding protein (TBP)-associated factor, 31 kDa | NM_015975 | CAGAGATGAACCAAGGTTA | SI03168480 | Hs_TAF9B_1 |
| 900029-10-A | single siRNA, 0.9 nmol | 1105 | 54876 | C4orf30 | chromosome 4 open reading frame 30 | NM_017741 | AAGGAAACAACTCGTACTGAA | SI00397250 | Hs_FLJ20280_4 |
| 900029-10-A | single siRNA, 0.9 nmol | 1106 | 56751 | BARHL1 | BarH-like 1 (Drosophila) | NM_020064 | AAGTGTATATGAAGTTATTTA | SI00310338 | Hs_BARHL1_4 |
| 900029-10-A | single siRNA, 0.9 nmol | 1107 | 58533 | SNX6 | sorting nexin 6 | NM_021249 NM_152233 | CCGCGGACTTAAAGCAATAAA | SI02778538 | Hs_SNX6_9 |
| 900029-10-A | single siRNA, 0.9 nmol | 1108 | 64780 | MICAL1 | microtubule associated monooxygenase, calponin and LIM domain containing 1 | NM_022765 | CTACAGCTCGTTGACAAGAAA | SI00658644 | Hs_NICAL_4 |
| 900029-10-A | single siRNA, 0.9 nmol | 1109 | 80005 | DOCK5 | dedicator of cytokinesis 5 | NM_024940 | AACATCCTAGACCCTGACGAA | SI03123645 | Hs_DOCK5_5 |
| 900029-10-A | single siRNA, 0.9 nmol | 1110 | 83481 | EPPK1 | epiplakin 1 | NM_031308 | AGGCTTCATCATCGACCCAAA | SI00380730 | Hs_EPPK1_4 |
| 900029-10-A | single siRNA, 0.9 nmol | 1111 | 25983 | NGDN | neuroguidin, EIF4E binding protein | NM_001042635 NM_015514 XM_033371 XM_932891 XM_932894 XM_932898 XM_932900 XM_932903 XM_932906 XM_941350 XM_945155 XM_945159 XM_945161 XM_945163 XM_945166 XM_945170 | CGGGAGAAGAAGCGTCTAGAA | SI00318598 | Hs_C14orf120_4 |
| 900029-10-A | single siRNA, 0.9 nmol | 1112 | 29123 | ANKRD11 | ankyrin repeat domain 11 | NM_013275 | CCCTCGGAGCACGAATATATA | SI03186925 | Hs_ANKRD11_6 |
| 900029-10-A | single siRNA, 0.9 nmol | 1113 | 51079 | NDUFA13 | NADH dehydrogenase (ubiquinone) 1 alpha | NM_015965 | CGCGGTCGATAGTTACACTA | SI00430941 | Hs_GRIM19_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-10-A | single siRNA, 0.9 nmol | 1114 | 51655 | RASD1 | RAS, dexamethasone-induced 1 | NM_016084 | GAGGGTGATTATCTTCTCA | SI03104115 | Hs RASD1 6 |
| 900029-10-A | single siRNA, 0.9 nmol | 1115 | 55236 | UBE1L2 | ubiquitin-activating enzyme E1-like 2 | NM_018227 | AAGGGAAACATCAGTAAGAAA | SI00389942 | Hs FLJ10808 4 |
| 900029-10-A | single siRNA, 0.9 nmol | 1116 | 56776 | FMN2 | formin 2 | NM_020066 XM_371352 | CTGGACCAGGATTCAACTACA | SI03210186 | Hs FMN2 8 |
| 900029-10-A | single siRNA, 0.9 nmol | 1117 | 60412 | EXOC4 | exocyst complex component 4 | NM_001037126 NM_021807 | TAGCCGAGTTGTGCAGCGTAA | SI03227595 | Hs EXOC4 1 |
| 900029-10-A | single siRNA, 0.9 nmol | 1118 | 64866 | CDCP1 | CUB domain containing protein 1 | NM_022842 NM_178181 | AACCCTGATGTCTGCCAACTA | SI00341446 | Hs CDCP1 4 |
| 900029-10-A | single siRNA, 0.9 nmol | 1119 | 80218 | NAT13 | N-acetyltransferase 13 | NM_025146 | CGGCGTTGATATCGGTGTAA | SI03196508 | Hs NAT13 1 |
| 900029-10-A | single siRNA, 0.9 nmol | 1120 | 83737 | ITCH | itchy homolog E3 ubiquitin protein ligase (mouse) | NM_031483 | TGCCGCCACAAATACAAATA | SI03118437 | Hs ITCH 6 |
| 900029-10-A | single siRNA, 0.9 nmol | 1121 | 26960 | NBEA | neurobeachin | NM_015678 | AAGAAATAAATTCACCAACAA | SI00655480 | Hs NBEA 4 |
| 900029-10-A | single siRNA, 0.9 nmol | 1122 | 29127 | RACGAP1 | Rac GTPase activating protein 1 | NM_013277 | CTGTAGATAGAAGAGCTAAA | SI02639840 | Hs RACGAP1 5 |
| 900029-10-A | single siRNA, 0.9 nmol | 1123 | 51343 | FZR1 | fizzy/cell division cycle 20 related 1 (Drosophila) | NM_016263 | CGGGTCGATCTTCCACATTCA | SI00114905 | Hs FZR1 1 |
| 900029-10-A | single siRNA, 0.9 nmol | 1124 | 53358 | SHC3 | SHC (Src homology 2 domain containing) transforming protein 3 | NM_016848 | CTCCAAACAGATCATAGCGAA | SI03199805 | Hs SHC3_5 |
| 900029-10-A | single siRNA, 0.9 nmol | 1125 | 55327 | LIN7C | lin-7 homolog C (C. elegans) | NM_018362 | TCAACCGTACATCAAATTATA | SI02778048 | Hs LIN7C 6 |
| 900029-10-A | single siRNA, 0.9 nmol | 1126 | 56907 | SPIRE1 | spire homolog 1 (Drosophila) | NM_020148 | TACGTGGGCTATACTGTATTA | SI03226027 | Hs SPIRE1 8 |
| 900029-10-A | single siRNA, 0.9 nmol | 1127 | 63920 | LOC63920 | transposon-derived Buster3 transposase-like | NM_022090 | AAAGAGATACCTCATATCGTA | SI03121783 | Hs LOC63920 5 |
| 900029-10-A | single siRNA, 0.9 nmol | 1128 | 79090 | DDX50 | DEAD (Asp-Glu-Ala-Asp) box polypeptide 50 | NM_024045 | AAGAAATCAAGAACAATTAA | SI00361662 | Hs DDX50 4 |
| 900029-10-A | single siRNA, 0.9 nmol | 1129 | 80336 | C20orf119 | chromosome 20 open reading frame 119 | XM_001130728 XM_001131956 | TCCCAATTAGTCTGTATCTAT | SI03020038 | Hs C20orf119 4 |
| 900029-10-A | single siRNA, 0.9 nmol | 1130 | 84790 | TUBA1C | tubulin, alpha 1c | NM_032704 | CTGTAAATGTCTATTGCCGTA | SI02654071 | Hs TUBA6 3 |
| 900029-10-A | single siRNA, 0.9 nmol | 1131 | 26986 | PABPC1 | poly(A) binding protein, cytoplasmic 1 | NM_002568 | TTAAAGCATTCCTTCTTTAA | SI03240111 | Hs PABPC1 6 |
| 900029-10-A | single siRNA, 0.9 nmol | 1132 | 29924 | EPN1 | epsin 1 | NM_013333 | CCGAAGACGCCGGAGTCATT | SI00380618 | Hs EPN1 4 |
| 900029-10-A | single siRNA, 0.9 nmol | 1133 | 51473 | DCDC2 | doublecortin domain containing 2 | NM_016356 | AAAGTCATATAGAAATATTAA | SI00360066 | Hs DCDC2 4 |
| 900029-10-A | single siRNA, 0.9 nmol | 1134 | 54206 | ERRFI1 | ERBB receptor feedback inhibitor 1 | NM_018948 | AACCAATTAGTTACTATCGTA | SI00645792 | Hs MIG-6 4 |
| 900029-10-A | single siRNA, 0.9 nmol | 1135 | 55824 | PAG1 | phosphoprotein associated with glycosphingolipid microdomains 1 | NM_018440 | CTGCTTGTATGAAACTGTGAA | SI02643305 | Hs PAG_8 |
| 900029-10-B | single siRNA, 0.9 nmol | 1136 | 57403 | RAB22A | RAB22A, member RAS oncogene family | NM_020673 | AAGGCCTATCAGCCAATTAAA | SI02662737 | Hs RAB22A 6 |
| 900029-10-B | single siRNA, 0.9 nmol | 1137 | 63932 | CXorf56 | chromosome X open reading frame 56 | NM_022101 | TAGACTAGCAAGCATTTA | SI03226818 | Hs CXorf56 2 |
| 900029-10-B | single siRNA, 0.9 nmol | 1138 | 79090 | TRAPPC6A | trafficking protein particle complex 6A | NM_024108 | TGGCGGTTGTTCCAGAAGCAGA | SI03238319 | Hs TRAPPC6A 2 |
| 900029-10-B | single siRNA, 0.9 nmol | 1139 | 80725 | SNIP | SNAP25-interacting protein | NM_025248 | TCCCATCATCGCAGAGCTAGA | SI03233727 | Hs SNIP 5 |
| 900029-10-B | single siRNA, 0.9 nmol | 1140 | 84918 | LRP11 | low density lipoprotein receptor-related protein 11 | NM_032832 | AAACATGATTCCTTTAATAAA | SI00623644 | Hs LRP11 4 |
| 900029-10-B | single siRNA, 0.9 nmol | 1141 | 23780 | PITPNB | phosphatidylinositol transfer protein, beta | NM_012399 | AAGGGACCAGTATACGCACAAA | SI03133788 | Hs PITPNB 7 |
| 900029-10-B | single siRNA, 0.9 nmol | 1142 | 27020 | NPTN | neuroplastin | NM_012428 NM_017455 | CTGGTACATAAAGATGAGTAA | SI02639672 | Hs SDFR1 9 |
| 900029-10-B | single siRNA, 0.9 nmol | 1143 | 30011 | SH3KBP1 | SH3-domain kinase binding protein 1 | NM_001024866 NM_031892 | CTCTGAGATCTCAATGCGAAA | SI00287896 | Hs SH3KBP1 5 |
| 900029-10-B | single siRNA, 0.9 nmol | 1144 | 51513 | ETV7 | ets variant gene 7 (TEL2 oncogene) | NM_016135 | CACGTGCAAGCCAGATGTGAA | SI03061590 | Hs ETV7 5 |
| 900029-10-B | single siRNA, 0.9 nmol | 1145 | 54567 | DLL4 | delta-like 4 (Drosophila) | NM_019074 | TTCGGGCTGTCATGAACAGAA | SI03023076 | Hs DLL4 5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-10-B | single siRNA, 0.9 nmol | 1146 | 55914 | ERBB2IP | erbb2 interacting protein | NM_001006800 | CCCGAAGAGCCAAATATAATA | SI02778188 | Hs_ERBB2IP_10 |
| 900029-10-B | single siRNA, 0.9 nmol | 1147 | 57561 | ARRDC3 | arrestin domain containing 3 | NM_018695 NM_020801 | CACGAAAGAGATGATGATAAT | SI00304598 | Hs_ARRDC3_4 |
| 900029-10-6 | single siRNA, 0.9 nmol | 1148 | 64130 | LIN7B | lin-7 homolog B (C. elegans) | NM_022165 | CTCCGCTATCCGAGAGGTGTA | SI03090066 | Hs_LIN7B_6 |
| 900029-10-B | single siRNA, 0.9 nmol | 1149 | 79718 | TBL1XR1 | transducin (beta)-like 1X-linked receptor 1 | NM_024665 | TAGCACCTTAGGCAGCATAA | SI03110905 | Hs_TBL1XR1_11 |
| 900029-10-B | single siRNA, 0.9 nmol | 1150 | 80821 | DDHD1 | DDHD domain containing 1 | NM_030637 | CAGGAAATACTGGAAGTCAA | SI00360682 | Hs_DDHD1_4 |
| 900029-10-B | single siRNA, 0.9 nmol | 1151 | 25759 | SHC2 | SHC (Src homology 2 domain containing) transforming protein 2 | XM_001129272 XM_939672 | ACGGAACCATTTCGCCTTTAA | SI02825256 | Hs_SHC2_6 |
| 900029-10-B | single siRNA, 0.9 nmol | 1152 | 28514 | DLL1 | delta-like 1 (Drosophila) | NM_005618 | CCCGTGTGCCTCAAGCACTA | SI00369719 | Hs_DLL1_3 |
| 900029-10-B | single siRNA, 0.9 nmol | 1153 | 50807 | DDEF1 | development and differentation enhancing factor 1 | NM_018482 | CACCTTCAAGTCAATTCATAA | SI00360591 | Hs_DDEF1_3 |
| 900029-10-B | single siRNA, 0.9 nmol | 1154 | 51582 | AZIN1 | antizyme inhibitor 1 | NM_015878 NM_148174 | CGGATTTGCTTGTTCCAGTAA | SI00112322 | Hs_OAZIN_4 |
| 900029-10-B | single siRNA, 0.9 nmol | 1155 | 54822 | TRPM7 | transient receptor potential cation channel, subfamily M, member 7 | NM_017672 | CCTGTAAGATCATCGTTCAA | SI03083549 | Hs_TRPM7_7 |
| 900029-10-B | single siRNA, 0.9 nmol | 1156 | 56288 | PARD3 | par-3 partitioning defective 3 homolog (C. elegans) | NM_019619 | CAGCTTAAGAAAGGTACAGAA | SI03173121 | Hs_PARD3_5 |
| 900029-10-B | single siRNA, 0.9 nmol | 1157 | 58513 | EPS15L1 | epidermal growth factor receptor pathway substrate 15-like 1 | NM_021235 | CACCGCCTAAATTTCACGACA | SI03058398 | Hs_EPS15L1_6 |
| 900029-10-1043 | single siRNA, 0.9 nmol | 1158 | 64319 | FBRS | fibrosin | NM_022452 | CAGGCTAAGGGTGGCCAGAGA | SI00385210 | Hs_FBS1_4 |
| 900029-10-B | single siRNA, 0.9 nmol | 1159 | 79801 | SHCBP1 | SHC SH2-domain binding protein 1 | NM_024745 | TTGCATAATACTTGTCTTAAA | SI00717857 | Hs_SHCBP1_3 |
| 900029-10-B | single siRNA, 0.9 nmol | 1160 | 81848 | SPRY4 | sprouty homolog 4 (Drosophila) | NM_030964 | CTGAATGTACTGATTTAGAAA | SI00732641 | Hs_SPRY4_3 |
| 900029-10-B | single siRNA, 0.9 nmol | 1161 | 25800 | SLC39A6 | solute carrier family 39 (zinc transporter), member 6 | NM_012319 | CTAGTTAAGGTTTAAATGCTA | SI02639371 | Hs_SLC39A6_6 |
| 900029-10-B | single siRNA, 0.9 nmol | 1162 | 28964 | GIT1 | G protein-coupled receptor kinase interactor 1 | NM_014030 | CAGCCTTGACTTATCCGAATT | SI02224467 | Hs_GIT1_5 |
| 900029-10-B | single siRNA, 0.9 nmol | 1163 | 50855 | PARD6A | par-6 partitioning defective 6 homolog alpha (C. elegans) | NM_001037281 NM_016948 | ATCGTCGAGGTGAAGAGCAAA | SI03048619 | Hs_PARD6A_6 |
| 900029-10-B | single sFINA, 0.9 nmol | 1164 | 51616 | TAF9B | TAF9B RNA polymerase II, TATA box binding protein (TBP)-associated factor, 31 kDa | NM_015975 | CAGAAGTTTCATCTTAGGATA | SI00739061 | Hs_TAF9L_3 |
| 900029-10-B | single siRNA, 0.9 nmol | 1165 | 54876 | C4orf30 | chromosome 4 open reading frame 30 | NM_017741 | CAGCAAGAGTCCTAACATCTA | SI00397243 | Hs_FLJ20280_3 |
| 900029-10-B | single siRNA, 0.9 nmol | 1166 | 56751 | BARHL1 | BarH-like 1 (Drosophila) | NM_020064 | CAGGACTAAATGGAAGCGACA | SI00310331 | Hs_BARHL1_3 |
| 900029-10-B | single siRNA, 0.9 nmol | 1167 | 58533 | SNX6 | sorting nexin 6 | NM_021249 NM_152233 | CAGGCCGGAAACTTCCCACCA | SI03070424 | Hs_SNX6_11 |
| 900029-10-B | single siRNA, 0.9 nmol | 1168 | 64780 | MICAL1 | microtubule associated monoxygenase, calponin and LIM domain containing 1 | NM_022765 | CCAGCGGTTGTCCTCCCTTAA | SI00658637 | Hs_NICAL_3 |
| 900029-10-B | single siRNA, 0.9 nmol | 1169 | 80005 | DOCK5 | dedicator of cytokinesis 5 | NM_024940 | CACATTCAGCTTATAATGGAA | SI00372666 | Hs_DOCK5_4 |
| 900029-10-B | single siRNA, 0.9 nmol | 1170 | 83481 | EPPK1 | epiplakin 1 | NM_031308 | AAGCAGGAAACCAGCAACAAA | SI00380723 | Hs_EPPK1_3 |
| 900029-10-B | single siRNA, 0.9 nmol | 1171 | 25983 | NGDN | neuroguidin, EIF4E binding protein | NM_001042635 NM_015514 XM_033371 XM_932891 XM_932894 XM_932898 XM_932900 XM_932903 | CTCTGTCATTCGTGAACTTAA | SI00318591 | Hs_C14orf120_3 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-10-B | single siRNA, 0.9 | nmol1172 | 29123 | ANKRD11 | ankyrin repeat domain 11 | XM_932906 XM_941350 XM_945155 XM_945159 XM_945161 XM_945163 XM_945166 XM_945170 | CACGAGAGCCTTCTAATGCCA | SI03163370 | Hs_ANKRD11_5 |
| 900029-10-B | single siRNA, 0.9 | nmol1173 | 51079 | NDUFA13 | NADH dehydrogenase (ubiquinone) 1 alpha subcomplex, 13 | NM_013275 NM_015965 | AGGGATTGGAACCCTGATCTA | SI00430934 | Hs_GRIM19_3 |
| 900029-10-B | single siRNA, 0.9 | nmol1174 | 51655 | RASD1 | RAS, dexamethasone-induced 1 | NM_016084 | CCCCAAGGTCTCCGTGCAGTA | SI03080483 | Hs_RASD1_5 |
| 900029-10-B | single siRNA, 0.9 | nmol1175 | 55236 | UBE1L2 | ubiquitin-activating enzyme E1-like 2 | NM_018227 | ATGGATCTATCAACAATAA | SI00389935 | Hs_FLJ10808_3 |
| 900029-10-B | single siRNA, 0.9 | nmol1176 | 56776 | FMN2 | formin 2 | NM_020066 XM_371352 | CTGATACTATCTCAAAGACGA | SI03208952 | Hs_FMN2_7 |
| 900029-10-B | single siRNA, 0.9 | nmol1177 | 60412 | EXOC4 | exocyst complex component 4 | NM_001037126 NM_021807 | CAGCAAGAAGATGAACCTTCA | SI00714301 | Hs_SEC8L1_3 |
| 900029-10-B | single siRNA, 0.9 | nmol1178 | 64866 | CDCP1 | CUB domain containing protein 1 | NM_022842 | AAGATGCAAGAAGGAGTGAAA | SI00341439 | Hs_CDCP1_3 |
| 900029-10-B | single siRNA, 0.9 | nmol1179 | 80218 | NAT13 | N-acetyltransferase 13 | NM_178181 NM_025146 | TTGGTGCAGTTAAGAATTAAA | SI00627200 | Hs_MAK3_4 |
| 900029-10-B | single siRNA, 0.9 | nmol1180 | 83737 | ITCH | itchy homolog E3 ubiquitin protein ligase (mouse) | NM_031483 | ATGGGTAGCCTCACCATGAAA | SI03051839 | Hs_ITCH_5 |
| 900029-10-B | single siRNA, 0.9 | nmol1181 | 26960 | NBEA | neurobeachin | NM_015678 | CGGGATGTGGATGATAGCAAA | SI00655473 | Hs_NBEA_3 |
| 900029-10-B | single siRNA, 0.9 | nmol1182 | 29127 | RACGAP1 | Rac GTPase activating protein 1 | NM_013277 | CAGGTGGATGTAGAGATCAAA | SI00101178 | Hs_RACGAP1_3 |
| 900029-10-B | single siRNA, 0.9 | nmol1183 | 51343 | FZR1 | fizzy/cell division cycle 20 related 1 (Drosophila) | NM_016263 | TGCAGTGACGCTGTCATTAAA | SI00114912 | Hs_FZR1_2 |
| 900029-10-B | single siRNA, 0.9 | nmol1184 | 53358 | SHC3 | SHC (Src homology 2 domain containing) transforming protein 3 | NM_016848 | CAGCAAACACCTTAAGGCAA | SI00717836 | Hs_SHC3_4 |
| 900029-10-B | single siRNA, 0.9 | nmol1185 | 55327 | LIN7C | lin-7 homolog C (C. elegans) | NM_018362 | TGGCATATTGACCCTATATAA | SI02778041 | Hs_LIN7C_5 |
| 900029-10-B | single siRNA, 0.9 | nmol1186 | 56907 | SPIRE1 | spire homolog 1 (Drosophila) | NM_020148 | TACGAGAATCAGTCTAACAGA | SI03225335 | Hs_SPIRE1_7 |
| 900029-10-B | single siRNA, 0.9 | nmol1187 | 63920 | LOC63920 | transposon-derived Buster3 transposase-like | NM_022090 | AAGCACTAGAATATCCAGCTA | SI00620284 | Hs_LOC63920_4 |
| 900029-10-B | single siRNA, 0.9 | nmol1188 | 79009 | DDX50 | DEAD (Asp-Glu-Ala-Asp) box polypeptide 50 | NM_024045 | CACAAGAATGGAACAAATCTA | SI00361655 | Hs_DDX50_3 |
| 900329-10-B | single siRNA, 0.9 | nmol1189 | 80336 | C20orf119 | chromosome 20 open reading frame 119 | XM_001130728 XM_001131956 | TCCATTGACAACAAGGCTTTA | SI03020031 | Hs_C20orf119_3 |
| 900029-10-B | single siRNA, 0.9 | nmol1190 | 84790 | TUBA1C | tubulin alpha 1c | NM_032704 | ATTGCCGTAAATGTTAATAA | SI02653777 | Hs_TUBA6_2 |
| 900029-10-B | single siRNA, 0.9 | nmol1191 | 26986 | PABPC1 | poly(A) binding protein, cytoplasmic 1 | NM_002568 | ATGCCAGGTCTAGCAAACATA | SI03152352 | Hs_PABPC1_5 |
| 900029-10-B | single siRNA, 0.9 | nmol1192 | 29924 | EPN1 | epsin 1 | NM_013333 | CCCGACGAGTTCTCTGACTTT | SI00380611 | Hs_EPN1_3 |
| 900029-10-B | single siRNA, 0.9 | nmol1193 | 51473 | DCDC2 | doublecortin domain containing 2 | NM_016356 | AAGCACATAGTTATTGCTGAA | SI00360059 | Hs_DCDC2_3 |
| 900029-10-B | single siRNA, 0.9 | nmol1194 | 54206 | ERRFI1 | ERBB receptor feedback inhibitor 1 | NM_018948 | TAGACTGTATTAATAAACATA | SI00645785 | Hs_MIG-6_3 |
| 900029-10-B | single siRNA, 0.9 | nmol1195 | 55824 | PAG1 | phosphoprotein associated with glycosphingolipid microdomains 1 | NM_018440 | AACAGAGAGCCTTAATCTTA | SI02643298 | Hs_PAG_7 |
| 900029-10-B | single siRNA, 0.9 | nmol1196 | 57403 | RAB22A | RAB22A, member RAS oncogene family | NM_020673 | CAGGTTTAATTTGATGGTCTA | SI02662184 | Hs_RAB22A_5 |
| 900029-10-B | single siRNA, 0.9 | nmol1197 | 63932 | CXorf56 | chromosome X open reading frame 56 | NM_022101 | CGGATTCCTATTTATGCCCTA | SI03195731 | Hs_CXorf56_1 |
| 900029-10-B | single siRNA, 0.9 | nmol1198 | 79090 | TRAPPC6A | trafficking protein particle complex 6A | NM_024108 | CAGGAAGTGGGTATCAAATTG | SI03173653 | Hs_TRAPPC6A_1 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-10-B | 0.9 nmol single siRNA, | 1199 | 80725 | SNIP | SNAP25-interacting protein | NM_025248 | CAGGCCACTAACCATCTAA | SI00728161 | Hs SNIP 3 |
| 900029-10-B | 0.9 nmol single siRNA, | 1200 | 84918 | LRP11 | low density lipoprotein receptor-related protein 11 | NM_032832 | CAGCAACTCATTTATATAT | SI00623637 | Hs LRP11 3 |
| 900029-11-A | 0.9 nmol single siRNA, | 1201 | 84962 | JUB | jub, ajuba homolog (Xenopus laevis) | NM_032876 NM_198086 | CCCAAAGATCATGATATTCCA | SI00450093 | Hs JUB 4 |
| 900029-11-A | 0.9 nmol single siRNA, | 1202 | 94030 | LRRC4B | leucine rich repeat containing 4B | NM_001080457 XM_292778 XM_936789 | GAGCAAGAACCTGGTGCGCAA | SI03102869 | Hs LRRC4B 5 |
| 900029-11-A | 0.9 nmol single siRNA, | 1203 | 144983 | RP11-78J21.1 | heterogeneous nuclear ribonucleoprotein A1-like | NM_001011724 NM_001011725 | TAGGACATGCTCCAAAGAAGA | SI03228127 | Hs RP11-78J21.1 4 |
| 900029-11-A | 0.9 nmol single siRNA, | 1204 | 284393 | LOC284393 | similar to ribosomal protein L10 | XM_209178 XM_934704 XM_934705 XM_934706 XM_939745 XM_944311 XM_944319 XM_944324 | CCGCACCAAGCTGCAGAACAA | SI02779523 | Hs LOC284393 5 |
| 900029-11-A | 0.9 nmol single siRNA, | 1205 | 642045 | LOC642045 | similar to myosin regulatory light chain-like | XM_936114 | GAGATGTGTCTATCCTAACCAA | SI02795142 | Hs LOC642045 4 |
| 900029-11-A | 0.9 nmol single siRNA, | 1206 | 648695 | LOC648695 | similar to retinoblastoma binding protein 4 | XM_944239 XM_944246 | TTCAACAAAGCTACAGAGTTA | SI03240524 | Hs LOC648695 4 |
| 900029-11-A | 0.9 nmol single siRNA, | 1207 | 731292 | LOC731292 | similar to Phosphatidylinositol-3,4,5-trisphosphate 3-phosphatase and dual-specificity protein phosphatase PTEN (Phosphatase and tensin homolog) (Mutated in multiple advanced cancers 1) | XM_001130021 | CACGATGGGAGGACAAGTTCA | SI03533467 | Hs LOC731292 4 |
| 900029-11-A | 0.9 nmol single siRNA, | 1208 | 84961 | MGC14376 | hypothetical protein MGC14376 | NM_001001870 NM_032895 | CTGGATGACAGTTGGGTGATA | SI03211068 | Hs MGC14376 6 |
| 900029-11-A | 0.9 nmol single siRNA, | 1209 | 103910 | MRLC2 | myosin regulatory light chain MRLC2 | NM_033546 | CAGGGCCAATCAATTTCACCA | SI03176495 | Hs MRLC2 5 |
| 900029-11-A | 0.9 nmol single siRNA, | 1210 | 150094 | SNF1LK | SNF1-like kinase | NM_173354 | TCCACACATCATAAAGCTTTA | SI02660490 | Hs SNF1LK 6 |
| 900029-11-A | 0.9 nmol single siRNA, | 1211 | 286887 | KRT6C | keratin 6C | NM_173086 | CAGGCTGAATGGCGAAGCAT | SI03175949 | Hs KRT6E 7 |
| 900029-11-A | 0.9 nmol single siRNA, | 1212 | 642954 | LOC642954 | similar to retinoblastoma binding protein 4 | XM_931847 XM_931860 | TTCAACAAAGCTACAGAGTTA | SI03240517 | Hs LOC842954 4 |
| 900029-11-A | 0.9 nmol single siRNA, | 1213 | 643997 | LOC643997 | similar to peptidylprolyl isomerase A isoform 1 | XM_939418 | CCAAGTCTGAGTCGTTGGATA | SI03180002 | Hs LOC650332 4 |
| 900029-11-A | 0.9 nmol single siRNA, | 1214 | 731751 | LOC731751 | similar to protein kinase, DNA-activated, catalytic polypeptide | XM_001129414 | CAGGATACTGTTTCCTTACTA | SI03528063 | Hs LOC731751 4 |
| 900029-11-A | 0.9 nmol single siRNA, | 1215 | 85021 | REPS1 | RALBP1 associated Eps domain containing 1 | NM_031922 | AACGCTCTTCAAGCTCACAAA | SI03125871 | Hs REPS1 5 |
| 900029-11-A | 0.9 nmol single siRNA, | 1216 | 121536 | AEBP2 | AE binding protein 2 | NM_153207 | CTGGATGCGATAAGACATCGA | SI03211145 | Hs AEBP2 5 |
| 900029-11-A | 0.9 nmol single siRNA, | 1217 | 151987 | PPP4R2 | protein phosphatase 4, regulatory subunit 2 | NM_174907 | CAAGGAGAAACTATACAGGAA | SI00691628 | Hs PPP4R2 4 |
| 900029-11-A | 0.9 nmol single siRNA, | 1218 | 343472 | BARHL2 | BarH-like 2 (Drosophila) | NM_020063 | CTCCCTGTTCGGAGATTGATA | SI03200540 | Hs BARHL2 5 |
| 900029-11-A | 0.9 nmol single siRNA, | 1219 | 643751 | LOC643751 | similar to cell division cycle 42 | XM_928854 XM_933237 XM_933245 XM_940814 XM_944817 | TGGAGTGTTCTGACTTACAA | SI03237640 | Hs LOC643751 4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-11-A | single siRNA, 0.9 nmol | 1220 | 727897 | MUC5B | mucin 5B, oligomeric mucus/gel-forming | XM_944820 | CCCGGCCTTCAACGAGTTCTA | SI03528147 | Hs_LOC649768_4 |
| 900029-11-A | single siRNA, 0.9 nmol | 1221 | 85458 | DIXDC1 | DIX domain containing 1 | XM_001126093 XM_001129427 NM_001037954 NM_033425 | AACTACCGAGATTATTTGATA | SI03126746 | Hs_DIXDC1_5 |
| 900029-11-A | single siRNA, 0.9 nmol | 1222 | 139322 | APOOL | apolipoprotein O-like | NM_198450 | TAGTTAAATTAGAATGTGTA | SI03229394 | Hs_FAM121A_2 |
| 900029-11-A | single siRNA, 0.9 nmol | 1223 | 253738 | EBF3 | early B-cell factor 3 | NM_001005463 | AAGTTGTAGCTAAATATTTA | SI03122511 | Hs_EBF3_1 |
| 900029-11-A | single siRNA, 0.9 nmol | 1224 | 387927 | LOC387927 | similar to NIMA (never in mitosis gene a)-related expressed kinase 5 | XM_370726 XM_941704 | ATGAAGCTCCAGGAACTTTAA | SI00510405 | Hs_LOC387927_4 |
| 900029-11-A | single siRNA, 0.9 nmol | 1225 | 643752 | hCG1757335 | hCG1757335 | XM_001129413 XM_928885 XM_938419 | CTAGAGTATGCAGCTGGTAAA | SI03198174 | Hs_LOC643752_4 |
| 900029-11-A | single siRNA, 0.9 nmol | 1226 | 728153 | LOC728153 | hypothetical protein LOC728153 | XM_001128002 XXM_001128014 | CCCGGCAGGGTTGTTCTTAA | SI03351610 | Hs_LOC728153_4 |
| 900029-11-A | single siRNA, 0.9 nmol | 1227 | 90665 | TBL1Y | transducin (beta)-like 1Y-linked | NM_033284 NM_134258 NM_134259 | TTCGCTCTGAAATGGAACAAA | SI03242407 | Hs_TBL1Y_5 |
| 900029-11-A | single siRNA, 0.9 nmol | 1228 | 140735 | DYNLL2 | dynein, light chain, LC8-type 2 | NM_080677 | CTGCATGGACTGTATACTCGA | SI00369390 | Hs_Dlc2_4 |
| 900029-11-A | single siRNA, 0.9 nmol | 1229 | 255324 | EPGN | epithelial mitogen homolog (mouse) | NM_001013442 | TTGGATTACTATTAAGTGGTT | SI03245004 | Hs_UNQ3072_4 |
| 900029-11-A | single siRNA, 0.9 nmol | 1230 | 389342 | LOC389342 | similar to ribosomal protein L10 | XM_171078 XM_371781 XM_926723 XM_931512 XM_931519 XM_931525 XM_931532 XM_931535 XM_942217 XM_945797 XM_945798 XM_945799 XM_945800 | CCGCCTGTTGTTACCGGTATT | SI03189249 | Hs_LOC389342_7 |
| 900029-11-A | single siRNA, 0.9 nmol | 1231 | 643997 | LOC643997 | similar to peptidylprolyl isomerase A isoform 1 | XM_292963 | CCAAGTCTGAGTGTTGGATA | SI02792762 | Hs_LOC643997_4 |
| 900029-11-A | single siRNA, 0.9 nmol | 1232 | 728198 | LOC728198 | similar to transcription associated factor 9B | XM_001126120 | CAGAGTATGAACCAAGGTTA | SI03499167 | Hs_LOC728198_4 |
| 900029-11-A | single siRNA, 0.9 nmol | 1233 | 92521 | SPECC1 | sperm antigen with calponin homology and coiled-coil domains 1 | NM_001033553 NM_001033554 NM_001033555 NM_152904 | CCAAATGTCGATCGAACATCA | SI03179883 | Hs_SPECC1_1 |
| 900029-11-A | single siRNA, 0.9 nmol | 1234 | 140801 | RPL10L | ribosomal protein L10-like | NM_080746 | CCAGAAGATTCATATCTCCAA | SI00705572 | Hs_RPL10L_4 |
| 900029-11-A | single siRNA, 0.9 nmol | 1235 | 283455 | KSR2 | kinase suppressor of ras 2 | NM_173598 | AAGGAAATCCATTACTTCCAA | SI02665551 | Hs_KSR2_6 |
| 900029-11-A | single siRNA, 0.9 nmol | 1236 | 390006 | LOC390006 | similar to peptidylprolyl isomerase A isoform 1 | NM_001130327 XM_372328 | CAAGATGAAAGAAGGCATAAA | SI00529053 | Hs_LOC390006_4 |
| 900029-11-A | single siRNA, 0.9 nmol | 1237 | 645691 | LOC645691 | similar to Heterogeneous nuclear ribonucleoprotein A1 (Helix-destabilizing protein) (Single-strand binding protein) (hnRNP core protein A1) (HDP-1) (Topoisomerase-inhibitor | XM_928701 XM_936790 | CATGGAATTATTGGTTATAAA | SI03179596 | Hs_LOC645691_4 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-11-A | single siRNA, 0.9 nmol | 1238 | 728024 | hCG1640171 | similar to hCG1640171 (suppressed) | XM_001129715 | CACAGAGAAGACGAAGAGACTAT | SI03530506 | Hs LOC731173_4 |
| 900029-11-B | single siRNA, 0.9 nmol | 1239 | 84962 | JUB | jub, ajuba homolog (Xenopus laevis) | NM_032876 NM_198086 | CTGCTAGGCAACCAAATTTAA | SI00450086 | Hs JUB_3 |
| 900029-11-B | single siRNA, 0.9 nmol | 1240 | 94030 | LRRC48 | leucine rich repeat containing 4B | NM_001080457 XM_292778 XM_936789 | CACCTCCATGACCTCCGTCAA | SI00624288 | Hs LRRC4B_4 |
| 900029-11-B | single siRNA, 0.9 nmol | 1241 | 144983 | RP11-78J21.1 | heterogeneous nuclear ribonucleoprotein A1-like | NM_001011724 NM_001011725 | ATGAAGCAGCTTCATATCTAA | SI03151204 | Hs RP11-78J21.1_3 |
| 900029-11-B | single siRNA, 0.9 nmol | 1242 | 284393 | LOC284393 | similar to ribosomal protein L10 | XM_209178 XM_934704 XM_934705 XM_934706 XM_939745 XM_944311 XM_944319 XM_944324 | TCCCTTCAGTGTGCCACTGAA | SI03114790 | Hs LOC284393_8 |
| 900029-11-B | single siRNA, 0.9 nmol | 1243 | 642045 | LOC642045 | similar to myosin regulatory light chain-like | XM_936114 | CAGAGAAGCGCTATTAACAA | SI02795135 | Hs LOC642045_3 |
| 900029-11-B | single siRNA, 0.9 nmol | 1244 | 648695 | LOC648695 | similar to retinoblastoma binding protein 4 | XM_939603 XM_944234 XM_944239 XM_944243 XM_944246 | GACCGAATGTCTAGGATTTAA | SI03216171 | Hs LOC648695_3 |
| 900029-11-B | single siRNA, 0.9 nmol | 1245 | 731292 | LOC731292 | similar to Phosphatidylinositol-3,4,5-trisphosphate 3-phosphatase and dual-specificity protein phosphatase PTEN (Phosphatase and tensin homolog) (Mutated in multiple advanced cancers 1) | XM_001130021 | ACGAACTGGTATAATGATTTA | SI03533460 | Hs LOC731292_3 |
| 900029-11-B | single siRNA, 0.9 nmol | 1246 | 84981 | MGC14376 | hypothetical protein MGC14376 | NM_001001870 NM_032895 | AGGAGTAGAAGGCTCAAACAA | SI03145779 | Hs MGC14376_5 |
| 900029-11-B | single siRNA, 0.9 nmol | 1247 | 103910 | MRLC2 | myosin regulatory light chain MRLC2 | NM_033546 | ACTGAAAGAACTTTAGCTAAA | SI00648025 | Hs MRLC2_3 |
| 900029-11-B | single siRNA, 0.9 nmol | 1248 | 150094 | SNF1LK | SNF1-like kinase | NM_173354 | TACCTCGGACGTCTACGGAAA | SI03109162 | Hs SNF1LK_9 |
| 900029-11-B | single siRNA, 0.9 nmol | 1249 | 286867 | KRT6C | keratin 6C | NM_173086 | CAGCCCTTCTCATCTCCTGGAA | SI03171028 | Hs KRT6E_6 |
| 900029-11-B | single siRNA, 0.9 nmol | 1250 | 642954 | LOC642954 | similar to retinoblastoma binding protein 4 | XM_927104 XM_931842 XM_931847 XM_931856 XM_931860 | GACCGAATGTCTAGGATTTAA | SI03216164 | Hs LOC642954_3 |
| 900029-11-B | single siRNA, 0.9 nmol | 1251 | 643997 | LOC643997 | similar to peptidylprolyl isomerase A isoform 1 | XM_939418 | CAGGTCCTGGCATATGTCCA | SI03177258 | Hs LOC650332_3 |
| 900029-11-B | single siRNA, 0.9 nmol | 1252 | 731751 | LOC731751 | similar to protein kinase, DNA-activated, catalytic polypeptide | XM_001129414 | CAACGTGTCAAGCTACTTAAA | SI03528056 | Hs LOC731751_3 |
| 900029-11-B | single siRNA, 0.9 nmol | 1253 | 85021 | REPS1 | RALBP1 associated Eps domain containing 1 | NM_031922 | ATGGCTATGATTACCAGAAA | SI00701288 | Hs REPS1_4 |
| 900029-11-B | single siRNA, 0.9 nmol | 1254 | 121536 | AEBP2 | AE binding protein 2 | NM_153207 | AAGCACCTTCTTTAACAATAA | SI00292890 | Hs AEBP2_4 |
| 900029-11-B | single siRNA, 0.9 nmol | 1255 | 151987 | PPP4R2 | protein phosphatase 4, regulatory subunit 2 | NM_174907 | AAGAGGCAAATTTGCAGCAAA | SI00691621 | Hs PPP4R2_3 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-11-B | 0.9 nmol single siRNA, | 1256 | 343472 | BARHL2 | BarH-like 2 (Drosophila) | NM_020063 | TCCGACCACCAGCTCAATCAA | SI00310366 | Hs_BARHL2_4 |
| 900029-11-B | 0.9 nmol single siRNA, | 1257 | 643751 | LOC643751 | similar to cell division cycle 42 | XM_928854 XM_933237 XM_940814 XM_944817 XM_944820 | GGCGATGGTGCTGTTAGTAAA | SI03221078 | Hs_LOC643751_3 |
| 900029-11-B | 0.9 nmol single siRNA, | 1258 | 727897 | MUC5B | mucin 5B, oligomeric mucus/gel-forming | XM_001126093 XM_001129427 XM_938837 | CCCGATGGGTTTCCTAAATTT | SI03528140 | Hs_LOC649768_3 |
| 900029-11-B | 0.9 nmol single siRNA, | 1259 | 85458 | DIXDC1 | DIX domain containing 1 | NM_033425 | CTGCTGAAATGTAAACAAGAA | SI00364259 | Hs_DIXDC1_3 |
| 900029-11-B | 0.9 nmol single siRNA, | 1260 | 139322 | APOOL | apolipoprotein O-like | NM_198450 | AAGAGTCACTCCTAAACCTA | SI03128951 | Hs_FAM121A_1 |
| 900029-11-B | 0.9 nmol single siRNA, | 1261 | 253738 | EBF3 | early B-cell factor 3 | NM_001005463 | TACACTACAATTGTTAATAAA | SI00368039 | Hs_DKFZp-667B0210_3 |
| 900029-11-B | 0.9 nmol single siRNA, | 1262 | 387927 | LOC387927 | similar to NIMA (never in mitosis gene a)-related expressed kinase 5 | XM_370726 XM_941704 | TTGGAGAATATTTCTACTACA | SI00510398 | Hs_LOC387927_3 |
| 900029-11-B | 0.9 nmol single siRNA, | 1263 | 643752 | hCG1757335 | hCG1757335 | XM_001129413 XM_928885 XM_938419 | CGCCCAGATTCAGGCGTGTAA | SI03193708 | Hs_LOC643752_3 |
| 900029-11-B | 0.9 nmol single siRNA, | 1264 | 728153 | LOC728153 | hypothetical protein LOC728153 | XM_001128002 XM_001128014 | AAAGGTAAATAAGCTCCCTAA | SI03351603 | Hs_LOC728153_3 |
| 900029-11-B | 0.9 nmol single siRNA, | 1265 | 90665 | TBL1Y | transducin (beta)-like 1Y-linked | NM_033284 NM_134258 NM_134259 | CAGGAGTGTATATGTTTCATA | SI00740460 | Hs_TBL1Y_4 |
| 900029-11-B | 0.9 nmol single siRNA, | 1266 | 140735 | DYNLL2 | dynein, light chain, LC8-type 2 | NM_080677 | TTGACAAGAAATATAAGCCTA | SI00369383 | Hs_Dlc2_3 |
| 900329-11-B | 0.9 nmol single siRNA, | 1267 | 255324 | EPGN | epithelial mitogen homolog (mouse) | NM_001013442 | CTGCTATATAAGAAAGAGGTA | SI03209052 | Hs_UNQ3072_3 |
| 900329-11-B | 0.9 nmol single siRNA, | 1268 | 389342 | LOC389342 | similar to ribosomal protein L10 | XM_371781 XM_926723 XM_931512 XM_931519 XM_931525 XM_931532 XM_931535 XM_942217 XM_945797 XM_945798 XM_945799 XM_945800 | CACCAATAAATTCTACTAACT | SI03160570 | Hs_LOC389342_5 |
| 900029-11-B | 0.9 nmol single siRNA, | 1269 | 643997 | LOC643997 | similar to peptidylprolyl isomerase A isoform 1 | XM_292963 | CAGGTCCTGGCATATTGTCCA | SI02797551 | Hs_LOC643997_3 |
| 900029-11-B | 0.9 nmol single siRNA, | 1270 | 728198 | LOC728198 | similar to transcription associated factor 9B | XM_001126120 | CAGAAGTTTCATCTTAGGATA | SI03499160 | Hs_LOC728198_3 |
| 900029-11-B | 0.9 nmol single siRNA, | 1271 | 92521 | SPECC1 | sperm antigen with calponin homology and coiled-coil domains 1 | NM_001033553 NM_001033554 NM_001033555 NM_152904 | CAGCAACAAATGTACAGGAA | SI00434777 | Hs_HCMOGT-1_4 |
| 900029-11-B | 0.9 nmol single siRNA, | 1272 | 140801 | RPL10L | ribosomal protein L10-like | NM_080746 | CCGTATTTGTGCAACAAATA | SI00705565 | Hs_RPL10L_3 |
| 900029-11-B | 0.9 nmol single siRNA, | 1273 | 283455 | KSR2 | kinase suppressor of ras 2 | NM_173598 | CAGGCTTACCGTGGACGCCTA | SI02655445 | Hs_KSR2_5 |

TABLE 3-continued

| Plate Id | Plate Name | SEQ ID NO: | Entrez Gene Id | NCBI gene symbol | Gene Description | mRNA Accessions | siRNA Target Sequence | Product Id | Product Name |
|---|---|---|---|---|---|---|---|---|---|
| 900029-11-B | single siRNA, 0.9 nmol | 1274 | 390006 | LOC390006 | similar to peptidylprolyl isomerase A isoform 1 | XM_001130327 XM_372328 | TTCTTCAACATTGCCATCAAT | SI00529048Hs | LOC390006_3 |
| 900029-11-B | single siRNA, 0.9 nmol | 1275 | 645691 | LOC645691 | similar to Heterogeneous nuclear ribonucleoprotein A1 (Helix-destabilizing protein) (Single-strand binding protein) (hnRNP core protein A1) (HDP-1) (Topoisomerase-inhibitor suppressed) | XM_928701 XM_936790 | ATCCTATGCAATATATCTAAA | SI03149713Hs_ | LOC645691_3 |
| 900029-11-B | single siRNA, 0.9 nmol | 1276 | 728024 | hCG_1640171 | hCG1640171 | XM_001129715 | TTGAACTACAGTACAGAAAGA | SI03283343Hs | LOC731173_3 |

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for modulating sensitivity to EGFR/MEK-1 targeting agents in cancer cells, comprising:
   a) providing cancer cells comprising genes present in an EGFR/NEDD9/TGF-β interactome, said genes being involved in cellular proliferation and EGFR/MEK-1 signalling;
   b) contacting said cancer cells with at least one compound which inhibits EGFR/NEDD9/TGF-β interactome gene SC4MOL; and
   c) contacting said cancer cells of step b) with at least one EGFR-MEK-1 targeting agent which is selected from erlotinib, and cetuximab, thereby increasing sensitivity to said EGFR/MEK-1 targeting agent in said cancer cells, wherein said cancer cells are squamous cell carcinoma cells.

2. The method of claim 1, wherein said compound is a siRNA that decreases SC4MOL expression.

* * * * *

UNITED STATES PATENT AND TRADEMARK OFFICE
CERTIFICATE OF CORRECTION

| | |
|---|---|
| PATENT NO. | : 10,450,613 B2 |
| APPLICATION NO. | : 15/171663 |
| DATED | : October 22, 2019 |
| INVENTOR(S) | : Igor Astsaturov et al. |

It is certified that error appears in the above-identified patent and that said Letters Patent is hereby corrected as shown below:

In the Specification

Column 1
Line 22, before the heading "FIELD OF THE INVENTION":
Insert --STATEMENT OF FEDERAL FUNDING
This invention was made with government support under CA188430 awarded by the National Institutes of Health. The government has certain rights in the invention.--

Signed and Sealed this
Twenty-second Day of August, 2023

Katherine Kelly Vidal
*Director of the United States Patent and Trademark Office*